(12) United States Patent
Kawakami et al.

(10) Patent No.: US 11,522,138 B2
(45) Date of Patent: Dec. 6, 2022

(54) HETEROCYCLIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Sachiko Kawakami, Kanagawa (JP); Yoshimi Ishiguro, Kanagawa (JP); Tatsuyoshi Takahashi, Kanagawa (JP); Takao Hamada, Toyama (JP)

(73) Assignee: Semiconductor Energy Laboratory Co., Ltd.

( * ) Notice: Subject to any disclaimer, the term of this patent is extended or adjusted under 35 U.S.C. 154(b) by 81 days.

(21) Appl. No.: 15/297,639

(22) Filed: Oct. 19, 2016

(65) Prior Publication Data

US 2017/0117487 A1    Apr. 27, 2017

(30) Foreign Application Priority Data

Oct. 23, 2015 (JP) .............................. JP2015-209351

(51) Int. Cl.
*H01L 51/00* (2006.01)
*C07D 409/10* (2006.01)
(Continued)

(52) U.S. Cl.
CPC ........ *H01L 51/0072* (2013.01); *C07D 403/10* (2013.01); *C07D 409/10* (2013.01);
(Continued)

(58) Field of Classification Search
CPC ......... H01L 51/003–0095; H01L 51/50–5296; H01L 2251/50–558; H01L 51/0071;
(Continued)

(56) References Cited

U.S. PATENT DOCUMENTS 7,449,980 B2   11/2008  Bates
8,318,322 B2   11/2012  Nomura et al.
(Continued)

FOREIGN PATENT DOCUMENTS

CN    102144313 A    8/2011
CN    102190653 A    9/2011
(Continued)

OTHER PUBLICATIONS

International Search Report re Application No. PCT/IB2016/056067, dated Dec. 27, 2016.
(Continued)

*Primary Examiner* — Dylan C Kershner
*Assistant Examiner* — Elizabeth M. Dahlburg
(74) *Attorney, Agent, or Firm* — Husch Blackwell LLP

(57) ABSTRACT

A novel heterocyclic compound is provided. In particular, a novel heterocyclic compound which can improve the element characteristics of a light-emitting element is provided. A novel light-emitting element with high emission efficiency and high heat resistance is provided. A heterocyclic compound represented by General Formula (G1). A represents any of a dibenzothiophenyl group, a dibenzofuranyl group, and a carbazolyl group. DBq represents a dibenzo[f,h]quinoxalinyl group. In addition, n is 0 or 1. Each of Ar1 to Ar4 independently represents a substituted or unsubstituted arylene group having 6 to 10 carbon atoms. In Ar1 to Ar4, the adjacent arylene groups may be bonded to each other to form a ring. When the adjacent arylene groups in Ar1 to Ar4 form a fluorene skeleton, the fluorene skeleton may have a substituent.

(G1)

$$DBq\text{-}Ar^1\text{—}Ar^2\text{—}Ar^3\text{\Large(}Ar^4\text{\Large)}_n A$$

13 Claims, 42 Drawing Sheets

(51) Int. Cl.
*H01L 51/50* (2006.01)
*H01L 27/32* (2006.01)
*C07D 403/10* (2006.01)
*C09K 11/02* (2006.01)

(52) U.S. Cl.
CPC ........ *C09K 11/025* (2013.01); *H01L 27/3255* (2013.01); *H01L 51/0074* (2013.01); *H01L 27/3244* (2013.01); *H01L 51/5012* (2013.01); *H01L 51/5056* (2013.01); *H01L 51/5072* (2013.01)

(58) Field of Classification Search
CPC ............. H01L 51/0072; H01L 27/3244; H01L 27/3255; H01L 51/5056; C07D 241/38; C07D 403/10; C07D 413/10; C07D 417/10; C09K 11/06; C09K 2211/00–188
USPC ................... 428/690, 691, 917; 427/58, 66; 313/498–512; 257/40, 88–103, 257/E51.001–E51.052; 252/301.16–301.35
See application file for complete search history.

(56) References Cited

U.S. PATENT DOCUMENTS

| | | | |
|---|---|---|---|
| 8,343,639 B2 | 1/2013 | Seo et al. | |
| 8,852,758 B2 | 10/2014 | Nomura et al. | |
| 9,079,879 B2 | 7/2015 | Kadoma et al. | |
| 9,133,169 B2 | 9/2015 | Kitano et al. | |
| 9,837,621 B2 * | 12/2017 | Inoue | C07D 409/10 |
| 2006/0078757 A1 * | 4/2006 | Boerner | C08G 61/123 428/690 |
| 2006/0088728 A1 * | 4/2006 | Kwong | C07D 209/82 428/690 |
| 2009/0284143 A1 | 11/2009 | Nomura et al. | |
| 2010/0060155 A1 | 3/2010 | Seo et al. | |
| 2011/0210316 A1 | 9/2011 | Kadoma et al. | |
| 2012/0126692 A1 * | 5/2012 | Ise | C09K 11/06 313/504 |
| 2013/0048971 A1 | 2/2013 | Kitano et al. | |
| 2013/0060033 A1 | 3/2013 | Seo et al. | |
| 2013/0112961 A1 | 5/2013 | Seo et al. | |
| 2014/0183503 A1 | 7/2014 | Kadoma et al. | |
| 2015/0060813 A1 | 3/2015 | Kawakami et al. | |
| 2015/0060818 A1 | 3/2015 | Ishiguro et al. | |
| 2015/0311454 A1 | 10/2015 | Inoue et al. | |
| 2015/0318493 A1 | 11/2015 | Kadoma et al. | |
| 2015/0318495 A1 | 11/2015 | Kawakami et al. | |
| 2016/0028022 A1 | 1/2016 | Seo et al. | |
| 2016/0240791 A1 * | 8/2016 | Lee | C07D 519/00 |

FOREIGN PATENT DOCUMENTS

| | | |
|---|---|---|
| CN | 103030632 A | 4/2013 |
| CN | 103765624 A | 4/2014 |
| CN | 105037332 A | 11/2015 |
| CN | 105304825 A | 2/2016 |
| CN | 105473577 A | 4/2016 |
| EP | 2 321 862 | 5/2011 |
| EP | 2 363 398 A1 | 9/2011 |
| JP | 2007-189001 A | 7/2007 |
| JP | 2009-298779 A | 12/2009 |
| JP | 2010-083876 A | 4/2010 |
| JP | 2011-201869 A | 10/2011 |
| JP | 2013-060459 A | 4/2013 |
| JP | 2013-063963 A | 4/2013 |
| JP | 2014-029973 A | 2/2014 |
| JP | 2014-058527 A | 4/2014 |
| JP | 2014-143412 A | 8/2014 |
| JP | 2015-063519 A | 4/2015 |
| JP | 2015-078228 A | 4/2015 |
| JP | 2015-128166 A | 7/2015 |
| JP | 2015-214539 A | 12/2015 |
| JP | 2015-227323 A | 12/2015 |
| JP | 2015-227328 A | 12/2015 |
| JP | 2016-032108 A | 3/2016 |
| JP | 2016-105485 A | 6/2016 |
| KR | 2011-0063749 A | 6/2011 |
| KR | 2011-0099173 A | 9/2011 |
| KR | 2013-0027426 A | 3/2013 |
| KR | 2013-0094762 A | 8/2013 |
| KR | 2014-0090142 A | 7/2014 |
| KR | 2014-0107700 A | 9/2014 |
| KR | 2015-0090836 A | 8/2015 |
| KR | 2015-0126555 A | 11/2015 |
| KR | 2016-0012948 A | 2/2016 |
| KR | 2016-0042920 A | 4/2016 |
| KR | 2016-0044491 A | 4/2016 |
| TW | 200630458 | 9/2006 |
| TW | 201202225 | 1/2012 |
| TW | 201315729 | 4/2013 |
| TW | 201512183 | 4/2015 |
| TW | 201518289 | 5/2015 |
| WO | WO 2006/047119 A1 | 5/2006 |
| WO | WO 2006/088728 A2 | 8/2006 |
| WO | WO 2010/027004 A1 | 3/2010 |
| WO | WO 2013/031527 A1 | 3/2013 |
| WO | WO 2015/029796 A1 | 3/2015 |
| WO | WO 2015/029807 A1 | 3/2015 |

OTHER PUBLICATIONS

Written Opinion re Application No. PCT/IB2016/056067, dated Dec. 27, 2016.
Taiwanese Office Action re Application No. TW 105133899, dated May 4, 2020.
Chinese Office Action (Application No. 201680061311.6) dated Dec. 3, 2020.

* cited by examiner

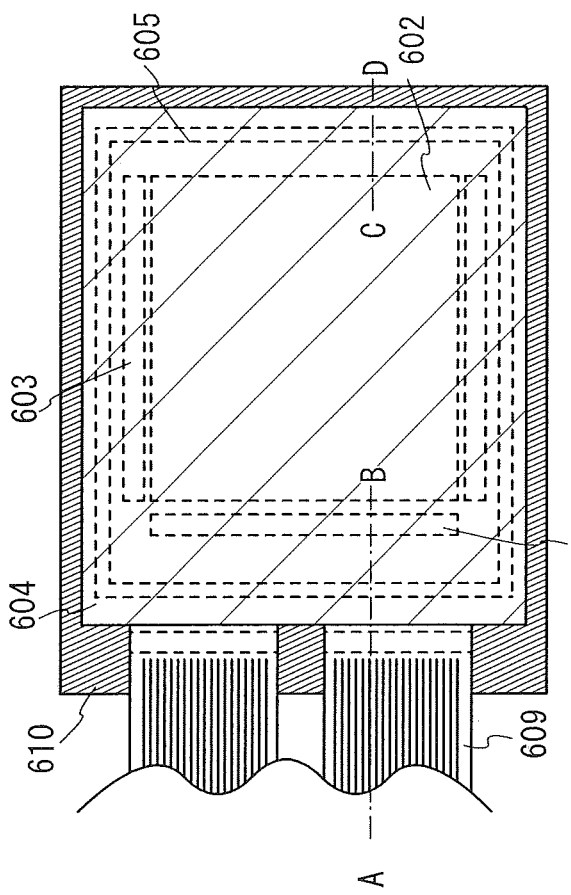
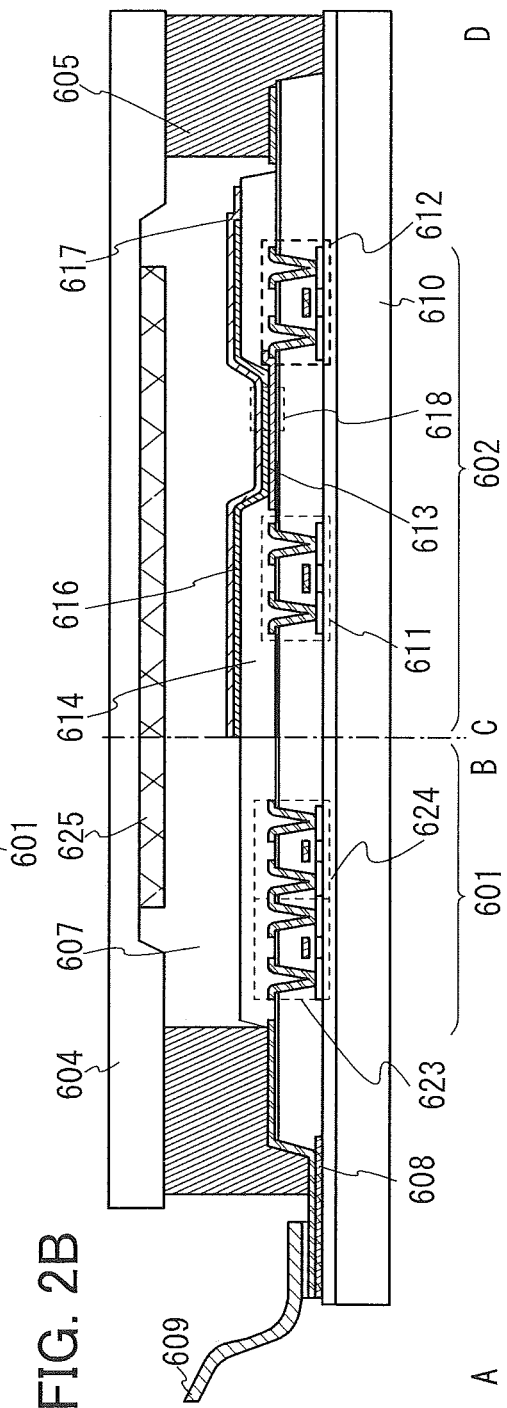
FIG. 2A
FIG. 2B

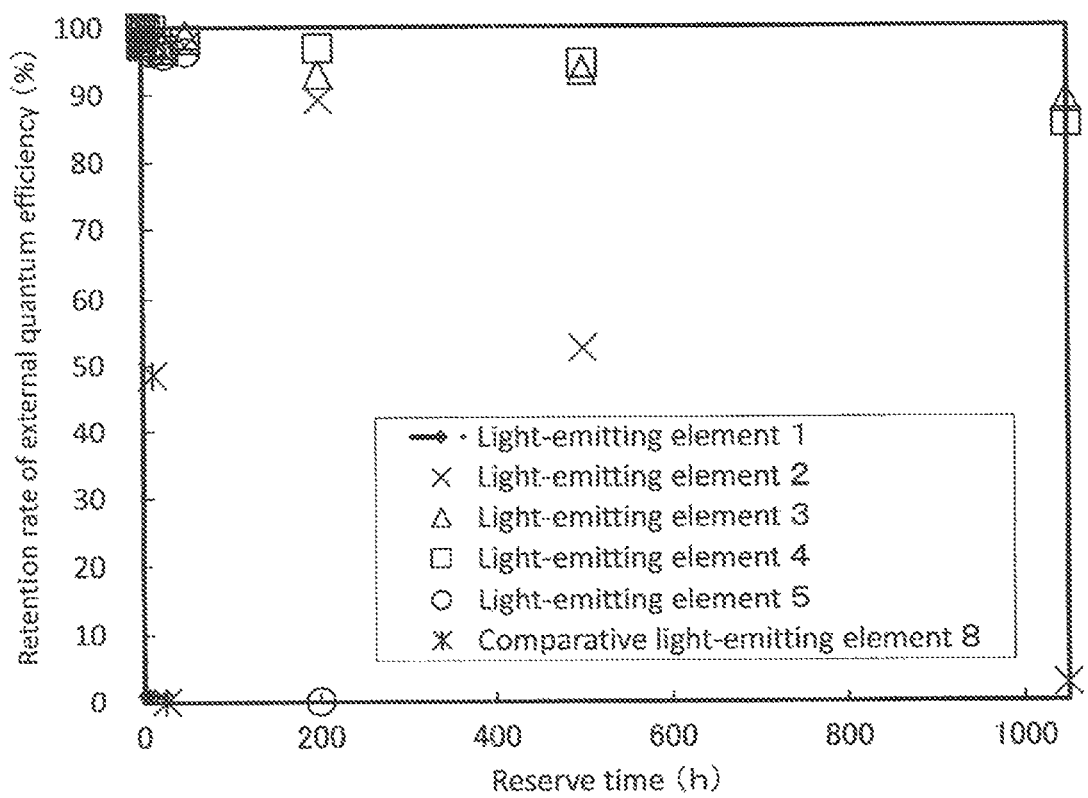

HETEROCYCLIC COMPOUND, LIGHT-EMITTING ELEMENT, LIGHT-EMITTING DEVICE, ELECTRONIC DEVICE, AND LIGHTING DEVICE

TECHNICAL FIELD

One embodiment of the present invention relates to an object, a method, and a manufacturing method. In addition, the present invention relates to a process, a machine, manufacture, or a composition of matter. In particular, one embodiment of the present invention relates to a semiconductor device, a light-emitting device, a display device, a lighting device, a light-emitting element, or a manufacturing method thereof. Further, one embodiment of the present invention relates to a heterocyclic compound and a novel method for synthesizing the heterocyclic compound. In addition, one embodiment of the present invention relates to a light-emitting element, a light-emitting device, an electronic device, and a lighting device that include the heterocyclic compound. Note that one embodiment of the present invention is not limited to the above technical field.

BACKGROUND ART

A light-emitting element using an organic compound as a luminous body, which has features such as thinness, lightness, high-speed response, and DC drive at low voltage, is expected to be applied to a next-generation flat panel display. A display device in which light-emitting elements are arranged in matrix is, in particular, considered to have advantages in a wide viewing angle and excellent visibility over a conventional liquid crystal display device.

It is said that the light emission mechanism of a light-emitting element is as follows: when a voltage is applied between a pair of electrodes with an EL layer including a luminous body provided therebetween, electrons injected from the cathode and holes injected from the anode recombine in the light emission center of the EL layer to form molecular excitons, and energy is released and light is emitted when the molecular excitons relax to the ground state. A singlet excited state and a triplet excited state are known as excited states, and it is thought that light emission can be achieved through either of the excited states.

An organic compound is mainly used in an EL layer in such a light-emitting element and greatly affects an improvement in the characteristics of the light-emitting element. For this reason, a variety of novel organic compounds have been developed (e.g., see Patent Document 1).

REFERENCE

Patent Document

[Patent Document 1] Japanese Published Patent Application No. 2007-189001

DISCLOSURE OF INVENTION

Compounds having a dibenzo[f,h]quinoxaline ring which are reported in Patent Document 1 are useful as materials that are used in light-emitting elements. However, compounds having structures with higher thermal stability have been demanded. Particularly when light-emitting elements for automobile use and light-emitting devices, electronic devices, and lighting devices that include the light-emitting elements are considered, the light-emitting elements desirably have heat resistance to withstand temperatures of 100° C. or higher; thus, an important object is to make light-emitting elements highly heat resistant. A possible solution is the use of a compound with an increased molecular mass; however, a compound whose molecular mass is increased simply by changing a substituent or the like also has an increased refractive index. When such a compound is used in an EL layer of a light-emitting element, light extraction efficiency is reduced, leading to a reduction in external quantum efficiency of the light-emitting element. Moreover, when heat resistance is increased by increasing molecular mass, thermal decomposition occurs at the time of deposition by evaporation or sublimation purification, and film purity might decrease. Accordingly, simply increasing the molecular mass of a compound can hardly enable the compound to have higher stability than the compound described in Patent Document 1 and enable an element including the compound to have improved characteristics at the same time.

In view of the above, an object of one embodiment of the present invention is to provide a novel heterocyclic compound. In particular, an object of one embodiment of the present invention is to provide a novel heterocyclic compound which can improve the element characteristics of a light-emitting element. An object of one embodiment of the present invention is to provide a novel light-emitting element with high emission efficiency and high heat resistance. An object of one embodiment of the present invention is to provide a novel heterocyclic compound that can be used in a light-emitting element. An object of one embodiment of the present invention is to provide a novel heterocyclic compound that can be used in an EL layer of a light-emitting element. An object of one embodiment of the present invention is to provide a novel light-emitting element. An object of one embodiment of the present invention is to provide a novel light-emitting device, a novel electronic device, or a novel lighting device. Note that the descriptions of these objects do not disturb the existence of other objects. In one embodiment of the present invention, there is no need to achieve all of these objects. Other objects will be apparent from and can be derived from the description of the specification, the drawings, the claims, and the like.

One embodiment of the present invention is a heterocyclic compound represented by General Formula (G1).

[Chemical formula 1]

(G1)

In the formula, A represents any of a substituted or unsubstituted dibenzothiophenyl group, a substituted or unsubstituted dibenzofuranyl group, and a substituted or unsubstituted carbazolyl group. DBq represents a substituted or unsubstituted dibenzo[f,h]quinoxalinyl group. In addition, n is 0 or 1. Each of $Ar^1$ to $Ar^4$ independently represents a substituted or unsubstituted arylene group having 6 to 10 carbon atoms. In $Ar^1$ to $Ar^4$, the adjacent arylene groups may be bonded to each other to form a ring. When the adjacent arylene groups in $Ar^1$ to $Ar^4$ form a fluorene skeleton, the fluorene skeleton may have a substituent.

Another embodiment of the present invention is a heterocyclic compound represented by General Formula (G2-1).

[Chemical Formula 2]

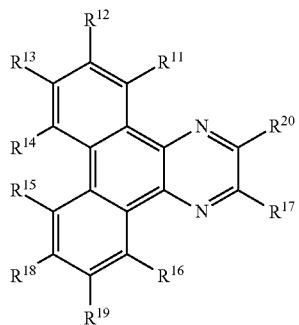

(G2-1)

In the formula, any one of $R^{18}$ to $R^{20}$ represents a substituent represented by General Formula (G2-2). Each of the other two of $R^{18}$ to $R^{20}$ and $R^{11}$ to $R^{17}$ independently represents hydrogen, an alkyl group having 1 to 4 carbon atoms, or a substituted or unsubstituted aryl group having 6 to 13 carbon atoms.

[Chemical Formula 3]

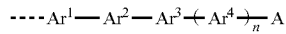

(G2-2)

In the formula, A represents any of a substituted or unsubstituted dibenzothiophenyl group, a substituted or unsubstituted dibenzofuranyl group, and a substituted or unsubstituted carbazolyl group. In addition, n is 0 or 1. Each of $Ar^1$ to $Ar^4$ independently represents a substituted or unsubstituted arylene group having 6 to 10 carbon atoms. In $Ar^1$ to $Ar^4$, the adjacent arylene groups may be bonded to each other to form a ring. When the adjacent arylene groups in $Ar^1$ to $Ar^4$ form a fluorene skeleton, the fluorene skeleton may have a substituent.

Another embodiment of the present invention is a heterocyclic compound represented by General Formula (G3-1).

[Chemical Formula 4]

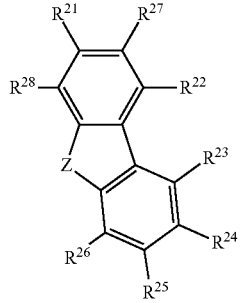

(G3-1)

In the formula, any one of $R^{27}$ and $R^{28}$ represents a substituent represented by General Formula (G3-2). Each of the other of $R^{27}$ and $R^{28}$ and $R^{21}$ to $R^{26}$ independently represents hydrogen, an alkyl group having 1 to 4 carbon atoms, or a substituted or unsubstituted aryl group having 6 to 13 carbon atoms. Z represents oxygen, sulfur, or nitrogen. When Z represents nitrogen, a substituent or no substituent may be bonded at the Z-position.

[Chemical Formula 5]

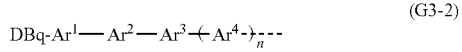

(G3-2)

In the formula, DBq represents a substituted or unsubstituted dibenzo[f,h]quinoxalinyl group. In addition, n is 0 or 1. Each of $Ar^1$ to $Ar^4$ independently represents a substituted or unsubstituted arylene group having 6 to 10 carbon atoms. In $Ar^1$ to $Ar^4$, the adjacent arylene groups may be bonded to each other to form a ring. When the adjacent arylene groups in $Ar^1$ to $Ar^4$ form a fluorene skeleton, the fluorene skeleton may have a substituent.

In this specification, the skeleton represented by General Formula (G3-1) is referred to as a dibenzofuran skeleton or a dibenzofuranyl group when Z represents oxygen, is referred to as a dibenzothiophenyl skeleton or a dibenzothiophenyl group when Z represents sulfur, and is referred to as a carbazole skeleton or a carbazolyl group when Z represents nitrogen.

Another embodiment of the present invention is a heterocyclic compound represented by General Formula (G4-1).

[Chemical Formula 6]

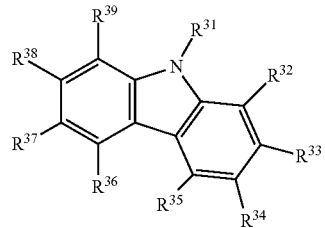

(G4-1)

In the formula, any one of $R^{31}$, $R^{33}$, and $R^{34}$ represents a substituent represented by General Formula (G4-2). Each of the other two of $R^{31}$, $R^{33}$, and $R^{34}$ to which the substituent represented by General Formula (G4-2) is not bonded, $R^{32}$, and $R^{35}$ to $R^{39}$ independently represents hydrogen, an alkyl group having 1 to 4 carbon atoms, or a substituted or unsubstituted aryl group having 6 to 13 carbon atoms.

[Chemical Formula 7]

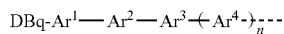

(G4-2)

In the formula, DBq represents a substituted or unsubstituted dibenzo[f,h]quinoxalinyl group. In addition, n is 0 or 1. Each of $Ar^1$ to $Ar^4$ independently represents a substituted or unsubstituted arylene group having 6 to 10 carbon atoms. In $Ar^1$ to $Ar^4$, the adjacent arylene groups may be bonded to each other to form a ring. When the adjacent arylene groups in $Ar^1$ to $Ar^4$ form a fluorene skeleton, the fluorene skeleton may have a substituent.

Another embodiment of the present invention is a heterocyclic compound represented by General Formula (G5-1).

[Chemical formula 8]

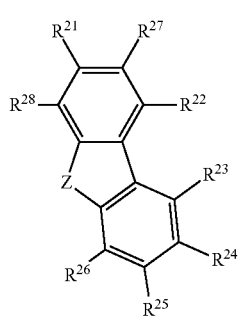

(G5-1)

In the formula, any one of $R^{27}$ and $R^{28}$ represents a substituent represented by General Formula (G5-2). Each of the other of $R^{27}$ and $R^{28}$ and $R^{21}$ to $R^{26}$ independently represents hydrogen, an alkyl group having 1 to 4 carbon atoms, or a substituted or unsubstituted aryl group having 6 to 13 carbon atoms. Z represents oxygen, sulfur, or nitrogen. When Z represents nitrogen, a substituent or no substituent may be bonded at the Z-position.

[Chemical Formula 9]

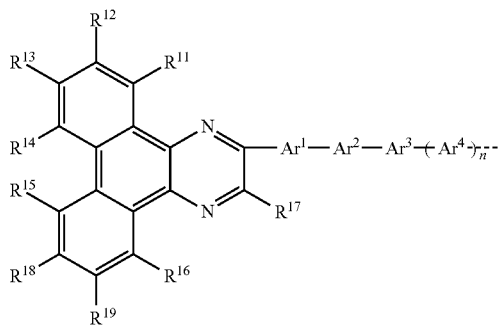

(G5-2)

In the formula, each of $R^{11}$ to $R^{19}$ independently represents hydrogen, an alkyl group having 1 to 4 carbon atoms, or a substituted or unsubstituted aryl group having 6 to 13 carbon atoms. In addition, n is 0 or 1. Each of $Ar^1$, $Ar^2$, $Ar^3$, and $Ar^4$ independently represents a substituted or unsubstituted arylene group having 6 to 10 carbon atoms. In $Ar^1$ to $Ar^4$, the adjacent arylene groups may be bonded to each other to form a ring. When the adjacent arylene groups in $Ar^1$ to $Ar^4$ form a fluorene skeleton, the fluorene skeleton may have a substituent.

Another embodiment of the present invention is a heterocyclic compound represented by General Formula (G6-1).

[Chemical formula 10]

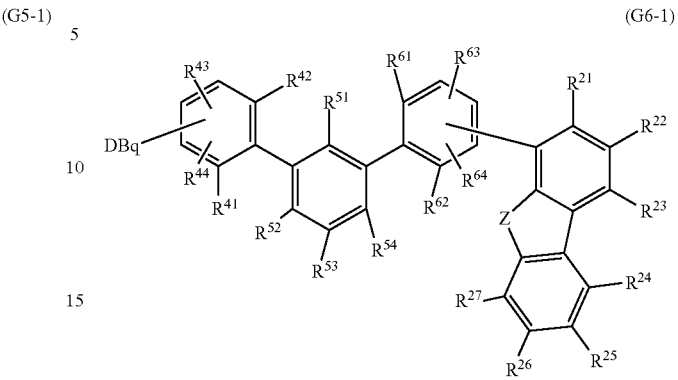

(G6-1)

In the formula, DBq represents a substituted or unsubstituted dibenzo[f,h]quinoxalinyl group. Z represents oxygen or sulfur. Each of $R^{21}$ to $R^{27}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G6-1) in which the site of substitution of DBq is a meta-position.

Another embodiment of the present invention is the heterocyclic compound represented by General Formula (G6-1) in which the site of substitution of DBq is a meta-position and the site of substitution of a dibenzothiophenyl group or a dibenzofuranyl group is a para-position.

Another embodiment of the present invention is a heterocyclic compound represented by General Formula (G6-2).

[Chemical formula 11]

(G6-2)

In the formula, DBq represents a substituted or unsubstituted dibenzo[f,h]quinoxalinyl group. Z represents oxygen or sulfur. Each of $R^{21}$ to $R^{27}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G6-3).

[Chemical formula 12]

(G6-3)

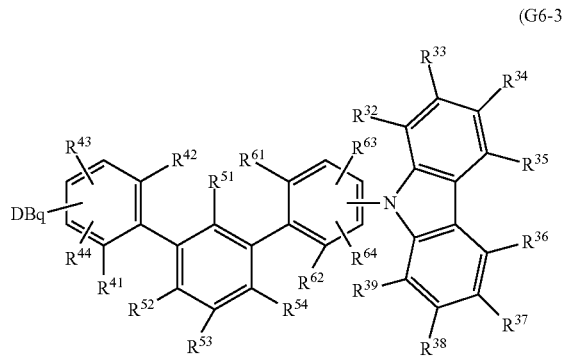

In the formula, DBq represents a substituted or unsubstituted dibenzo[f,h]quinoxalinyl group. Each of $R^{32}$ to $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G6-3) in which the site of substitution of DBq is a meta-position.

Another embodiment of the present invention is the heterocyclic compound represented by General Formula (G6-3) in which the site of substitution of DBq is a meta-position and the site of substitution of a carbazolyl group is a para-position.

Another embodiment of the present invention is a heterocyclic compound represented by General Formula (G6-4).

[Chemical formula 13]

(G6-4)

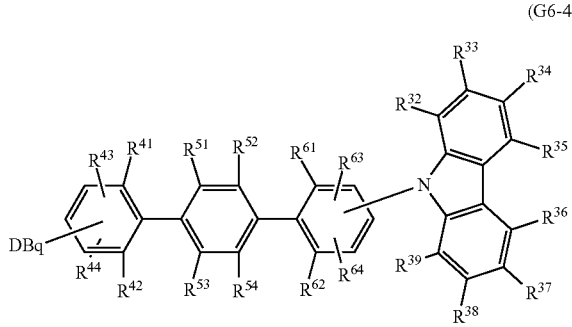

In the formula, DBq represents a substituted or unsubstituted dibenzo[f,h]quinoxalinyl group. Each of $R^{32}$ to $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G6-5).

[Chemical Formula 14]

(G6-5)

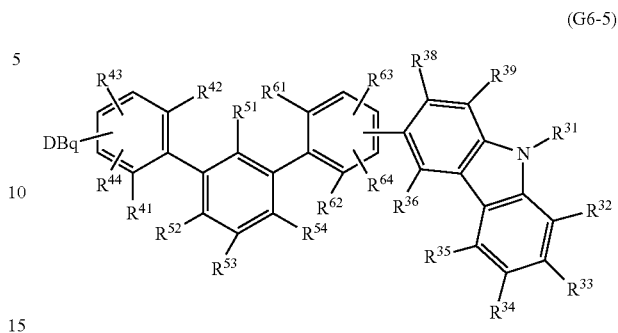

In the formula, DBq represents a substituted or unsubstituted dibenzo[f,h]quinoxalinyl group. $R^{31}$ represents an alkyl group having 1 to 4 carbon atoms or a substituted or unsubstituted aryl group having 6 to 13 carbon atoms. Each of $R^{32}$ to $R^{36}$, $R^{38}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G6-5) in which the site of substitution of DBq is a meta-position.

Another embodiment of the present invention is the heterocyclic compound represented by General Formula (G6-5) in which the site of substitution of DBq is a meta-position and the site of substitution of a carbazolyl group is a para-position.

Another embodiment of the present invention is a heterocyclic compound represented by General Formula (G6-6).

[Chemical Formula 15]

(G6-6)

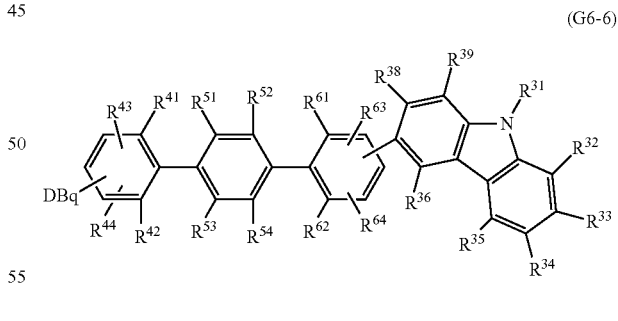

In the formula, DBq represents a substituted or unsubstituted dibenzo[f,h]quinoxalinyl group. $R^{31}$ represents an alkyl group having 1 to 4 carbon atoms or a substituted or unsubstituted aryl group having 6 to 13 carbon atoms. Each of $R^{32}$ to $R^{36}$, $R^{38}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G6-7).

[Chemical Formula 16]

(G6-7)

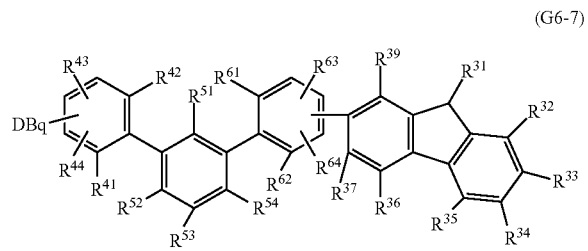

In the formula, DBq represents a substituted or unsubstituted dibenzo[f,h]quinoxalinyl group. $R^{31}$ represents an alkyl group having 1 to 4 carbon atoms or a substituted or unsubstituted aryl group having 6 to 13 carbon atoms. Each of $R^{32}$ to $R^{37}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G6-7) in which the site of substitution of DBq is a meta-position.

Another embodiment of the present invention is the heterocyclic compound represented by General Formula (G6-7) in which the site of substitution of DBq is a meta-position and the site of substitution of a carbazolyl group is a para-position.

Another embodiment of the present invention is a heterocyclic compound represented by General Formula (G6-8).

[Chemical Formula 17]

(G6-8)

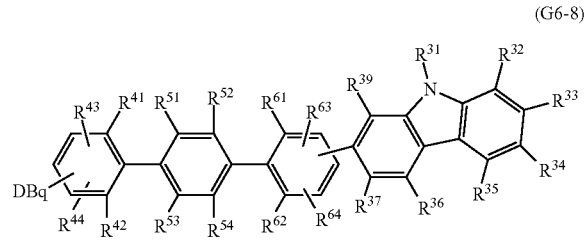

In the formula, DBq represents a substituted or unsubstituted dibenzo[f,h]quinoxalinyl group. $R^{31}$ represents an alkyl group having 1 to 4 carbon atoms or a substituted or unsubstituted aryl group having 6 to 13 carbon atoms. Each of $R^{32}$ to $R^{37}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G7-1).

[Chemical formula 18]

(G7-1)

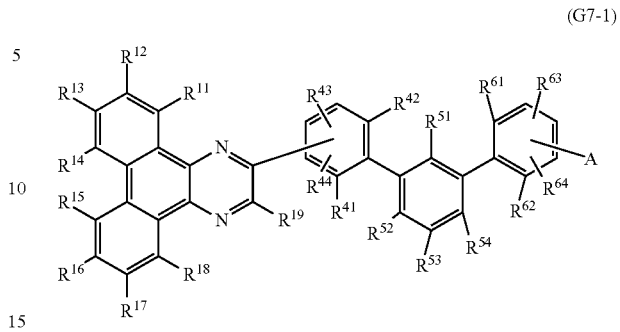

In the formula, A represents any of a substituted or unsubstituted dibenzothiophenyl group, a substituted or unsubstituted dibenzofuranyl group, and a substituted or unsubstituted carbazolyl group. Each of $R^{11}$ to $R^{19}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G7-1) in which the site of substitution of DBq is a meta-position.

Another embodiment of the present invention is the heterocyclic compound represented by General Formula (G7-1) in which the site of substitution of DBq is a meta-position and the site of substitution of A is a para-position.

Another embodiment of the present invention is a heterocyclic compound represented by General Formula (G7-2).

[Chemical Formula 19]

(G7-2)

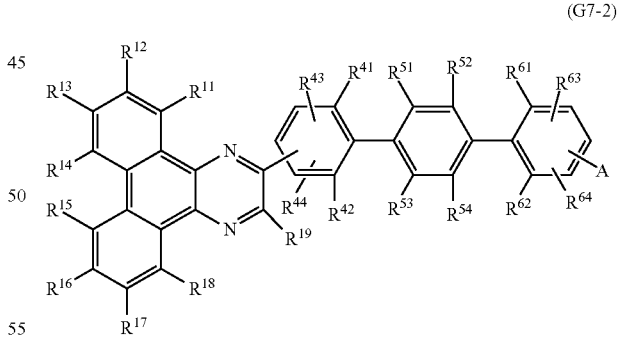

In the formula, A represents any of a substituted or unsubstituted dibenzothiophenyl group, a substituted or unsubstituted dibenzofuranyl group, and a substituted or unsubstituted carbazolyl group. Each of $R^{11}$ to $R^{19}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G8-1).

[Chemical Formula 20]

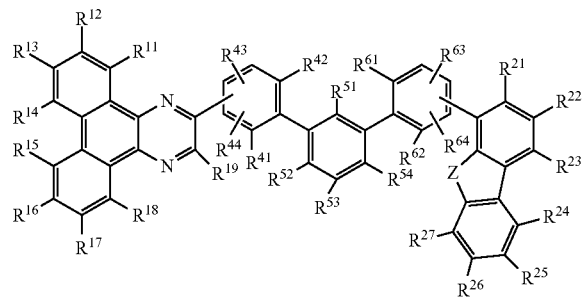

(G8-1)

In the formula, Z represents oxygen or sulfur. Each of $R^{11}$ to $R^{19}$, $R^{21}$ to $R^{27}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G8-1) in which the site of substitution of DBq is a meta-position.

Another embodiment of the present invention is the heterocyclic compound represented by General Formula (G8-1) in which the site of substitution of DBq is a meta-position and the site of substitution of a dibenzothiophenyl group or a dibenzofuranyl group is a para-position.

Another embodiment of the present invention is a heterocyclic compound represented by General Formula (G8-2).

[Chemical formula 21]

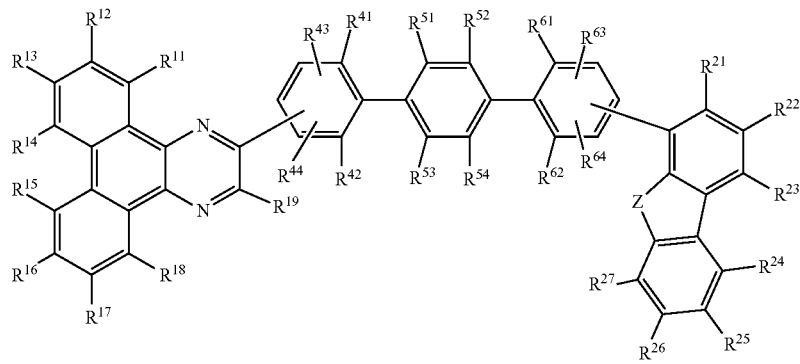

(G8-2)

In the formula, Z represents oxygen or sulfur. Each of $R^{11}$ to $R^{19}$, $R^{21}$ to $R^{27}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G8-3).

[Chemical Formula 22]

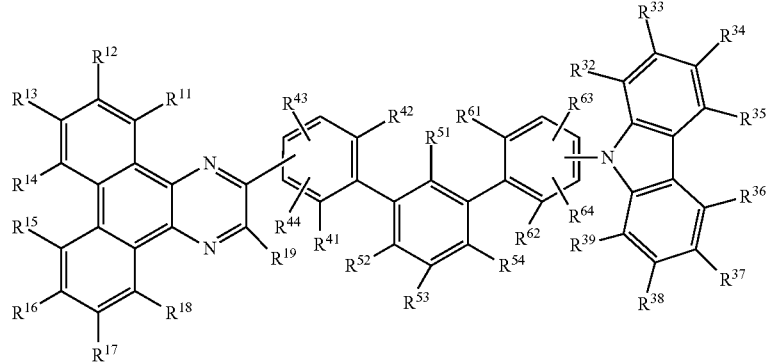

(G8-3)

In the formula, each of $R^{11}$ to $R^{19}$, $R^{32}$ to $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G8-3) in which the site of substitution of DBq is a meta-position.

Another embodiment of the present invention is the heterocyclic compound represented by General Formula (G8-3) in which the site of substitution of DBq is a meta-position and the site of substitution of a carbazolyl group is a para-position.

Another embodiment of the present invention is a heterocyclic compound represented by General Formula (G8-4).

In the formula, each of $R^{11}$ to $R^{19}$, $R^{32}$ to $R^{36}$, $R^{38}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms. $R^{31}$ represents an alkyl group having 1 to 4 carbon atoms or a substituted or unsubstituted aryl group having 6 to 13 carbon atoms.

Another embodiment of the present invention is the heterocyclic compound represented by General Formula (G8-5) in which the site of substitution of DBq is a meta-position.

Another embodiment of the present invention is the heterocyclic compound represented by General Formula

[Chemical Formula 23]

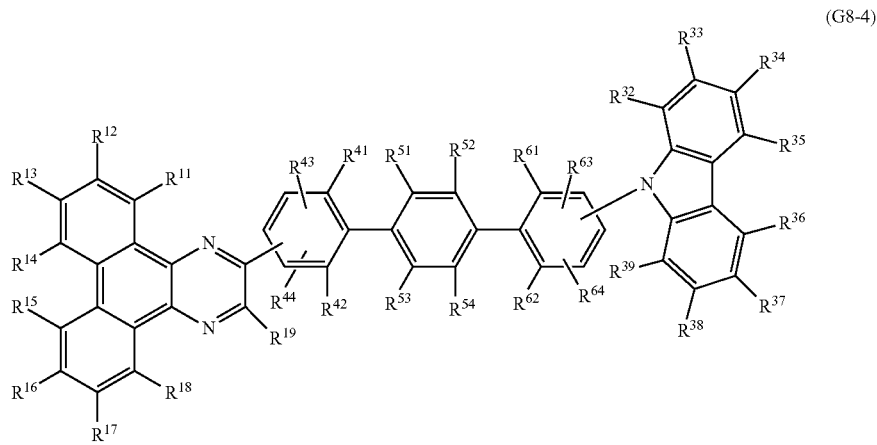

(G8-4)

In the formula, each of $R^{11}$ to $R^{19}$, $R^{32}$ to $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G8-5).

(G8-5) in which the site of substitution of DBq is a meta-position and the site of substitution of a carbazolyl group is a para-position.

Another embodiment of the present invention is a heterocyclic compound represented by General Formula (G8-6).

[Chemical Formula 24]

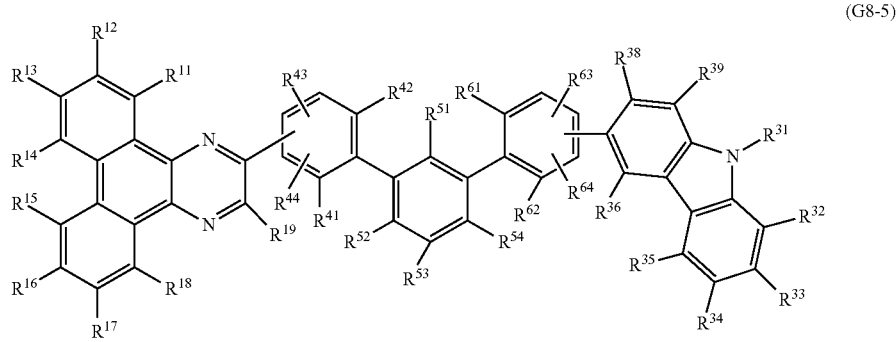

(G8-5)

[Chemical Formula 25]

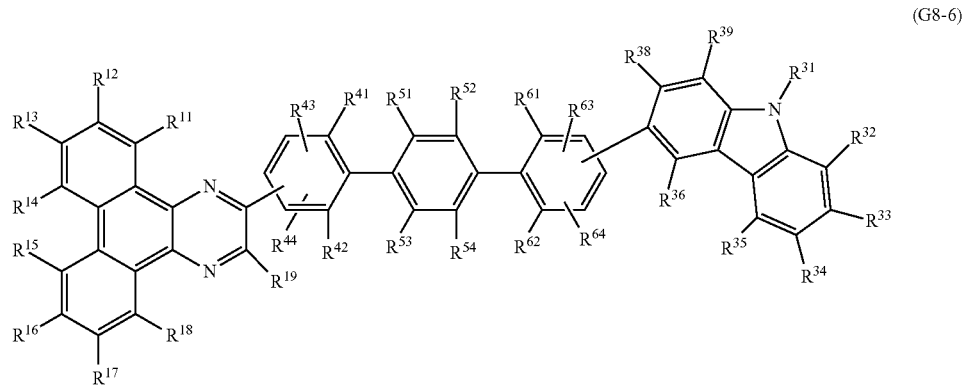

(G8-6)

In the formula, each of $R^{11}$ to $R^{19}$, $R^{32}$ to $R^{36}$, $R^{38}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms. $R^{31}$ represents an alkyl group having 1 to 4 carbon atoms or a substituted or unsubstituted aryl group having 6 to 13 carbon atoms.

Another embodiment of the present invention is a heterocyclic compound represented by General Formula (G8-7).

[Chemical formula 26]

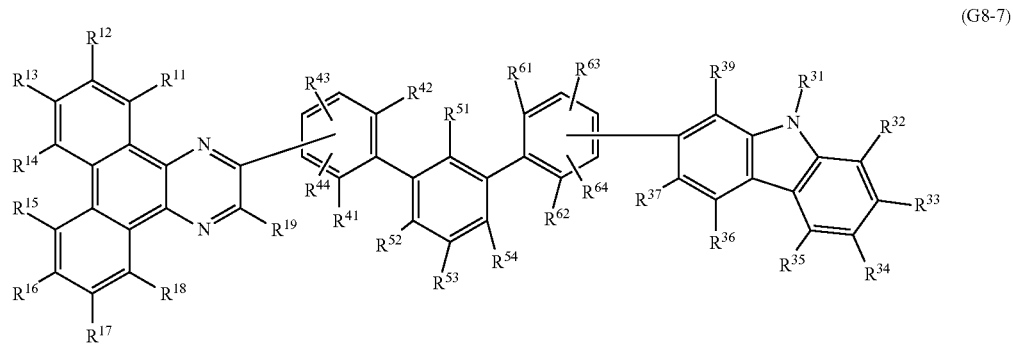

(G8-7)

In the formula, each of $R^{11}$ to $R^{19}$, $R^{32}$ to $R^{37}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms. $R^{31}$ represents an alkyl group having 1 to 4 carbon atoms or a substituted or unsubstituted aryl group having 6 to 13 carbon atoms.

Another embodiment of the present invention is the heterocyclic compound represented by General Formula (G8-7) in which the site of substitution of DBq is a meta-position.

Another embodiment of the present invention is the heterocyclic compound represented by General Formula (G8-7) in which the site of substitution of DBq is a meta-position and the site of substitution of a carbazolyl group is a para-position.

Another embodiment of the present invention is a heterocyclic compound represented by General Formula (G8-8).

[Chemical Formula 27]

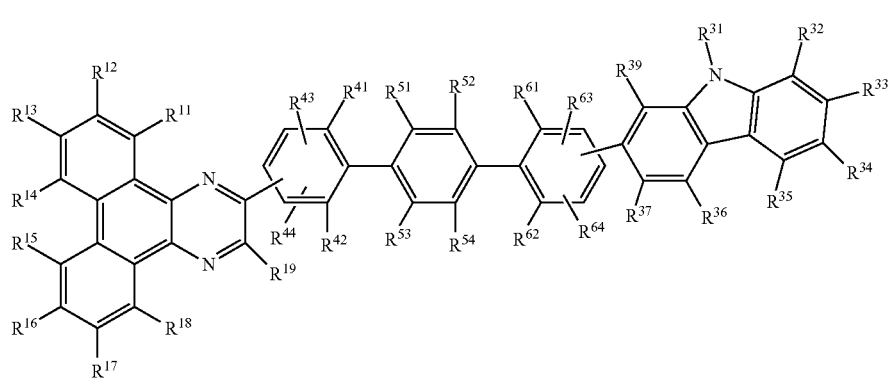

(G8-8)

In the formula, each of $R^{11}$ to $R^{19}$, $R^{32}$ to $R^{37}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms. $R^{31}$ represents an alkyl group having 1 to 4 carbon atoms or a substituted or unsubstituted aryl group having 6 to 13 carbon atoms.

Another embodiment of the present invention is a heterocyclic compound represented by General Formula (G9-1).

[Chemical formula 28]

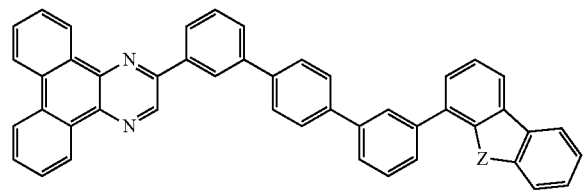

(G9-1)

In the formula, Z represents oxygen or sulfur.
Another embodiment of the present invention is a heterocyclic compound represented by General Formula (G9-2).

[Chemical formula 29]

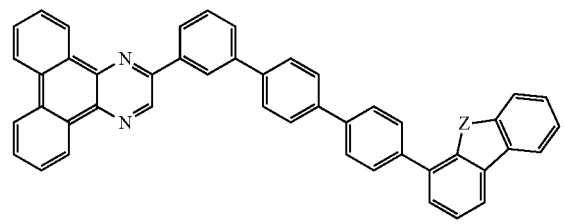

(G9-2)

In the formula, Z represents oxygen or sulfur.

Another embodiment of the present invention is a heterocyclic compound represented by General Formula (G9-3).

[Chemical formula 30]

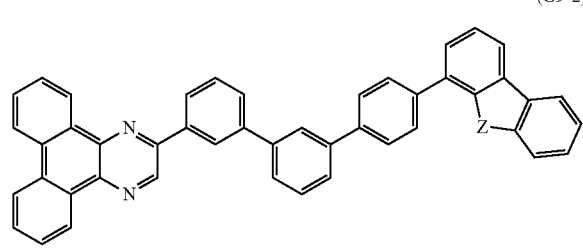

(G9-3)

In the formula, Z represents oxygen or sulfur.
Another embodiment of the present invention is a heterocyclic compound represented by General Formula (G9-4).

[Chemical formula 31]

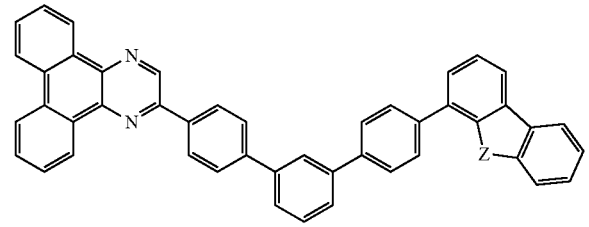

(G9-4)

In the formula, Z represents oxygen or sulfur.

Another embodiment of the present invention is a heterocyclic compound represented by General Formula (G9-5).

[Chemical formula 32]

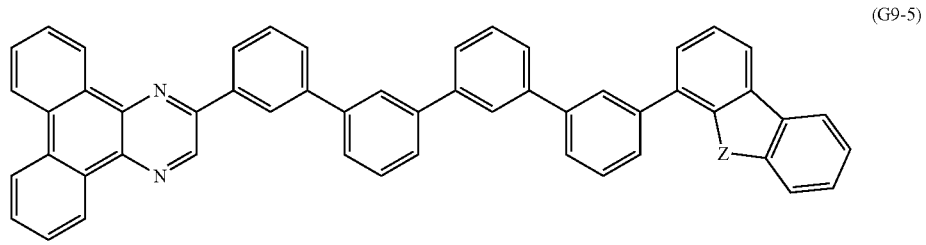

(G9-5)

In the formula, Z represents oxygen or sulfur.

Another embodiment of the present invention is a heterocyclic compound represented by General Formula (G10-1).

[Chemical formula 33]

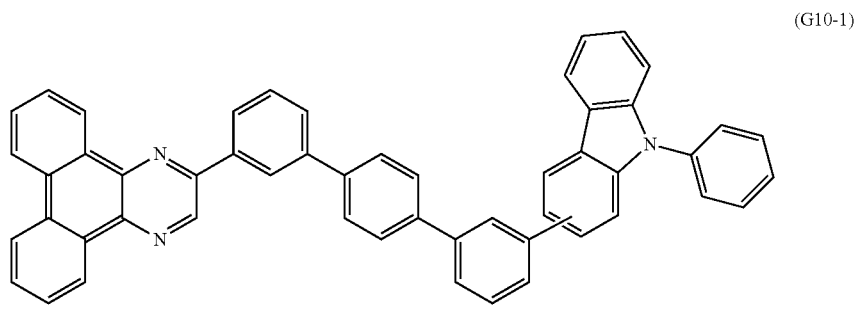

(G10-1)

Another embodiment of the present invention is a heterocyclic compound represented by General Formula (G10-2).

[Chemical formula 34]

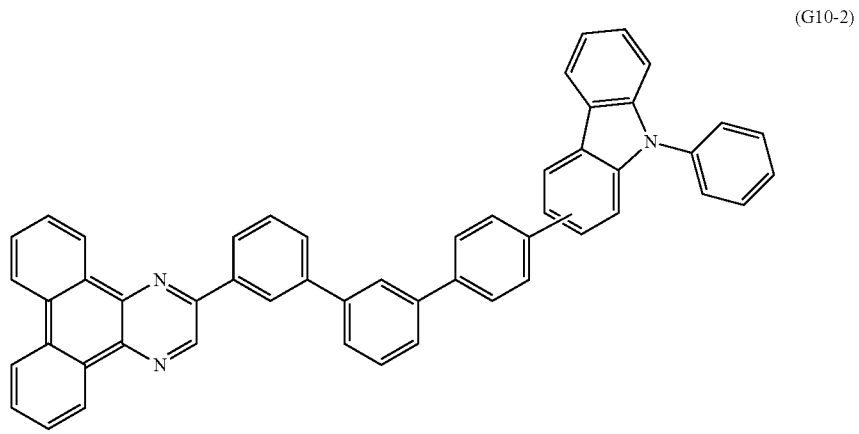

(G10-2)

Another embodiment of the present invention is a heterocyclic compound represented by General Formula (G10-3).

[Chemical formula 35]

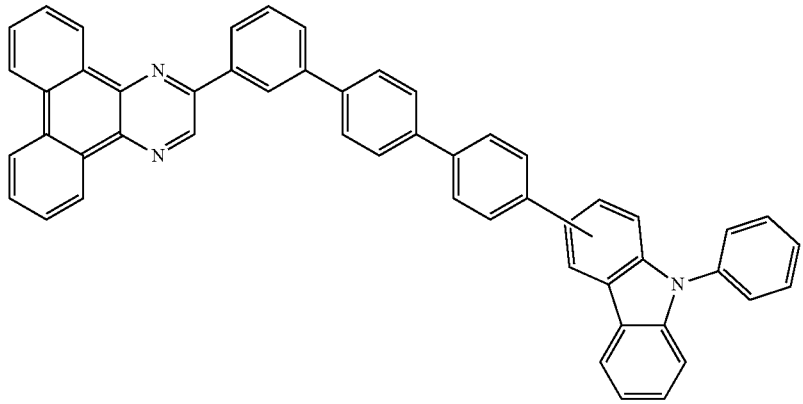

(G10-3)

Another embodiment of the present invention is a heterocyclic compound represented by General Formula (G10-4).

[Chemical formula 36]

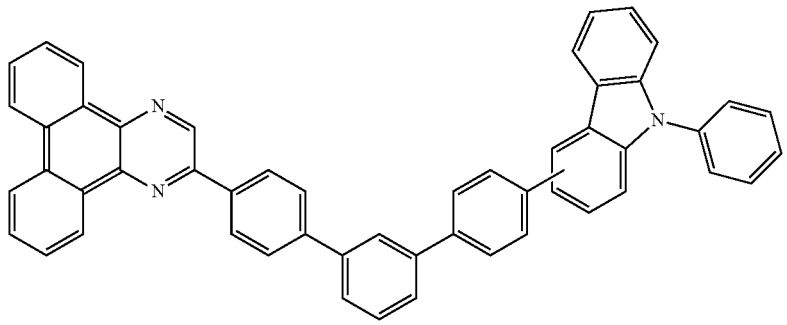

(G10-4)

Another embodiment of the present invention is a heterocyclic compound represented by General Formula (G10-5).

[Chemical formula 37]

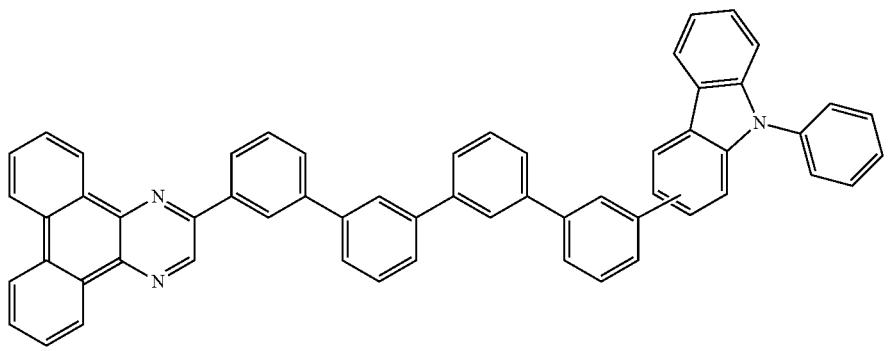

(G10-5)

Another embodiment of the present invention is a light-emitting element including a compound in which a dibenzo[f,h]quinoxaline ring and a hole-transport skeleton are bonded through a terphenylene group.

Another embodiment of the present invention is a light-emitting element including, in a light-emitting layer, a light-emitting material and a compound in which a dibenzo[f,h]quinoxaline ring and a hole-transport skeleton are bonded through a terphenylene group.

In a light-emitting element of another embodiment of the present invention, the hole-transport skeleton may include a π-electron rich heteroaromatic ring.

In a light-emitting element of another embodiment of the present invention, the π-electron rich heteroaromatic ring may be a carbazole ring, a dibenzofuran ring, or a dibenzothiophene ring.

Another embodiment of the present invention is a light-emitting element that includes a heterocyclic compound of one embodiment of the present invention and an electrode.

Another embodiment of the present invention is a light-emitting element that includes, in a light-emitting layer, a light-emitting substance and a heterocyclic compound of one embodiment of the present invention.

Another embodiment of the present invention is a light-emitting device that includes a light-emitting portion including a light-emitting element of one embodiment of the present invention, and a substrate.

Another embodiment of the present invention is an electronic device that includes a display portion including the light-emitting device of one embodiment of the present invention, and an antenna, a battery, a housing, a speaker, a microphone, or an operation key.

Another embodiment of the present invention is a lighting device that includes a light-emitting device of one embodiment of the present invention, and a housing, a connection terminal, or a protective cover.

With one embodiment of the present invention, a novel heterocyclic compound can be provided. In particular, a novel heterocyclic compound which can improve the element characteristics of a light-emitting element can be provided. With one embodiment of the present invention, a novel light-emitting element with high emission efficiency and high heat resistance can be provided. With one embodiment of the present invention, a novel heterocyclic compound that can be used in a light-emitting element can be provided. With one embodiment of the present invention, a novel heterocyclic compound that can be used in an EL layer of a light-emitting element can be provided. With one embodiment of the present invention, a novel light-emitting element can be provided. With one embodiment of the present invention, a novel light-emitting device, a novel electronic device, or a novel lighting device can be provided.

Note that the descriptions of these effects do not disturb the existence of other effects. In one embodiment of the present invention, there is no need to achieve all of these effects. Other effects will be apparent from and can be derived from the description of the specification, the drawings, the claims, and the like.

BRIEF DESCRIPTION OF DRAWINGS

FIGS. 2A and 2B are schematic views of an active matrix light-emitting device.

FIGS. 3A and 3B are schematic views of active matrix light-emitting devices.

FIG. 55 shows evaluation results of thermophysical properties of light-emitting elements.

BEST MODE FOR CARRYING OUT THE INVENTION

Figure 1A:
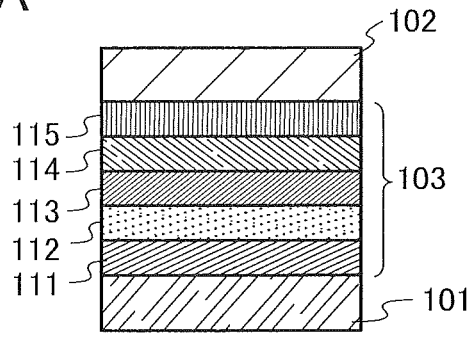
FIGS. 1A and 1B are schematic views of light-emitting elements.

Embodiments of the present invention will be described below. Note that it is easily understood by those skilled in the art that modes and details disclosed herein can be modified in various ways without departing from the spirit and scope of the present invention. Therefore, the present invention is not construed as being limited to the description of the following embodiments.

Note that in each drawing described in this specification, the size, the thickness, and the like of components such as an anode, an EL layer, an intermediate layer, and a cathode are exaggerated for clarity in some cases. Therefore, the sizes of the components are not limited to the sizes in the drawings and relative sizes between the components.

In this specification and the like, ordinal numbers such as "first", "second", and "third" are used for convenience and do not denote the order of steps or the stacking order of layers. Therefore, for example, description can be made even when "first" is replaced with "second" or "third", as appropriate. In addition, the ordinal numbers in this specification and the like are not necessarily the same as those which specify one embodiment of the present invention.

In the structures of the present invention described in this specification and the like, the same portions or portions having similar functions in different drawings are denoted by the same reference numerals, and description of such portions is not repeated. Furthermore, the same hatching pattern is applied to portions having similar functions, and the portions are not especially denoted by reference numerals in some cases.

In this specification, color is defined by three aspects of hue (corresponding to the wavelength of light of a single color), chroma (saturation, i.e., the degree to which it differs from white), and value (brightness, i.e., the intensity of light). In this specification, color may be defined by only one of the above three aspects or two of the aspects which are selected arbitrarily. In this specification, a difference between two colors of light means a difference in at least one of the above three aspects and includes a difference in the shapes of two spectra of light or in the distributions of the relative intensity of the peaks in the spectra.

Note that the terms "film" and "layer" can be interchanged with each other depending on the case or circumstances. For example, the term "conductive layer" can be changed into the term "conductive film" in some cases, and the term "insulating film" can be changed into the term "insulating layer" in some cases.

Embodiment 1

In this embodiment, a heterocyclic compound of one embodiment of the present invention is described.

One embodiment of the present invention is a heterocyclic compound represented by General Formula (G1).

[Chemical formula 38]

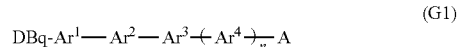

(G1)

In the formula, A represents any of a substituted or unsubstituted dibenzothiophenyl group, a substituted or unsubstituted dibenzofuranyl group, and a substituted or unsubstituted carbazolyl group. DBq represents a substituted or unsubstituted dibenzo[f,h]quinoxalinyl group. In addition, n is 0 or 1. Each of $Ar^1$ to $Ar^4$ independently represents a substituted or unsubstituted arylene group having 6 to 10 carbon atoms. In $Ar^1$ to $Ar^4$, the adjacent arylene groups may be bonded to each other to form a ring. When the adjacent arylene groups in $Ar^1$ to $Ar^4$ form a fluorene skeleton, the fluorene skeleton may have a substituent.

Another embodiment of the present invention is a heterocyclic compound represented by General Formula (G2-1). The heterocyclic compound is useful in terms of simplicity of the synthesis and synthesis cost.

[Chemical formula 39]

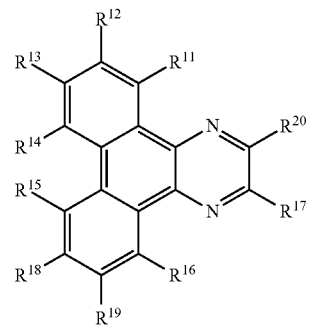

(G2-1)

In the formula, any one of $R^{18}$ to $R^{20}$ represents a substituent represented by General Formula (G2-2). Each of the other two of $R^{18}$ to $R^{20}$ and $R^{11}$ to $R^{17}$ independently represents hydrogen, an alkyl group having 1 to 4 carbon atoms, or a substituted or unsubstituted aryl group having 6 to 13 carbon atoms.

[Chemical formula 40]

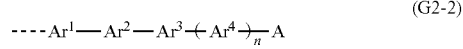

(G2-2)

In the formula, A represents any of a substituted or unsubstituted dibenzothiophenyl group, a substituted or unsubstituted dibenzofuranyl group, and a substituted or unsubstituted carbazolyl group. In addition, n is 0 or 1. Each of $Ar^1$ to $Ar^4$ independently represents a substituted or unsubstituted arylene group having 6 to 10 carbon atoms. In $Ar^1$ to $Ar^4$, the adjacent arylene groups may be bonded to each other to form a ring. When the adjacent arylene groups in $Ar^1$ to $Ar^4$ form a fluorene skeleton, the fluorene skeleton may have a substituent.

Another embodiment of the present invention is a heterocyclic compound represented by General Formula (G3-1).

[Chemical formula 41]

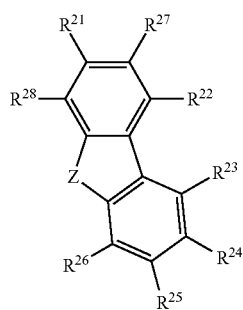

(G3-1)

In the formula, any one of $R^{27}$ and $R^{28}$ represents a substituent represented by General Formula (G3-2). Each of the other of $R^{27}$ and $R^{28}$ and $R^{21}$ to $R^{26}$ independently represents hydrogen, an alkyl group having 1 to 4 carbon atoms, or a substituted or unsubstituted aryl group having 6 to 13 carbon atoms. Z represents oxygen, sulfur, or nitrogen. When Z represents nitrogen, a substituent or no substituent may be bonded at the Z-position.

[Chemical formula 42]

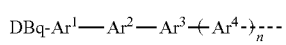

(G3-2)

In the formula, DBq represents a substituted or unsubstituted dibenzo[f,h]quinoxalinyl group. In addition, n is 0 or 1. Each of $Ar^1$ to $Ar^4$ independently represents a substituted or unsubstituted arylene group having 6 to 10 carbon atoms. In $Ar^1$ to $Ar^4$, the adjacent arylene groups may be bonded to each other to form a ring. When the adjacent arylene groups in $Ar^1$ to $Ar^4$ form a fluorene skeleton, the fluorene skeleton may have a substituent.

Another embodiment of the present invention is a heterocyclic compound represented by General Formula (G4-1).

[Chemical formula 43]

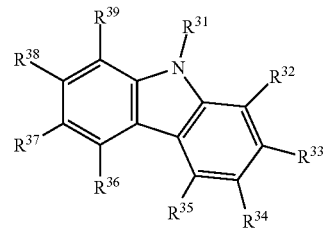

(G4-1)

In the formula, any one of $R^{31}$, $R^{33}$, and $R^{34}$ represents a substituent represented by General Formula (G4-2). Each of the other two of $R^{31}$, $R^{33}$, and $R^{34}$ to which the substituent represented by General Formula (G4-2) is not bonded, $R^{32}$, and $R^{35}$ to $R^{39}$ independently represents hydrogen, an alkyl group having 1 to 4 carbon atoms, or a substituted or unsubstituted aryl group having 6 to 13 carbon atoms.

[Chemical formula 44]

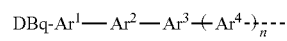

(G4-2)

In the formula, DBq represents a substituted or unsubstituted dibenzo[f,h]quinoxalinyl group. In addition, n is 0 or 1. Each of $Ar^1$ to $Ar^4$ independently represents a substituted or unsubstituted arylene group having 6 to 10 carbon atoms. In $Ar^1$ to $Ar^4$, the adjacent arylene groups may be bonded to each other to form a ring. When the adjacent arylene groups in $Ar^1$ to $Ar^4$ form a fluorene skeleton, the fluorene skeleton may have a substituent.

Another embodiment of the present invention is a heterocyclic compound represented by General Formula (G5-1). The heterocyclic compound is useful in terms of simplicity of the synthesis and synthesis cost.

[Chemical formula 45]

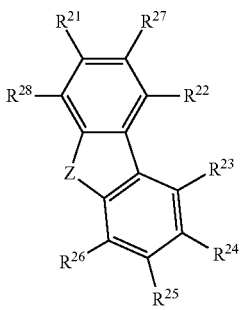

(G5-1)

In the formula, any one of $R^{27}$ and $R^{28}$ represents a substituent represented by General Formula (G5-2). Each of the other of $R^{27}$ and $R^{28}$ and $R^{21}$ to $R^{26}$ independently represents hydrogen, an alkyl group having 1 to 4 carbon atoms, or a substituted or unsubstituted aryl group having 6 to 13 carbon atoms. Z represents oxygen, sulfur, or nitrogen. When Z represents nitrogen, a substituent or no substituent may be bonded at the Z-position.

[Chemical formula 46]

(G5-2)

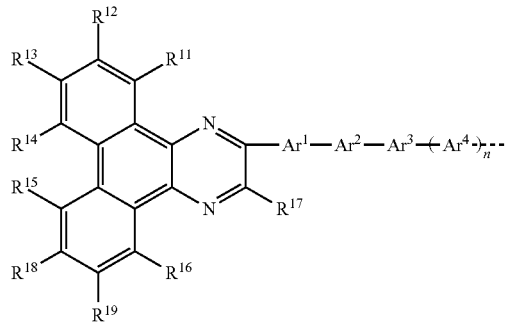

In the formula, each of $R^{11}$ to $R^{19}$ independently represents hydrogen, an alkyl group having 1 to 4 carbon atoms, or a substituted or unsubstituted aryl group having 6 to 13 carbon atoms. In addition, n is 0 or 1. Each of $Ar^1$ to $Ar^4$ independently represents a substituted or unsubstituted arylene group having 6 to 10 carbon atoms. In $Ar^1$ to $Ar^4$, the adjacent arylene groups may be bonded to each other to form a ring. When the adjacent arylene groups in $Ar^1$ to $Ar^4$ form a fluorene skeleton, the fluorene skeleton may have a substituent.

Another embodiment of the present invention is a heterocyclic compound represented by General Formula (G6-1). The heterocyclic compound is useful in terms of a high carrier-transport property and high reliability.

[Chemical formula 47]

(G6-1)

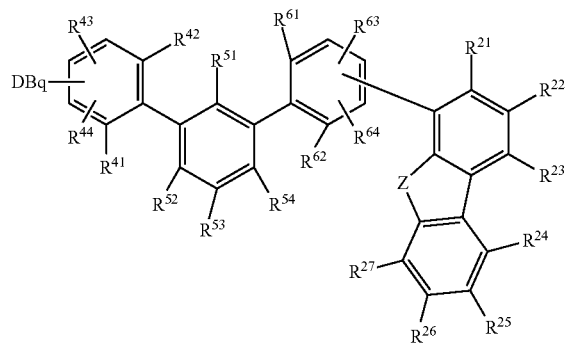

In the formula, DBq represents a substituted or unsubstituted dibenzo[f,h]quinoxalinyl group. Z represents oxygen or sulfur. Each of $R^{21}$ to $R^{27}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G6-1) in which the site of substitution of DBq is a meta-position.

Another embodiment of the present invention is the heterocyclic compound represented by General Formula (G6-1) in which the site of substitution of DBq is a meta-position and the site of substitution of a dibenzothiophenyl group or a dibenzofuranyl group is a para-position.

Another embodiment of the present invention is a heterocyclic compound represented by General Formula (G6-2). The heterocyclic compound is useful in terms of a high carrier-transport property and high reliability.

[Chemical formula 48]

(G6-2)

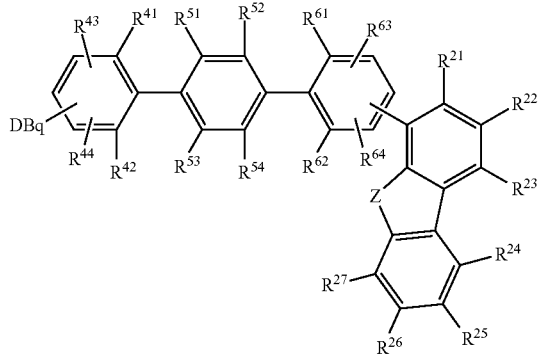

In the formula, DBq represents a substituted or unsubstituted dibenzo[f,h]quinoxalinyl group. Z represents oxygen or sulfur. Each of $R^{21}$ to $R^{27}$, $R^{41}$ to $R^{44}$, $R^{51}$ to and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G6-3). The heterocyclic compound is useful in terms of a high carrier-transport property and high reliability.

[Chemical formula 49]

(G6-3)

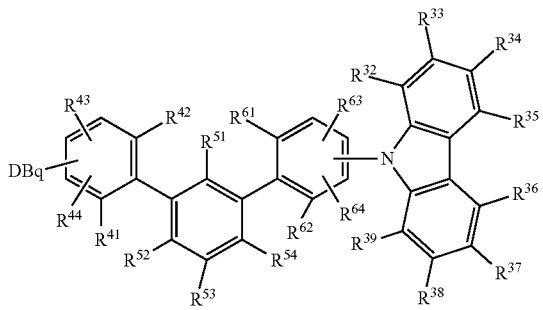

In the formula, DBq represents a substituted or unsubstituted dibenzo[f,h]quinoxalinyl group. Each of $R^{32}$ to $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G6-3) in which the site of substitution of DBq is a meta-position.

Another embodiment of the present invention is the heterocyclic compound represented by General Formula (G6-3) in which the site of substitution of DBq is a meta-position and the site of substitution of a carbazolyl group is a para-position.

Another embodiment of the present invention is a heterocyclic compound represented by General Formula (G6-4). The heterocyclic compound is useful in terms of a high carrier-transport property and high reliability.

[Chemical formula 50]

(G6-4)

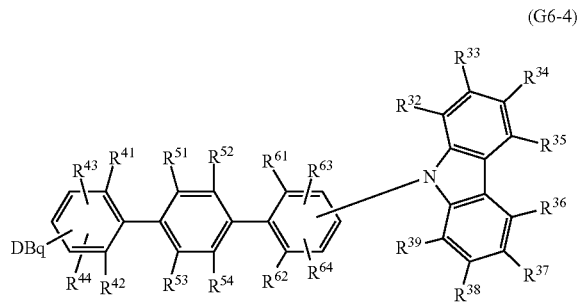

In the formula, DBq represents a substituted or unsubstituted dibenzo[f,h]quinoxalinyl group. Each of $R^{32}$ to $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G6-5). The heterocyclic compound is useful in terms of a high carrier-transport property and high reliability.

[Chemical formula 51]

(G6-5)

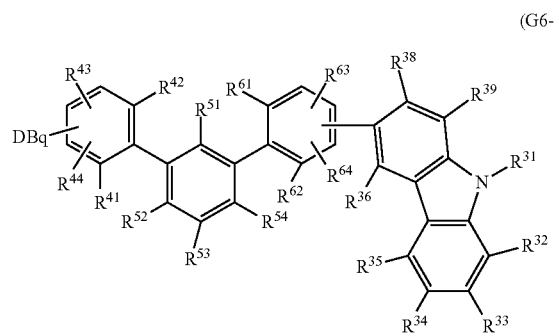

In the formula, DBq represents a substituted or unsubstituted dibenzo[f,h]quinoxalinyl group. $R^{31}$ represents an alkyl group having 1 to 4 carbon atoms or a substituted or unsubstituted aryl group having 6 to 13 carbon atoms. Each of $R^{32}$ to $R^{36}$, $R^{38}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G6-5) in which the site of substitution of DBq is a meta-position.

Another embodiment of the present invention is the heterocyclic compound represented by General Formula (G6-5) in which the site of substitution of DBq is a meta-position and the site of substitution of a carbazolyl group is a para-position.

Another embodiment of the present invention is a heterocyclic compound represented by General Formula (G6-6). The heterocyclic compound is useful in terms of a high carrier-transport property and high reliability.

[Chemical formula 52]

(G6-6)

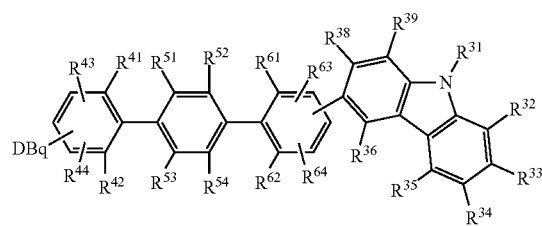

In the formula, DBq represents a substituted or unsubstituted dibenzo[f,h]quinoxalinyl group. $R^{31}$ represents an alkyl group having 1 to 4 carbon atoms or a substituted or unsubstituted aryl group having 6 to 13 carbon atoms. Each of $R^{32}$ to $R^{36}$, $R^{38}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G6-7). The heterocyclic compound is useful in terms of a high carrier-transport property and high reliability.

[Chemical formula 53]

(G6-7)

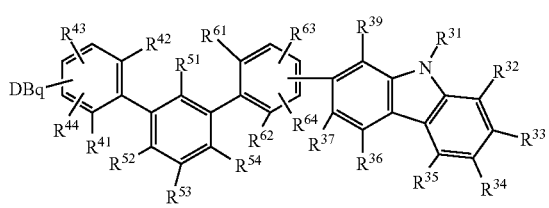

In the formula, DBq represents a substituted or unsubstituted dibenzo[f,h]quinoxalinyl group. $R^{31}$ represents an alkyl group having 1 to 4 carbon atoms or a substituted or unsubstituted aryl group having 6 to 13 carbon atoms. Each of $R^{32}$ to $R^{37}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G6-7) in which the site of substitution of DBq is a meta-position.

Another embodiment of the present invention is the heterocyclic compound represented by General Formula (G6-7) in which the site of substitution of DBq is a meta-position and the site of substitution of a carbazolyl group is a para-position.

Another embodiment of the present invention is a heterocyclic compound represented by General Formula (G6-8). The heterocyclic compound is useful in terms of a high carrier-transport property and high reliability.

[Chemical formula 54]

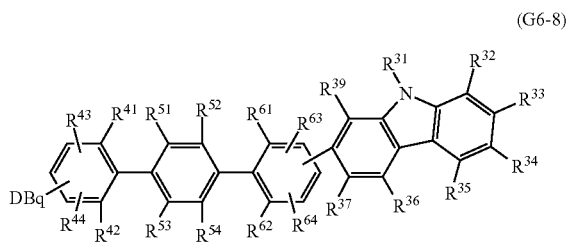

(G6-8)

In the formula, DBq represents a substituted or unsubstituted dibenzo[f,h]quinoxalinyl group. $R^{31}$ represents an alkyl group having 1 to 4 carbon atoms or a substituted or unsubstituted aryl group having 6 to 13 carbon atoms. Each of $R^{32}$ to $R^{37}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G7-1). The heterocyclic compound is useful in terms of a high carrier-transport property and high reliability.

[Chemical formula 55]

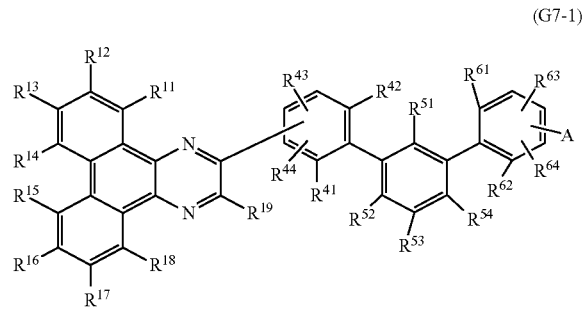

(G7-1)

In the formula, A represents any of a substituted or unsubstituted dibenzothiophenyl group, a substituted or unsubstituted dibenzofuranyl group, and a substituted or unsubstituted carbazolyl group. Each of $R^{11}$ to $R^{19}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G7-1) in which the site of substitution of DBq is a meta-position.

Another embodiment of the present invention is the heterocyclic compound represented by General Formula (G7-1) in which the site of substitution of DBq is a meta-position and the site of substitution of A is a para-position.

Another embodiment of the present invention is a heterocyclic compound represented by General Formula (G7-2). The heterocyclic compound is useful in terms of a high carrier-transport property and high reliability.

[Chemical formula 56]

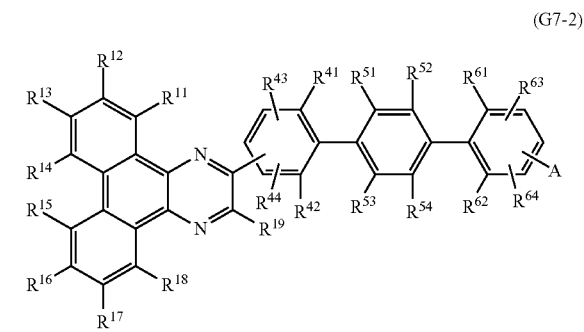

(G7-2)

In the formula, A represents any of a substituted or unsubstituted dibenzothiophenyl group, a substituted or unsubstituted dibenzofuranyl group, and a substituted or unsubstituted carbazolyl group. Each of $R^{11}$ to $R^{19}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G8-1). The heterocyclic compound is useful in terms of a high carrier-transport property and high reliability.

[Chemical formula 57]

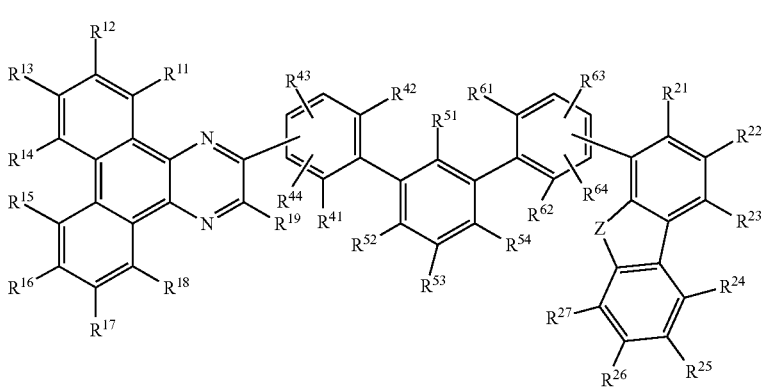

(G8-1)

In the formula, Z represents oxygen or sulfur. Each of $R^{11}$ to $R^{19}$, $R^{21}$ to $R^{27}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G8-1) in which the site of substitution of DBq is a meta-position.

Another embodiment of the present invention is the heterocyclic compound represented by General Formula (G8-1) in which the site of substitution of DBq is a meta-position and the site of substitution of a dibenzothiophenyl group or a dibenzofuranyl group is a para-position.

Another embodiment of the present invention is a heterocyclic compound represented by General Formula (G8-2). The heterocyclic compound is useful in terms of a high carrier-transport property and high reliability.

[Chemical formula 58]

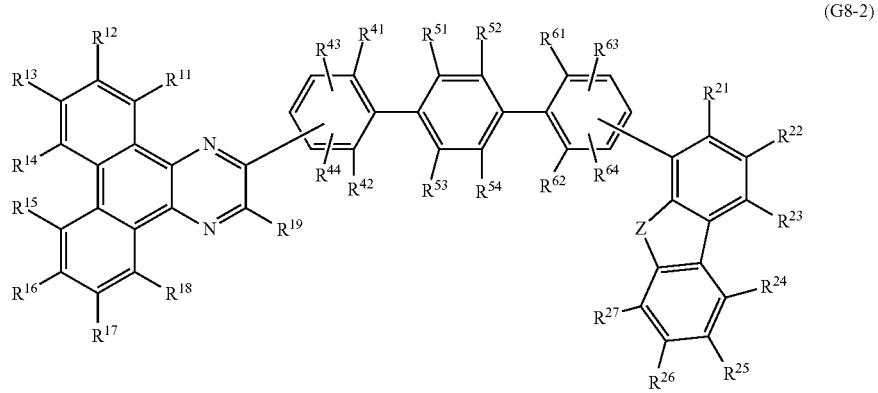

(G8-2)

In the formula, Z represents oxygen or sulfur. Each of $R^{11}$ to $R^{19}$, $R^{21}$ to $R^{27}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G8-3). The heterocyclic compound is useful in terms of a high carrier-transport property and high reliability.

[Chemical formula 59]

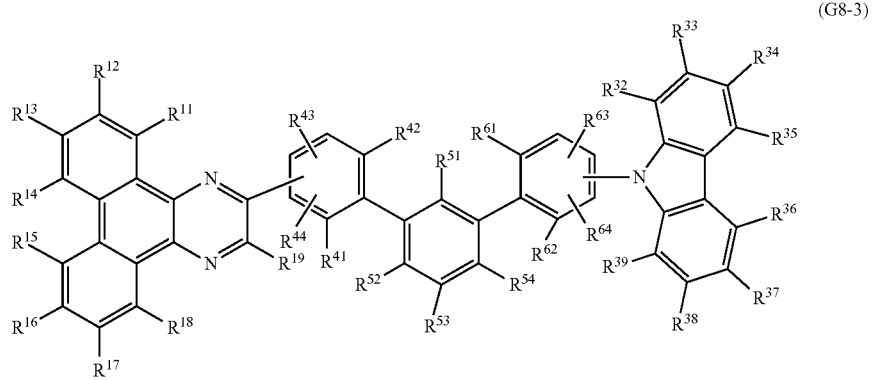

(G8-3)

In the formula, each of $R^{11}$ to $R^{19}$, $R^{32}$ to $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is the heterocyclic compound represented by General Formula (G8-3) in which the site of substitution of DBq is a meta-position.

Another embodiment of the present invention is the heterocyclic compound represented by General Formula (G8-3) in which the site of substitution of DBq is a meta-position and the site of substitution of a carbazolyl group is a para-position.

Another embodiment of the present invention is a heterocyclic compound represented by General Formula (G8-4). The heterocyclic compound is useful in terms of a high carrier-transport property and high reliability.

[Chemical formula 60]

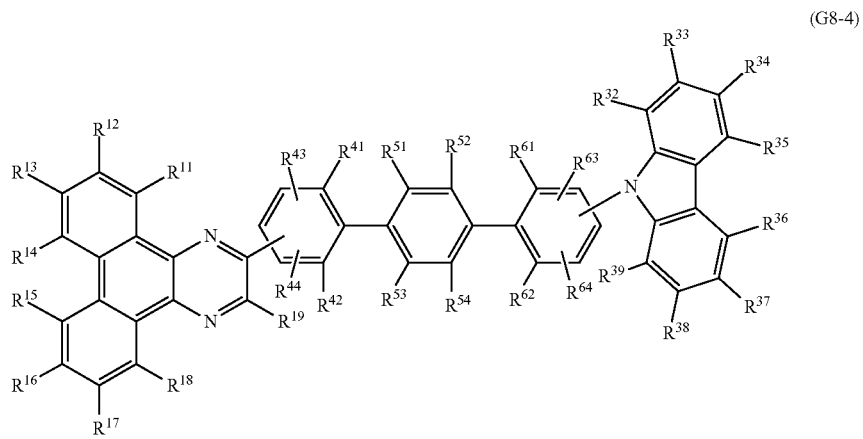

(G8-4)

In the formula, each of $R^{11}$ to $R^{19}$, $R^{32}$ to $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

Another embodiment of the present invention is a heterocyclic compound represented by General Formula (G8-5). The heterocyclic compound is useful in terms of a high carrier-transport property and high reliability.

In the formula, each of $R^{11}$ to $R^{19}$, $R^{32}$ to $R^{36}$, $R^{38}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms. $R^{31}$ represents an alkyl group having 1 to 4 carbon atoms or a substituted or unsubstituted aryl group having 6 to 13 carbon atoms.

Another embodiment of the present invention is the heterocyclic compound represented by General Formula (G8-5) in which the site of substitution of DBq is a meta-position.

Another embodiment of the present invention is the heterocyclic compound represented by General Formula (G8-5) in which the site of substitution of DBq is a meta-position and the site of substitution of a carbazolyl group is a para-position.

Another embodiment of the present invention is a heterocyclic compound represented by General Formula (G8-6). The heterocyclic compound is useful in terms of a high carrier-transport property and high reliability.

[Chemical formula 61]

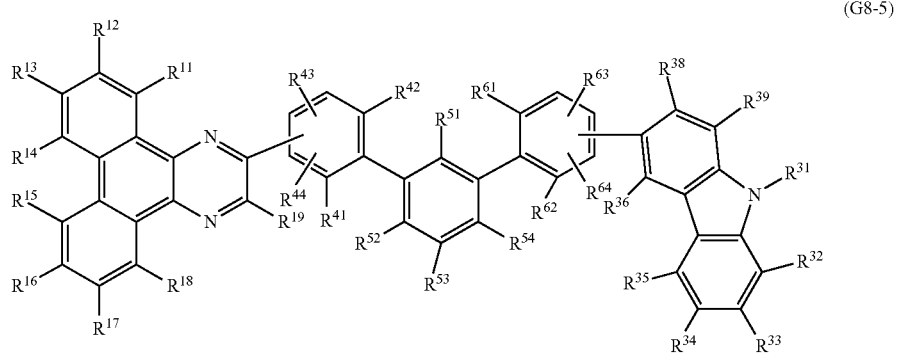

(G8-5)

[Chemical formula 62]

(G8-6)

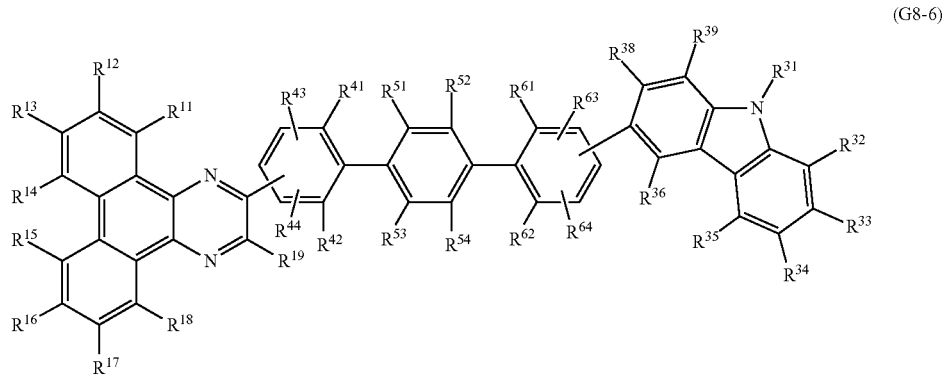

In the formula, each of $R^{11}$ to $R^{19}$, $R^{32}$ to $R^{36}$, $R^{38}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms. $R^{31}$ represents an alkyl group having 1 to 4 carbon atoms or a substituted or unsubstituted aryl group having 6 to 13 carbon atoms.

Another embodiment of the present invention is a heterocyclic compound represented by General Formula (G8-7). The heterocyclic compound is useful in terms of a high carrier-transport property and high reliability.

[Chemical formula 63]

(G8-7)

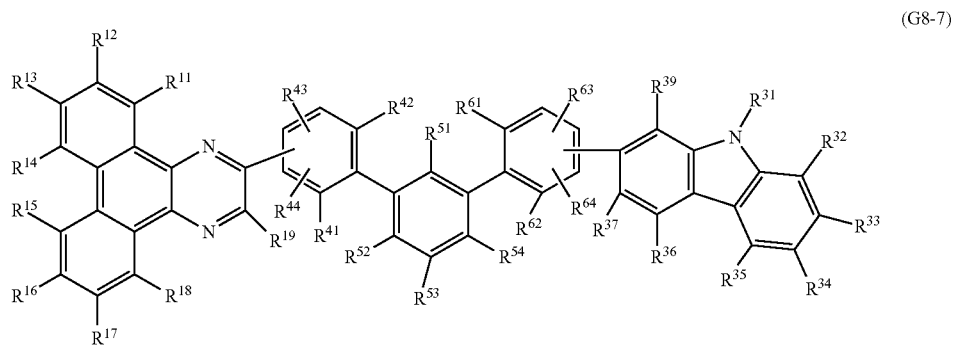

In the formula, each of $R^{11}$ to $R^{19}$, $R^{32}$ to $R^{37}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms. $R^{31}$ represents an alkyl group having 1 to 4 carbon atoms or a substituted or unsubstituted aryl group having 6 to 13 carbon atoms.

Another embodiment of the present invention is the heterocyclic compound represented by General Formula (G8-7) in which the site of substitution of DBq is a meta-position.

Another embodiment of the present invention is the heterocyclic compound represented by General Formula (G8-7) in which the site of substitution of DBq is a meta-position and the site of substitution of a carbazolyl group is a para-position.

Another embodiment of the present invention is a heterocyclic compound represented by General Formula (G8-8). The heterocyclic compound is useful in terms of a high carrier-transport property and high reliability.

[Chemical formula 64]

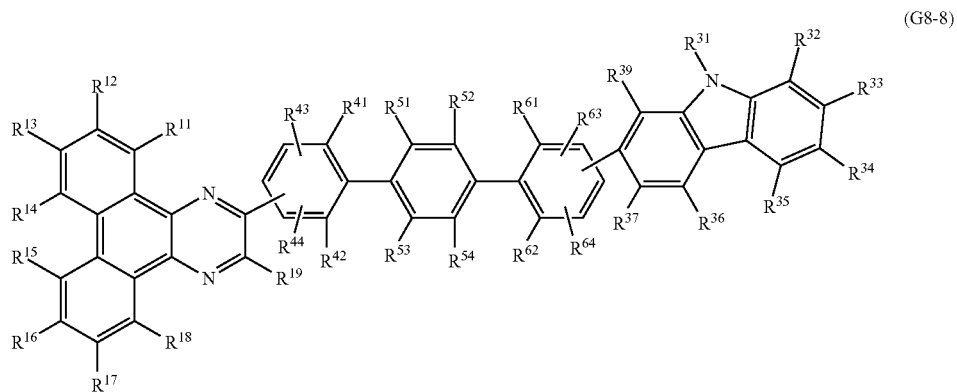

(G8-8)

In the formula, each of $R^{11}$ to $R^{19}$, $R^{32}$ to $R^{37}$, $R^{39}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms. $R^{31}$ represents an alkyl group having 1 to 4 carbon atoms or a substituted or unsubstituted aryl group having 6 to 13 carbon atoms.

Another embodiment of the present invention is a heterocyclic compound represented by General Formula (G9-1). The heterocyclic compound is useful in terms of a high T1 level, a high carrier-transport property, high heat resistance, and high reliability.

[Chemical formula 65]

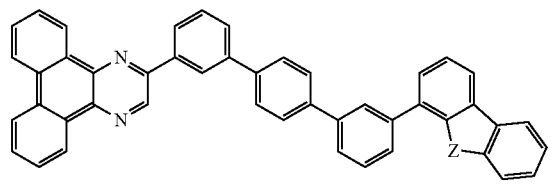

(G9-1)

In the formula, Z represents oxygen or sulfur.

Another embodiment of the present invention is a heterocyclic compound represented by General Formula (G9-2). The heterocyclic compound is useful in terms of a high T1 level, a high carrier-transport property, high heat resistance, and high reliability.

[Chemical formula 66]

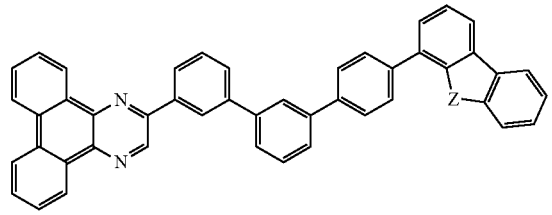

(G9-2)

In the formula, Z represents oxygen or sulfur.

Another embodiment of the present invention is a heterocyclic compound represented by General Formula (G9-3). The heterocyclic compound is useful in terms of a high T1 level, a high carrier-transport property, high heat resistance, and high reliability.

[Chemical formula 67]

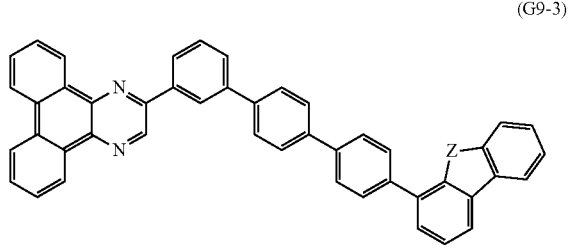

(G9-3)

In the formula, Z represents oxygen or sulfur.

Another embodiment of the present invention is a heterocyclic compound represented by General Formula (G9-4). The heterocyclic compound is useful in terms of a high T1 level, a high carrier-transport property, high heat resistance, and high reliability.

[Chemical formula 68]

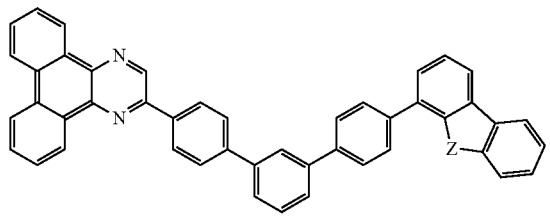

(G9-4)

In the formula, Z represents oxygen or sulfur.

Another embodiment of the present invention is a heterocyclic compound represented by General Formula (G9-5). The heterocyclic compound is useful in terms of a high T1 level, a high carrier-transport property, high heat resistance, and high reliability.

[Chemical formula 69]

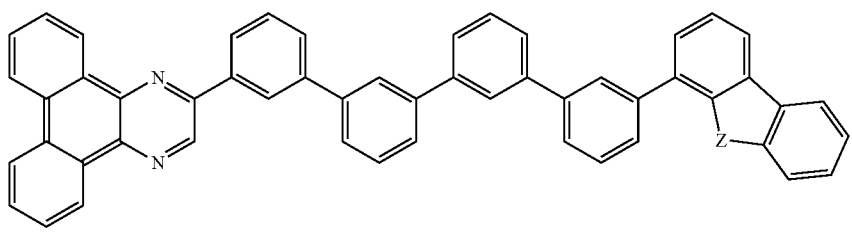

(G9-5)

In the formula, Z represents oxygen or sulfur.

Another embodiment of the present invention is a heterocyclic compound represented by General Formula (G10-1). The heterocyclic compound is useful in terms of a high T1 level, a high carrier-transport property, high heat resistance, and high reliability.

[Chemical formula 70]

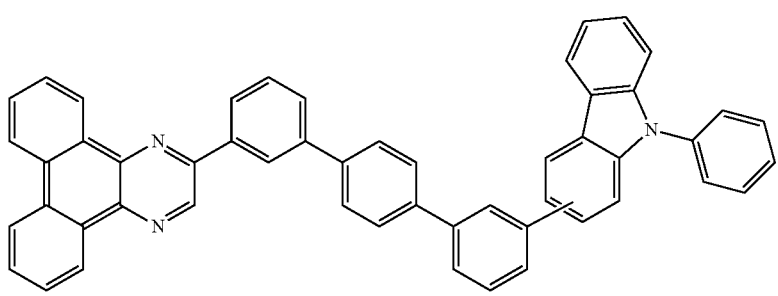

(G10-1)

Another embodiment of the present invention is a heterocyclic compound represented by General Formula (G10-2). The heterocyclic compound is useful in terms of a high T1 level, a high carrier-transport property, high heat resistance, and high reliability.

[Chemical formula 71]

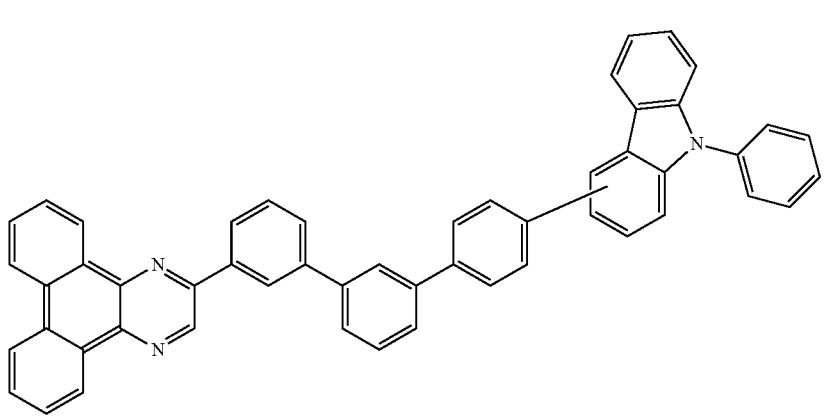

(G10-2)

Another embodiment of the present invention is a heterocyclic compound represented by General Formula (G10-3). The heterocyclic compound is useful in terms of a high T1 level, a high carrier-transport property, high heat resistance, and high reliability.

[Chemical formula 72]

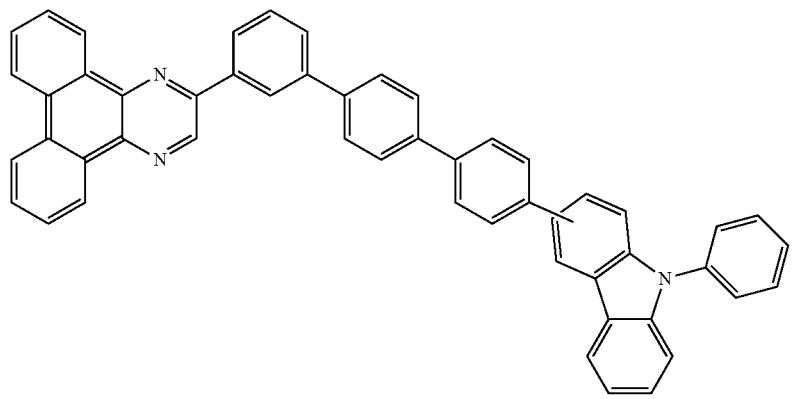

(G10-3)

Another embodiment of the present invention is a heterocyclic compound represented by General Formula (G10-4). The heterocyclic compound is useful in terms of a high carrier-transport property, high heat resistance, and high reliability.

[Chemical formula 73]

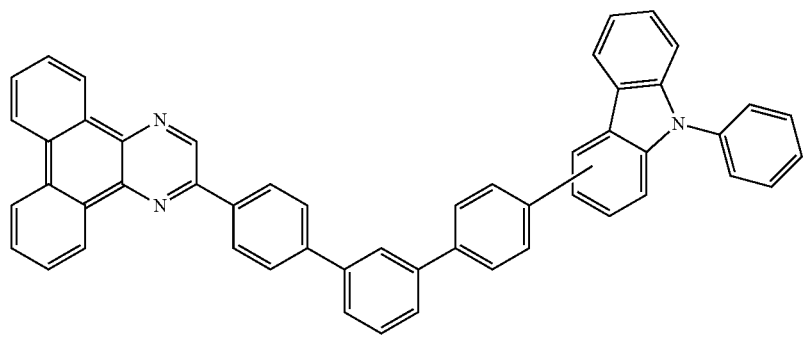

(G10-4)

Another embodiment of the present invention is a heterocyclic compound represented by General Formula (G10-5). The heterocyclic compound is useful in terms of a high T1 level, a high carrier-transport property, high heat resistance, and high reliability.

[Chemical formula 74]

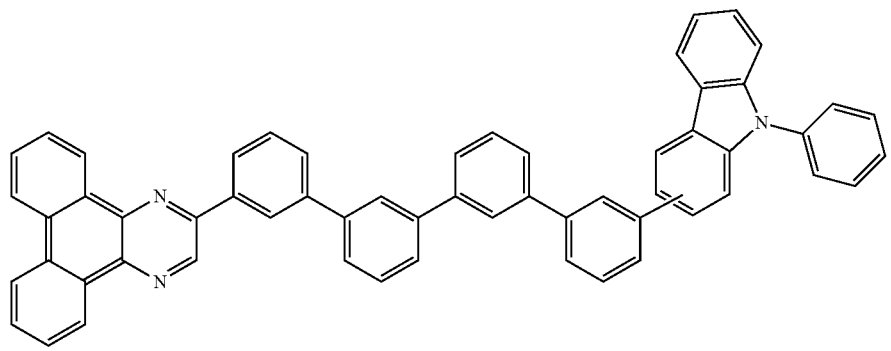

(G10-5)

Examples of the substituents included in the heterocyclic compound of one embodiment of the present invention are shown below. Formulae (S01) to (S25) represent specific examples of $R^{11}$ to $R^{19}$, $R^{21}$ to $R^{27}$, $R^{32}$ to $R^{39}$, $R^{41}$ to $R^{44}$, $R^{51}$ to $R^{54}$, and $R^{61}$ to $R^{64}$, and Formulae (S02) to (S25) represent specific examples of $R^{31}$. Formulae (S31) to (S46) represent examples of $Ar^1$ to $Ar^4$. Note that one embodiment of the present invention is not limited to the examples below.

[Chemical formula 75]

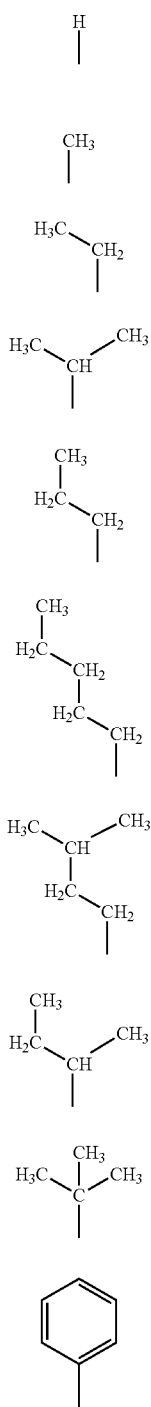

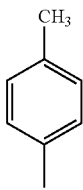

(S11)

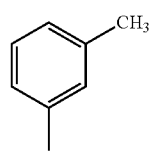

(S12)

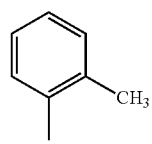

(S13)

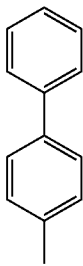

(S14)

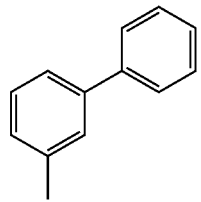

(S15)

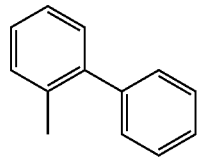

(S16)

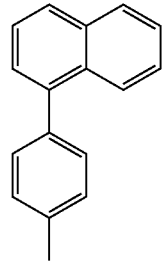

(S17)

(S18) 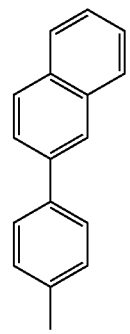
(S19) 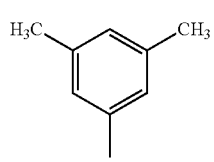
(S20) 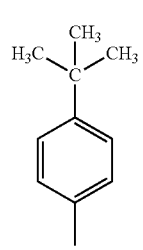
(S21) 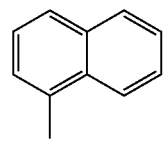
(S22) 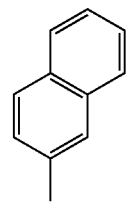
(S23) 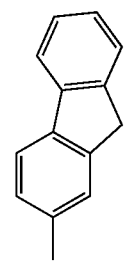
(S24) 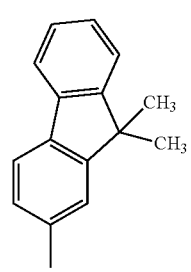
(S25) 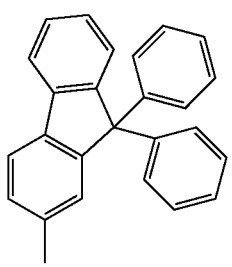
[Chemical formula 76]
(S31) 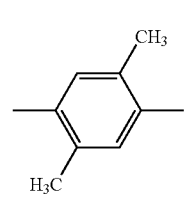
(S32) 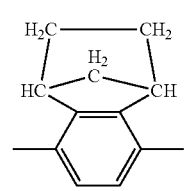
(S33) 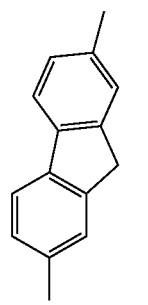
(S34) 
(S35) 
(S36)

(S37) 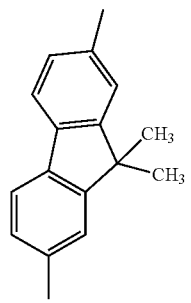
(S38) 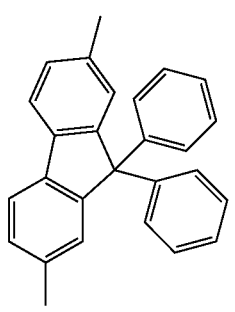
(S39) 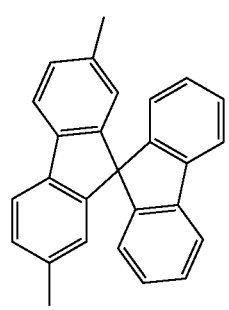
(S40) 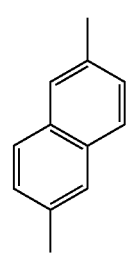
(S41) 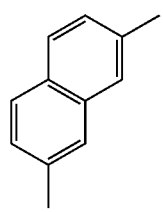
(S42) 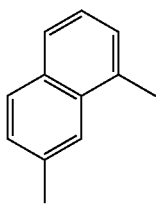
(S43) 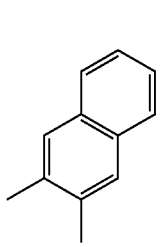
(S44) 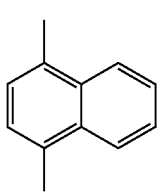
(S45) 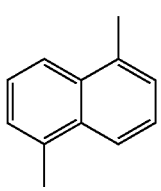
(S46) 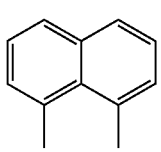
Specific structures of heterocyclic compounds of embodiments of the present invention are shown below. Note that heterocyclic compounds of embodiments of the present invention are not limited to the examples below.

[Chemical formula 77]
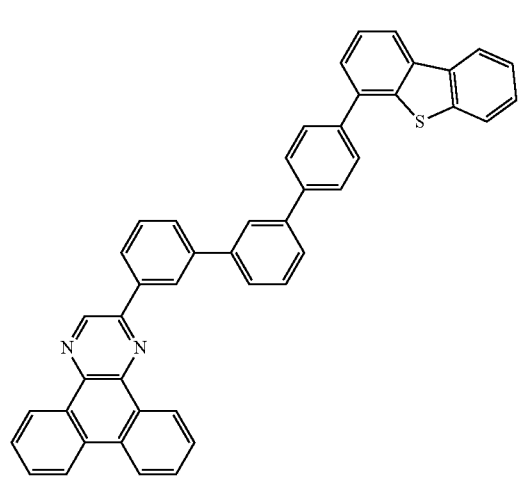
(001)
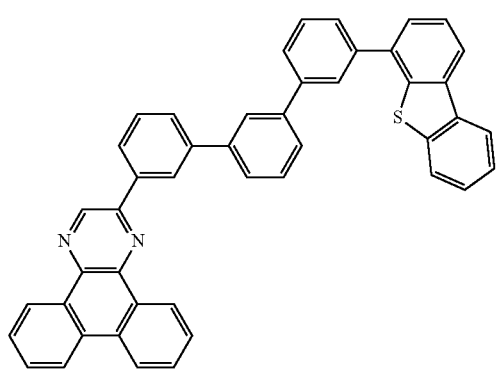
(002)
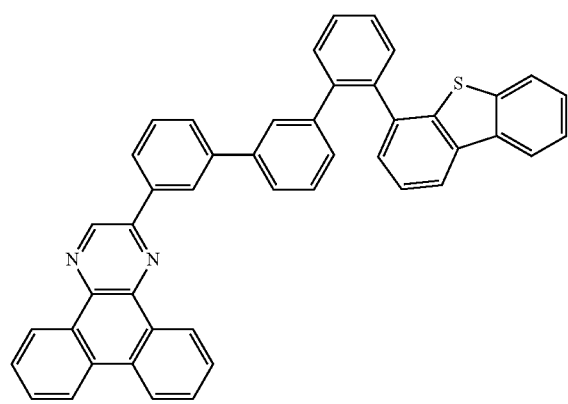
(003)
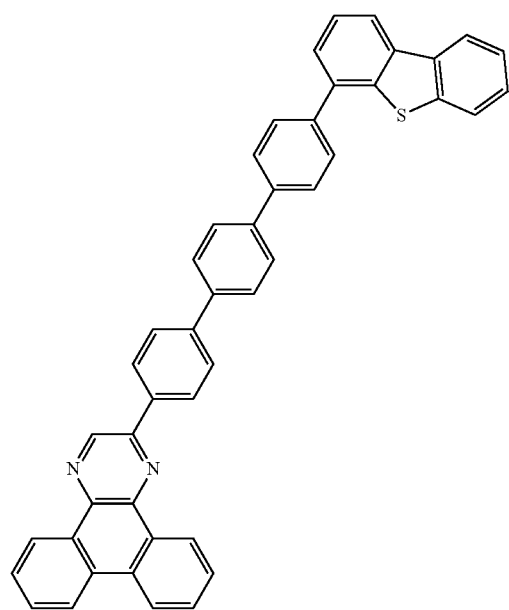
(004)

-continued
(005)
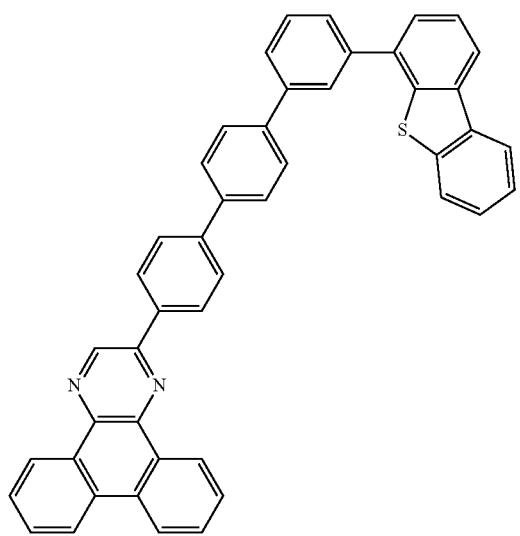
(006)
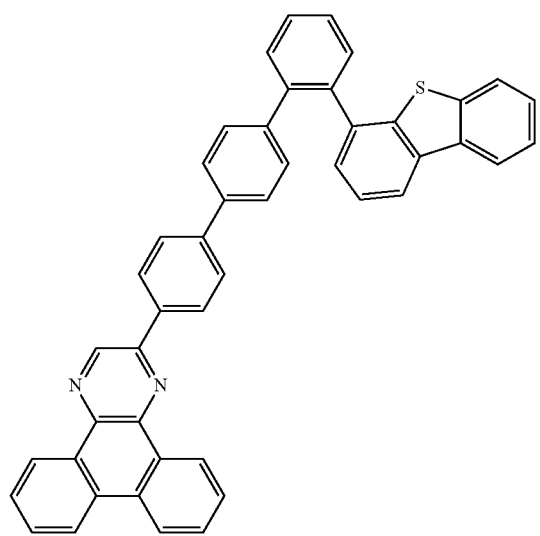
(007)
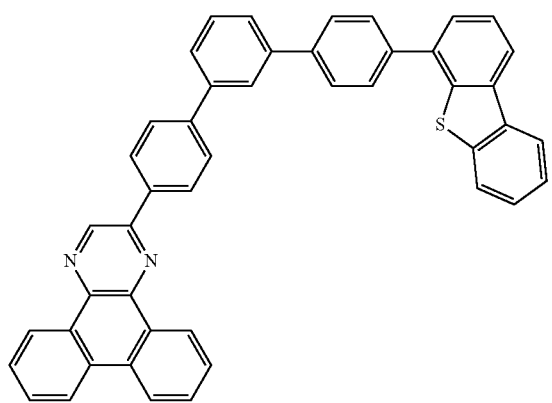
(008)
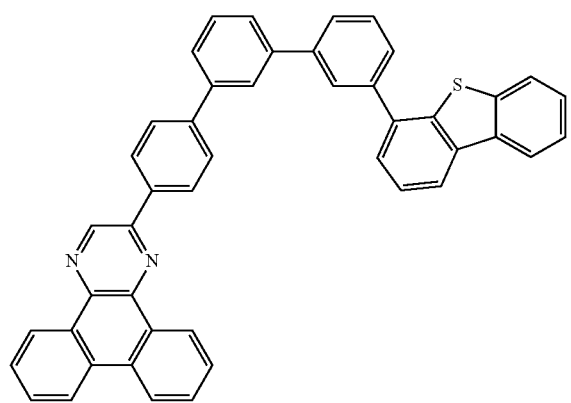
(009)
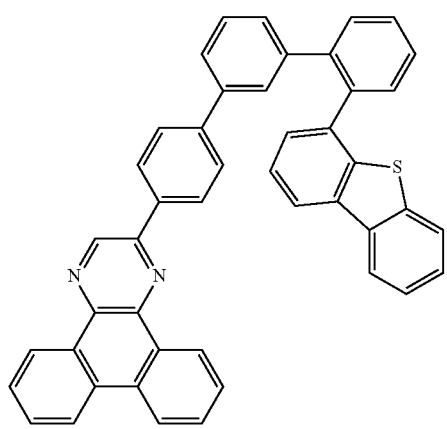

[Chemical formula 78]
(010)
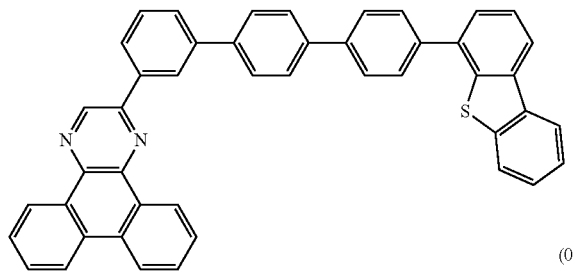
(011)
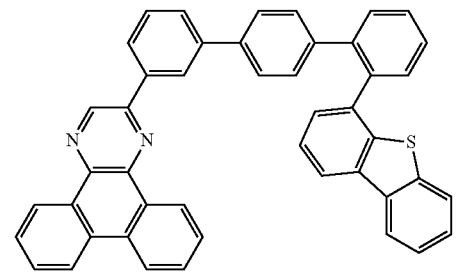
(012)
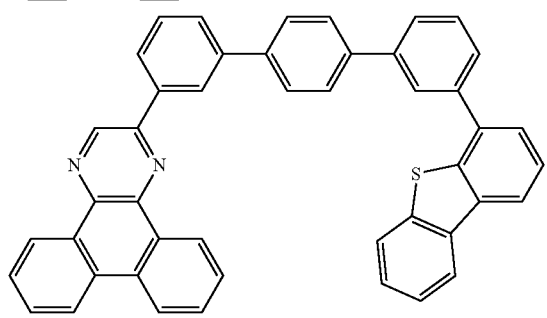
(013)
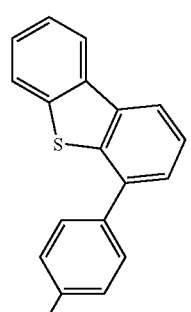
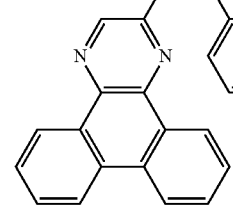
(014)
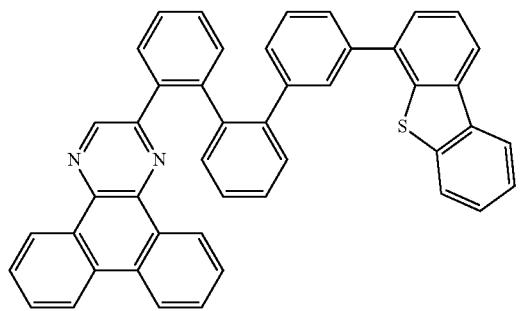
(015)
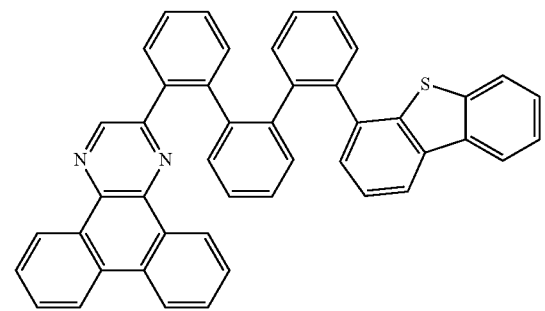
(016)
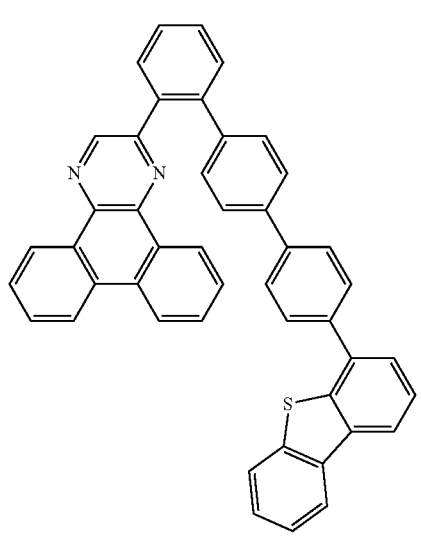
(017)
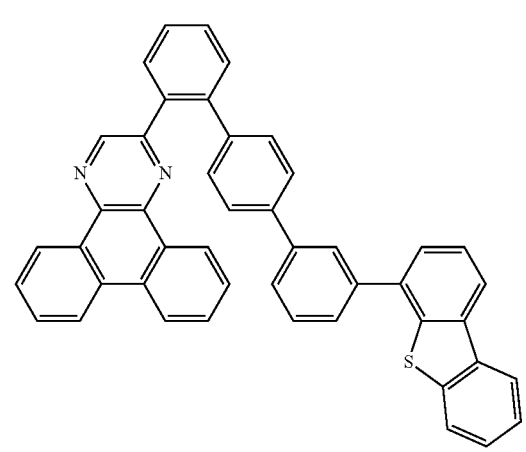

-continued
(018)
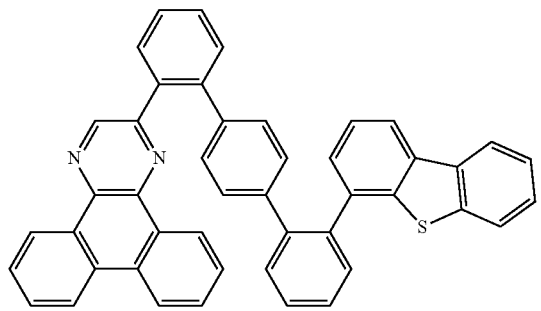
[Chemical formula 79]
(019)
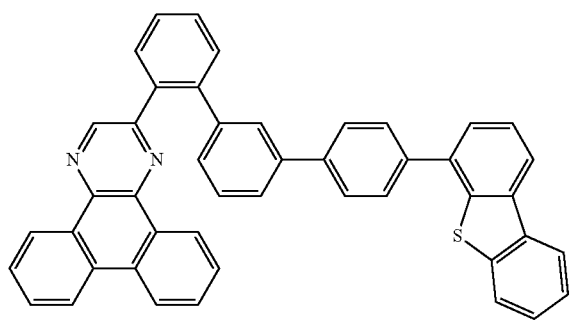
(020)
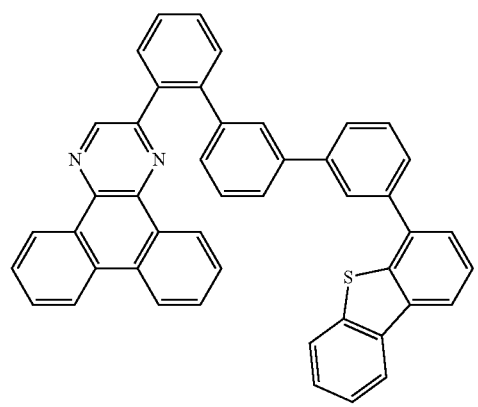
(021)
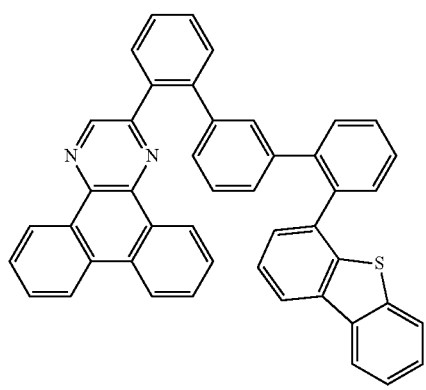
(022)
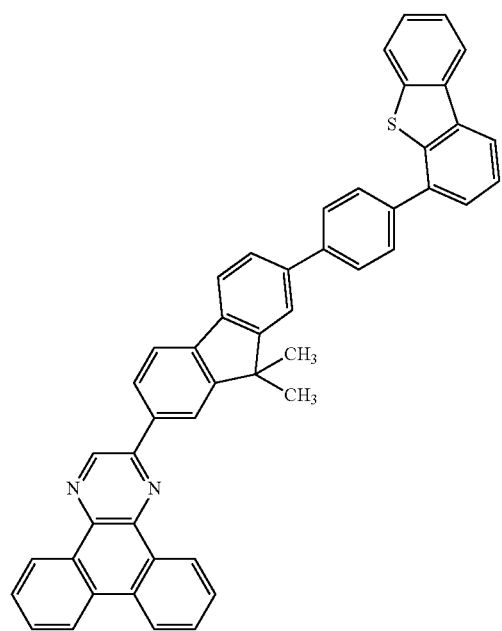

-continued
(023)
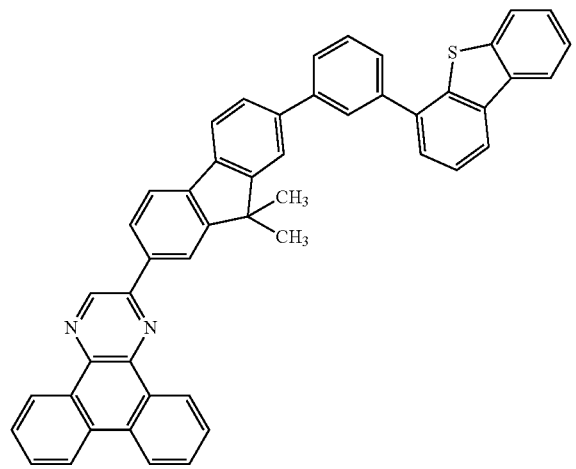
(024)
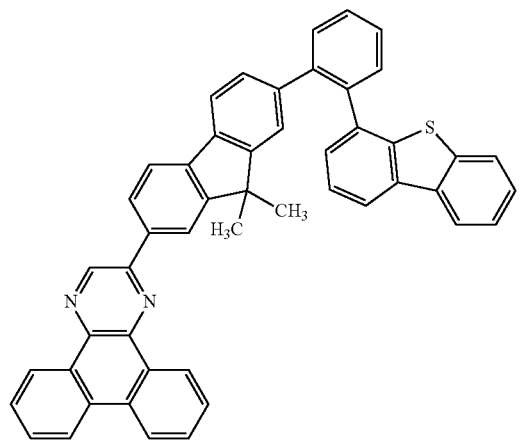
(025)
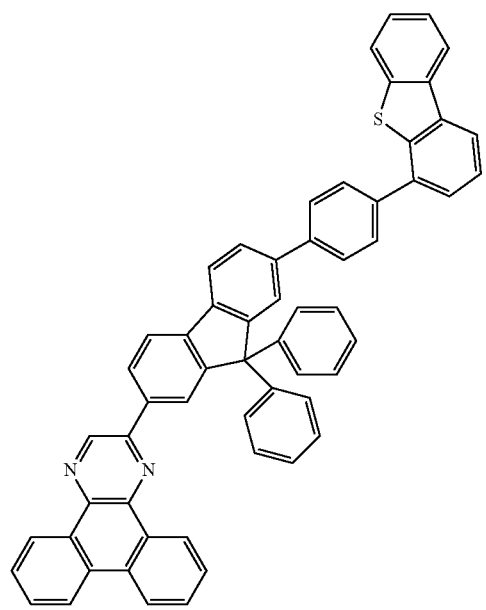
(026)
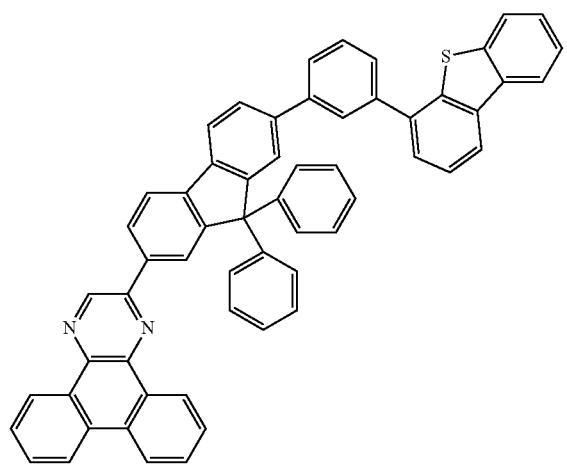

[Chemical formula 80]
(027)
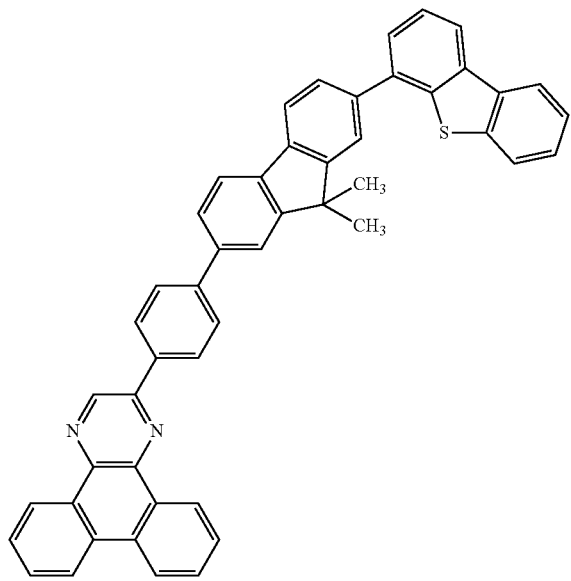
(028)
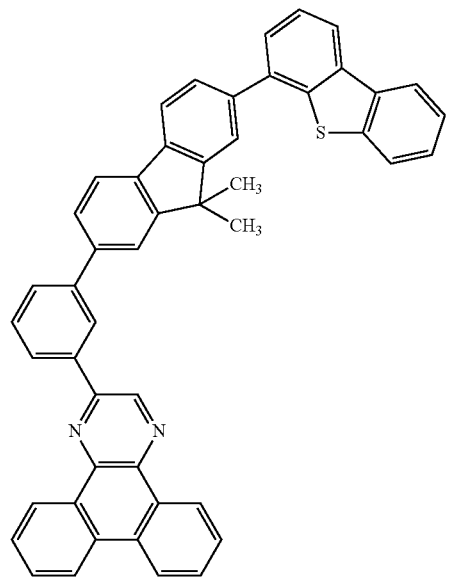
(029)
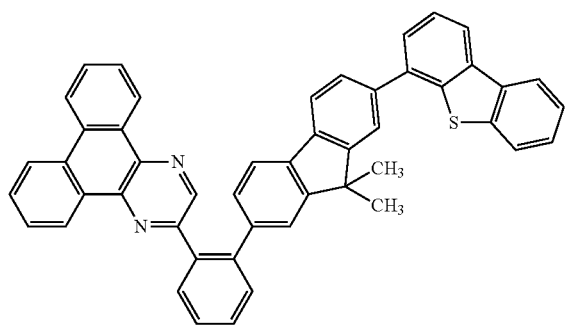
(030)
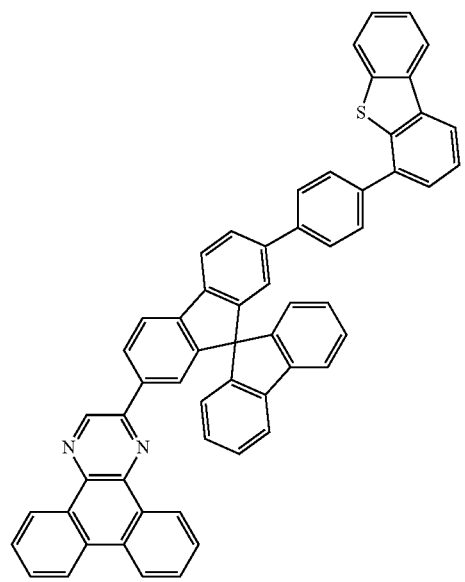

-continued
(031)
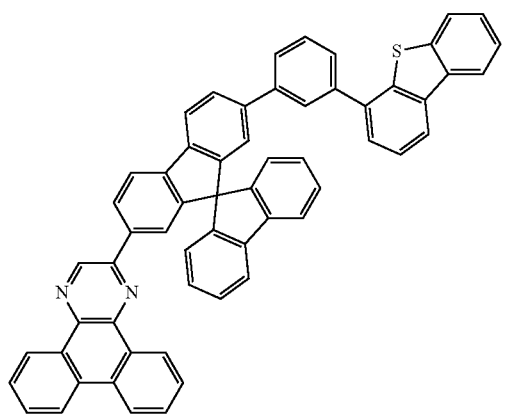
(032)
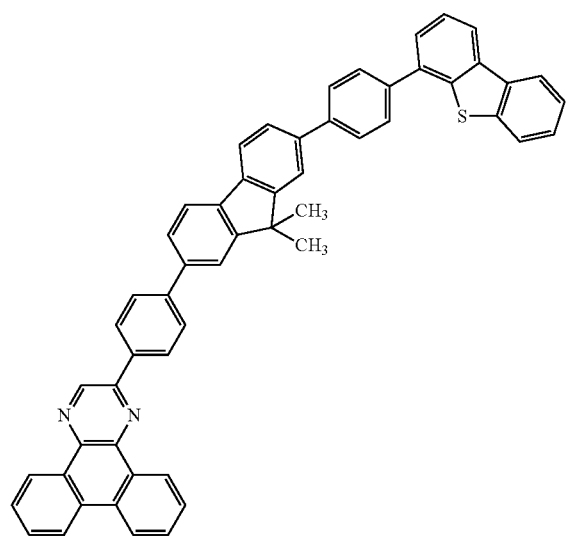
(033)
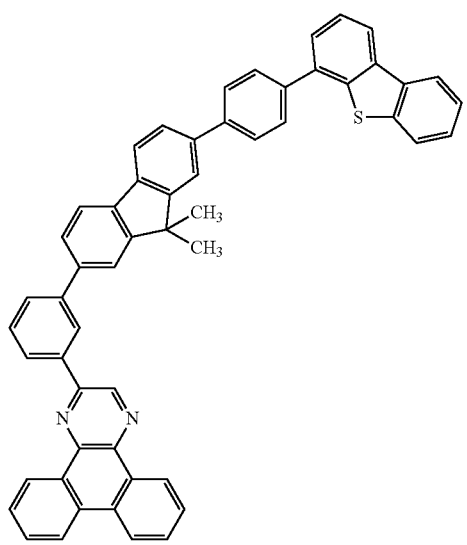
(034)
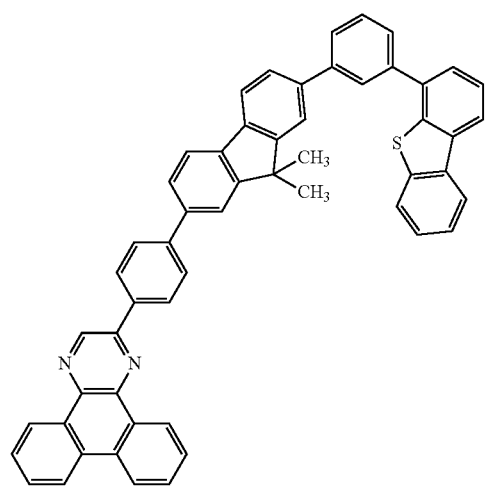

(035)
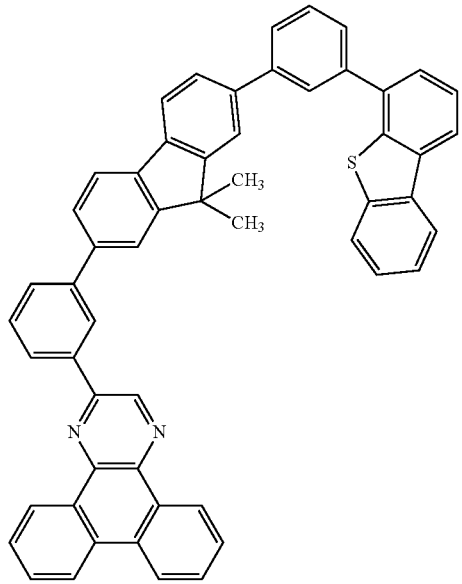
[Chemical formula 81]
(036)
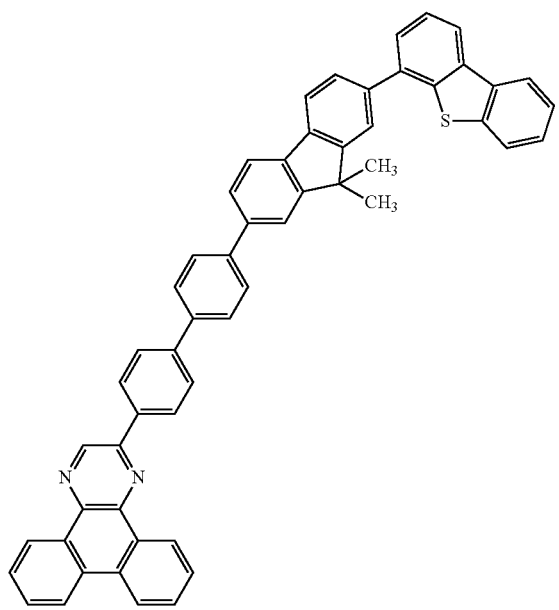
(037)
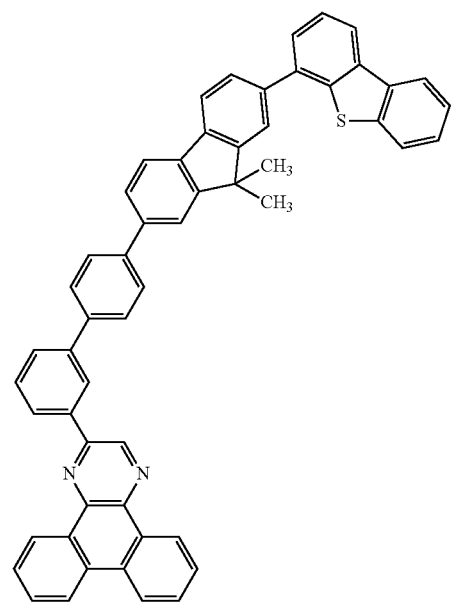
(038)
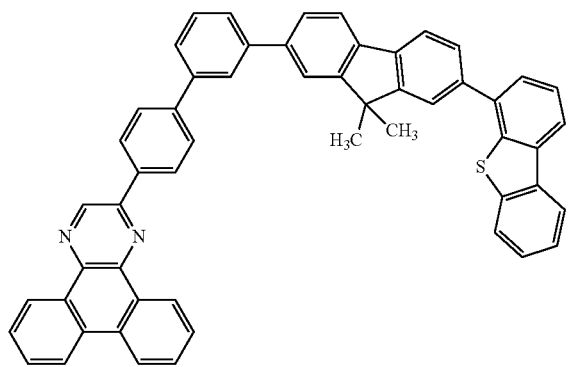
(039)
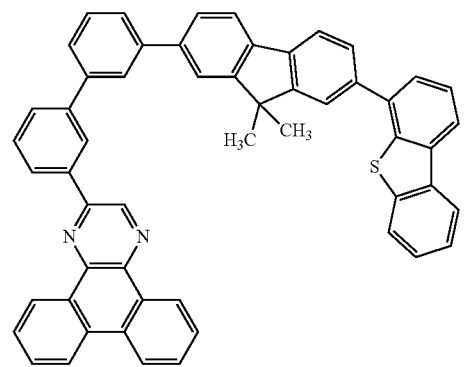

-continued
(040)
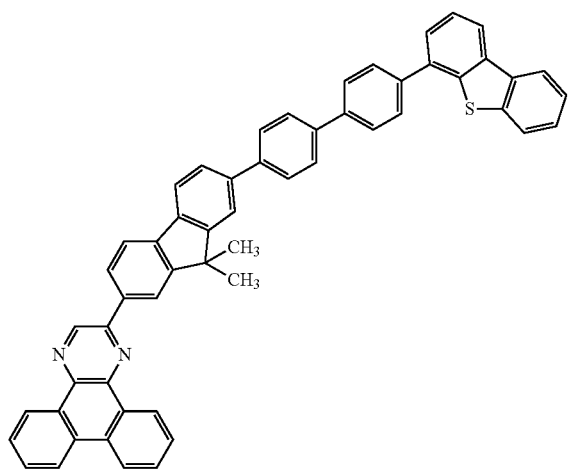
(041)
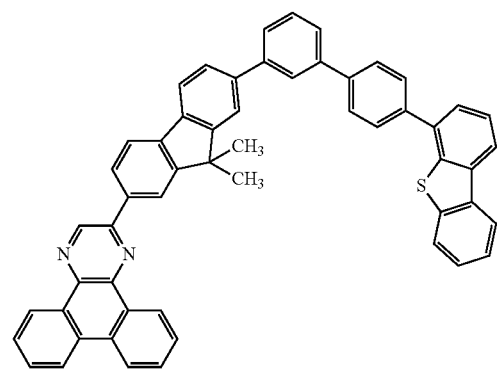
(042)
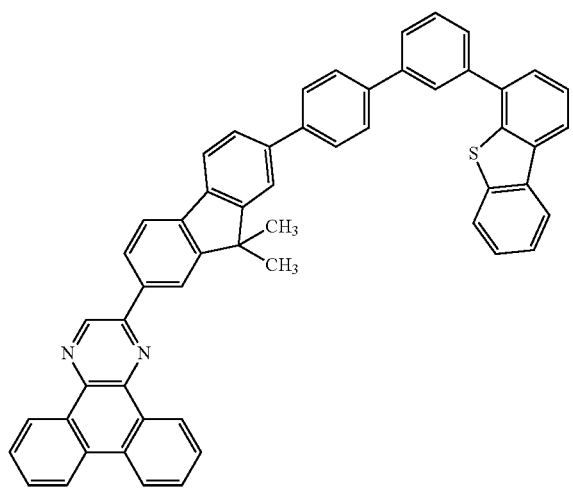
(043)
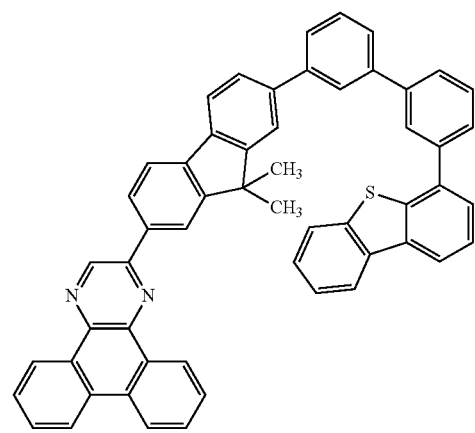
[Chemical formula 82]
(044)
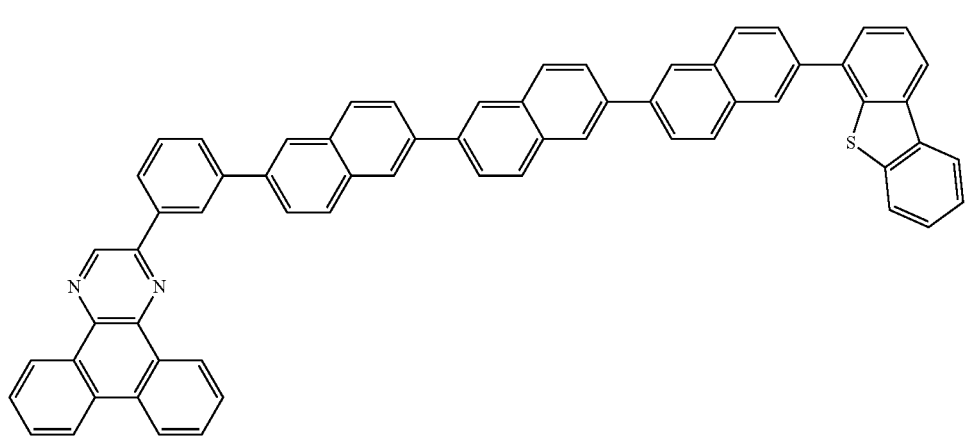

-continued
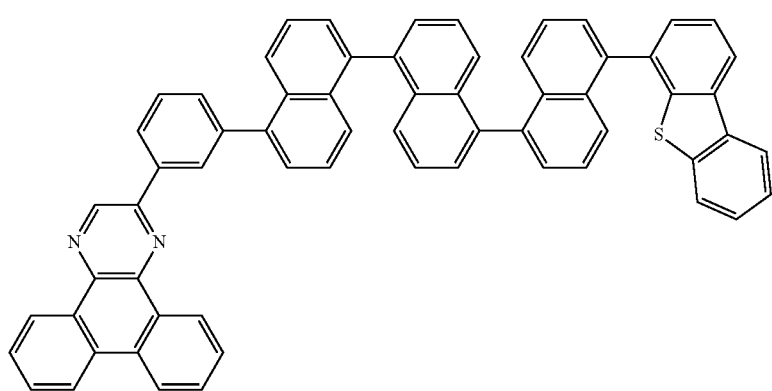 (045)
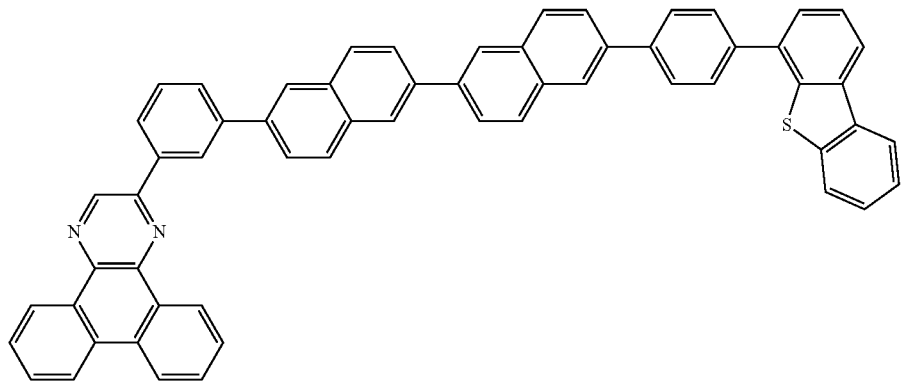 (046)
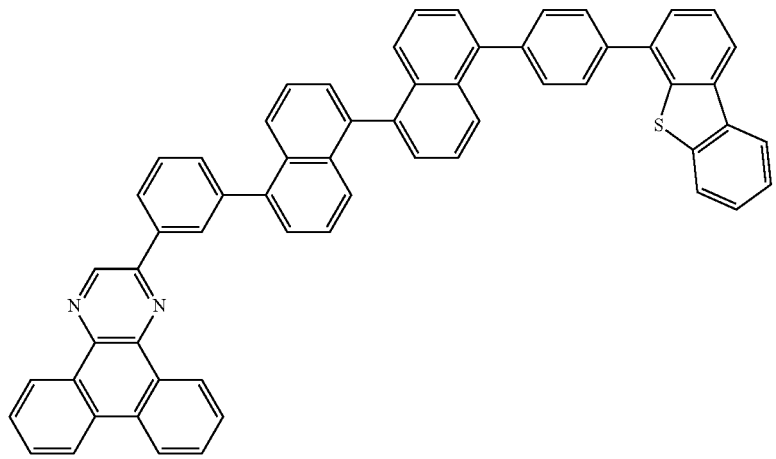 (047)

-continued
(048)
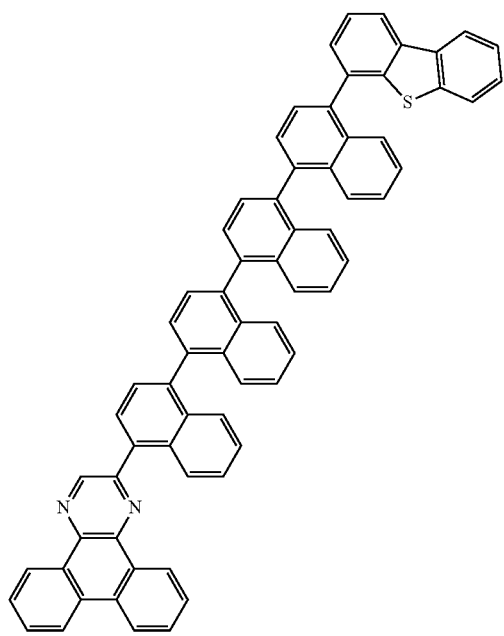
(049)
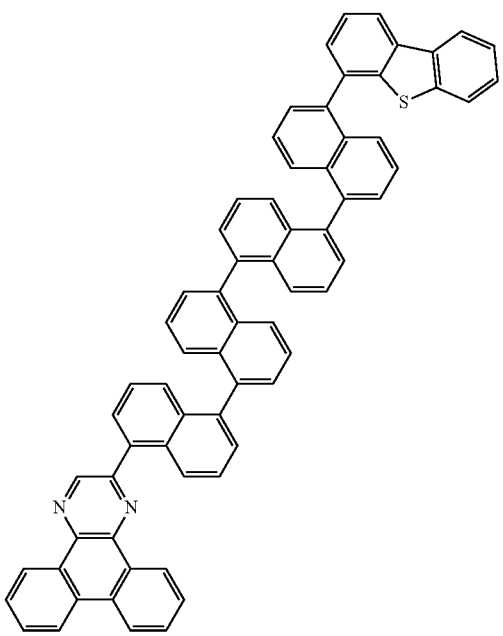
(050)
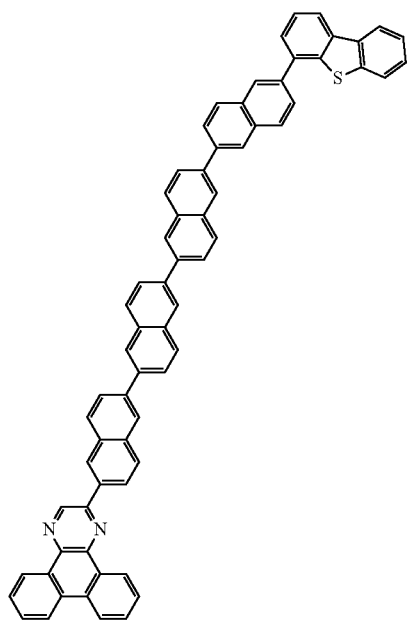
[Chemical formula 83]
(051)
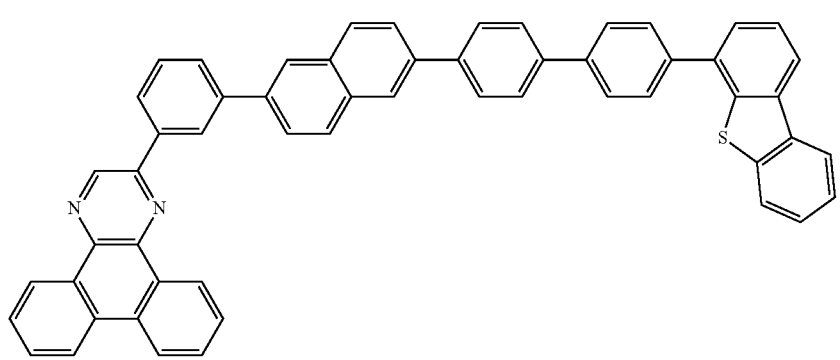

-continued
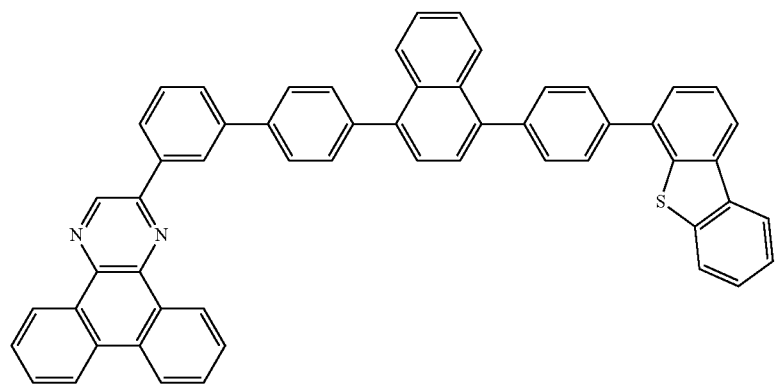
(052)
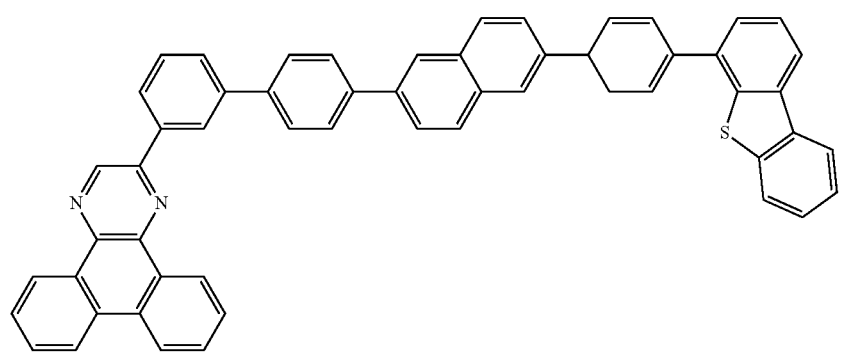
(053)
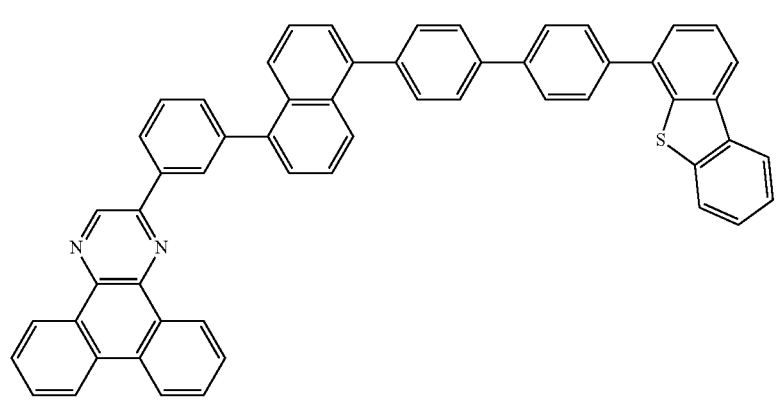
(054)

-continued
(055)
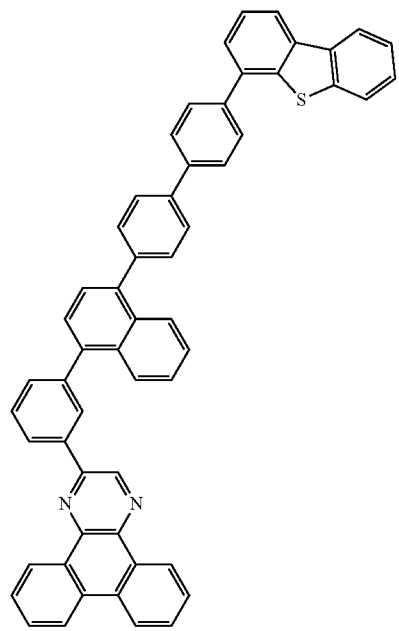
(056)
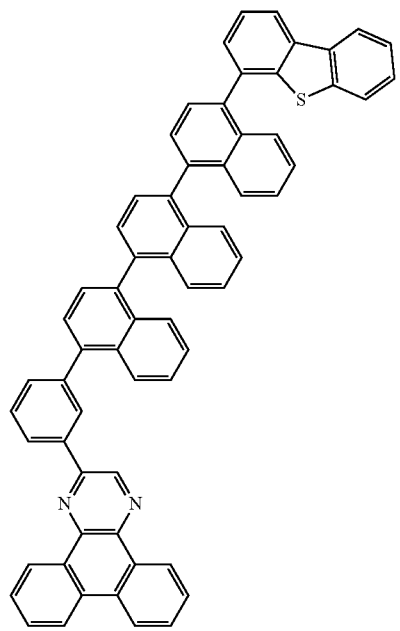
(056)
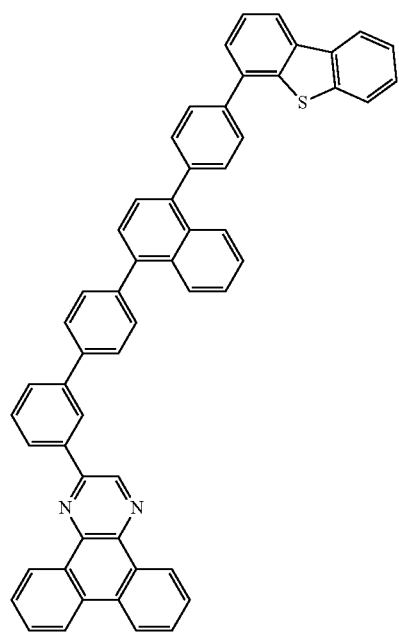
(058)
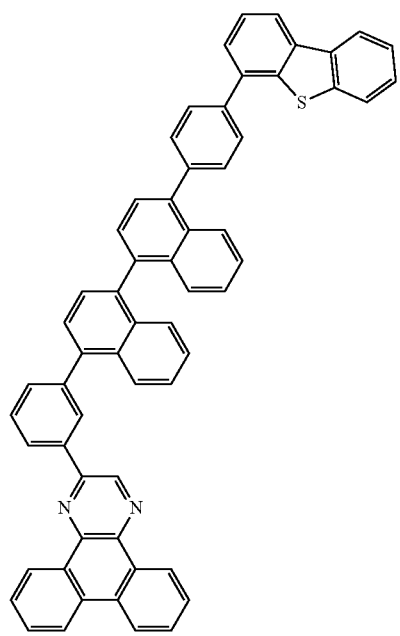
[Chemical formula 84]
(059)
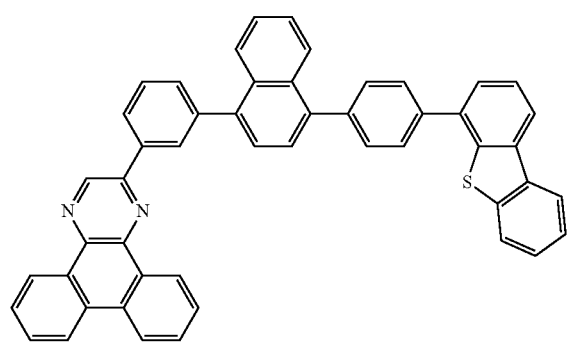
(060)
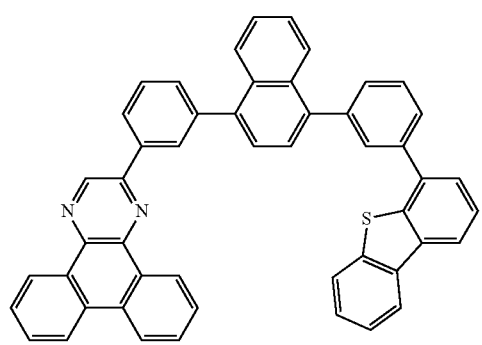

-continued
(061)
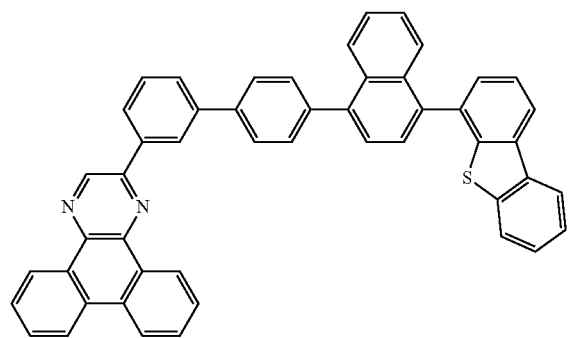
(062)
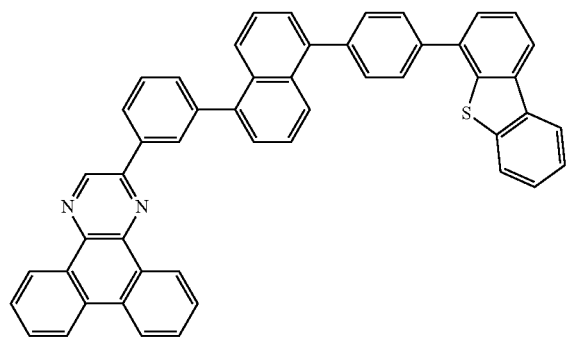
(063)
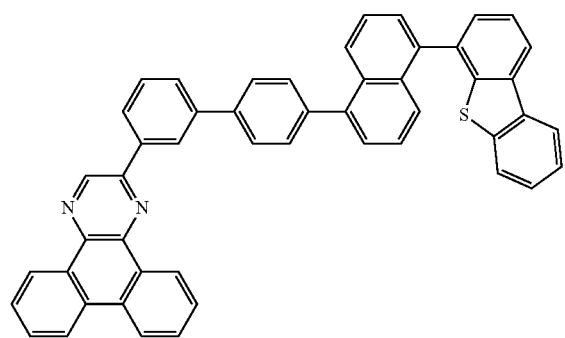
(064)
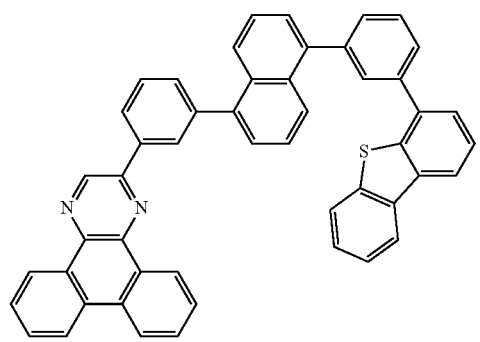
(065)
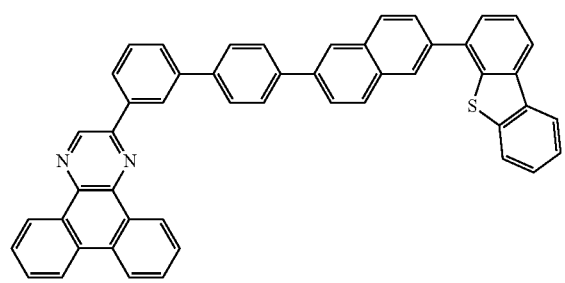
(066)
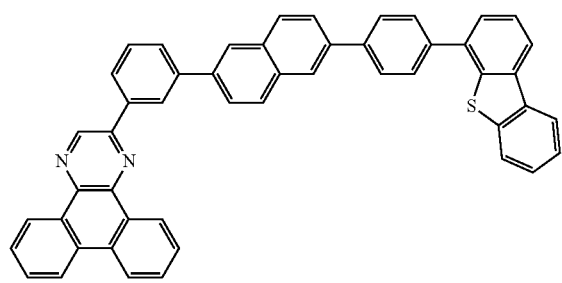
(067)
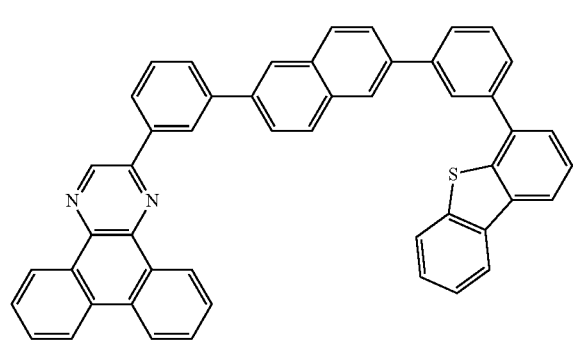

[Chemical formula 85]
(068)
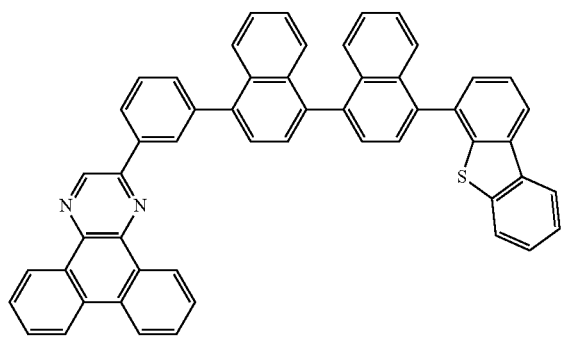
(069)
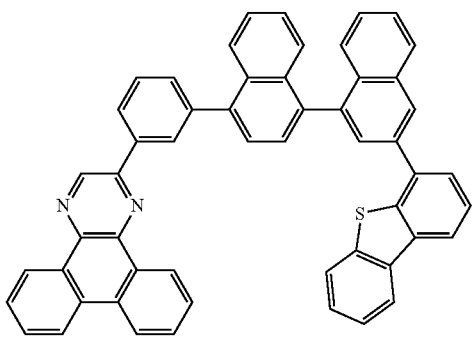
(070)
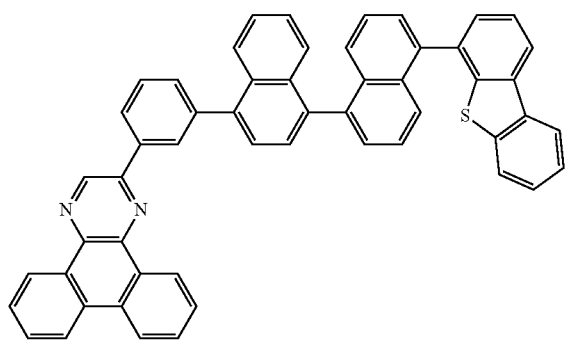
(071)
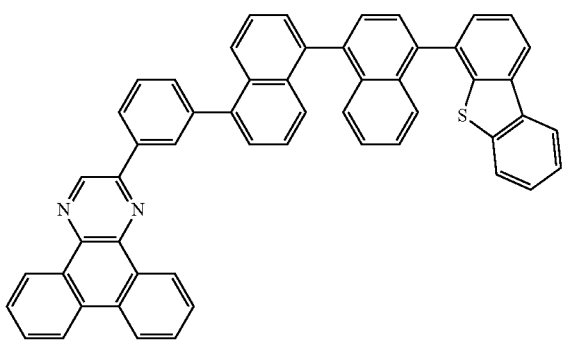
(072)
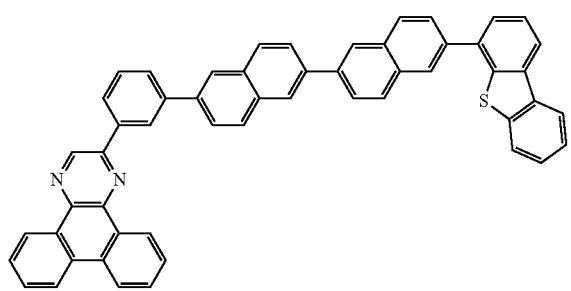
(073)
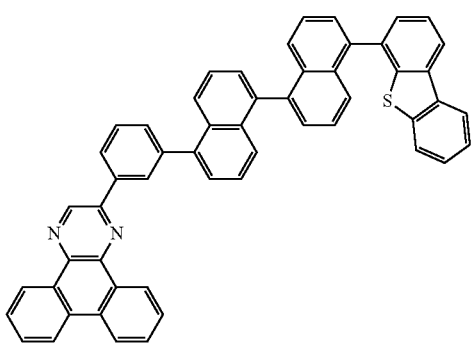

-continued
(074)
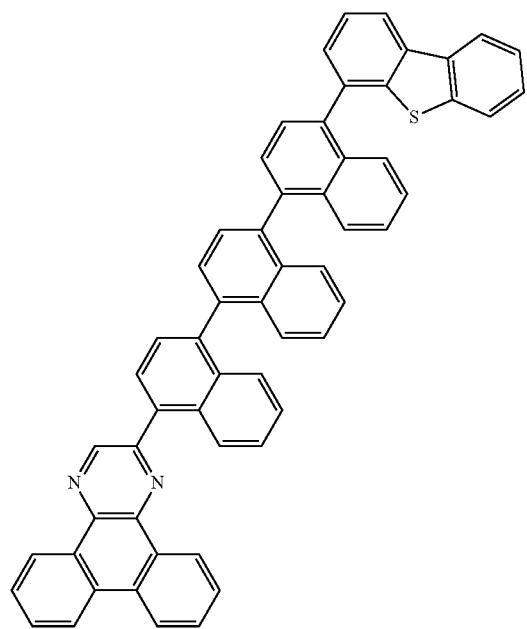
(075)
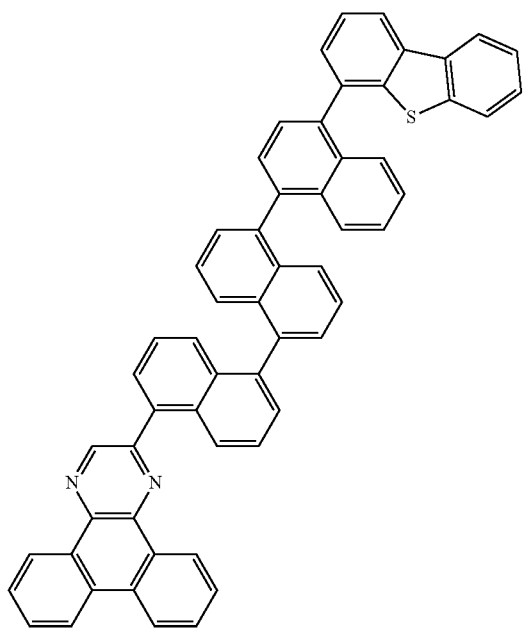
(076)
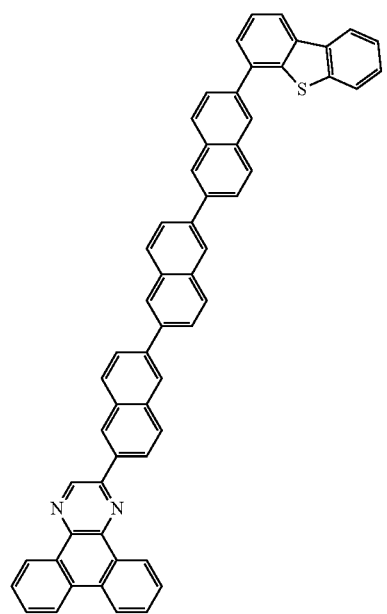

[Chemical formula 86]
(077)
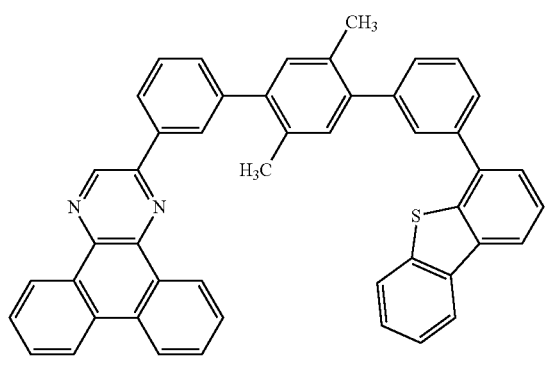
(078)
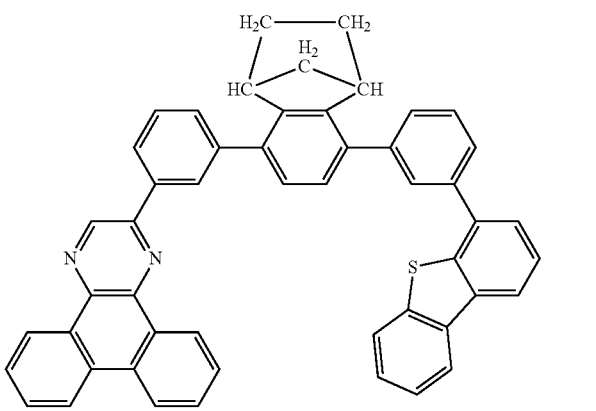
(079)
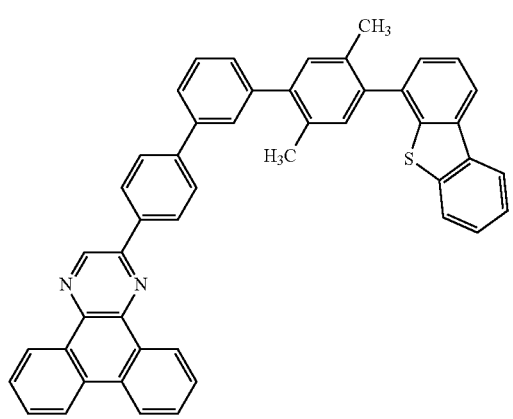
(080)
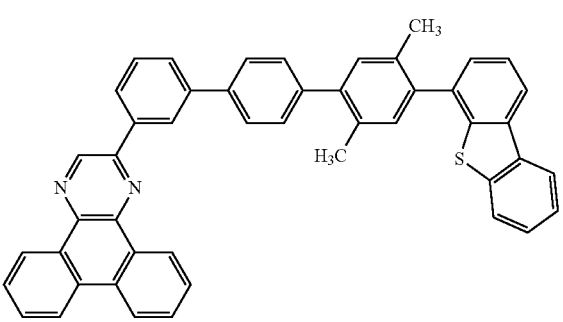
(081)
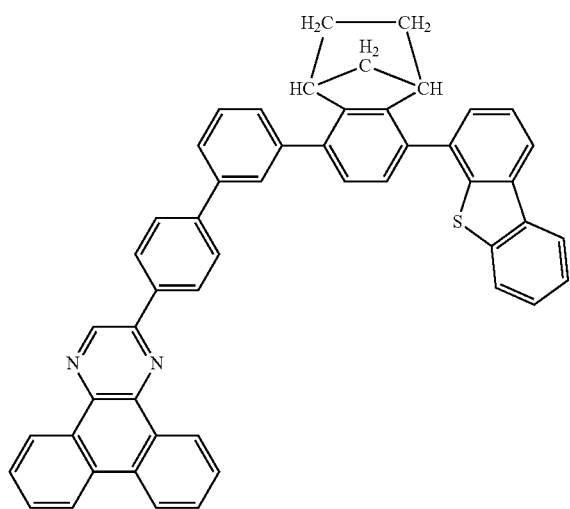
(082)
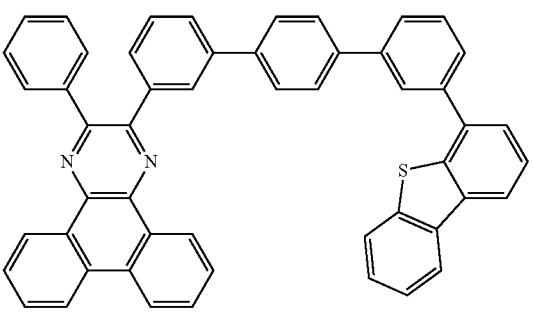

-continued
(083)
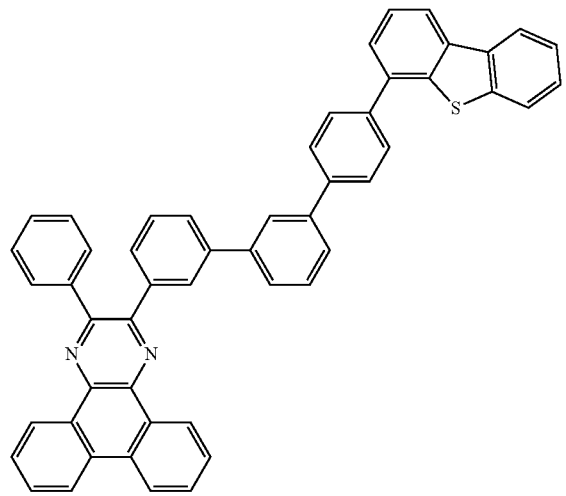
(084)
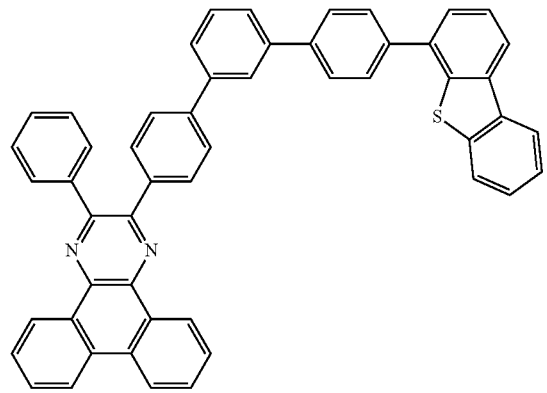
(085)
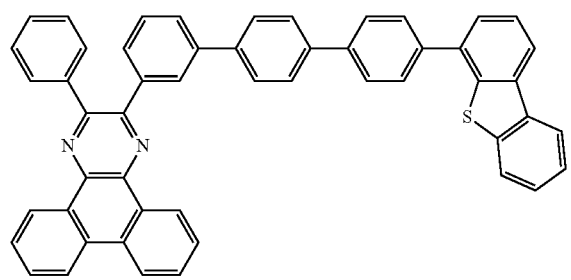
(086)
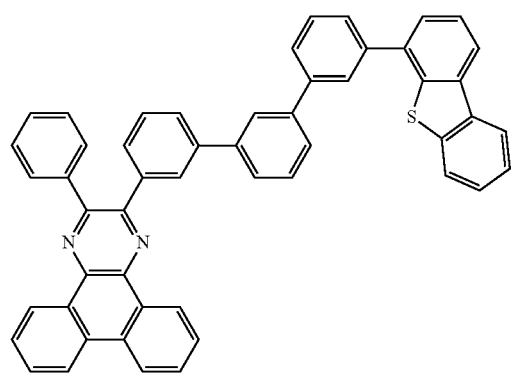
[Chemical formula 87]
(087)
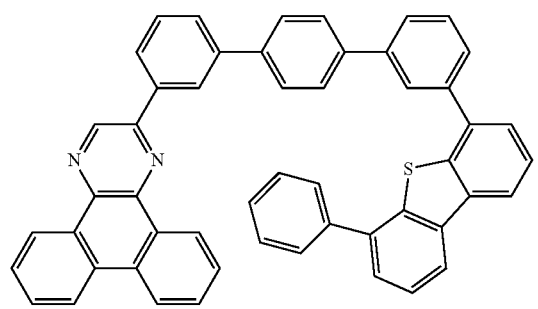
(088)
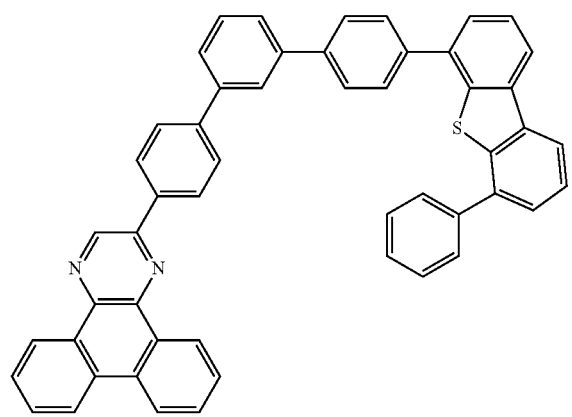

-continued
(089)
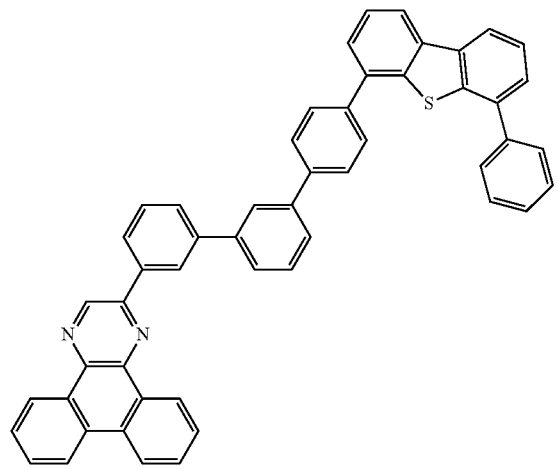
(090)
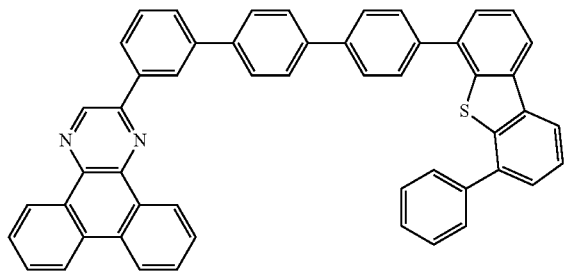
(091)
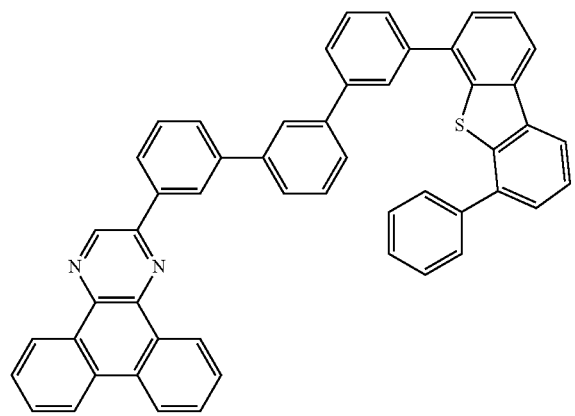
(092)
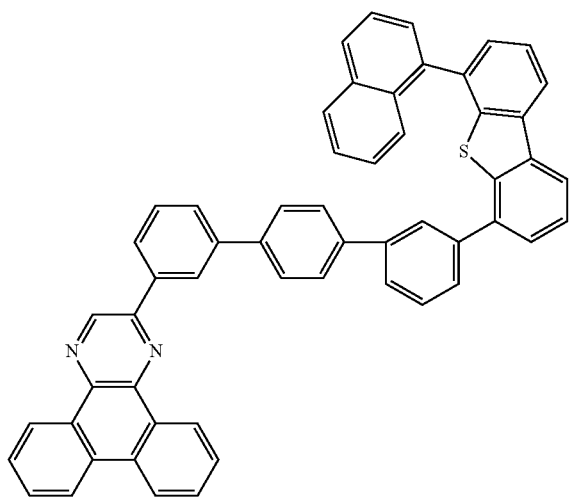
(093)
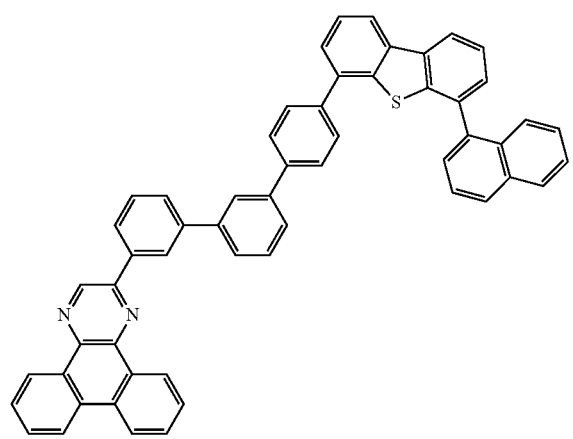
(094)
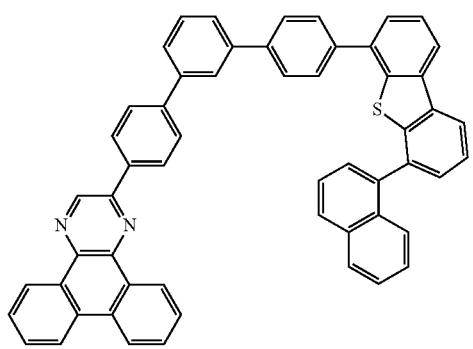

-continued
(095)
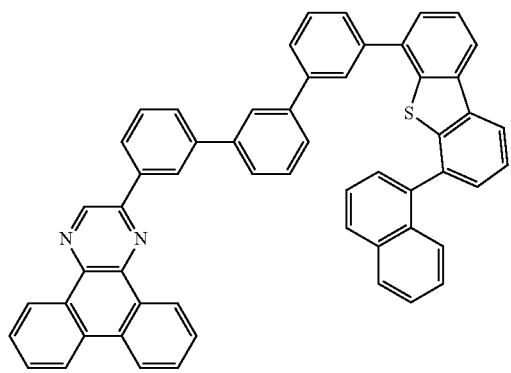
(096)
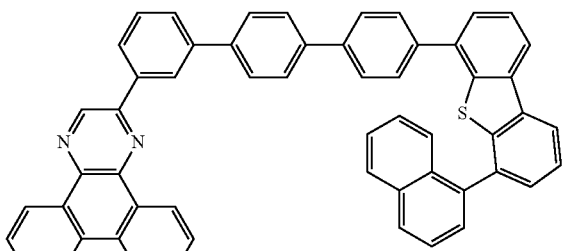
[Chemical formula 88]
(097)
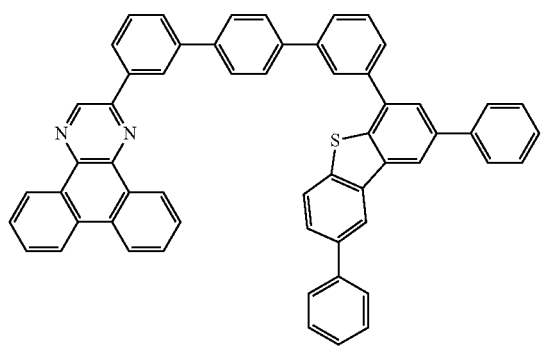
(098)
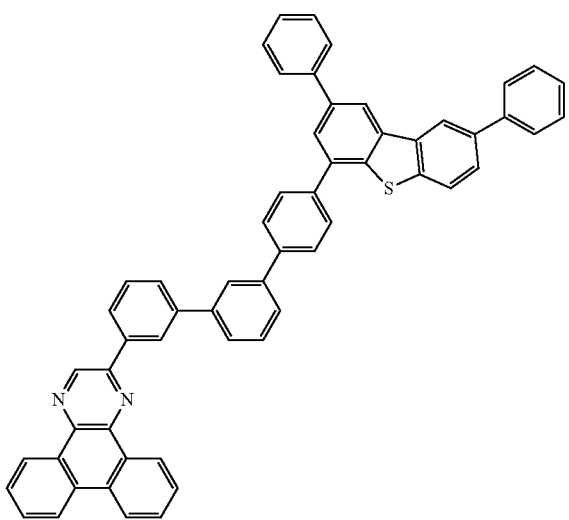
(099)
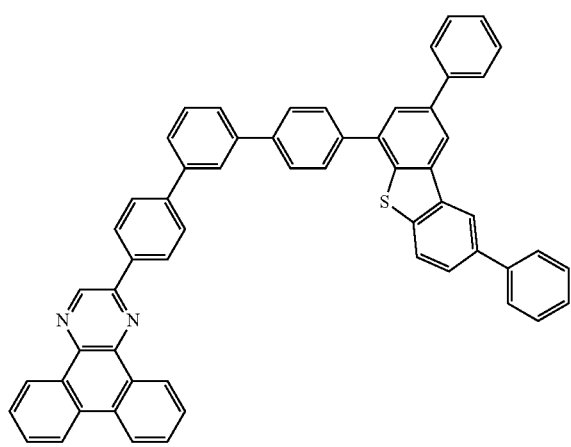
(100)
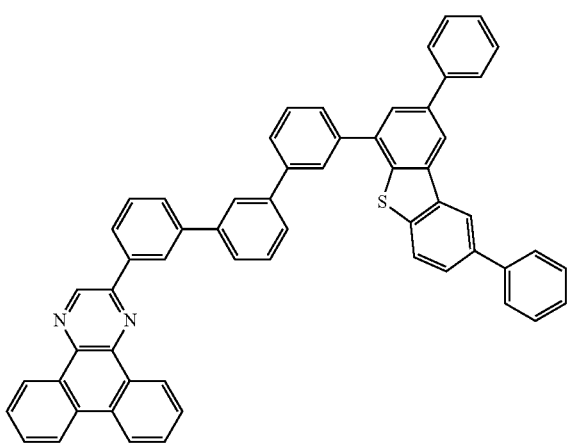

-continued
(101)
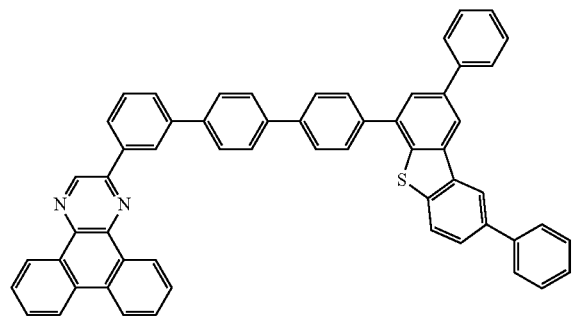
(102)
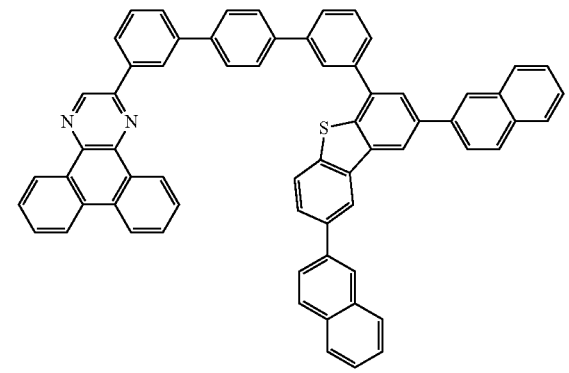
(103)
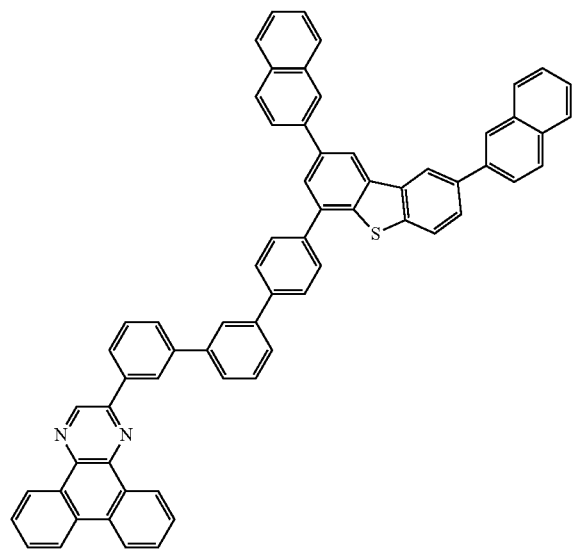
(014)
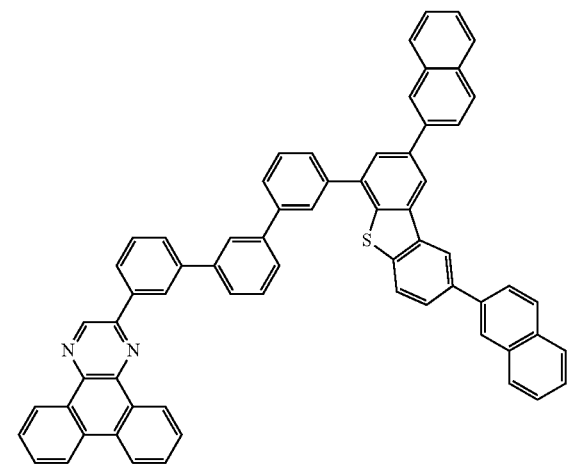
[Chemical formula 89]
(105)
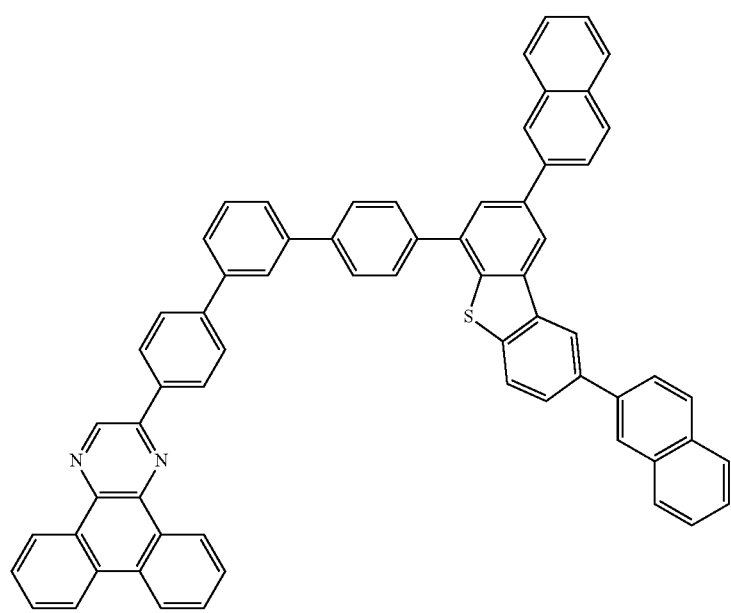

-continued
(106)
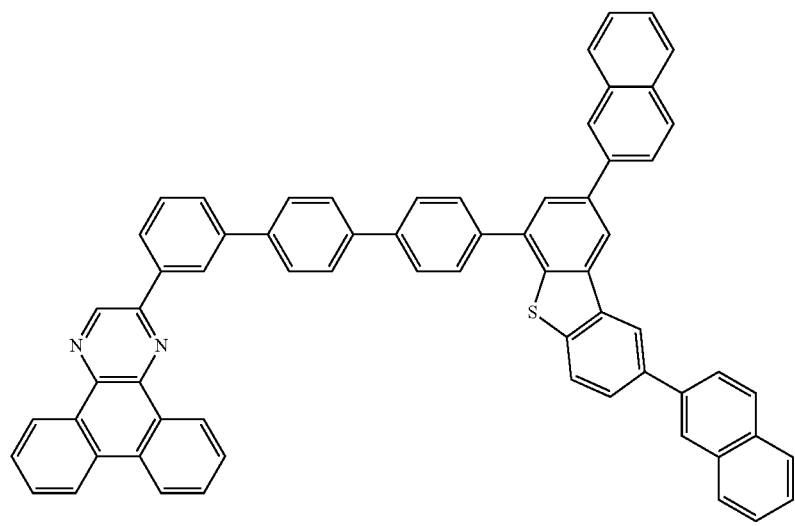
(107)
(108)
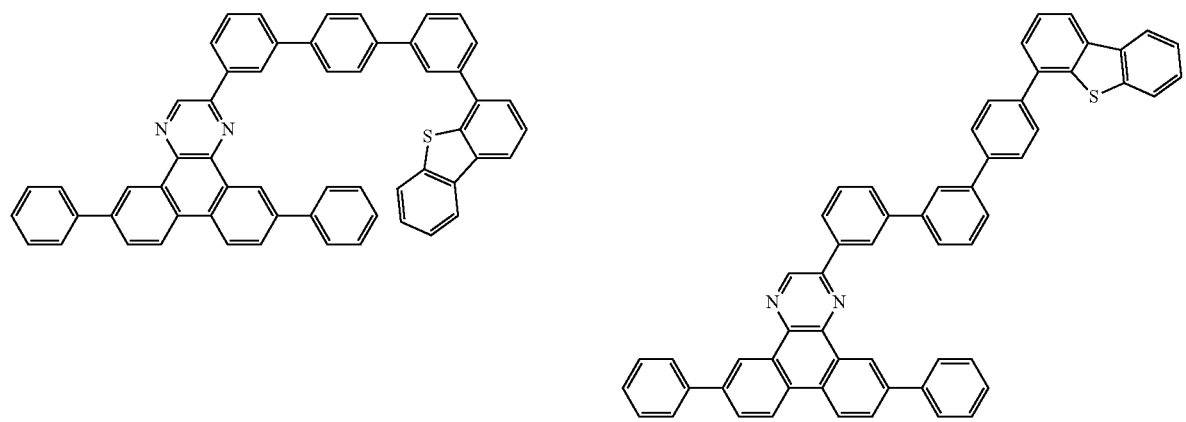
(109)
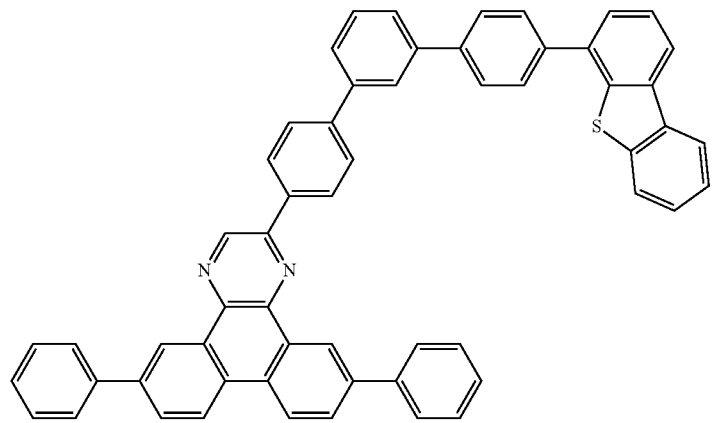

-continued
(110)
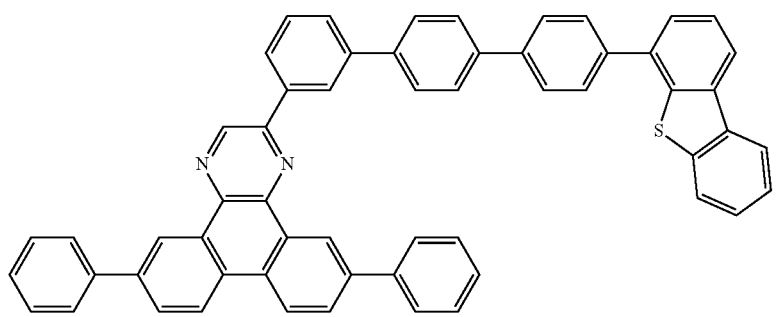
(111)
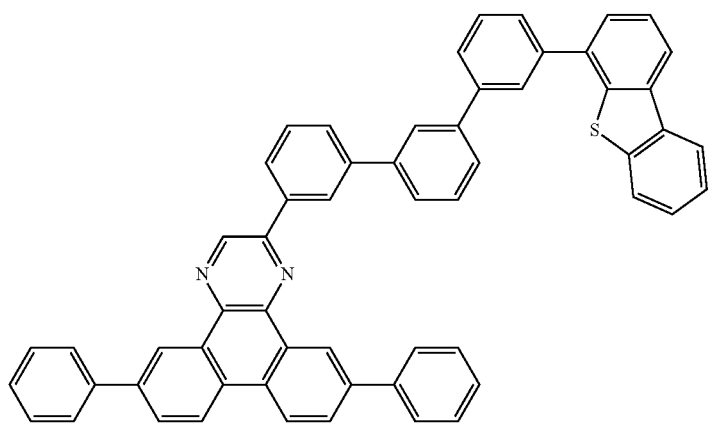
[Chemical formula 90]
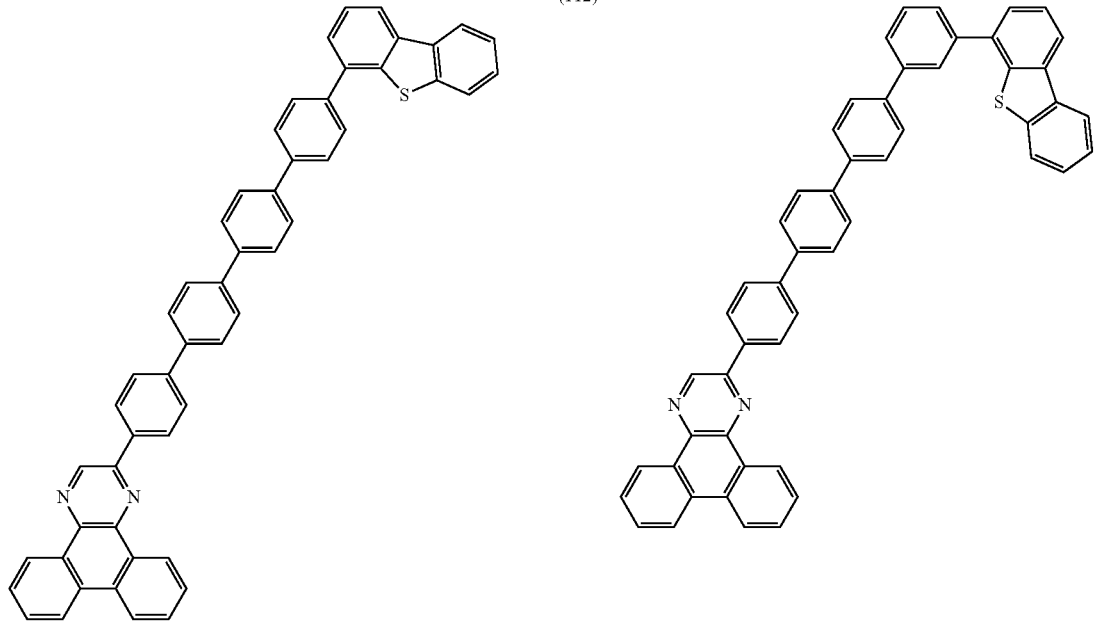

-continued
(114)
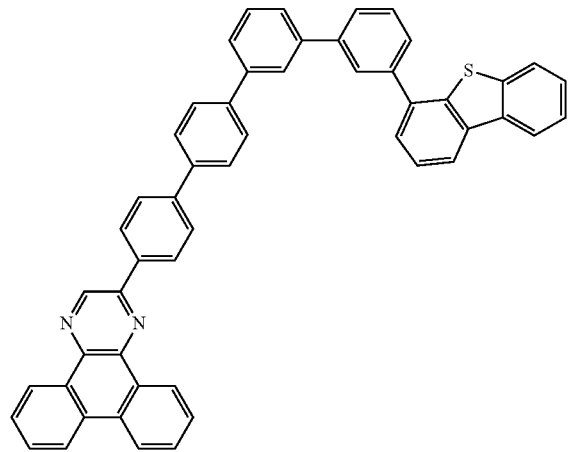
(115)
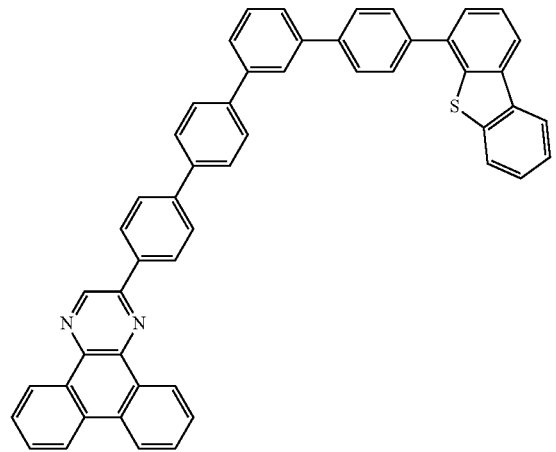
(116)
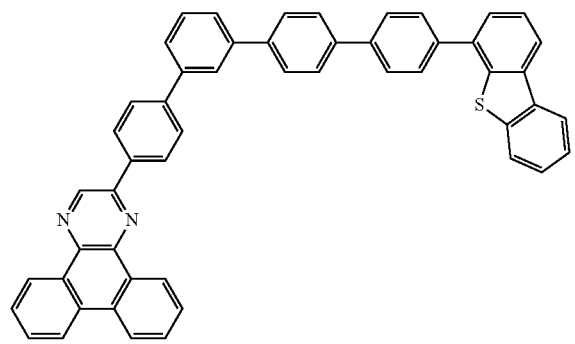
(117)
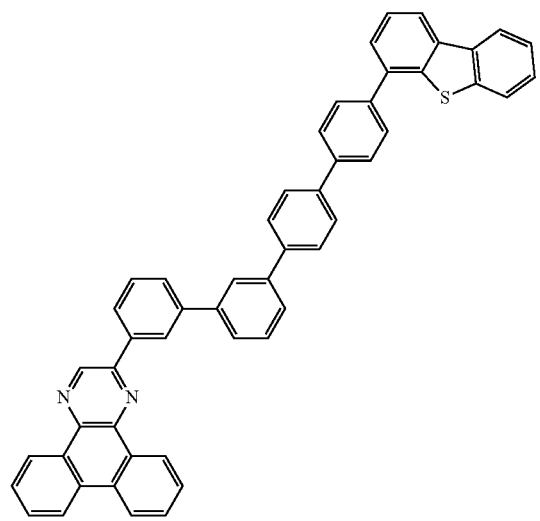
(118)
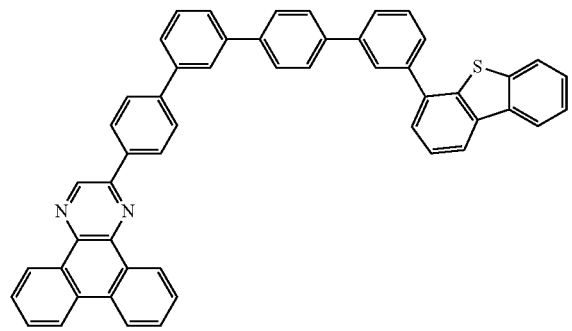
(119)
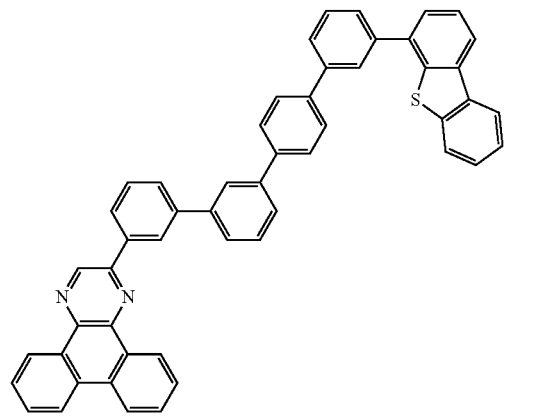

[Chemical formula 91]
(120)
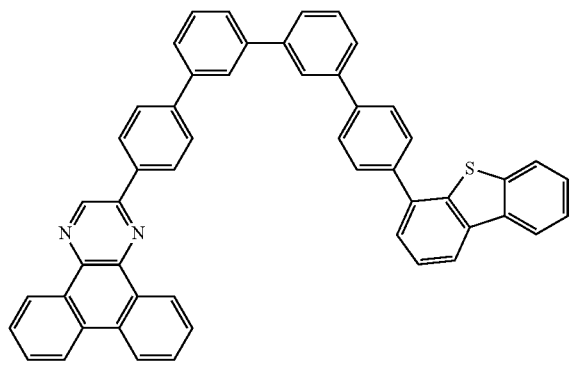
(121)
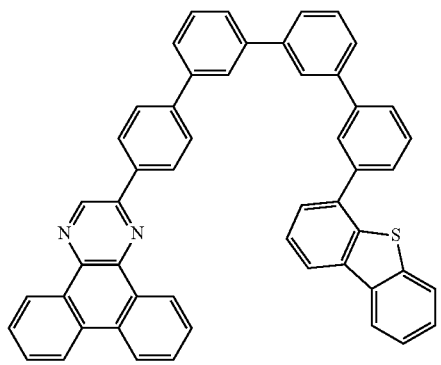
(122)
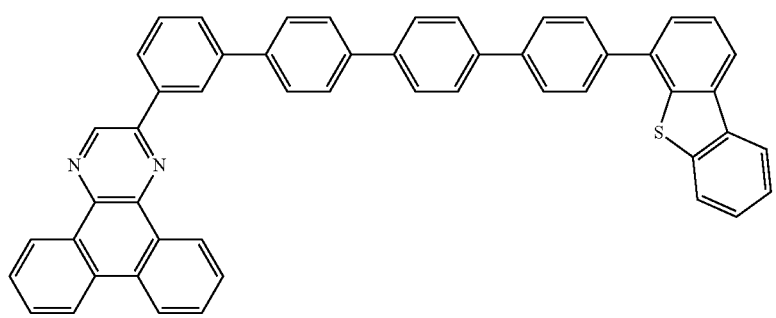
(123)
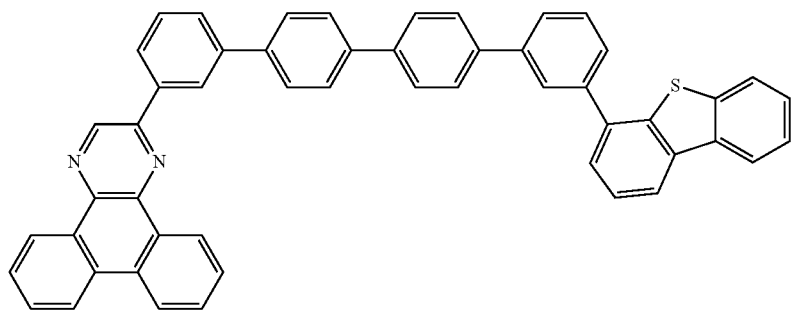
(124)
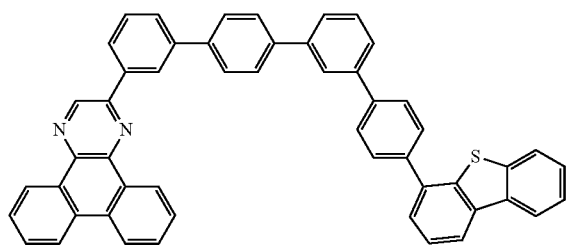
(125)
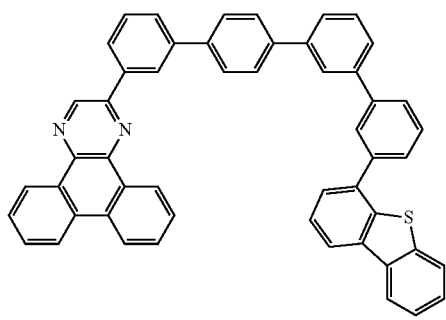

-continued
(126)
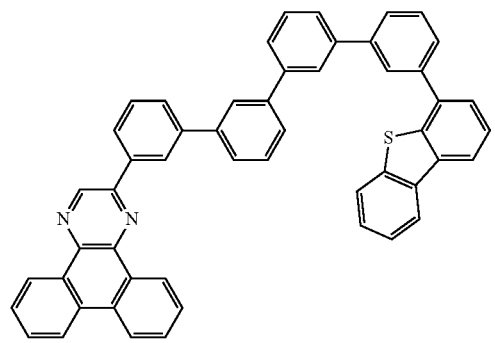
(127)
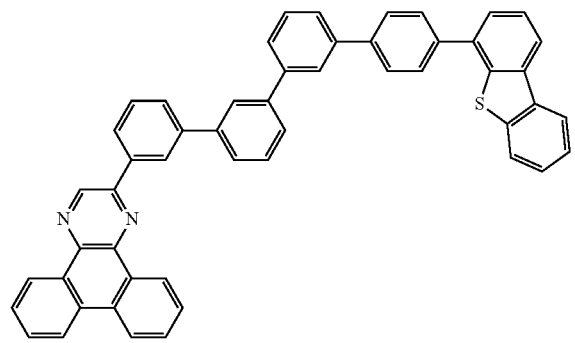
[Chemical formula 92]
(128)
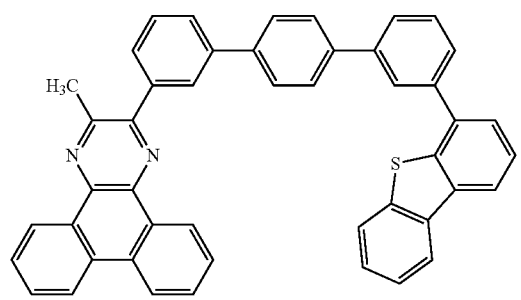
(129)
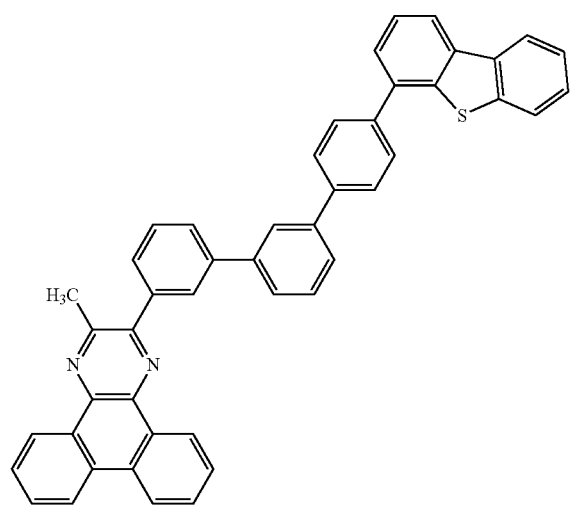
(130)
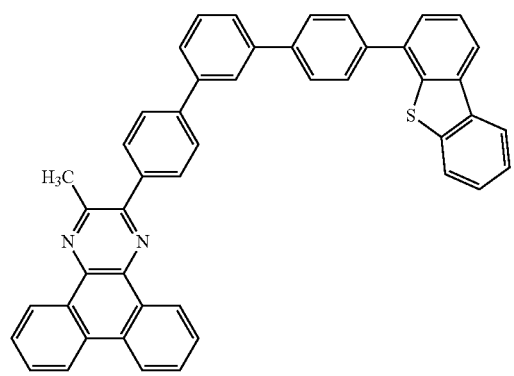
(131)
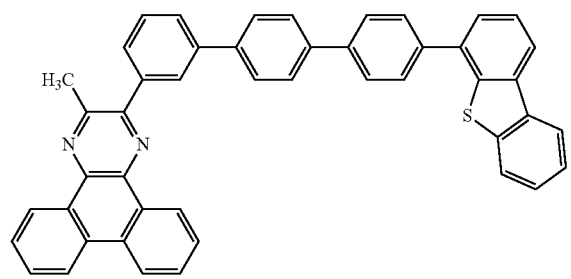

-continued
(132)
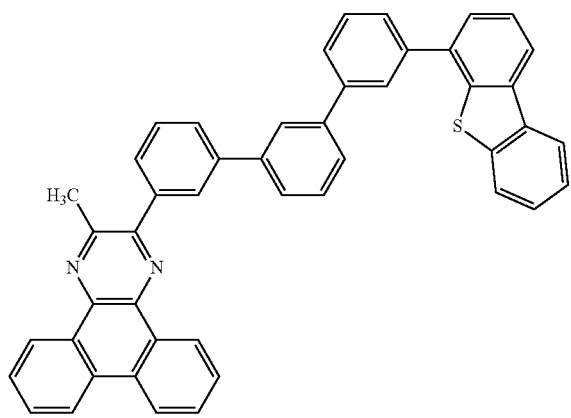
(133)
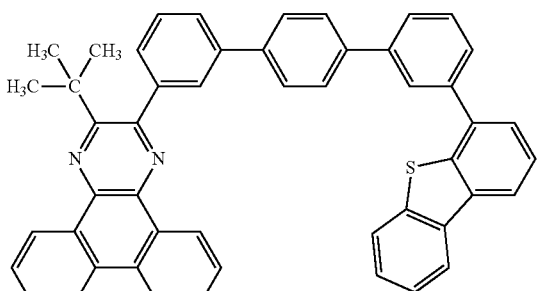
(134)
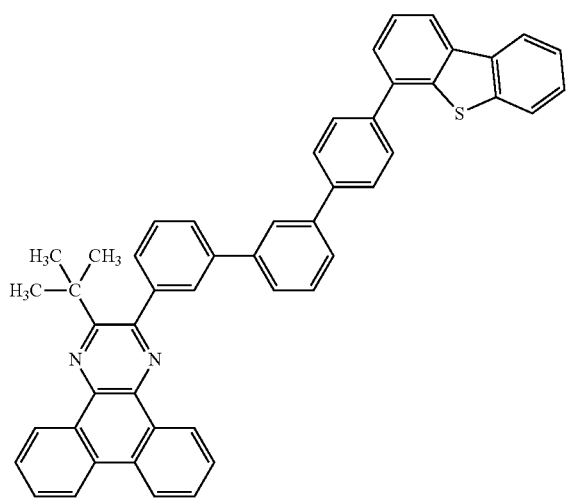
(135)
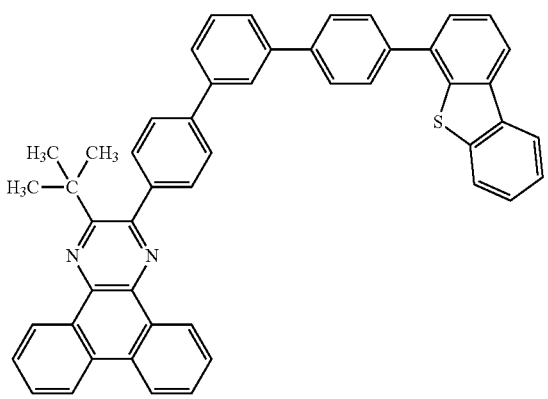
(136)
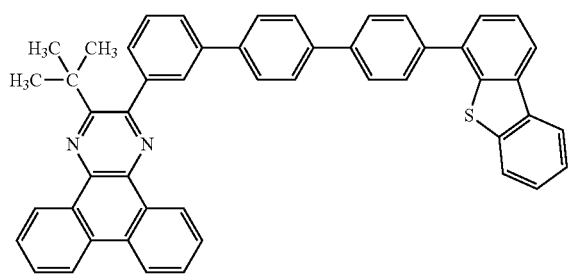
(137)
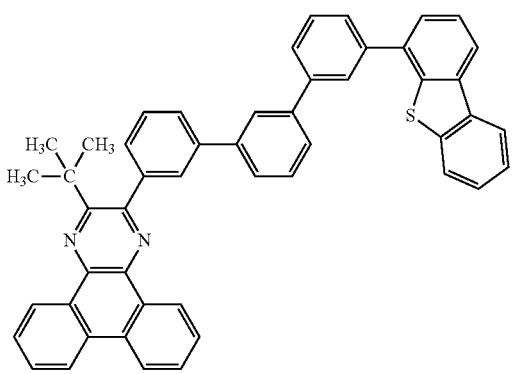

[Chemical formula 93]
(138)
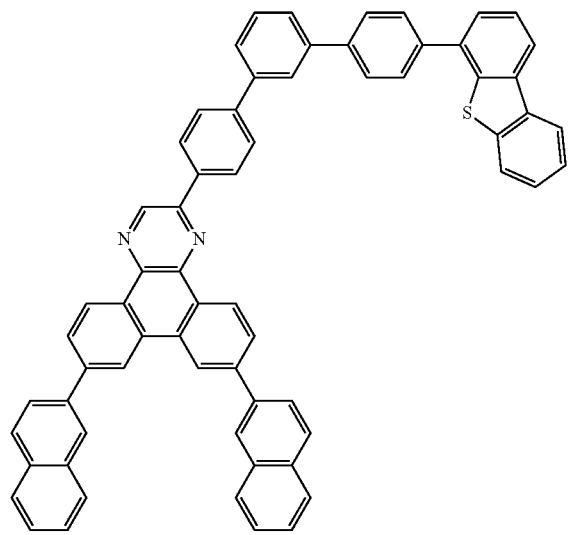
(139)
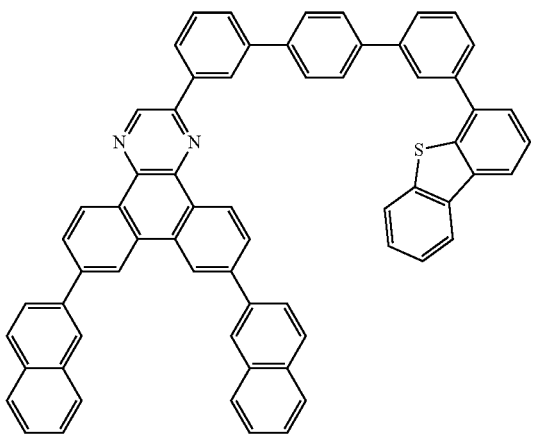
(140)
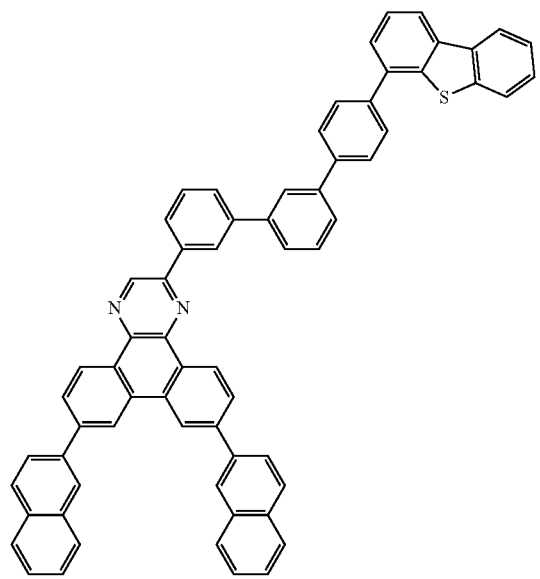
(141)
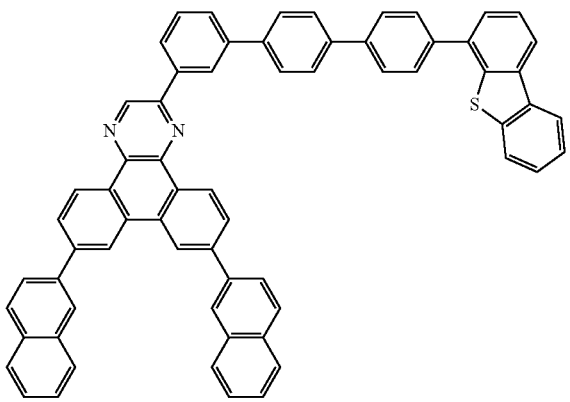

(142)
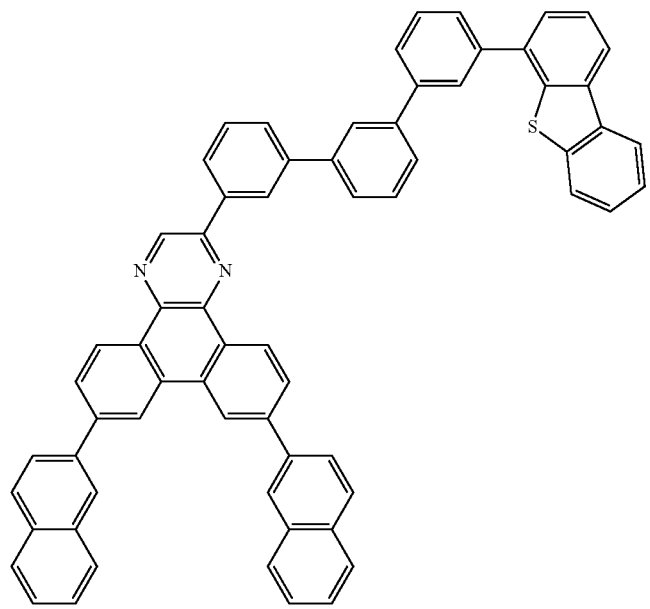
[Chemical formula 94]
(143)
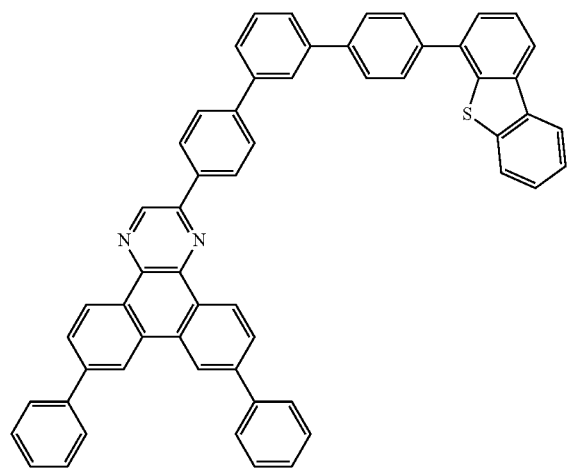
(144)
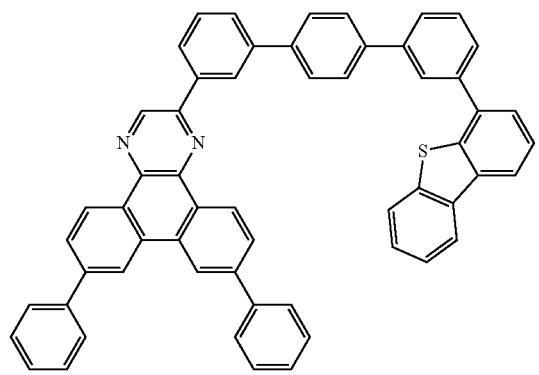
(145)
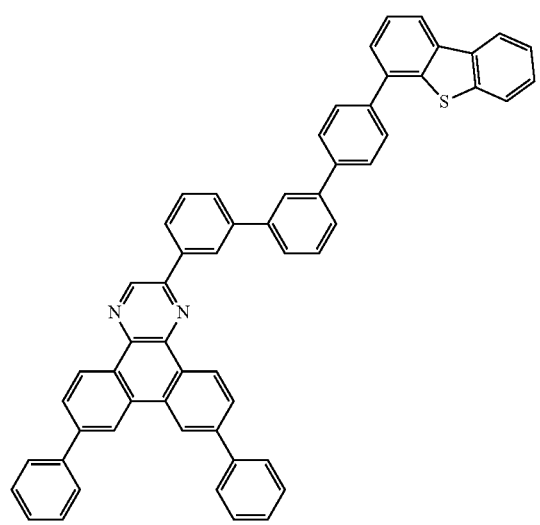
(146)
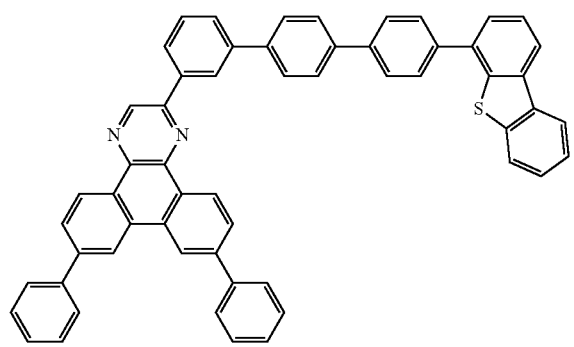

(147)
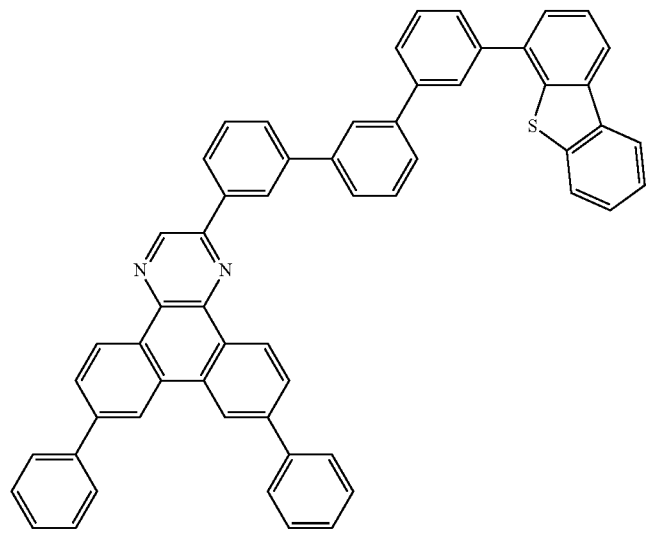
[Chemical formula 95]
(148)
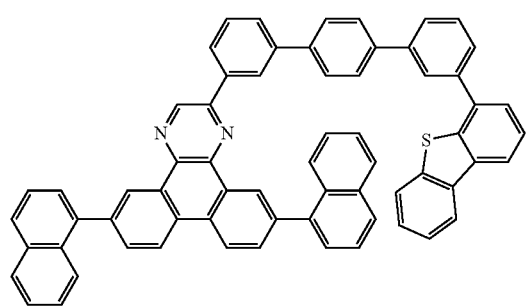
(149)
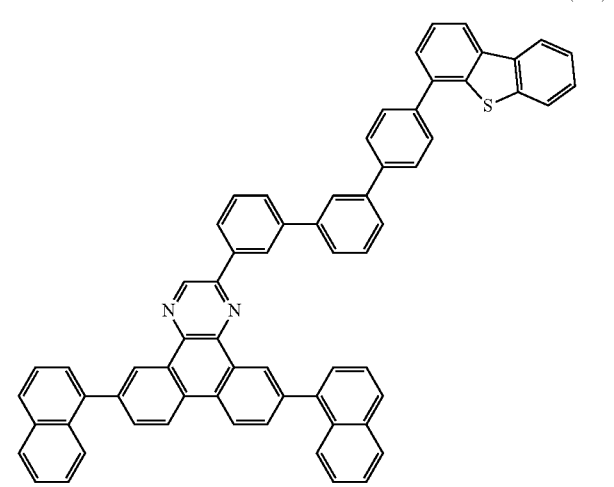
(150)
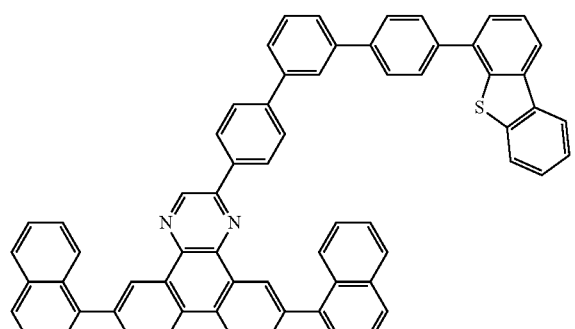
(151)
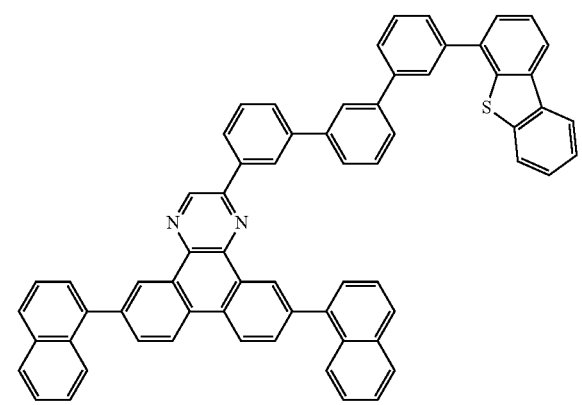

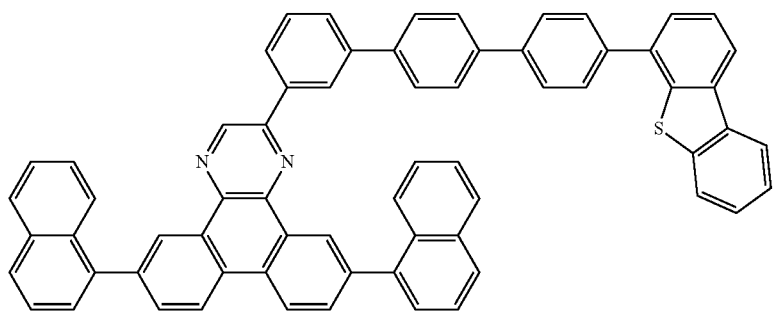
(152)
[Chemical formula 96]
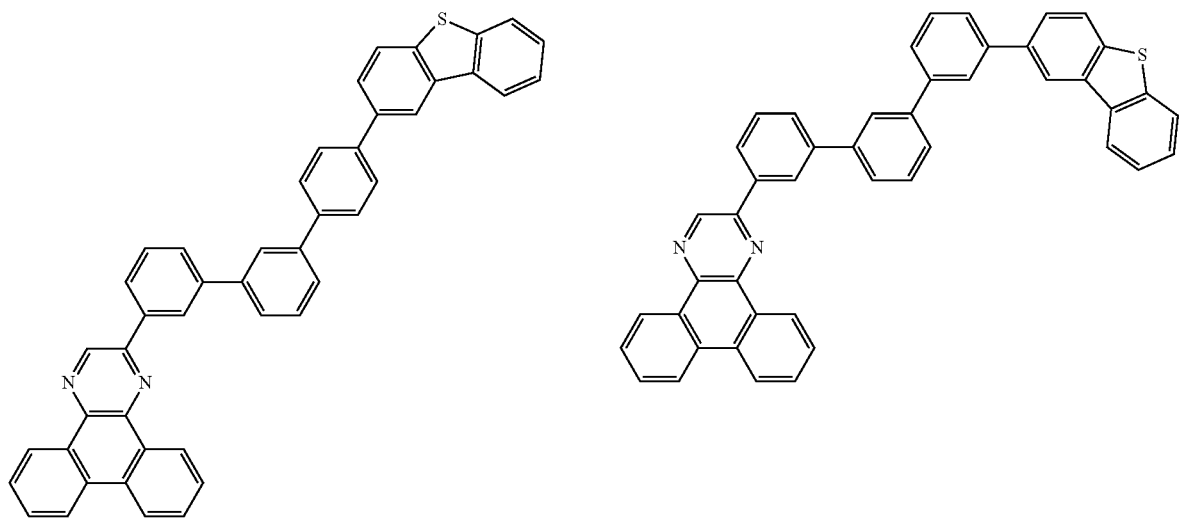
(153) (154)
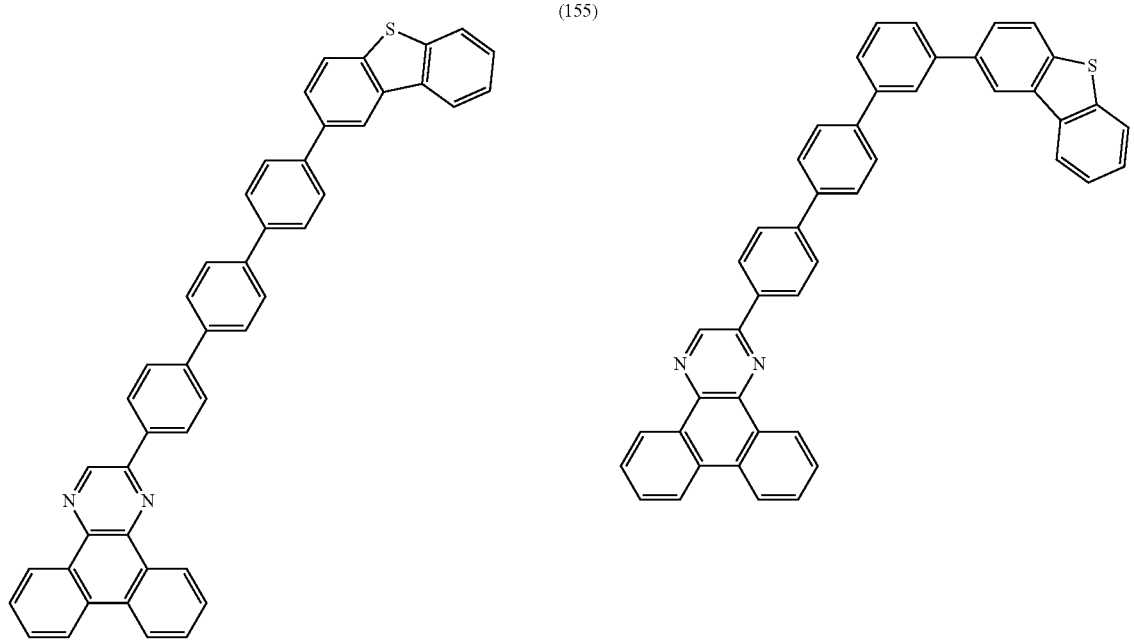
(155) (156)

(157)
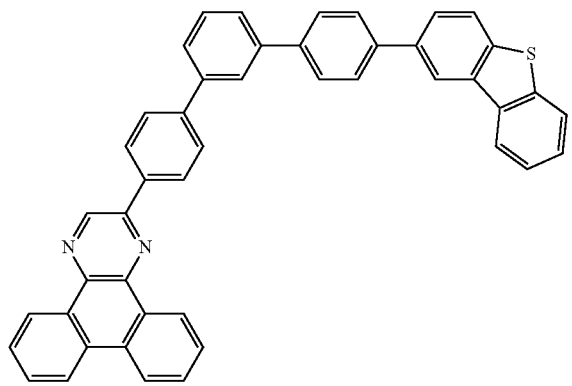
(158)
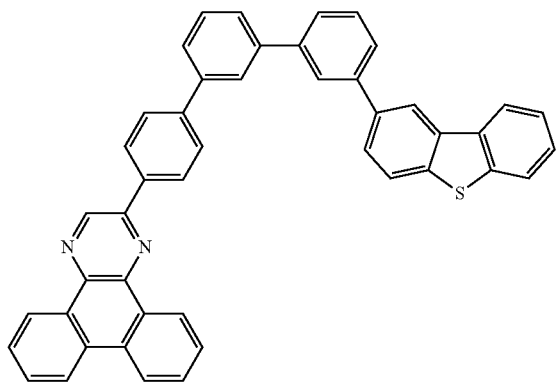
[Chemical formula 97]
(159)
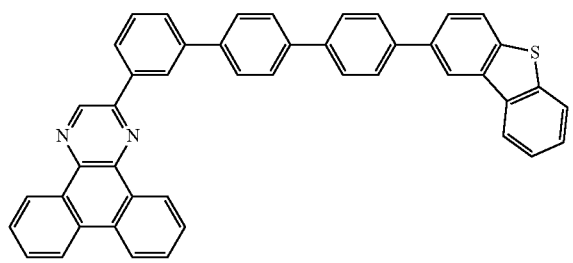
(1609
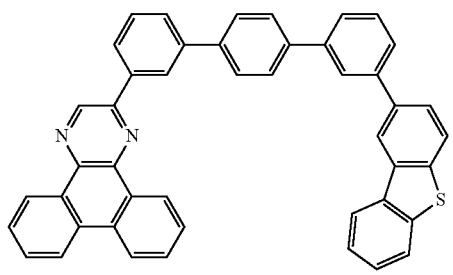
(161)
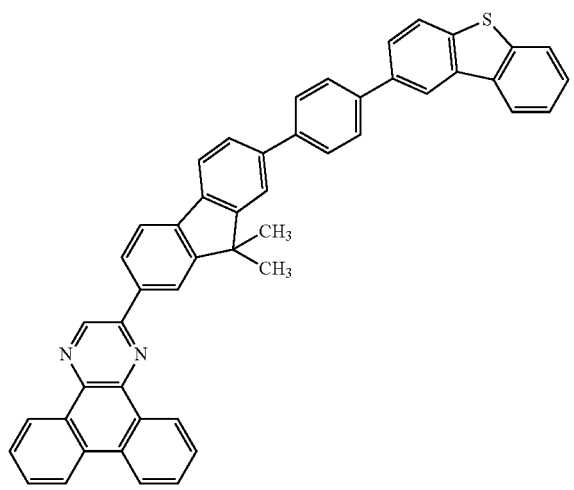
(162)
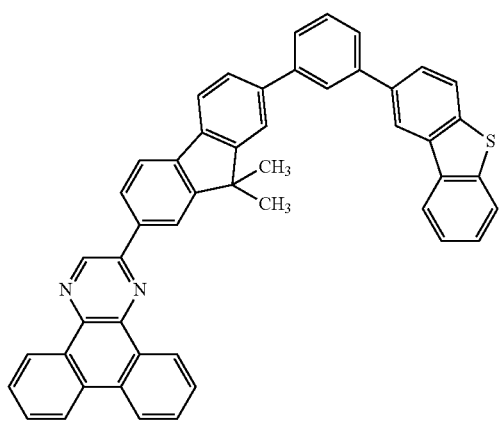

-continued
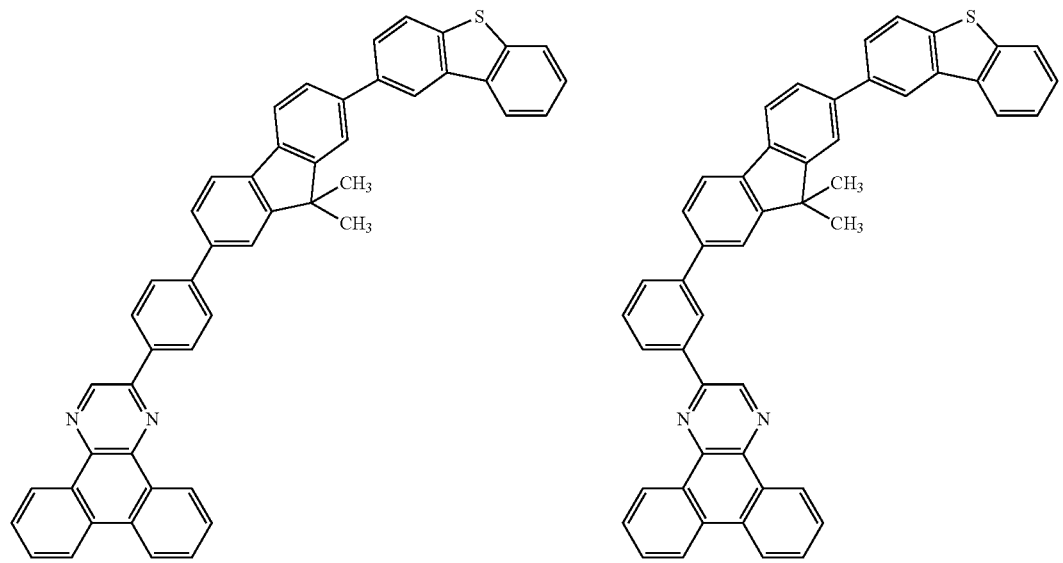
[Chemical formula 98]
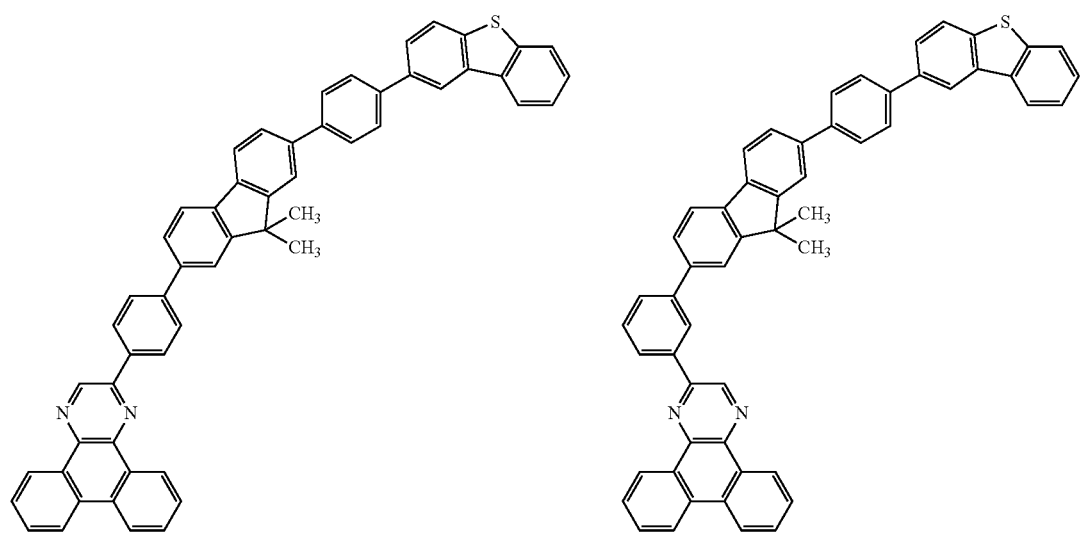

-continued
(167)
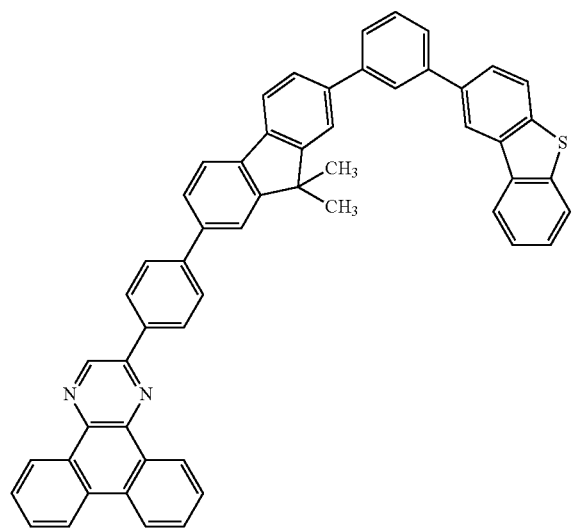
(168)
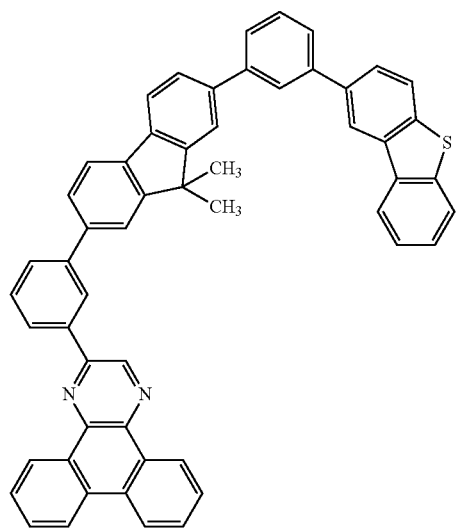
[Chemical formula 99]
(169)
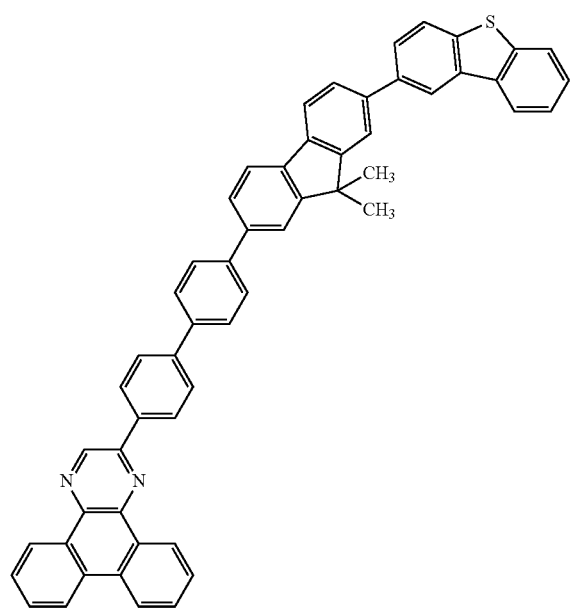
(170)
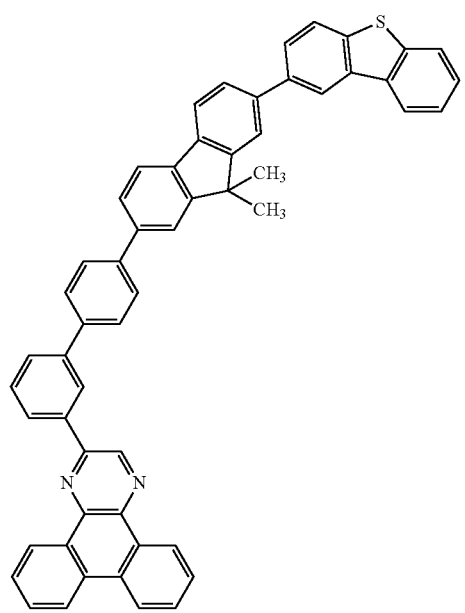
(171)
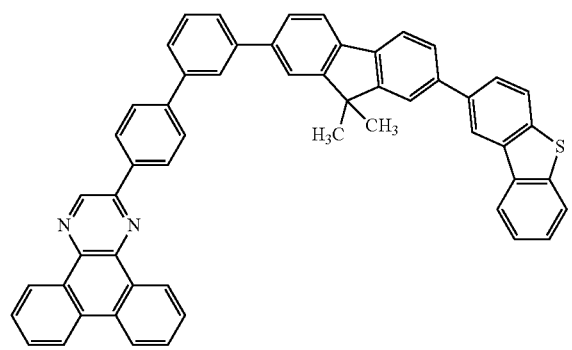
(172)
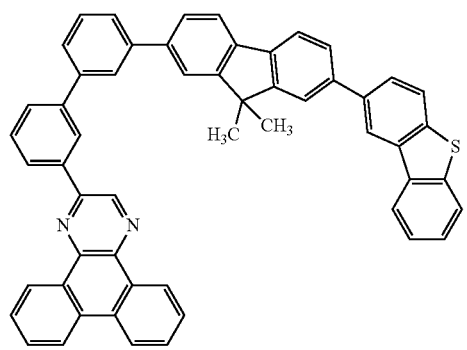

-continued
(173)
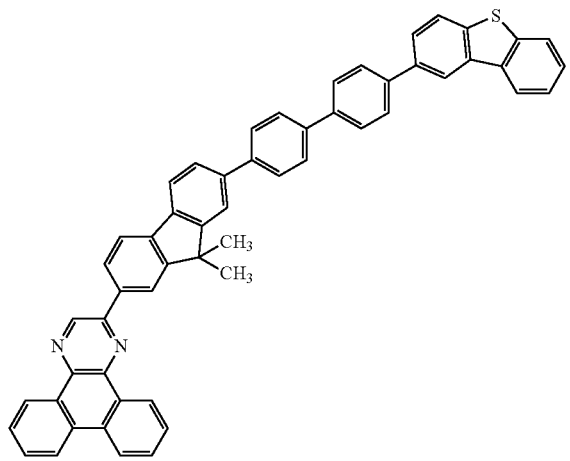
(174)
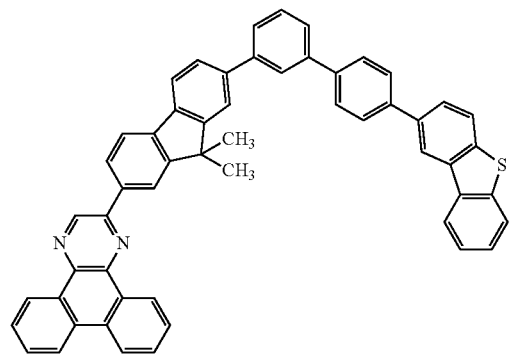
(175)
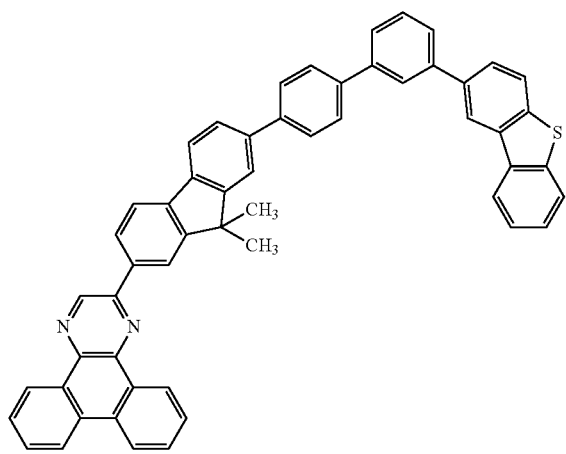
(176)
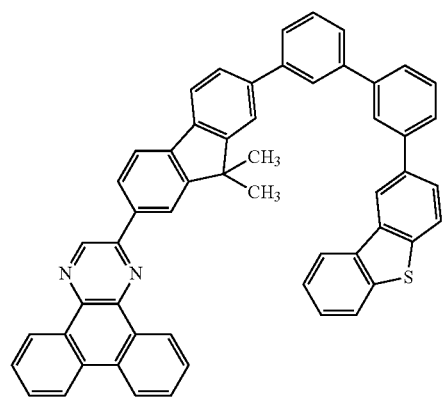
[Chemical formula 100]
(177)
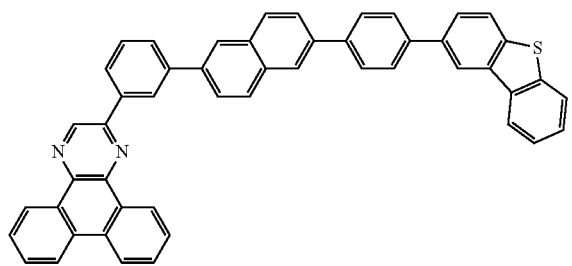
(178)
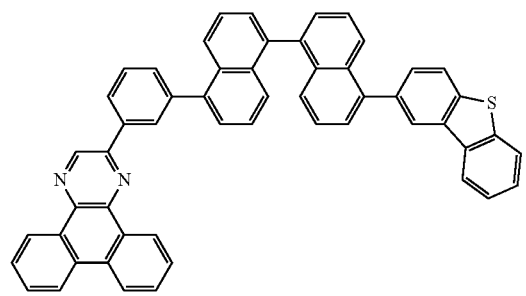

-continued
(179)
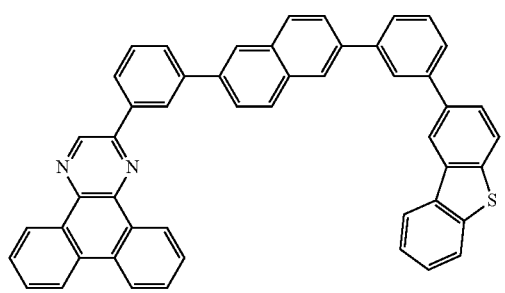
(180)
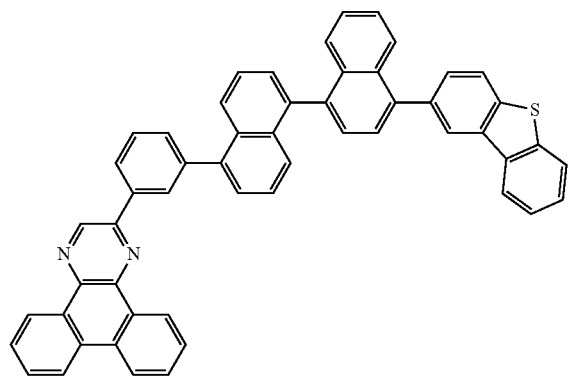
(181)
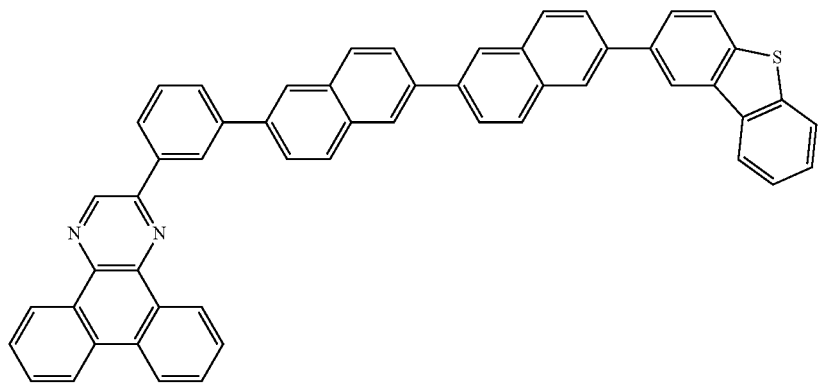
(182)
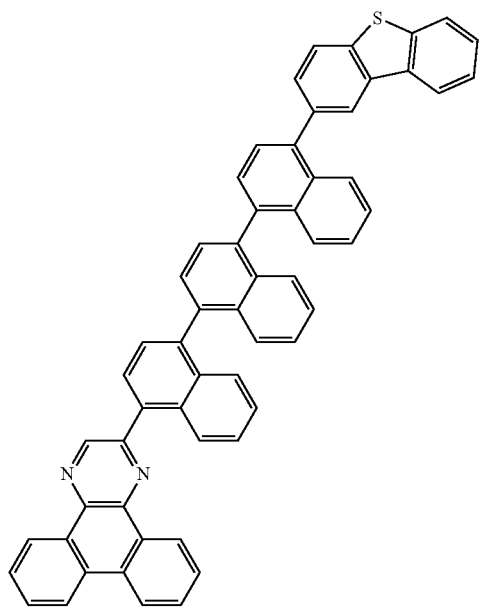
(183)
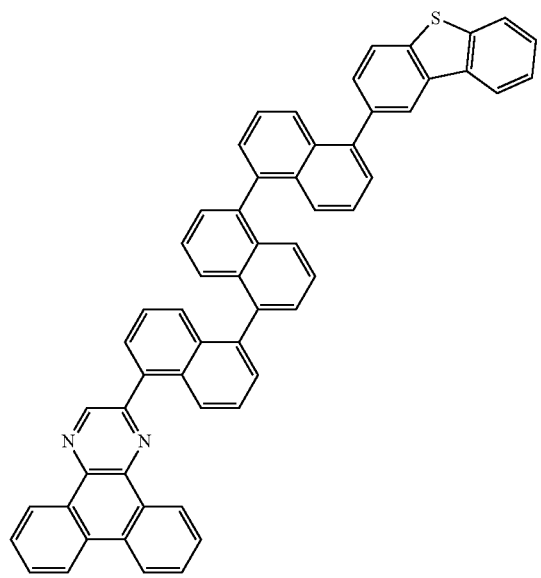

-continued
(184)
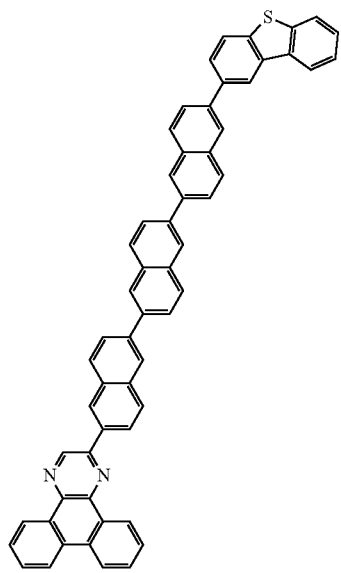
(185)
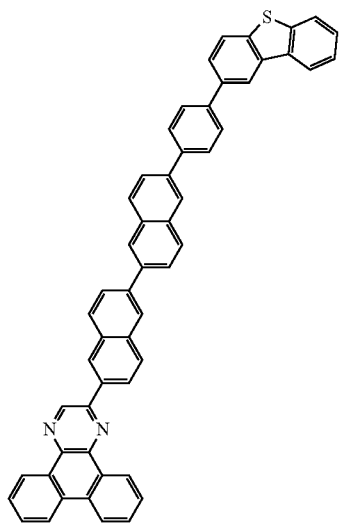
[Chemical formula 101]
(186)
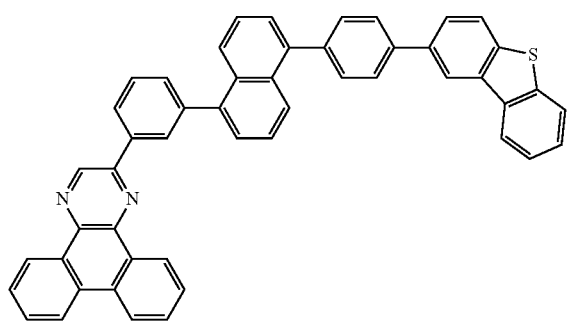
(187)
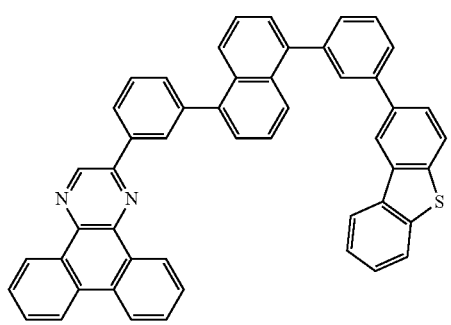
(188)
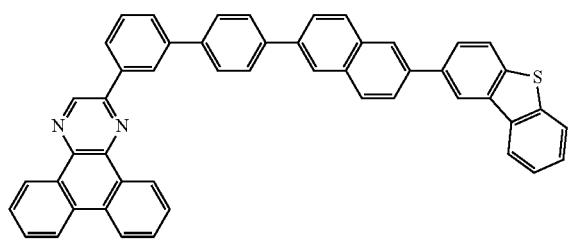
(189)
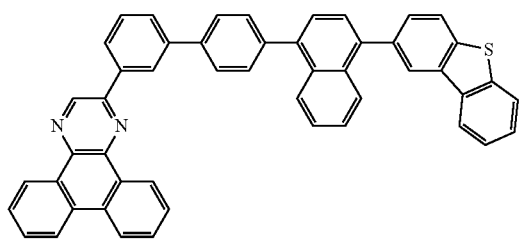
(190)
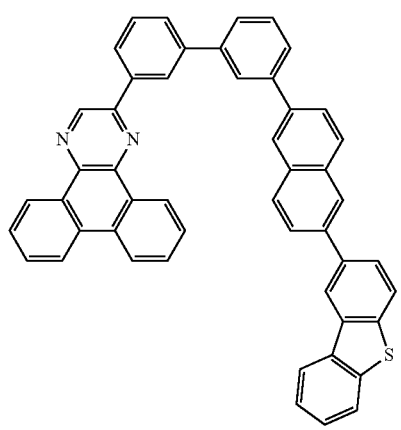
(191)
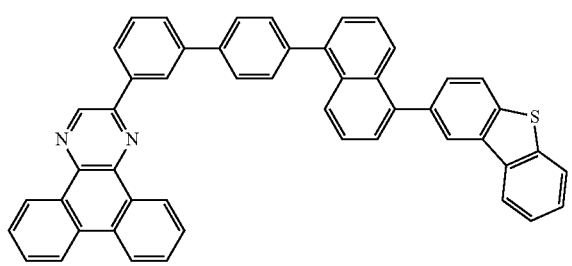

-continued
(192)
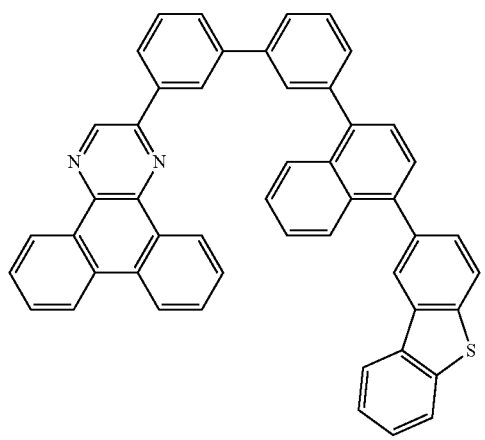
(193)
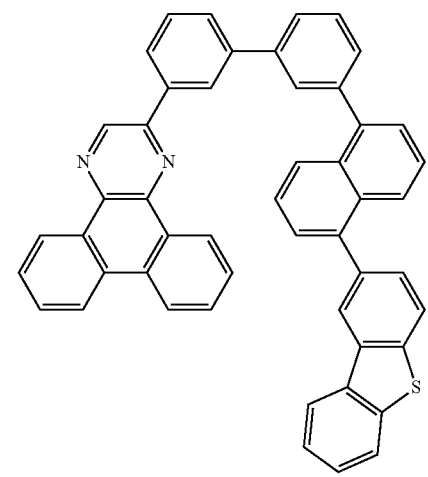
[Chemical formula 102]
(194)
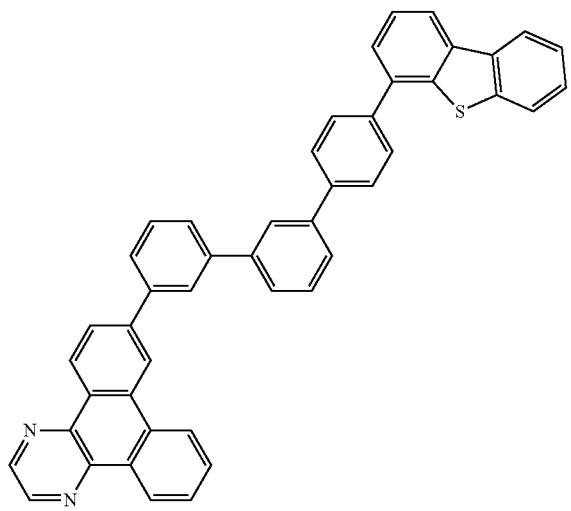
(195)
(196)
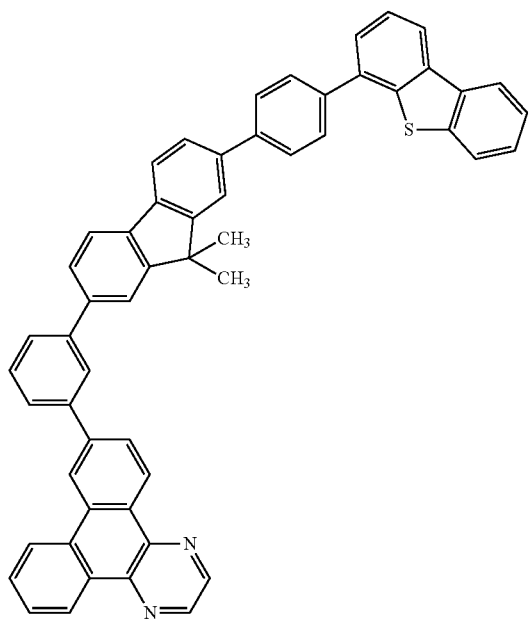
(197)
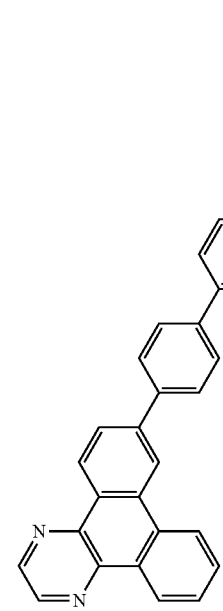

-continued
(198)
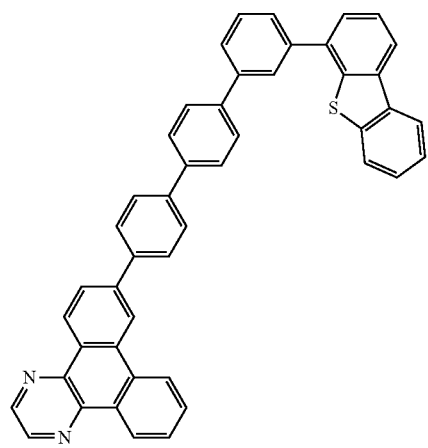
(199)
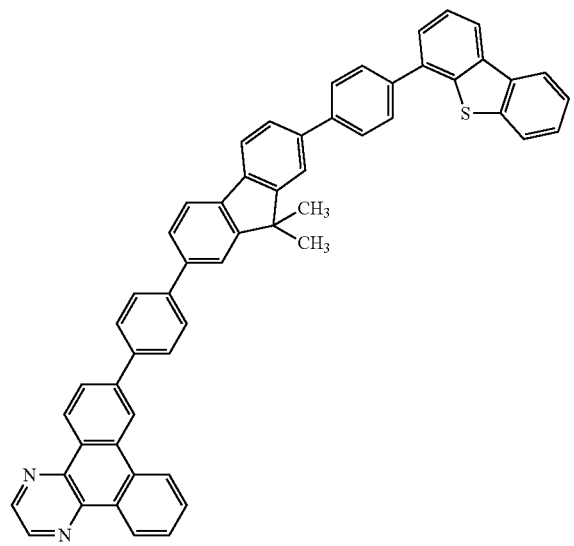
(200)
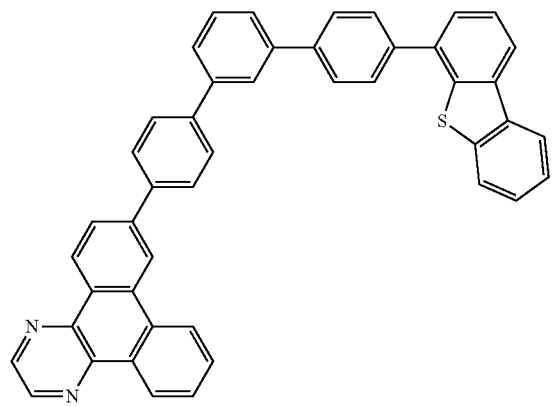
(201)
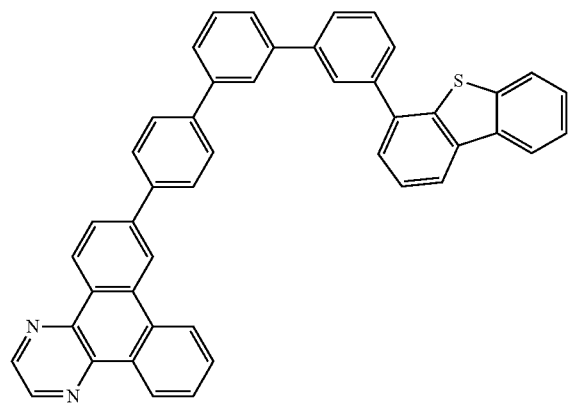
(202)
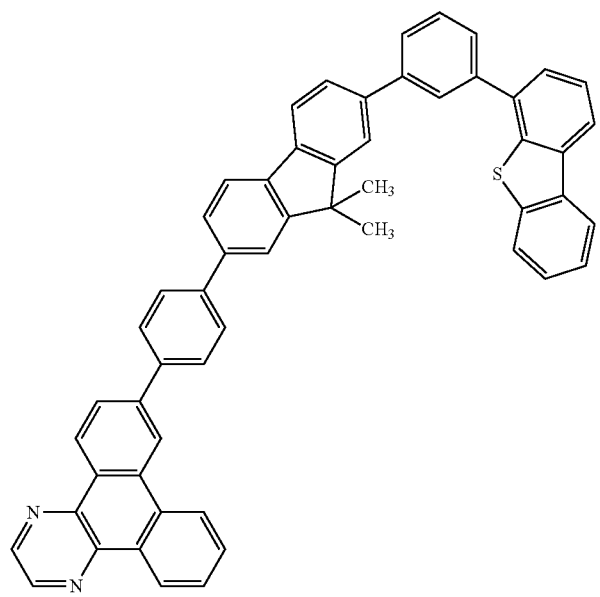

[Chemical formula 103]
(203)
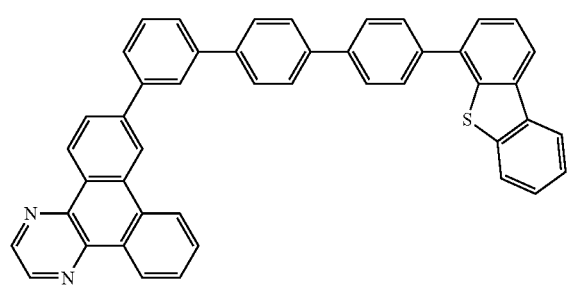
(204)
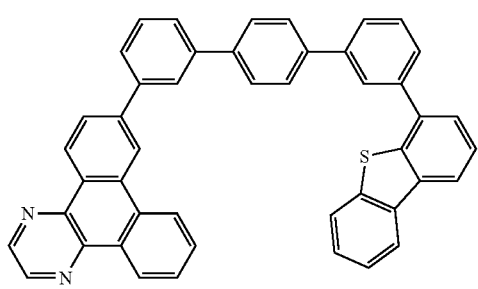
(205)
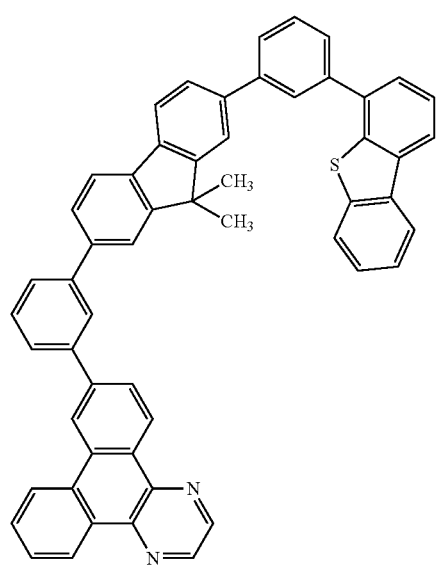
(206)
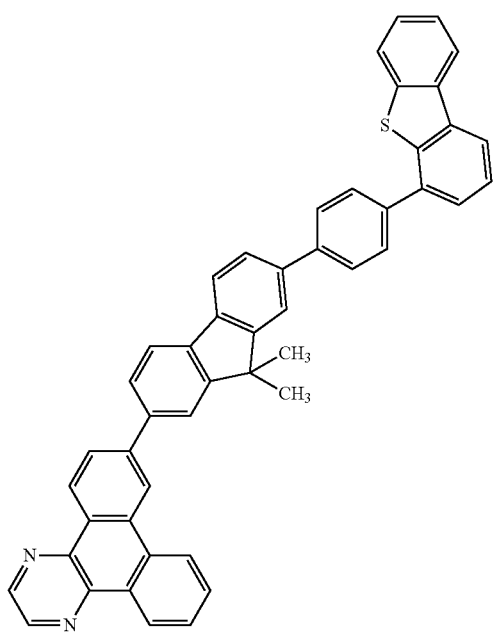
(207)
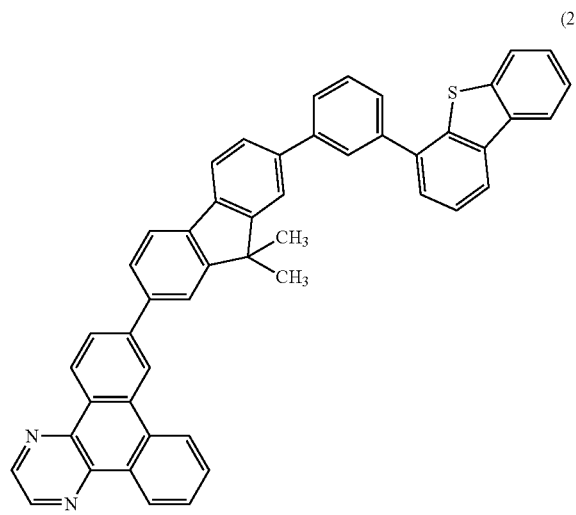
(208)
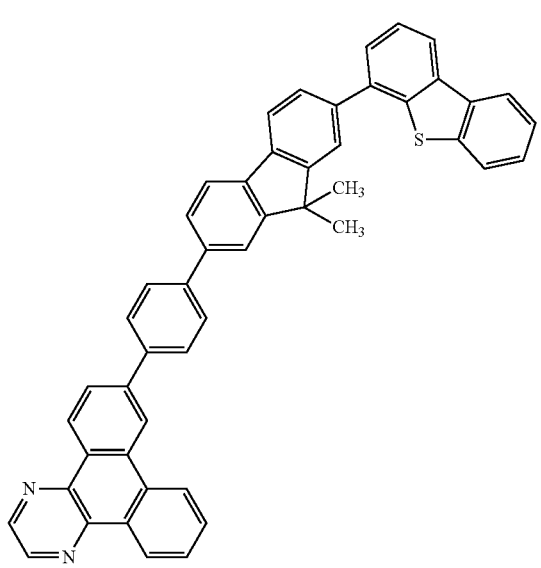

(209)
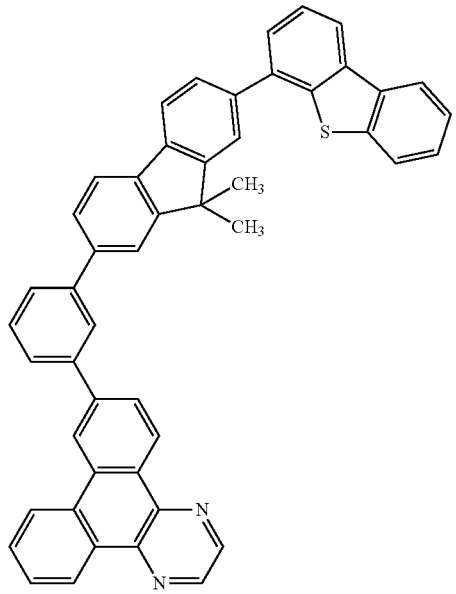
[Chemical formula 104]
(210)
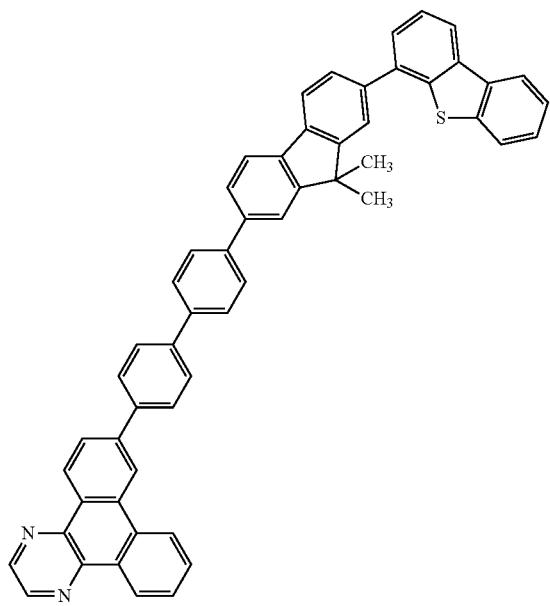
(211)
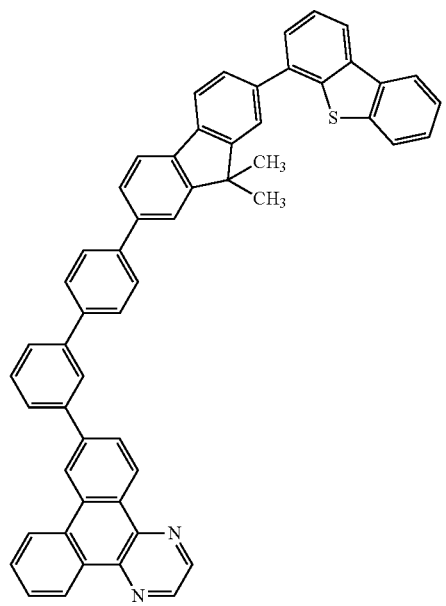
(212)
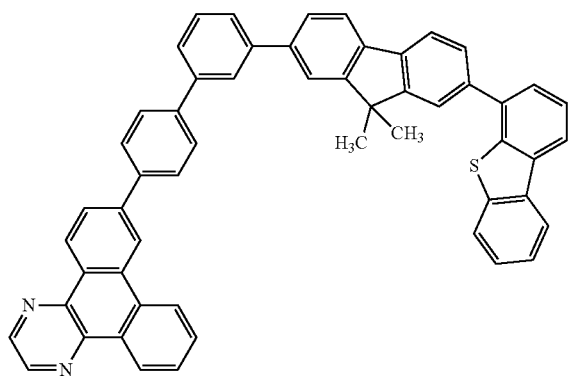
(213)
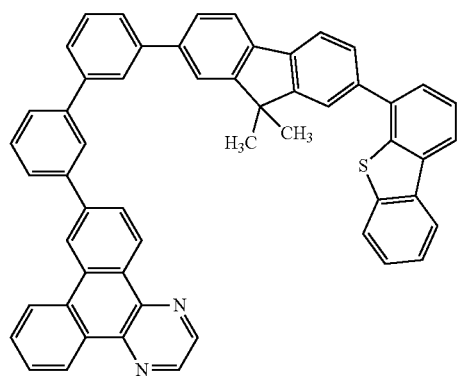

-continued
(214)
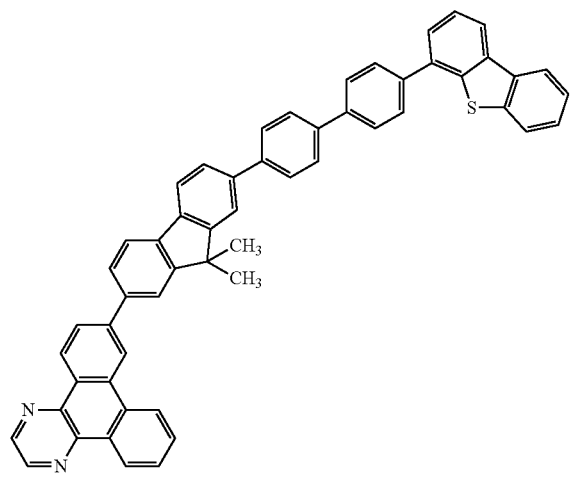
(215)
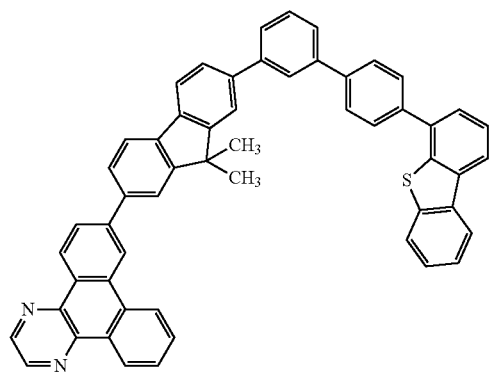
(216)
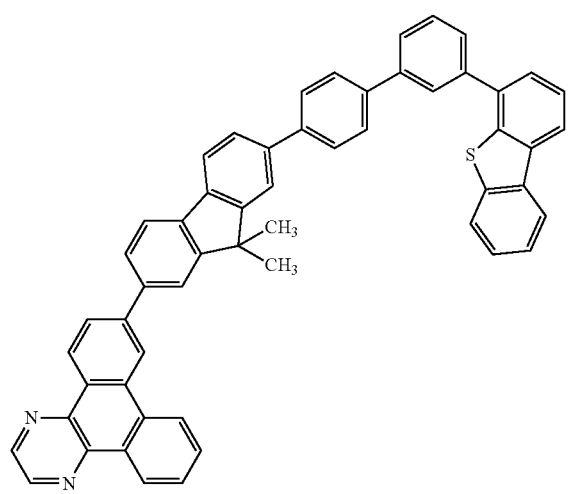
(217)
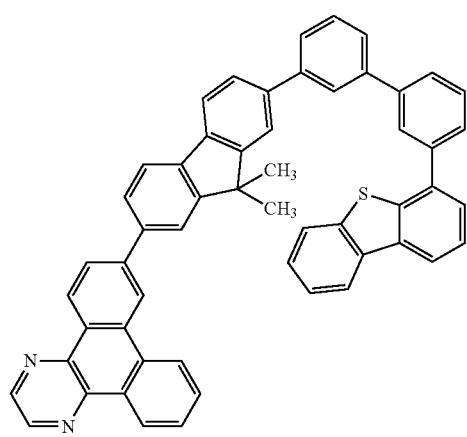
[Chemical formula 105]
(218)
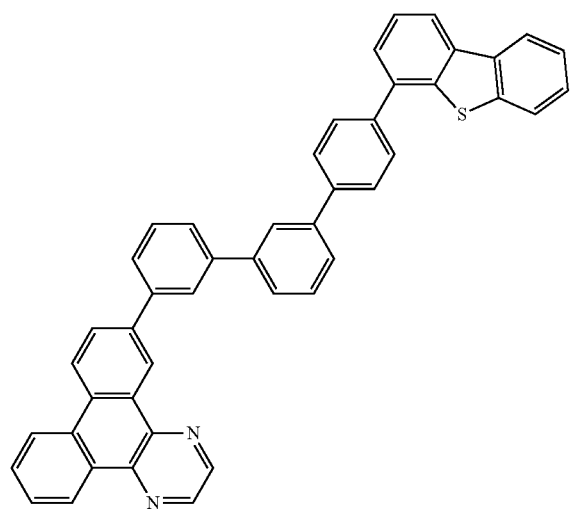
(219)
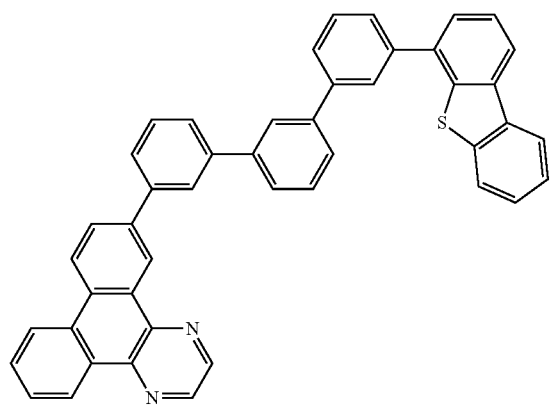

-continued
(220)
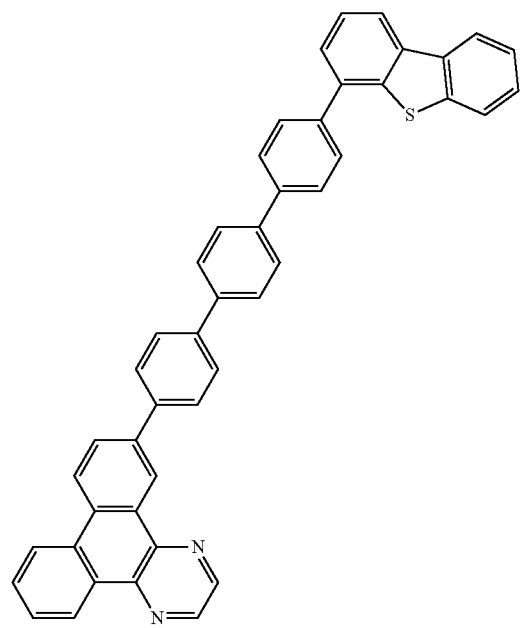
(221)
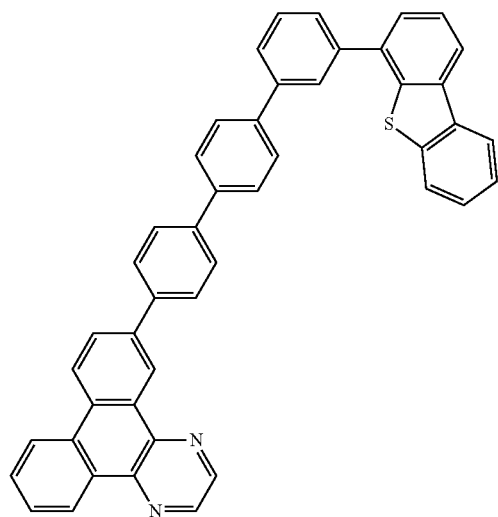
(222)
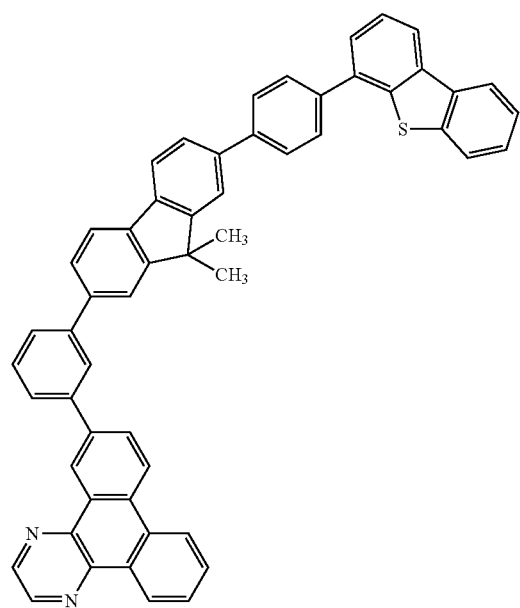
(223)

-continued
(224)
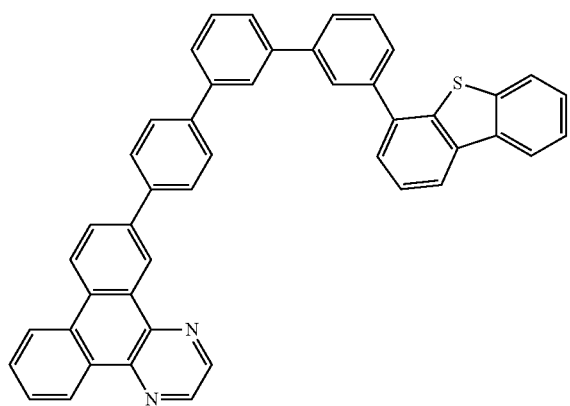
(225)
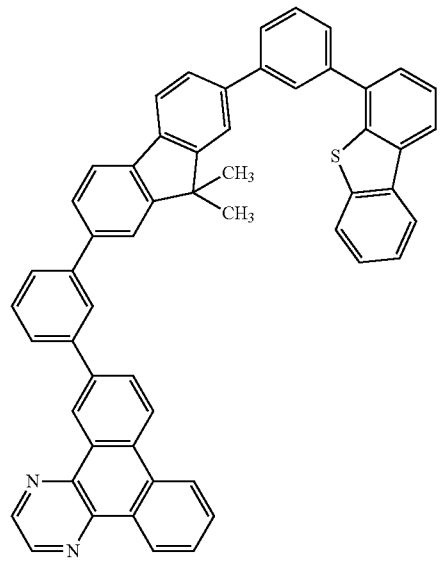
(226)
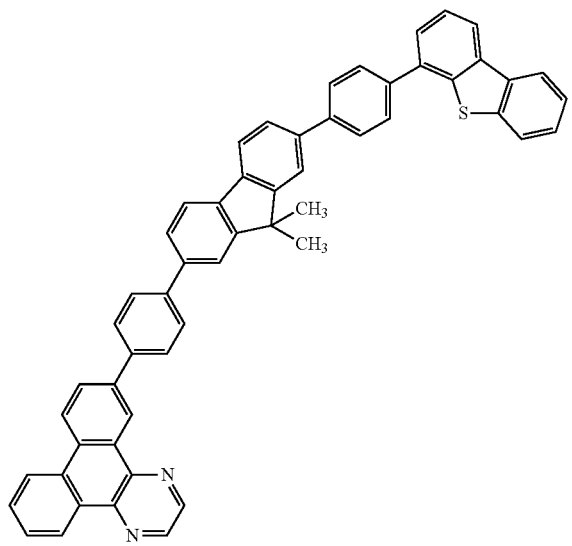
(227)
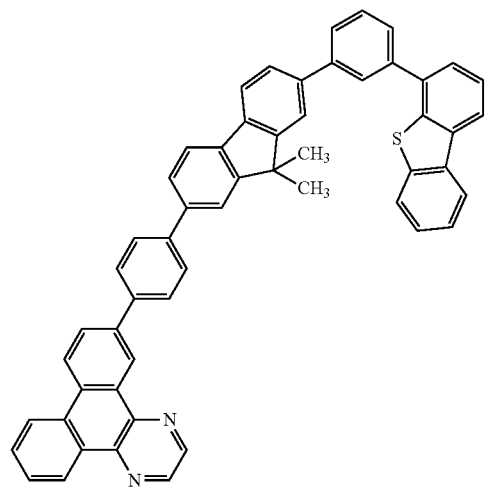
[Chemical formula 106]
(228)
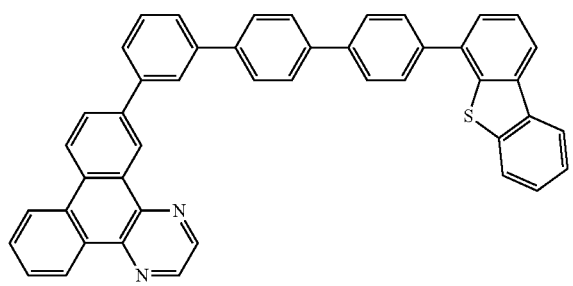
(229)
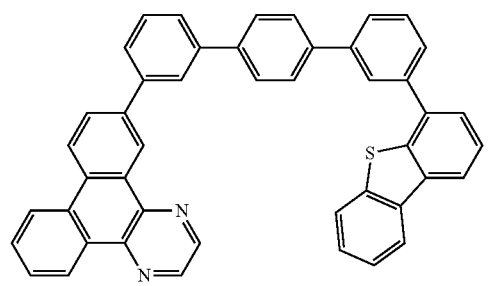

-continued
(230)
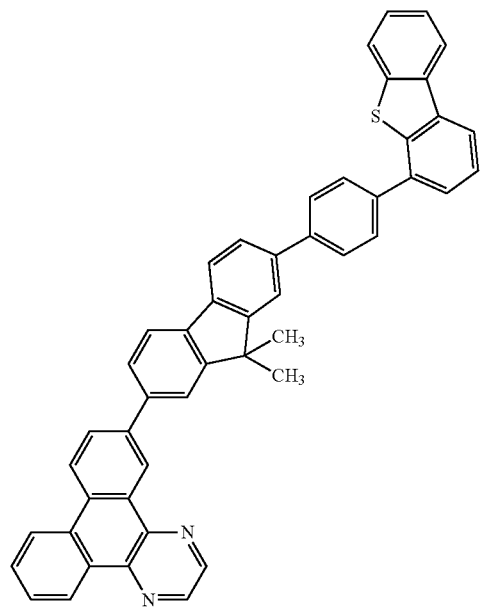
(231)
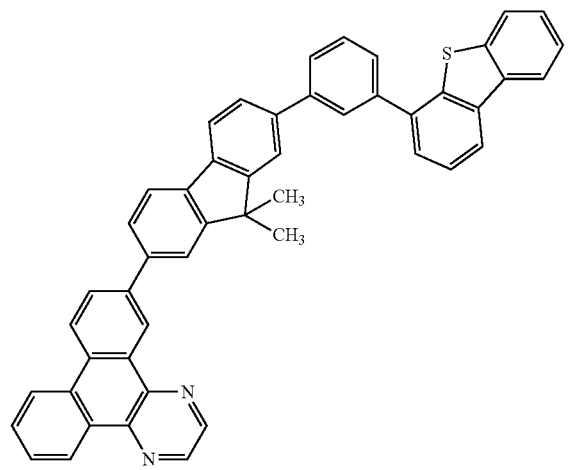
(232)
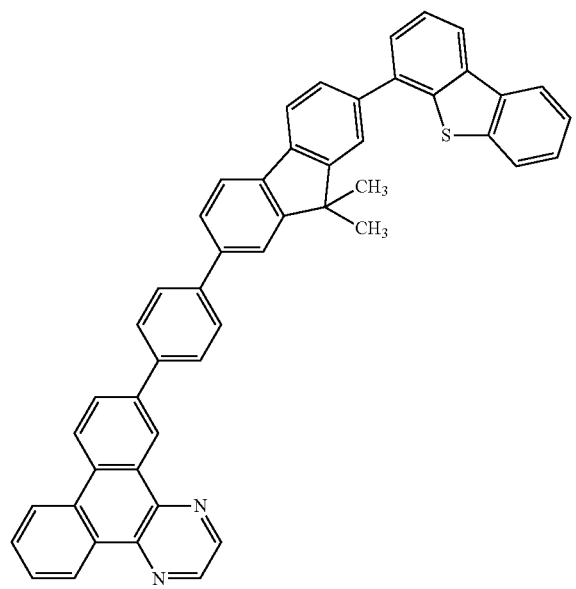
(233)
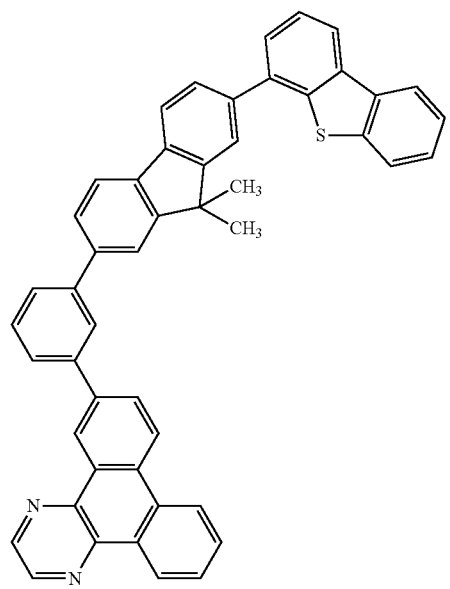

[Chemical formula 107]
(234)
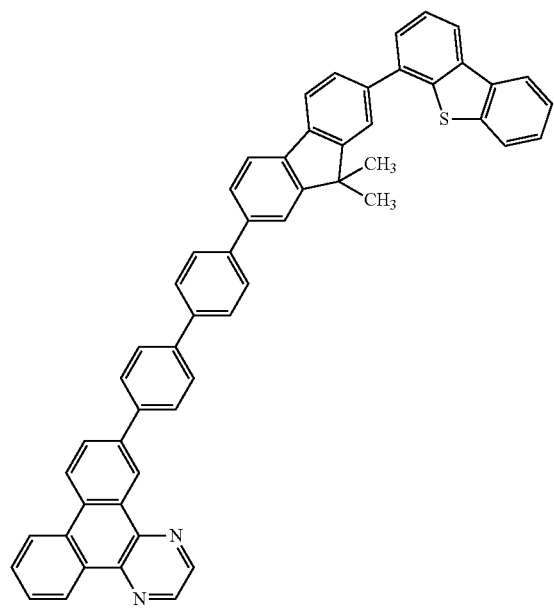
(235)
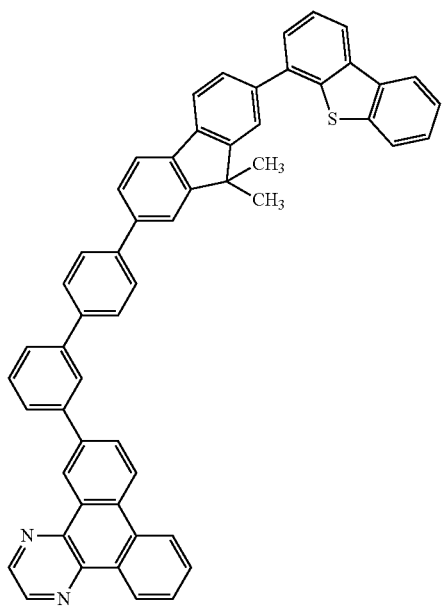
(236)
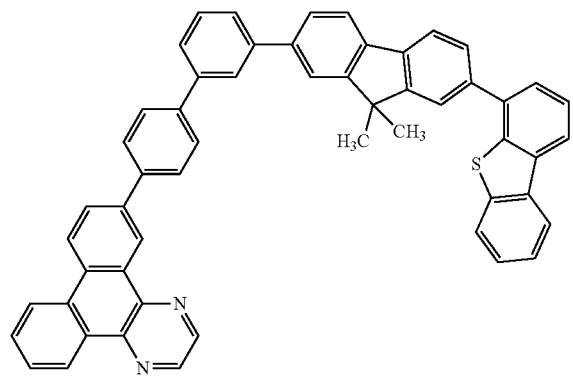
(237)
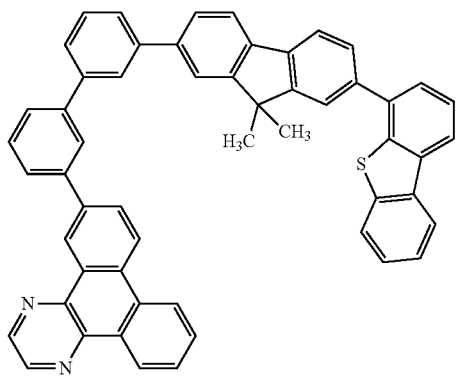
(238)
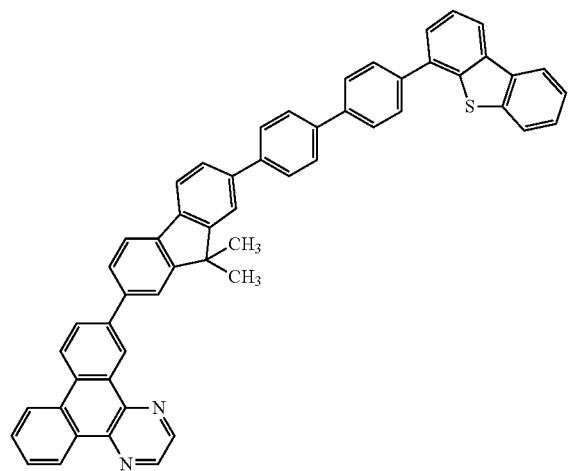
(239)
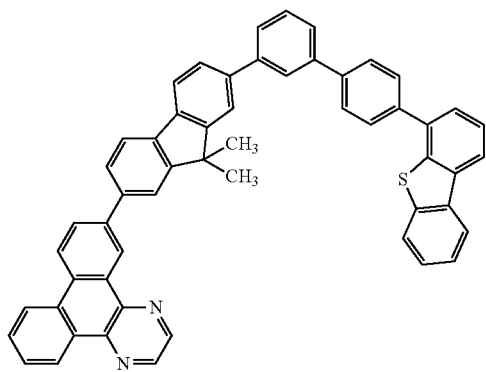

-continued
(240)
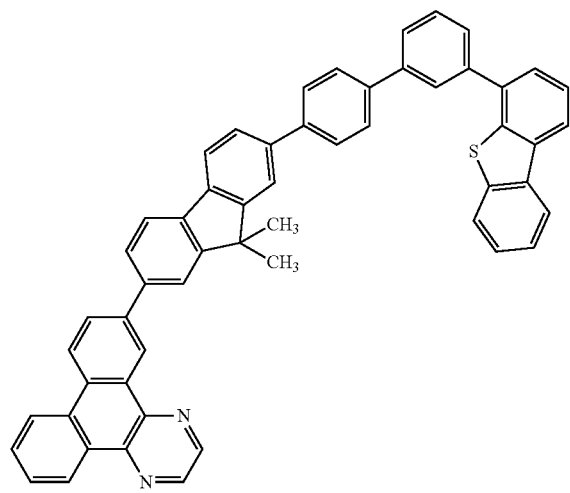
(241)
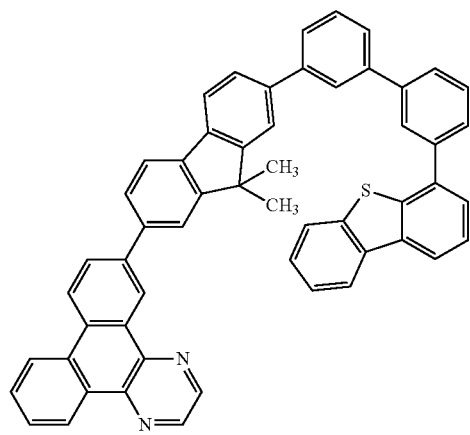
[Chemical formula 108]
(242)
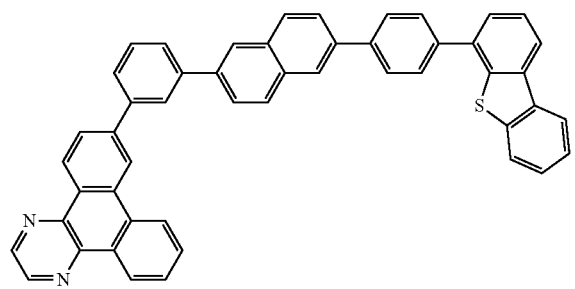
(243)
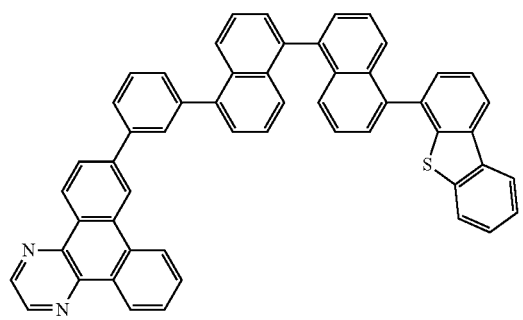
(244)
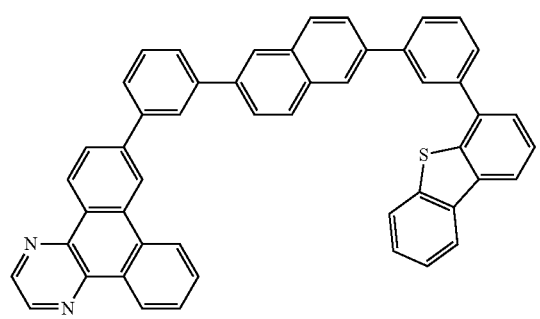
(245)
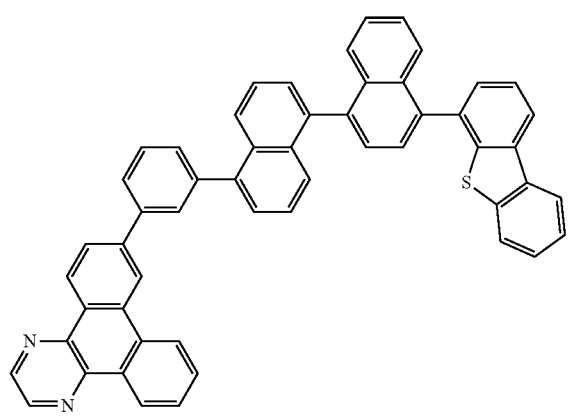

-continued
(246)
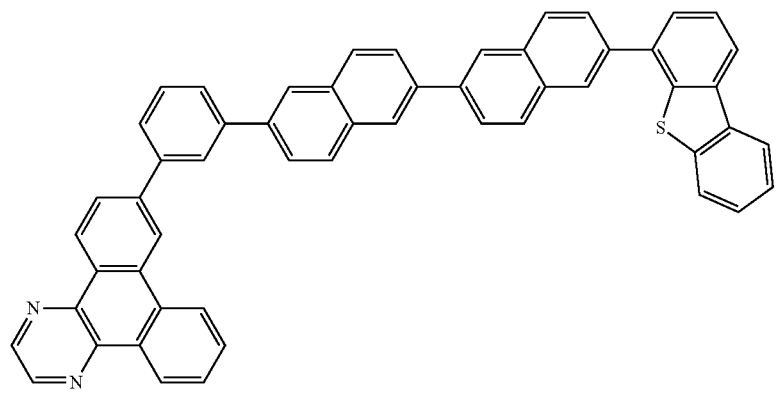
(247)
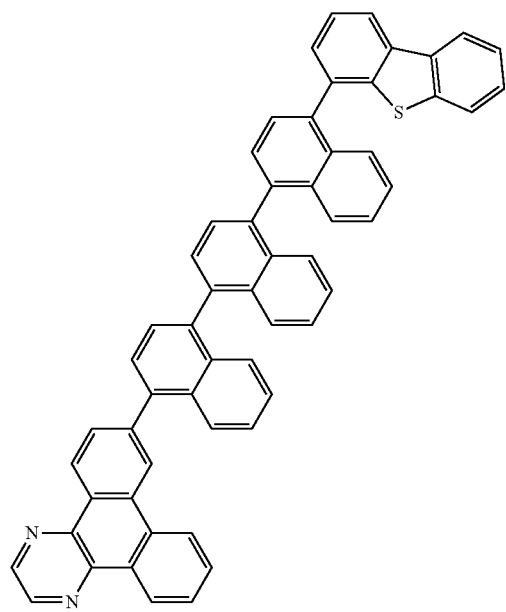
(248)
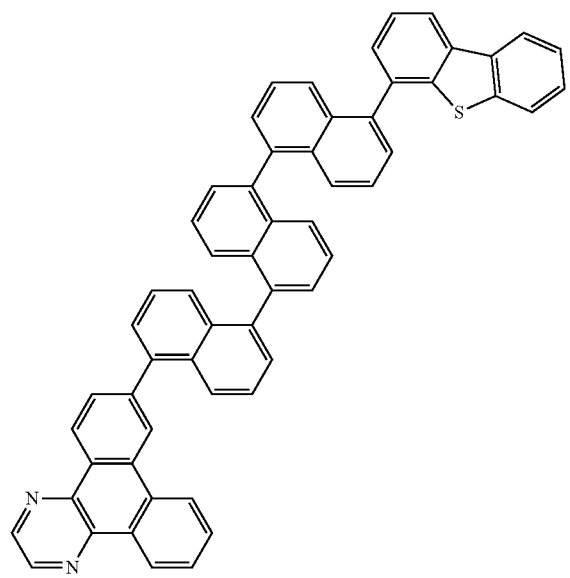
(249)
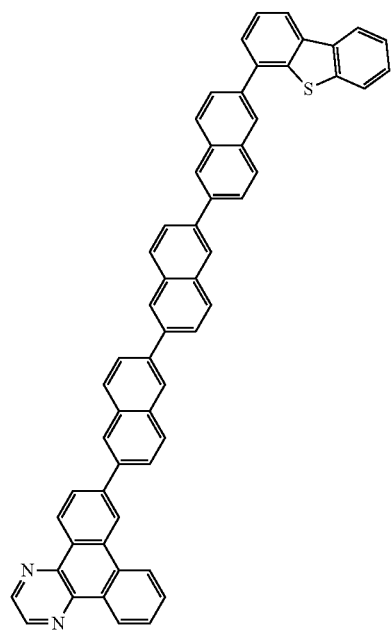
(250)
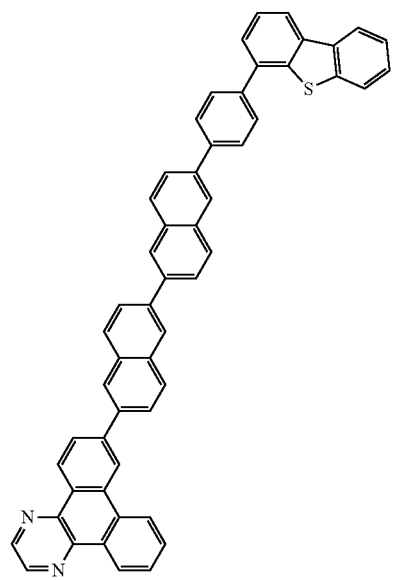

[Chemical formula 109]
(251) 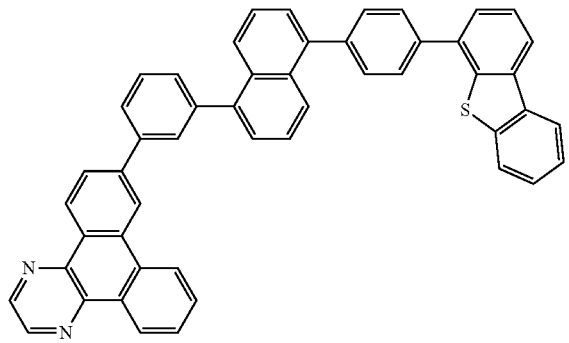
(252) 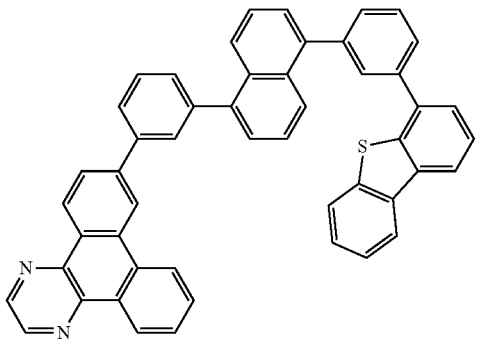
(253) 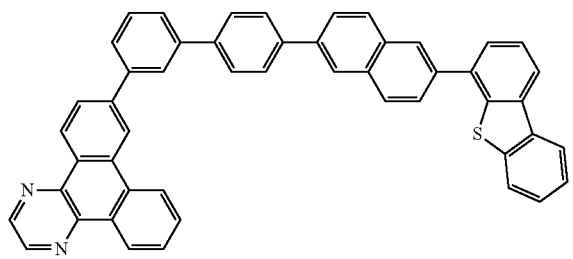
(254) 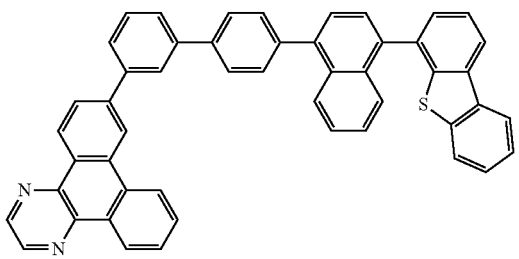
(255) 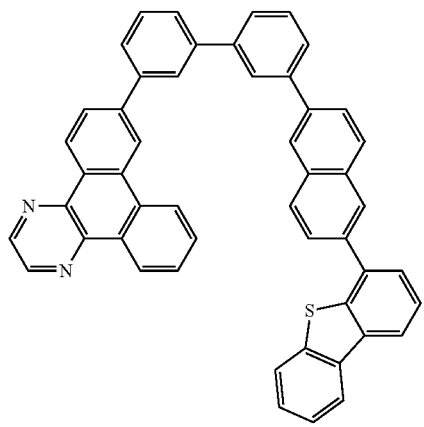
(256) 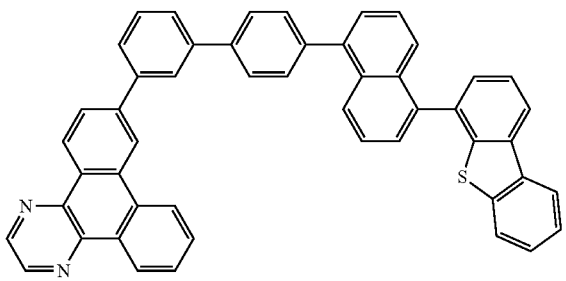
(257) 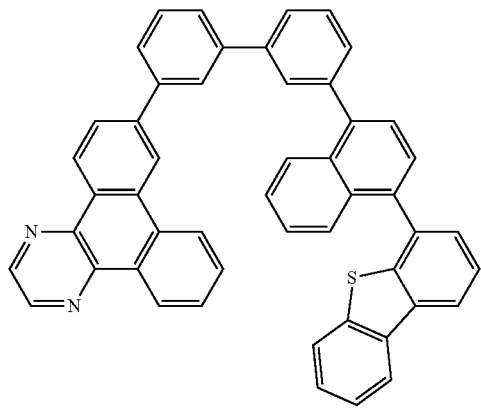
(258) 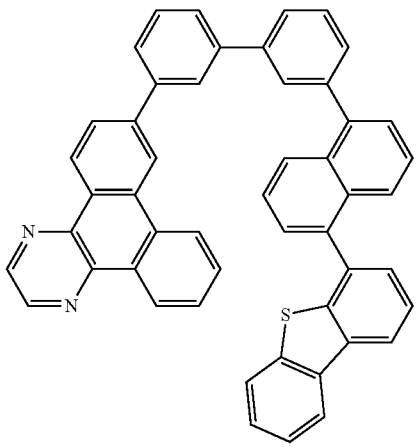

[Chemical formula 110]
(259)
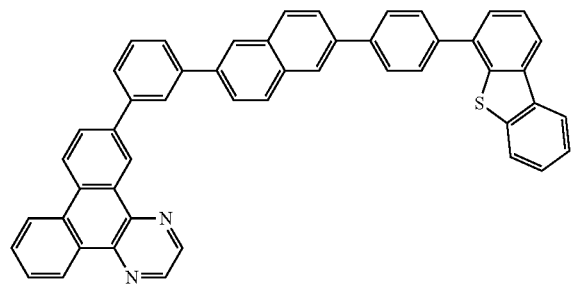
(260)
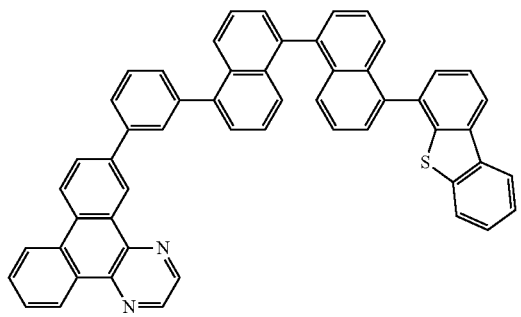
(261)
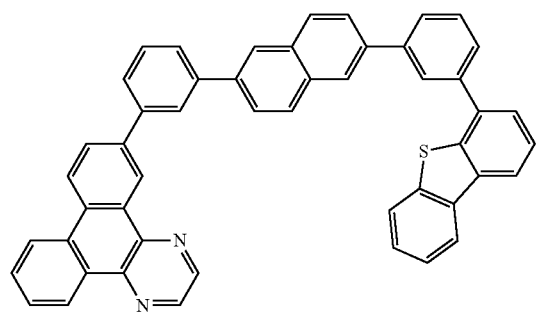
(262)
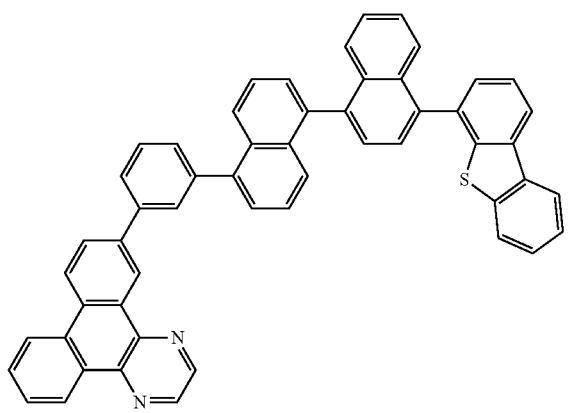
(263)
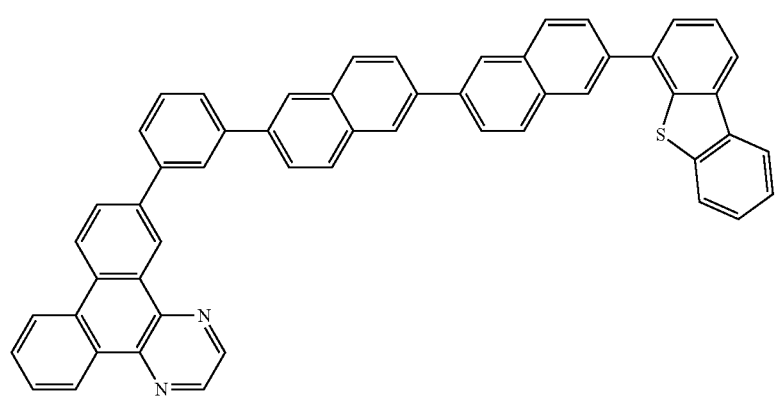

-continued
(264)
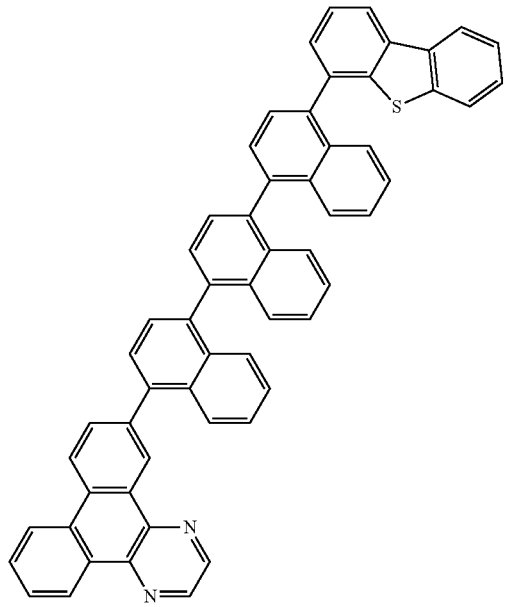
(265)
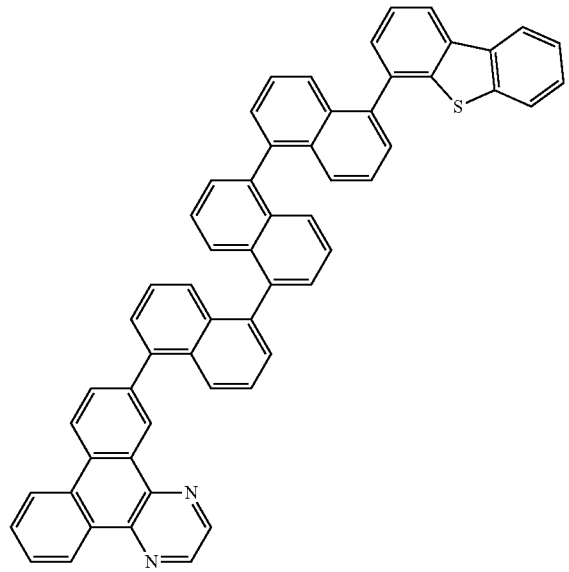
(266)
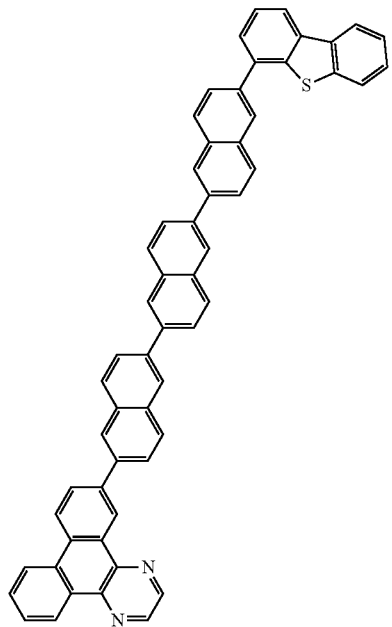
(267)
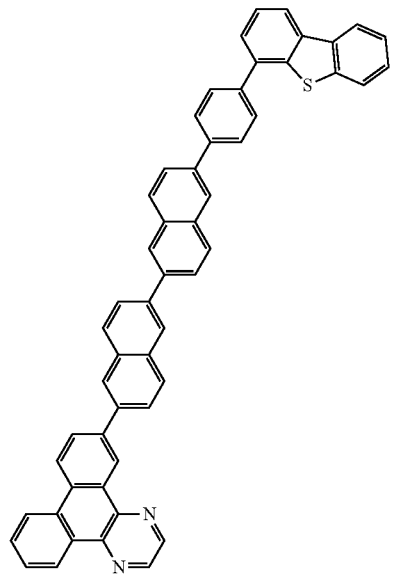
[Chemical formula 111]
(268)
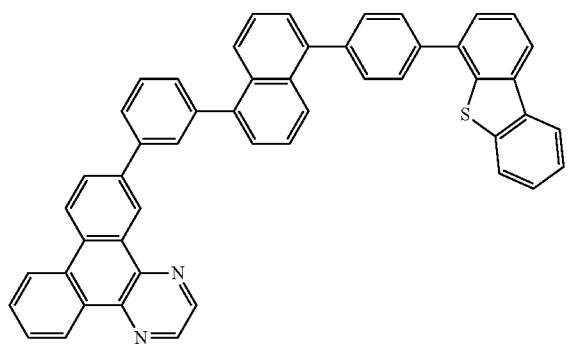
(269)
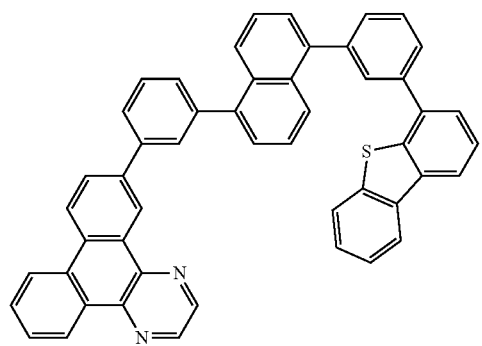

-continued
(270)
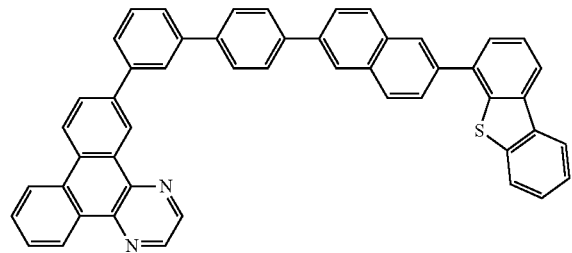
(271)
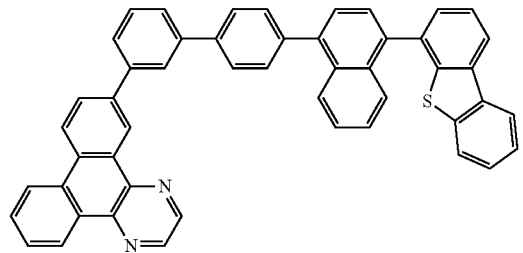
(272)
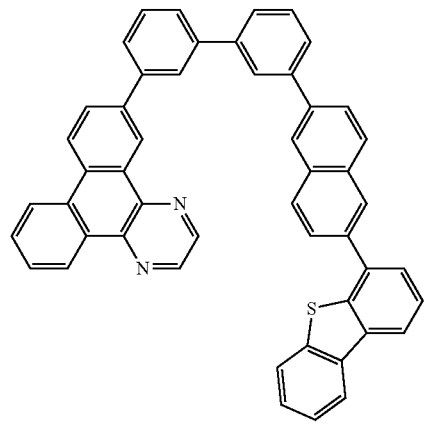
(273)
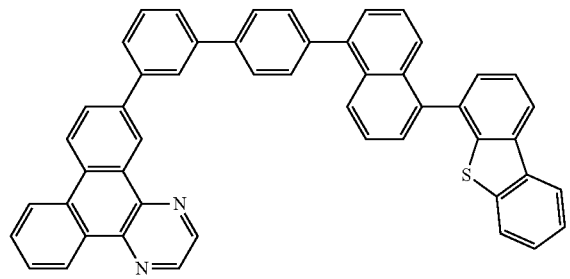
(274)
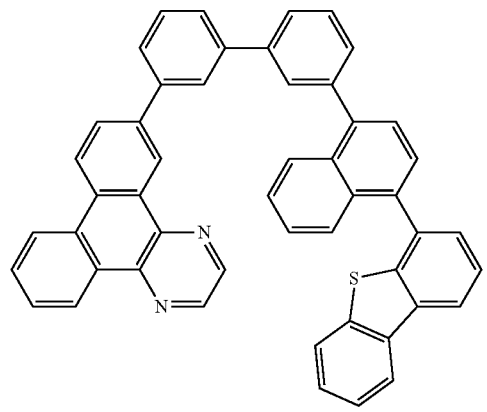
(275)
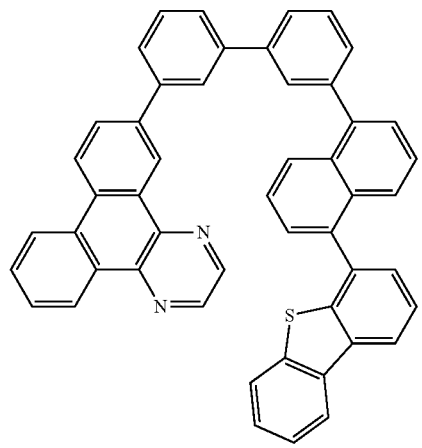

[Chemical formula 112]
(301)
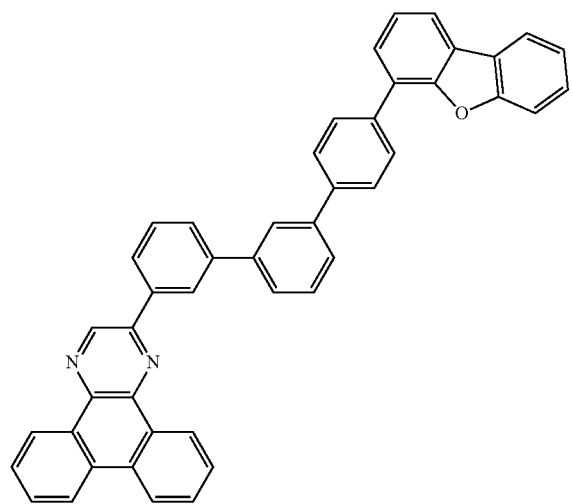
(302)
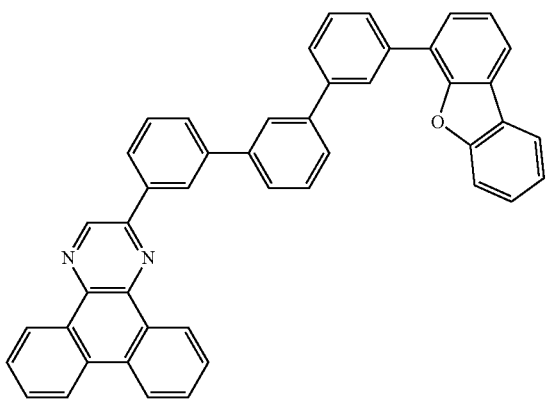
(303)
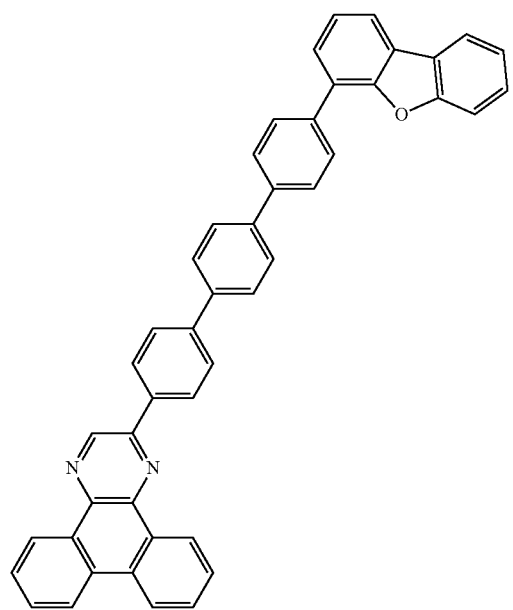
(304)
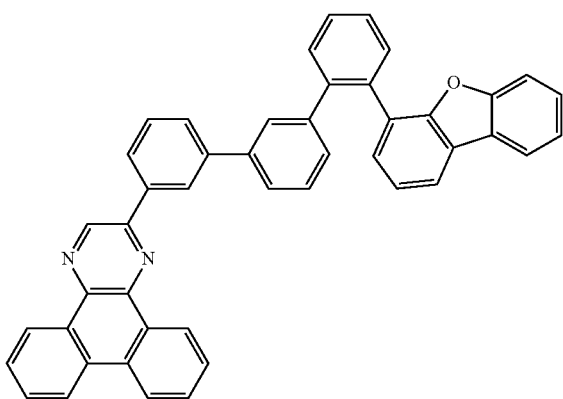

-continued
(305)
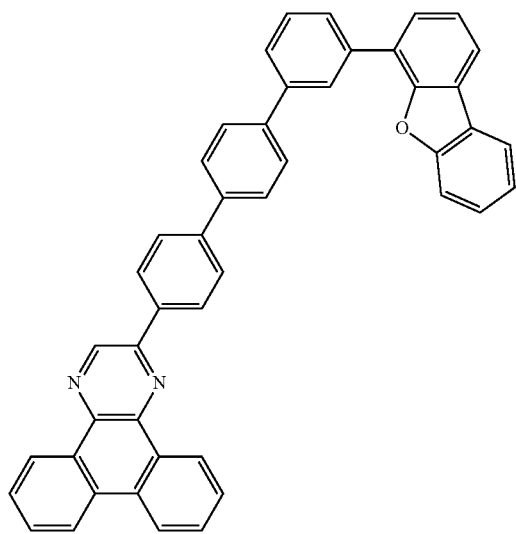
(306)
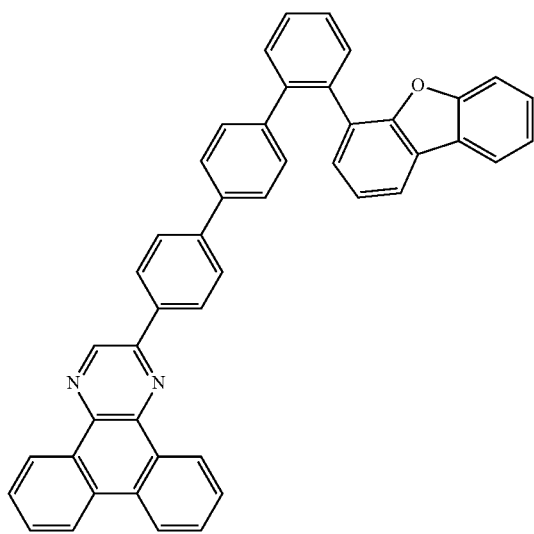
(307)
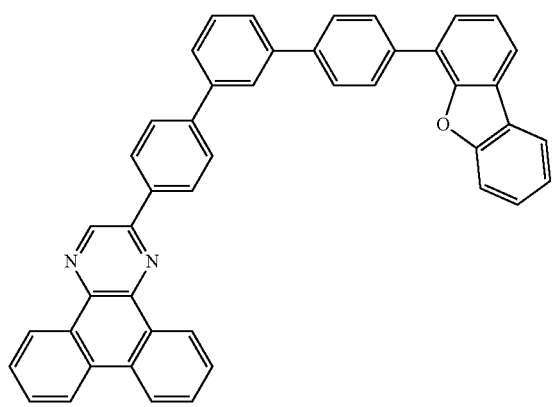
(308)
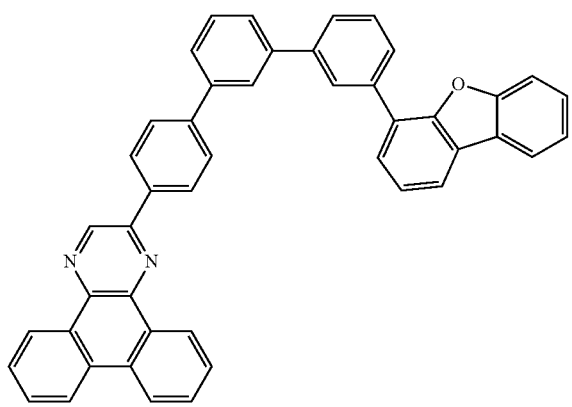
(309)
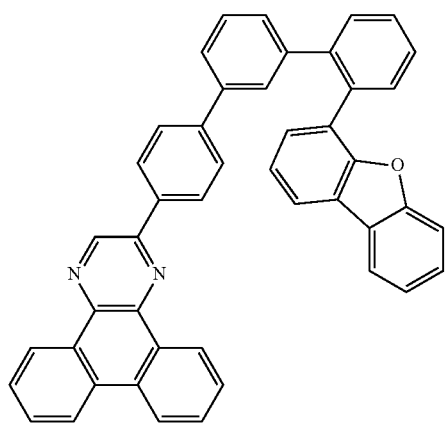

[Chemical formula 113]
(310)
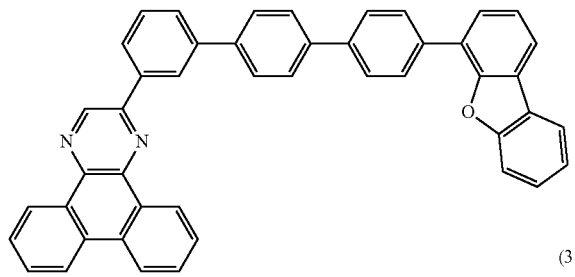
(311)
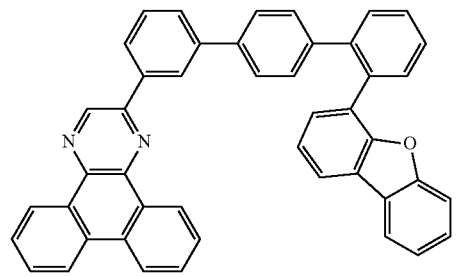
(312)
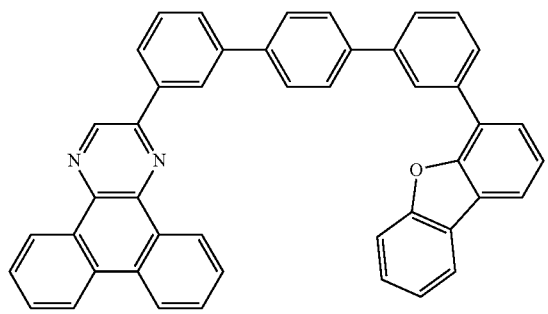
(313)
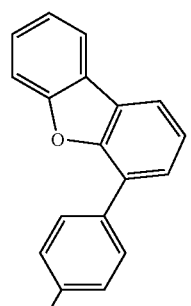
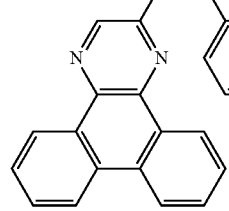
(314)
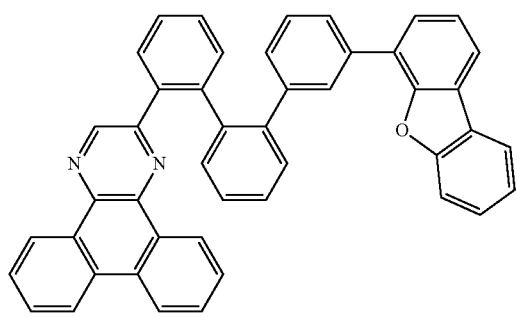
(315)
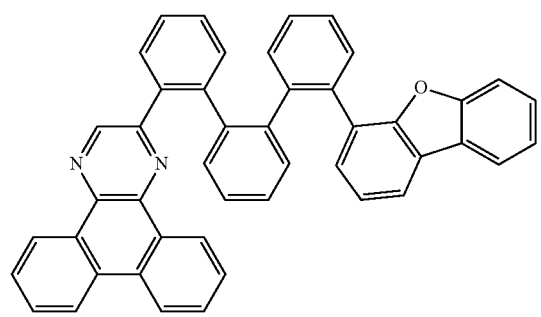
(316)
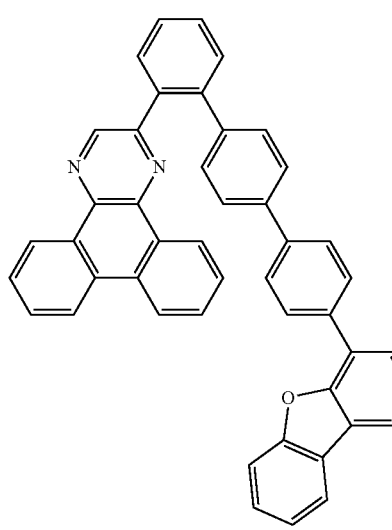
(317)
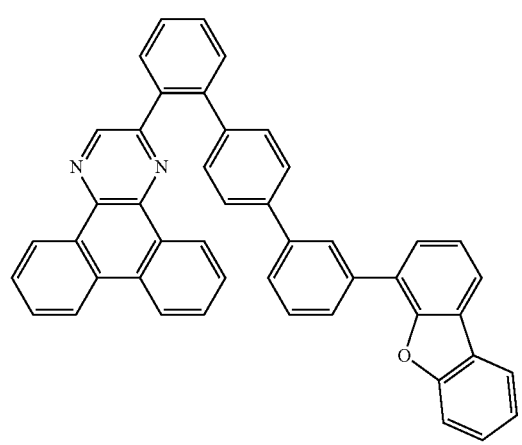

-continued
(318)
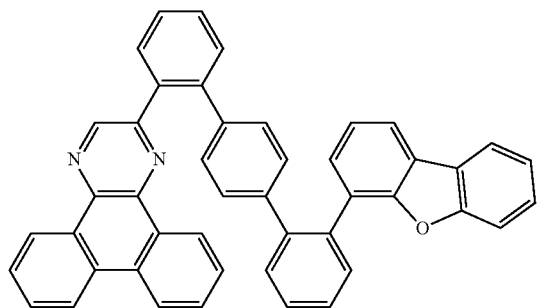
[Chemical formula 114]
(319)
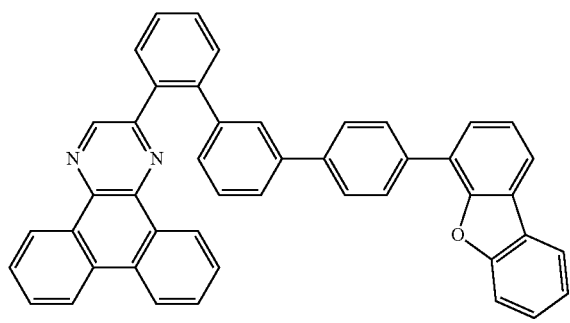
(320)
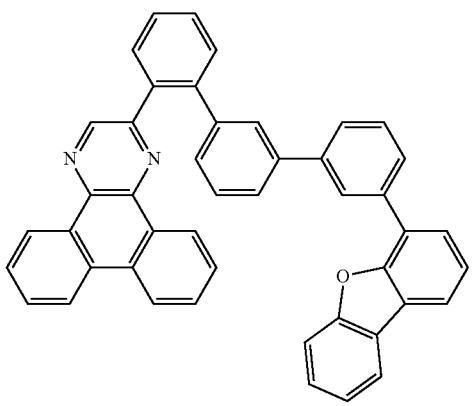
(321)
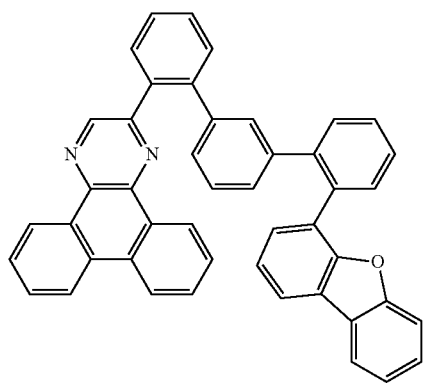
(322)
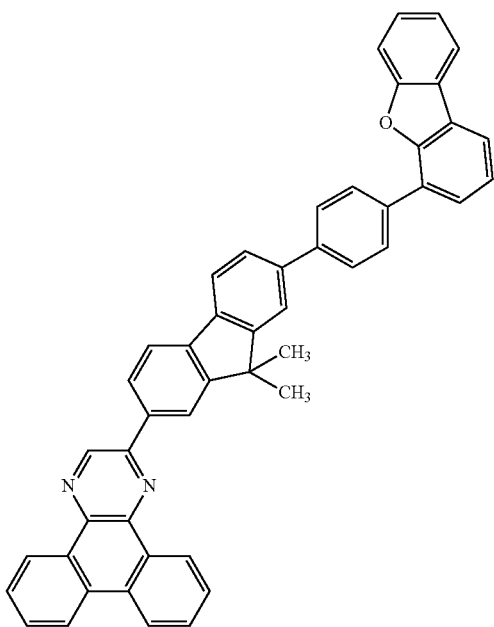

-continued
(323)
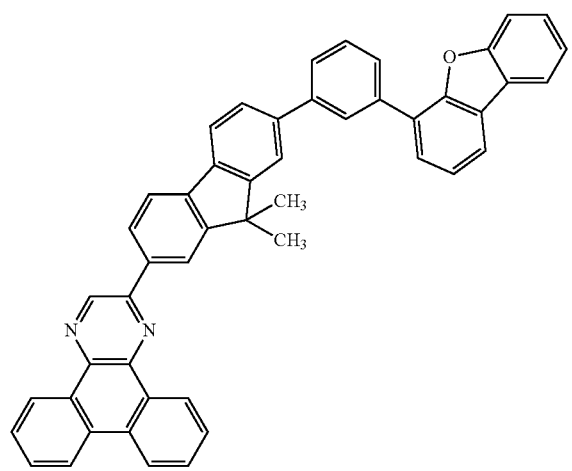
(324)
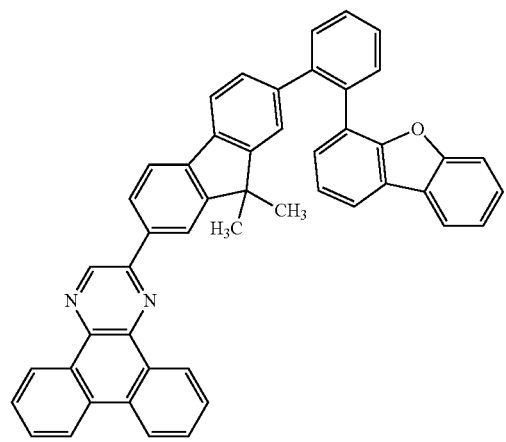
(325)
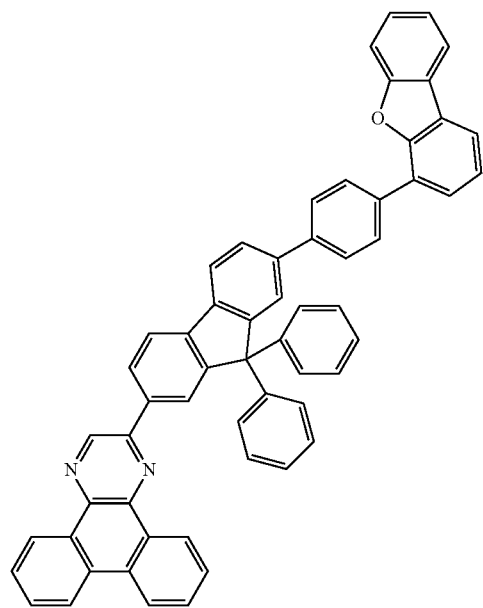
(326)
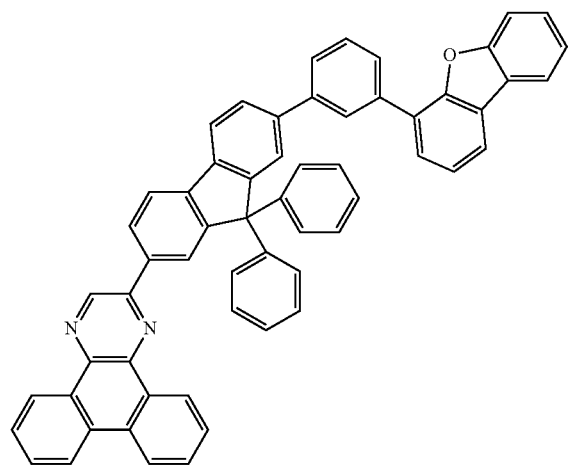

[Chemical formula 115]
(327)
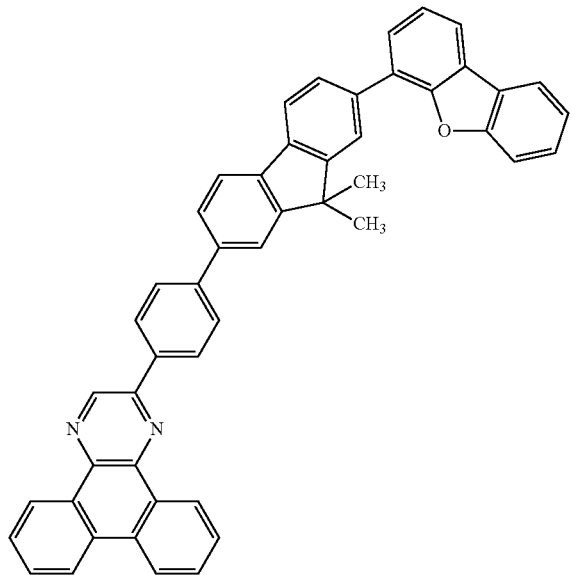
(328)
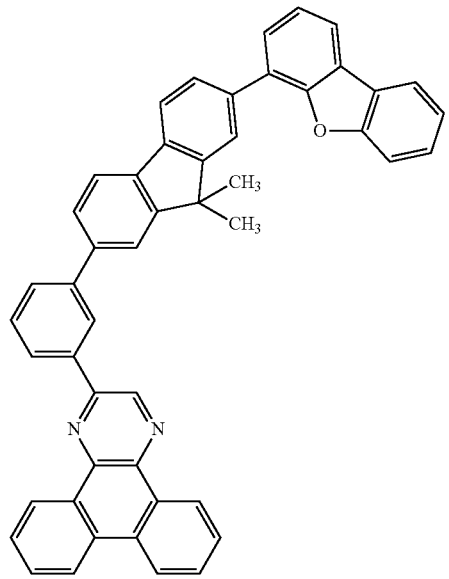
(329)
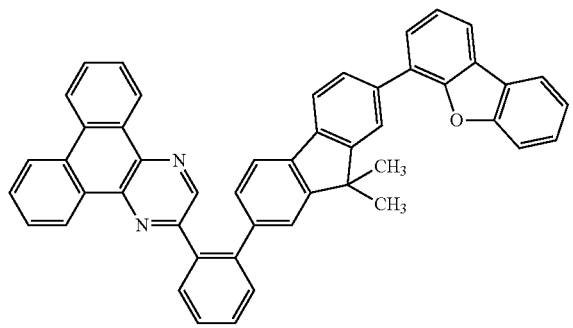
(330)
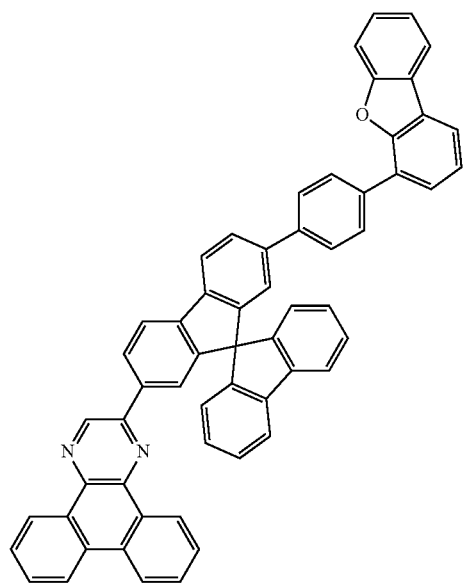

-continued
(331)
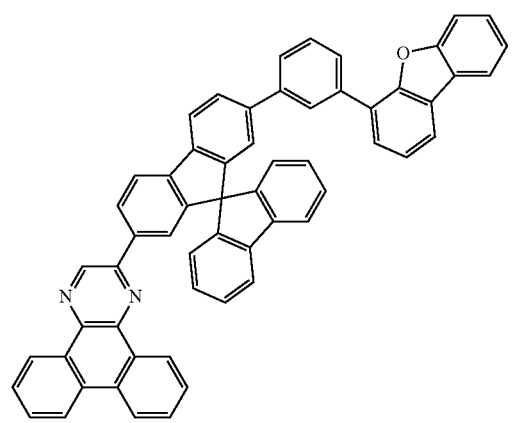
(332)
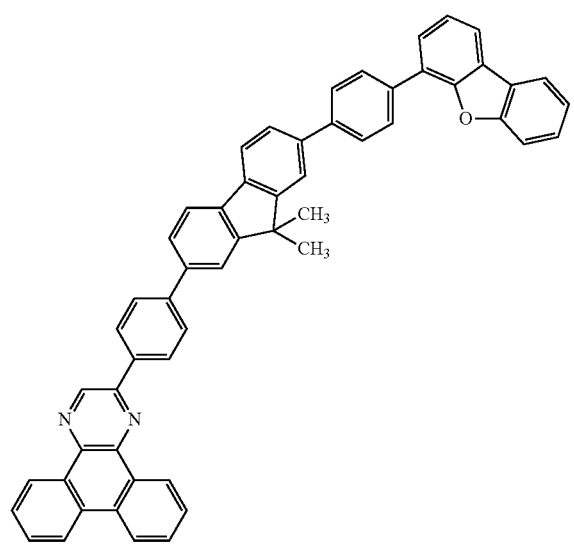
(333)
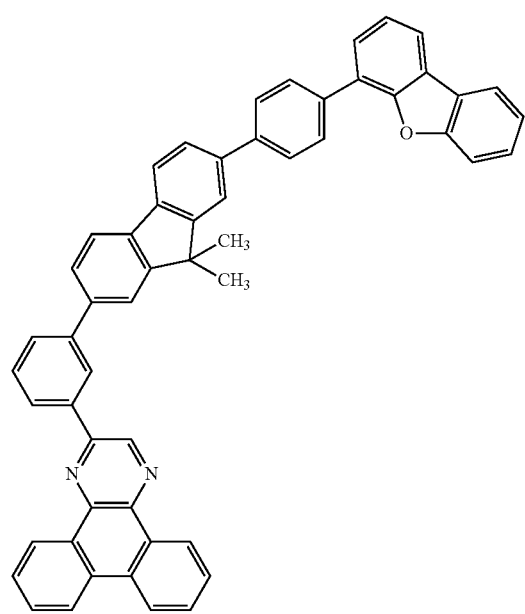
(334)

(335)
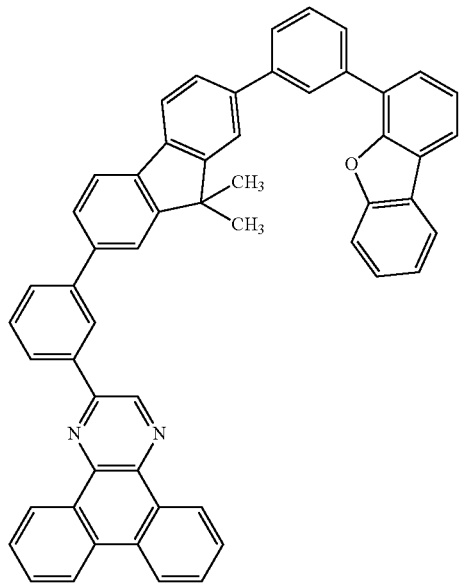
[Chemical formula 116]
(336)
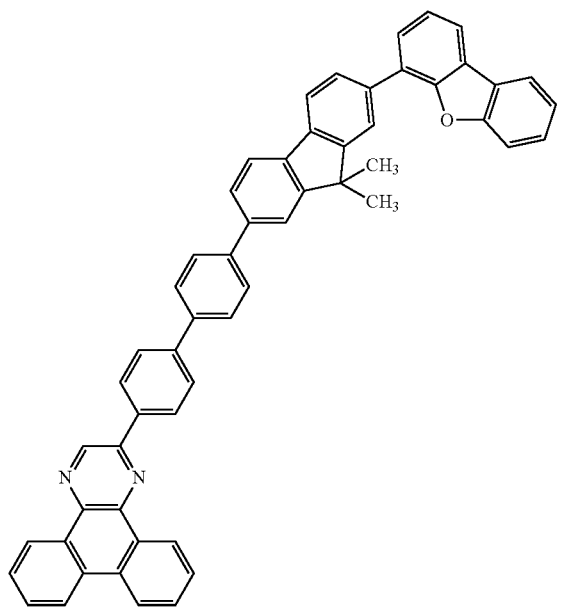
(337)
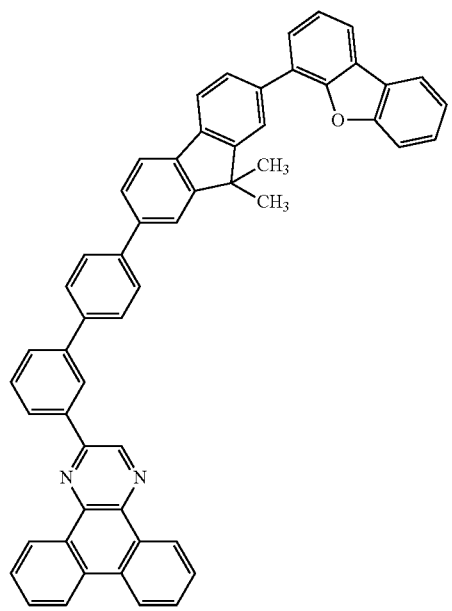
(338)
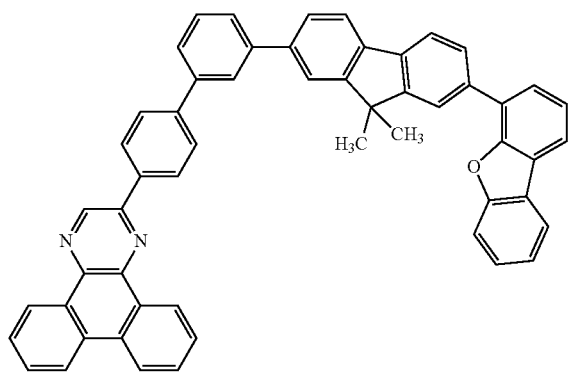
(339)
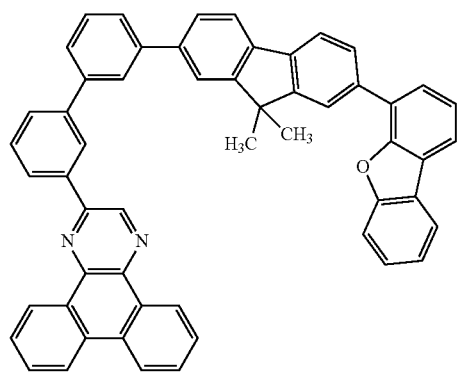

-continued
(340)
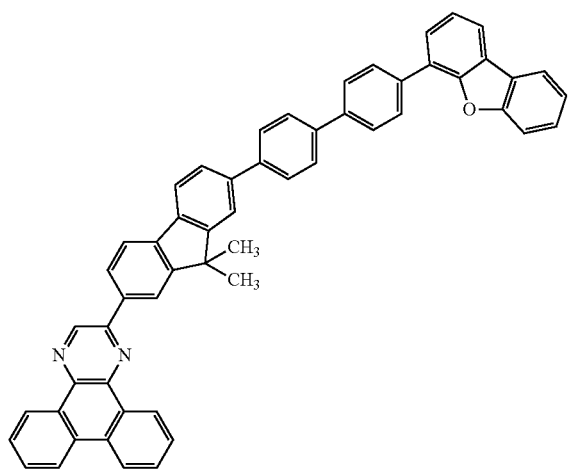
(341)
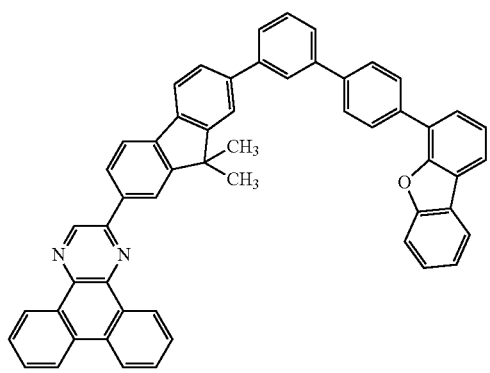
(342)
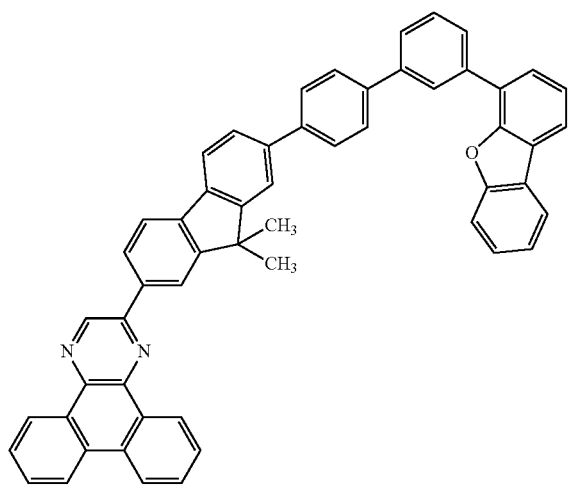
(343)
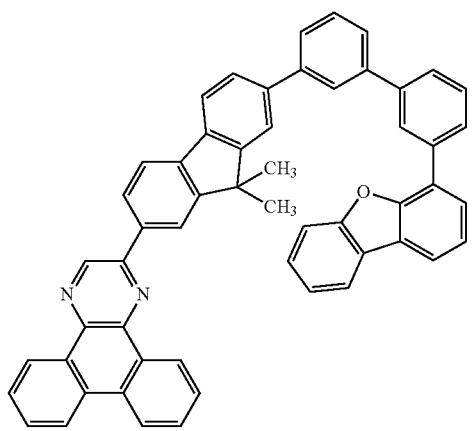
[Chemical formula 117]
(344)
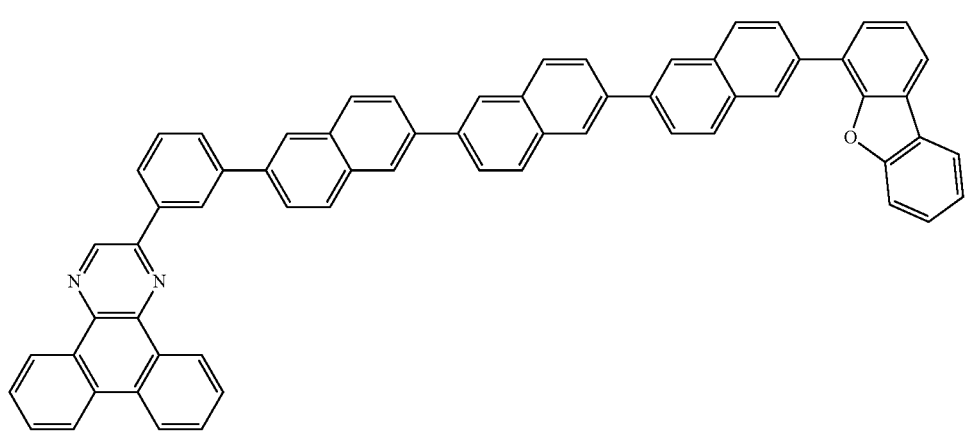

-continued
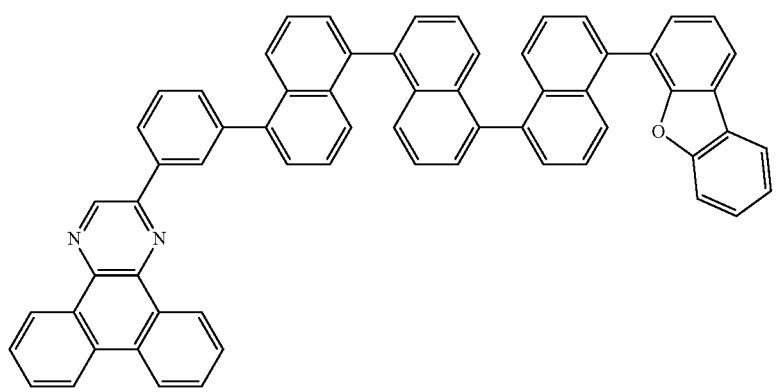
(345)
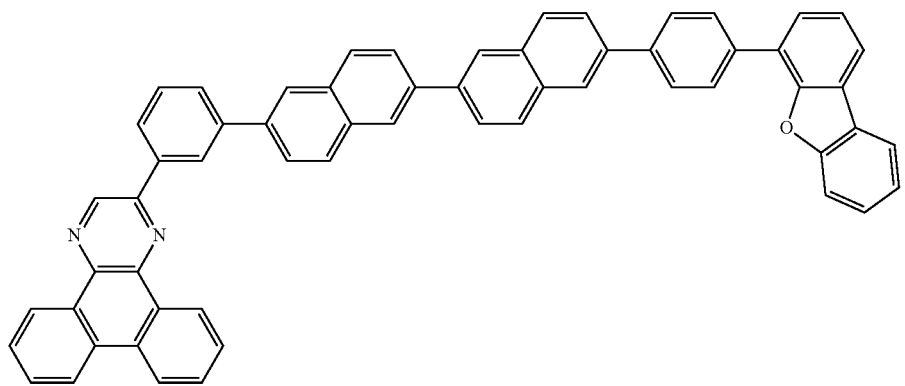
(346)
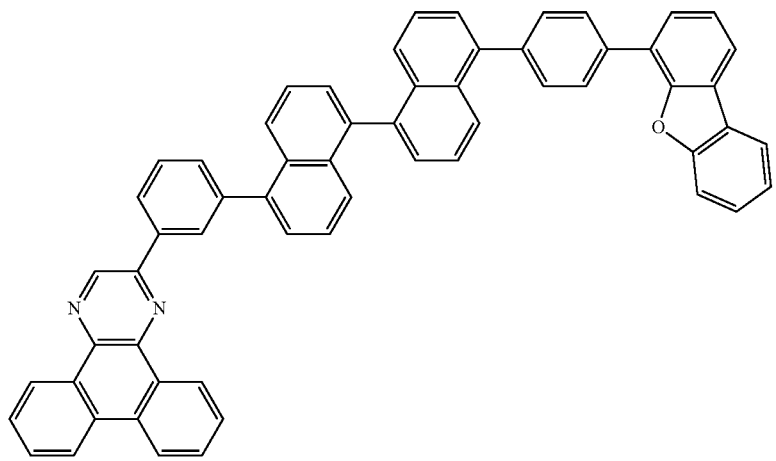
(347)

-continued
(348)
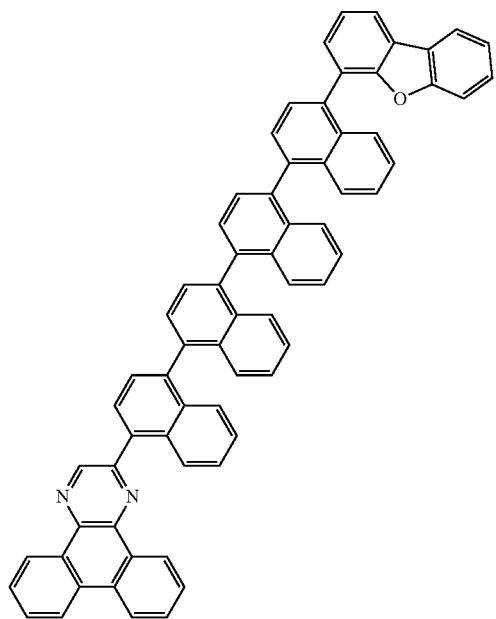
(349)
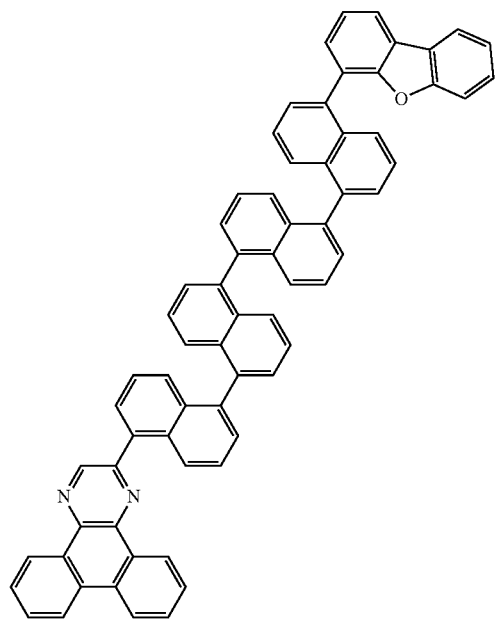
(350)
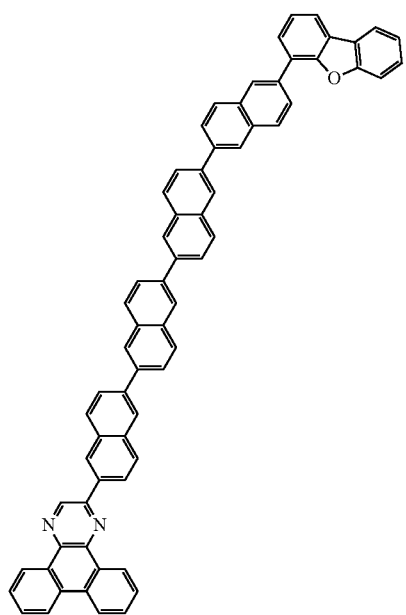
[Chemical formula 118]
(351)
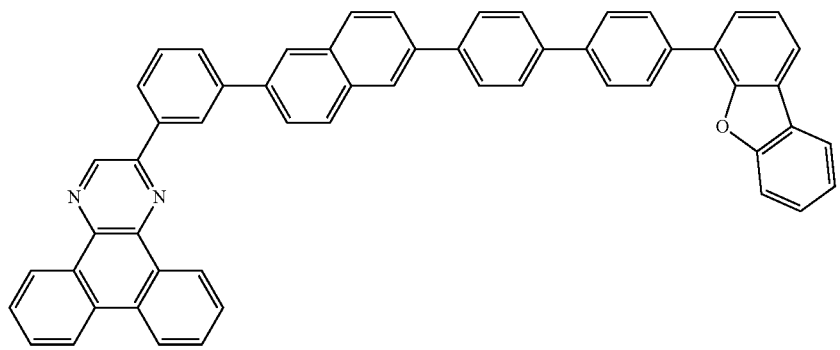

-continued
(352)
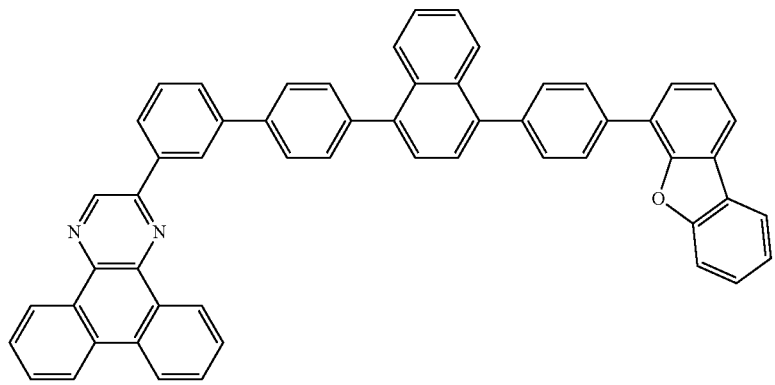
(353)
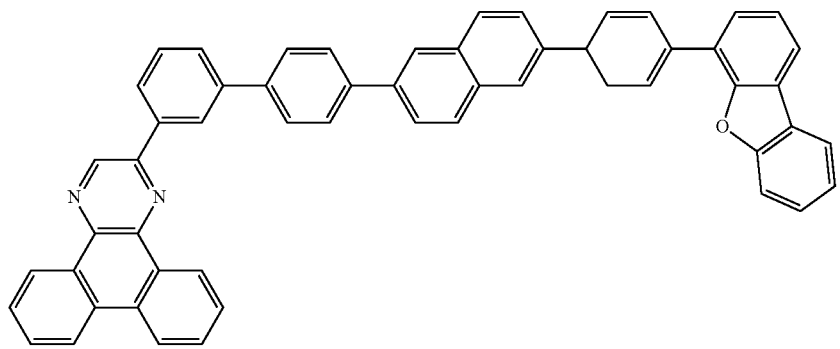
(354)
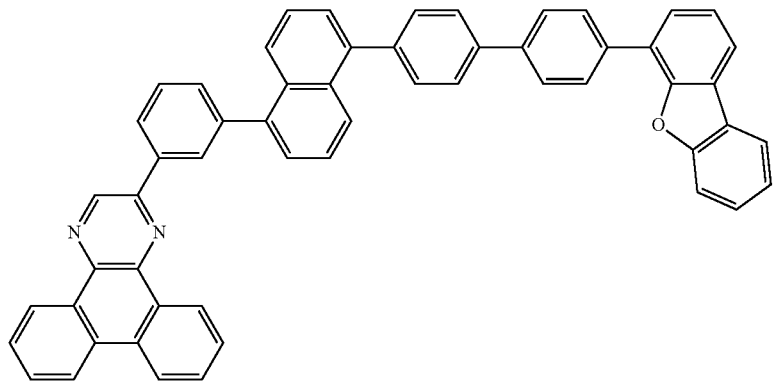

-continued
(355)
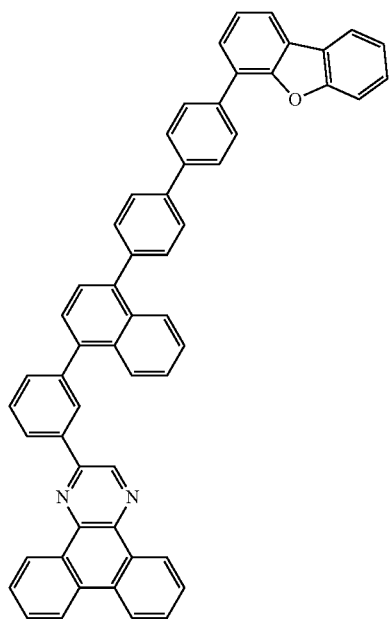
(356)
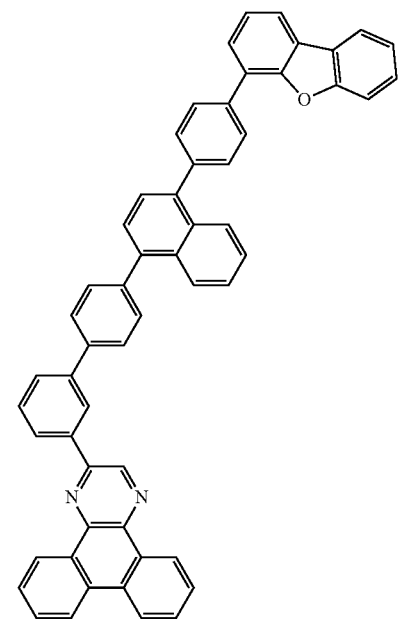
(357)
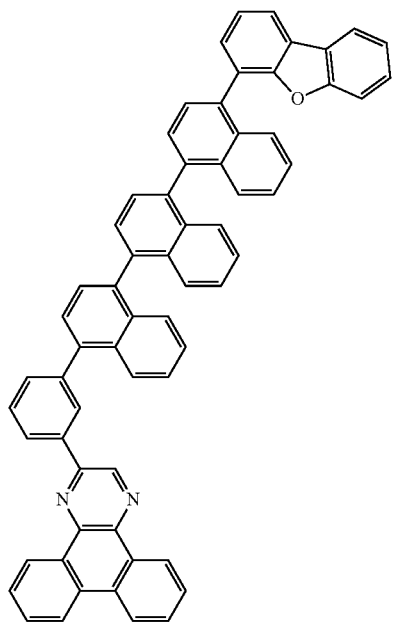
(358)
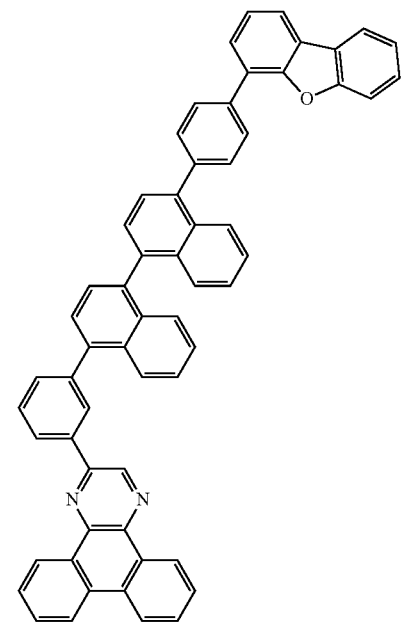
[Chemical formula 119]
(359)
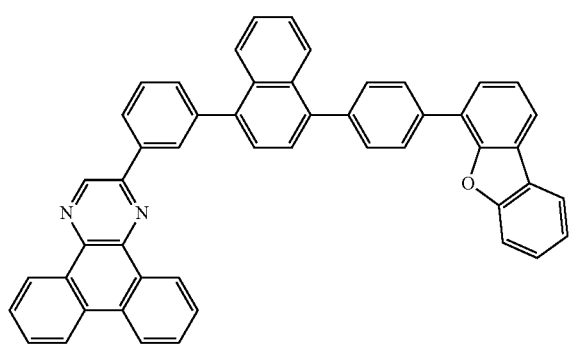
(360)
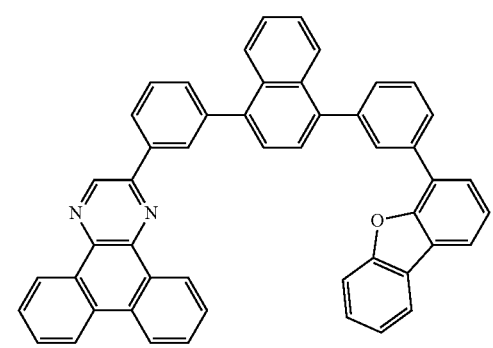

-continued
(361)
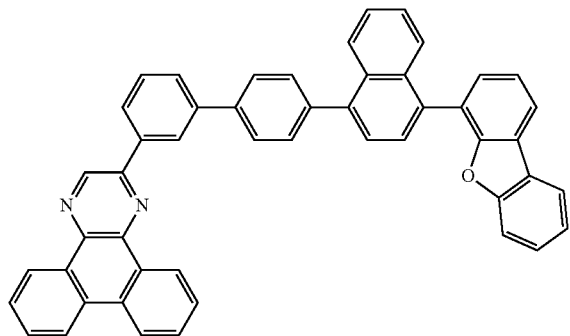
(362)
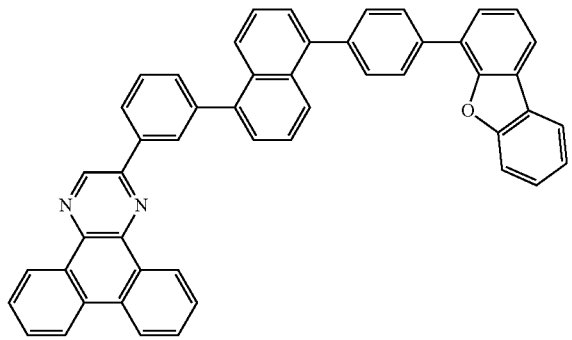
(363)
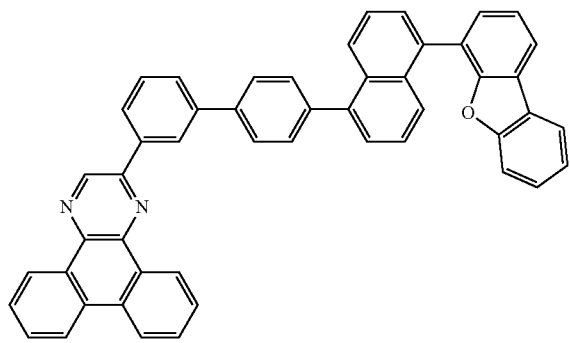
(364)
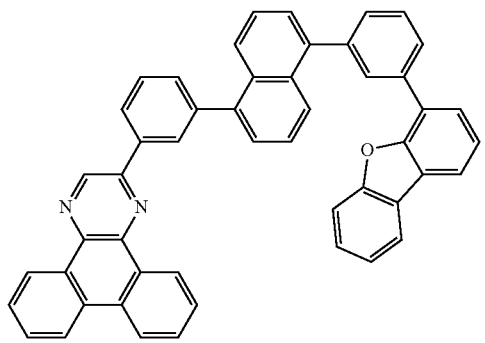
(365)
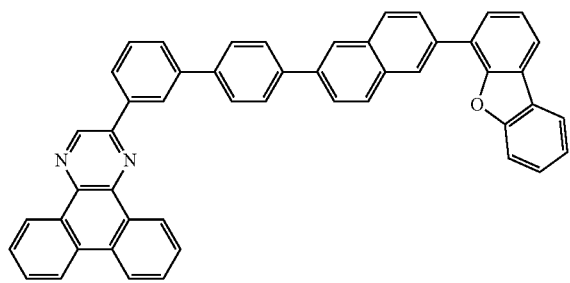
(366)
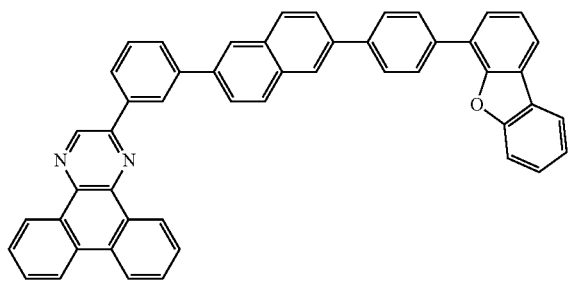
(367)
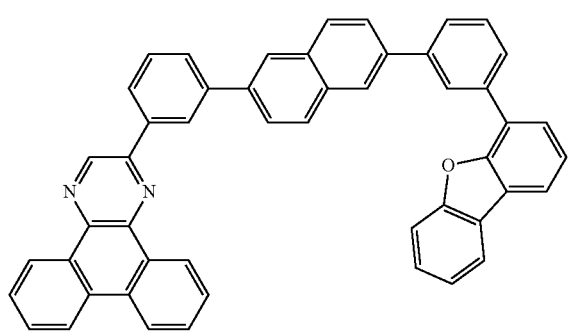

[Chemical formula 120]
(368)
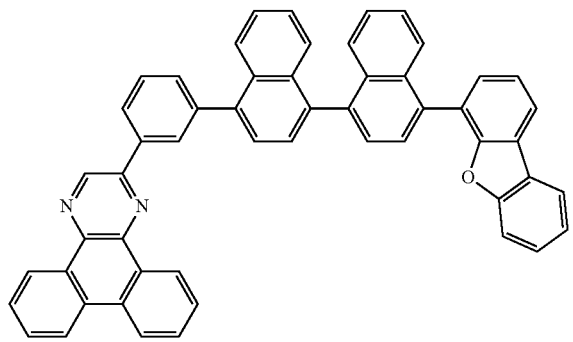
(369)
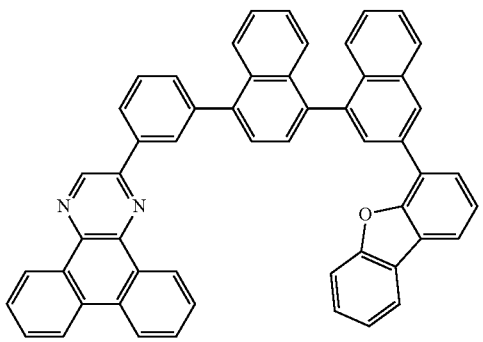
(370)
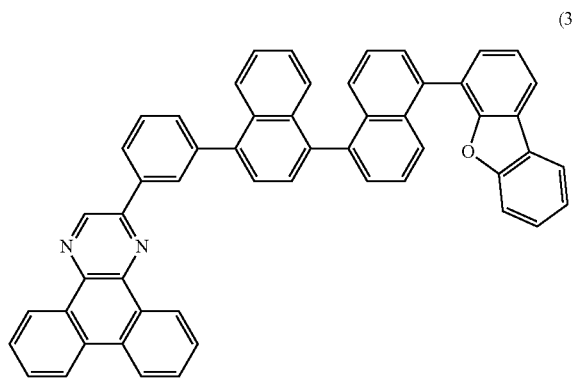
(371)
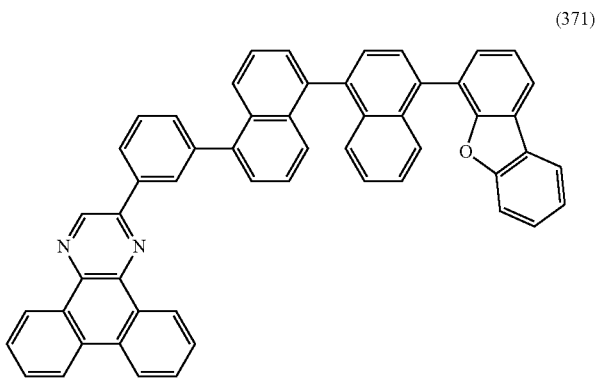
(372)
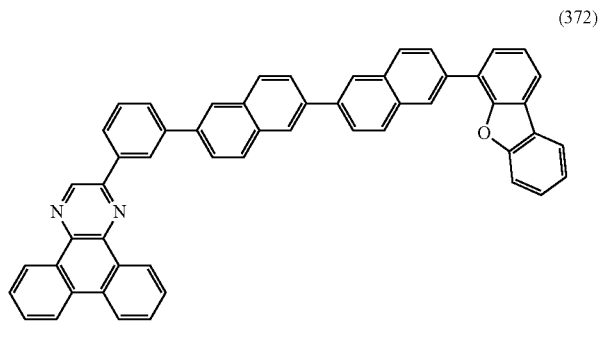
(373)
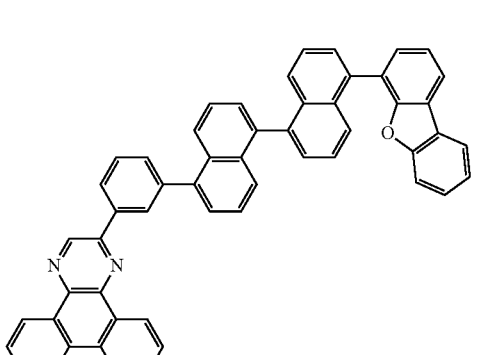

-continued
(374)
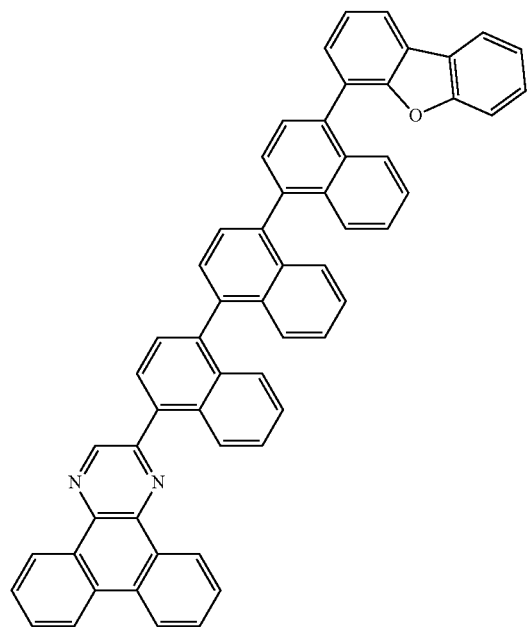
(375)
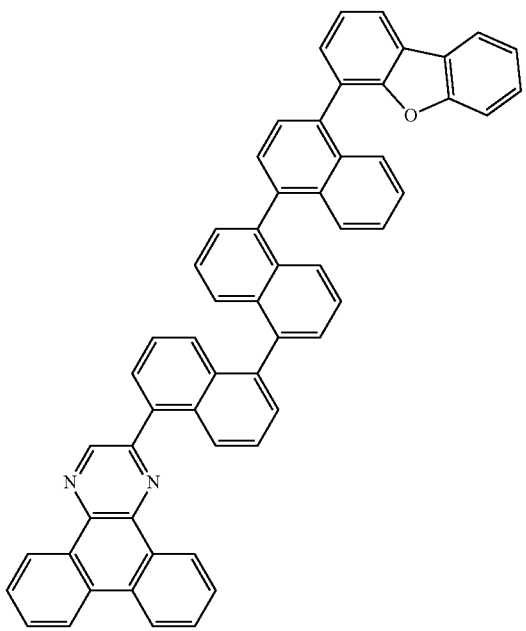
(376)
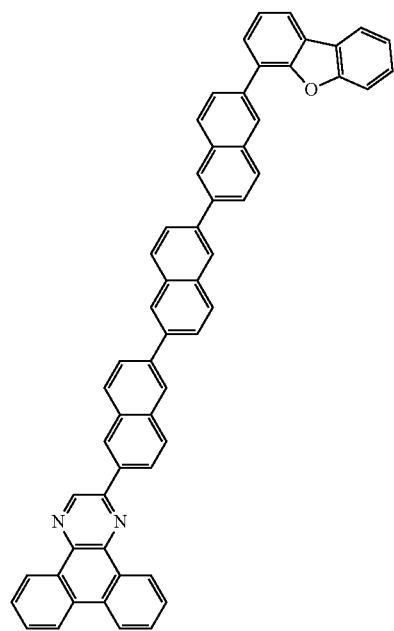

[Chemical formula 121]
(377)
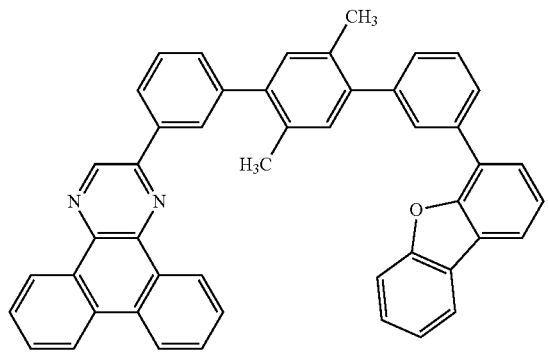
(378)
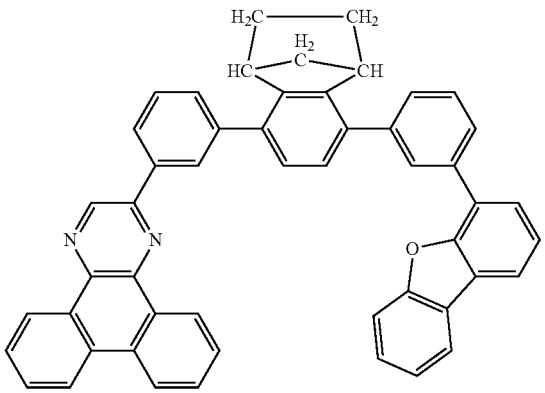
(379)
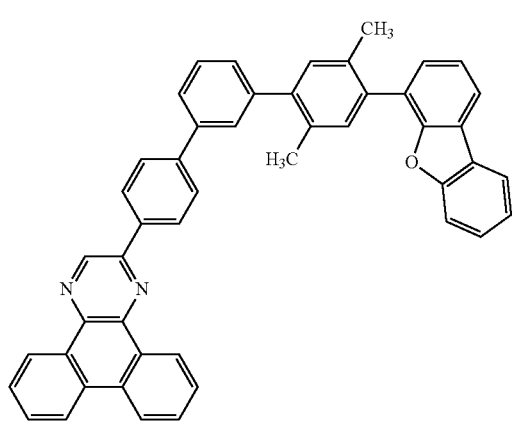
(380)
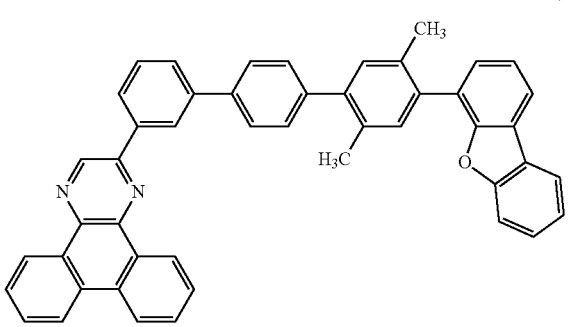
(381)
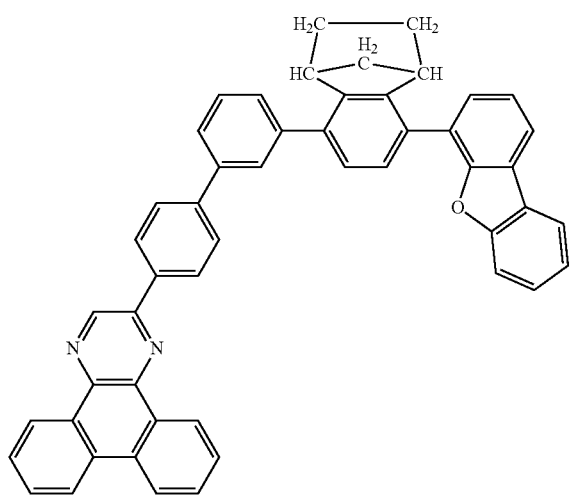
(382)
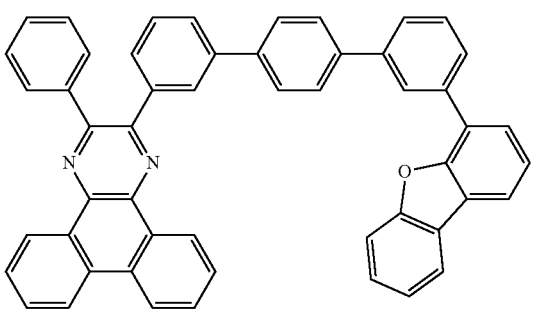

-continued
(383)
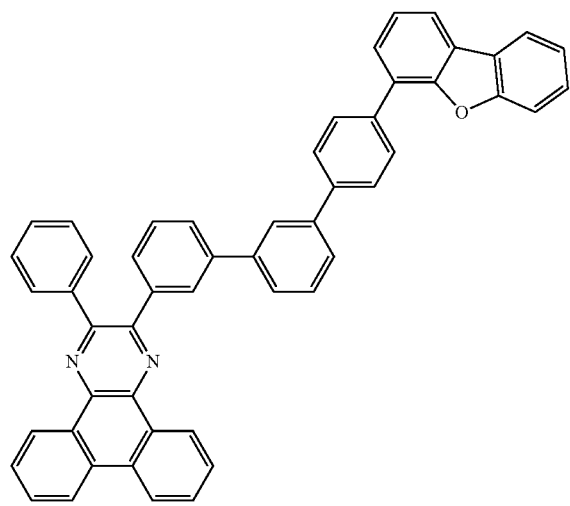
(384)
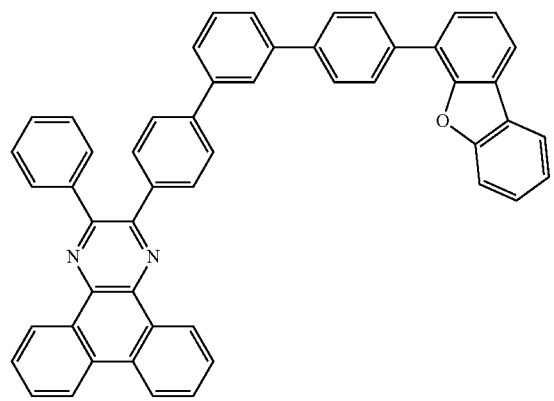
(385)
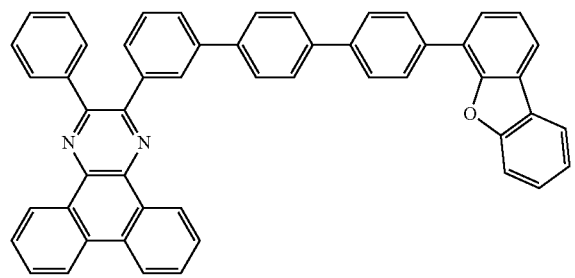
(386)
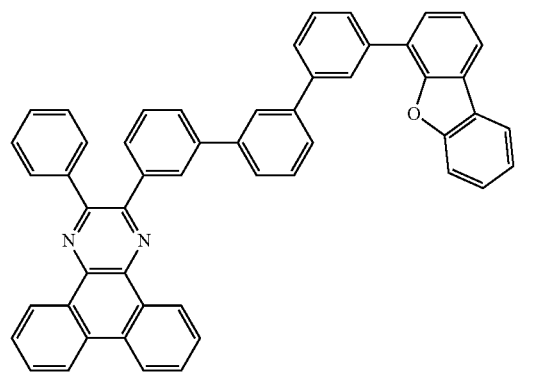
[Chemical formula 122]
(387)
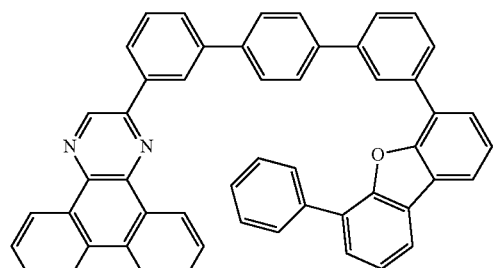
(388)
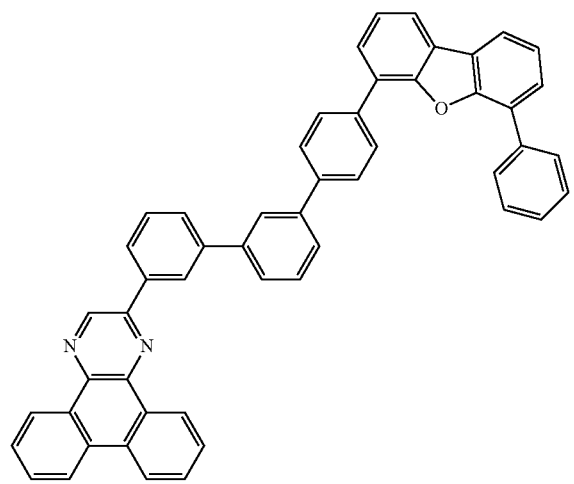

-continued
(389)
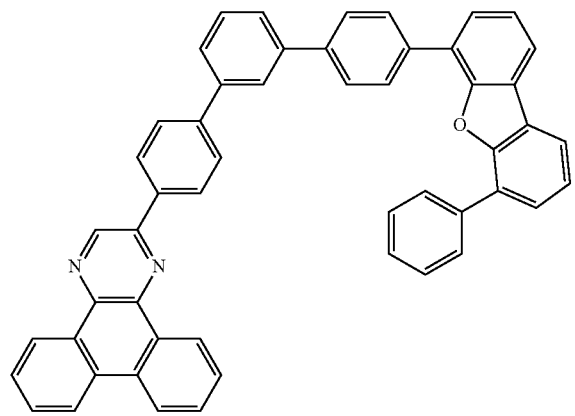
(390)
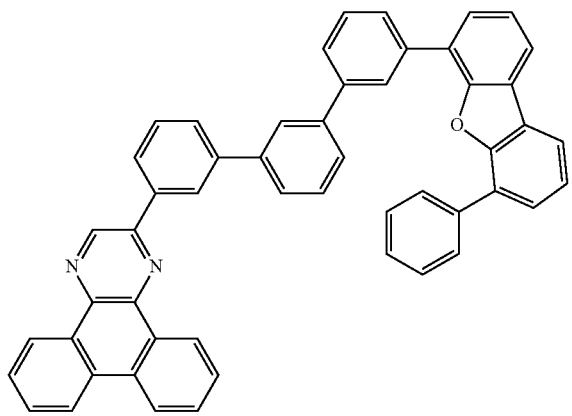
(391)
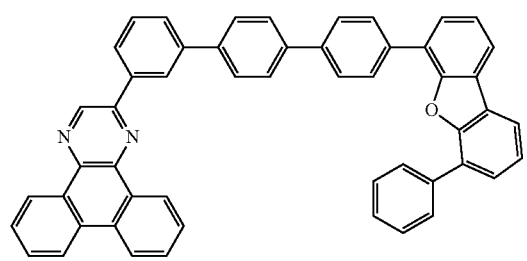
(392)
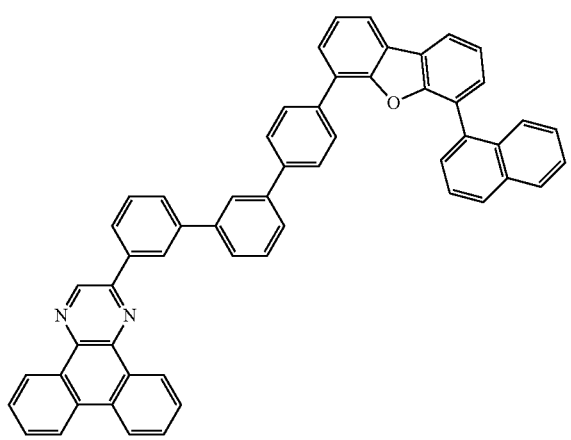
(393)
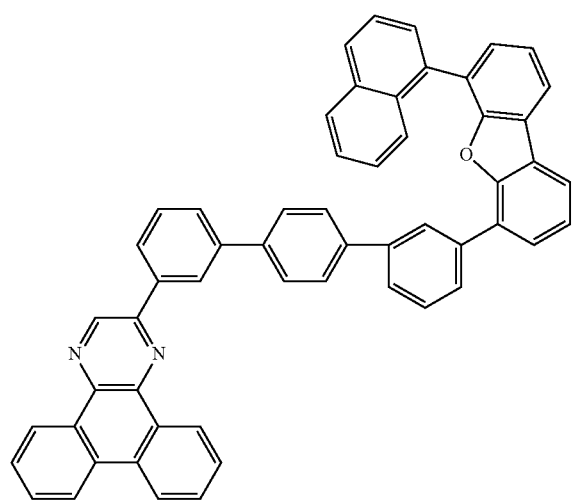
(394)
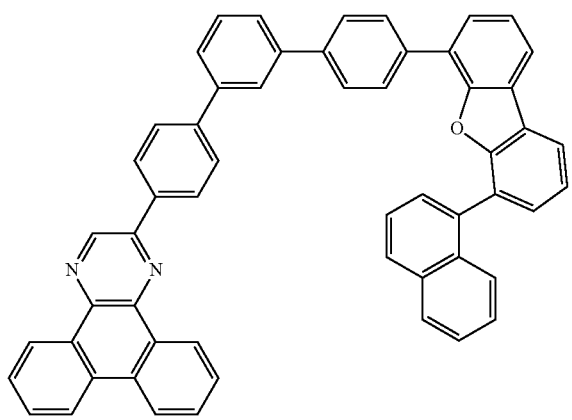

-continued
(395)
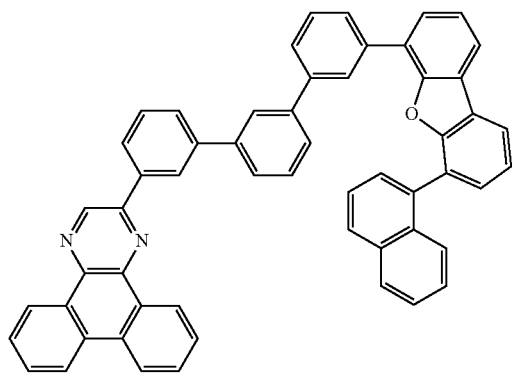
(396)
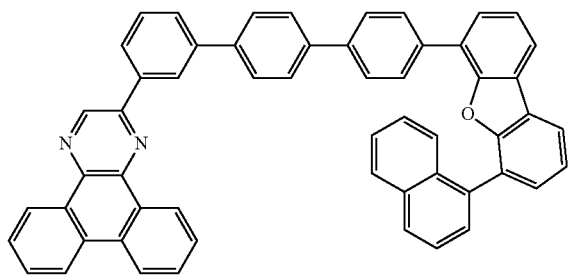
[Chemical formula 123]
(397)
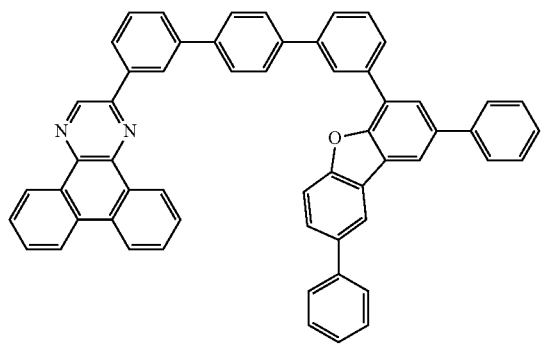
(398)
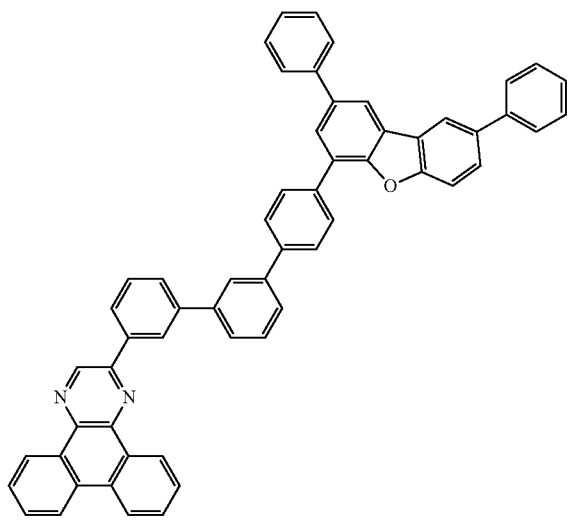
(399)
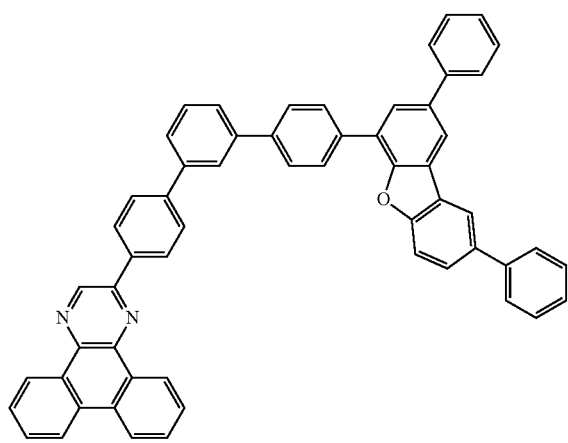
(400)
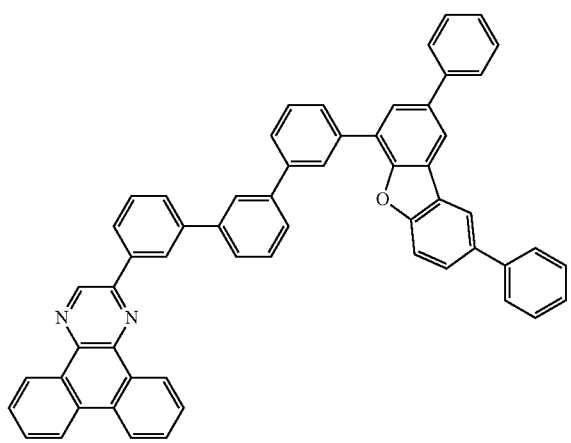

-continued
(401)
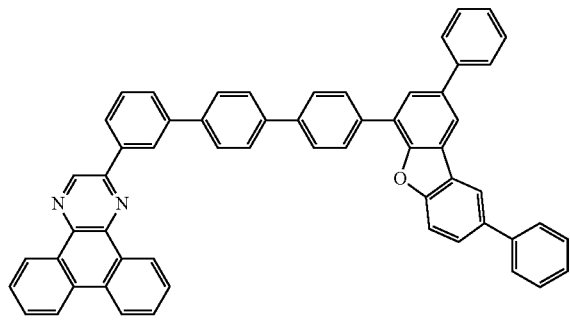
(402)
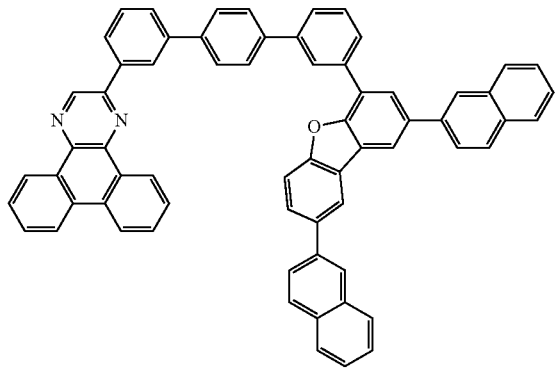
(403)
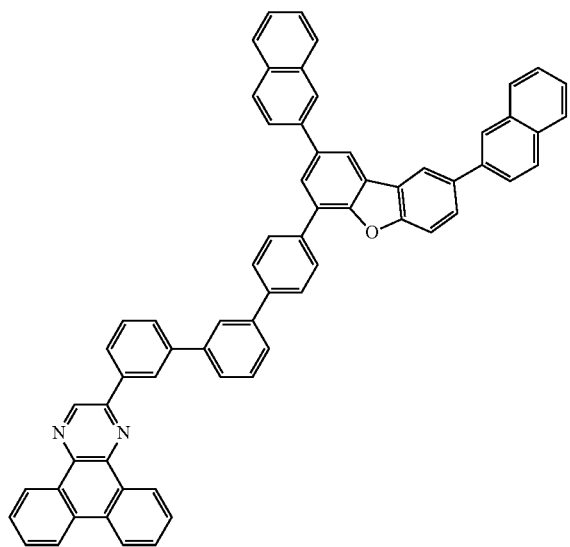
(404)
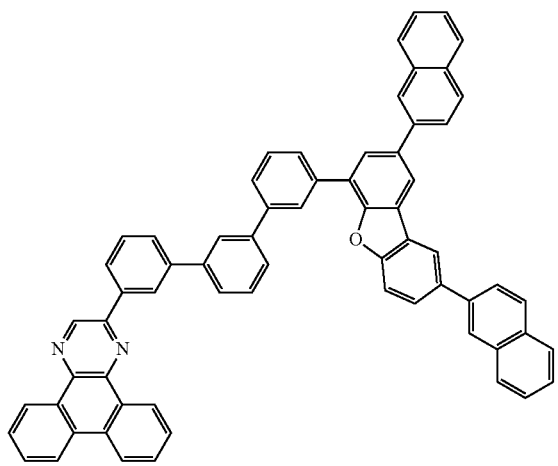
[Chemical formula 124]
(405)
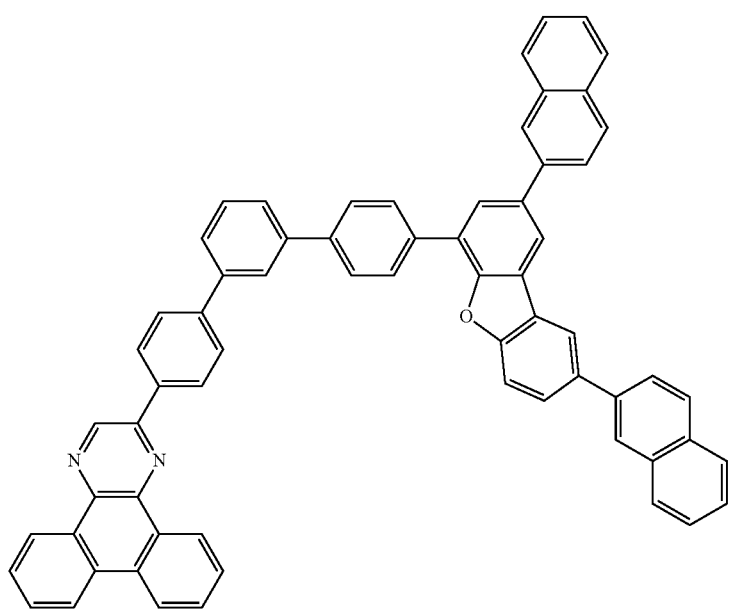

-continued
(406)
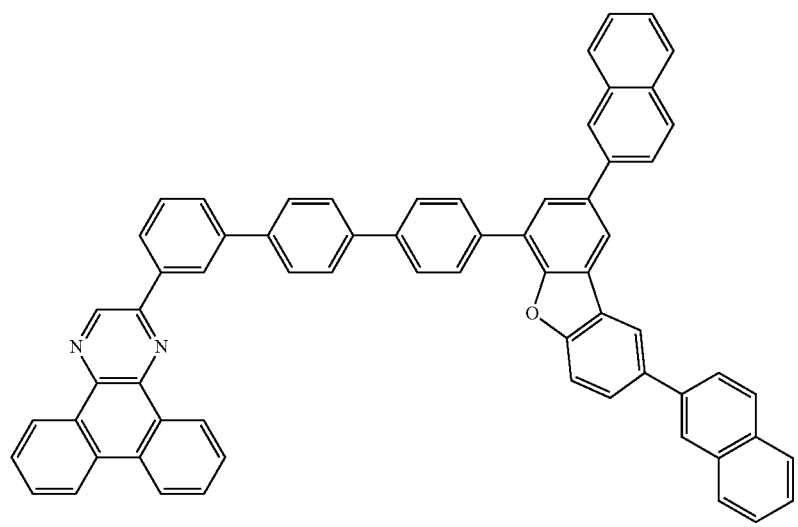
(407)
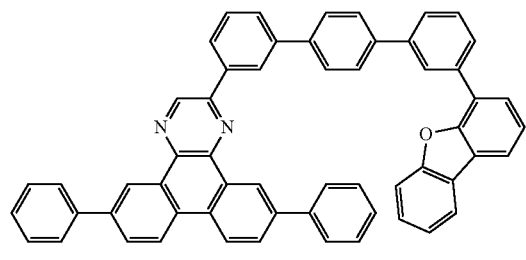
(408)
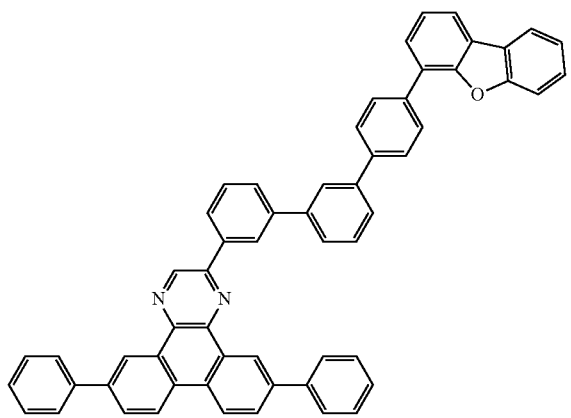
(409)
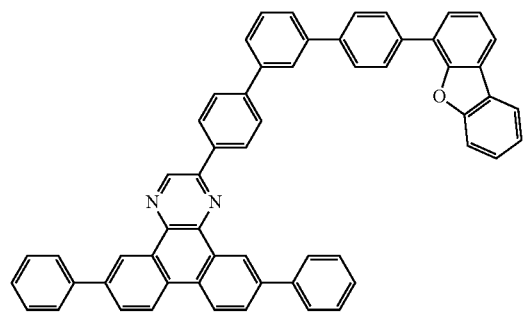
(410)
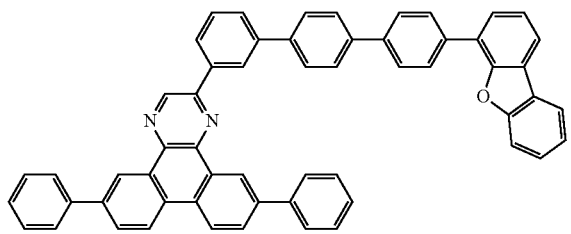

(411)
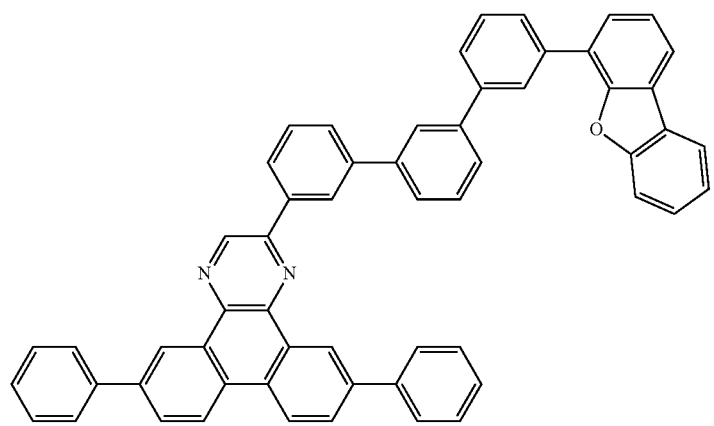
[Chemical formula 125]
(412)　(413)
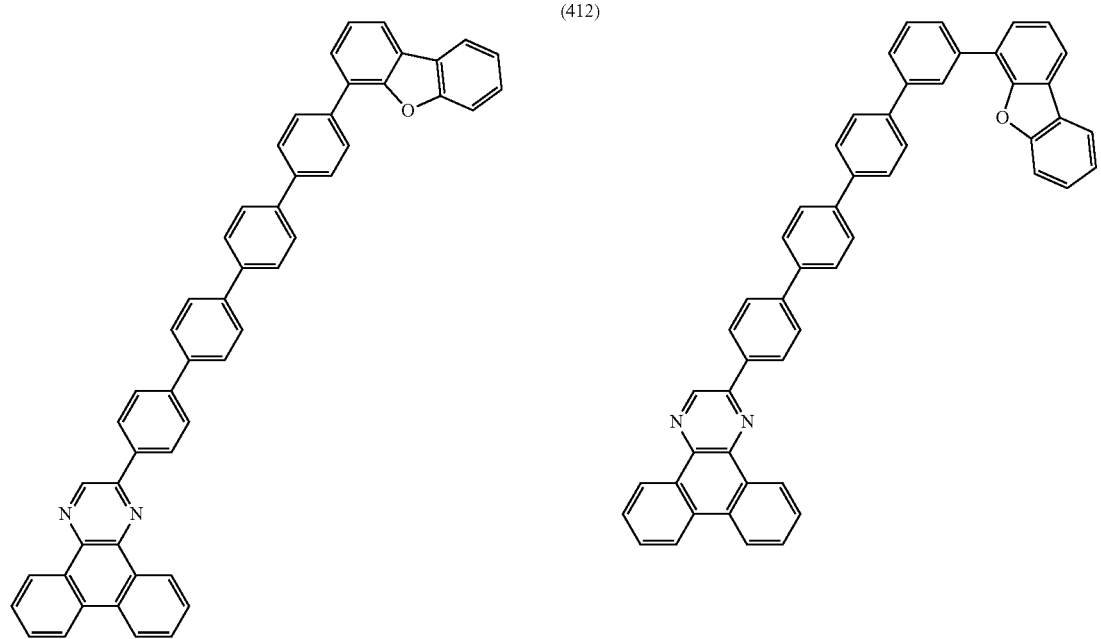
(414)　(415)
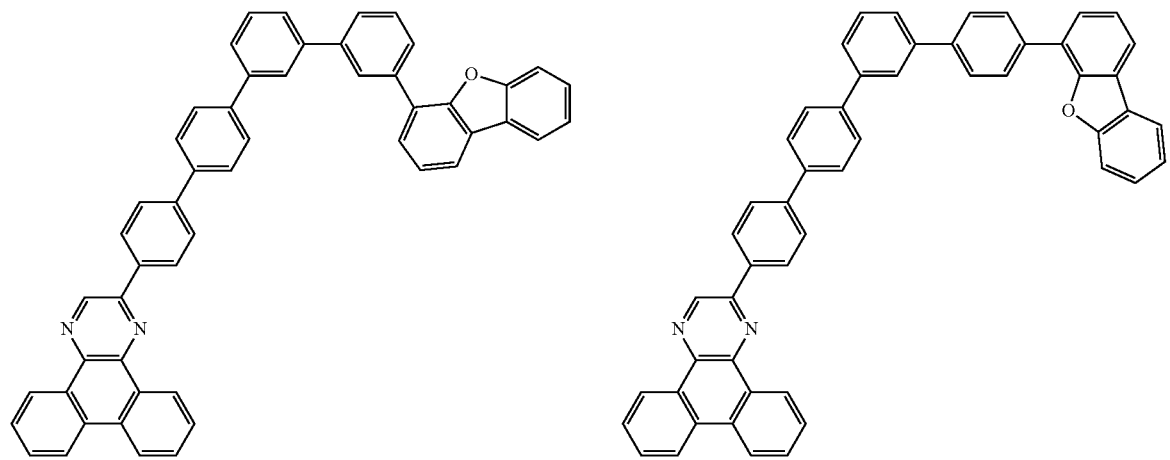

-continued
(416)
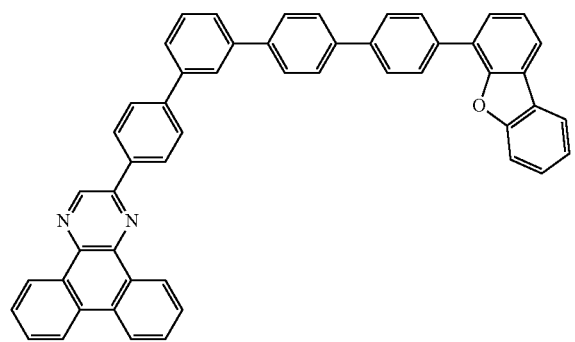
(417)
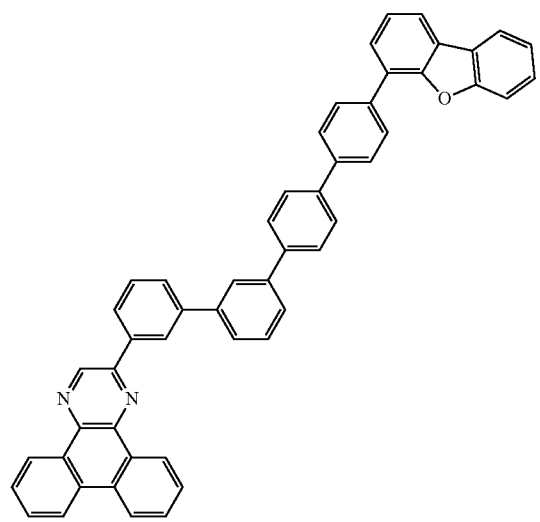
(418)
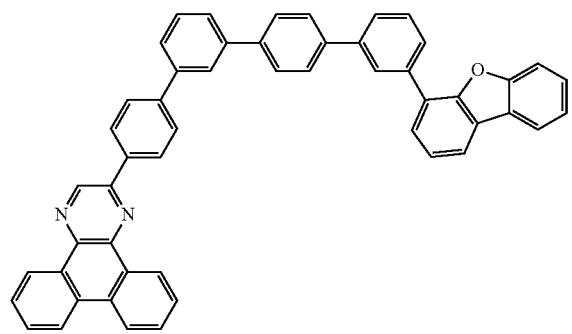
(419)
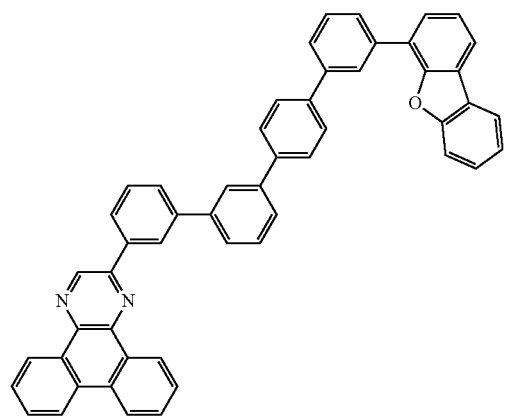
[Chemical formula 126]
(420)
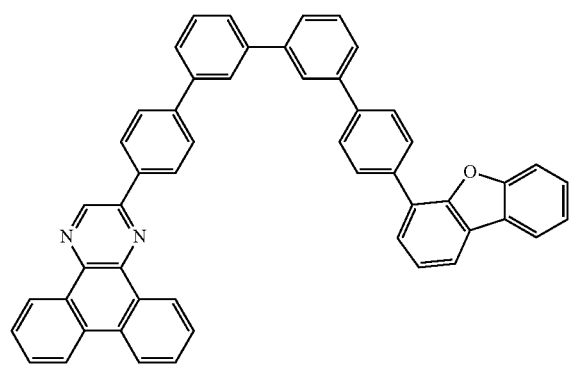
(421)
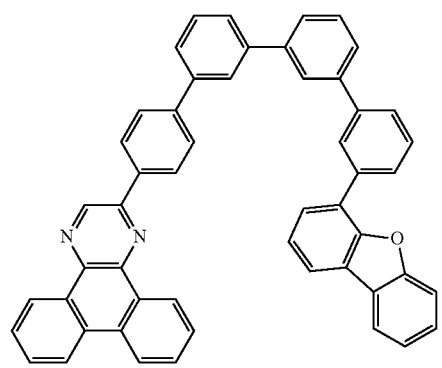

-continued
(422)
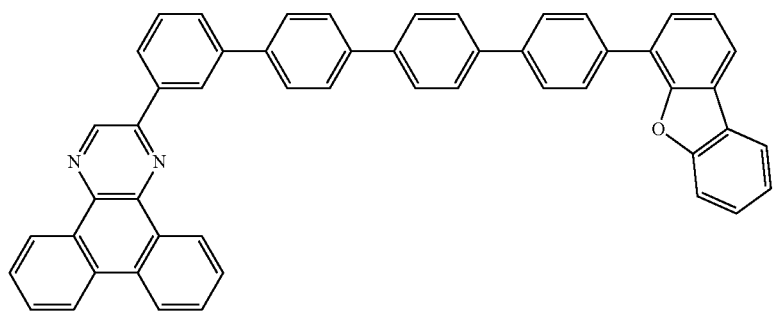
(423)
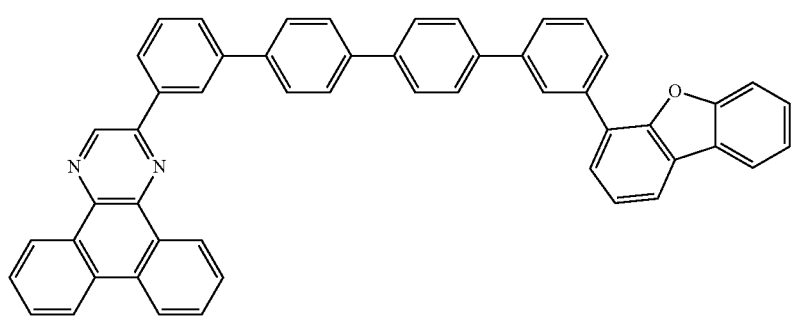
(424)
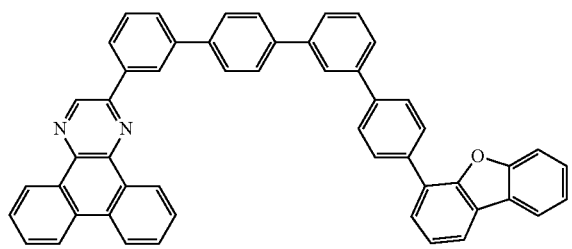
(425)
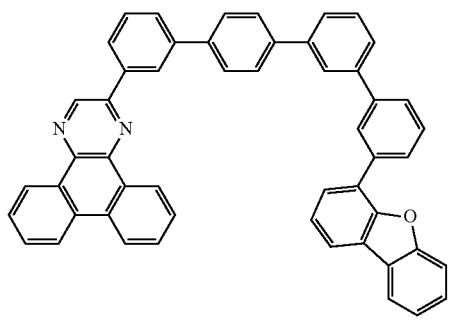
(426)
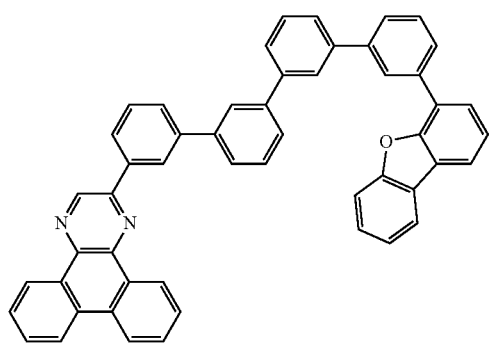
(427)
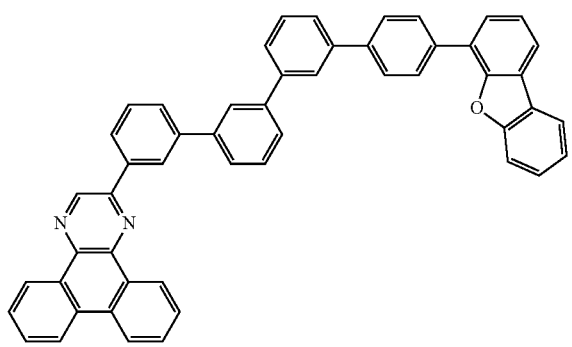

[Chemical formula 127]
(428)
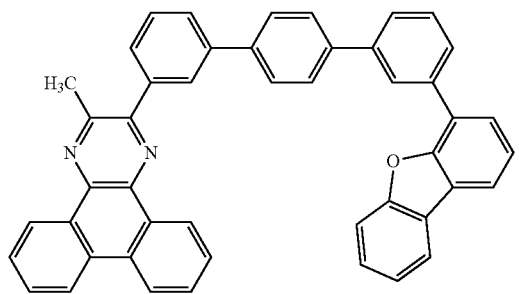
(429)
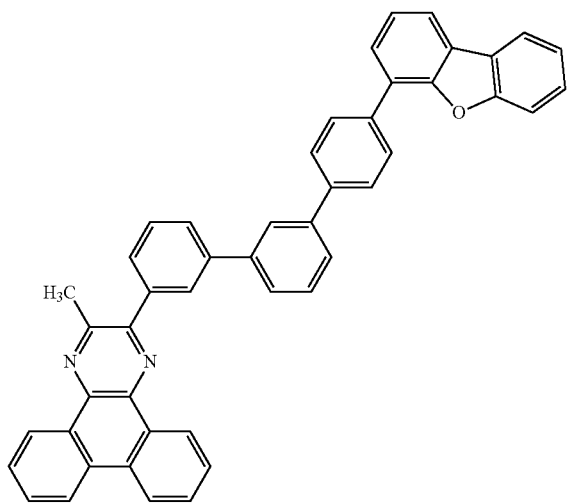
(430)
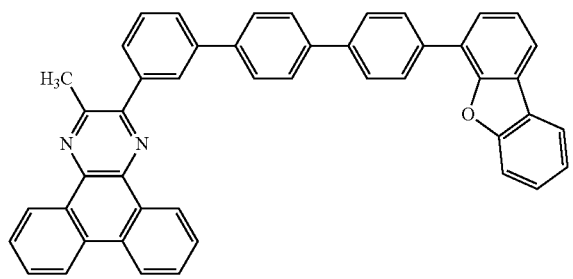
(431)
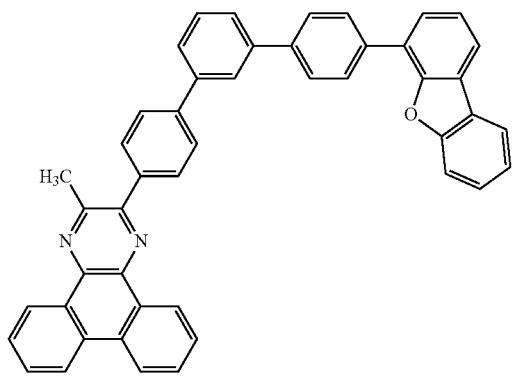
(432)
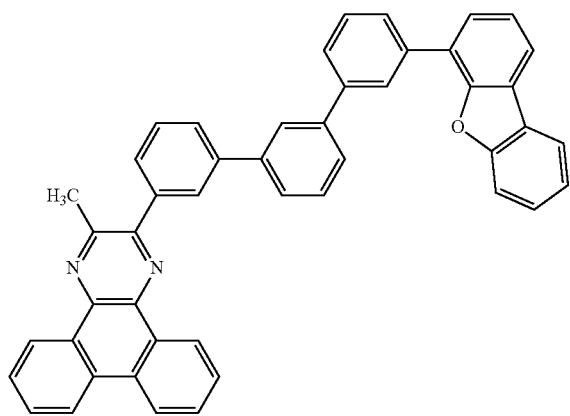
(433)
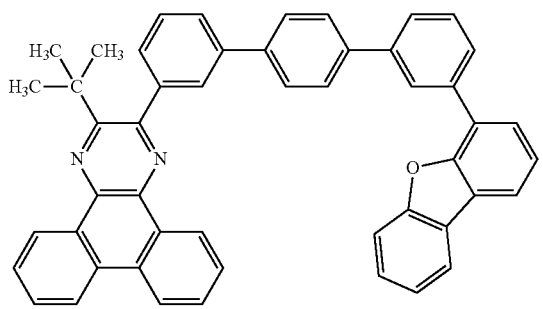

-continued
(434)
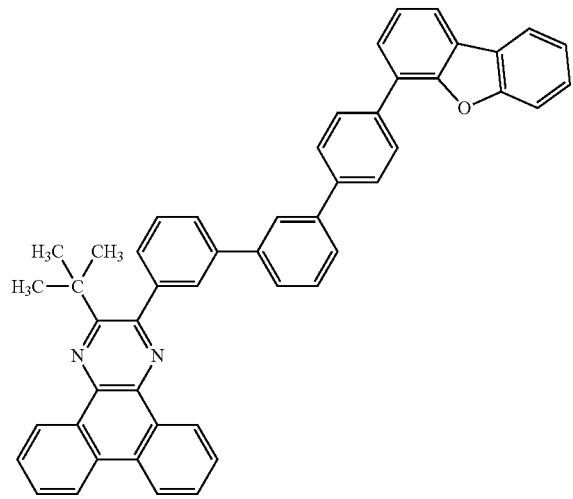
(435)
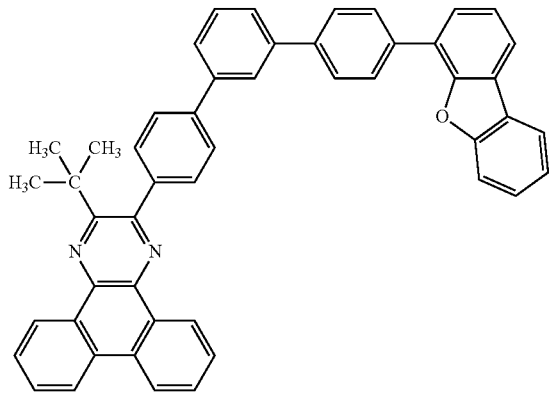
(436)
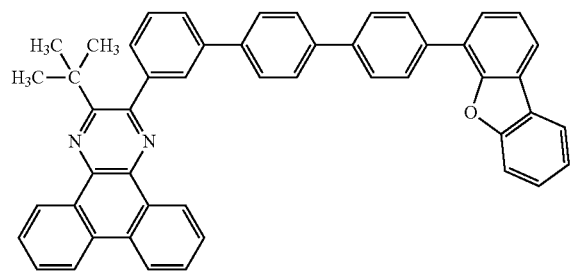
(437)
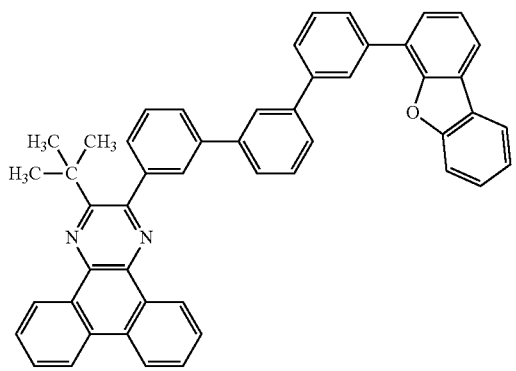
[Chemical formula 128]
(438)
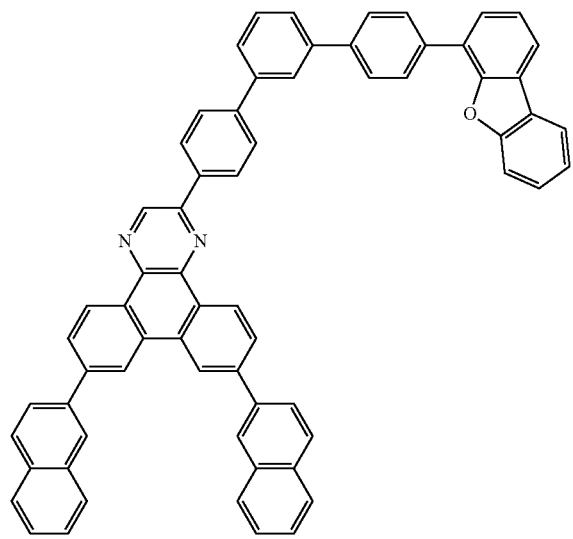
(439)
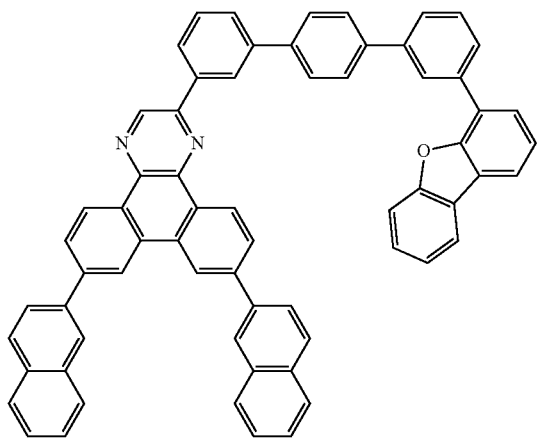

-continued
211
(440)
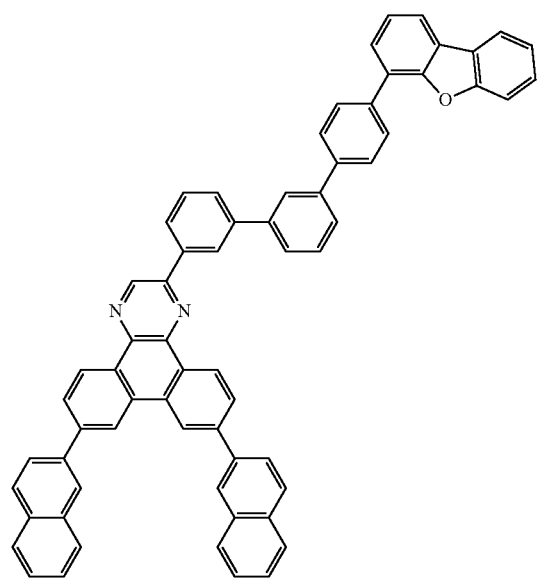
212
(441)
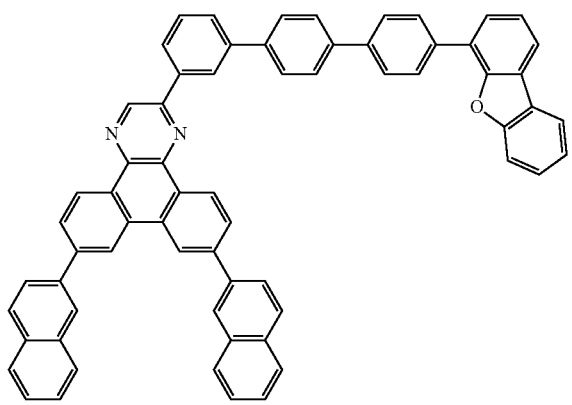
(442)
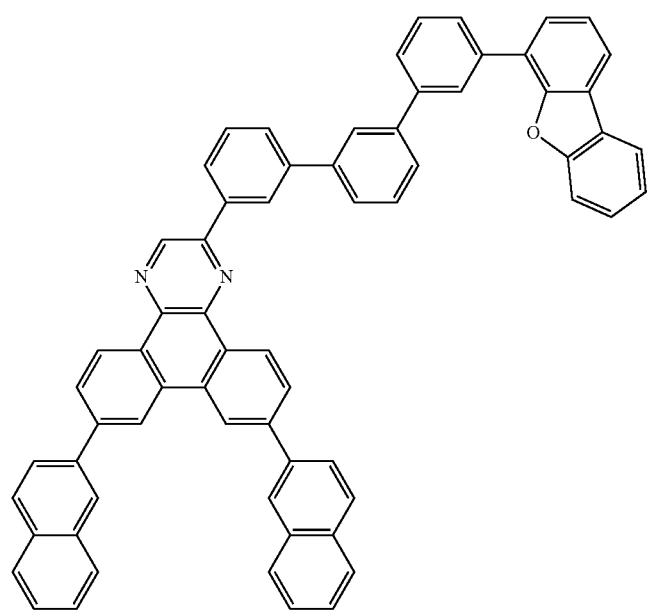

[Chemical formula 129]
(443)
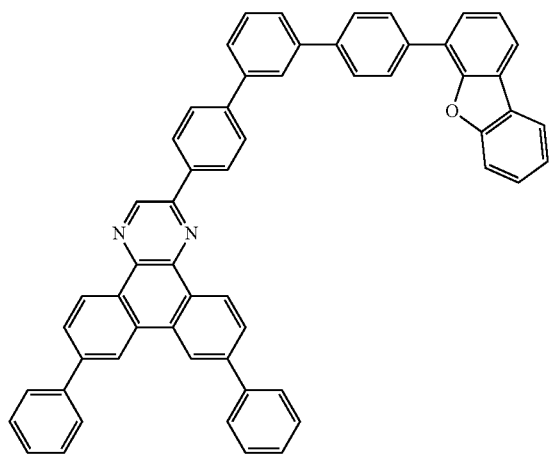
(444)
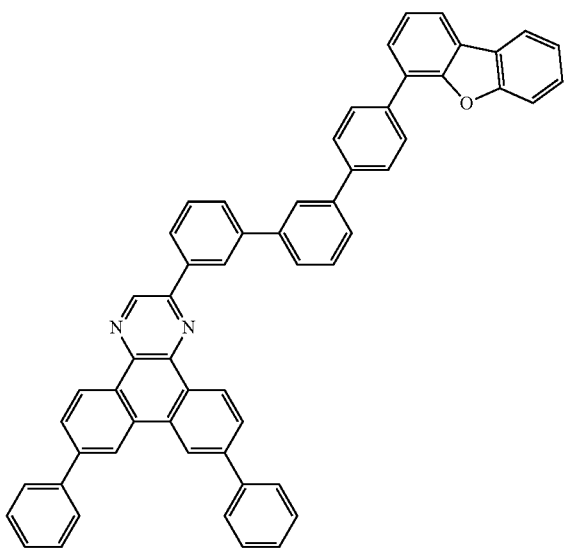
(445)
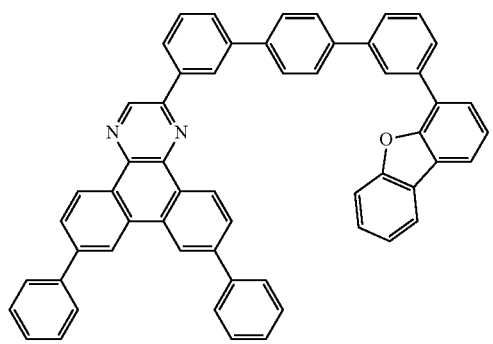
(446)
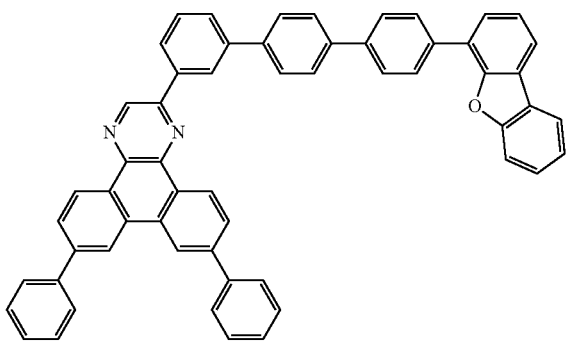
(447)
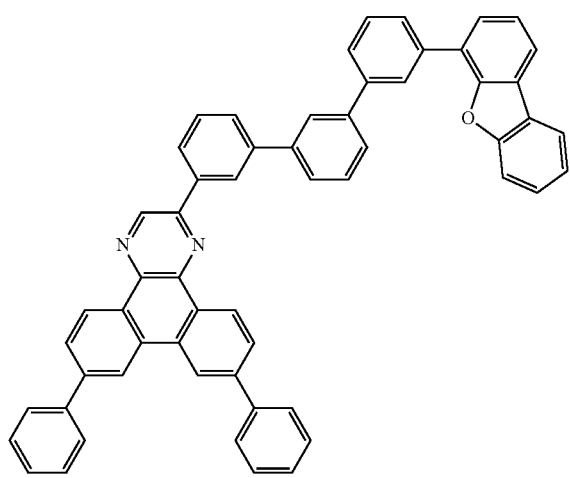

[Chemical formula 130]
(448)
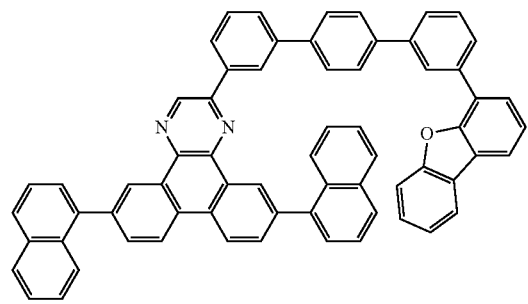
(449)
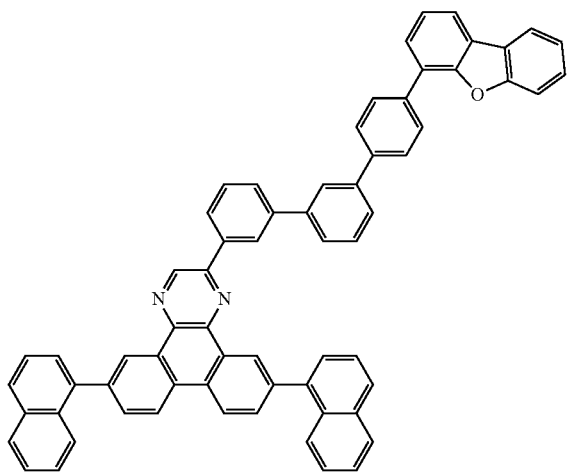
(450)
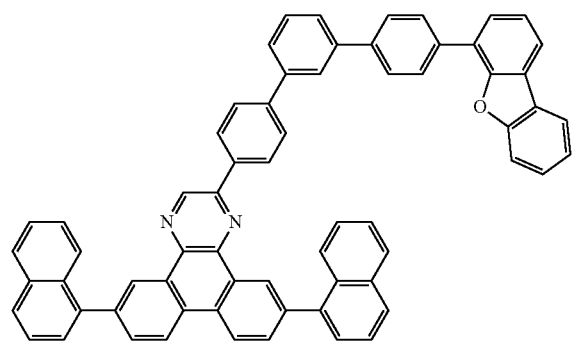
(451)
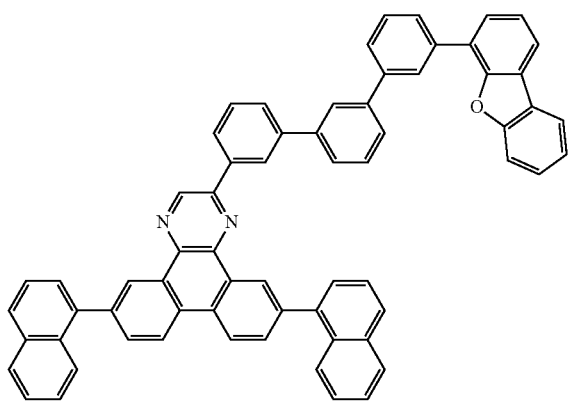
(452)
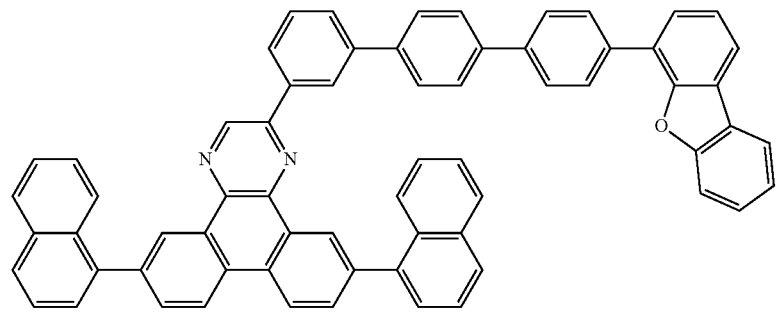

[Chemical formula 131]
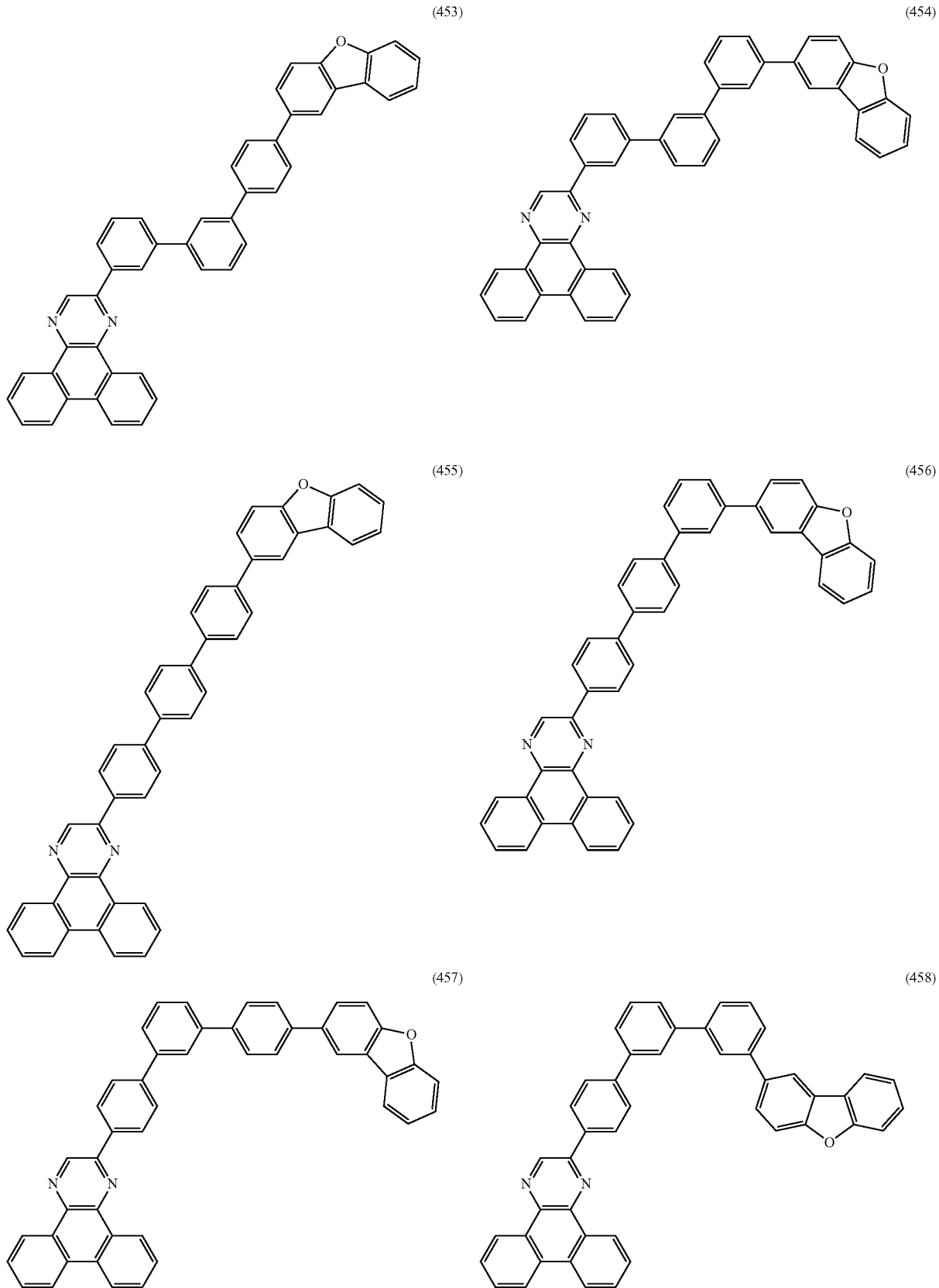

[Chemical formula 132]
(459)
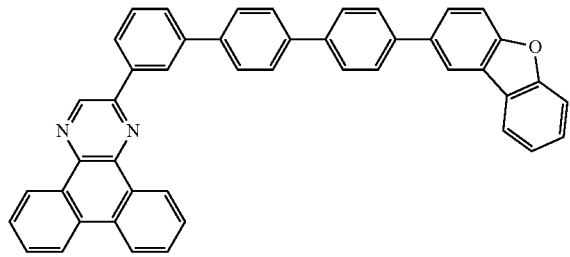
(460)
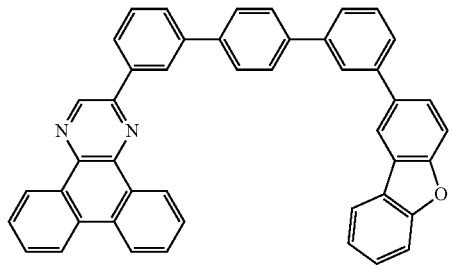
-continued
(461)
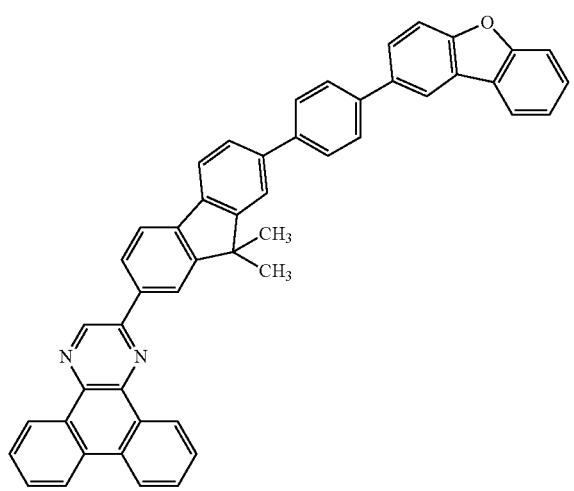
(462)
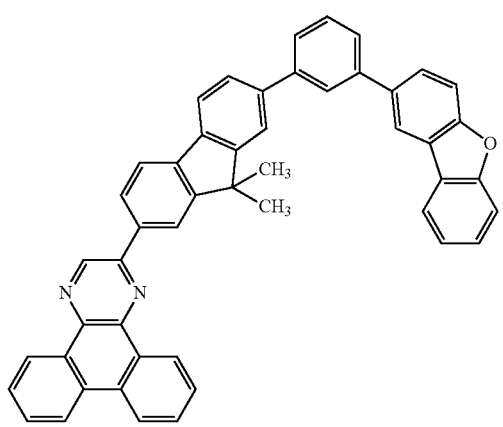
(463)
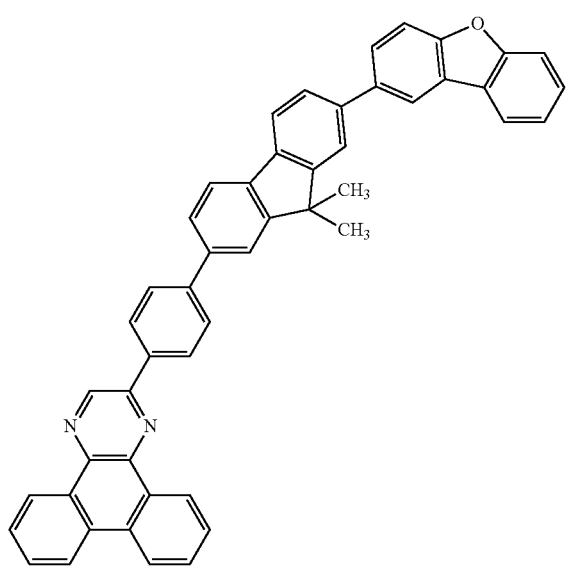
(464)
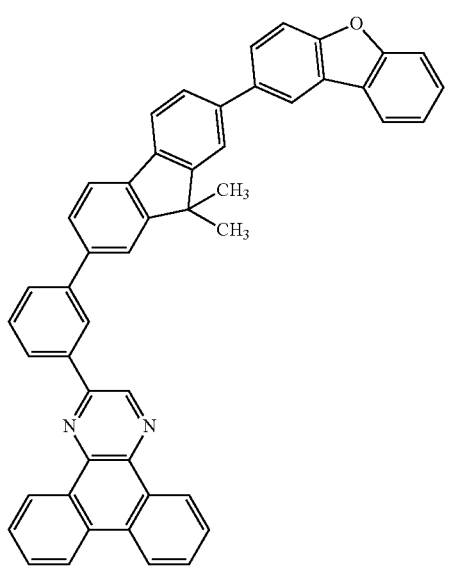

[Chemical formula 133]
(465)
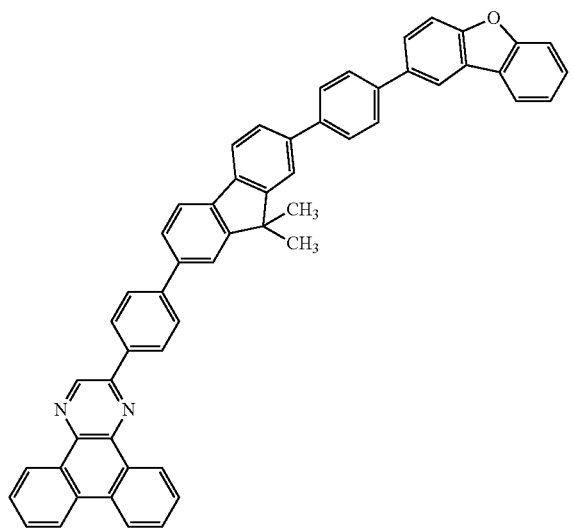
(466)
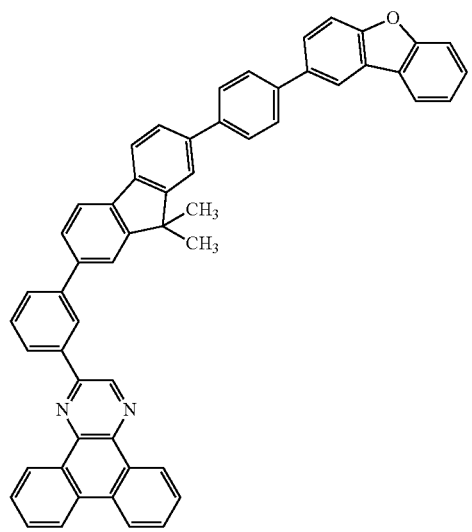
(467)
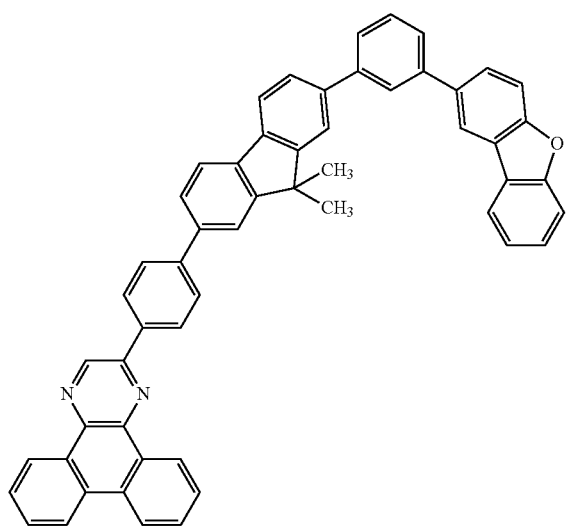
(468)
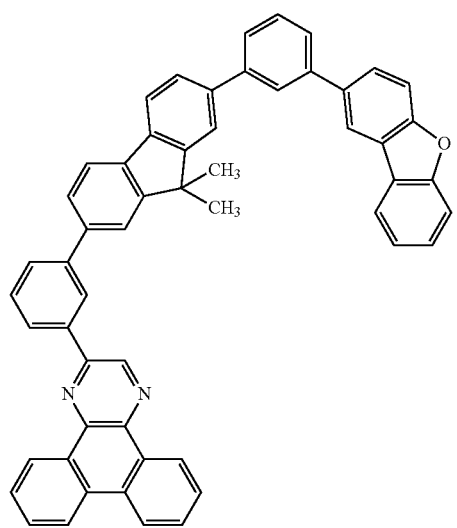

[Chemical formula 134]
(469) 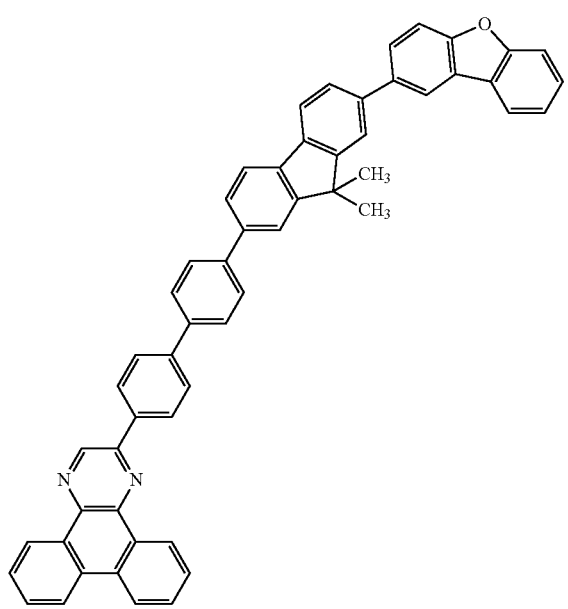
(470) 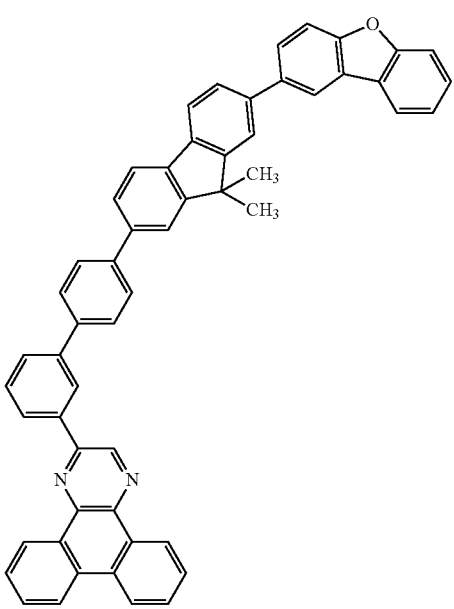
(471) 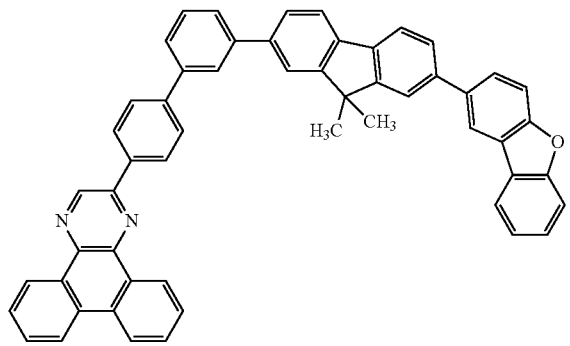
(472) 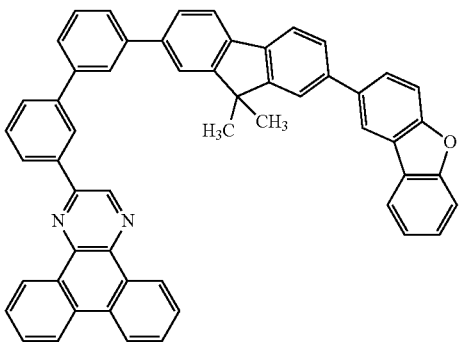
(473) 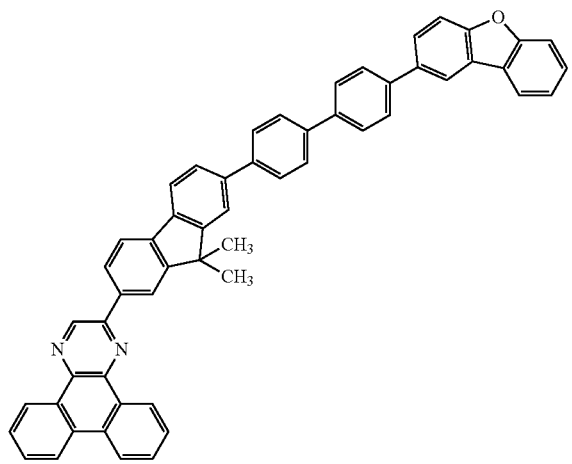
(474) 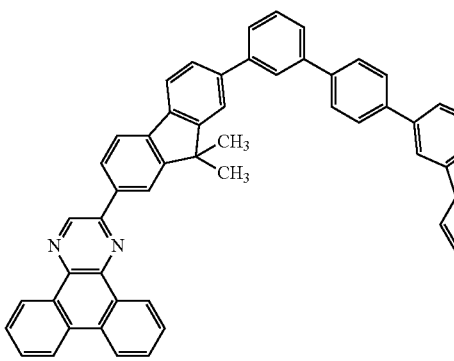

-continued
(475)
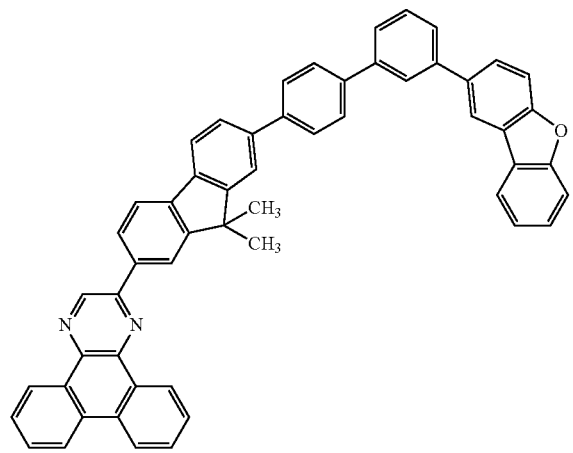
(476)
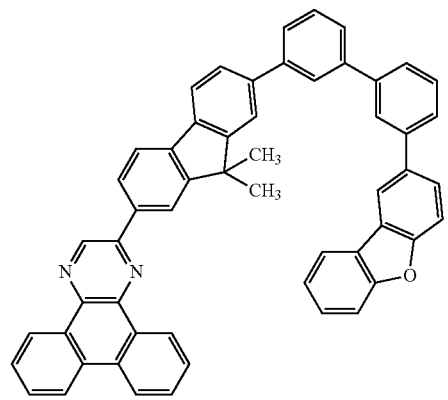
[Chemical formula 135]
(477)
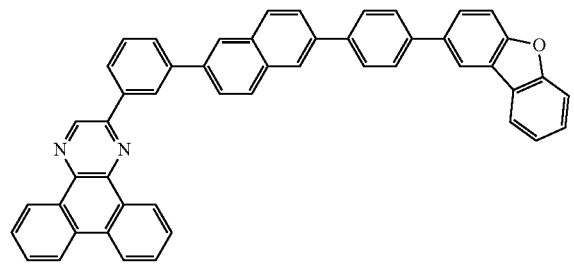
(478)
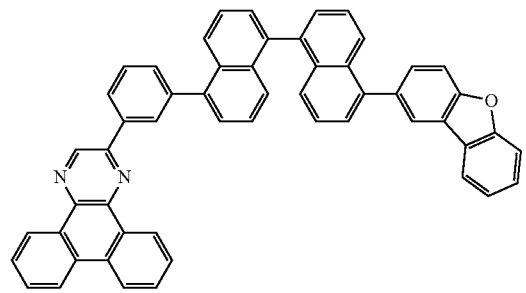
(479)
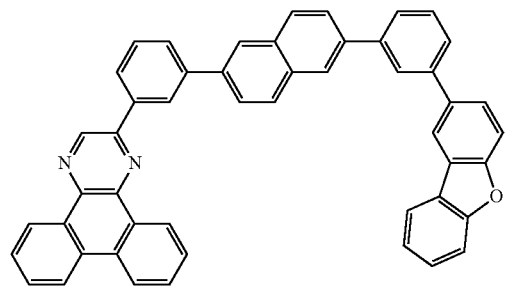
(480)
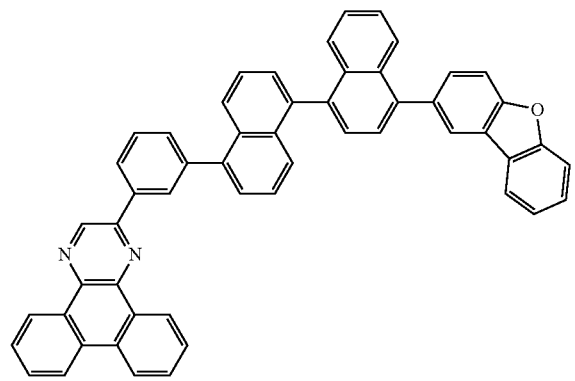
(481)
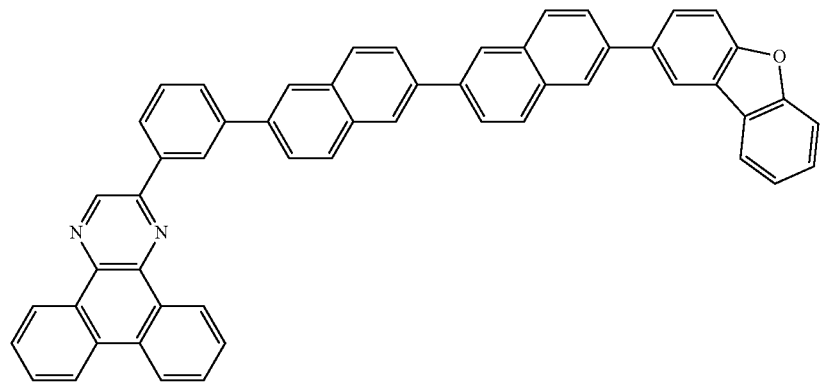

-continued
(482)
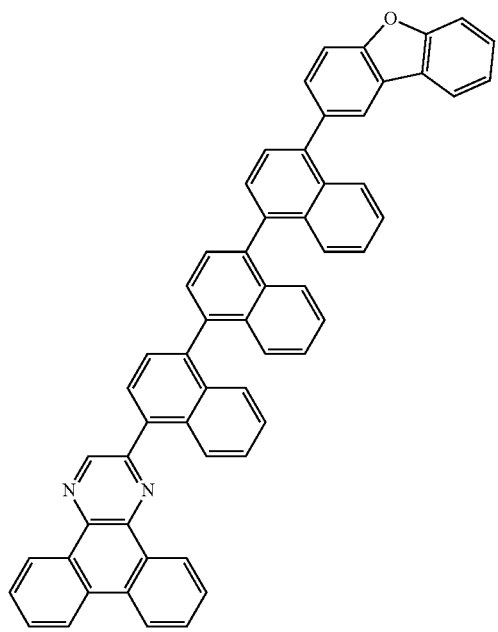
(483)
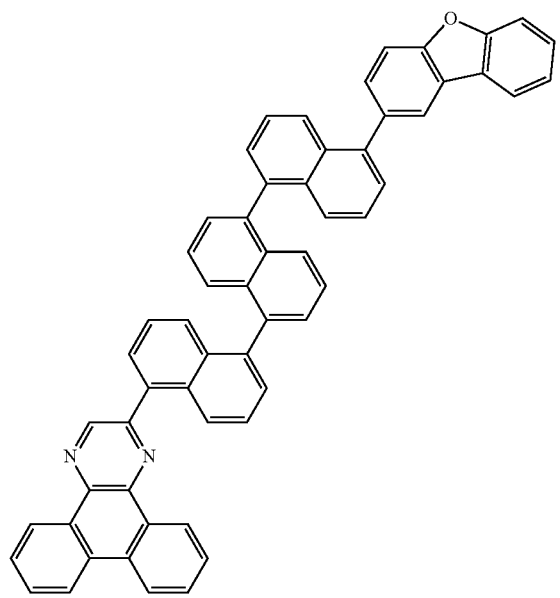
(484)
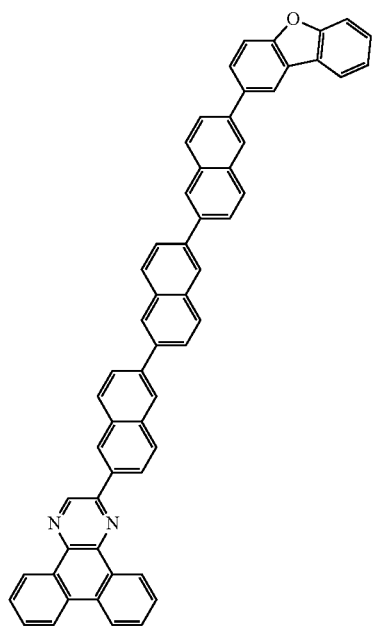
(485)
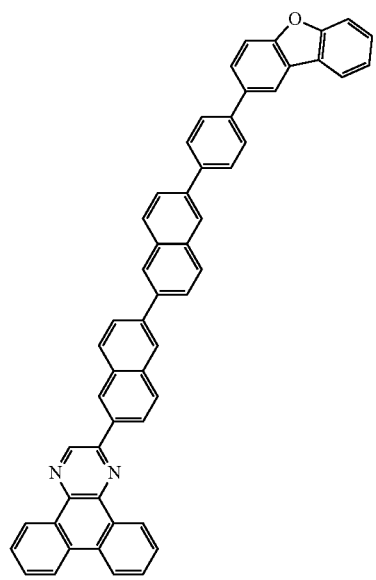
[Chemical formula 136]
(486)
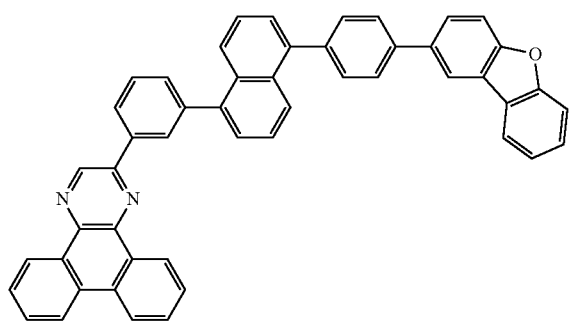
(487)
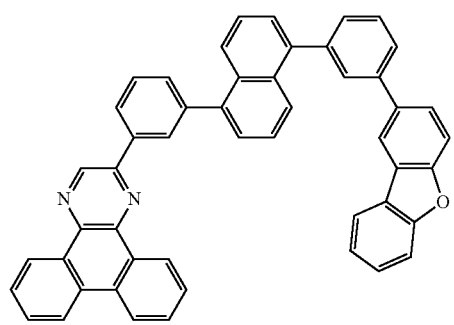

-continued
(488)
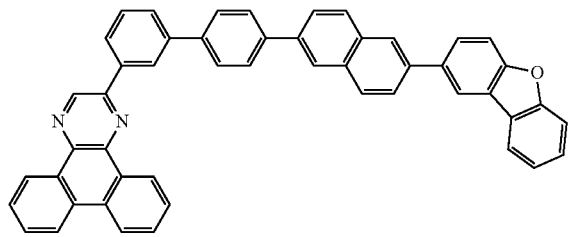
(489)
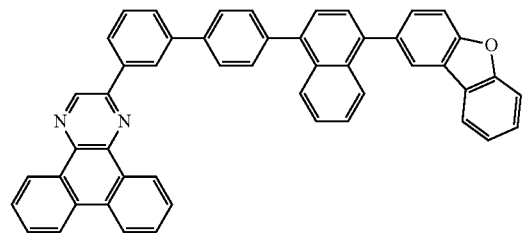
(490)
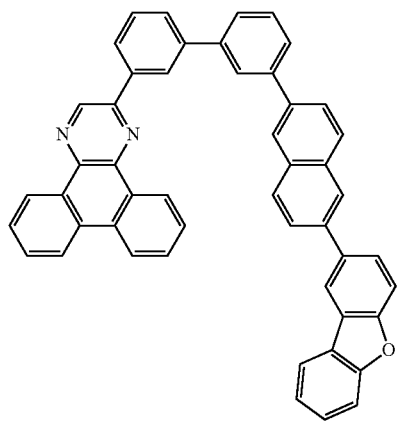
(491)
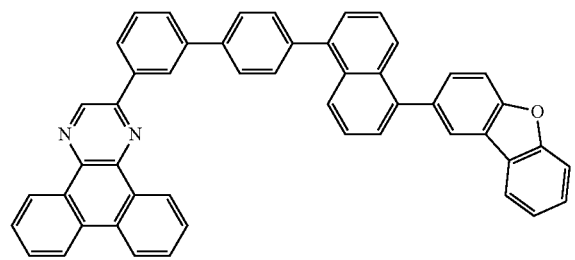
(492)
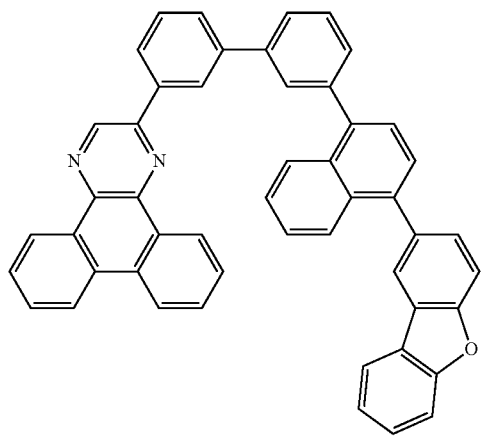
(493)
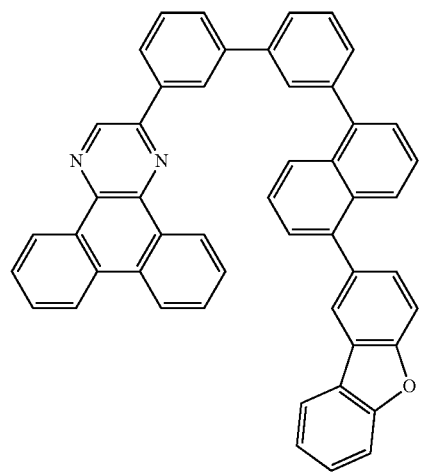

[Chemical formula 137]
(494)
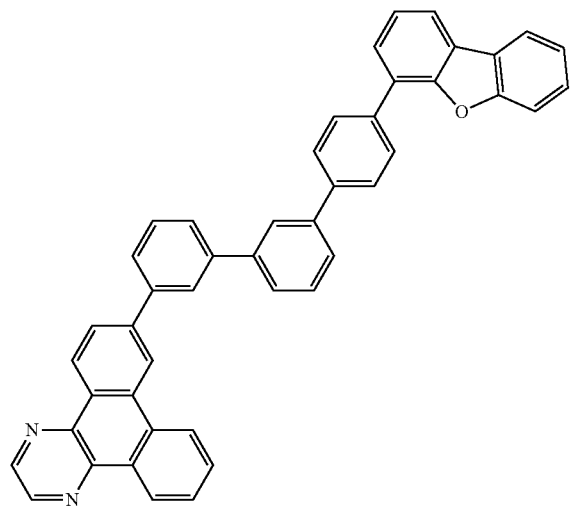
(495)
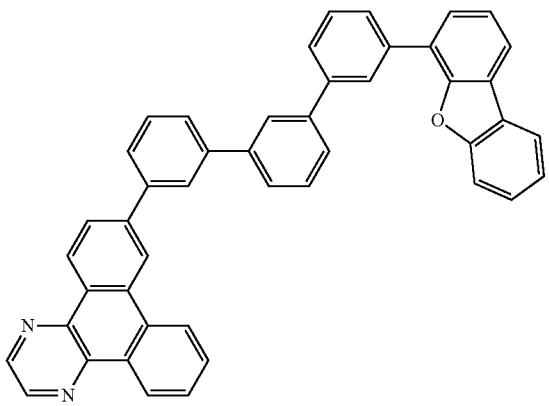
(496)
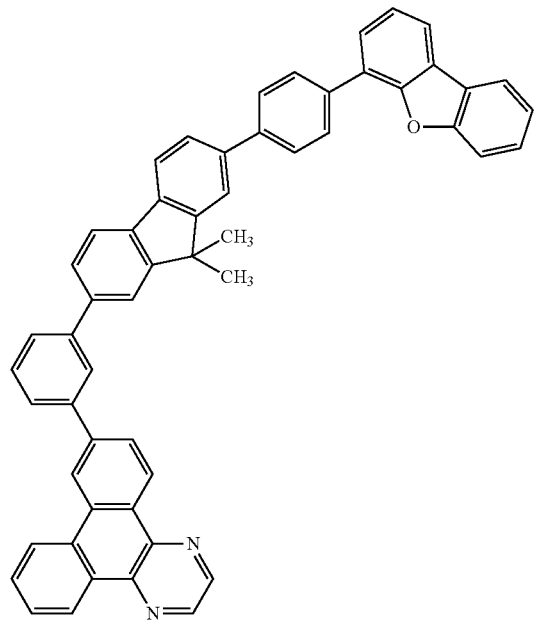
(497)
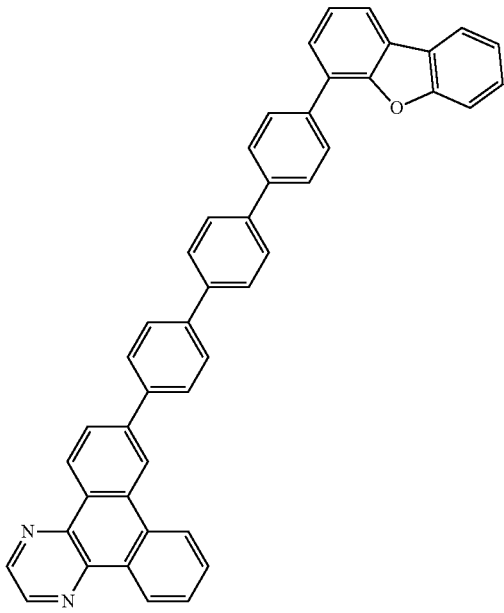

-continued
(498)
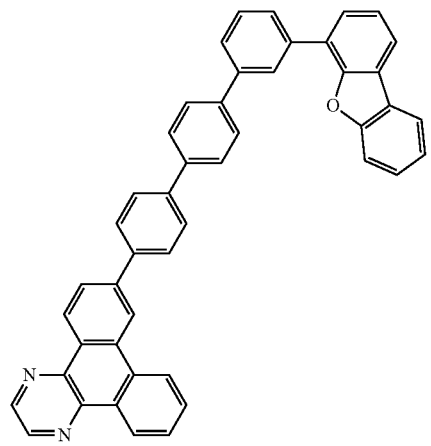
(499)
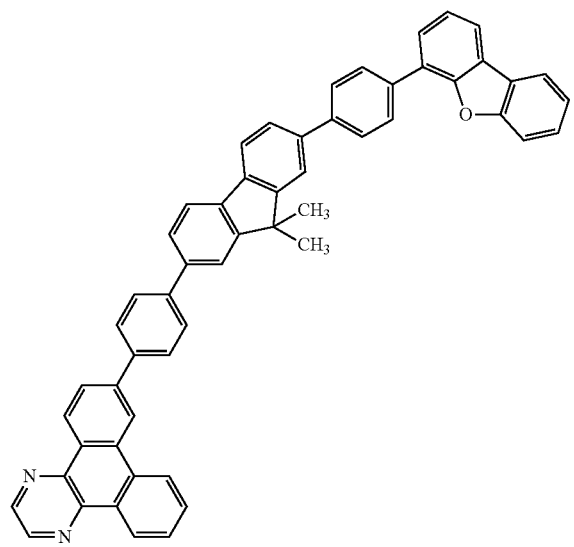
(500)
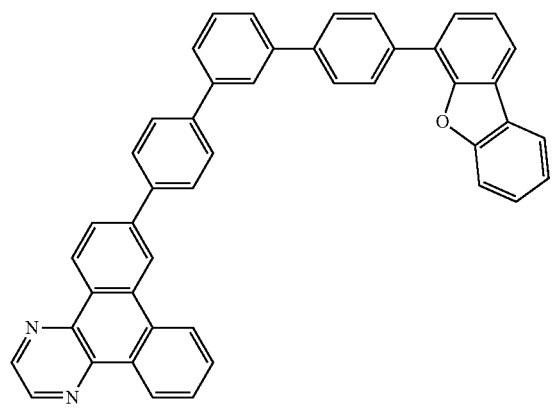
(501)
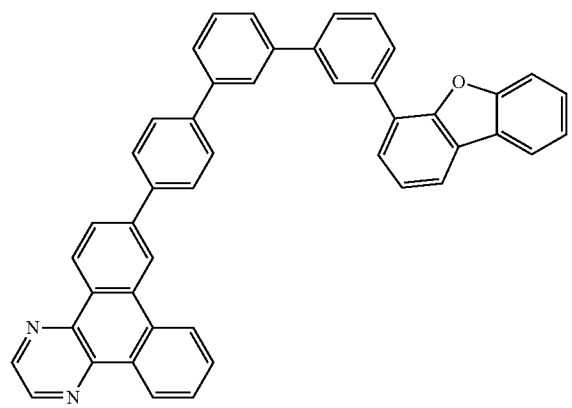
(502)
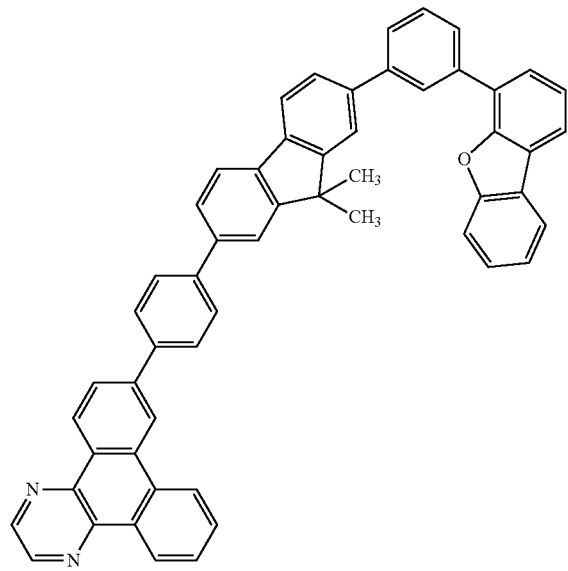

[Chemical formula 138]
(503)
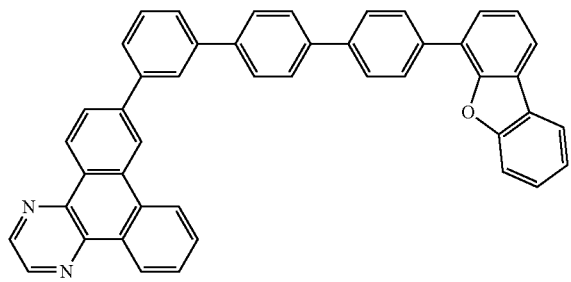
(504)
(505)
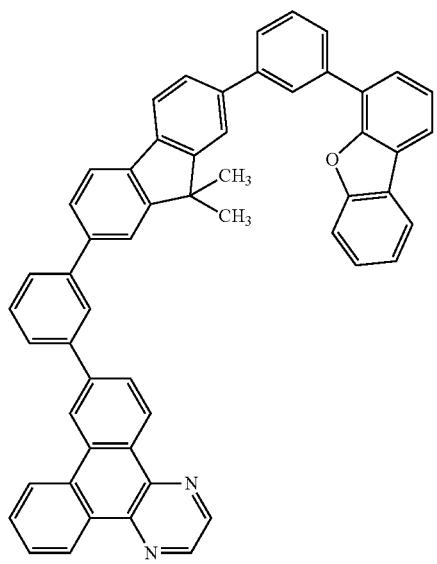
(506)
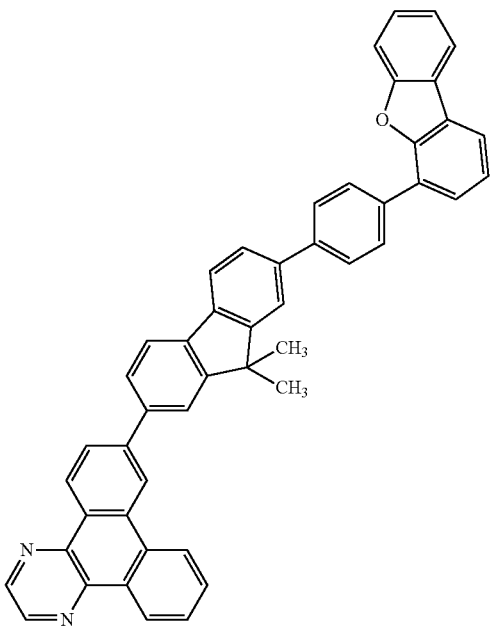
(507)
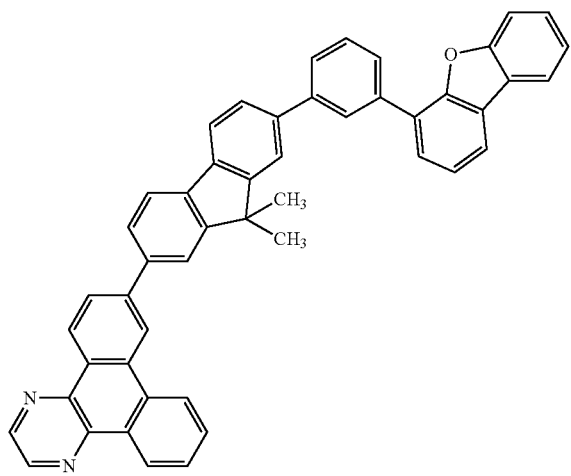
(508)
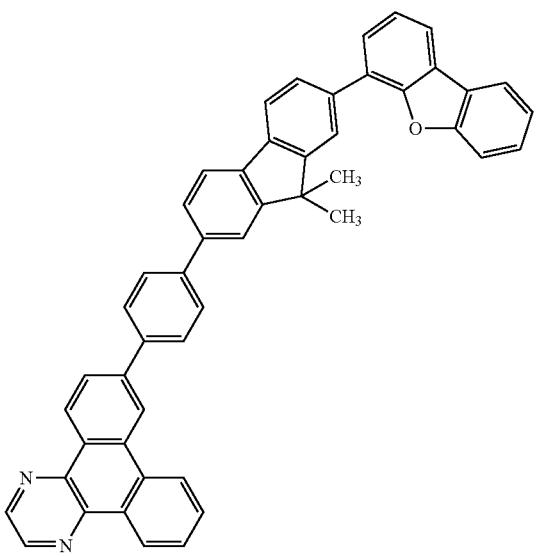

(509)
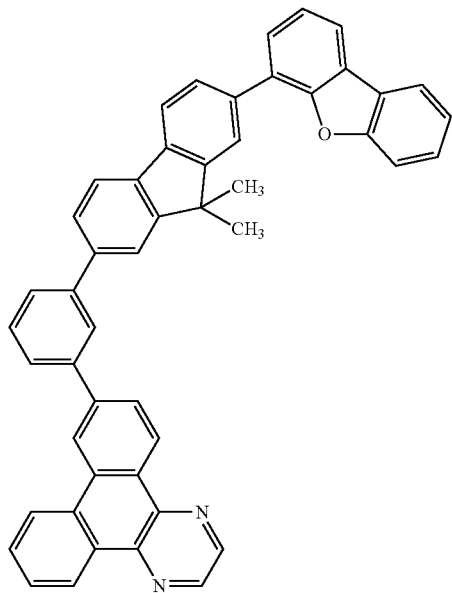
[Chemical formula 139]
(510)
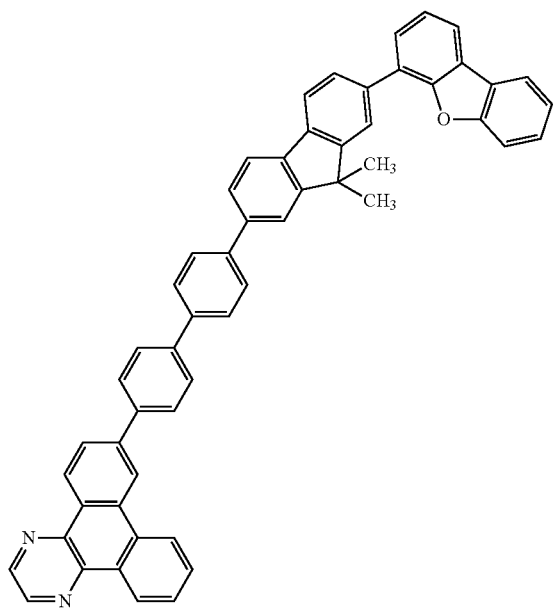
(511)
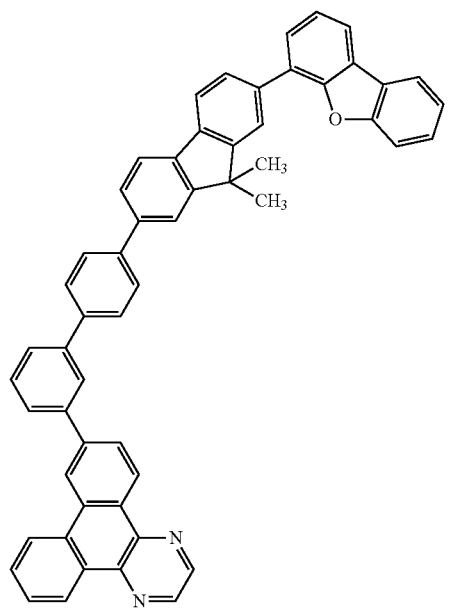
(512)
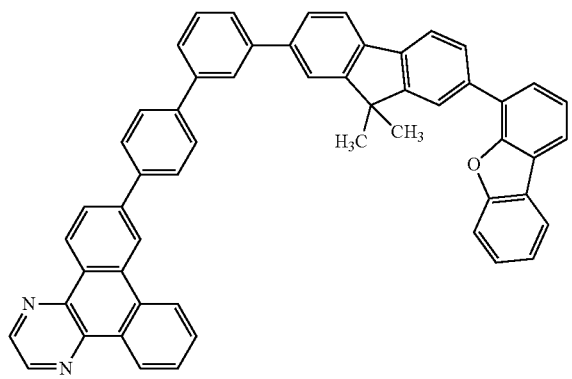
(513)
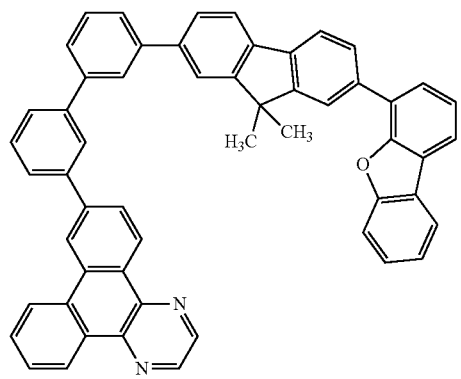

-continued
(514)
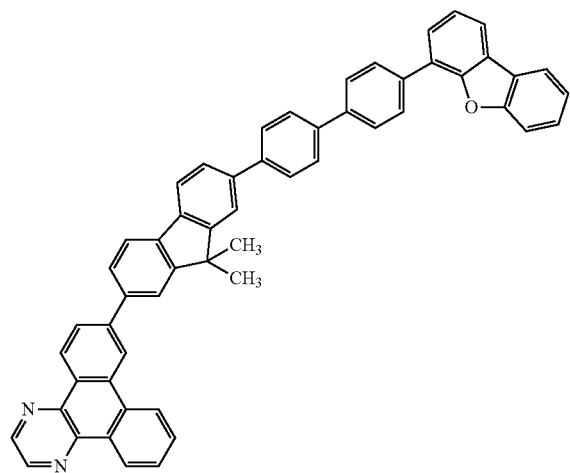
(515)
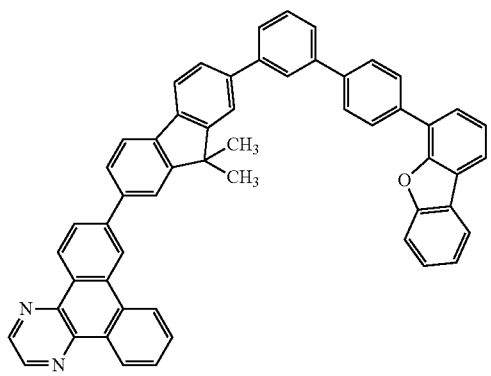
(516)
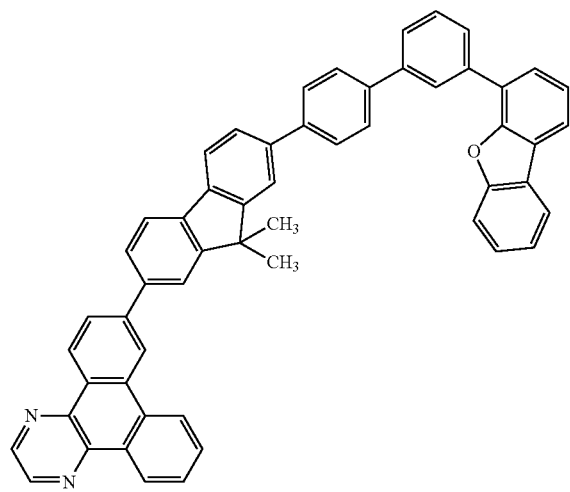
(517)
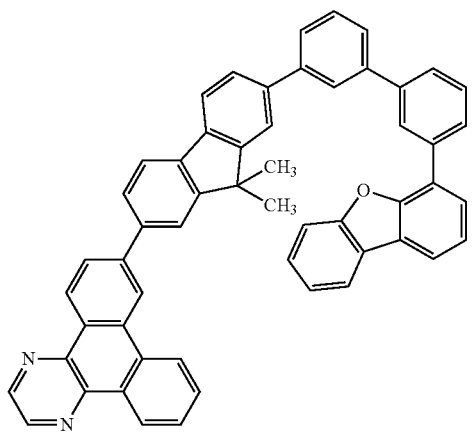
[Chemical formula 140]
(518)
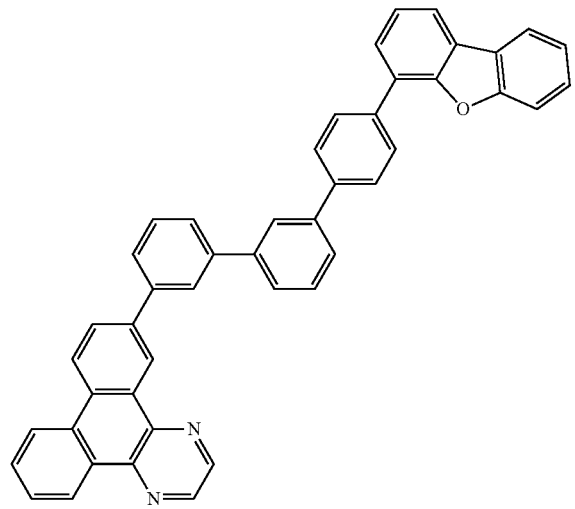
(519)
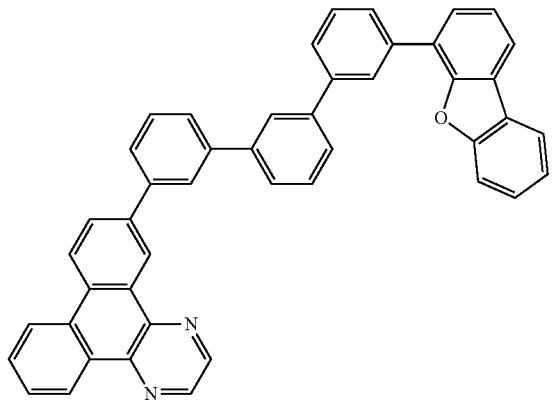

-continued
(520)
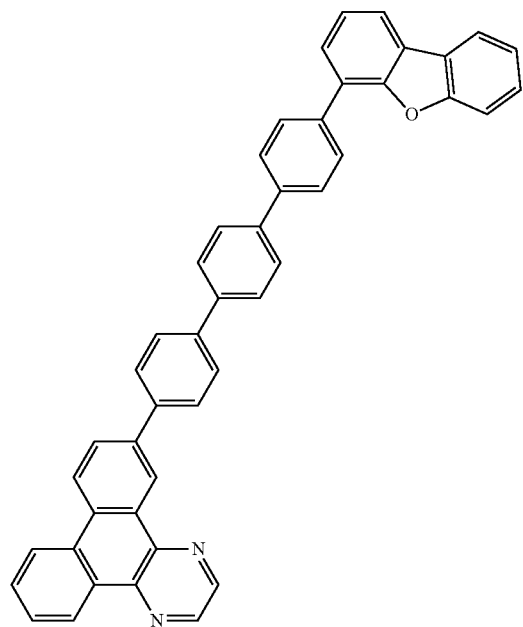
(521)
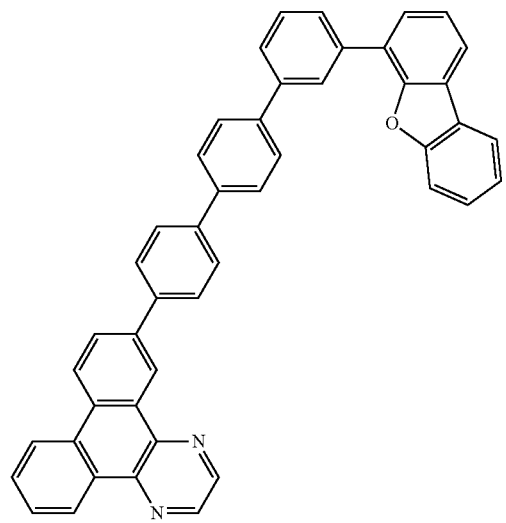
(522)
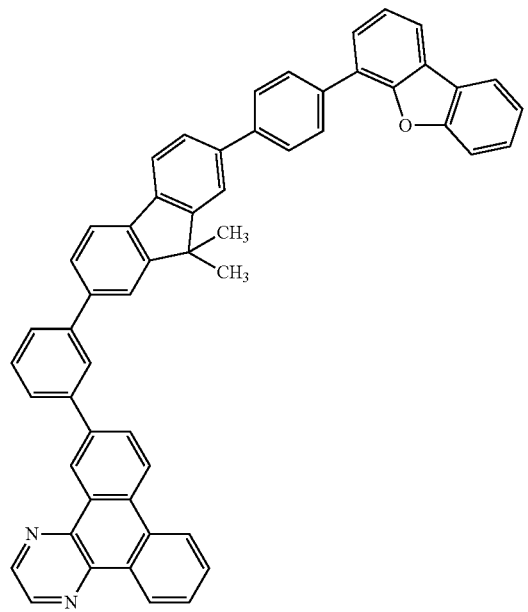
(523)

-continued
(524)
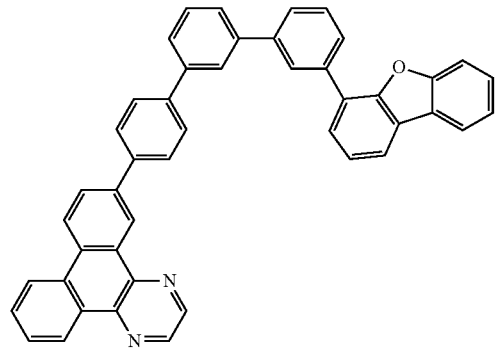
(525)
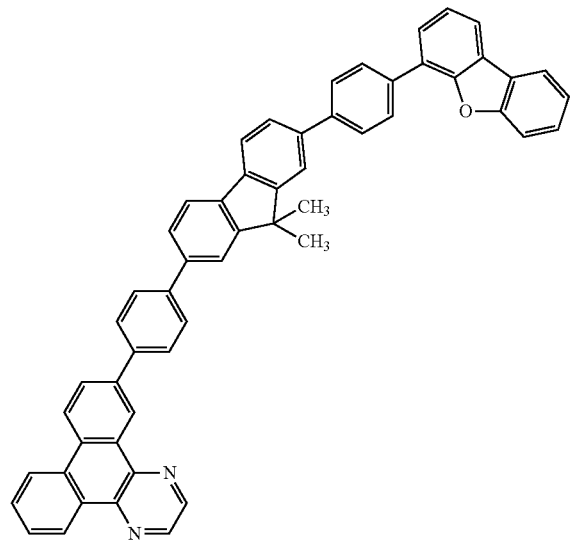
(525)
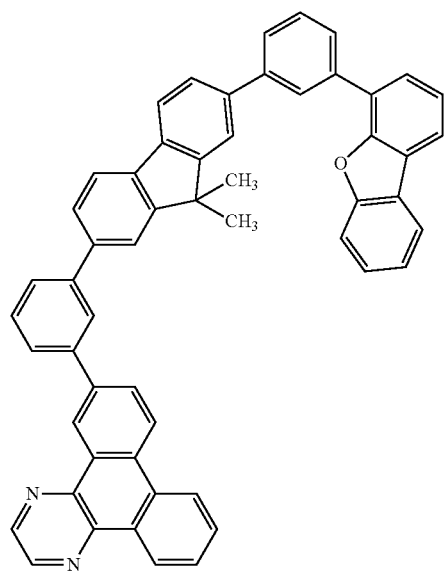
(526)
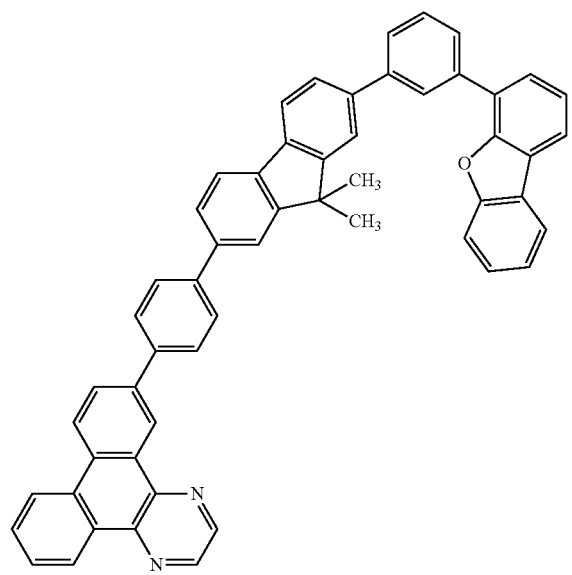
[Chemical formula 141]
(527)
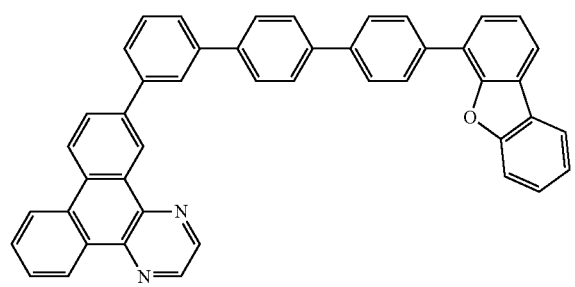
(528)
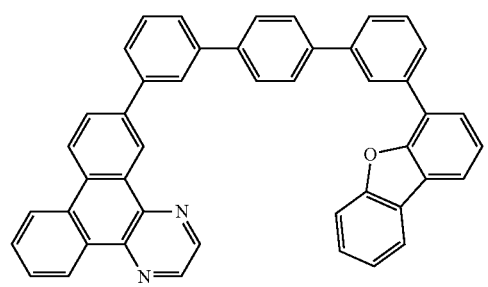

(529)
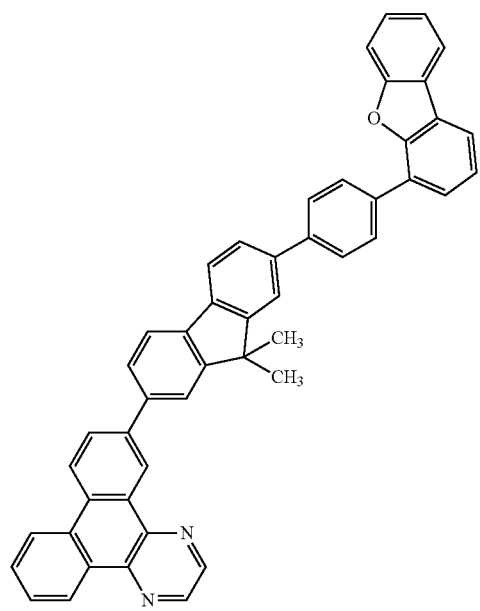
(530)
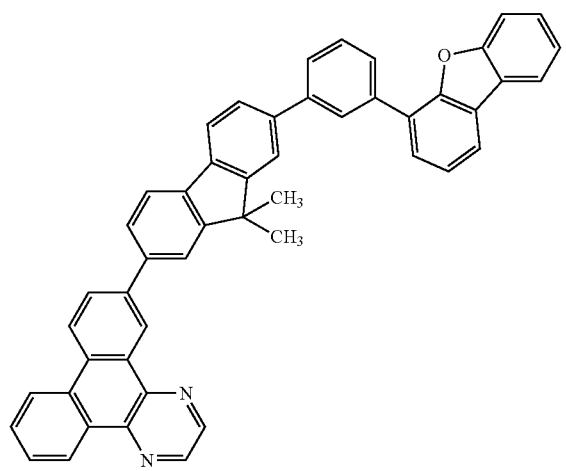
(531)
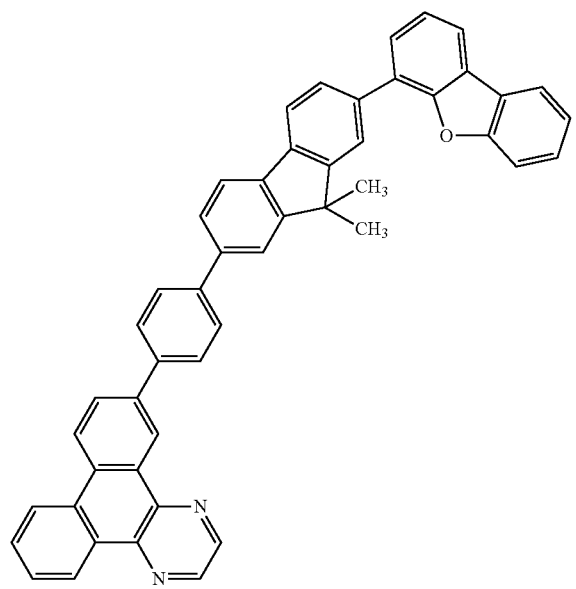
(532)
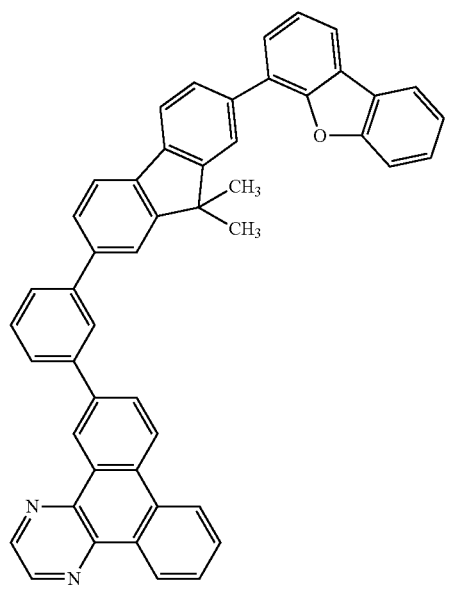

[Chemical formula 142]
(533)
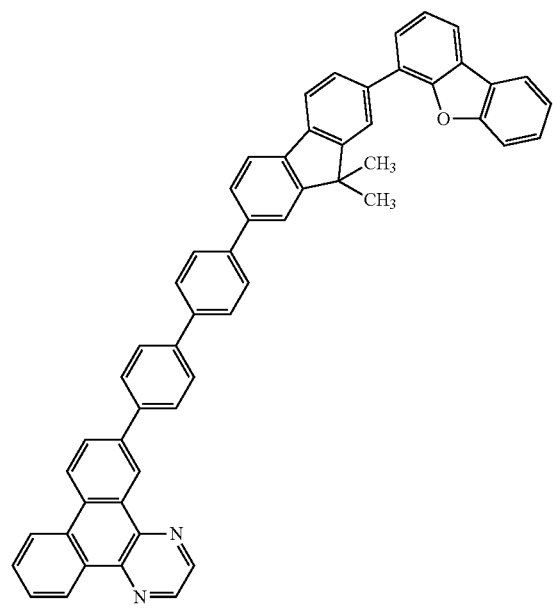
(534)
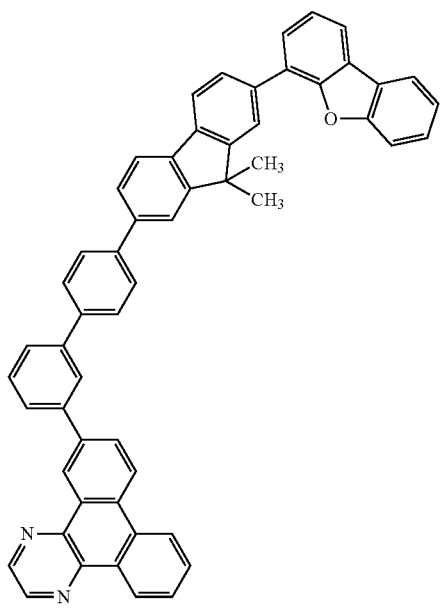
(535)
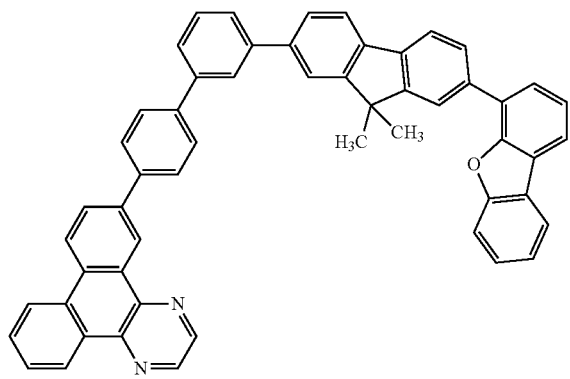
(536)
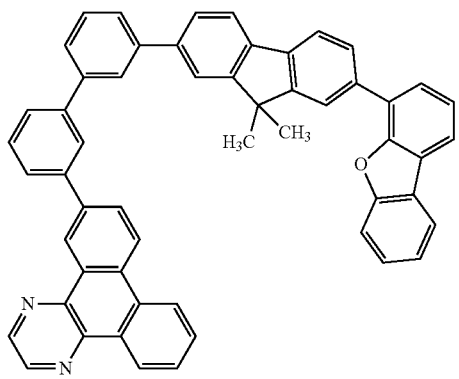
(537)
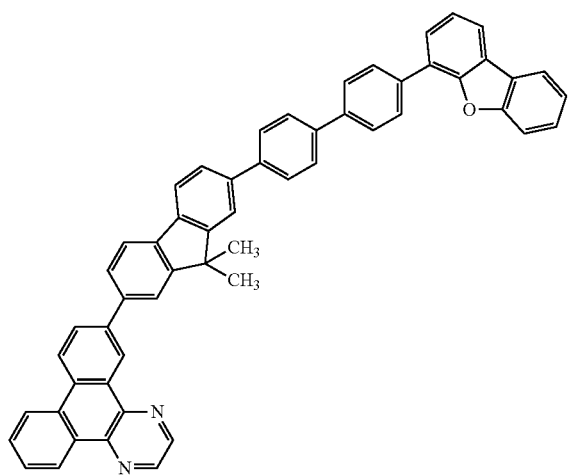
(538)
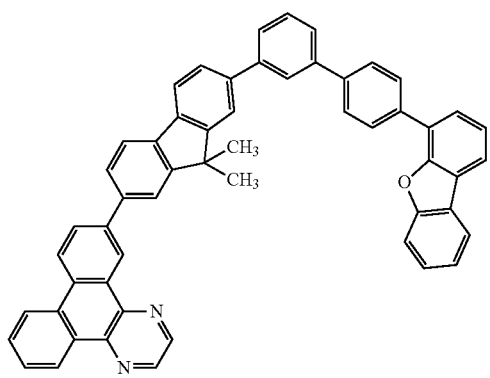

(539)
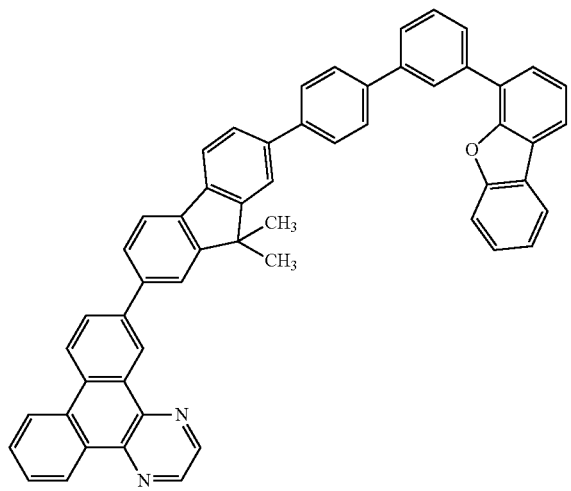
(540)
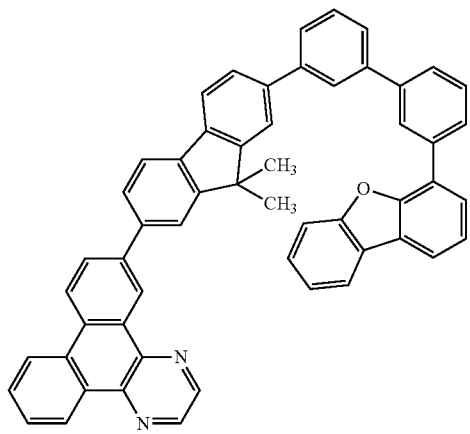
[Chemical formula 143]
(541)
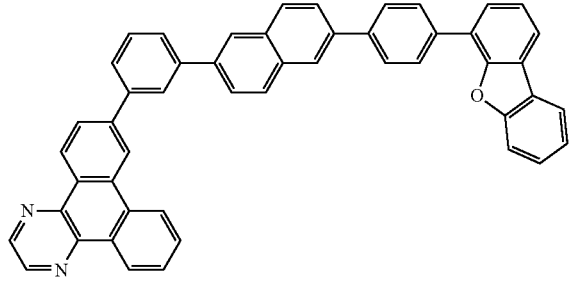
(542)
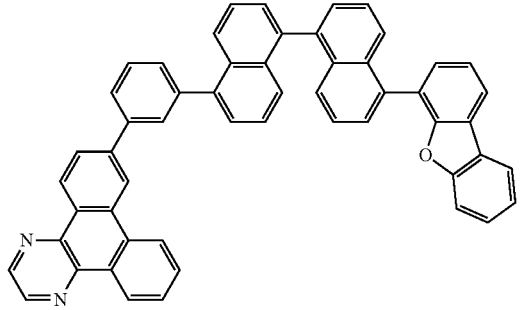
(543)
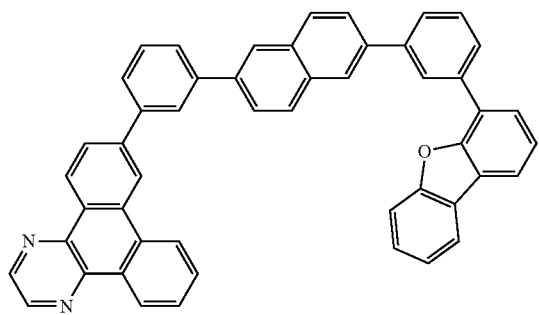
(544)
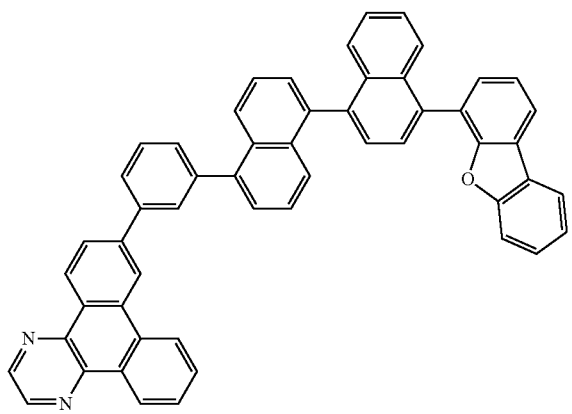

(545)
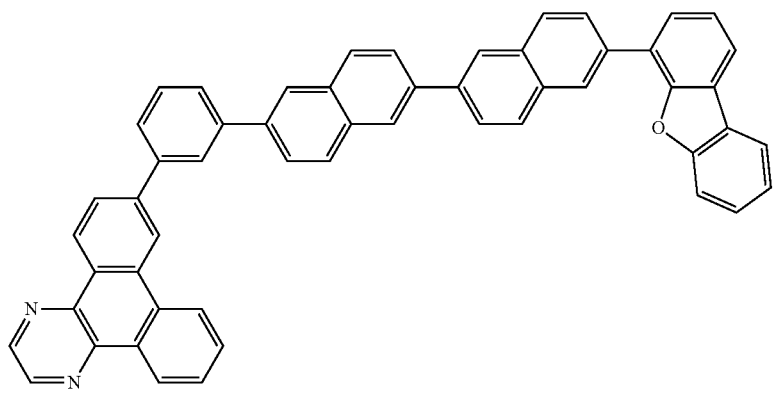
(546)
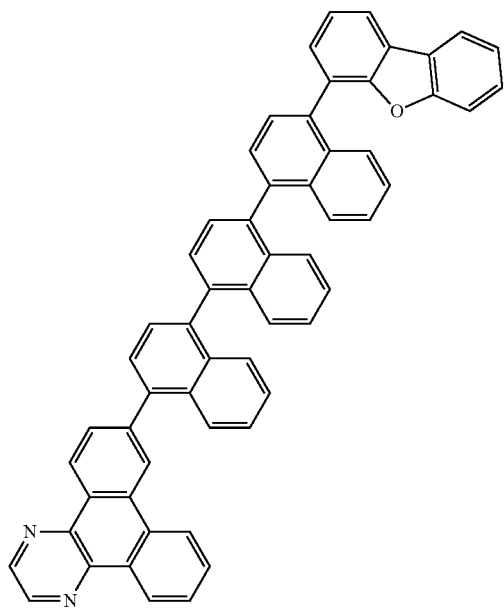
(547)
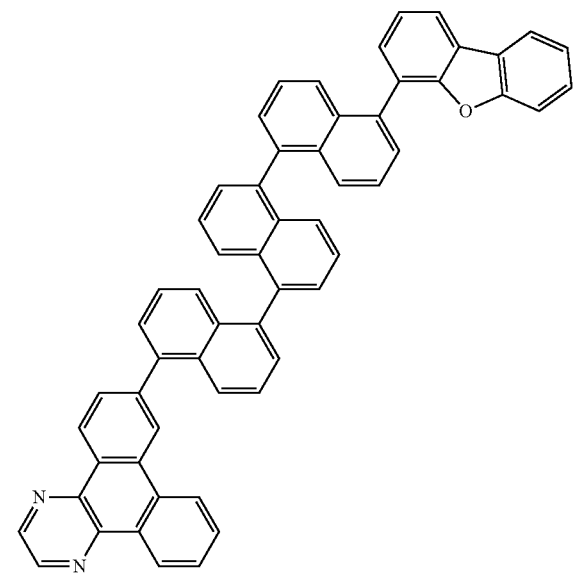
(548)
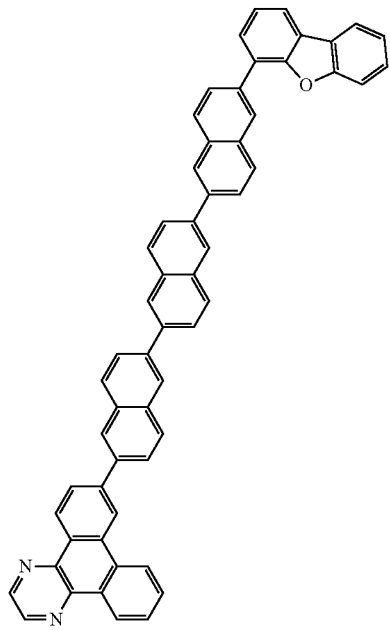
(549)
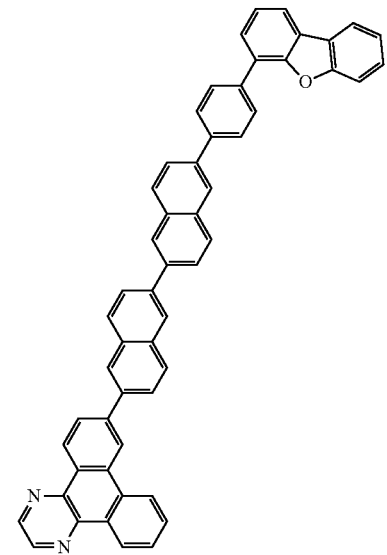

-continued
(550)
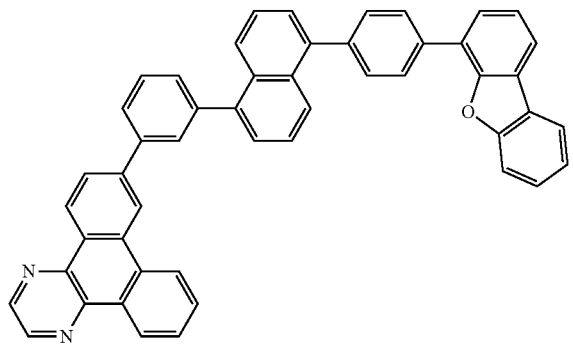
(551)
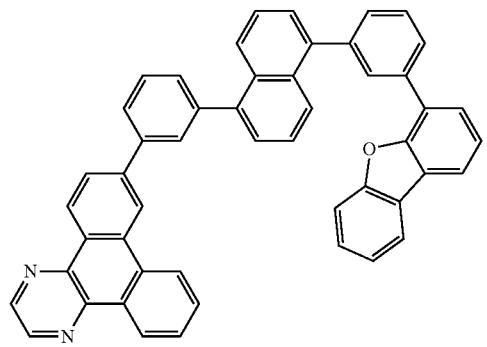
[Chemical formula 144]
(552)
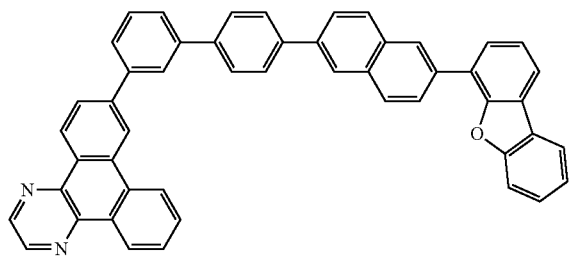
(553)
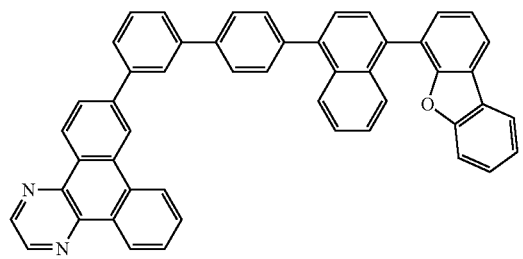
(554)
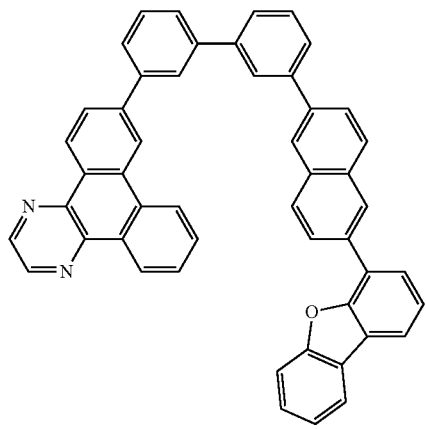
(555)
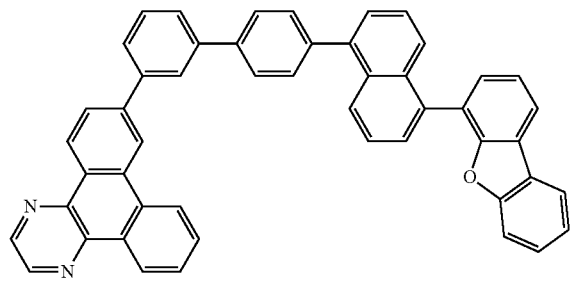
(556)
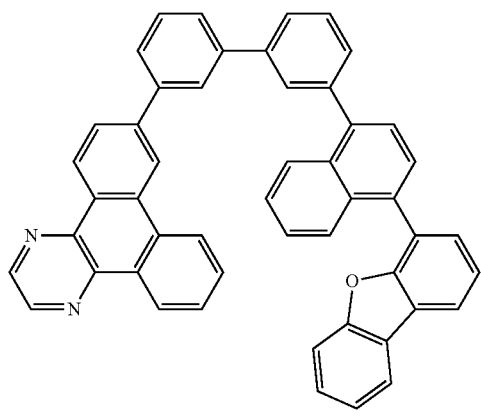
(557)
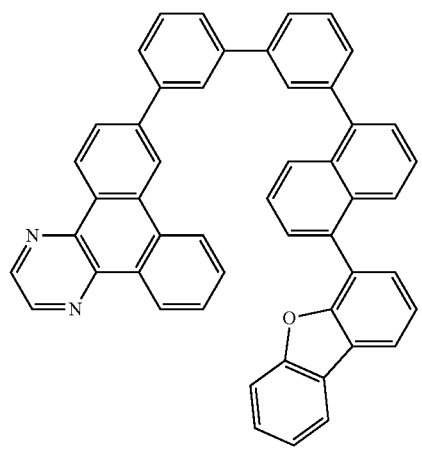

[Chemical formula 145]
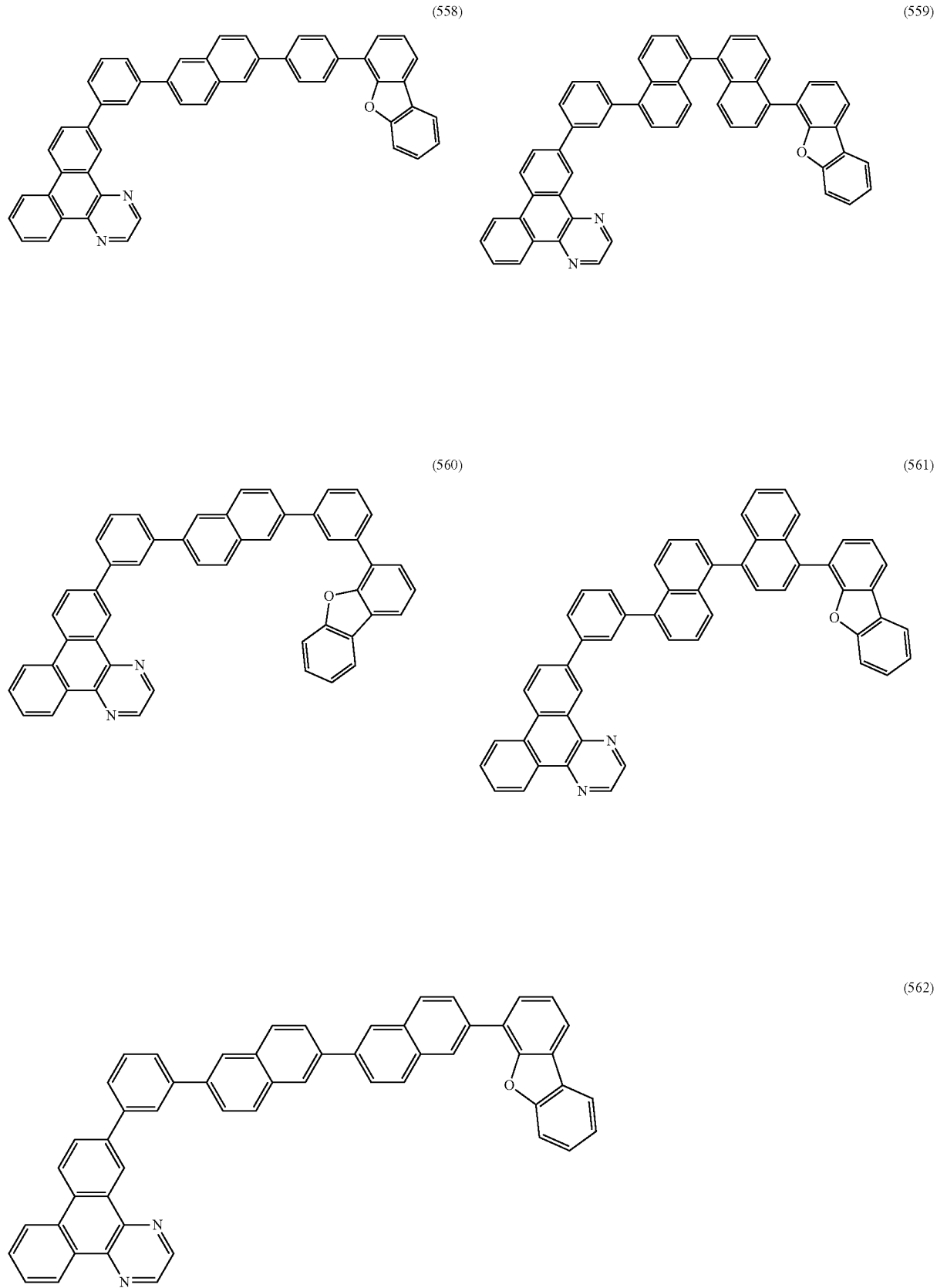

-continued
(563)
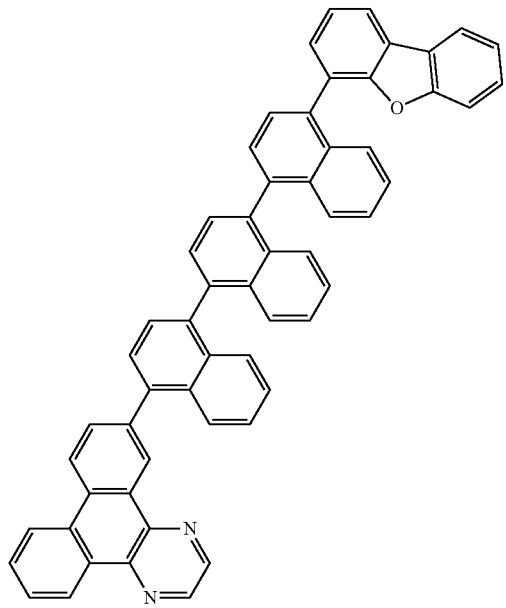
(564)
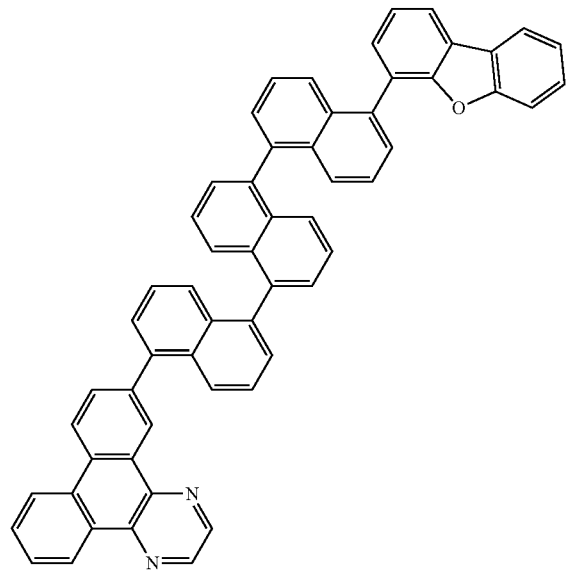
(565)
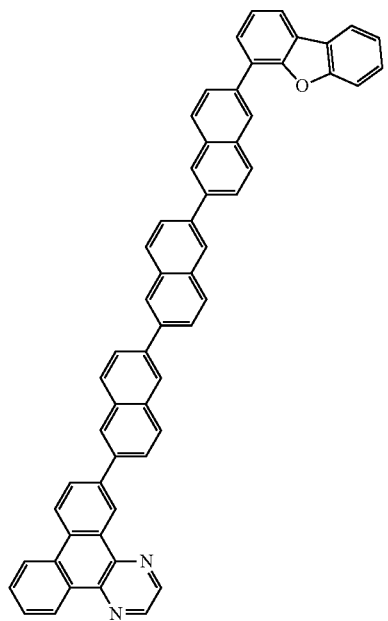
(566)
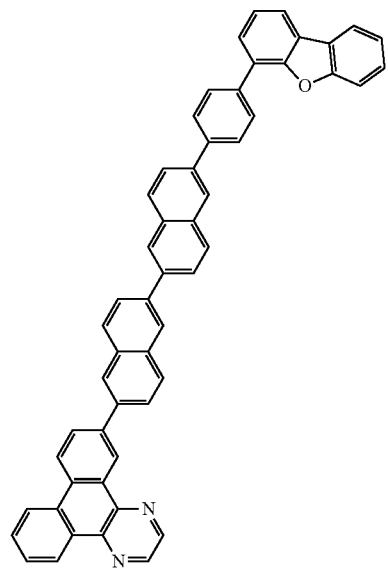
[Chemical formula 146]
(567)
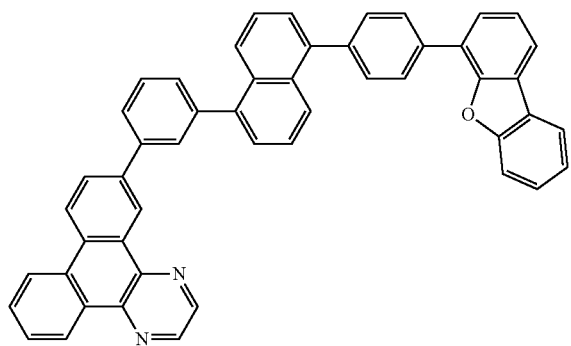
(568)
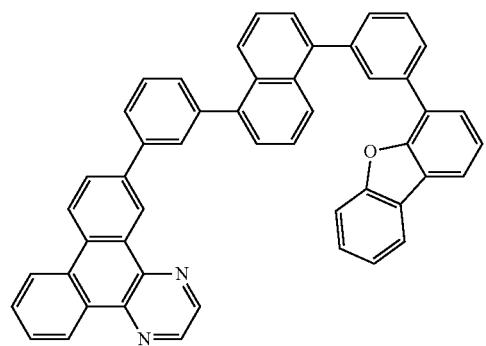

-continued
(569)
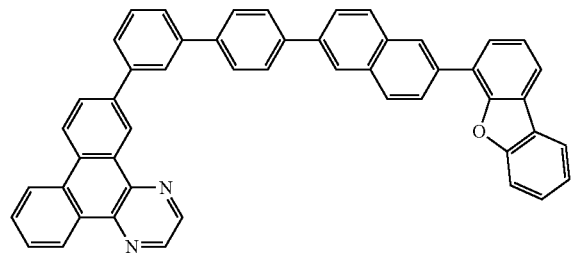
(570)
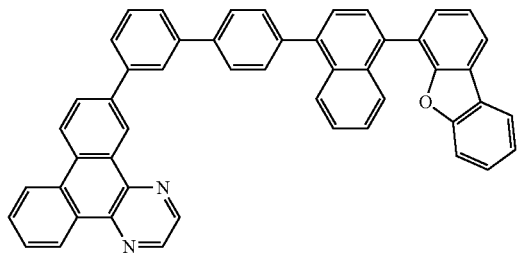
(571)
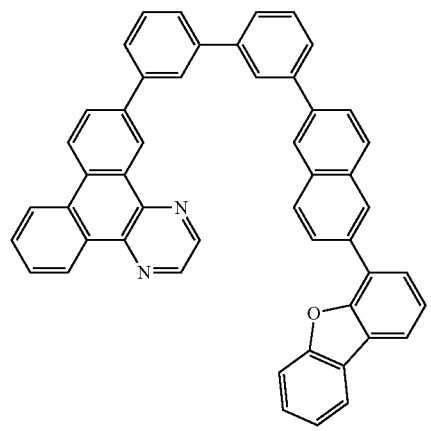
(572)
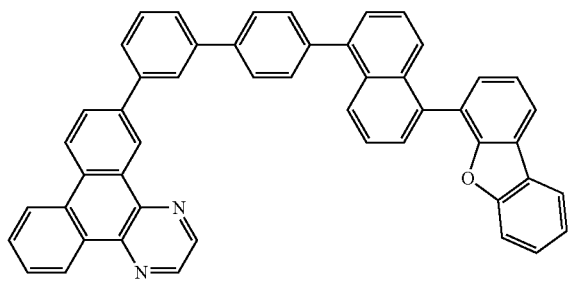
(573)
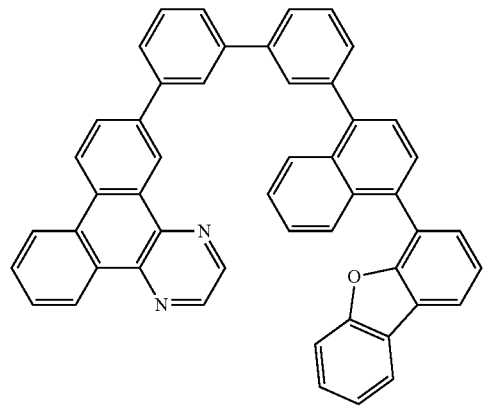
(574)
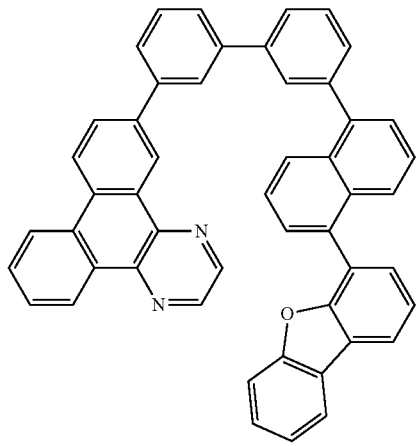

[Chemical formula 147]
(600)
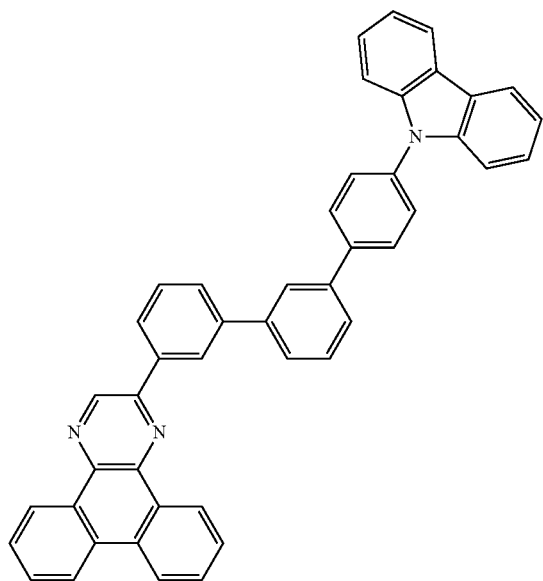
(601)
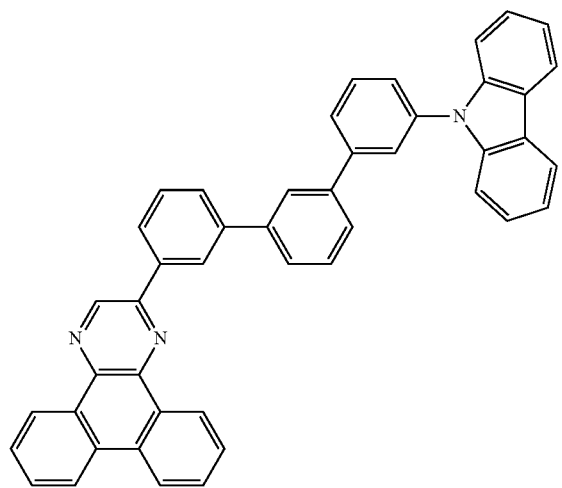
(602)
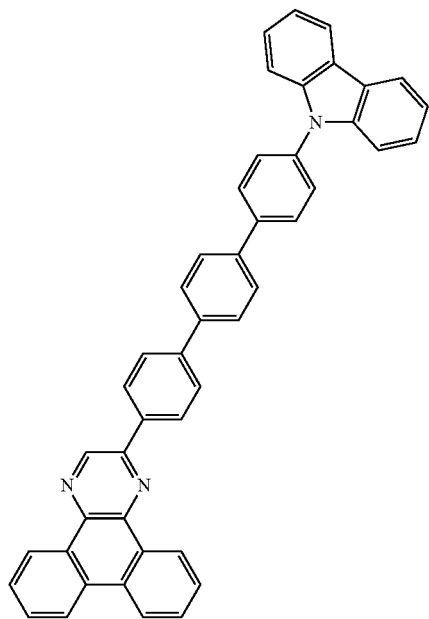
(603)
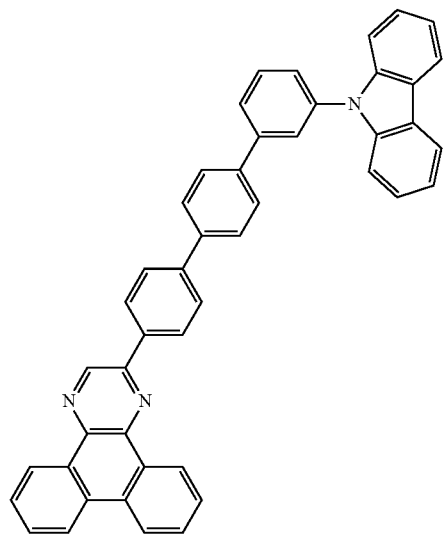

-continued
(604)
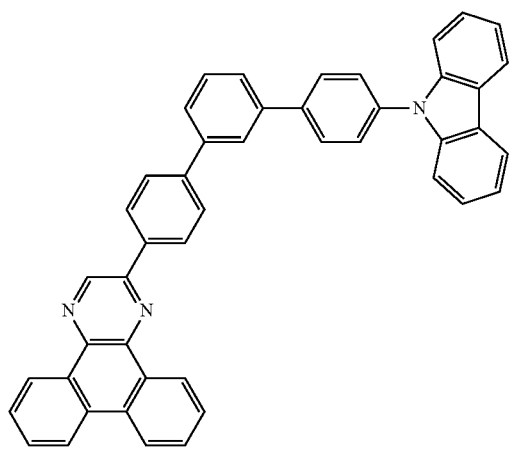
(605)
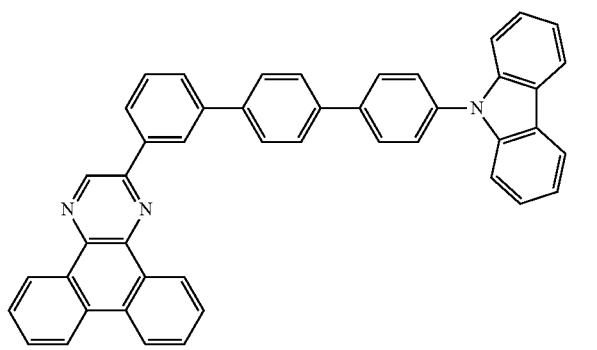
(606)
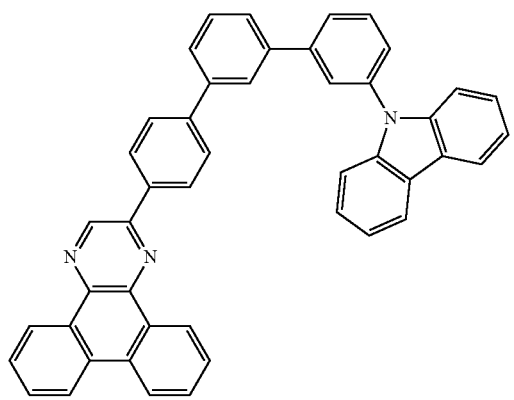
(607)
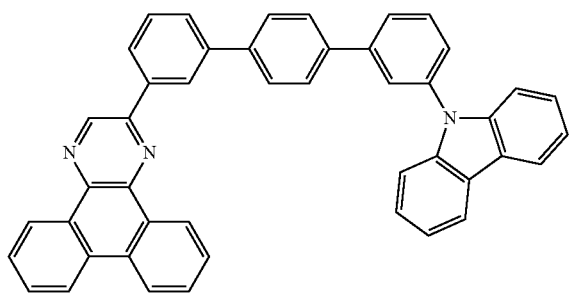
(608)
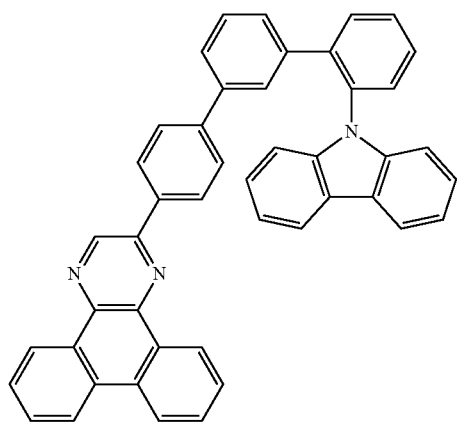
(609)
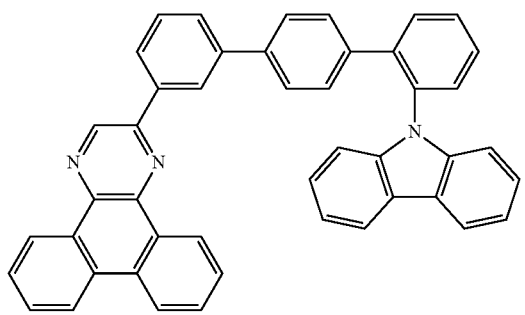

[Chemical formula 148]
(610)
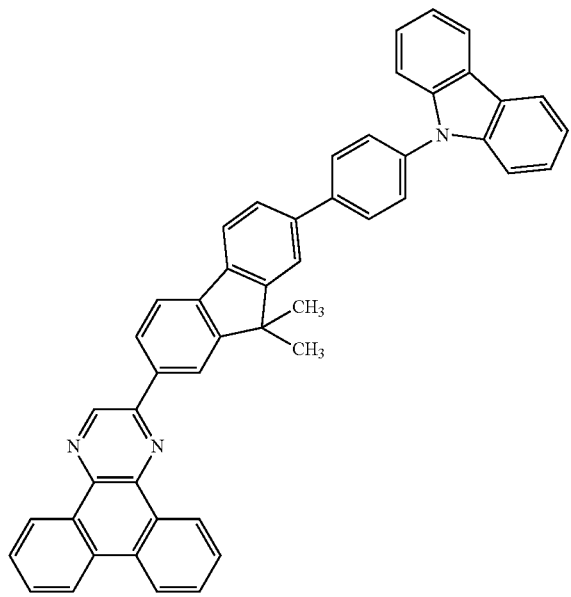
(611)
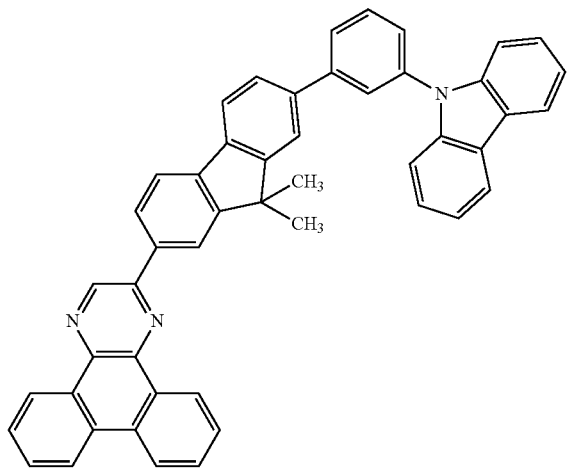
(612)
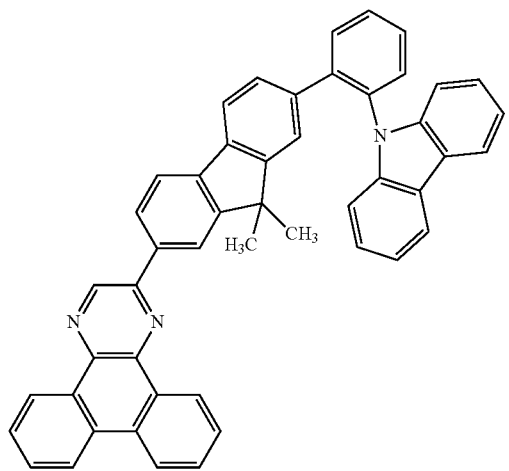
(613)
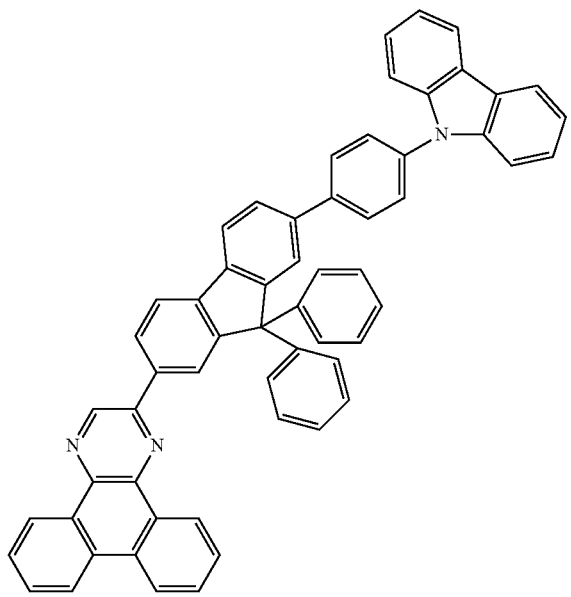

-continued
(614)
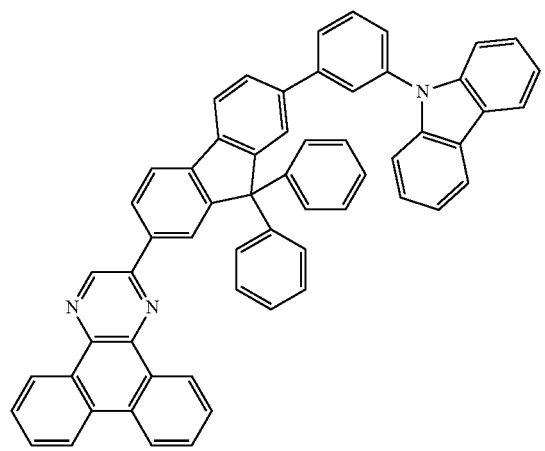
(615)
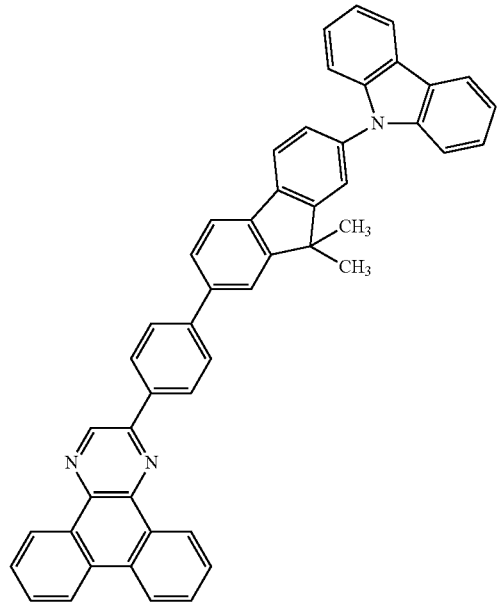
(616)
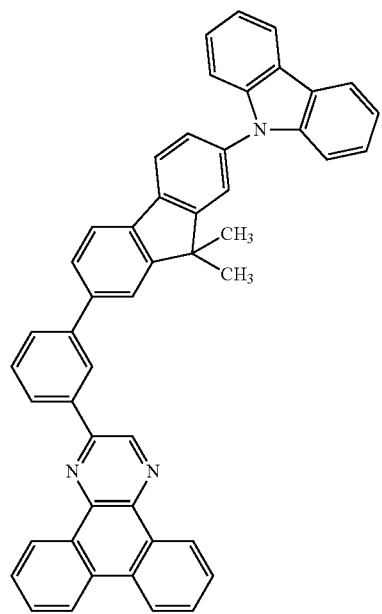

[Chemical formula 149]
(617)
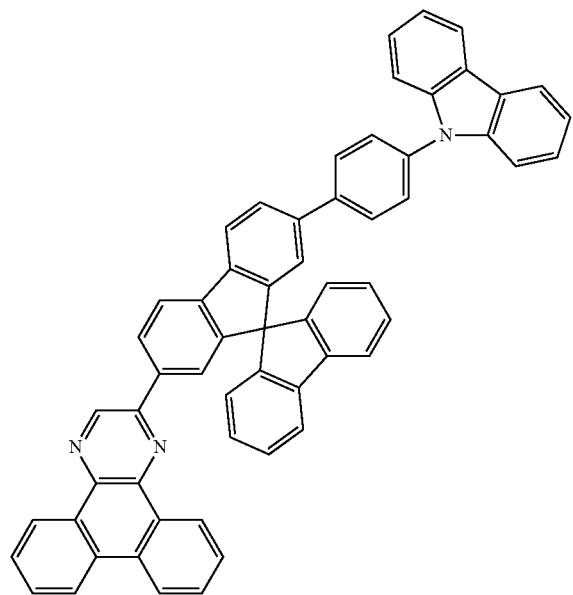
(618)
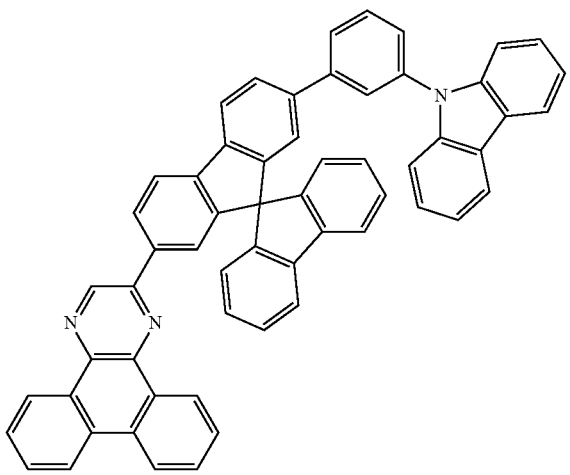
(619)
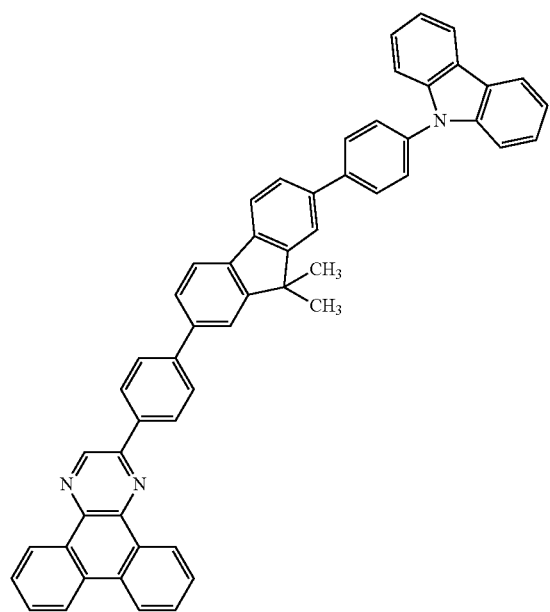
(620)
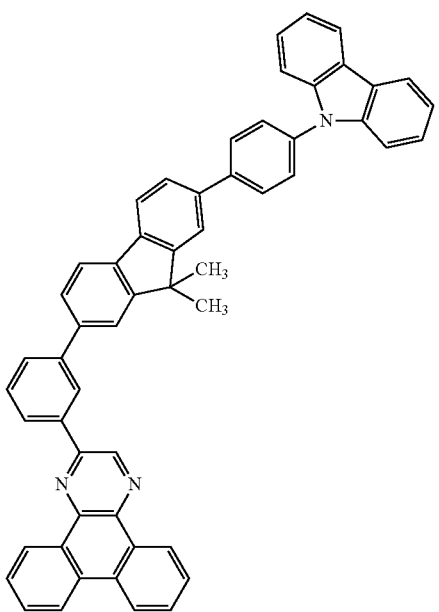

-continued
(621)
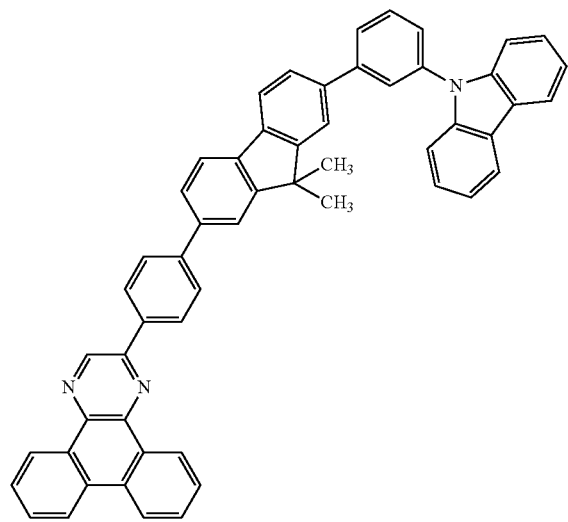
(622)
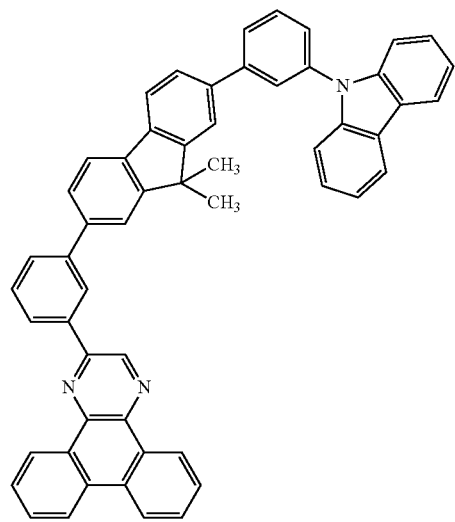
[Chemical formula 150]
(623)
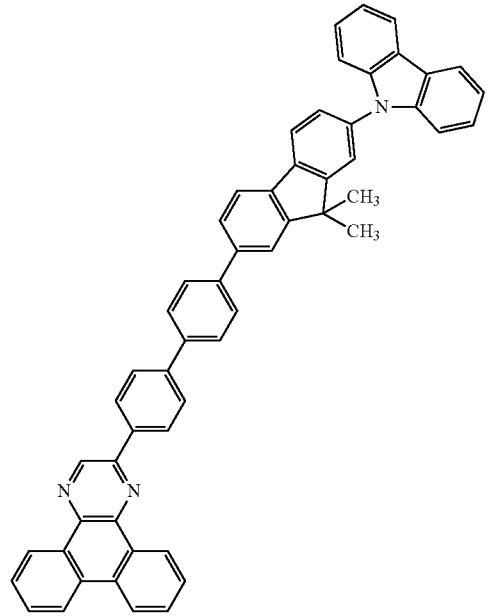
(624)
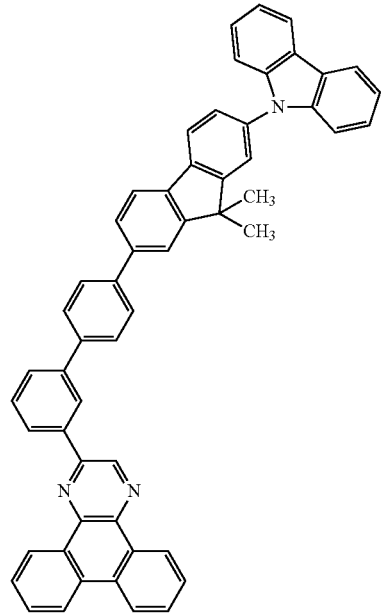
(625)
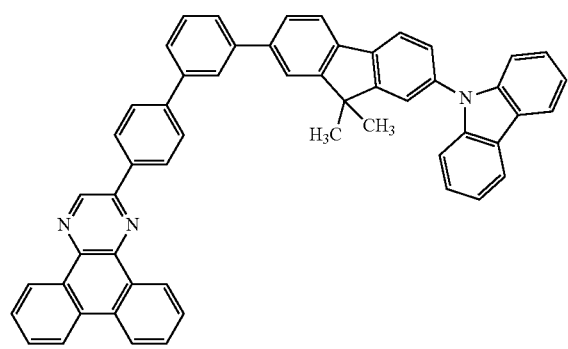
(626)
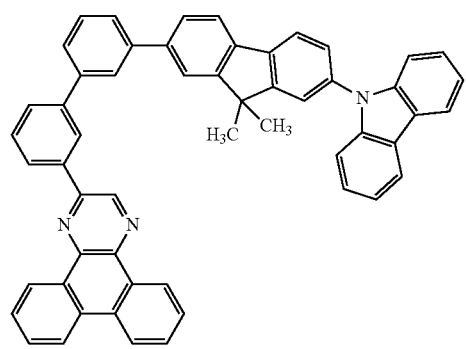

-continued
(627)
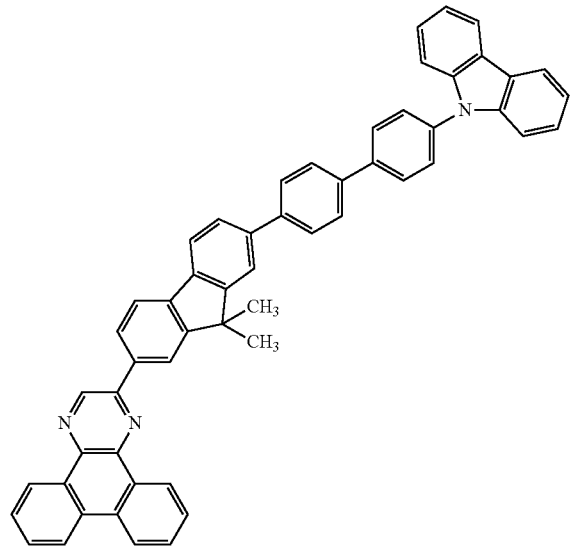
(628)
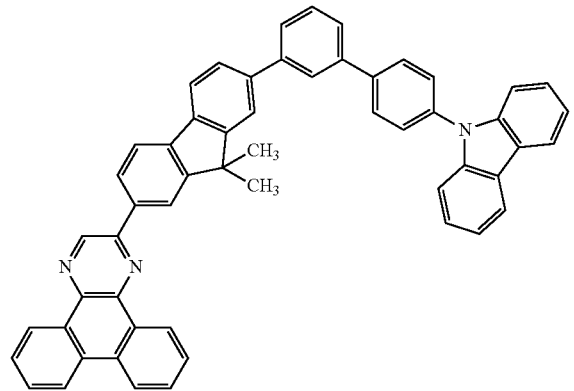
(629)
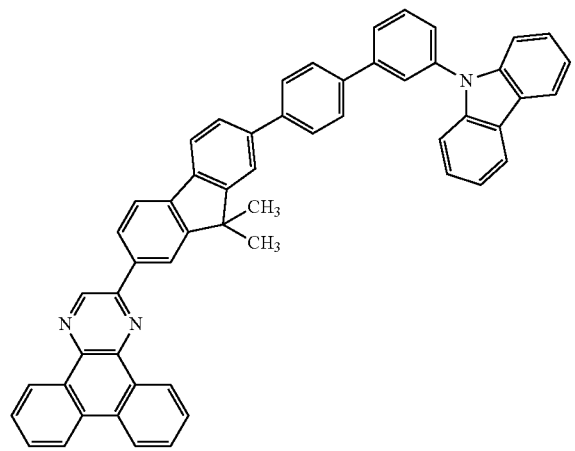
(630)
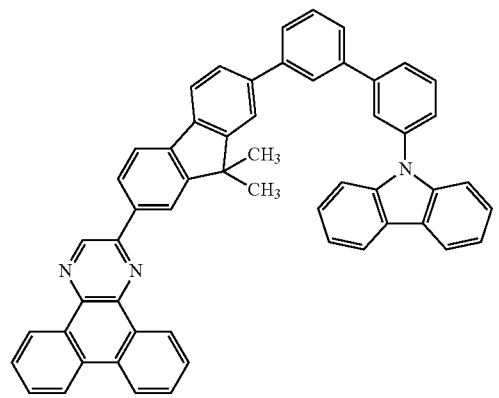
[Chemical formula 151]
(631)
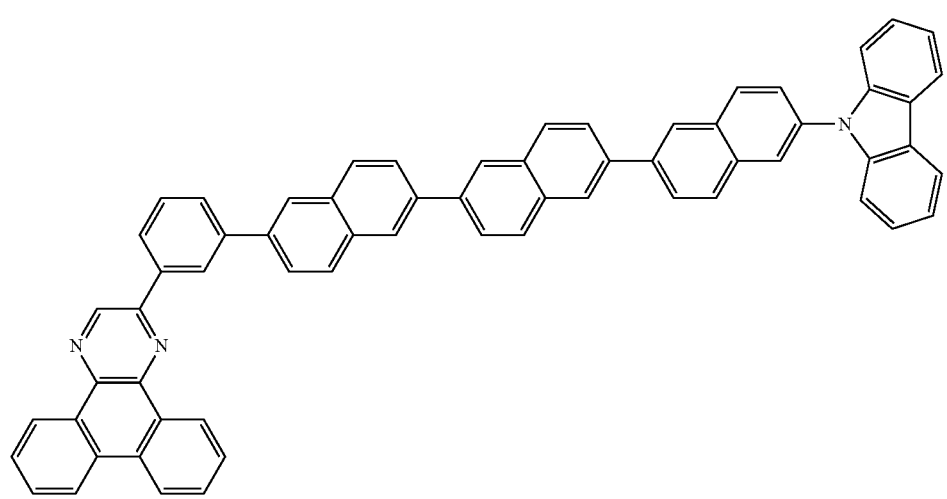

(632)
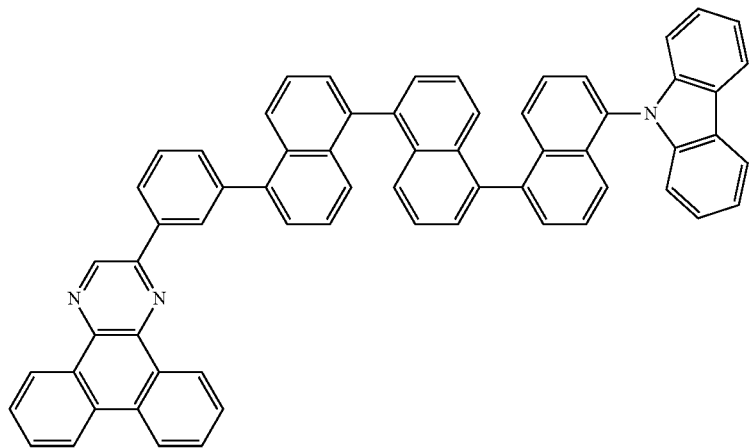
(633)
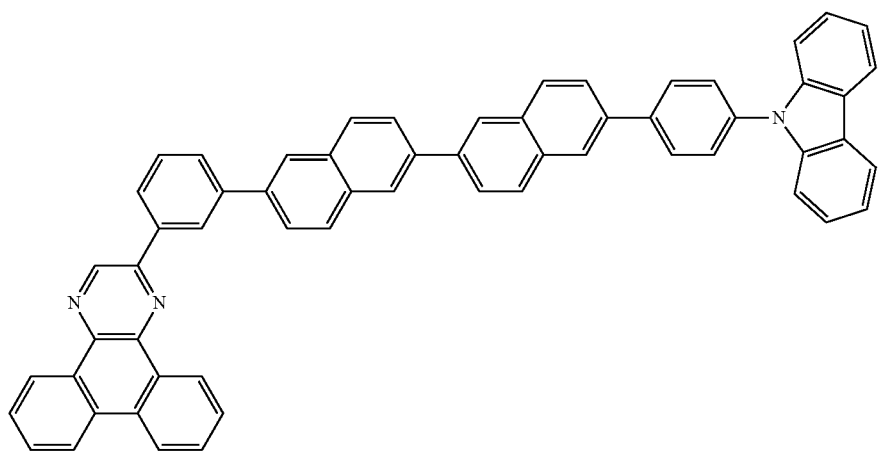
(634)
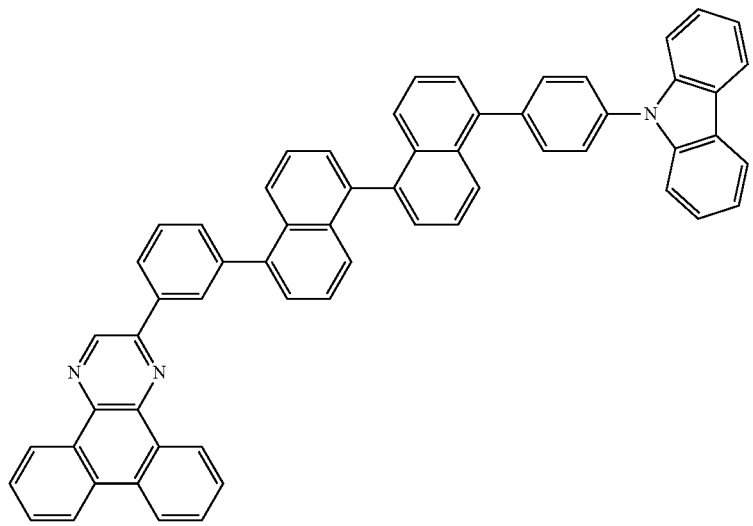

-continued
277
(635)
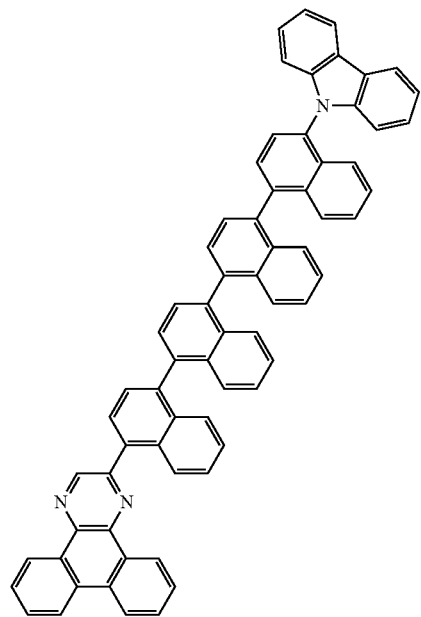
278
(636)
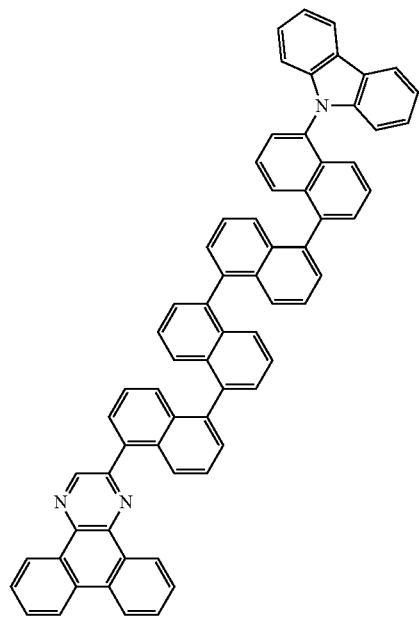
(637)
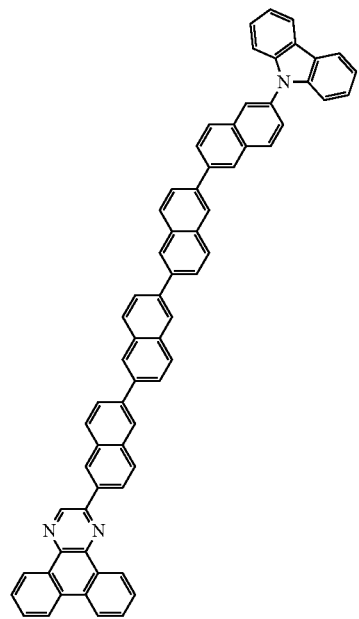

[Chemical formula 152]
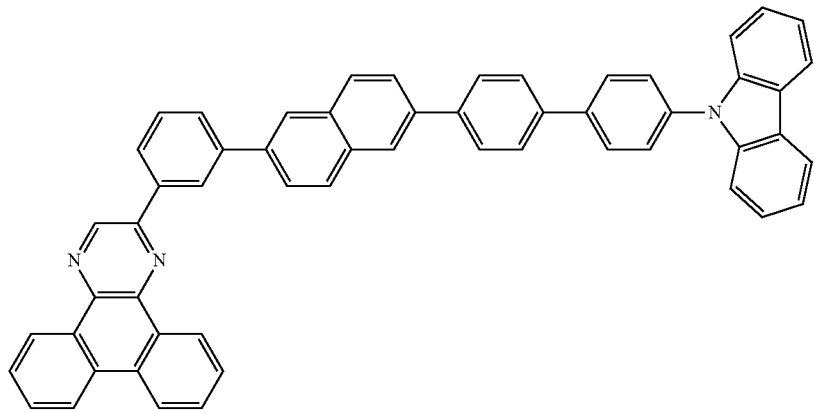
(637)
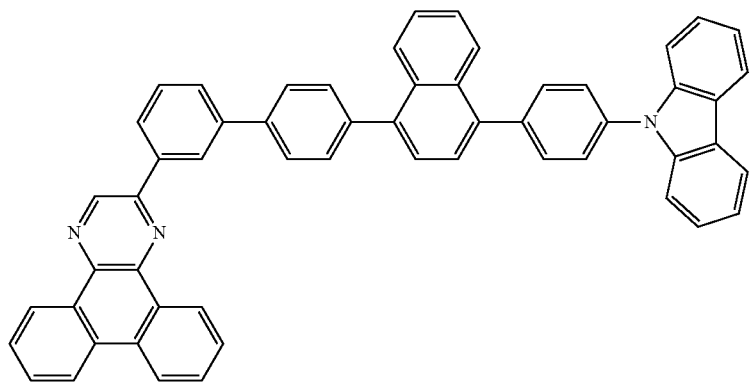
(638)
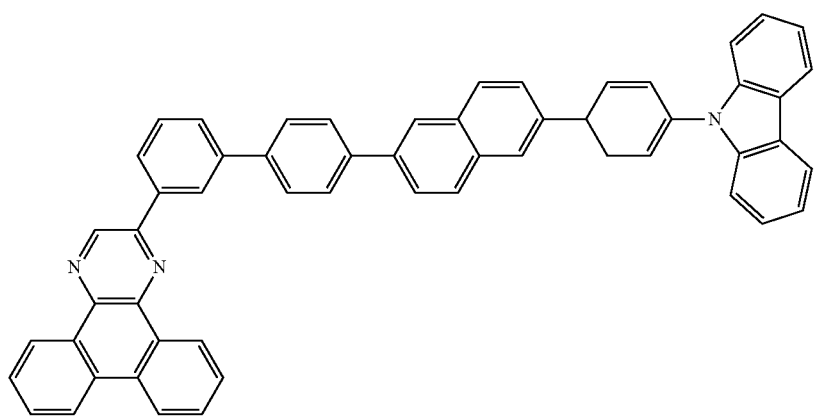
(639)

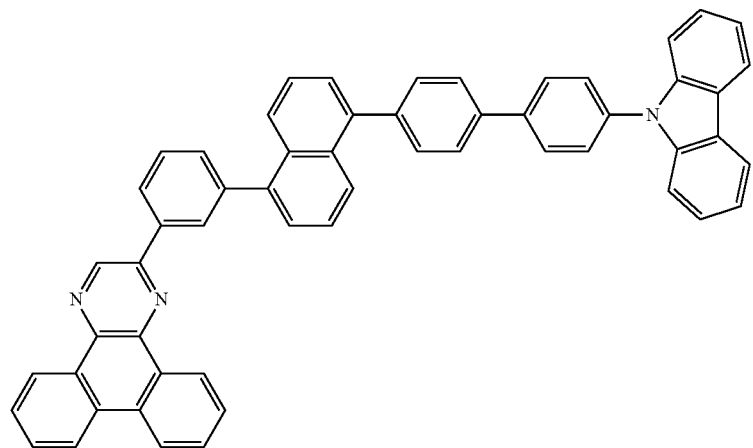
(640)
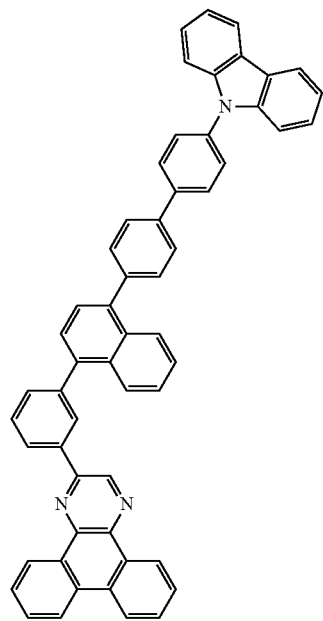
(641)
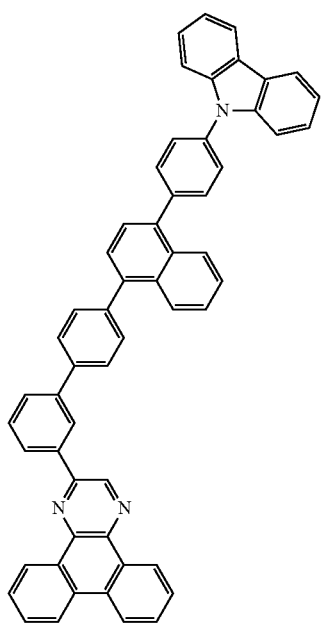
(642)

(643)
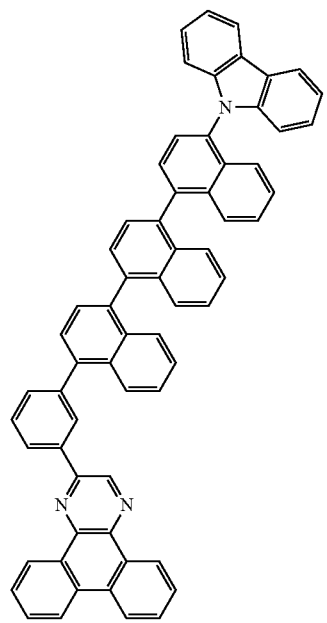
(644)
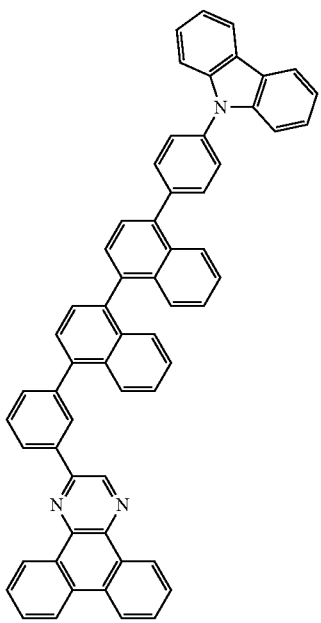
[Chemical formula 153]
(645)
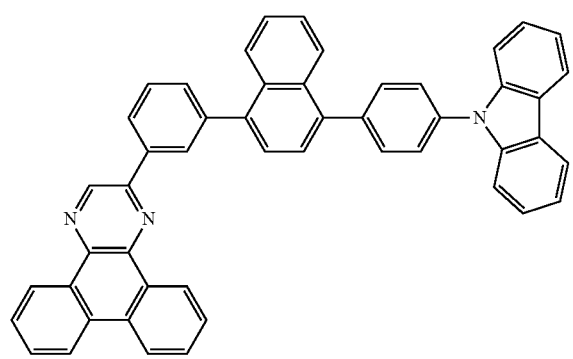
(646)
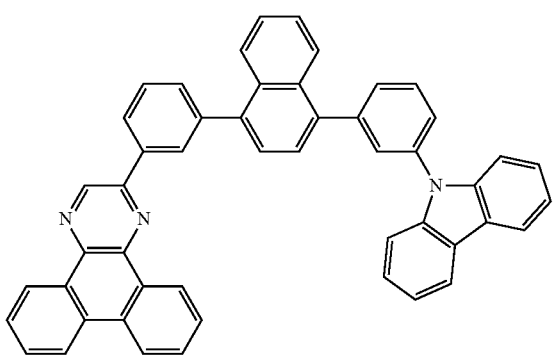
(647)
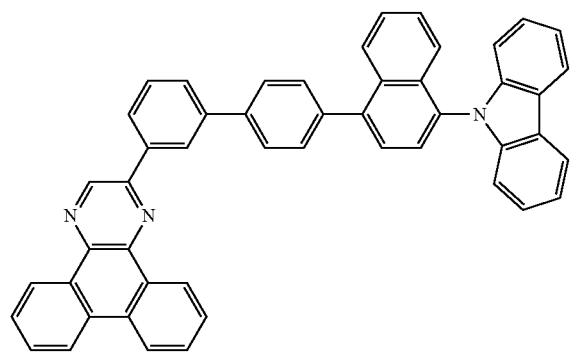
(648)
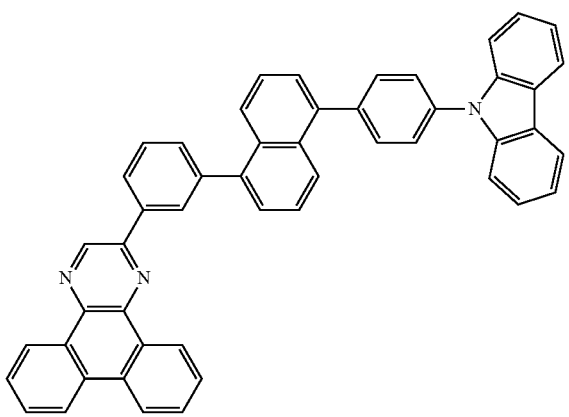

-continued
(649)
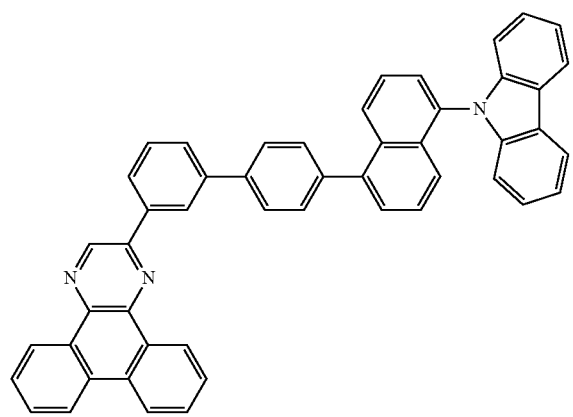
(650)
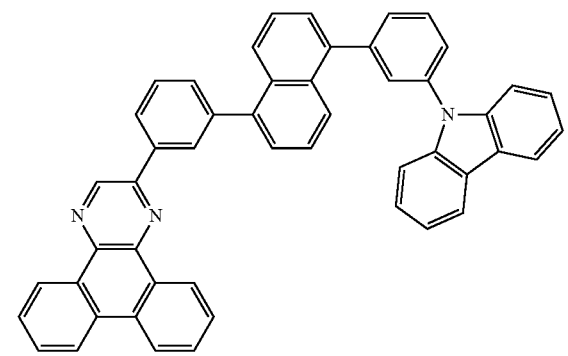
(651)
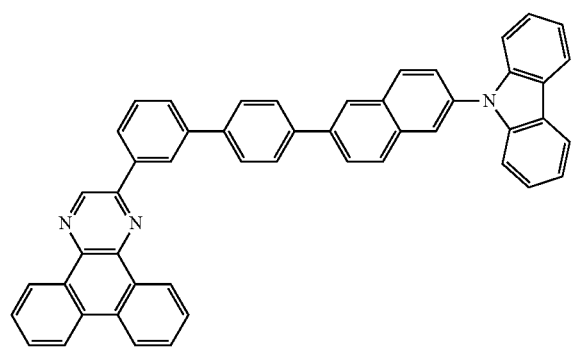
(652)
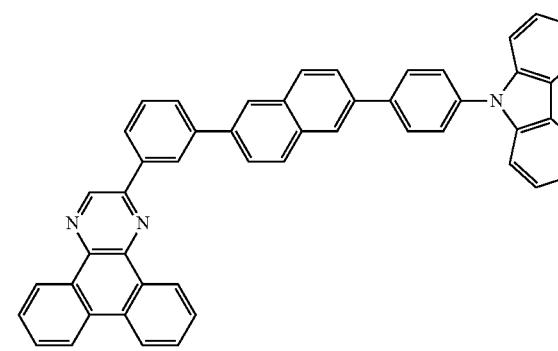
(653)
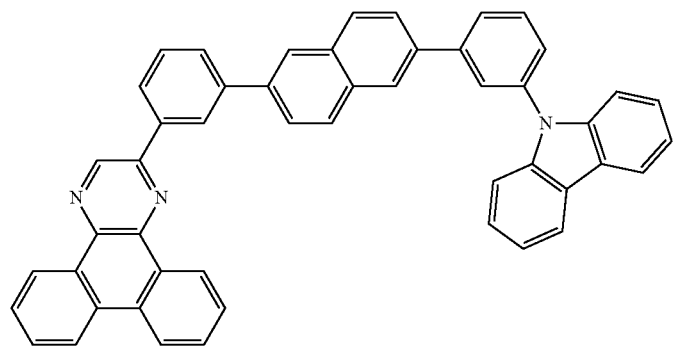
[Chemical formula 154]
(654)
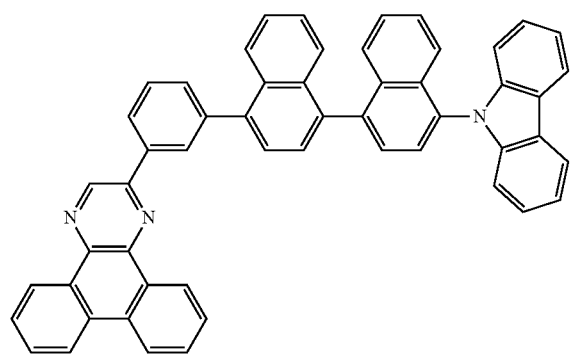
(655)
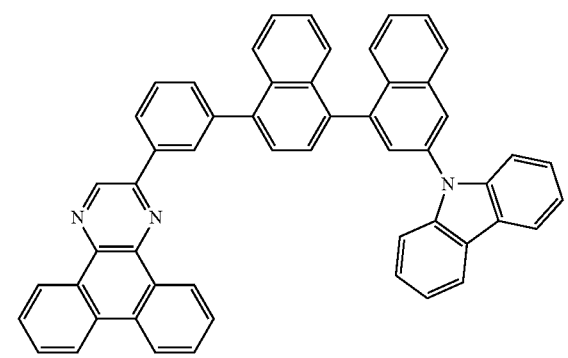

-continued
(656)
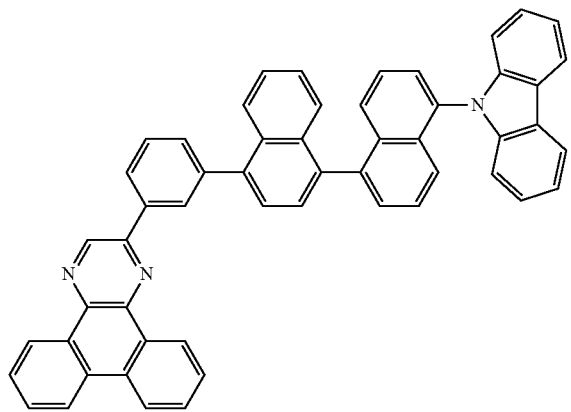
(657)
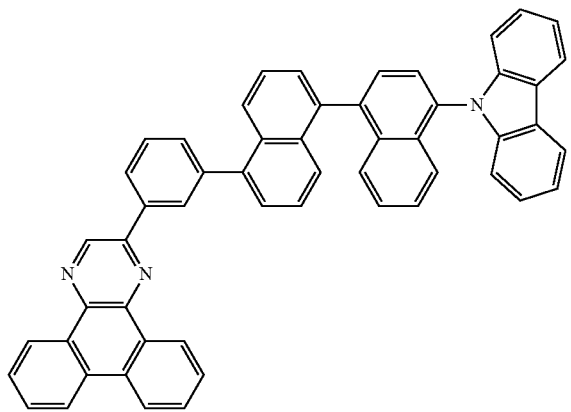
(658)
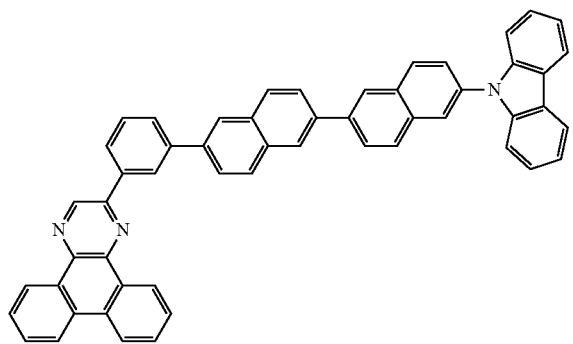
(659)
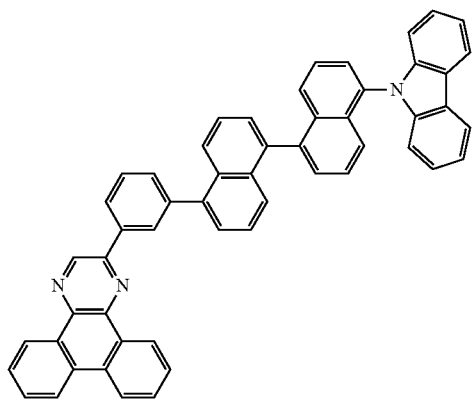
(660)
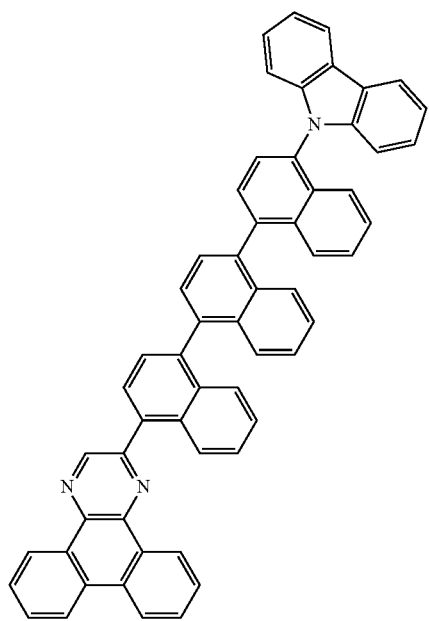
(661)
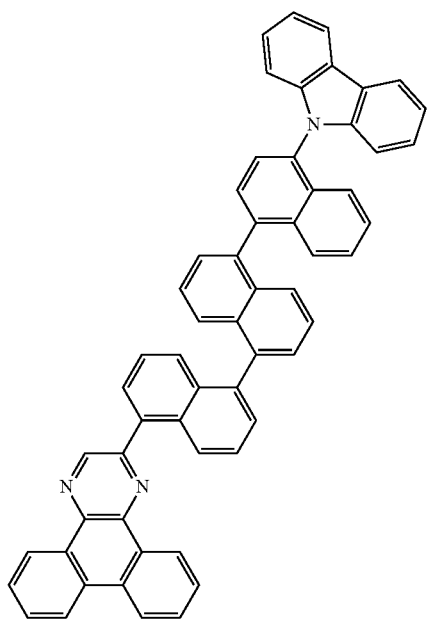

-continued
(662)
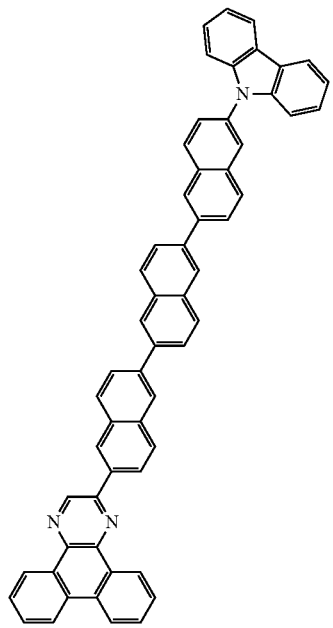
[Chemical formula 155]
(663)
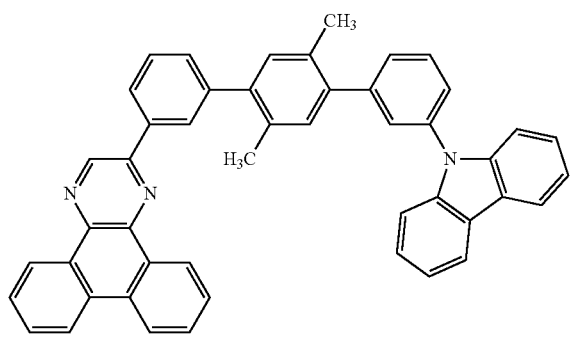
(664)
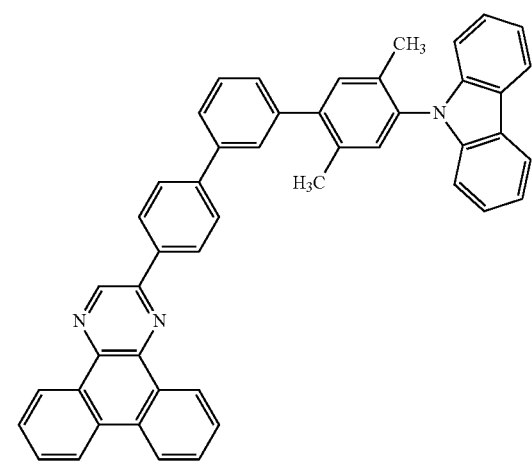
(665)
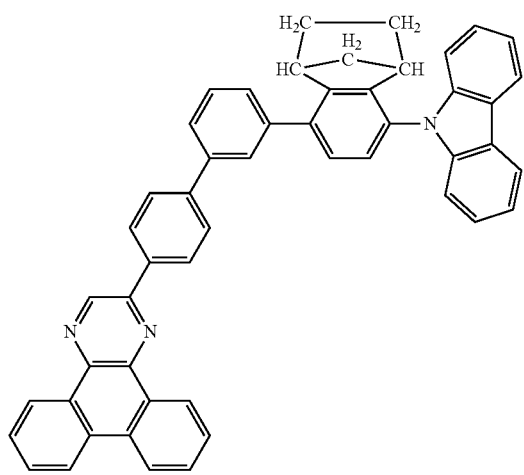
(667)
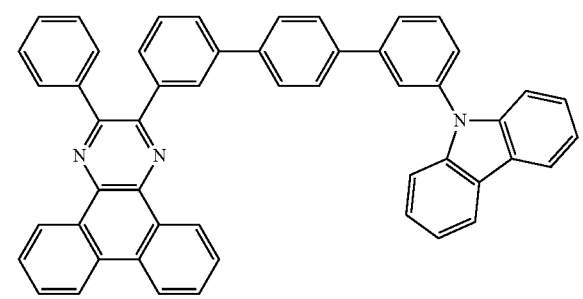

[Chemical formula 156]
(668)
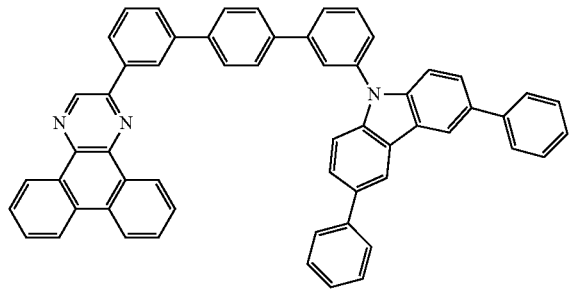
(669)
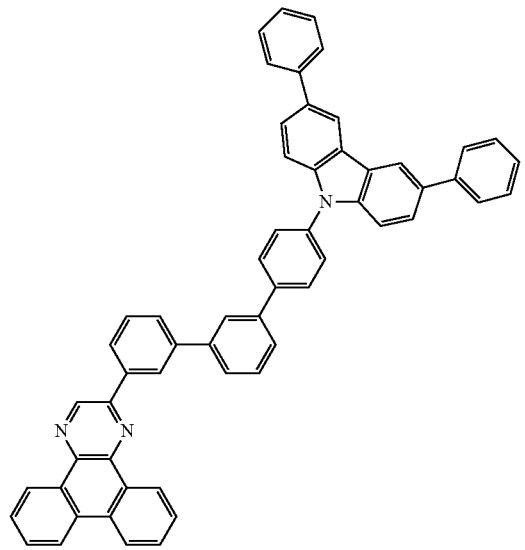
(670)
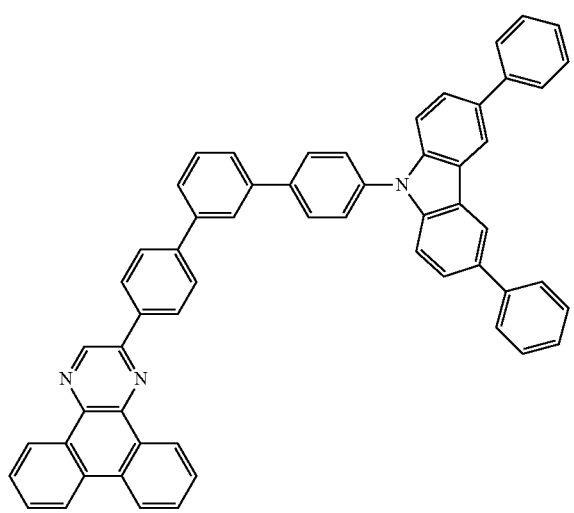
(671)
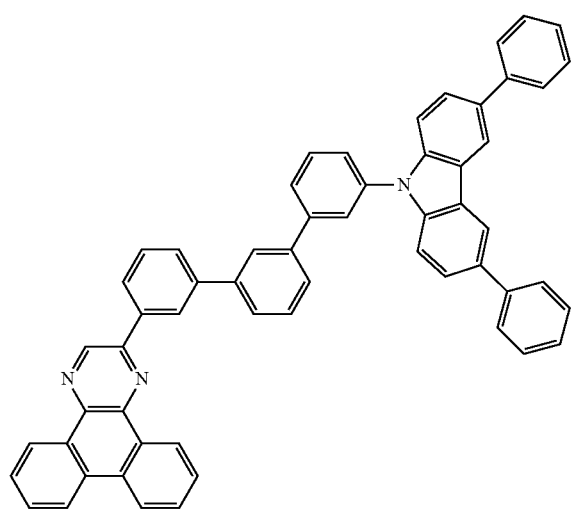

-continued
(672)
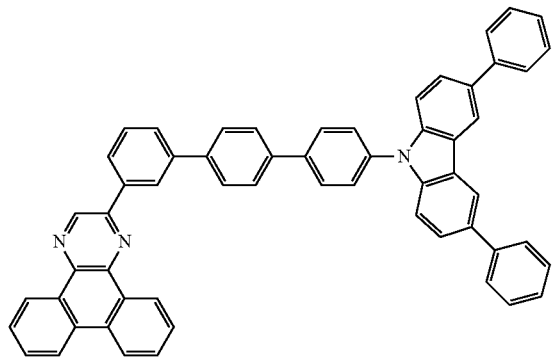
(673)
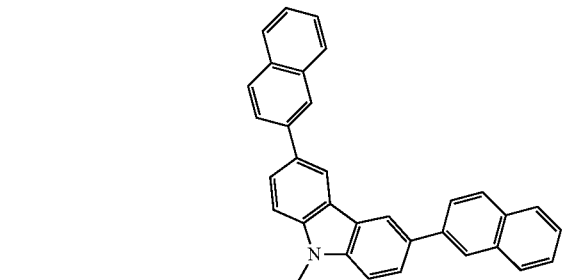
(674)
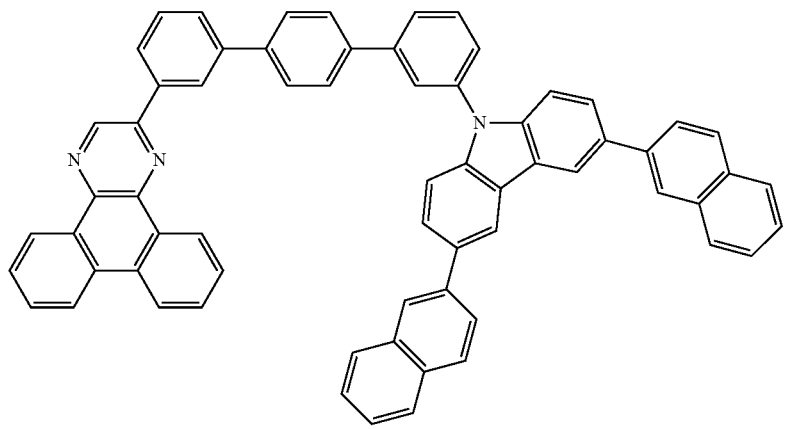
(675)
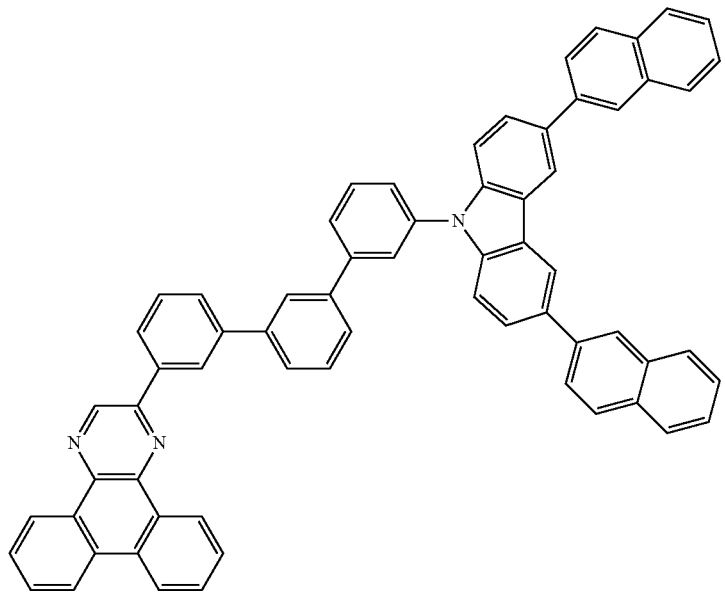

[Chemical formula 157]
(676)
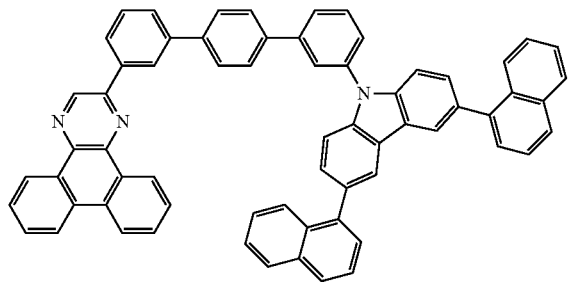
(677)
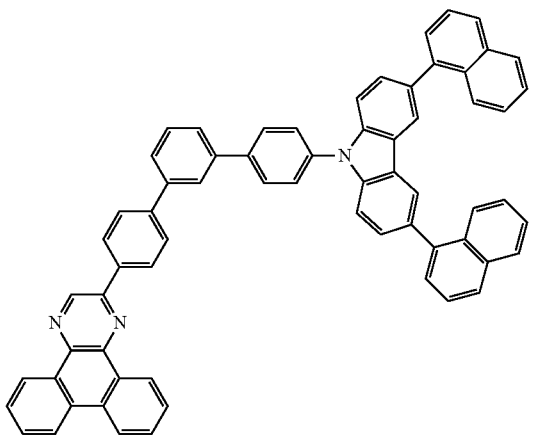
(678)
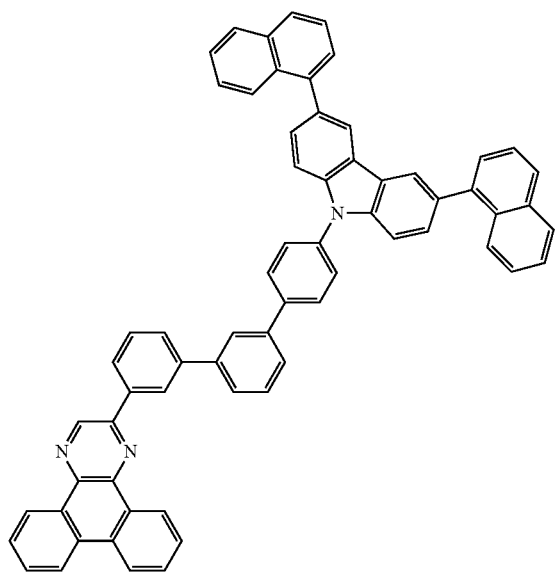
(679)
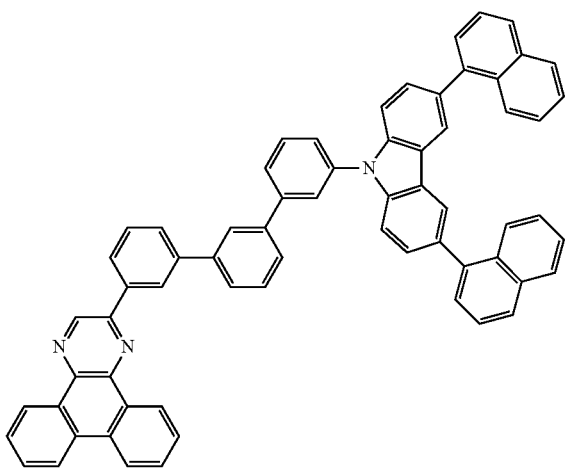
(680)
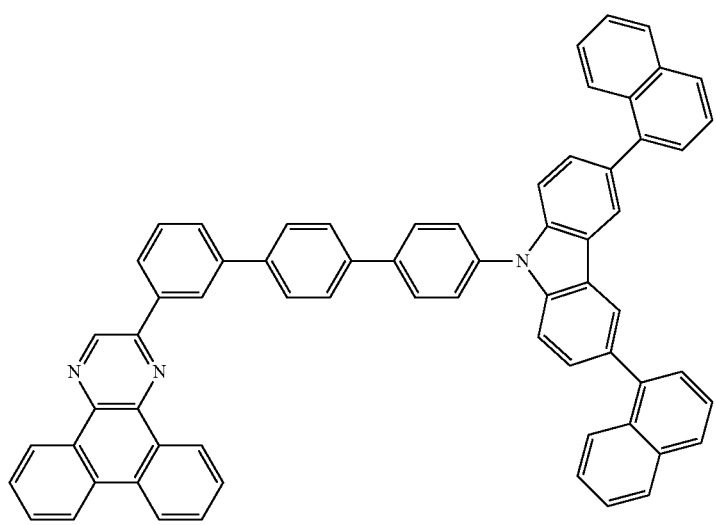

(681) (682)
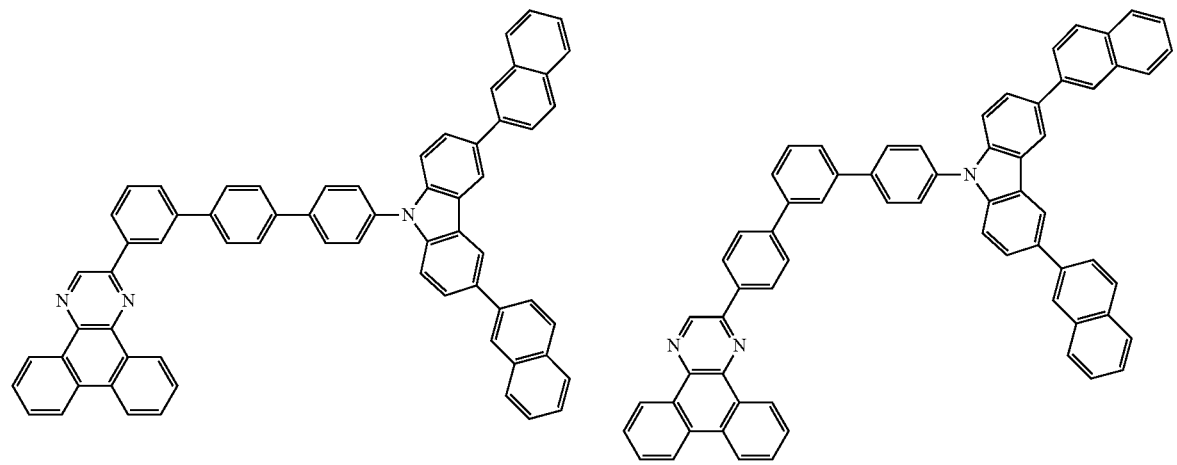
[Chemical formula 158]
(683) (684)
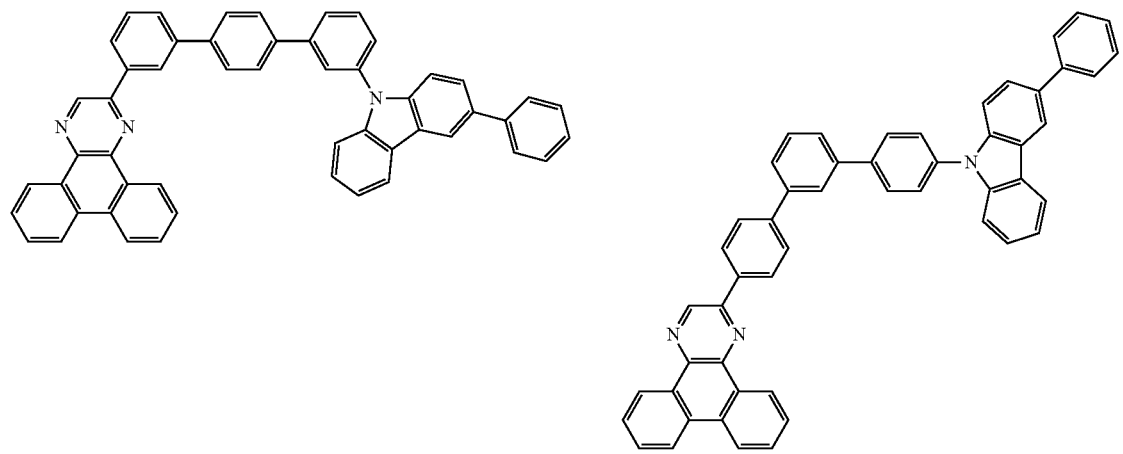
(685)
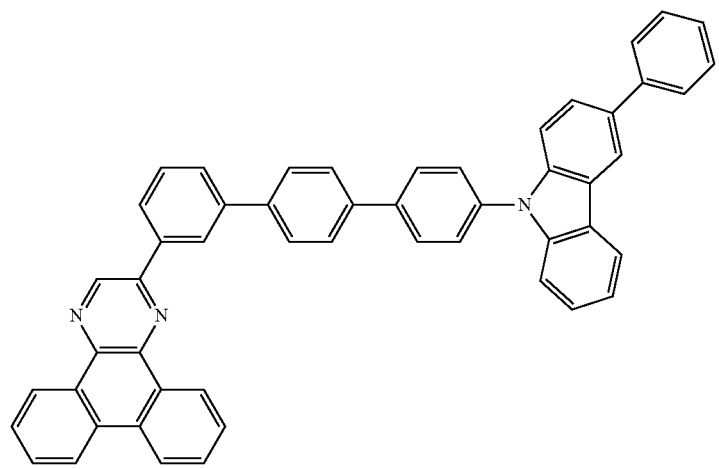

-continued
(686)
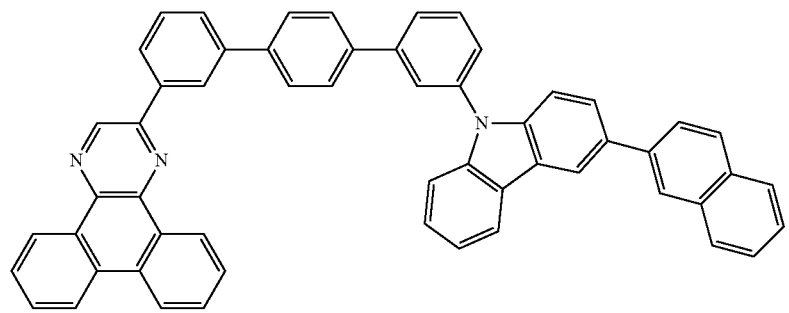
(687)
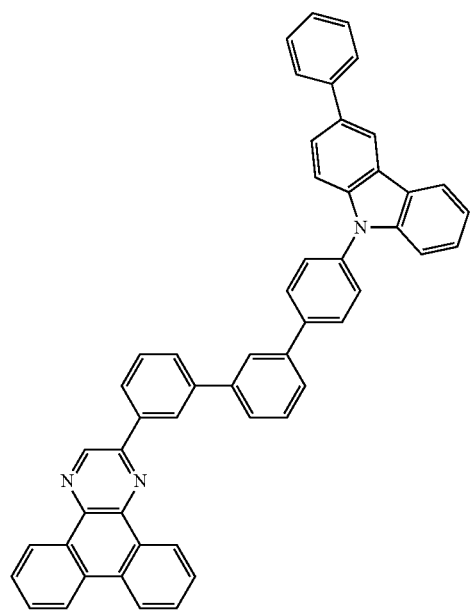
(688)
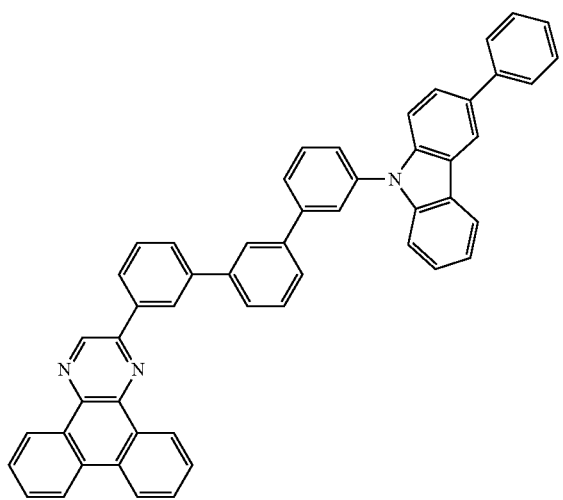
(689)
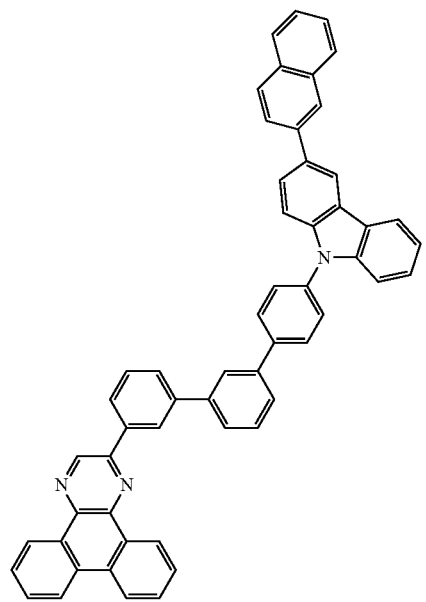
(670)
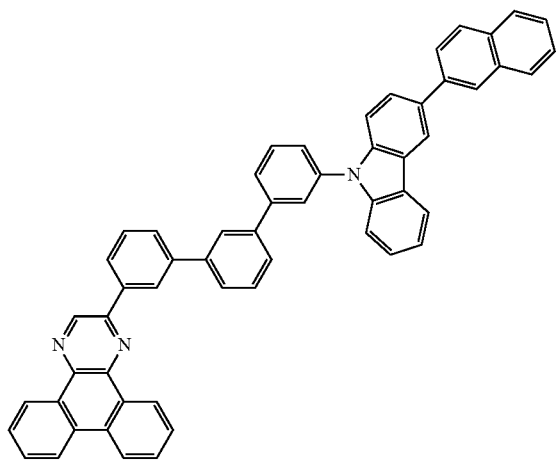

[Chemical formula 159]
(671)
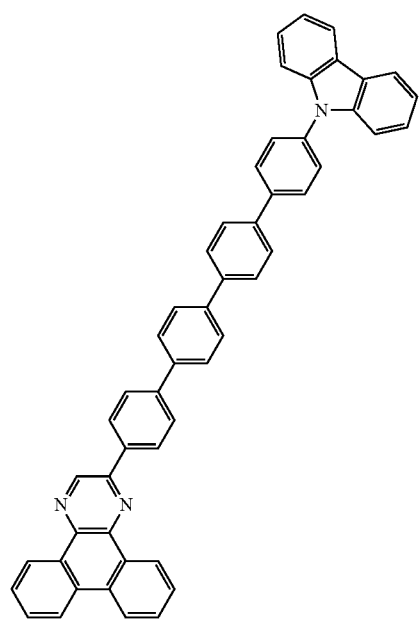
(672)
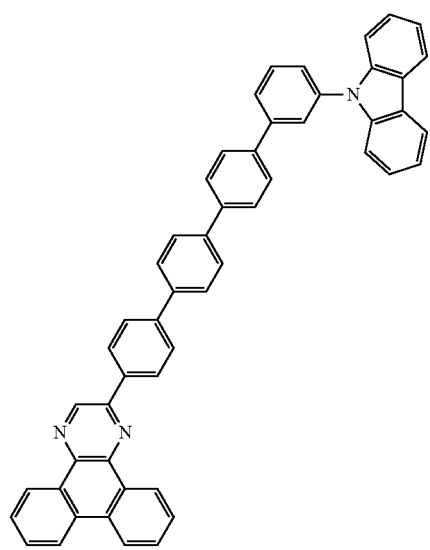
-continued
(673)
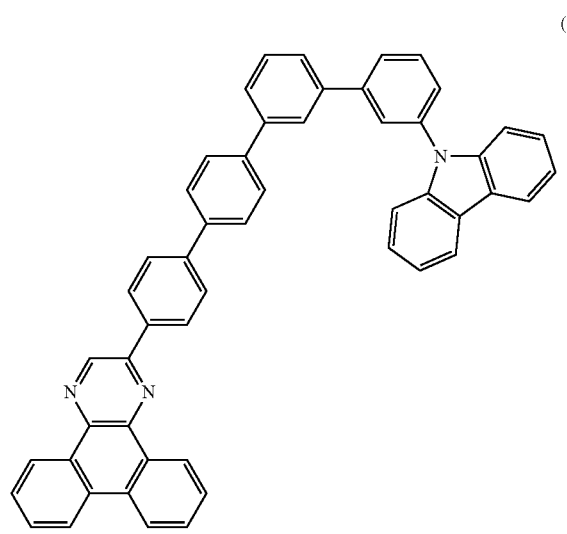
(674)
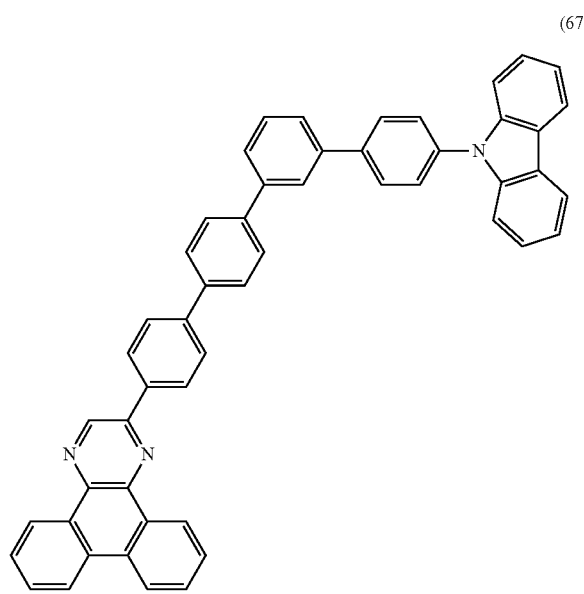

-continued
(675)
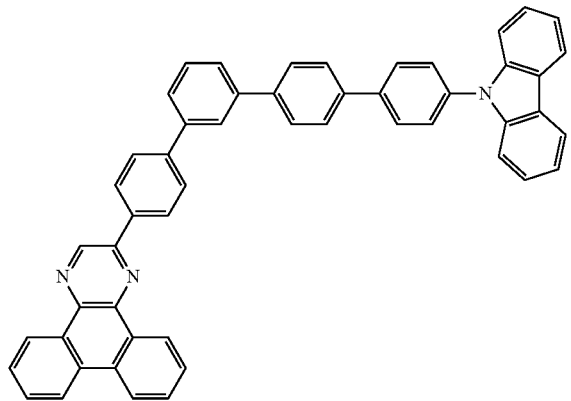
(676)
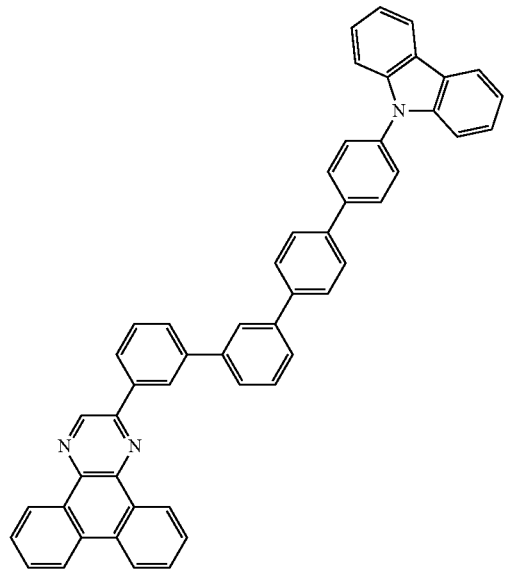
(677)
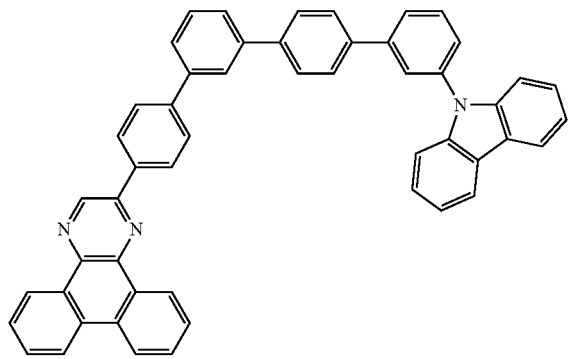
(678)
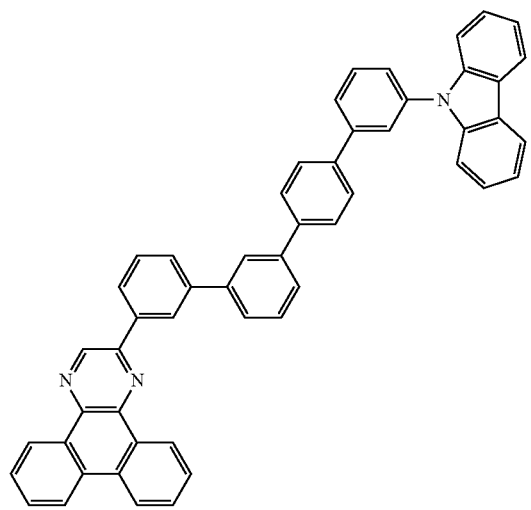
[Chemical formula 160]
(679)
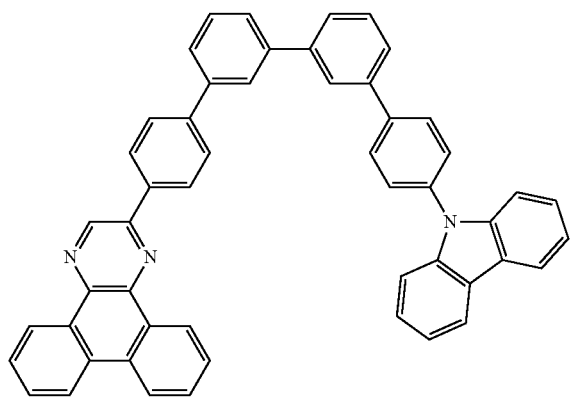
(680)
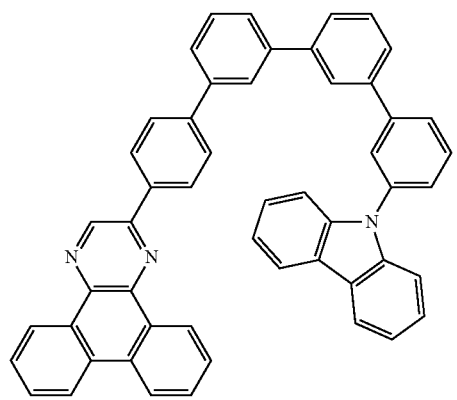

-continued
(681)
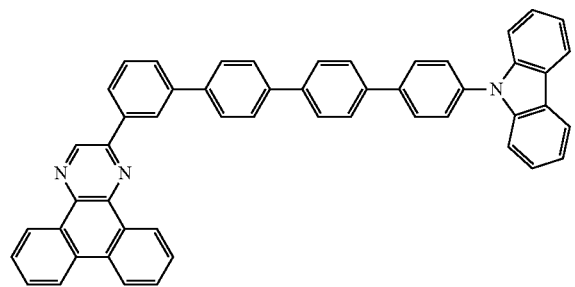
(682)
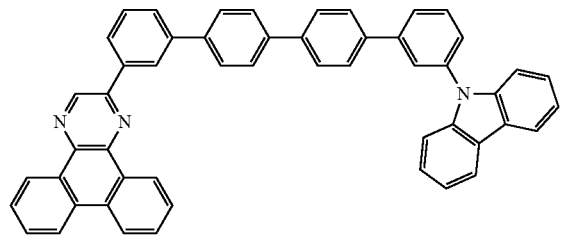
(683)
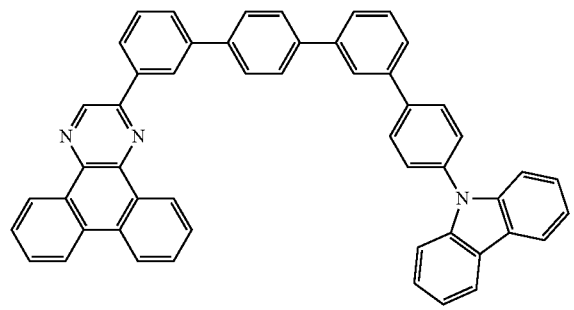
(684)
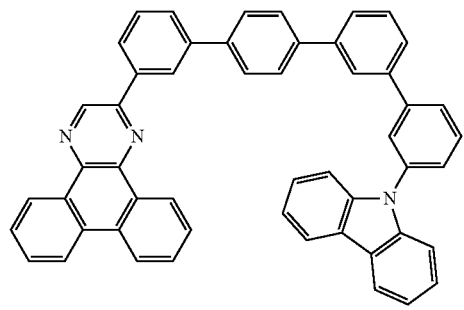
(685)
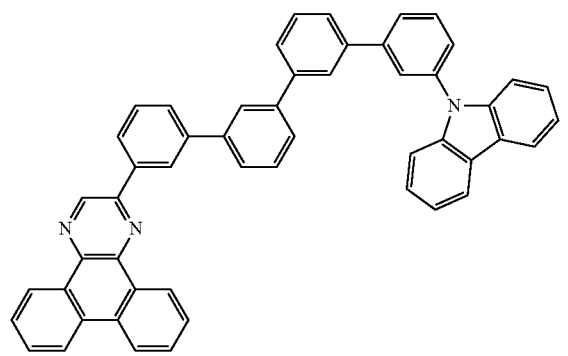
(686)
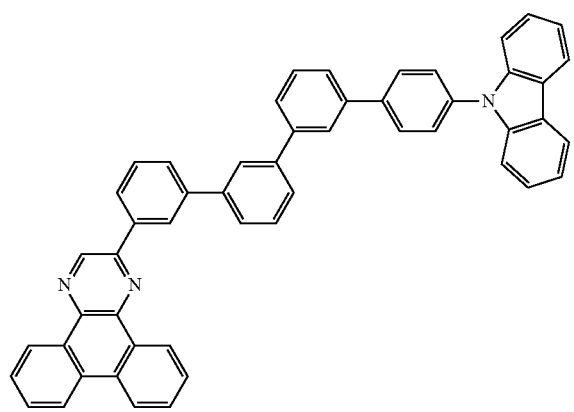

[Chemical formula 161]
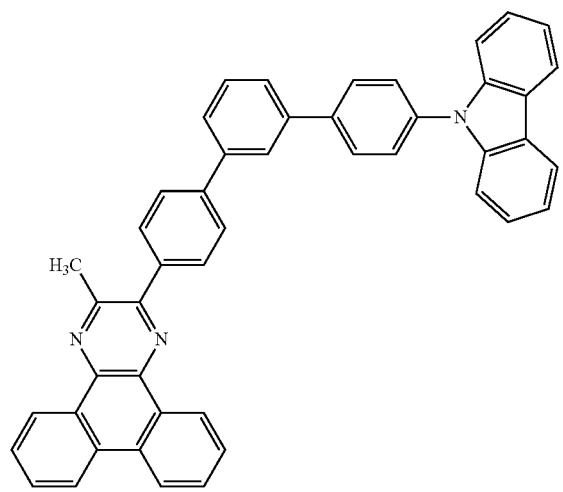

-continued
(691)
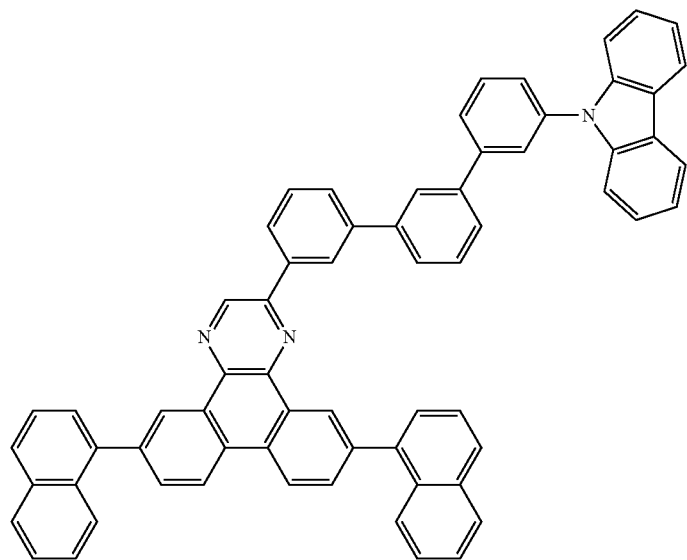
[Chemical formula 162]
(692)
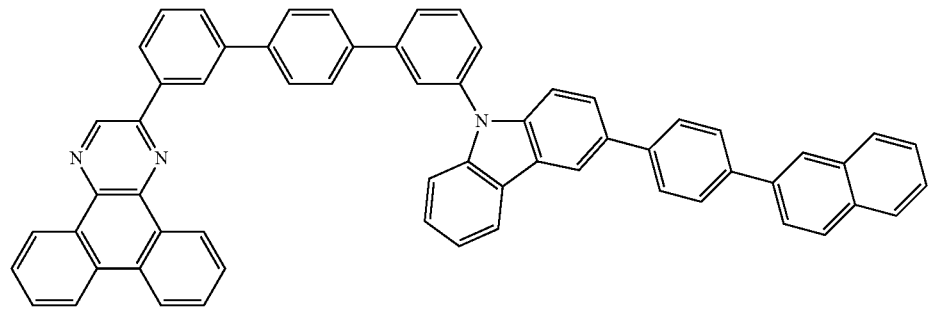
(693)
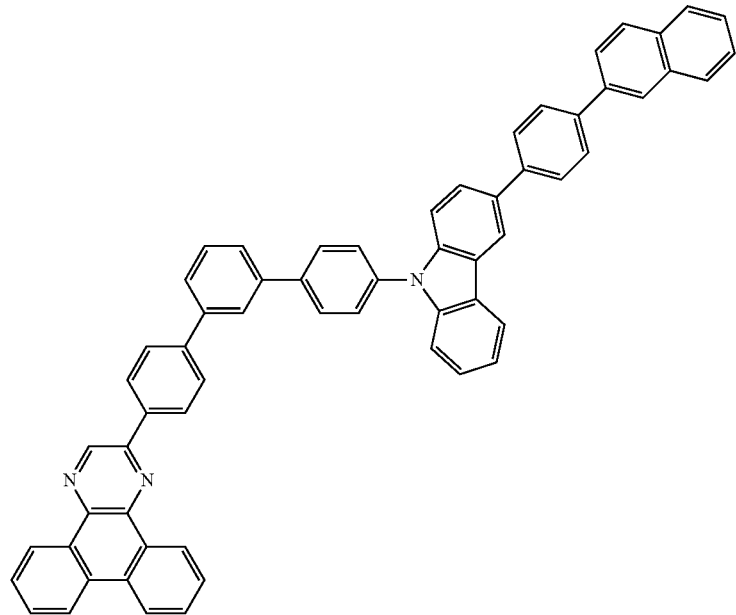

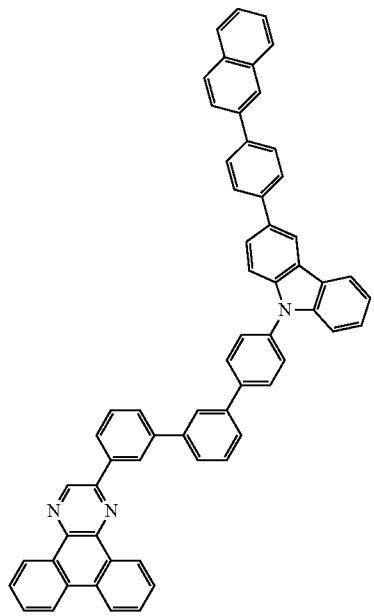
(694)
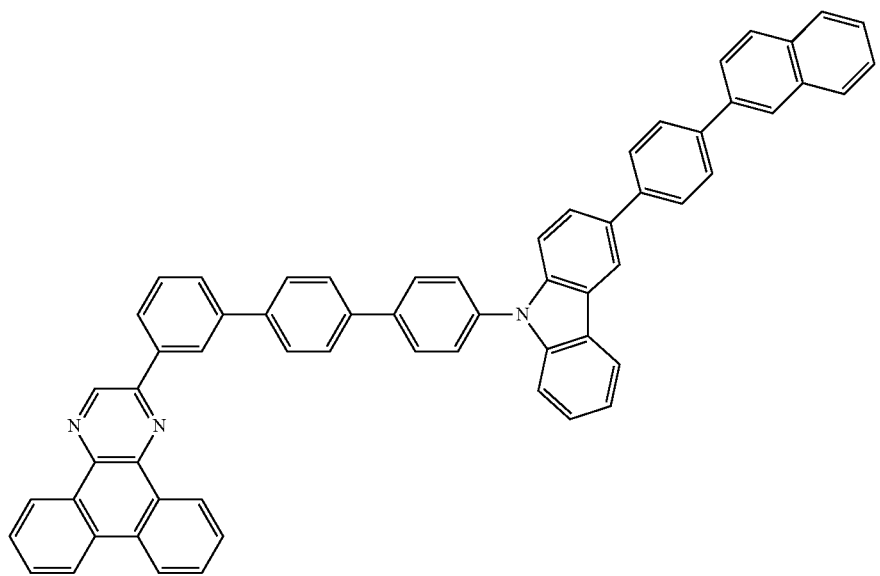
(695)

(696)
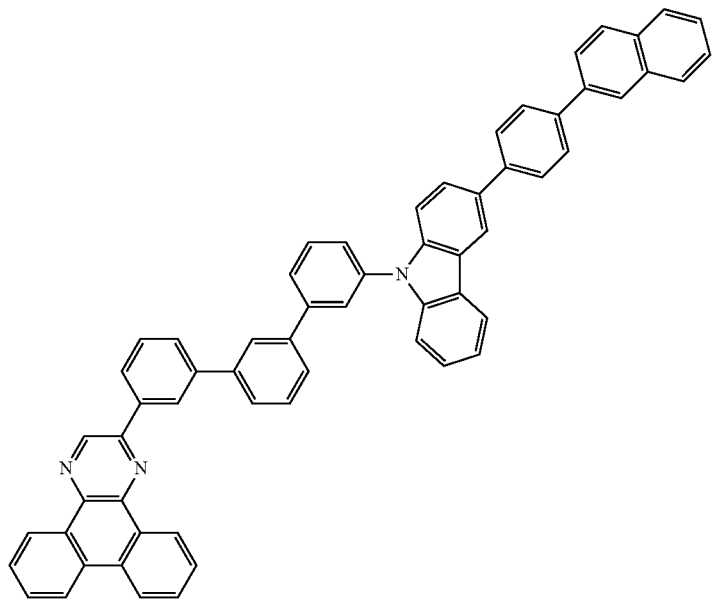
[Chemical formula 163]
(697)
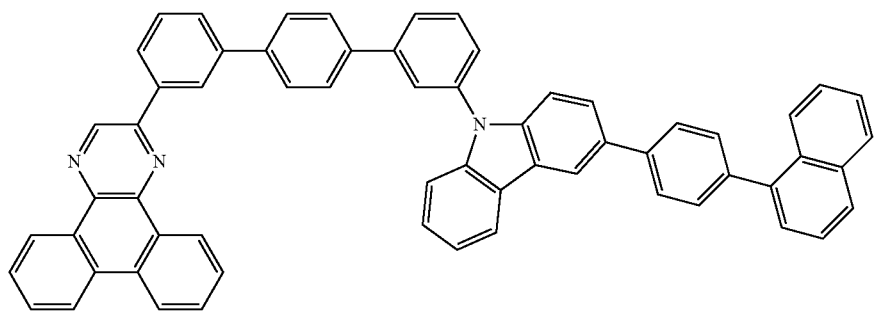
(698)
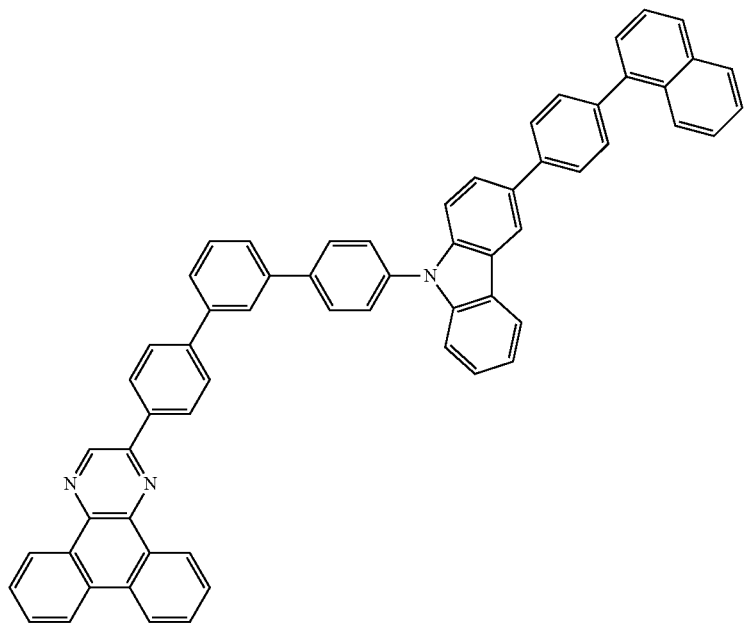

-continued
(699)
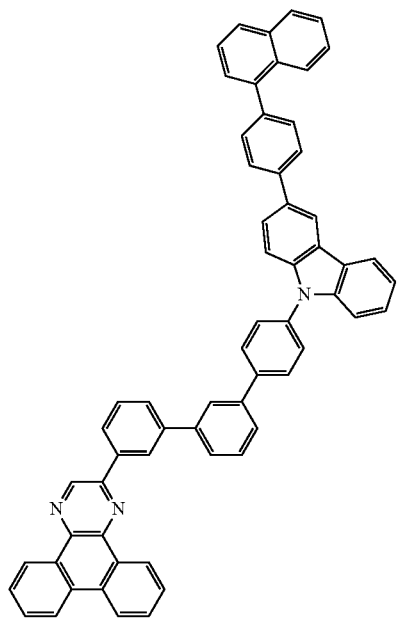
(700)
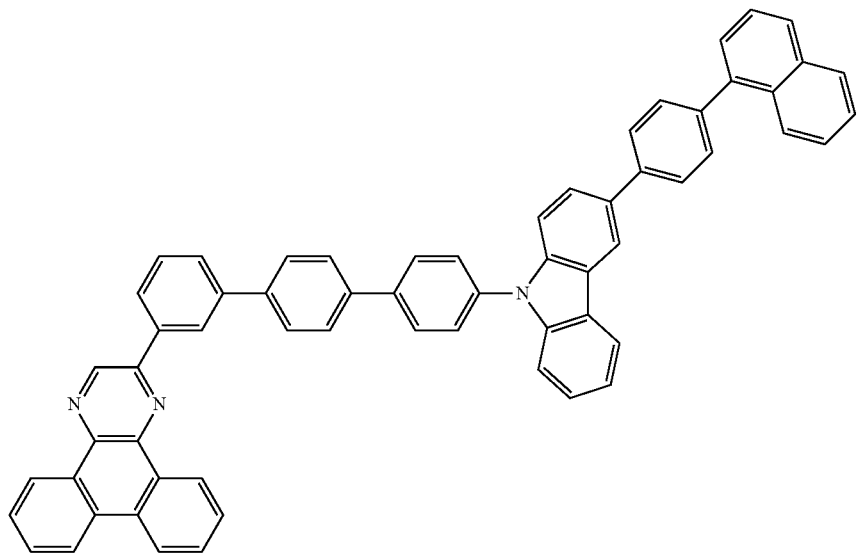

-continued
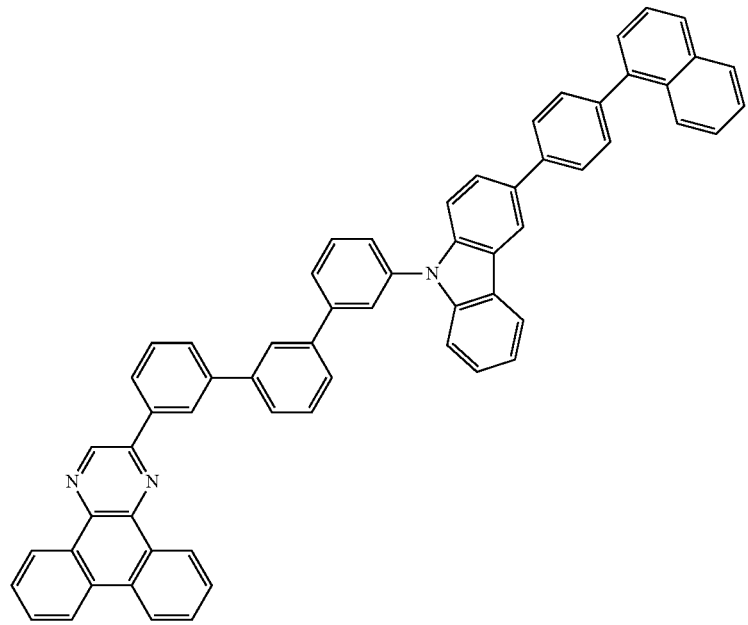
(701)
[Chemical formula 164]
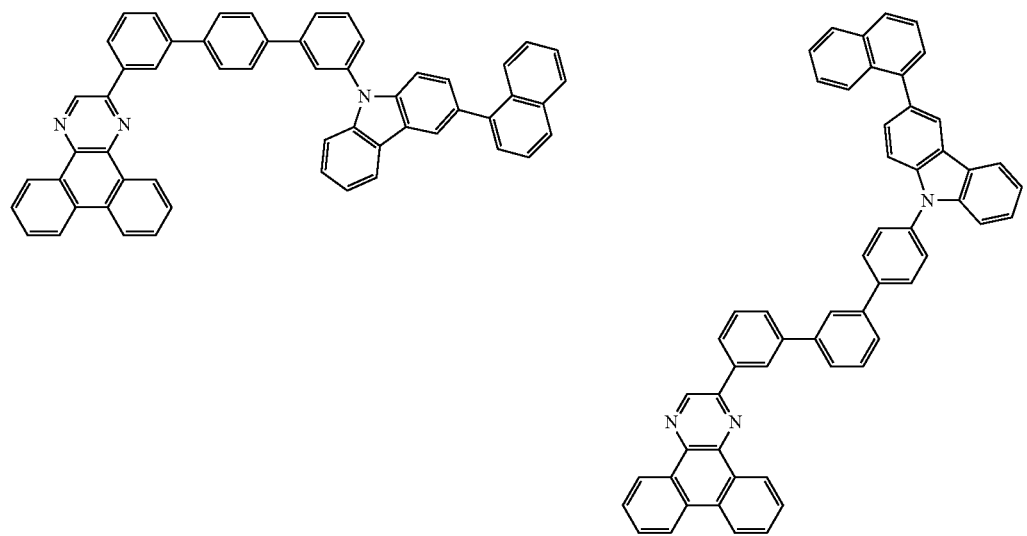

-continued
(704)
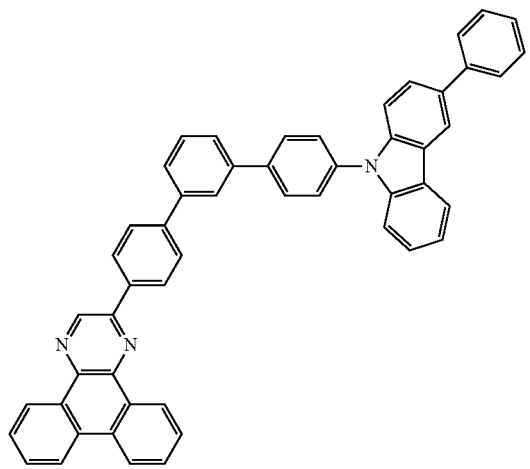
(705)
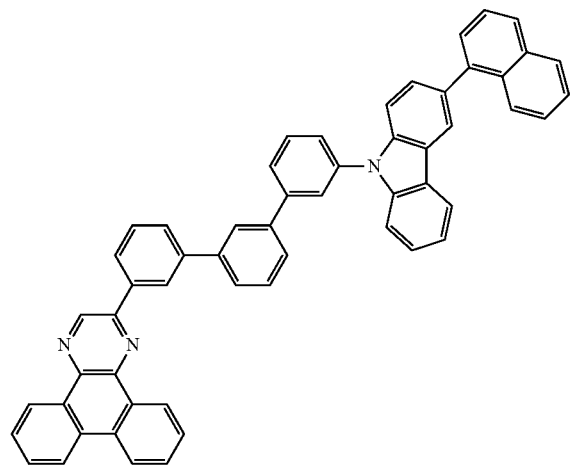
(706)
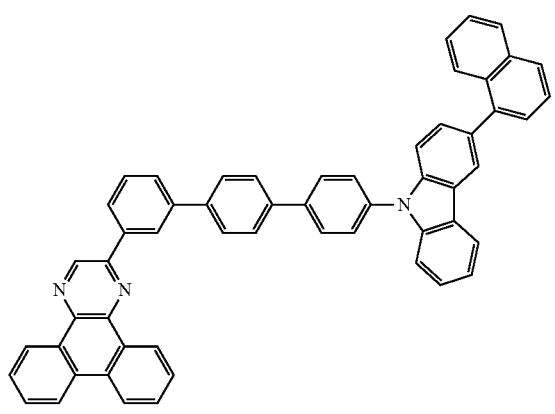
(707)
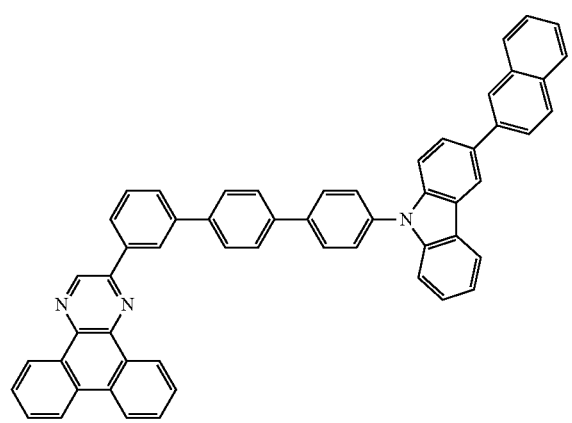
(708)
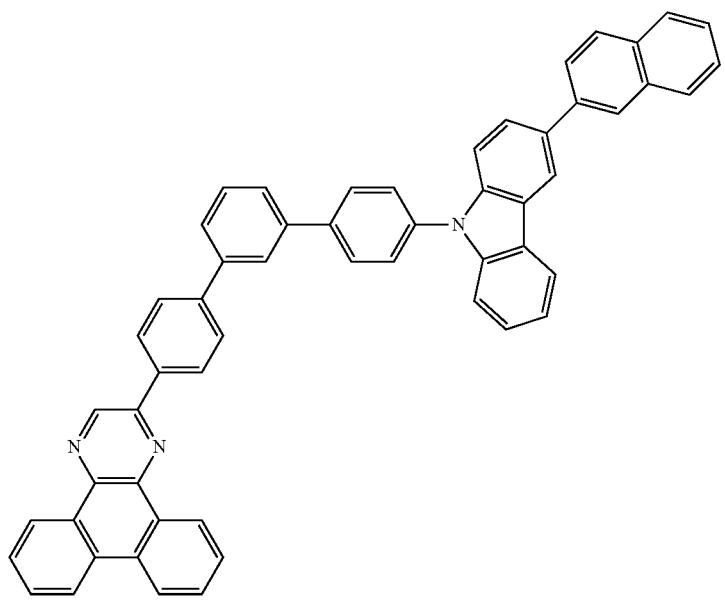

[Chemical formula 165]
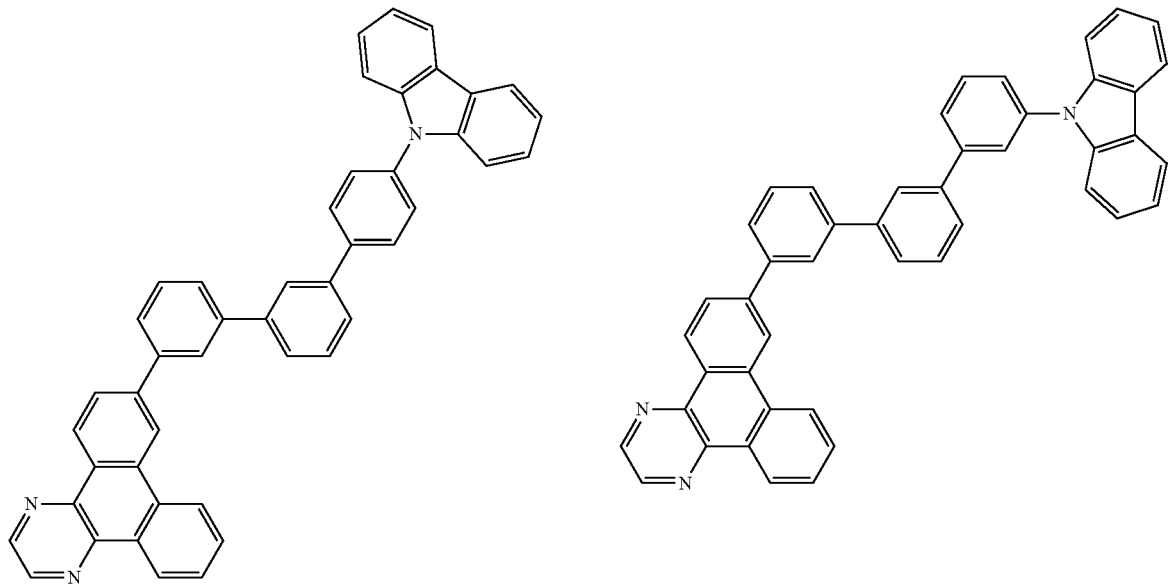
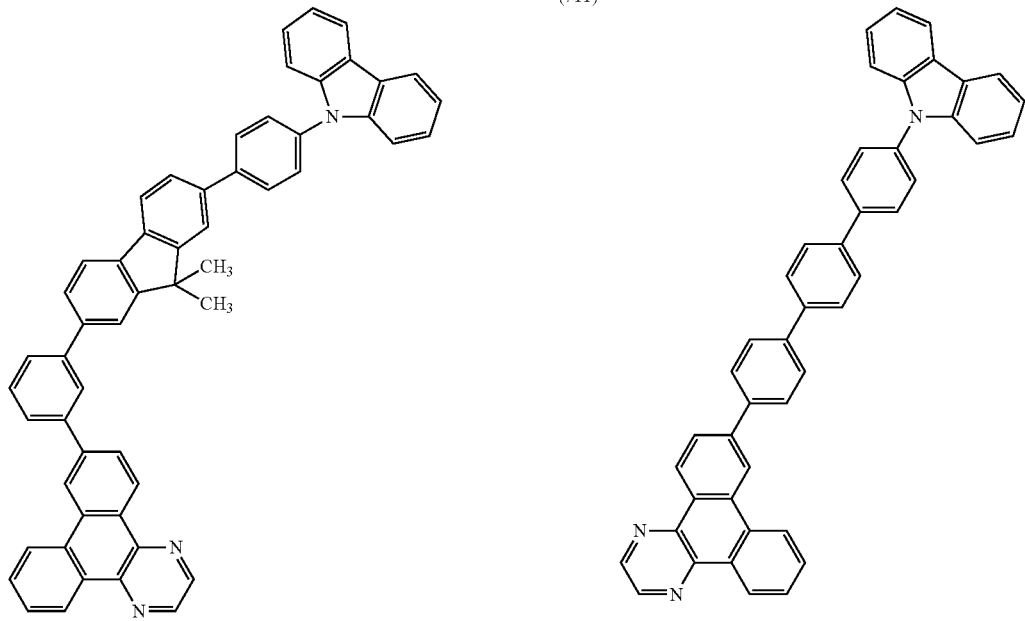

-continued
(713)
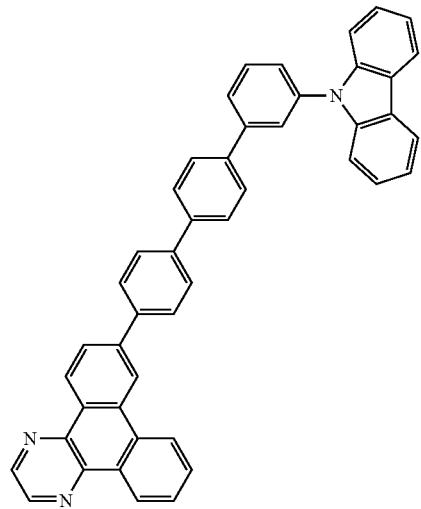
(714)
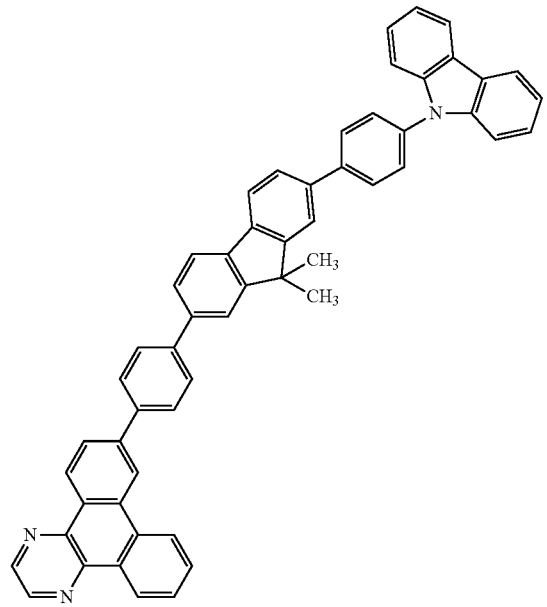
(715)
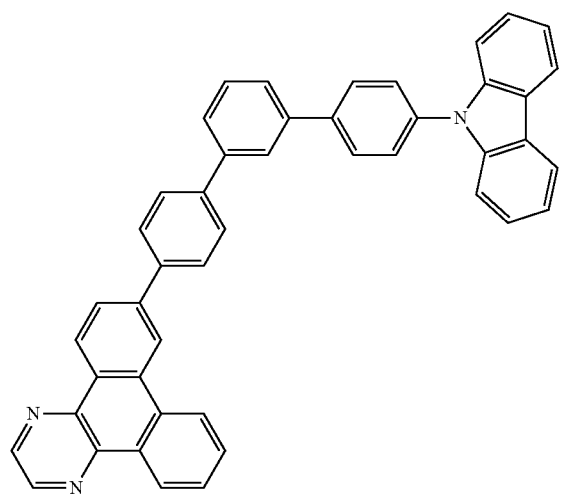
(716)
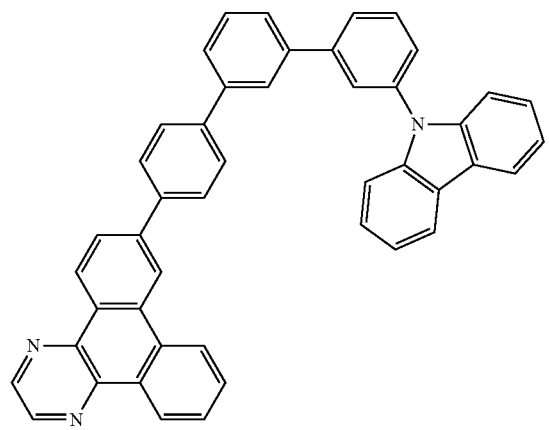

-continued
(717)
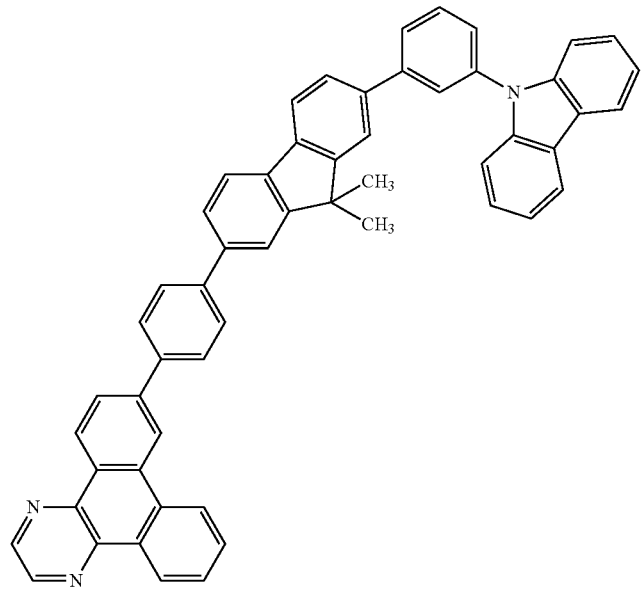
[Chemical formula 166]
(718) (719)
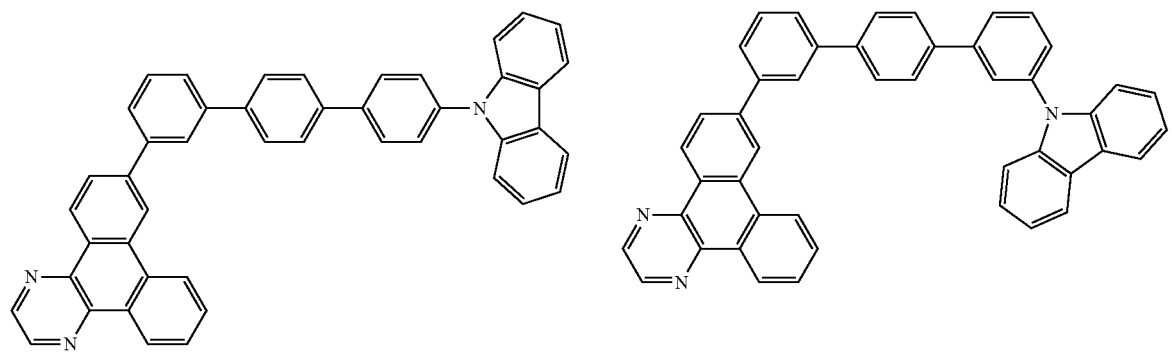
(720) (721)
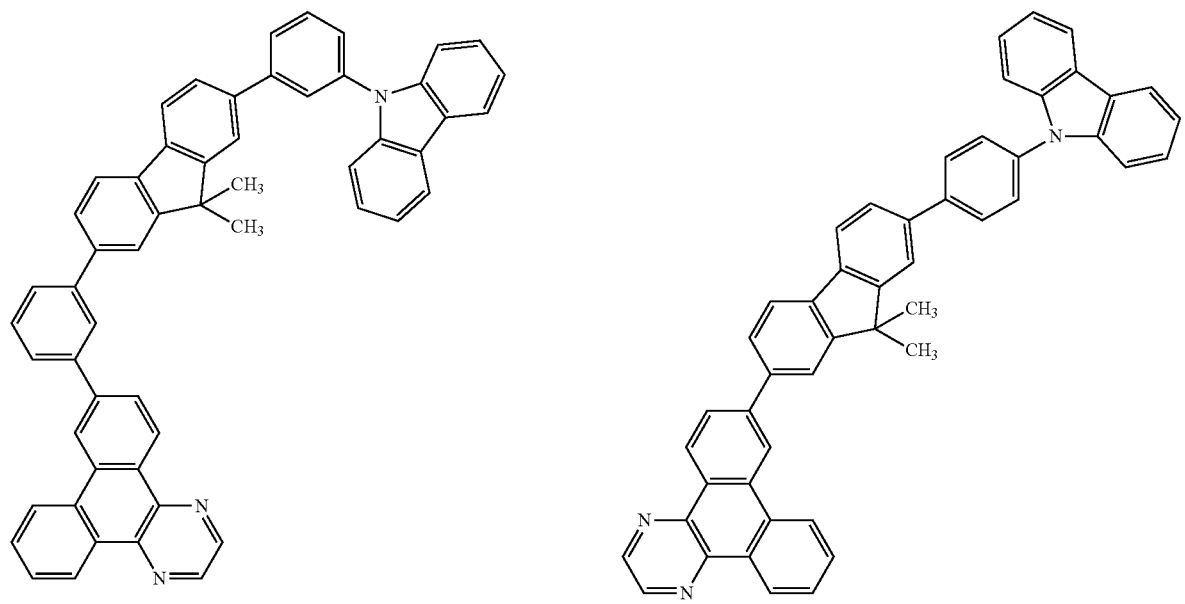

-continued
(722)
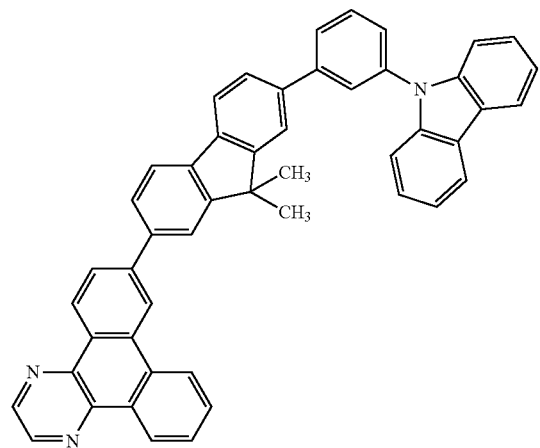
(723)
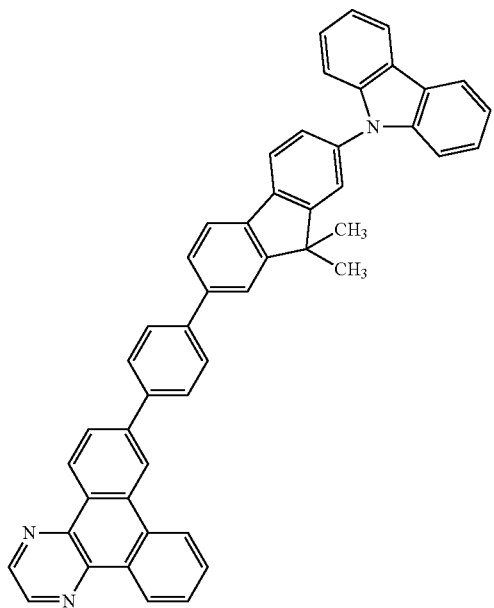
(724)
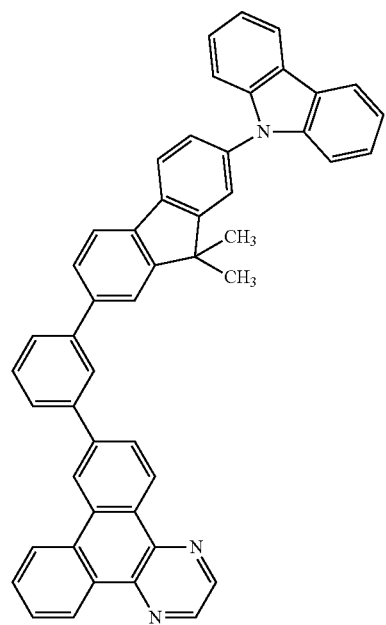

[Chemical formula 167]
(725) 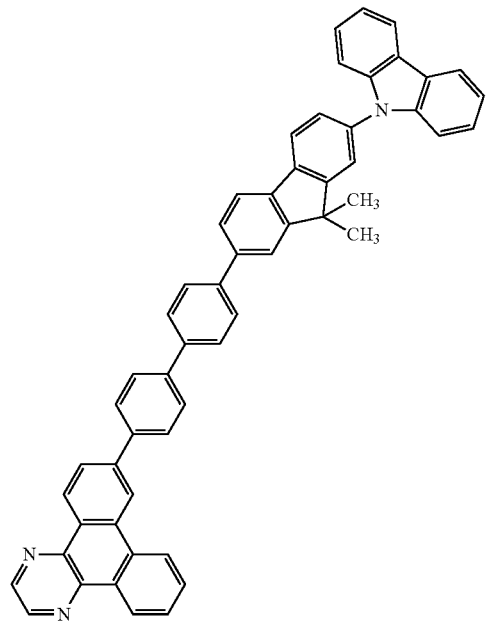
(726) 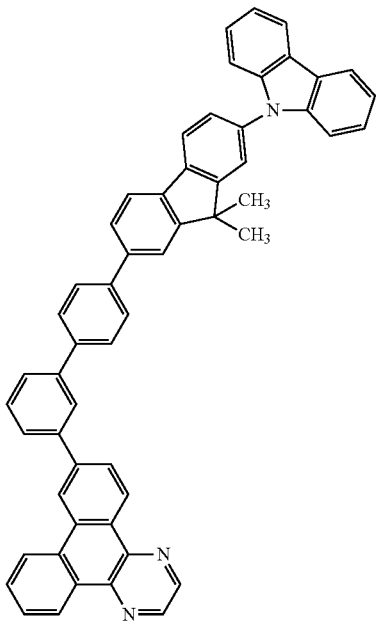
(727) 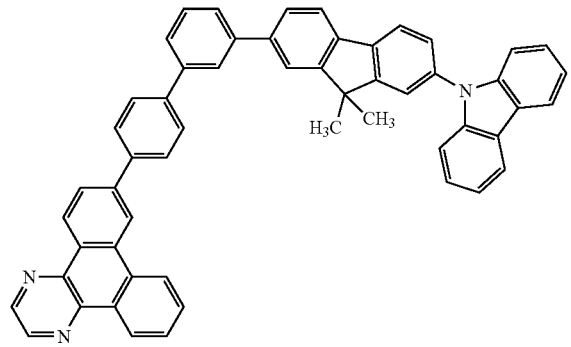
(728) 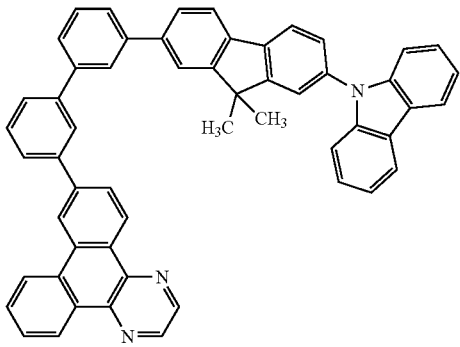
(729) 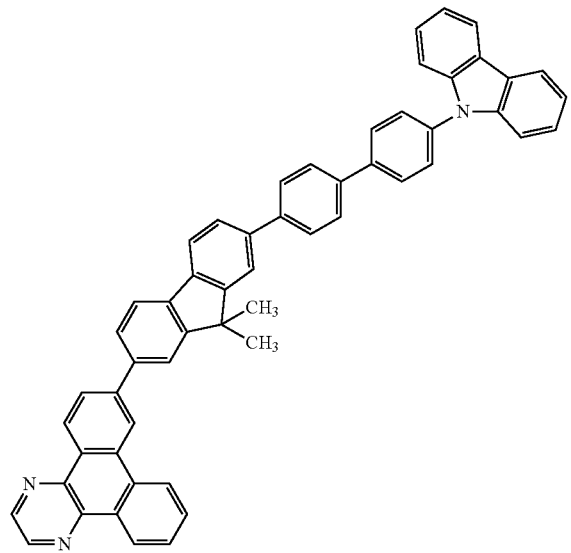
(730) 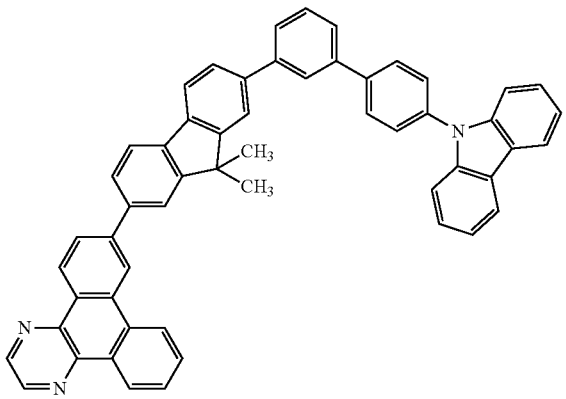

-continued
(731)
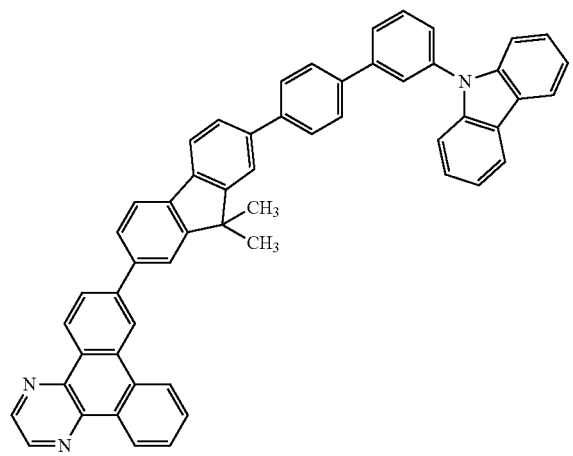
(732)
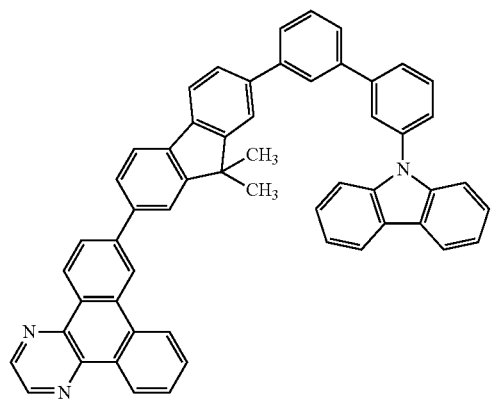
[Chemical formula 168]
(733)
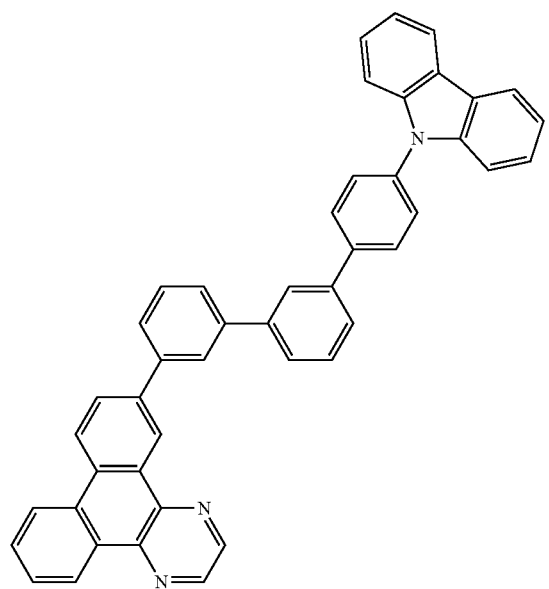
(734)
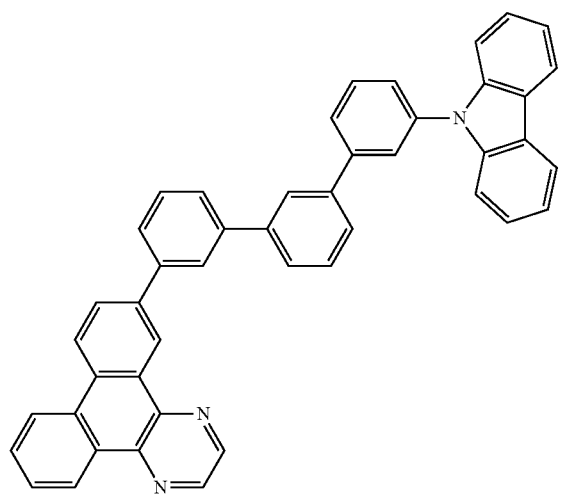

333
-continued
(735)
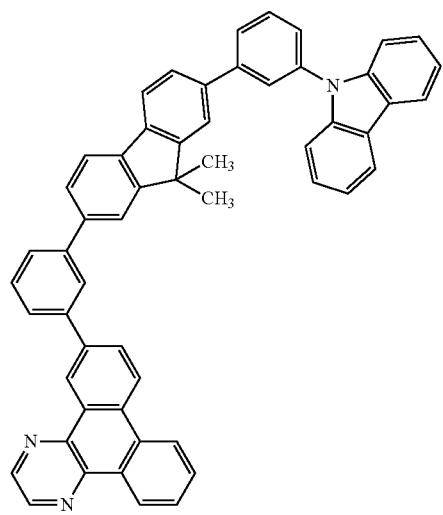
334
(736)
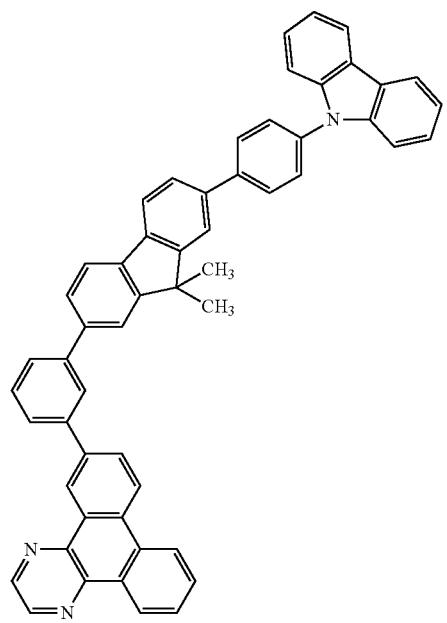
(737)
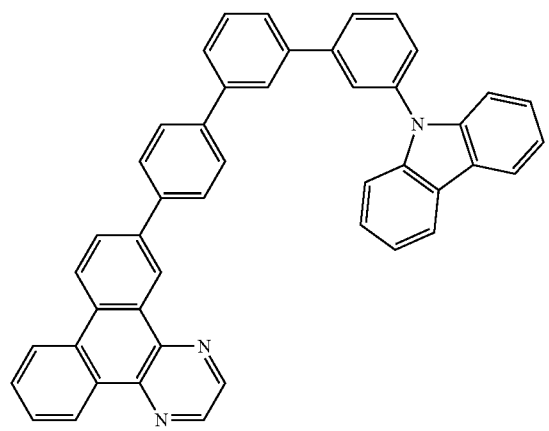
[Chemical formula 169]
(738)
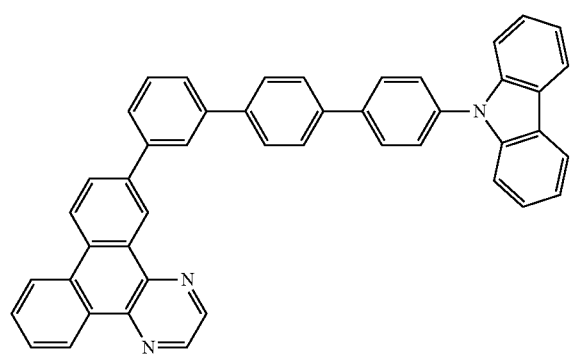
(739)
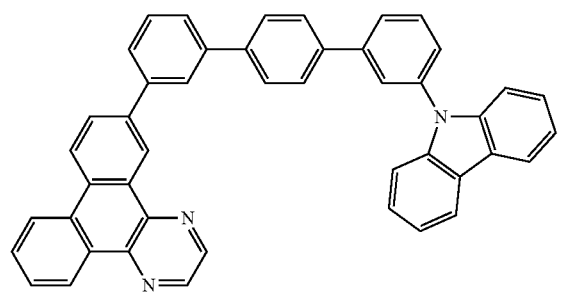

-continued
(740)
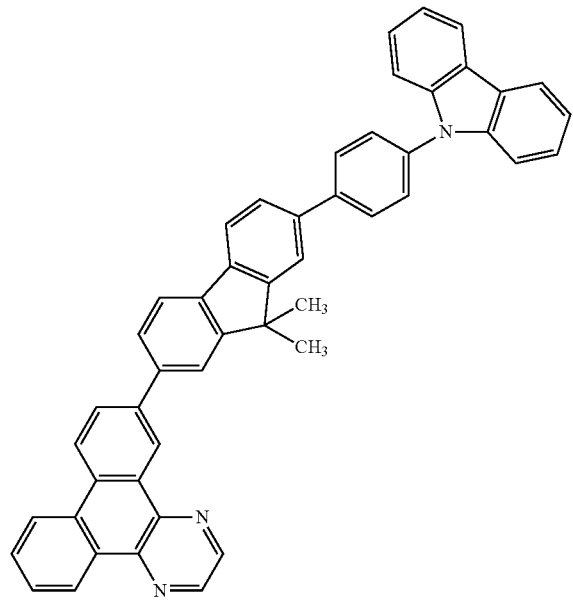
(741)
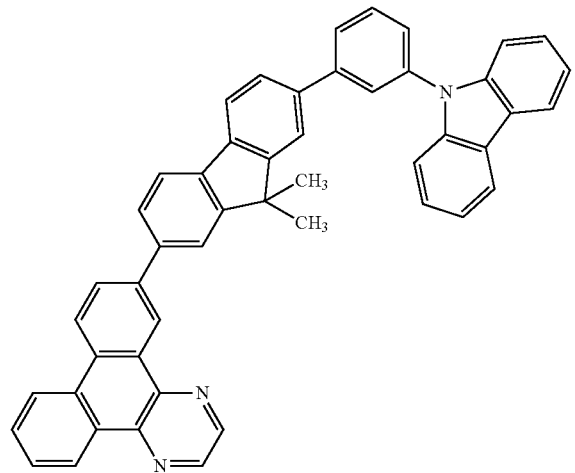
(742)
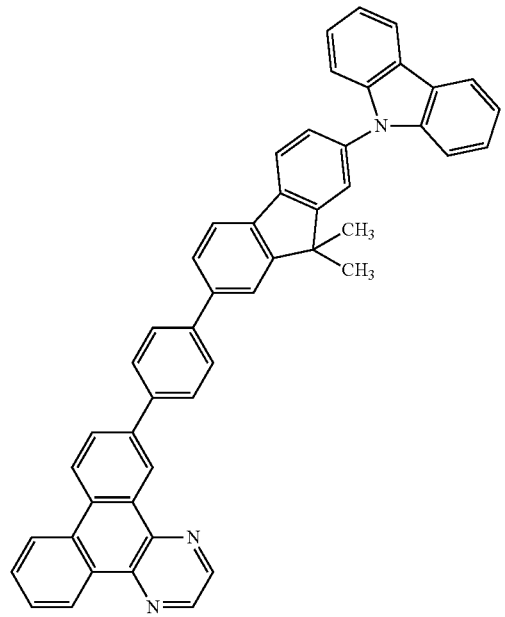
(743)
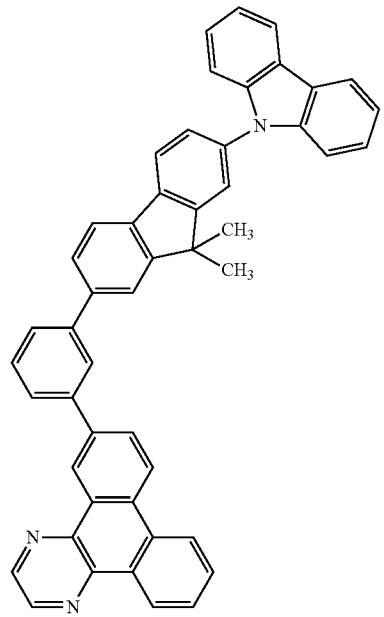

[Chemical formula 170]
(744)
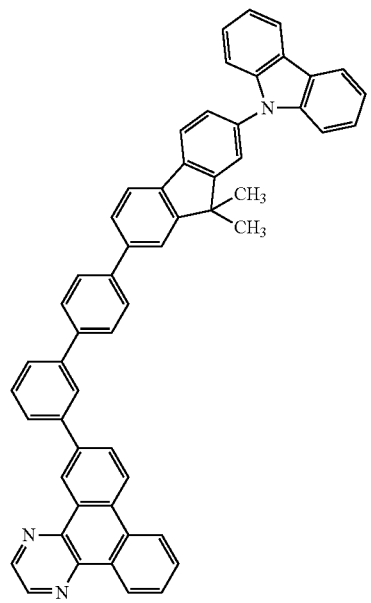
(745)
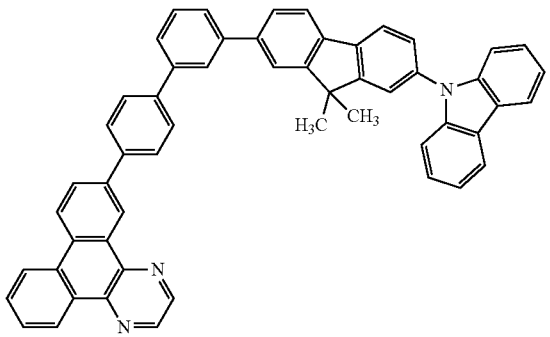
(746)
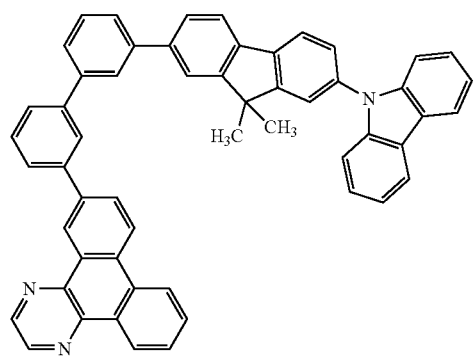
(747)
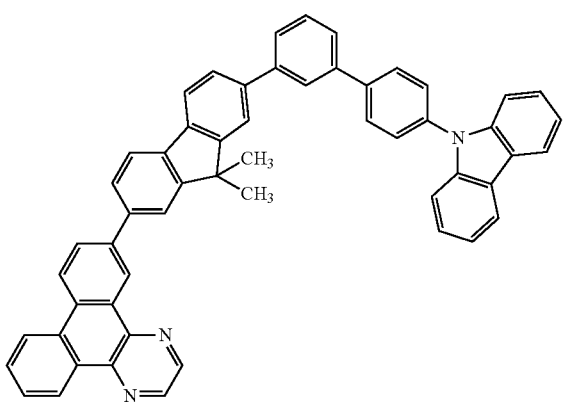
(748)
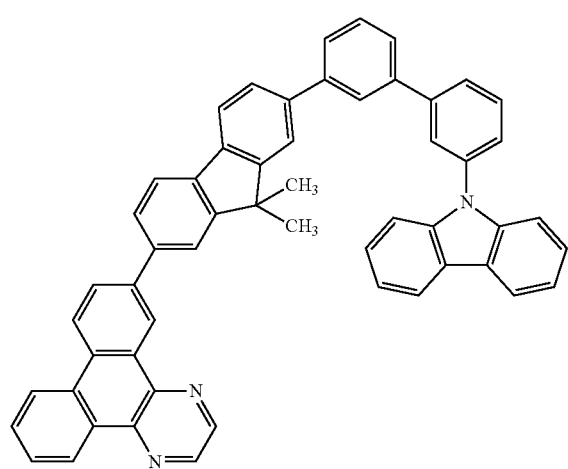

[Chemical formula 171]
(749)
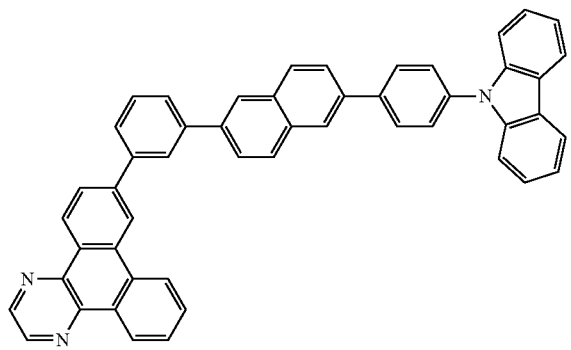
(750)
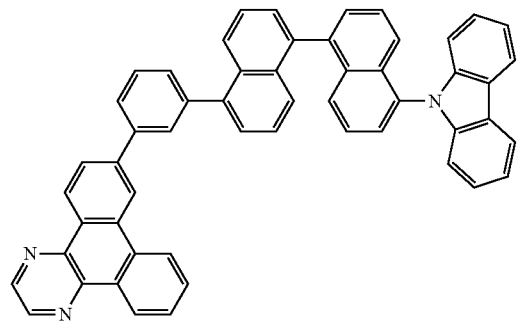
(751)
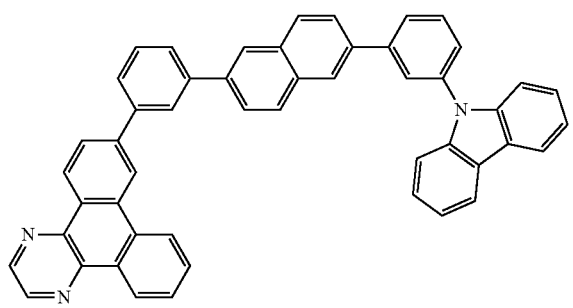
(752)
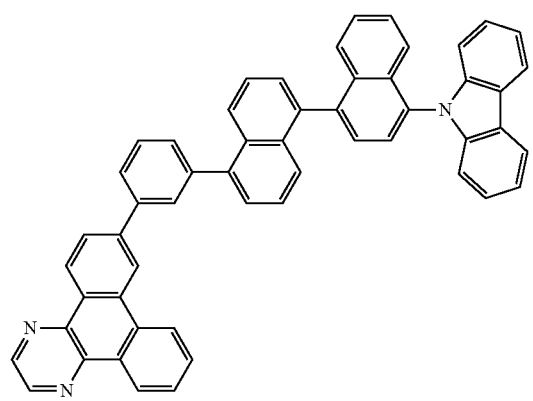
(753)
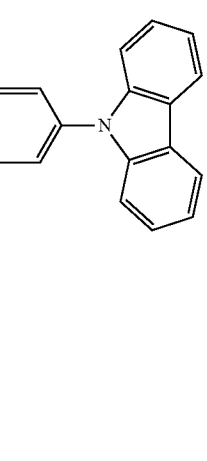

-continued
(754)
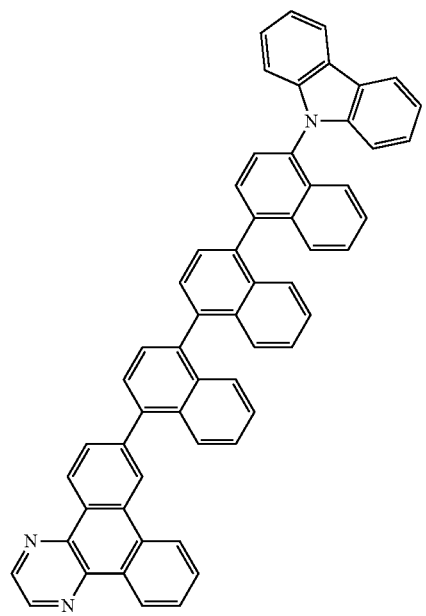
(755)
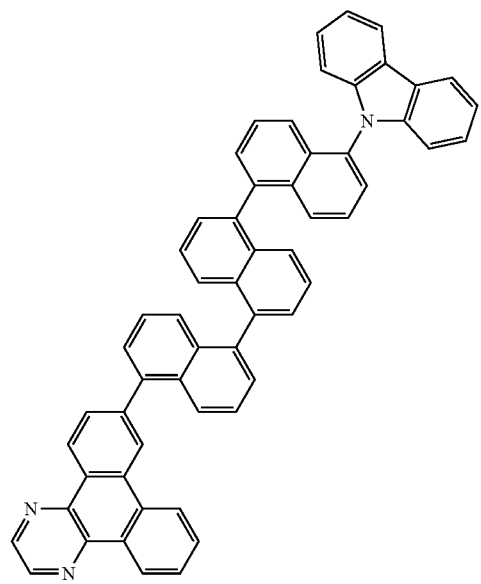
(756)
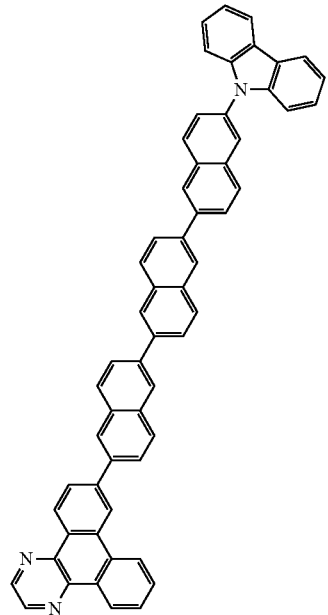
(757)
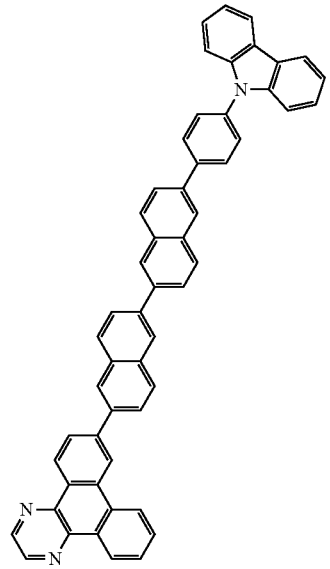

[Chemical formula 172]
(758) 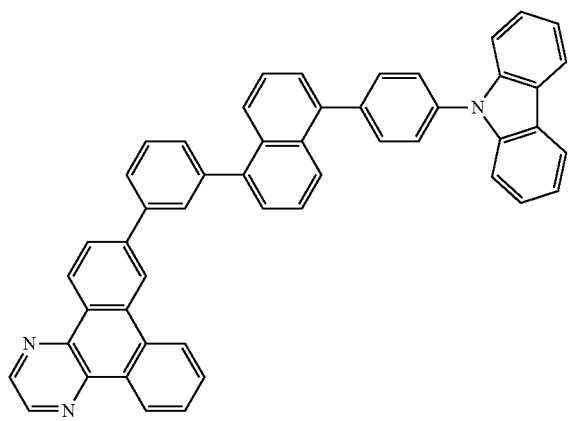
(759) 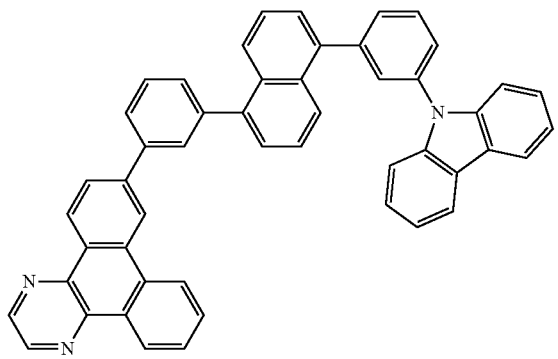
(760) 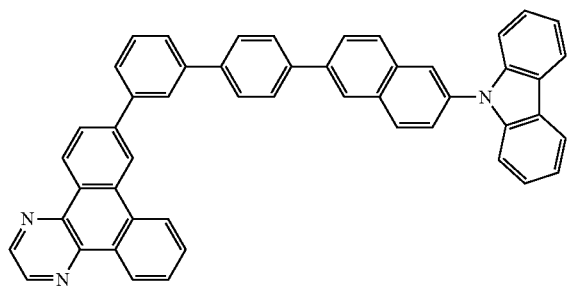
(761) 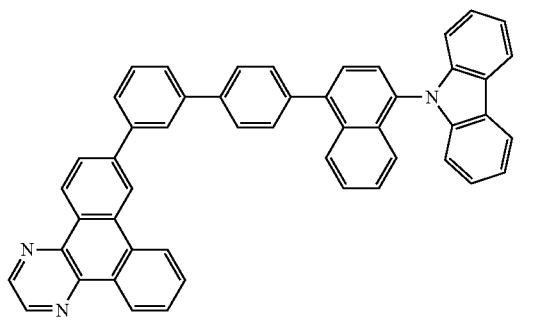
(762) 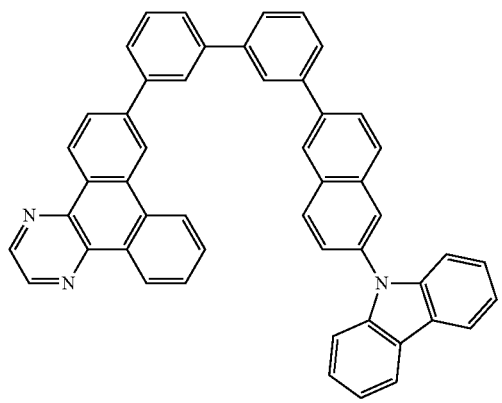
(763) 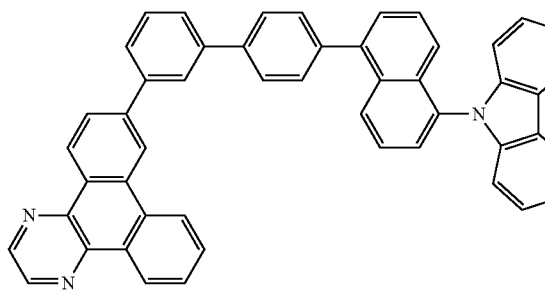
(764) 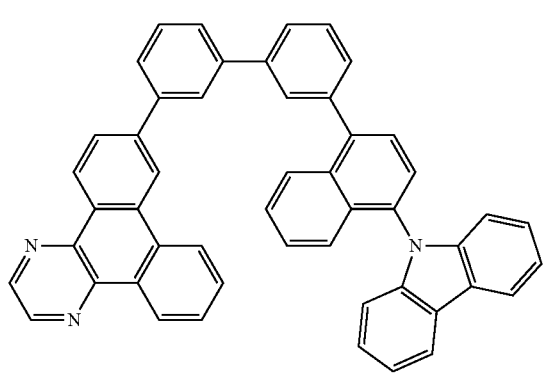
(765) 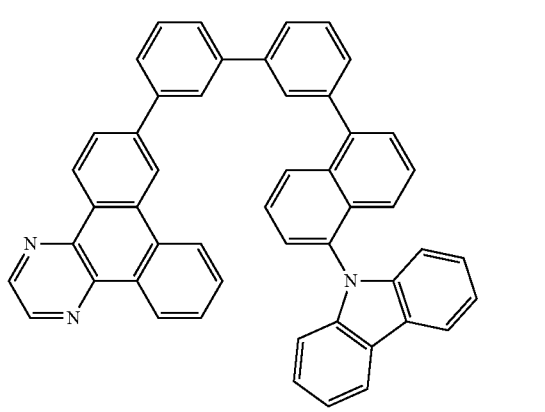

[Chemical formula 173]
(766) 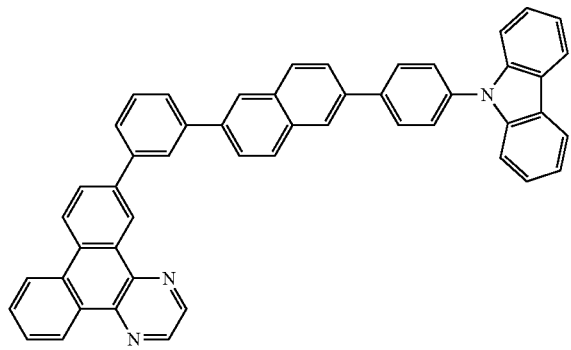
(767) 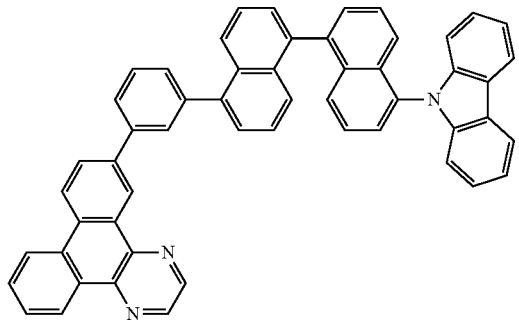
(768) 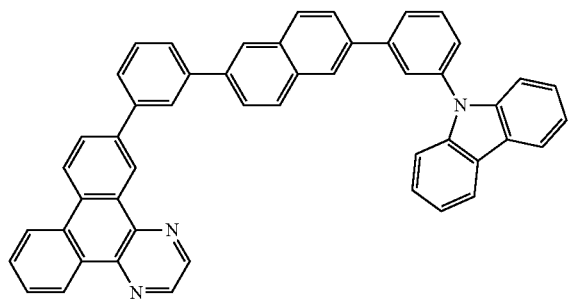
(769) 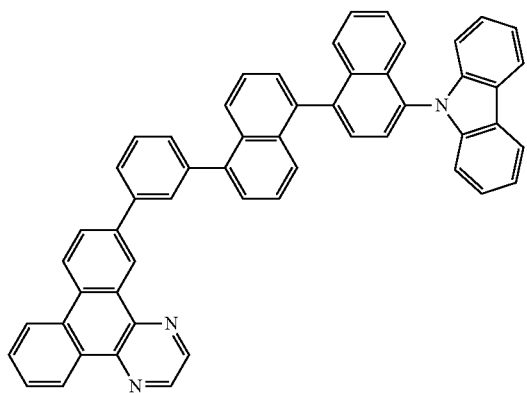
(770) 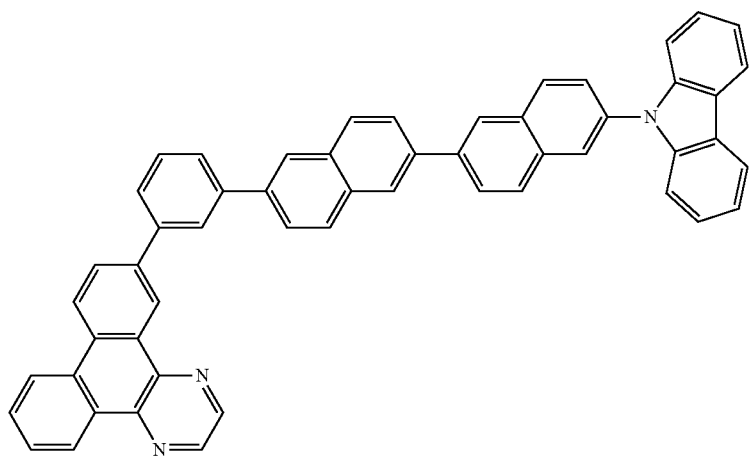

-continued
347 (771)
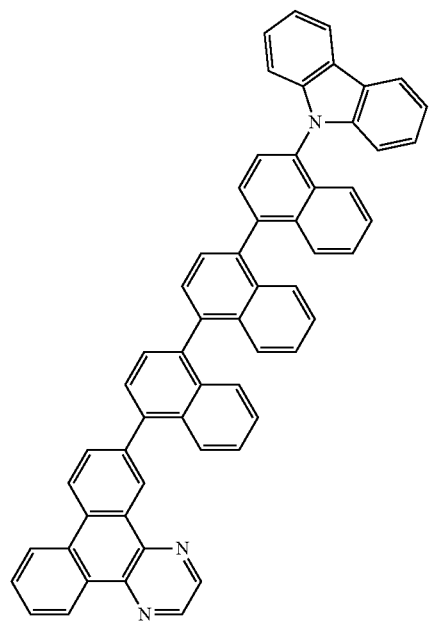
348 (772)
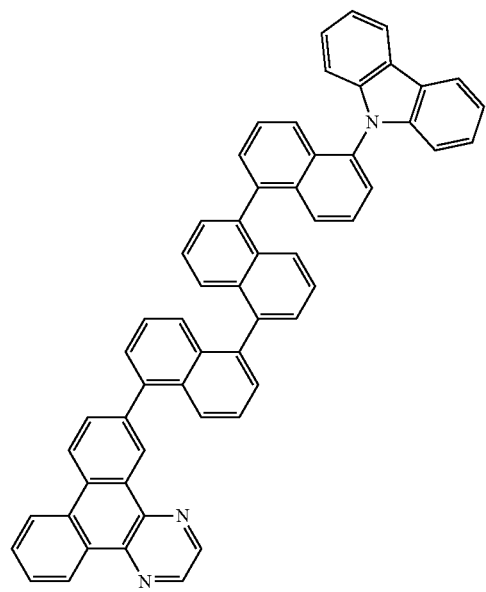
(773)
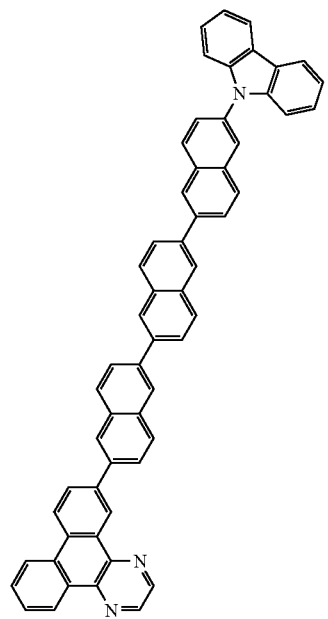
(774)
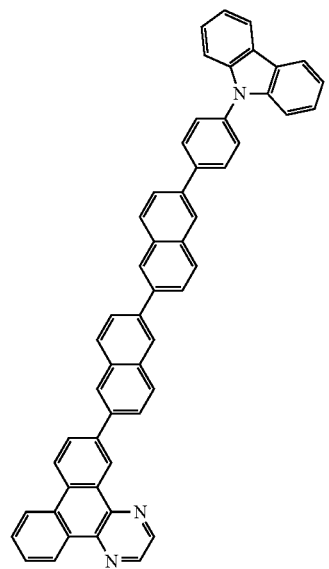

[Chemical formula 174]
(775)
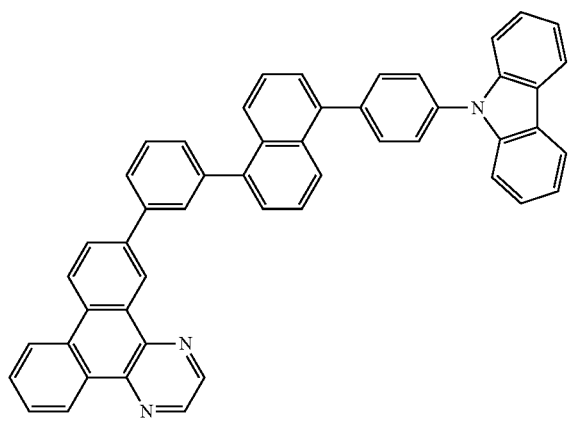
(776)
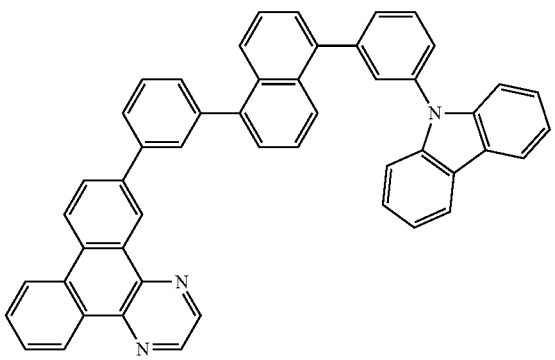
(777)
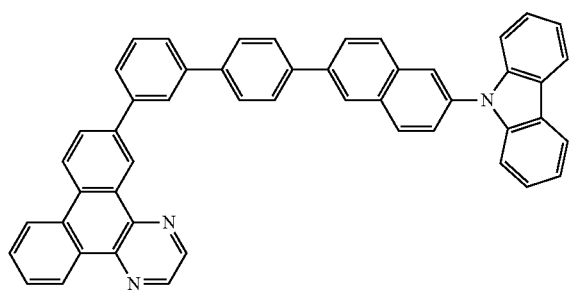
(778)
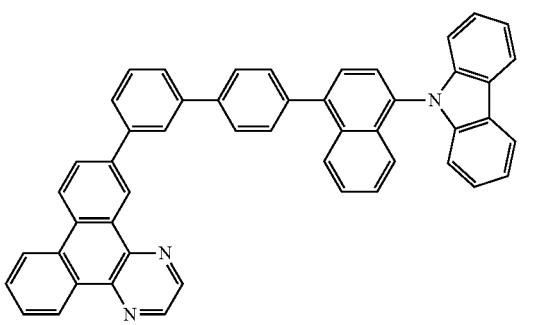
(779)
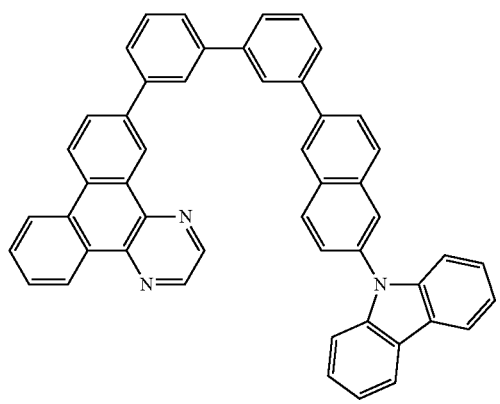
(780)
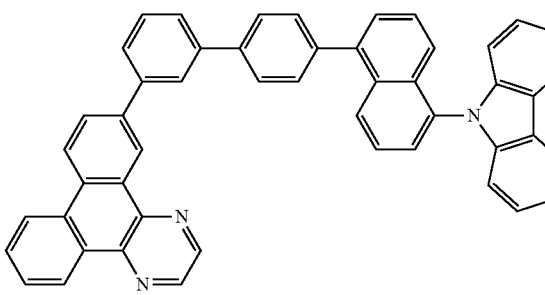
(781)
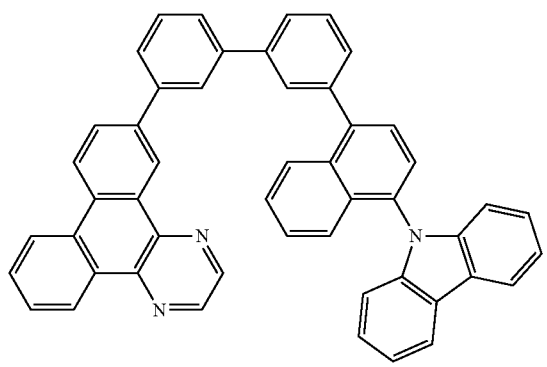
(782)
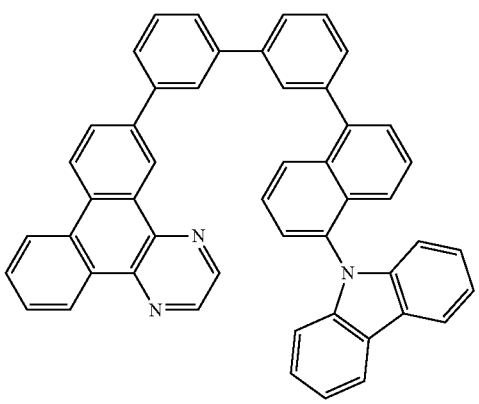

[Chemical formula 175]
(783)
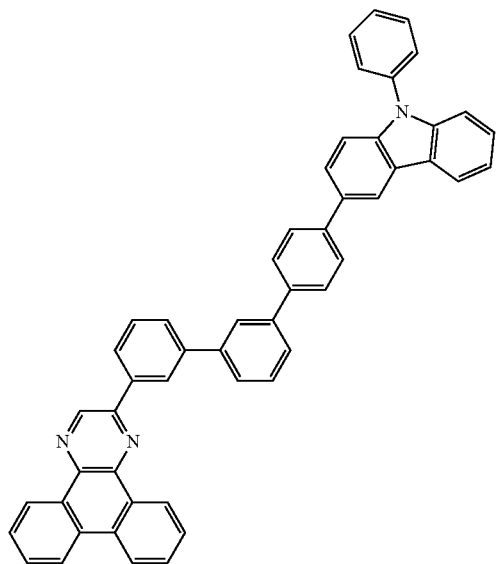
(784)
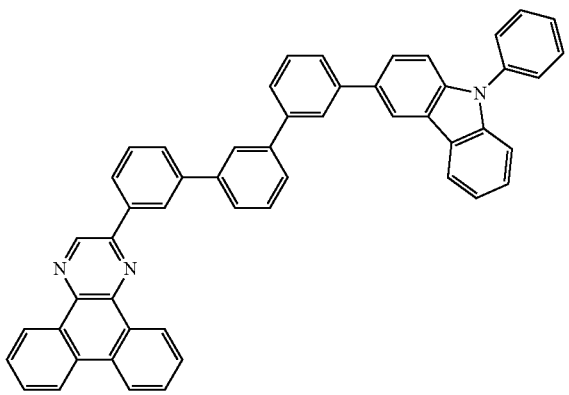
(785)
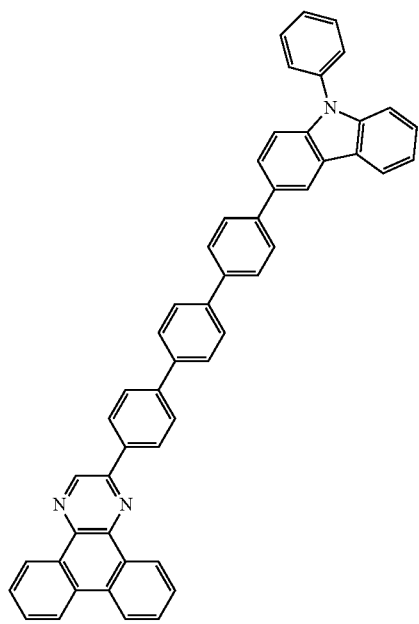
(786)
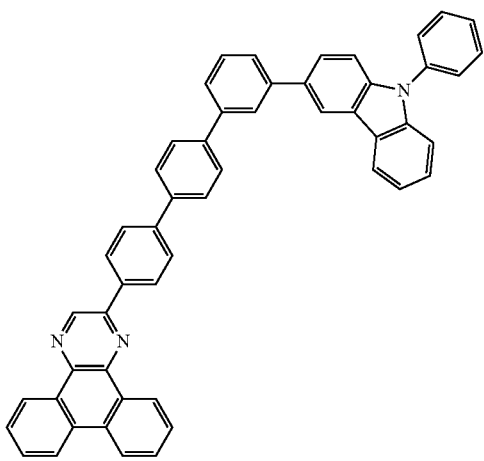
(787)
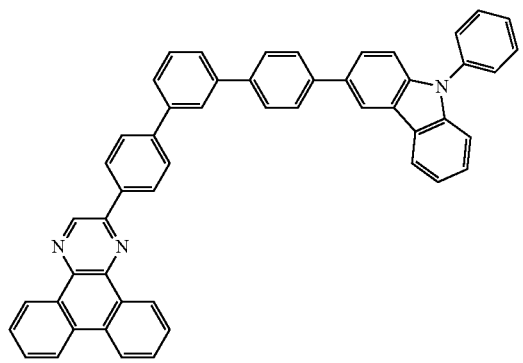
(788)
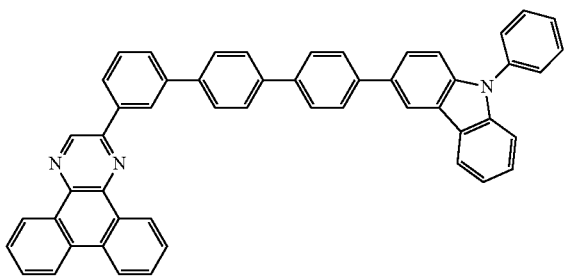

-continued
(789)
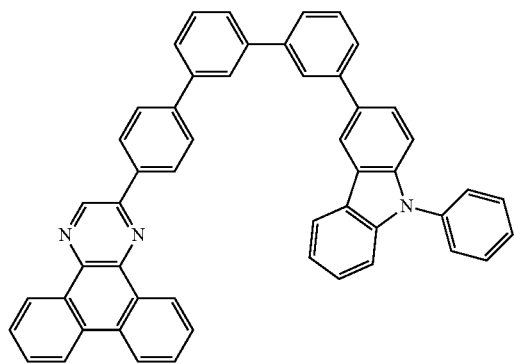
(790)
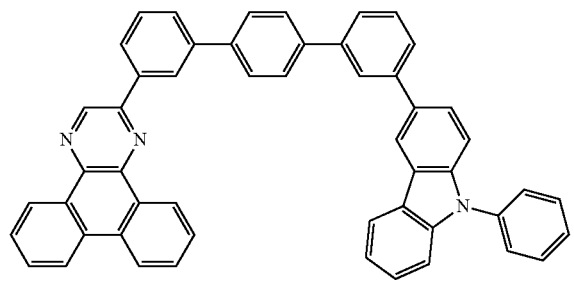
(791)
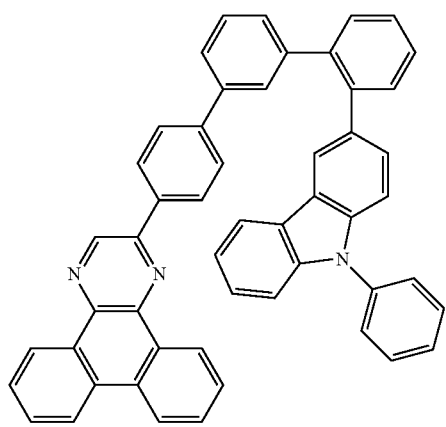
(792)
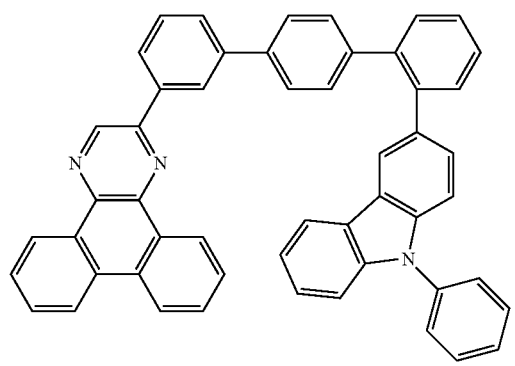
[Chemical formula 176]
(793)
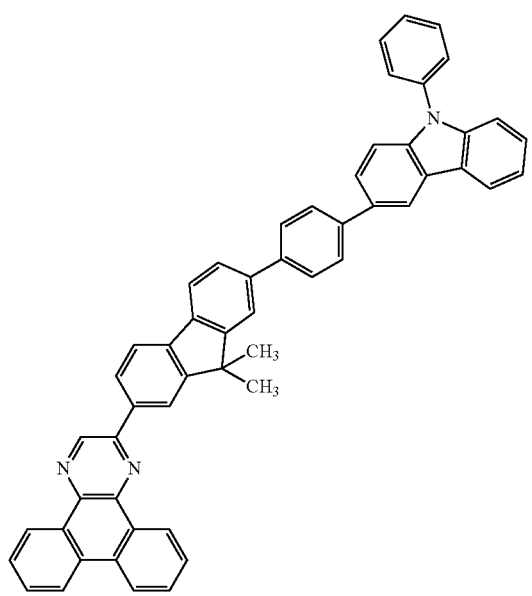
(794)
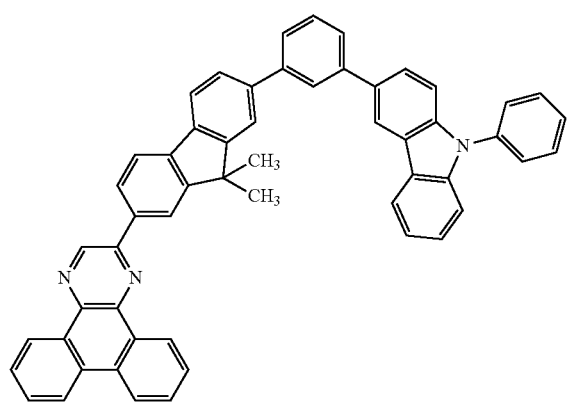

-continued
(795)
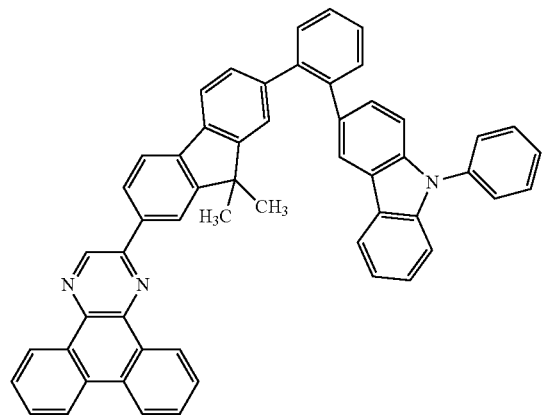
(796)
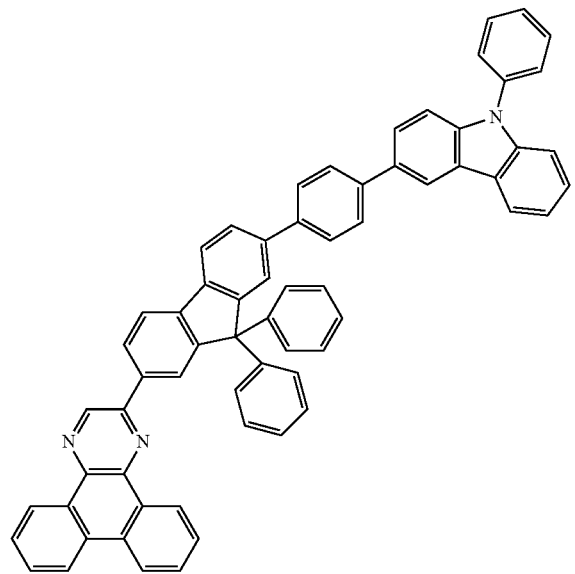
(797)
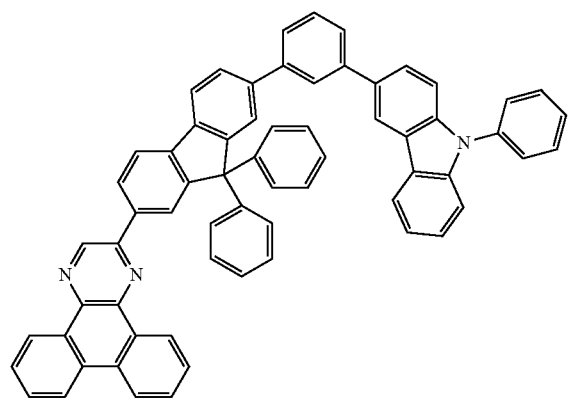
(798)
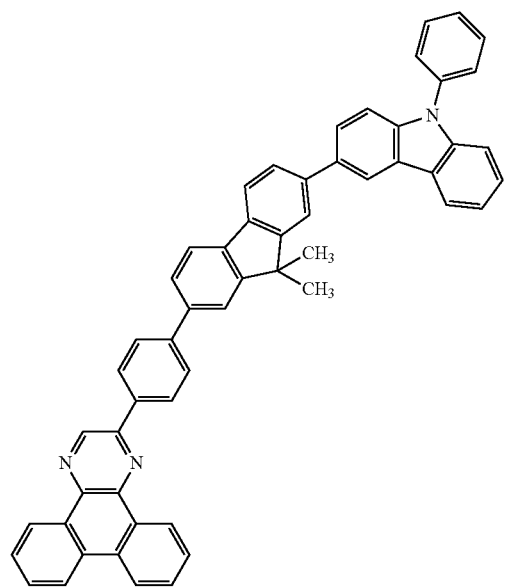

(799)
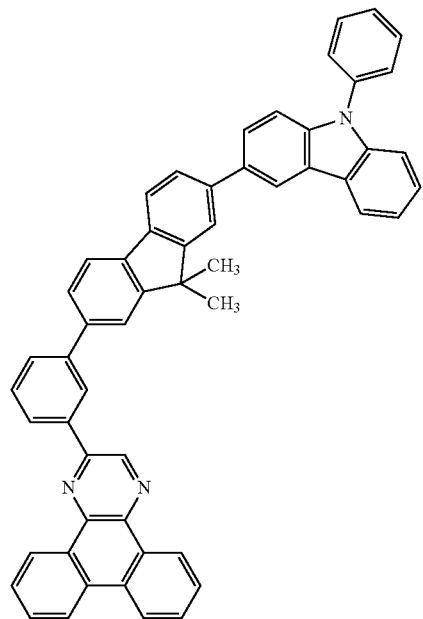
[Chemical formula 177]
(800)
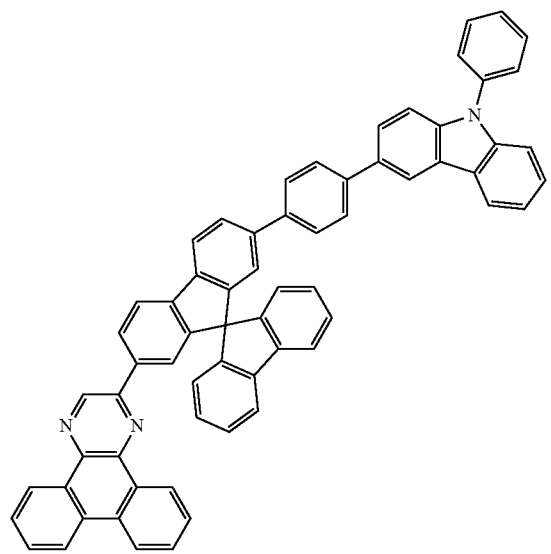
(801)
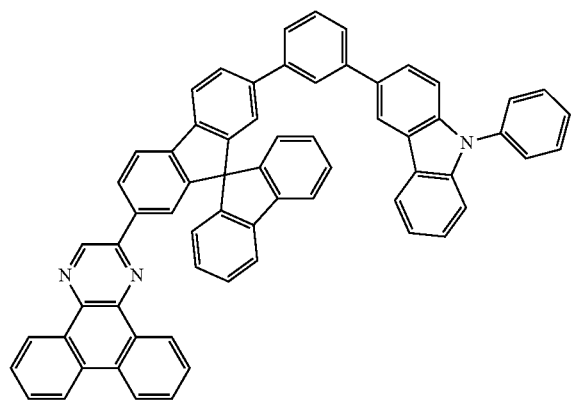

-continued
(802) (803)
(804) (805)
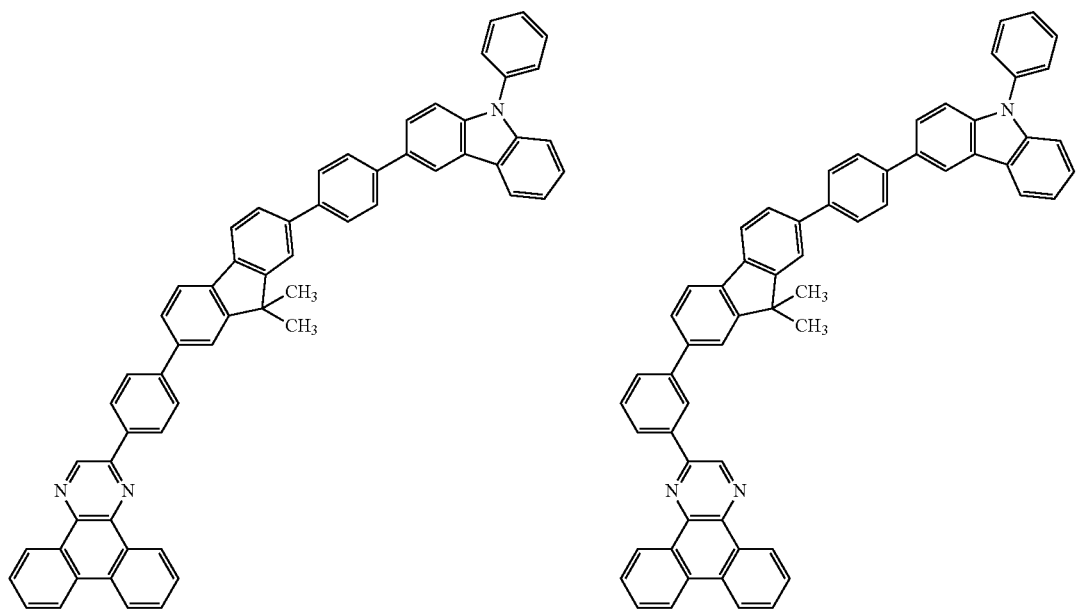
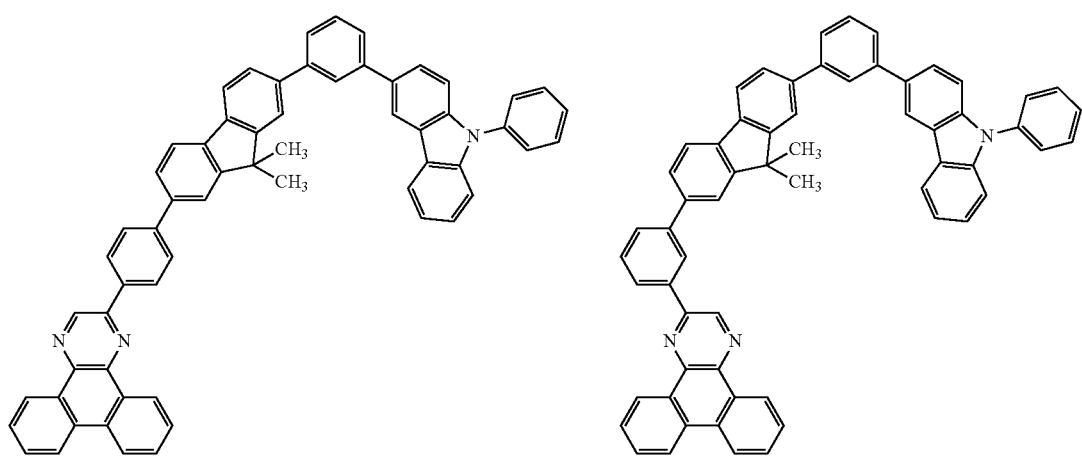

[Chemical formula 178]
(806) 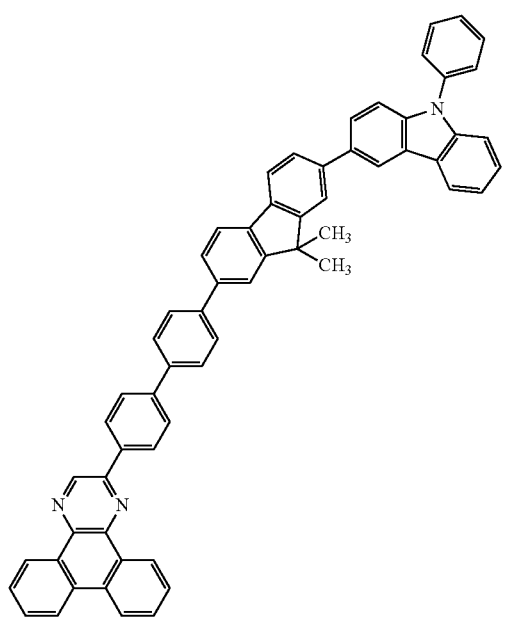
(807) 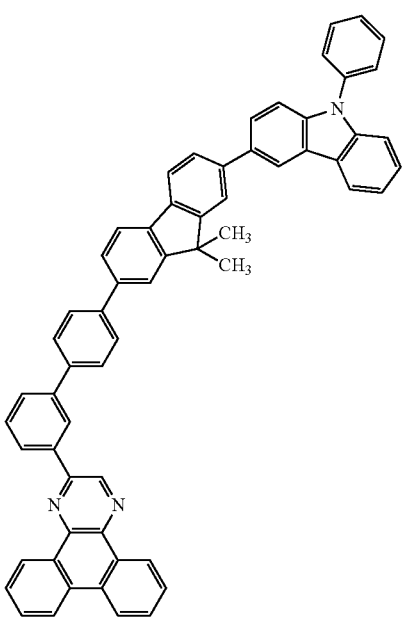
(808) 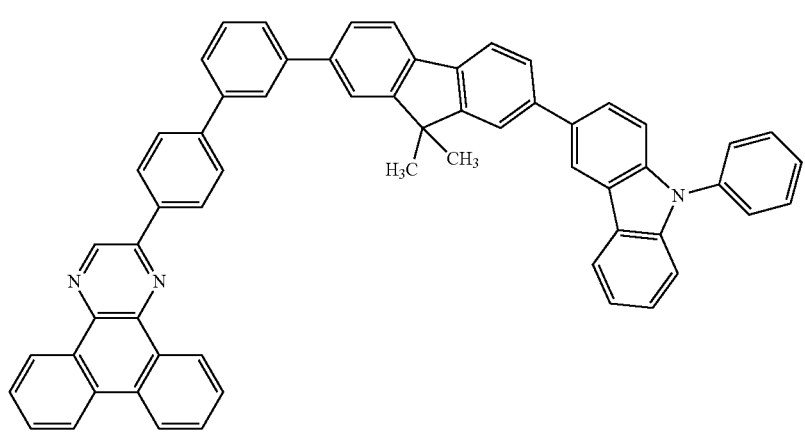
(809) 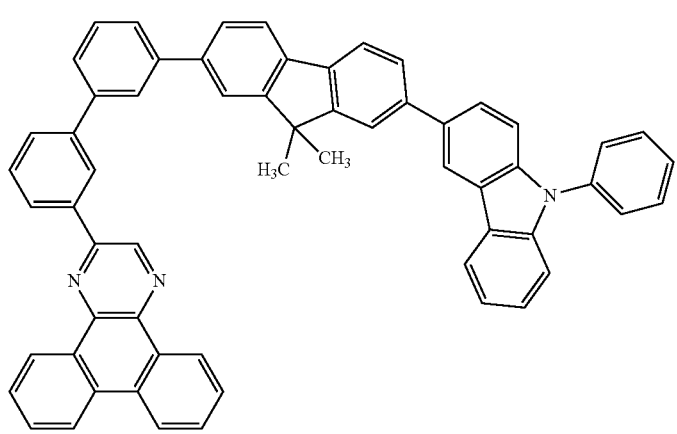

-continued
(810)
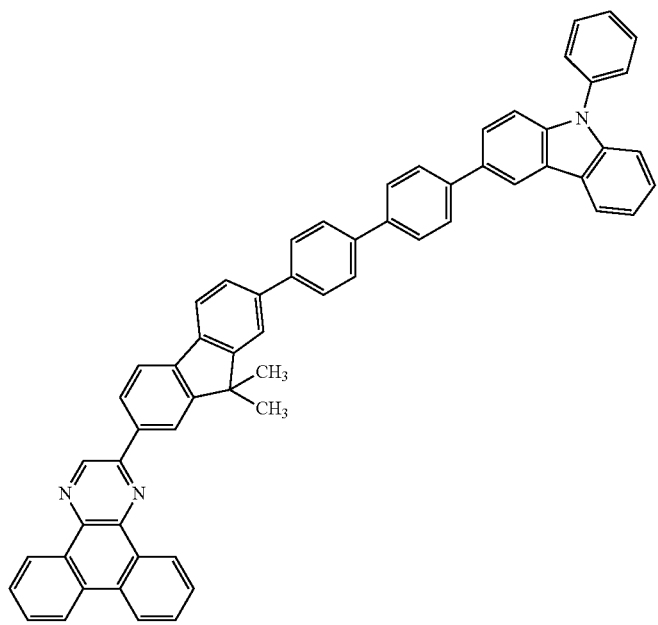
(811)
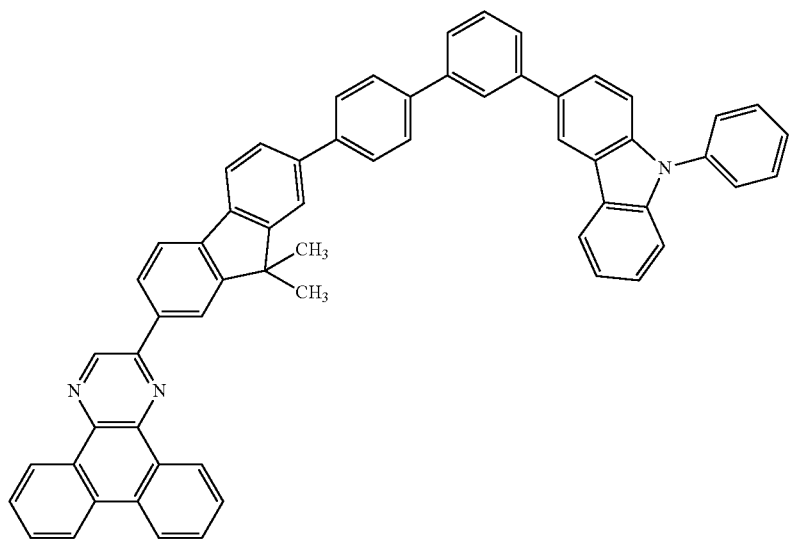
(812)
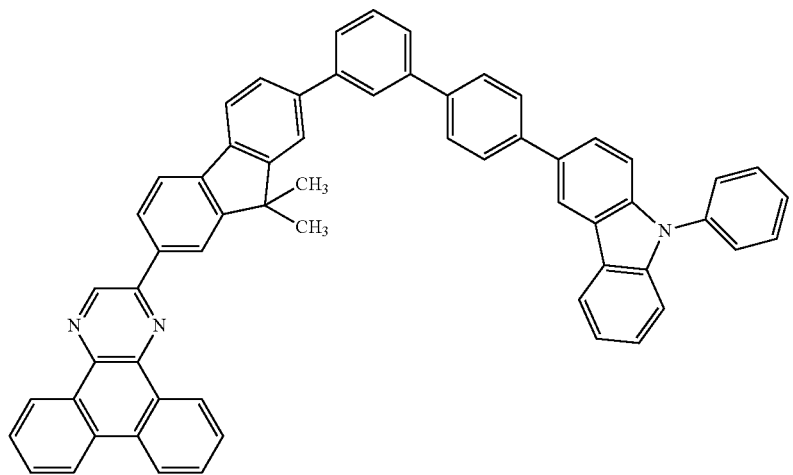

(813)
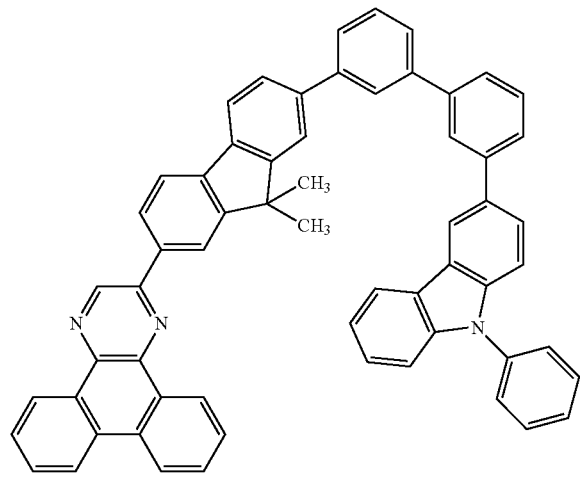
[Chemical formula 179]
(814)
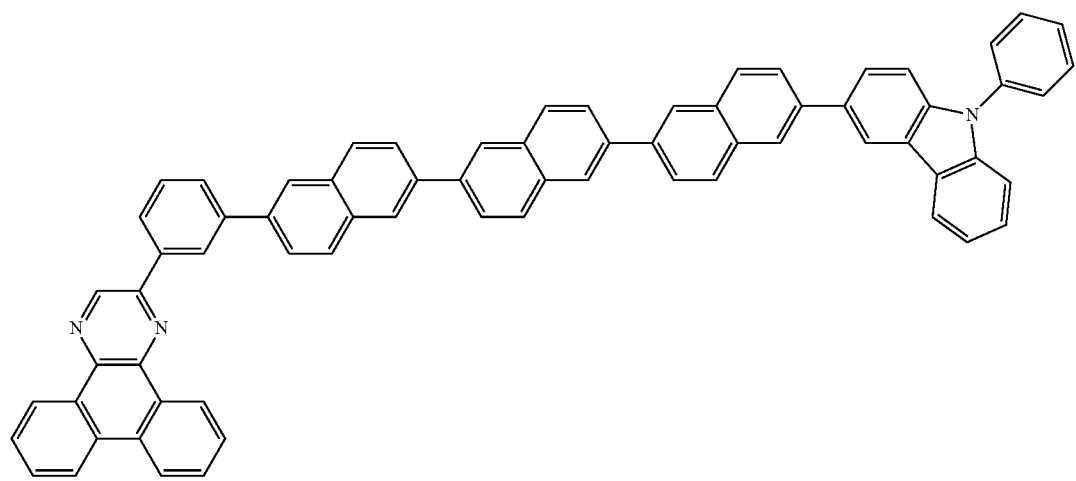
(815)
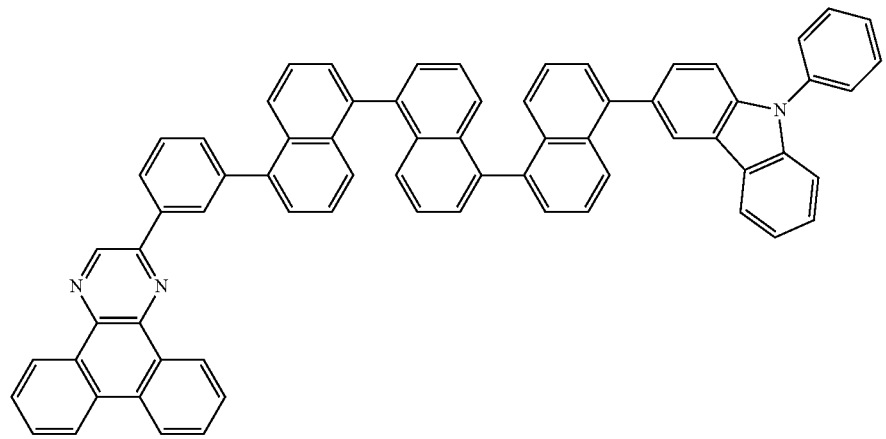

(816)
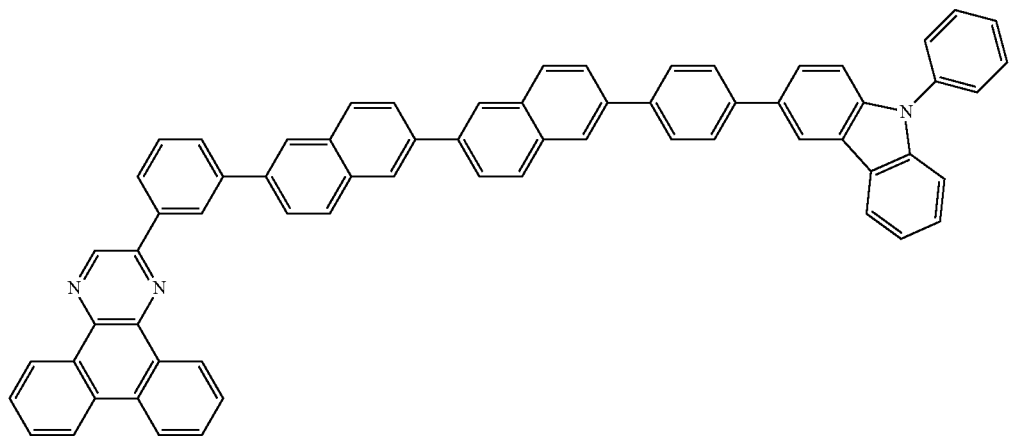
(817)
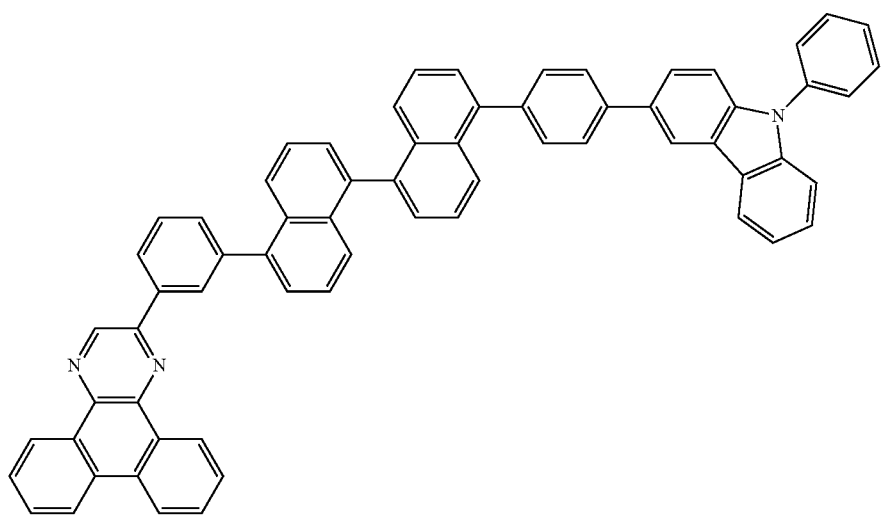
(818)
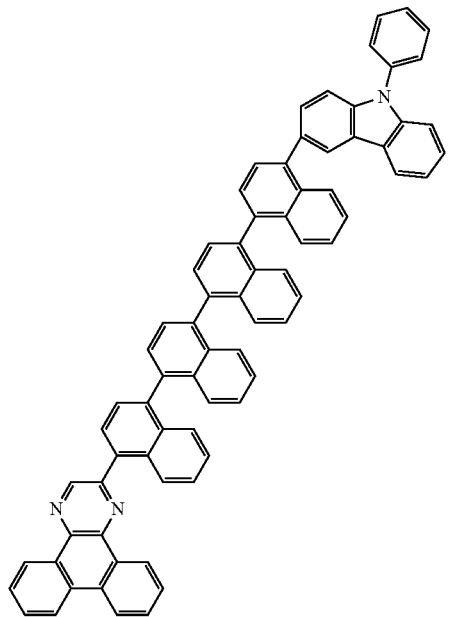
(819)
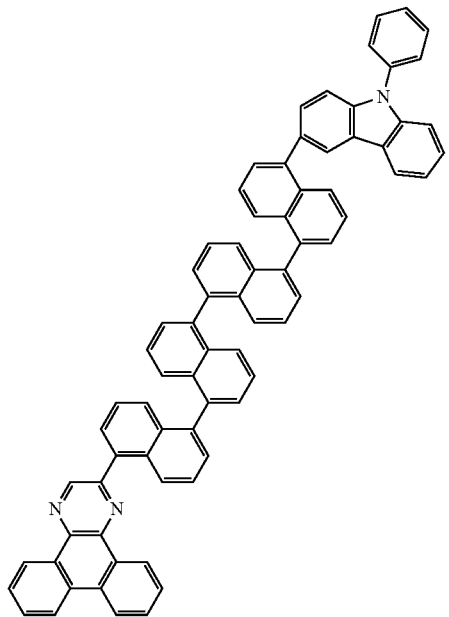

(820)
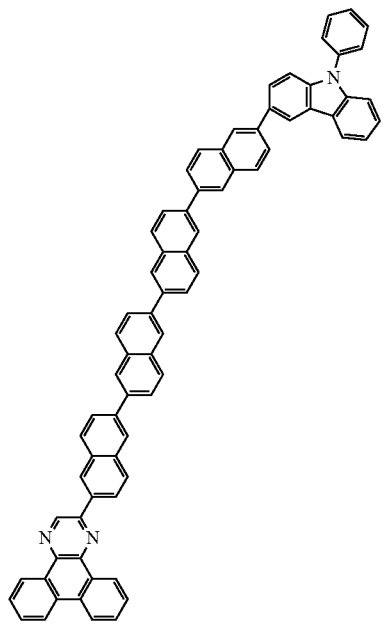
[Chemical formula 180]
(821)
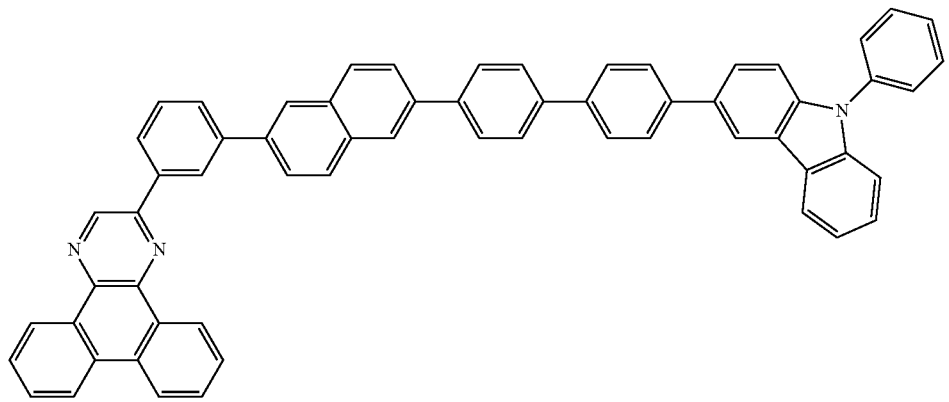
(822)
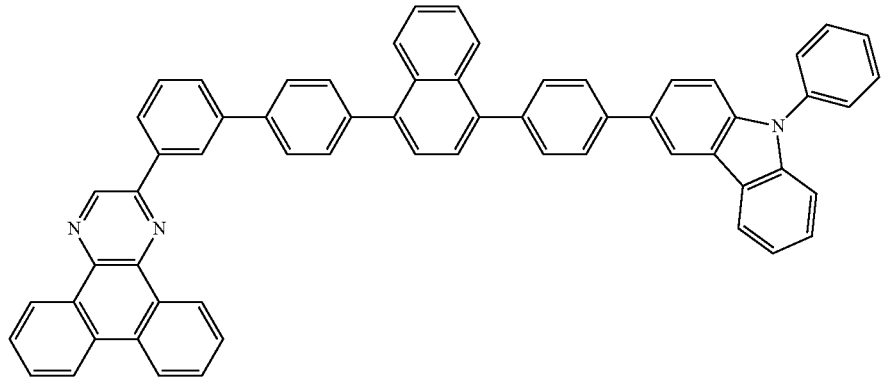

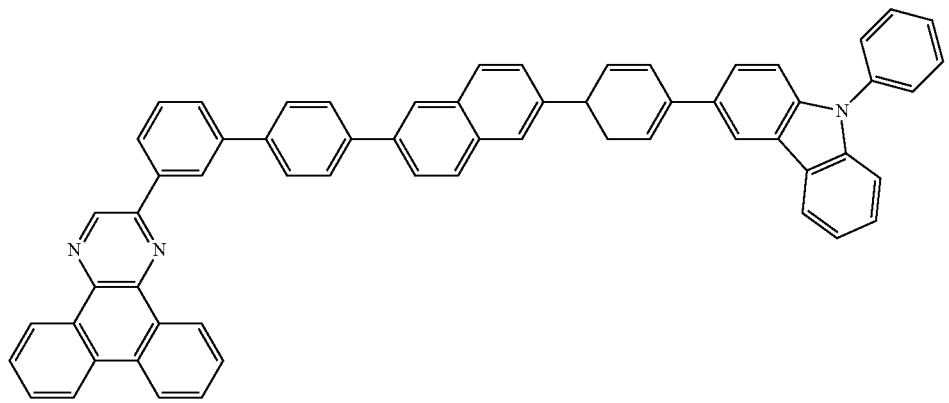
(823)
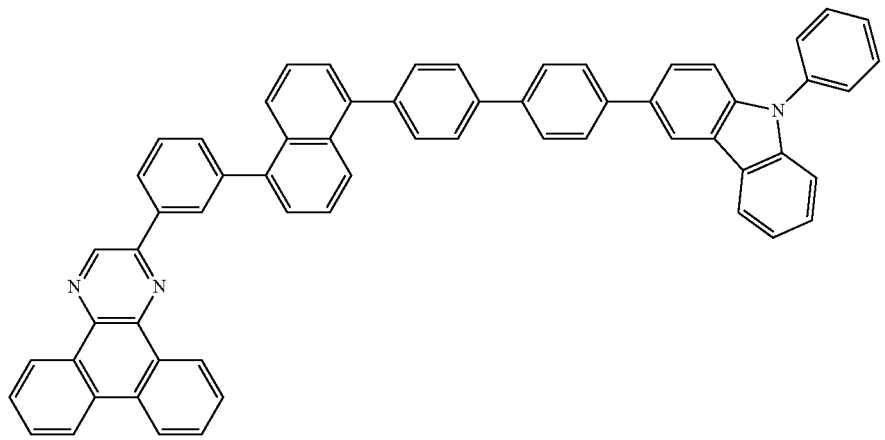
(824)
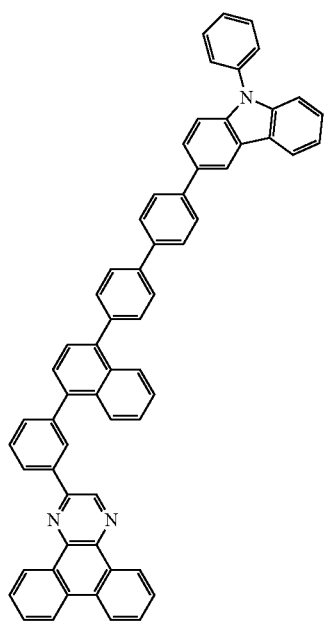
(825)
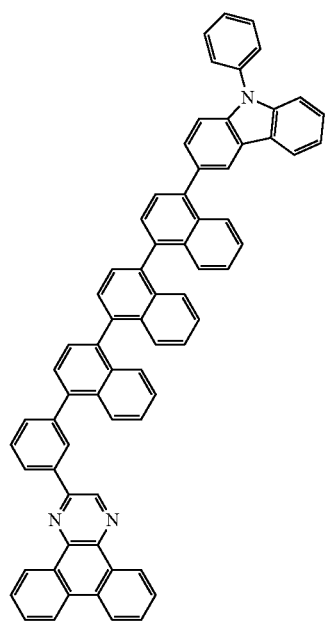
(826)

-continued
(827)
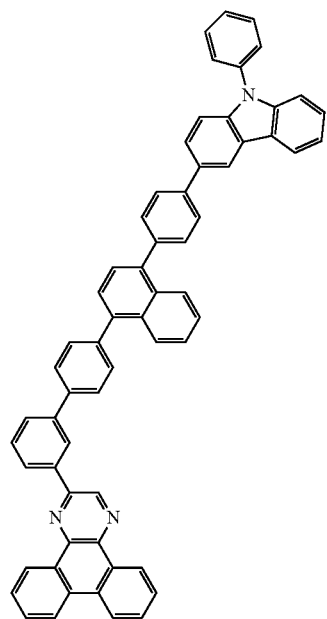
(828)
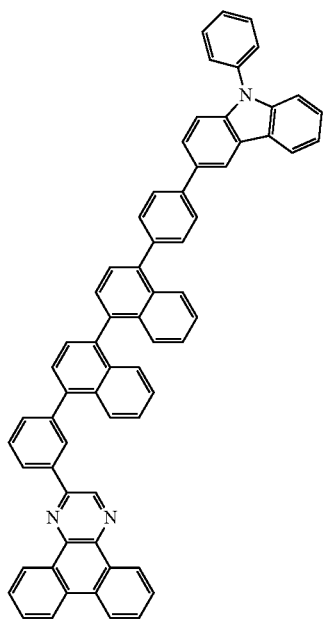
[Chemical formula 181]
(829)
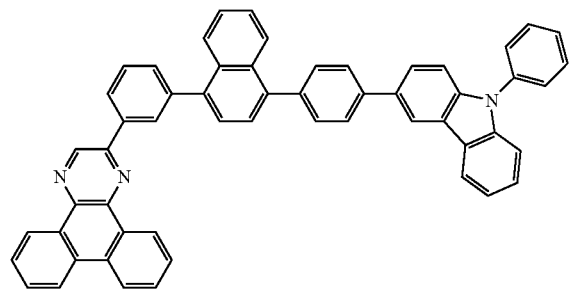
(830)
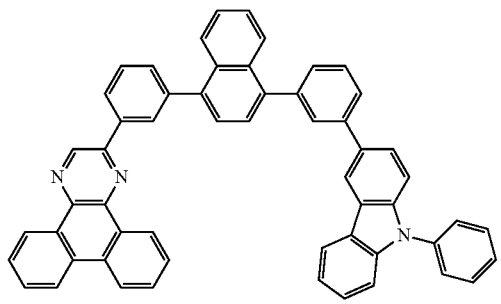
(831)
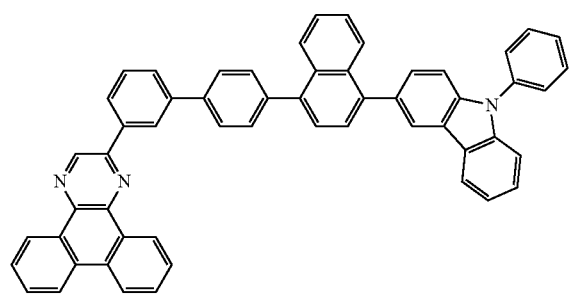
(832)
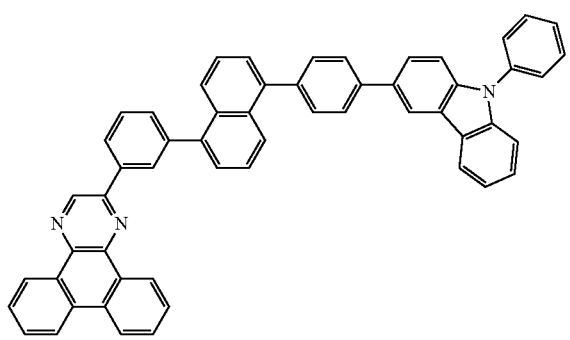

-continued
(833)
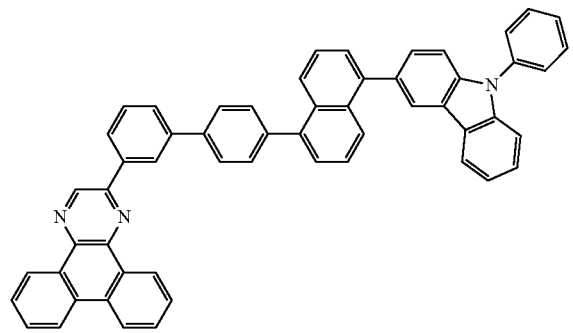
(834)
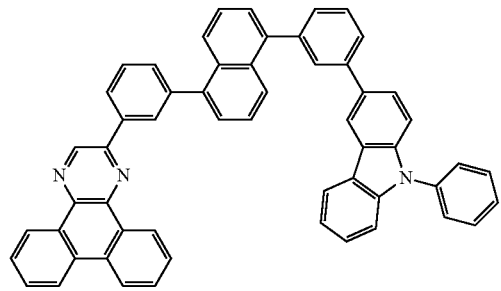
(835)
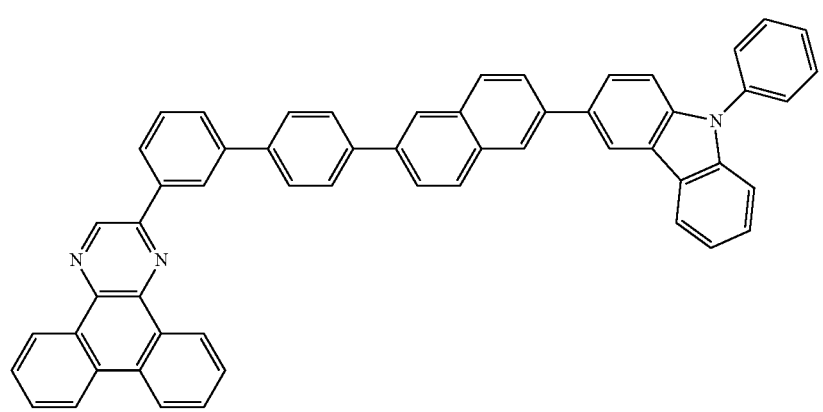
(836)
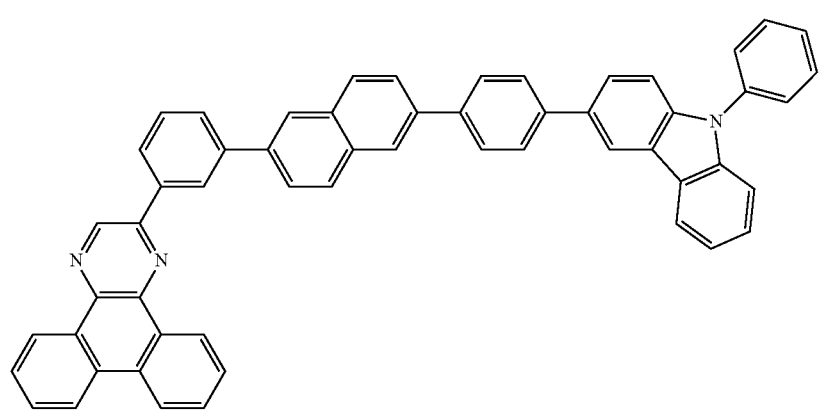
(837)
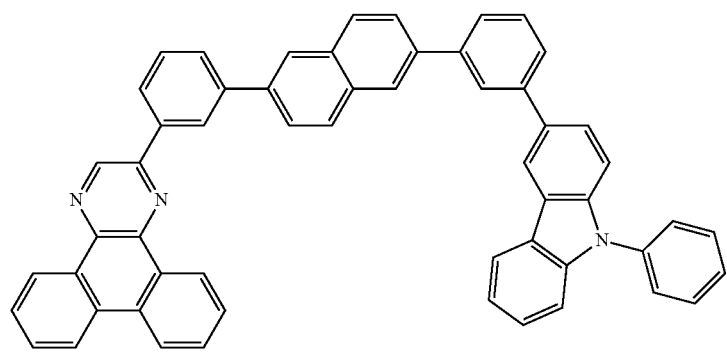

[Chemical formula 182]
(838)
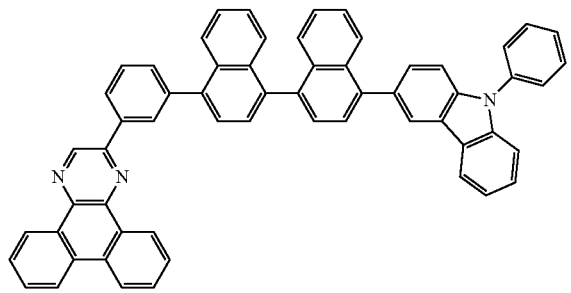
(839)
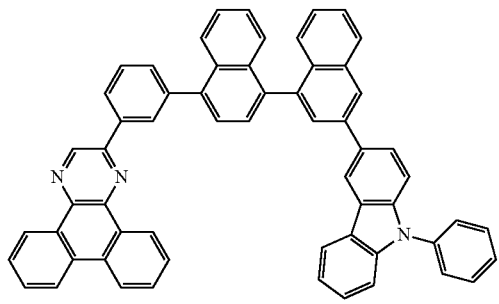
(840)
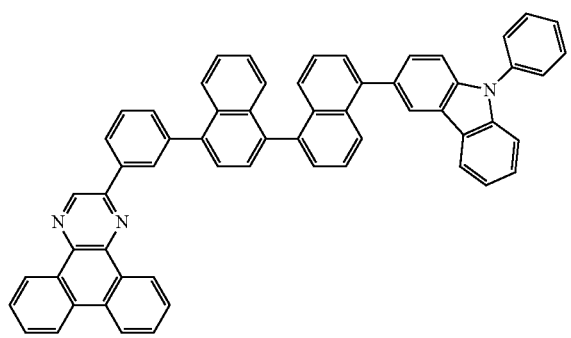
(841)
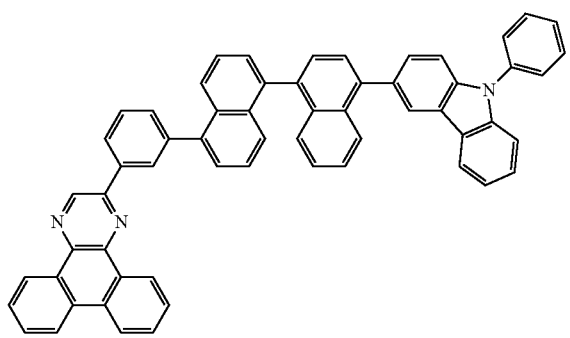
(842)
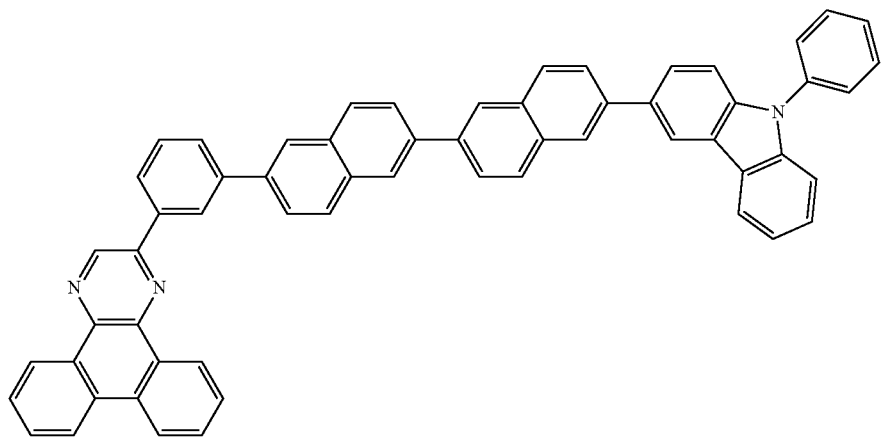

-continued
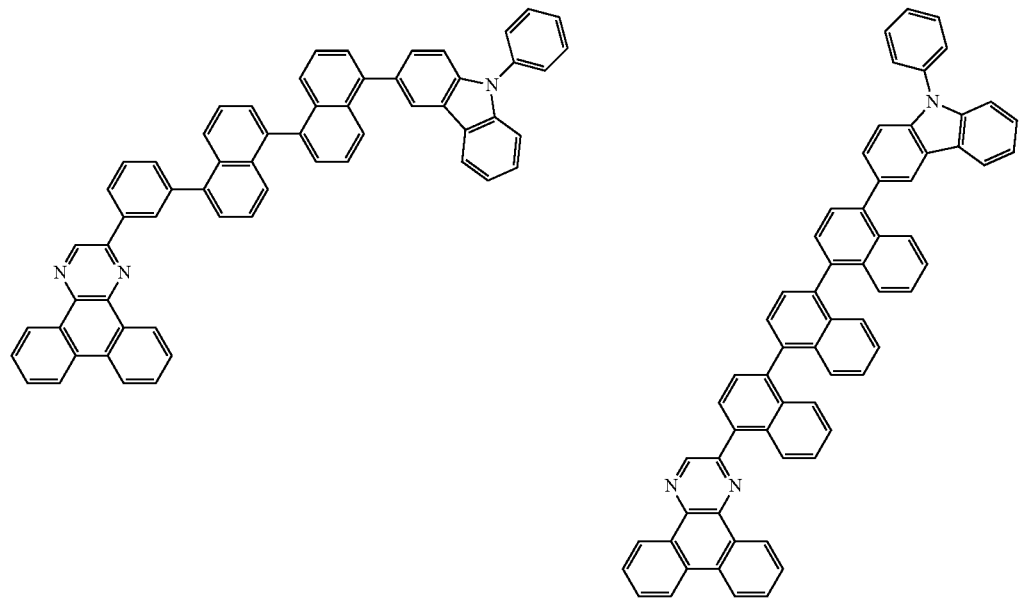
[Chemical formula 183]
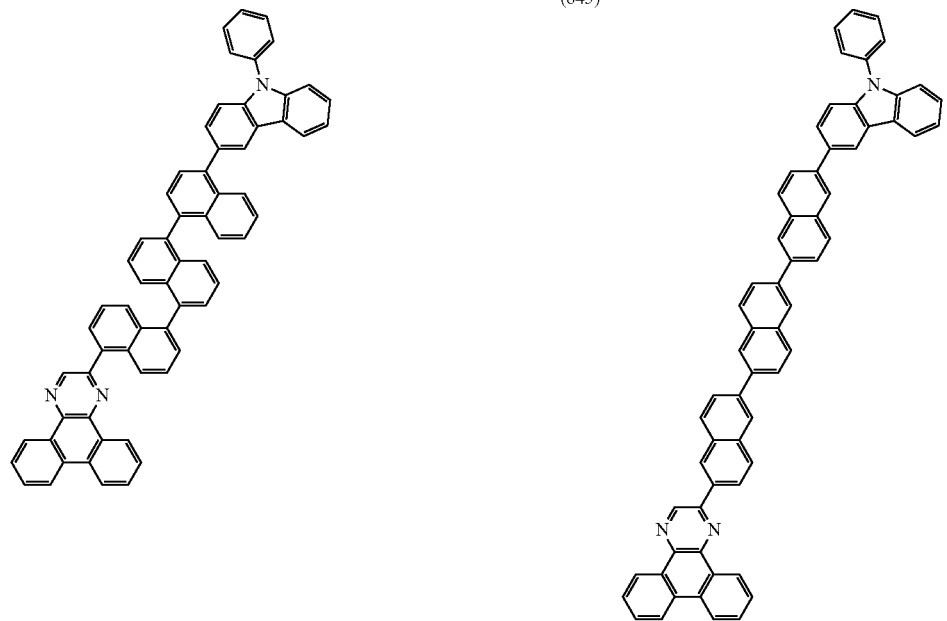

-continued
(847)
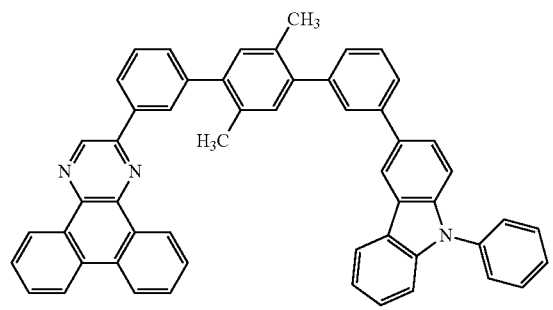
(848)
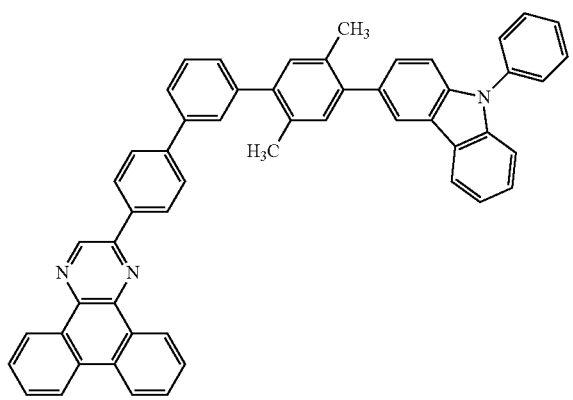
(849)
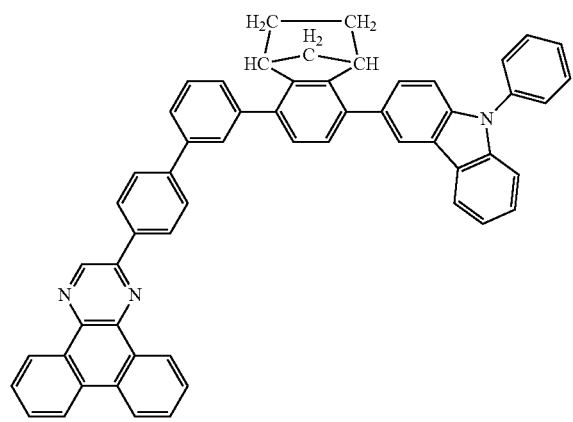
(850)
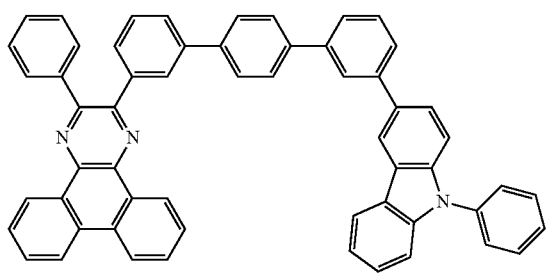
[Chemical formula 184]
(851)
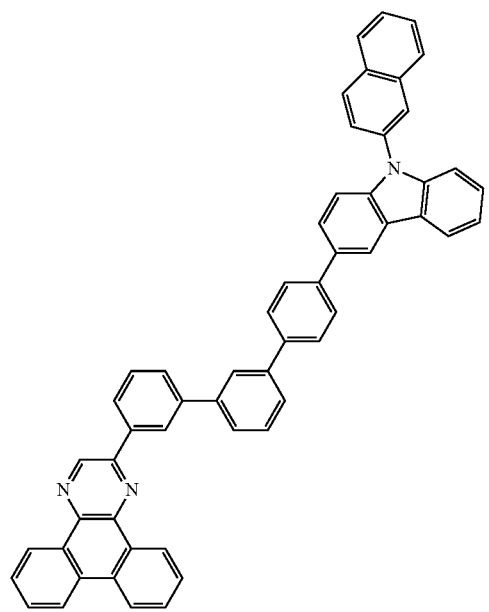
(852)
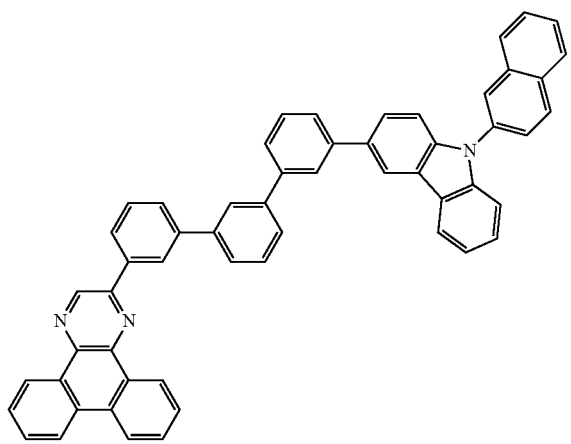

(853)
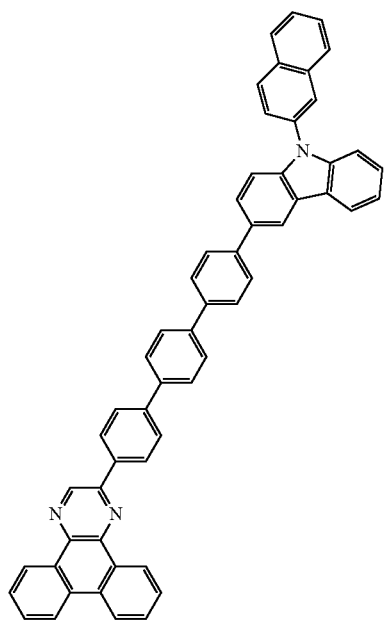
(854)
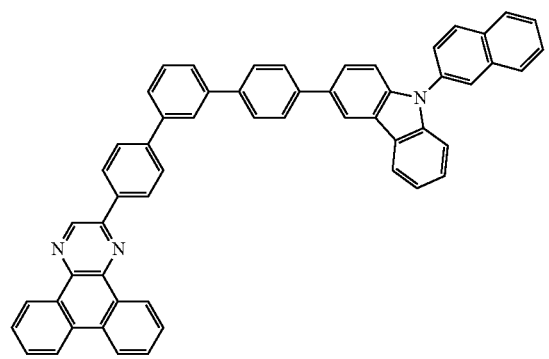
(855)
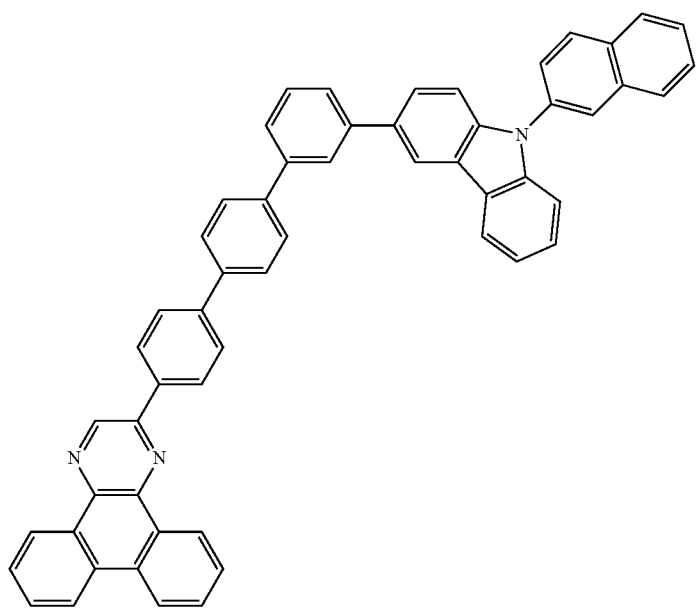
(856)
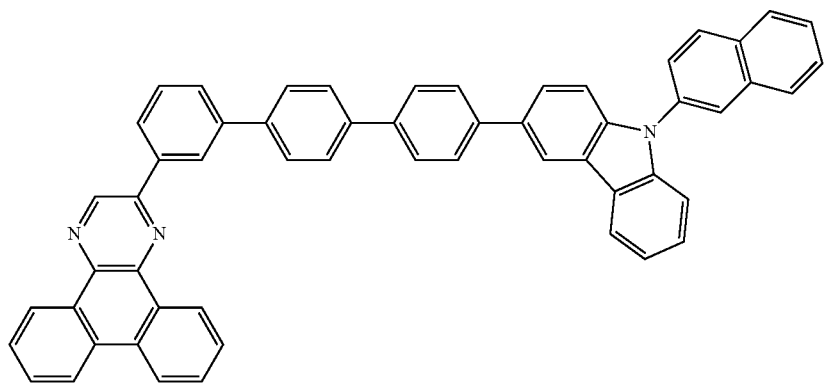

385 386
-continued
(857) 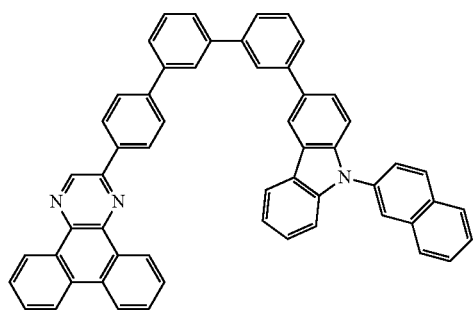 (858) 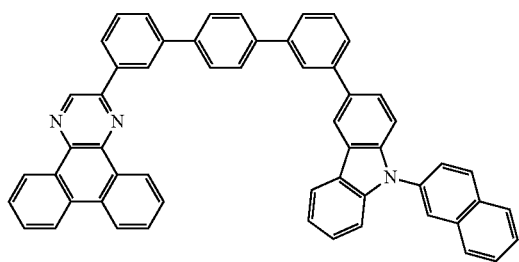
[Chemical formula 185]
(859) 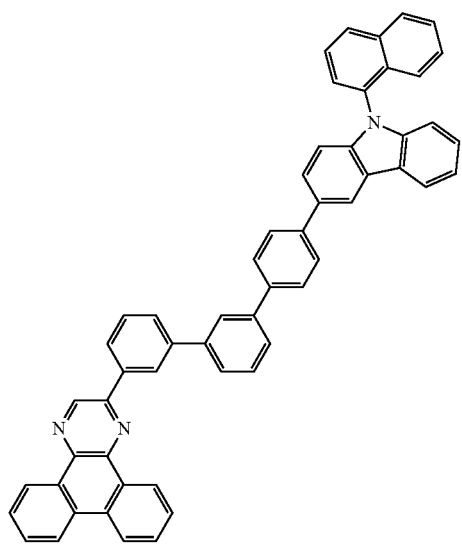 (860) 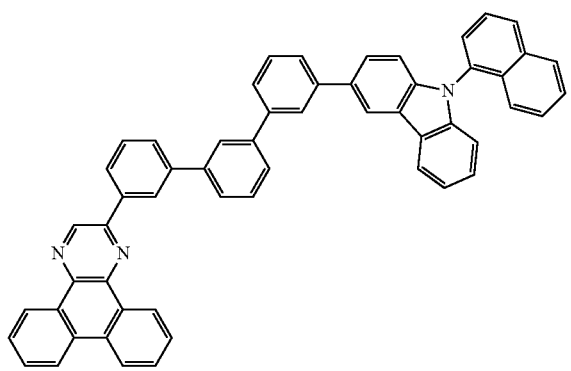
(861) 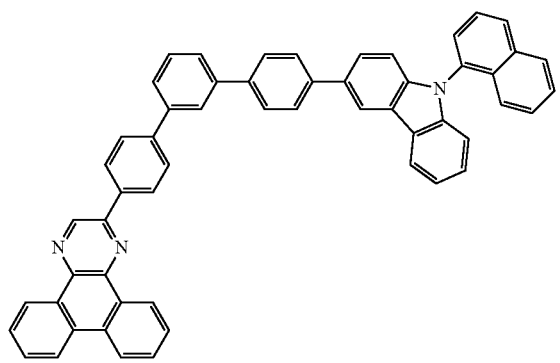 (862) 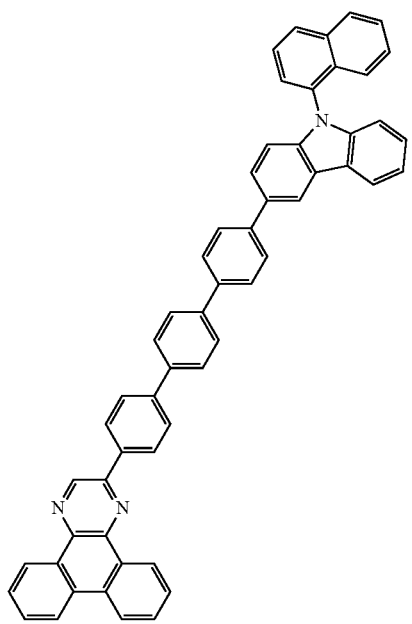

-continued
(863)
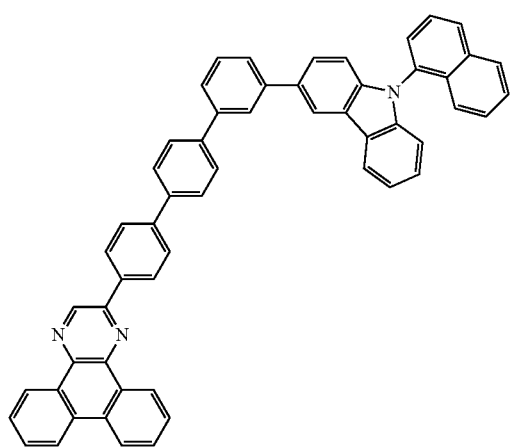
(864)
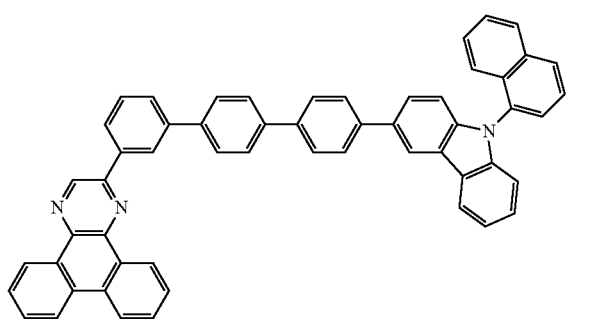
(865)
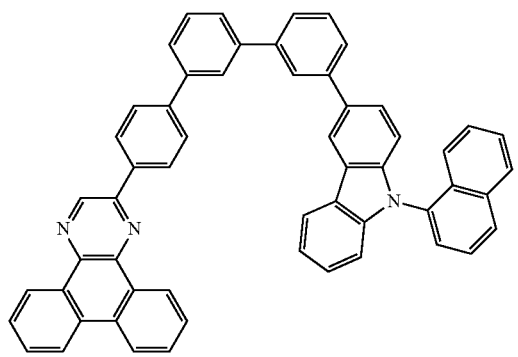
(866)
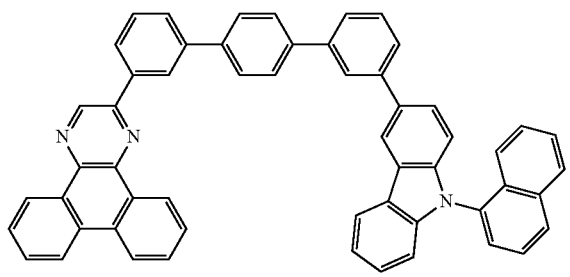
[Chemical formula 186]
(867)
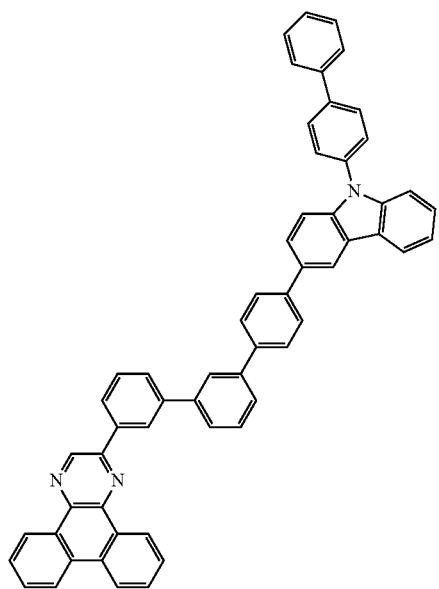
(868)
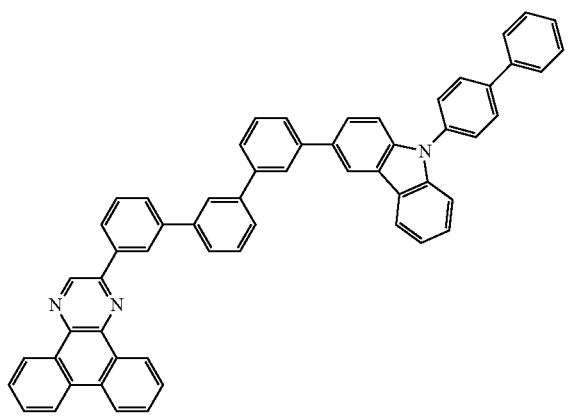

-continued
(869)
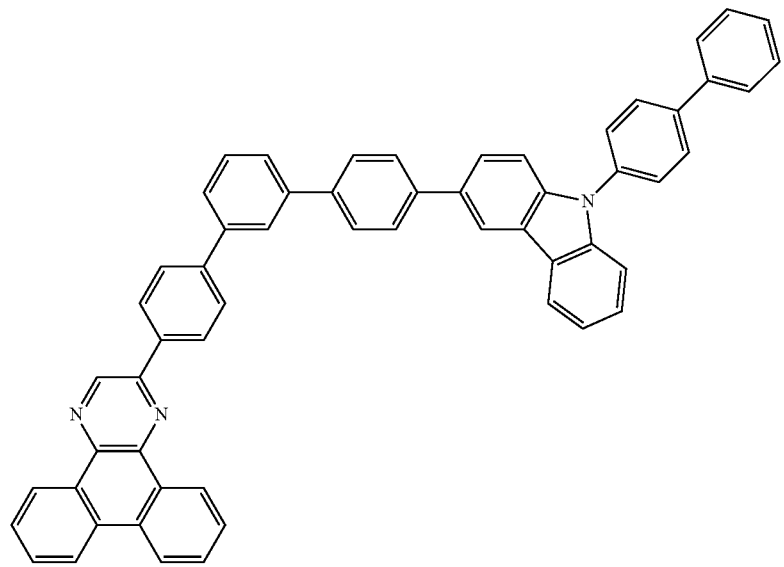
(870)
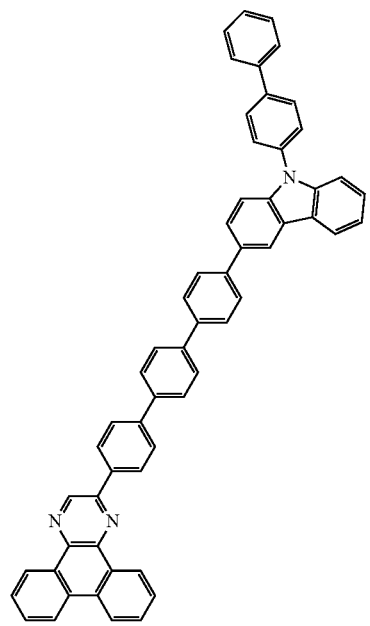
(871)
(872)
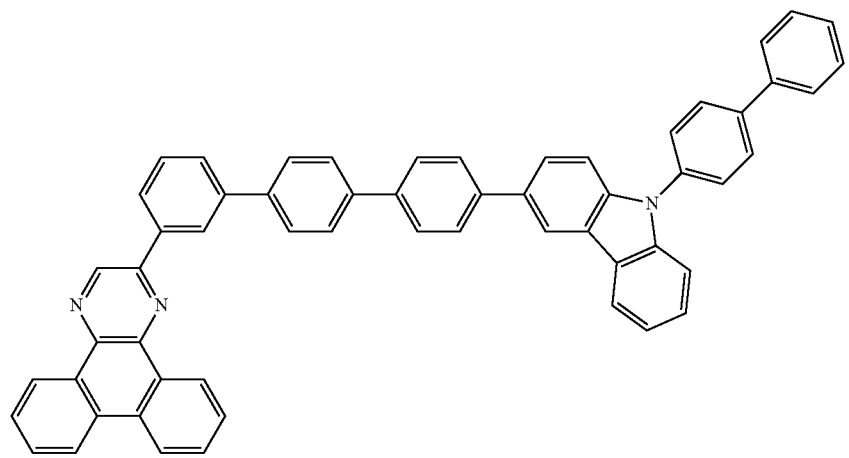

(873)
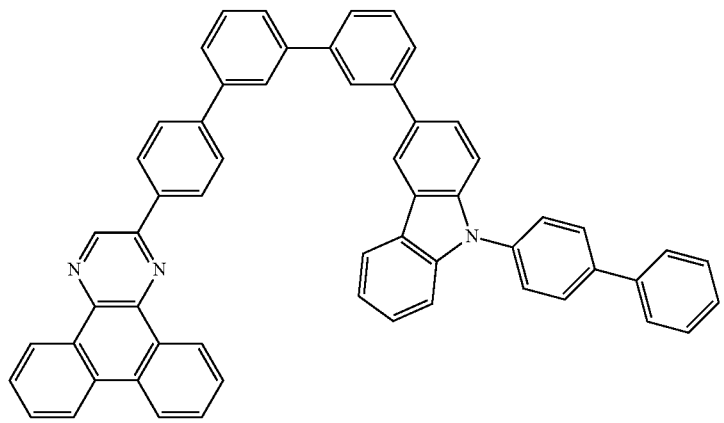
(874)
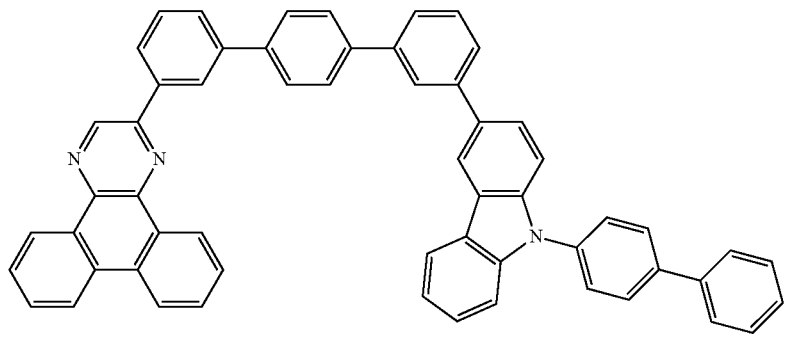
[Chemical formula 187]
(875)
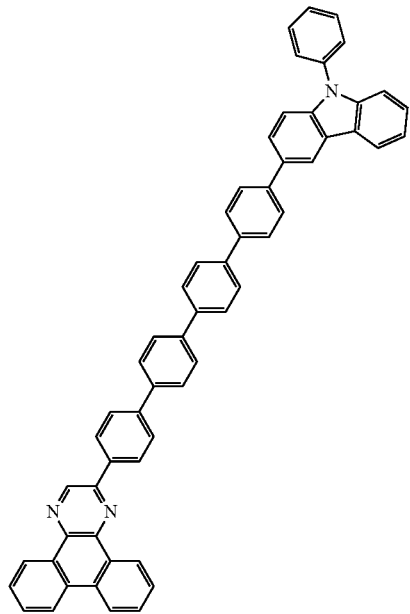
(876)
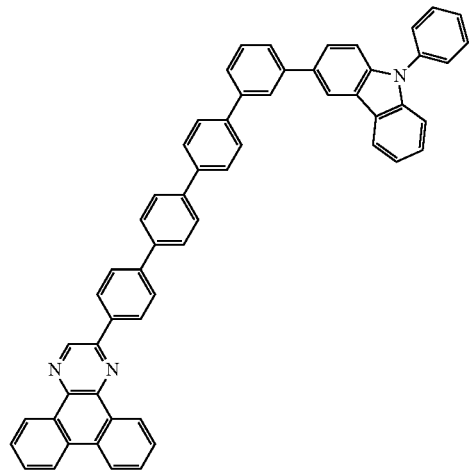

-continued
(877)
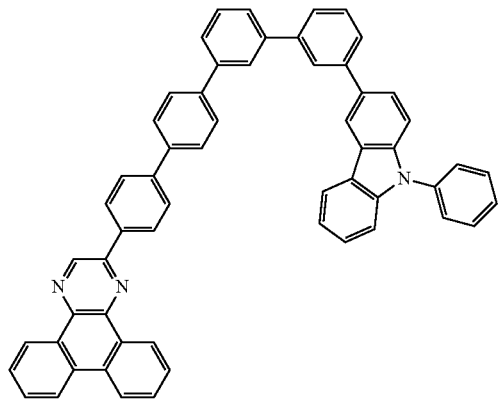
(878)
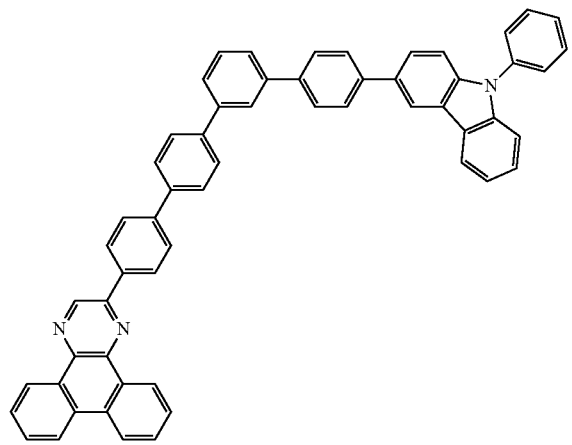
(879)
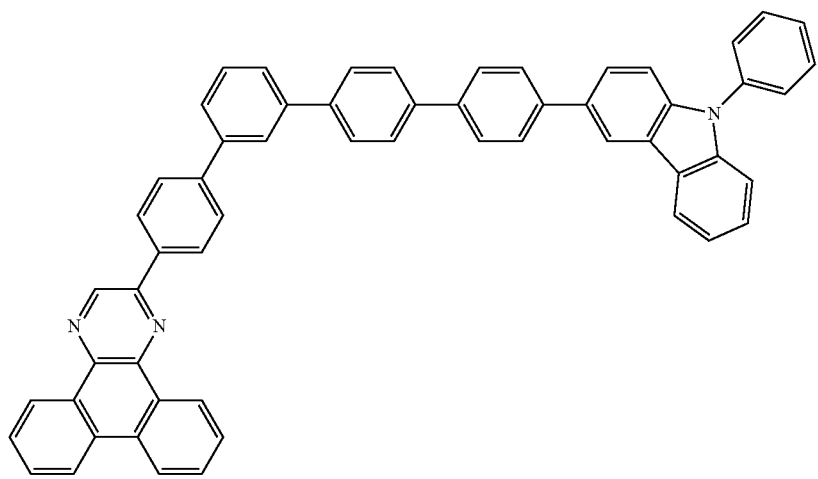
(880)
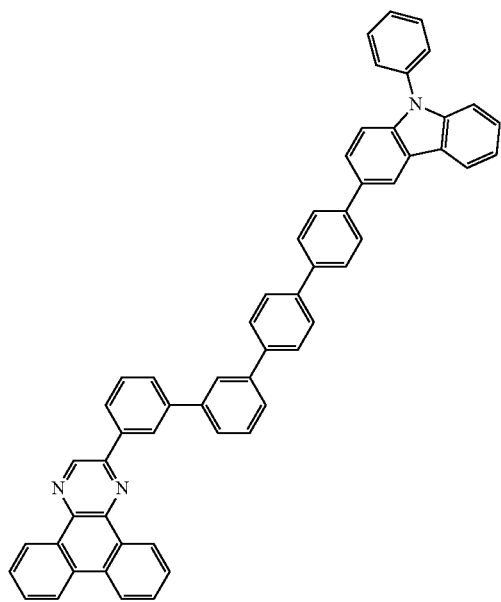
(881)
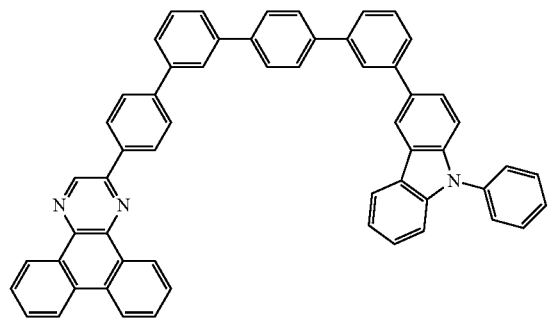

-continued
(882)
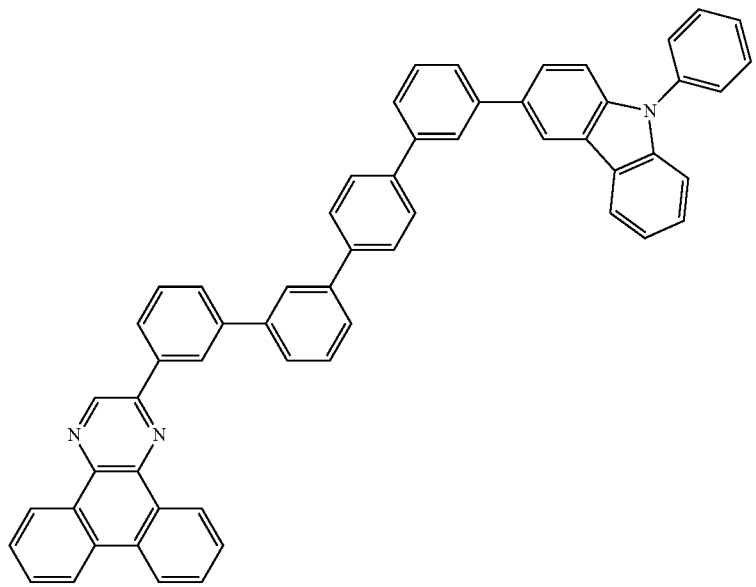
[Chemical formula 188]
(883) (884)
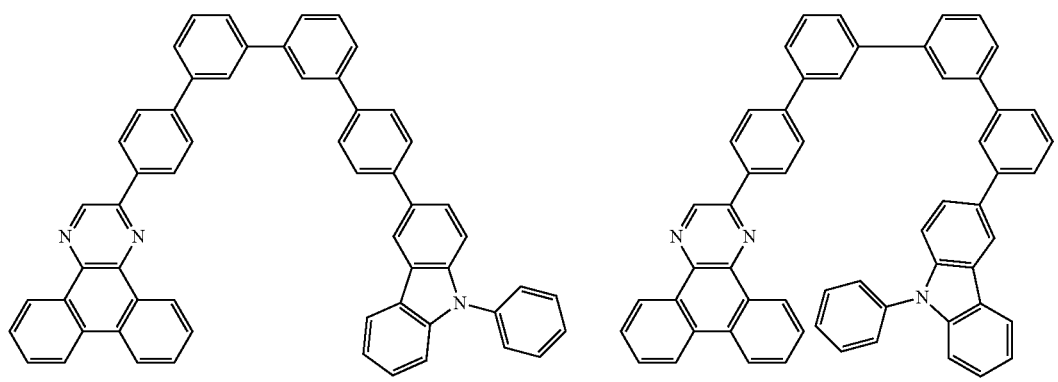
(885)
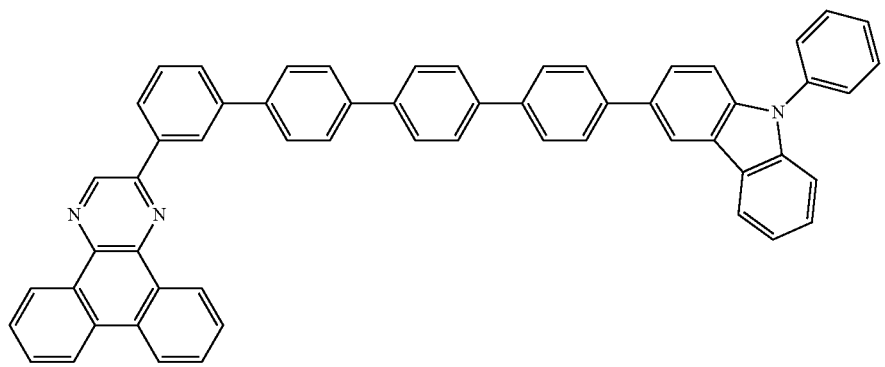

(886)
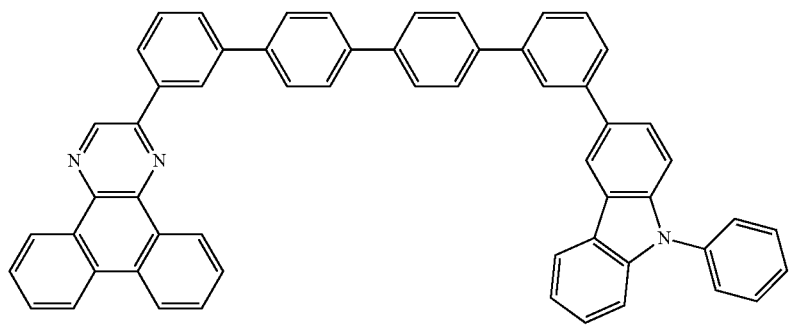
(887)
(888)
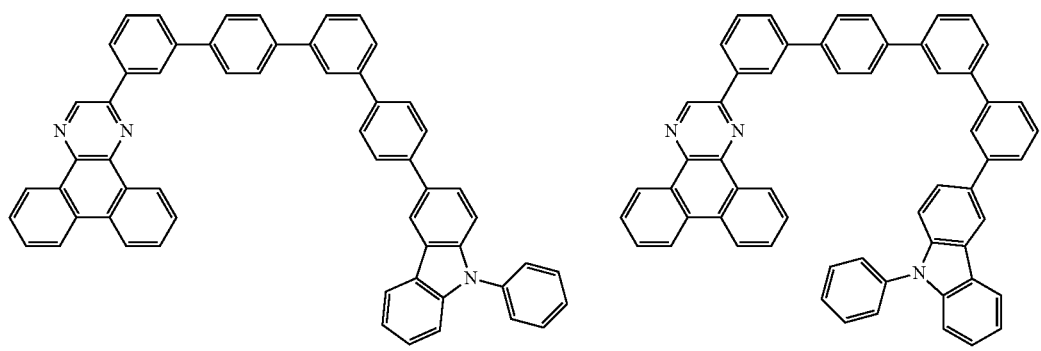
(889)
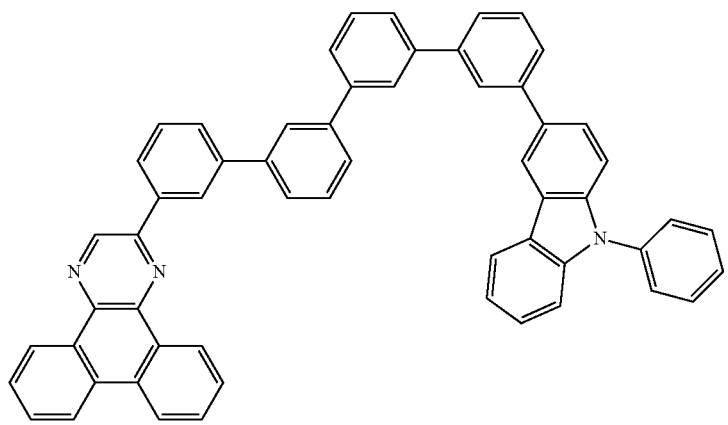
(890)
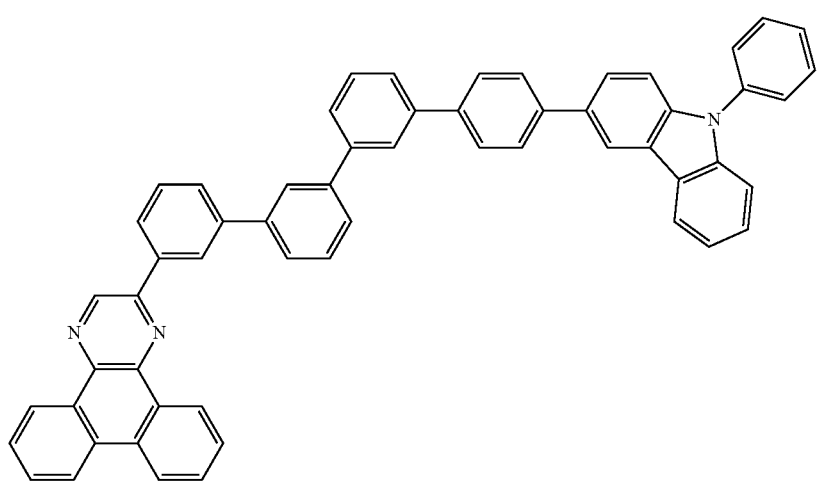

-continued
[Chemical formula 189]
(891)
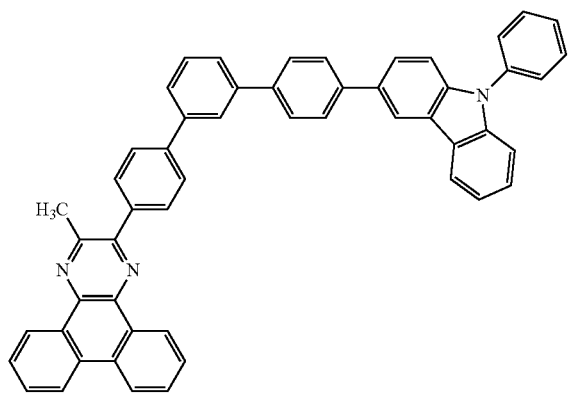
(892)
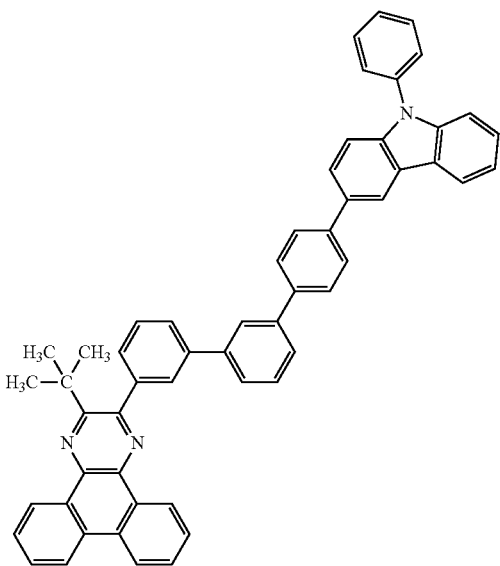
(893)
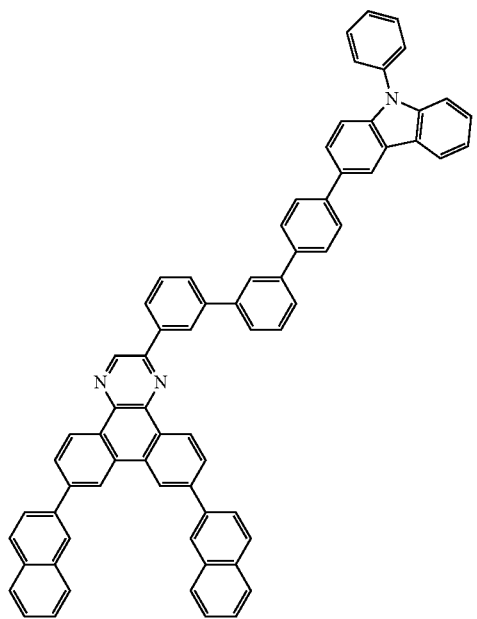
(894)
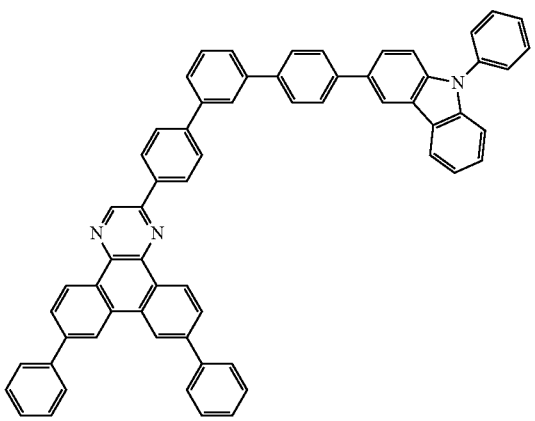

-continued
(895)
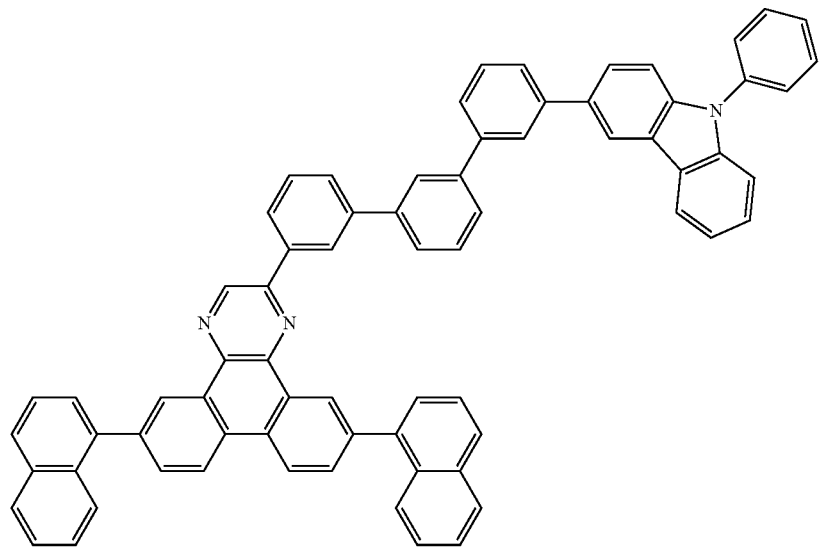
[Chemical formula 190]
(896)
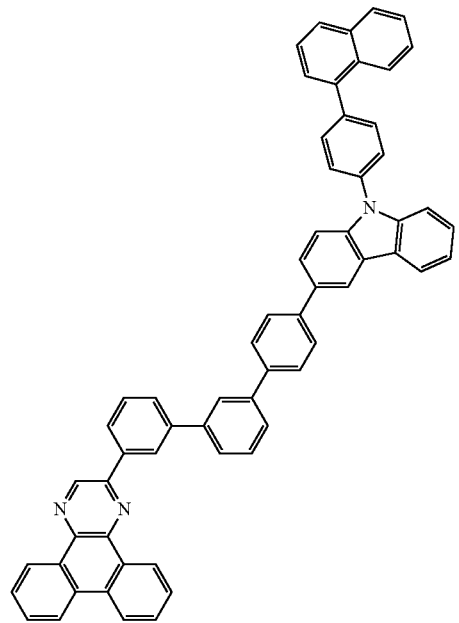

(897)
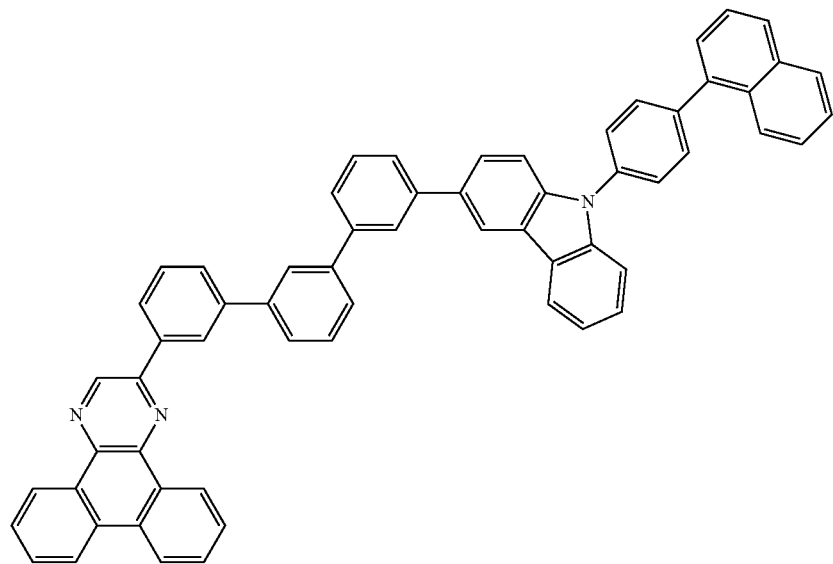
(898)
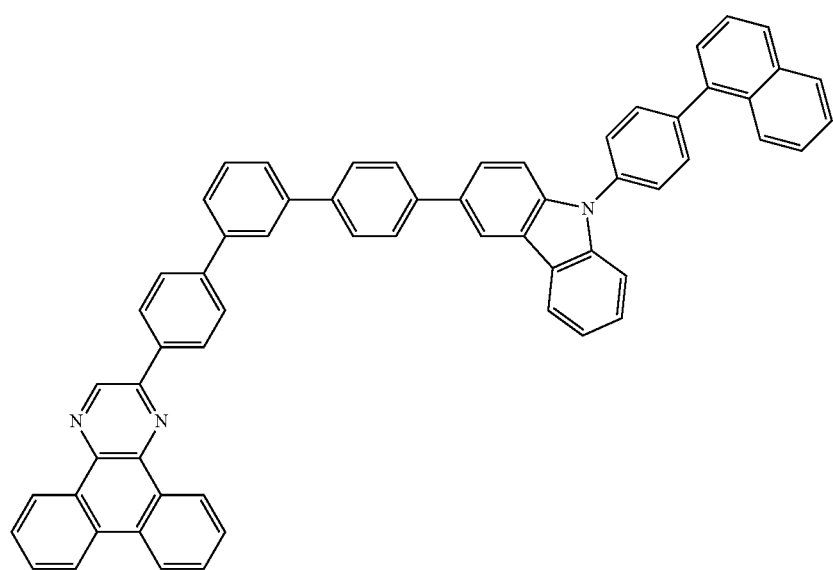

-continued
405 (899)
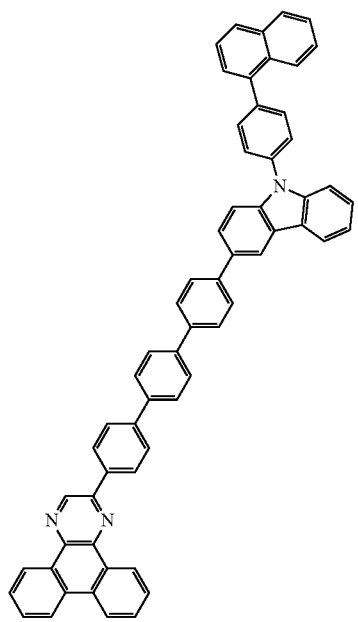
406 (900)
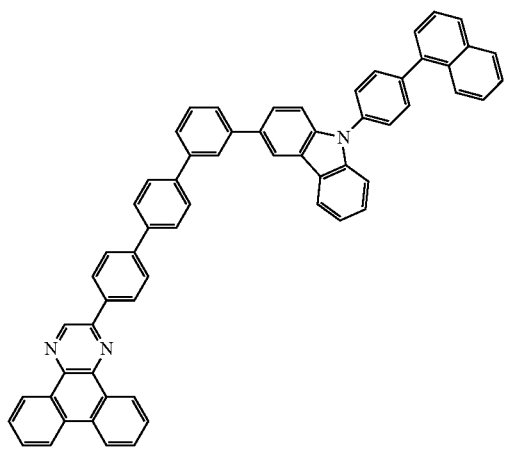
(901)
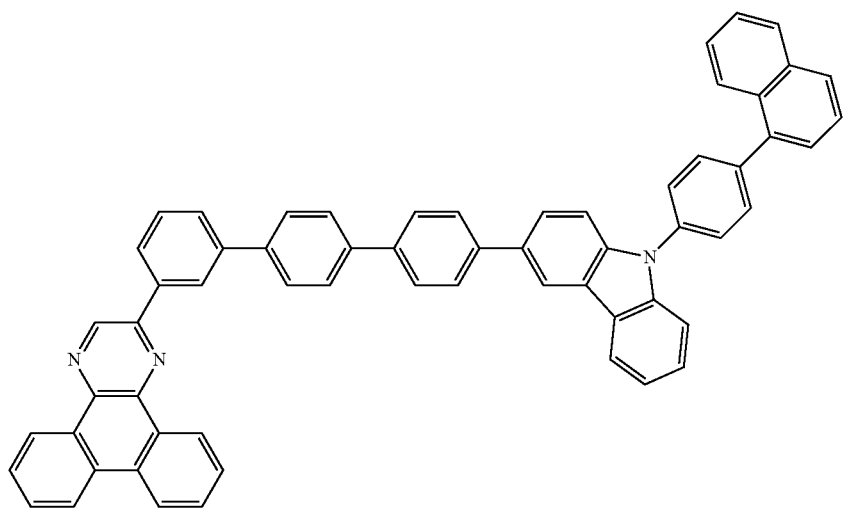
(902)
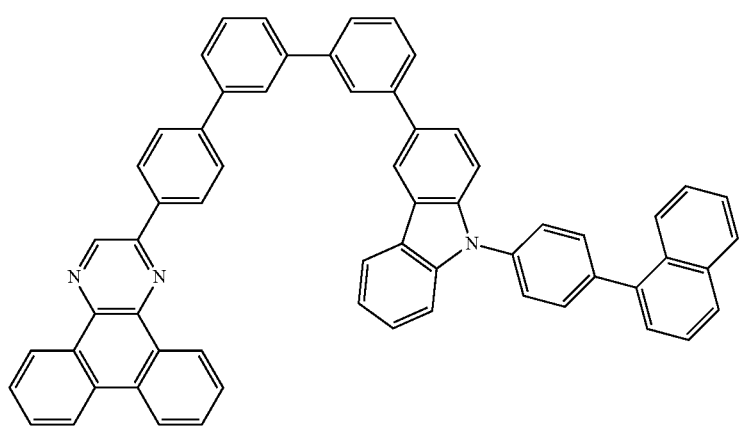

(903)
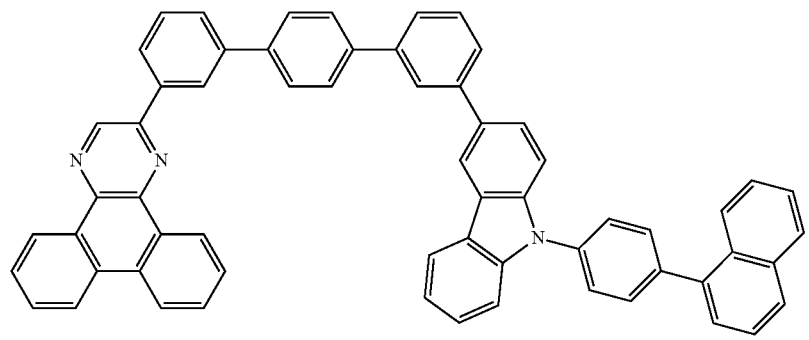
[Chemical formula 191]
(904)
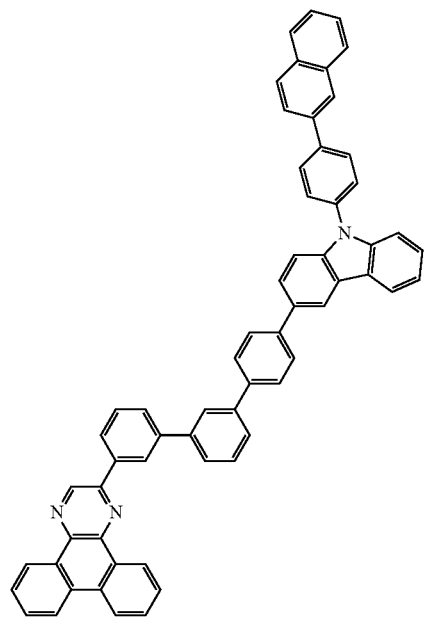
(905)
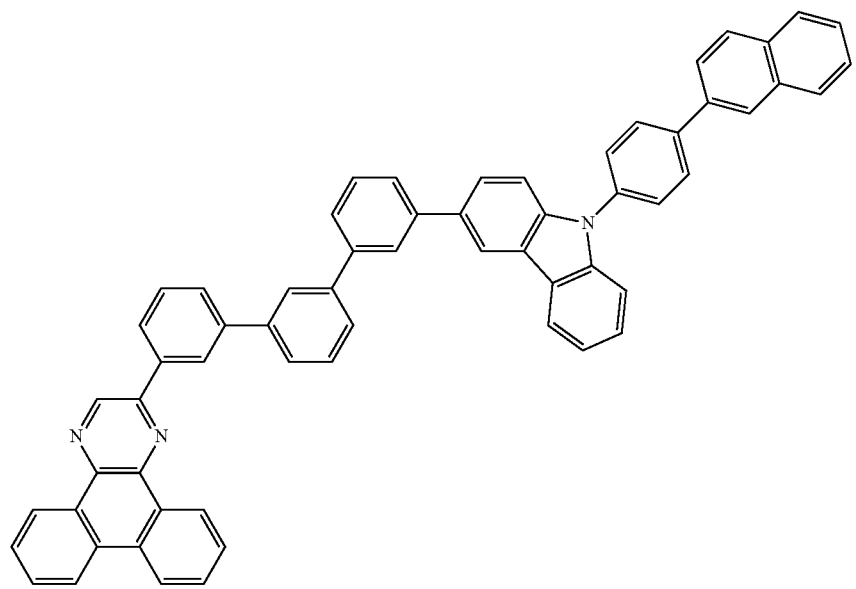

-continued
(906)
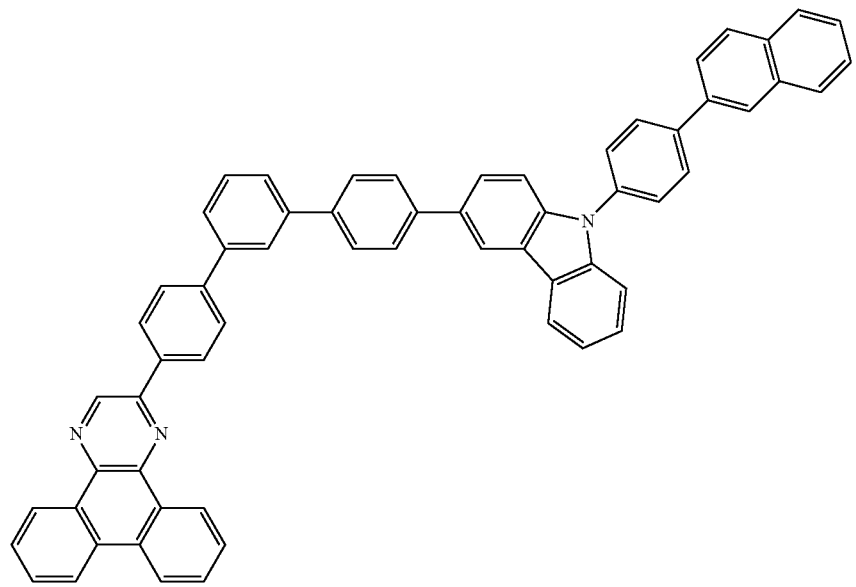
(907)
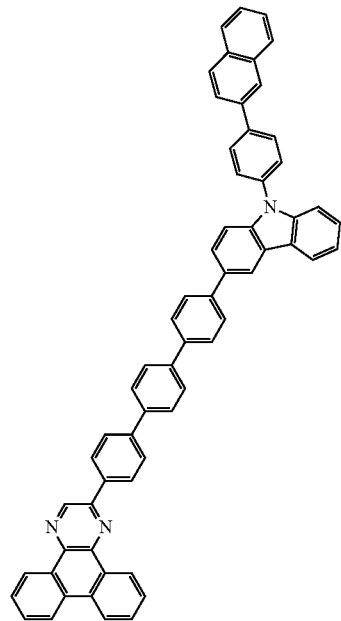
(908)
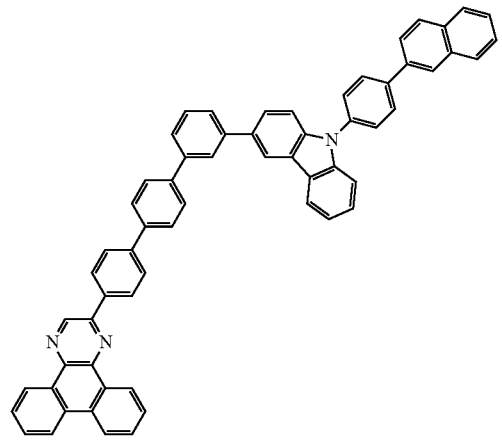

-continued
(909)
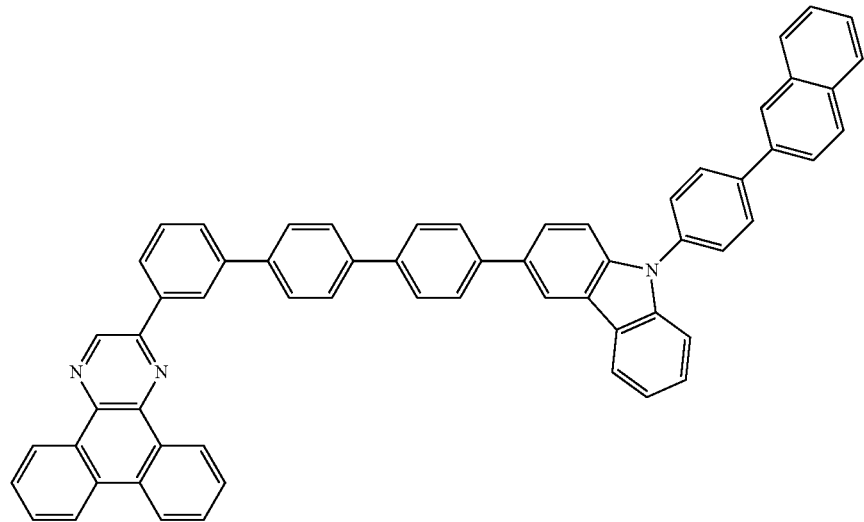
(910)
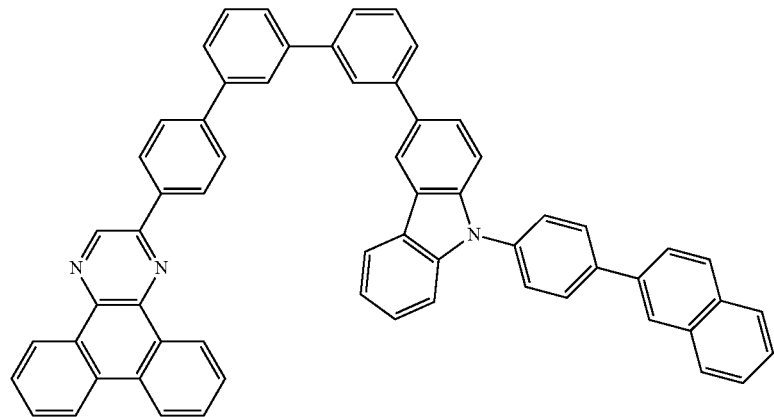
(911)
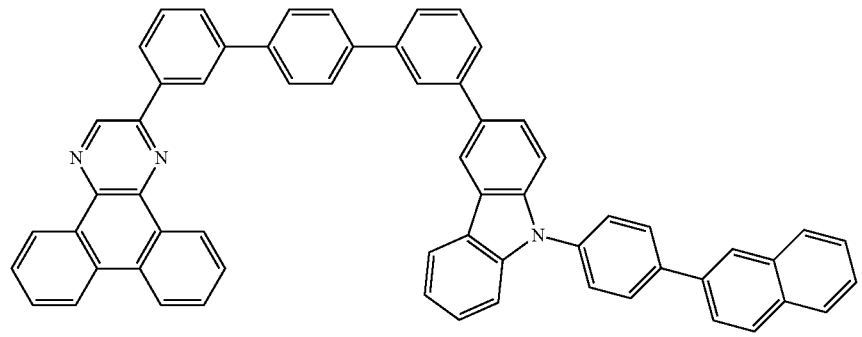

[Chemical formula 192]
(912)
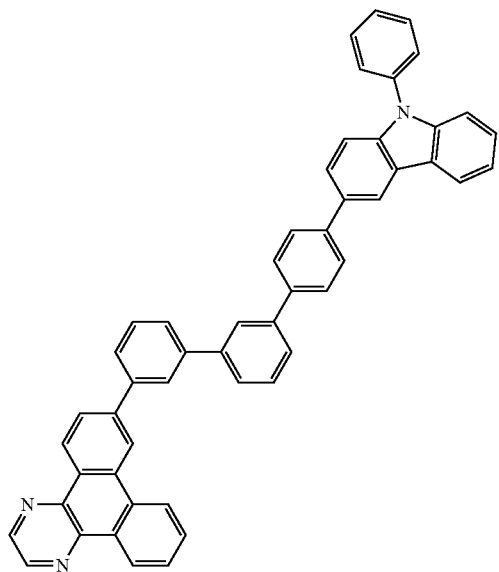
(913)
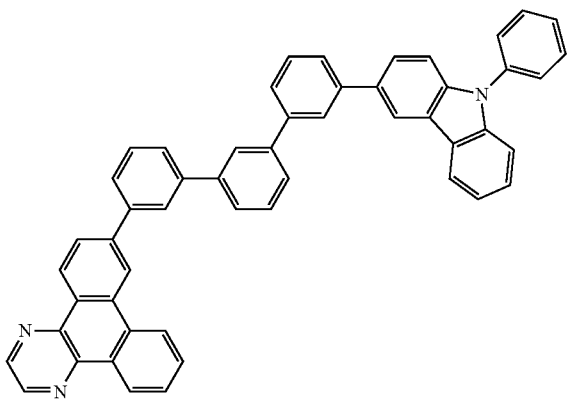
(914)
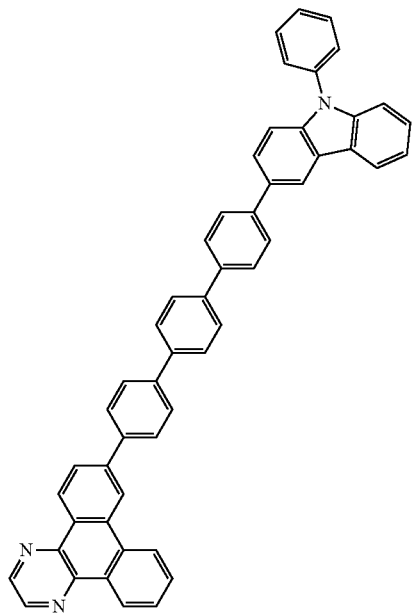
(915)
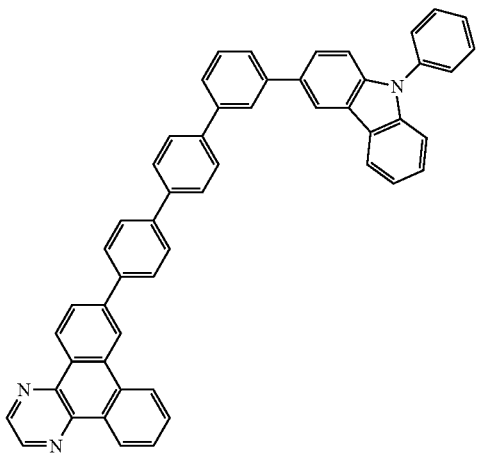

-continued
(916)
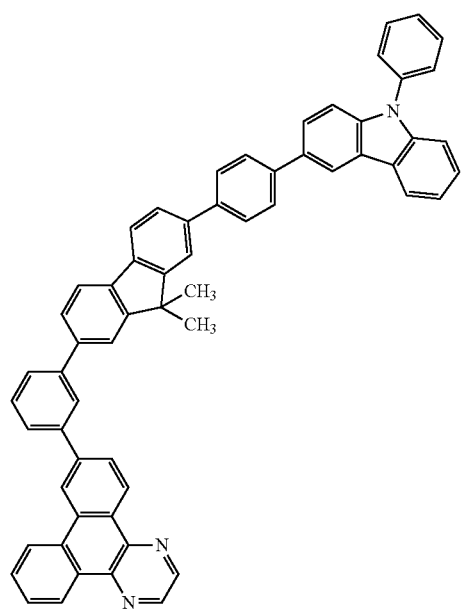
(917)
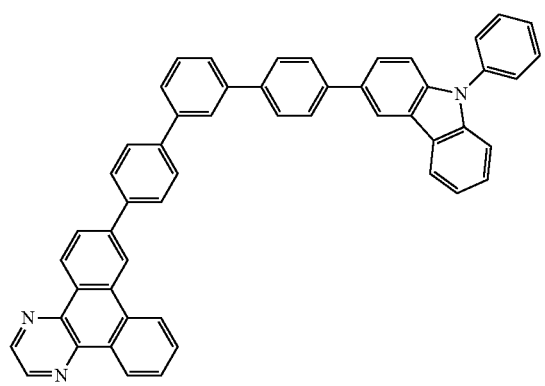
(918)
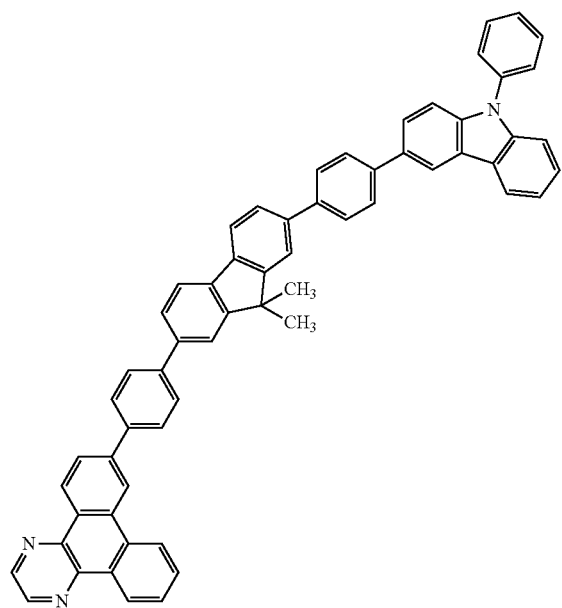
(919)
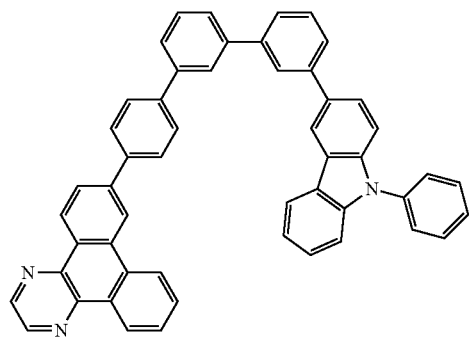

(920)
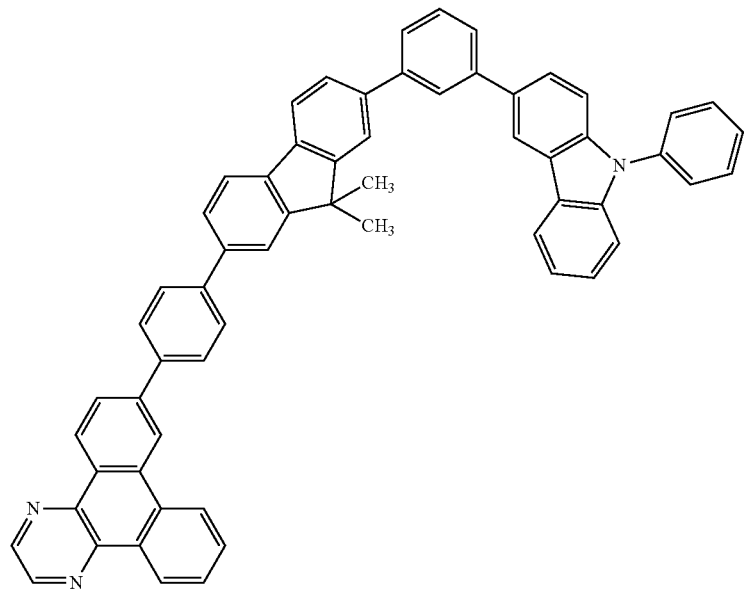
[Chemical formula 193]
(921)
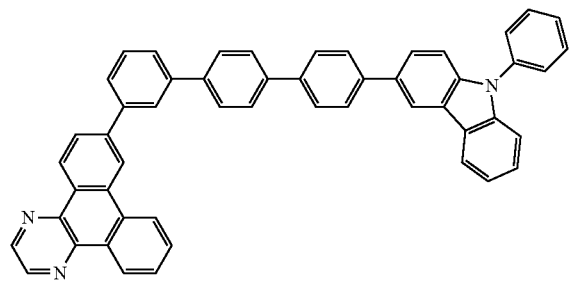
(922)
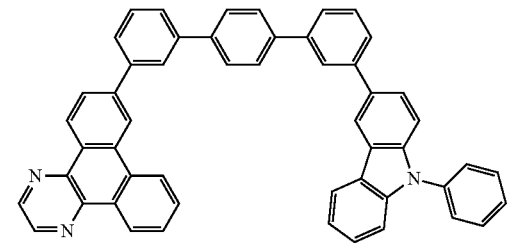
(923)
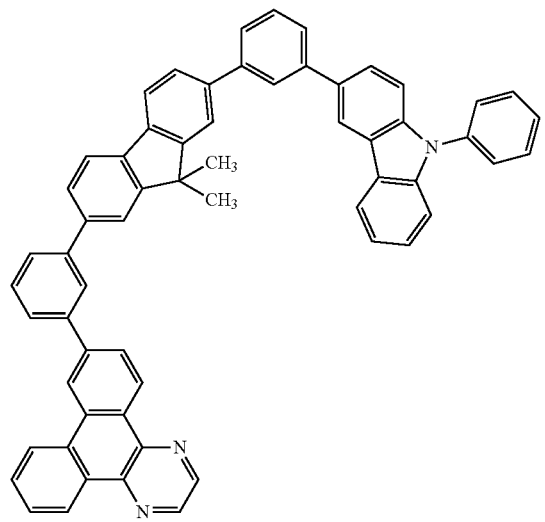
(924)
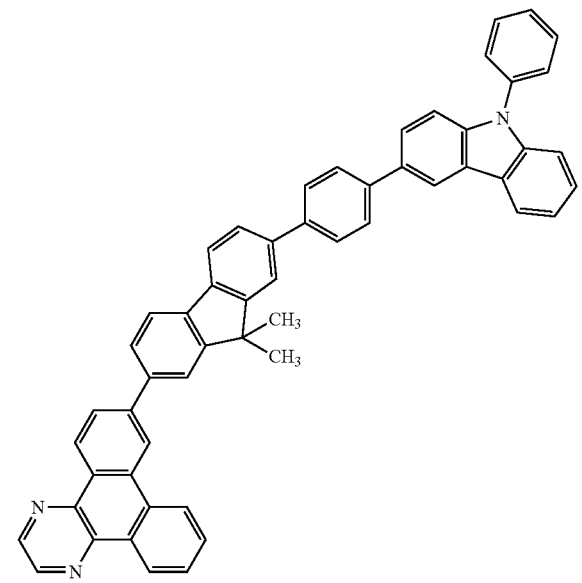

(925)
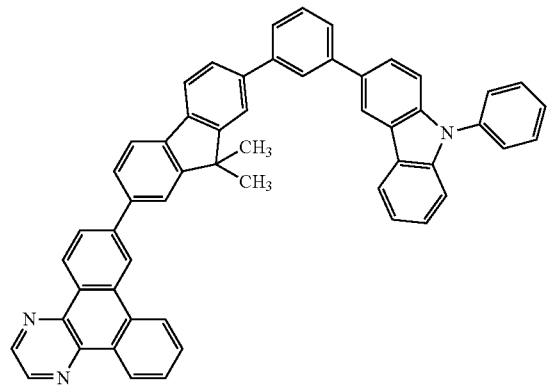
(926)
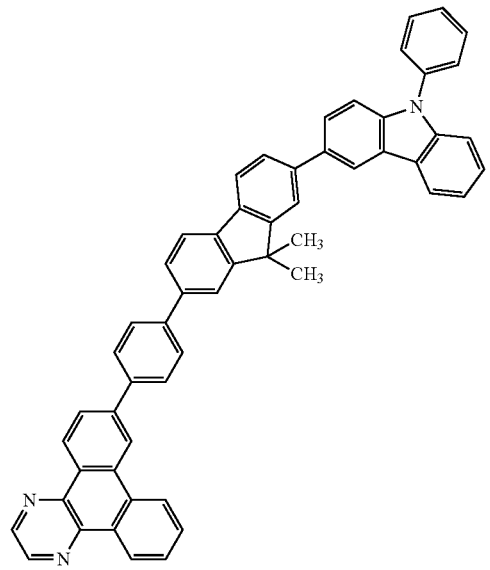
(927)
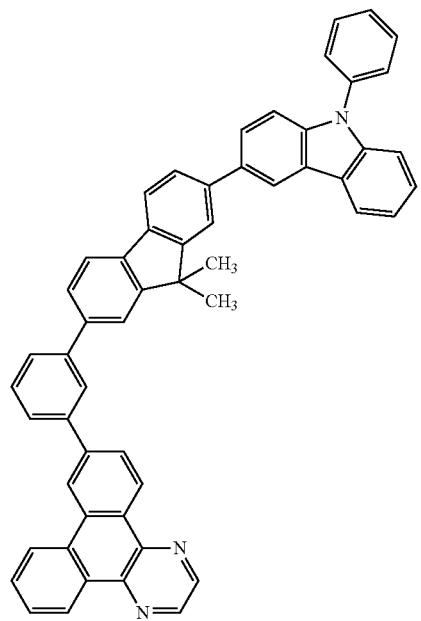

[Chemical formula 194]
(928)
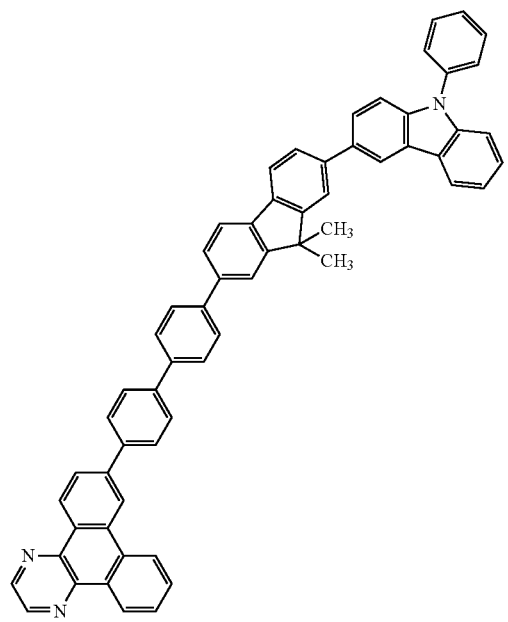
(929)
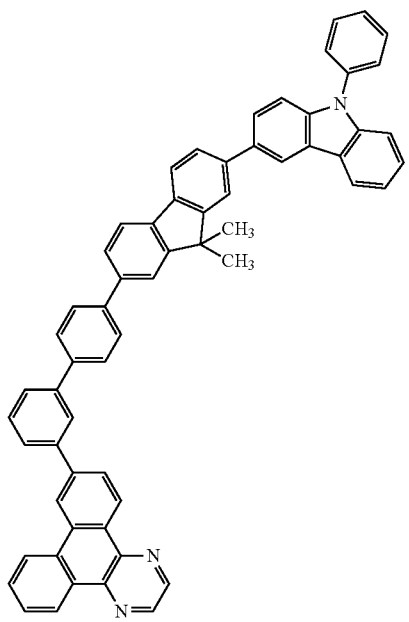
(930)
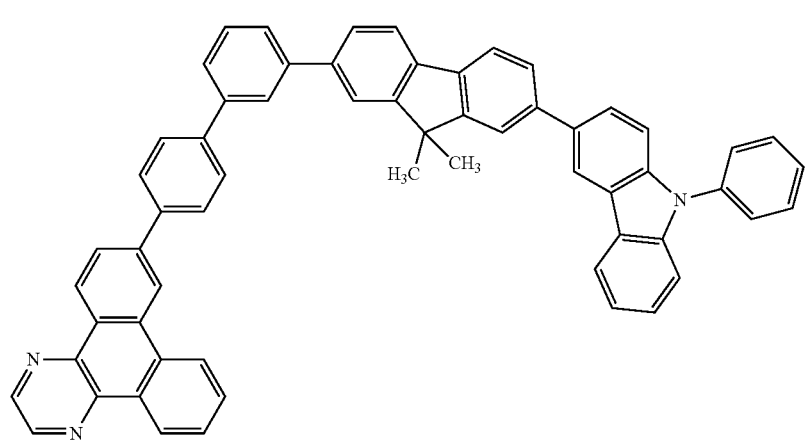
(931)
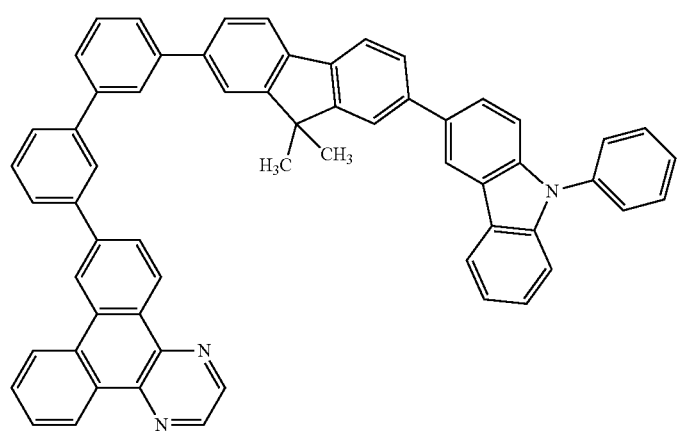

-continued
(932)
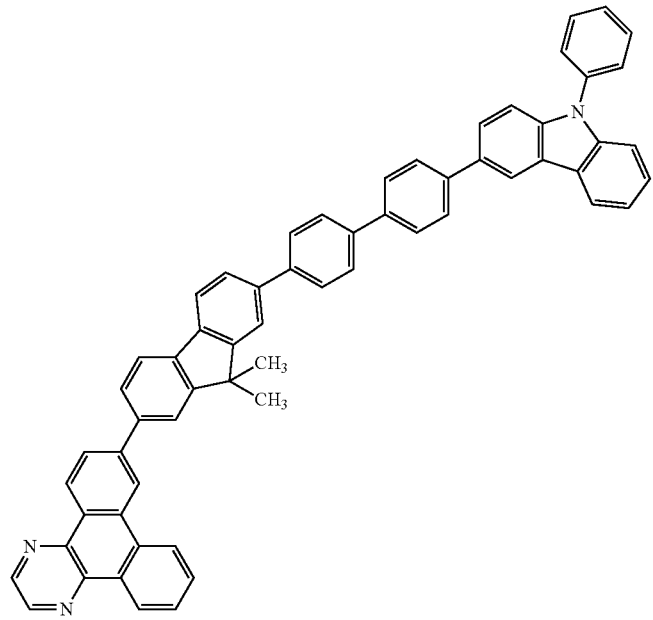
(933)
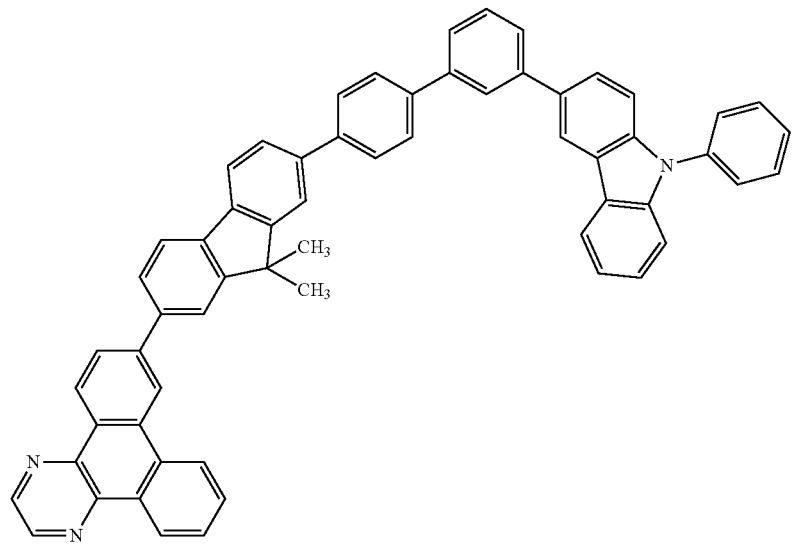
(934)
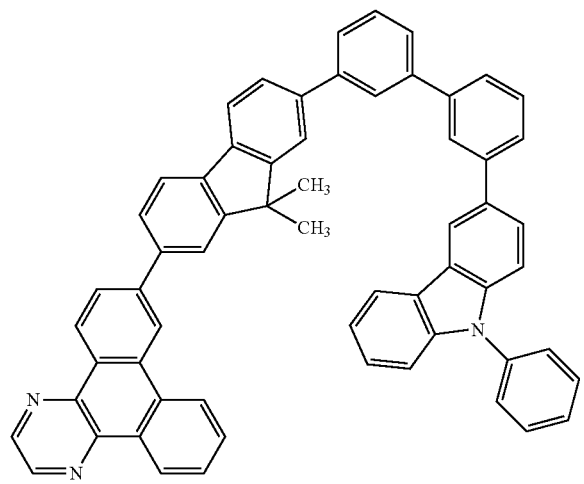

[Chemical formula 195]
(935)
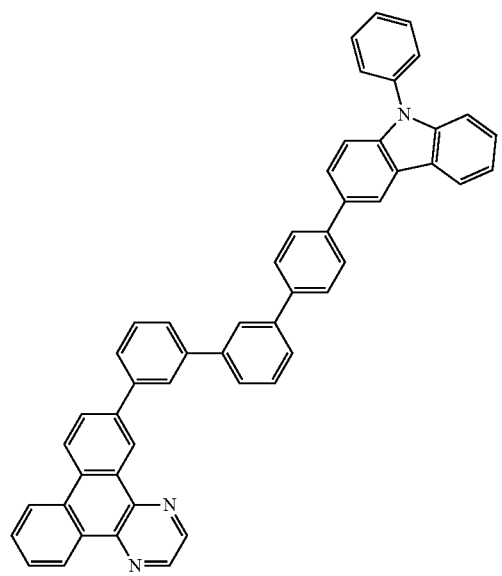
(936)
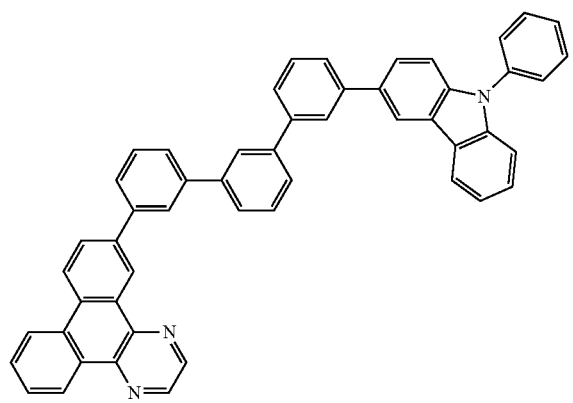
(937)
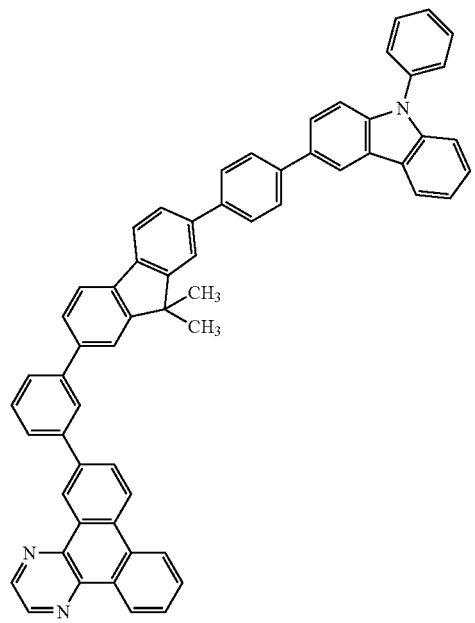
(938)
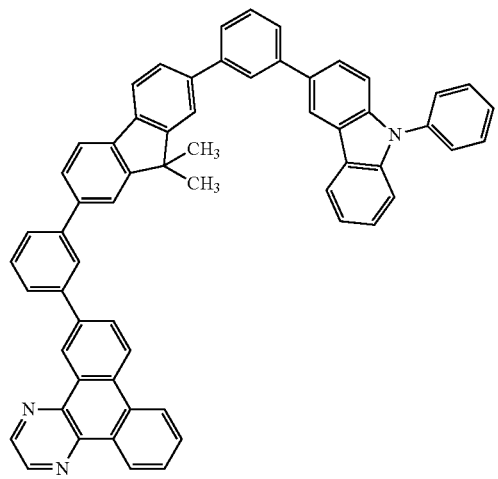

(939)
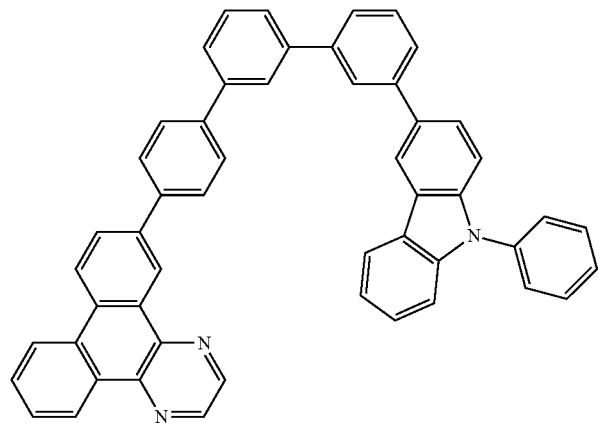
(940)
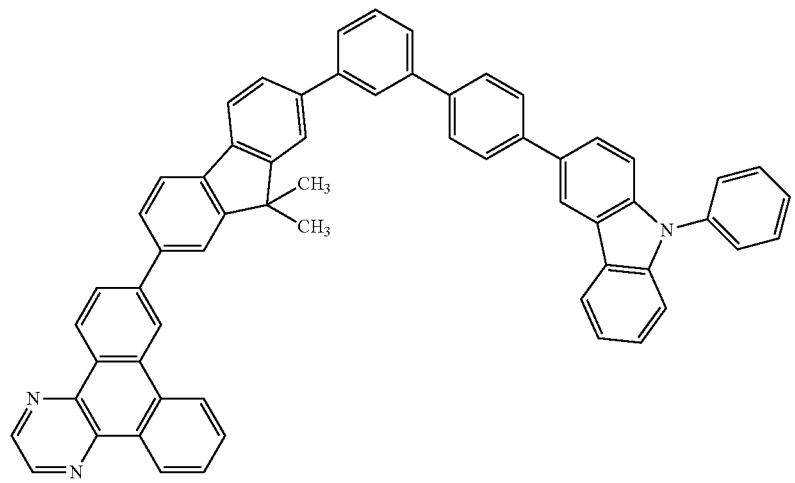
[Chemical formula 196]
(941)
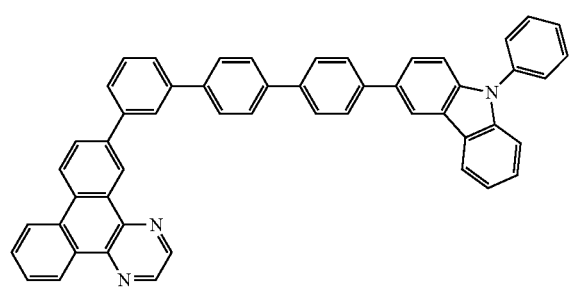
(942)
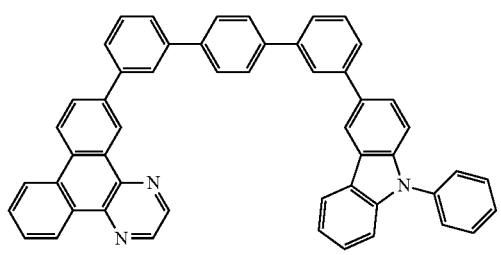

-continued
(943)
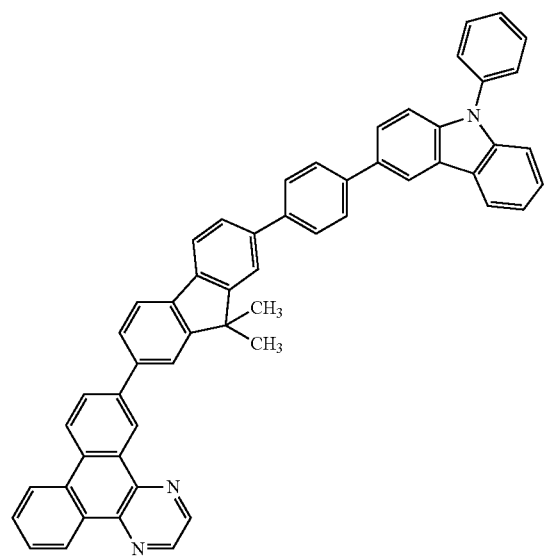
(944)
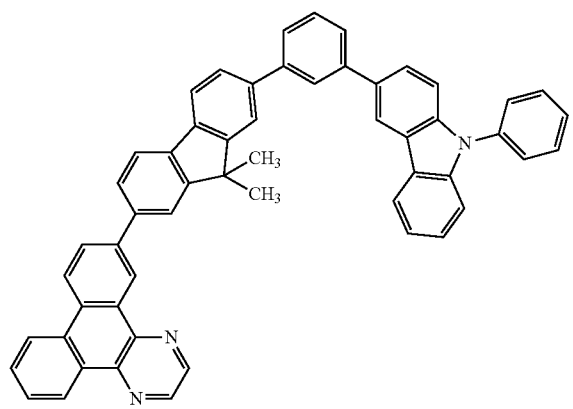
(945)
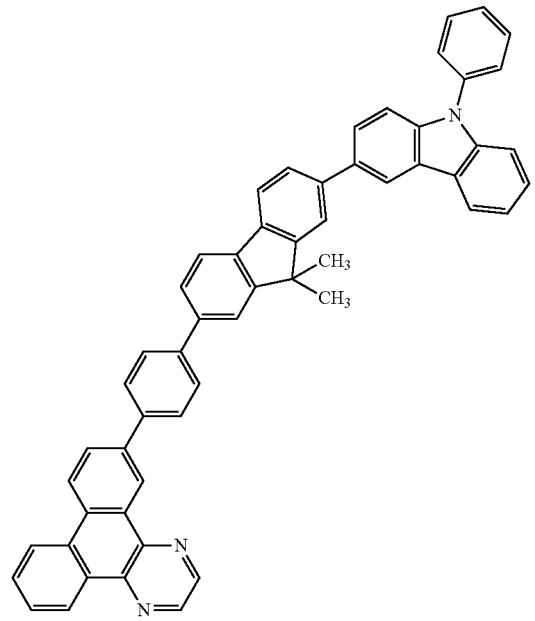
(946)
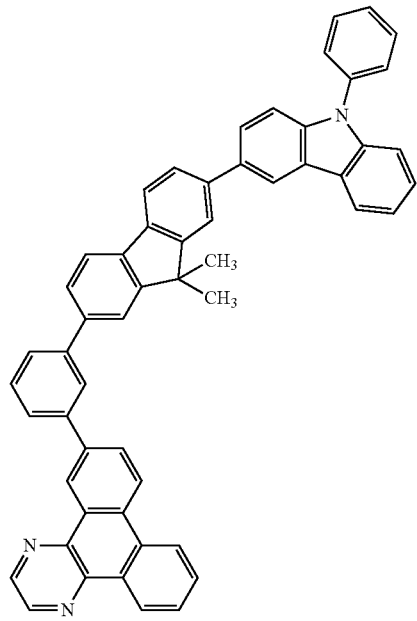

[Chemical formula 197]
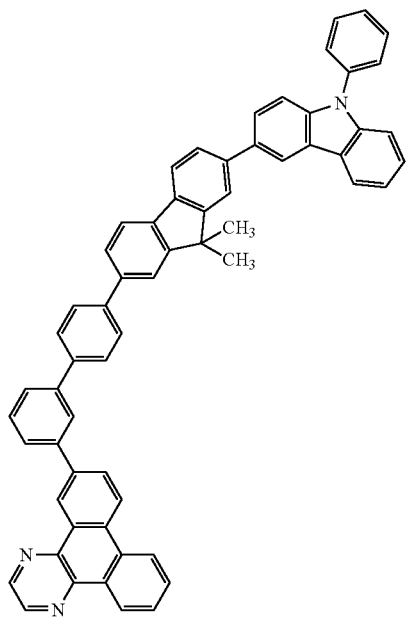
(947)
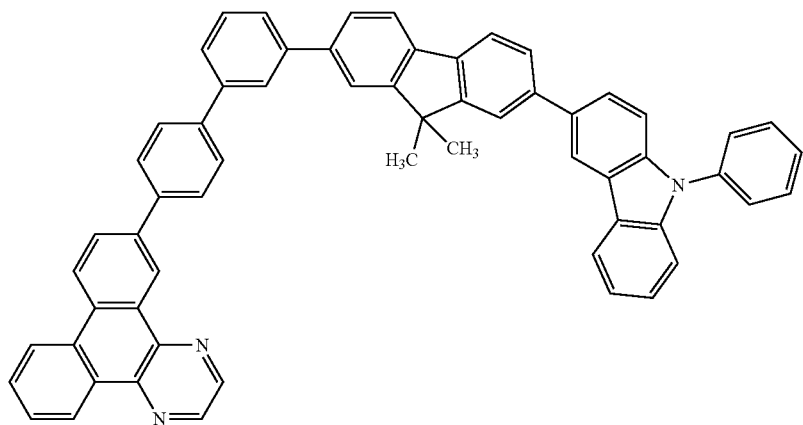
(948)
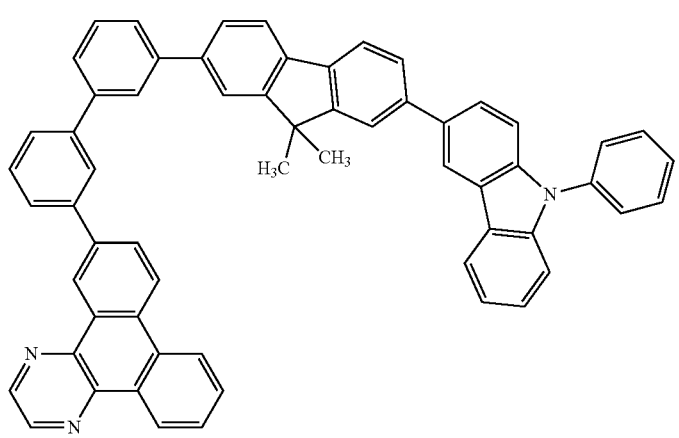
(949)

(950)
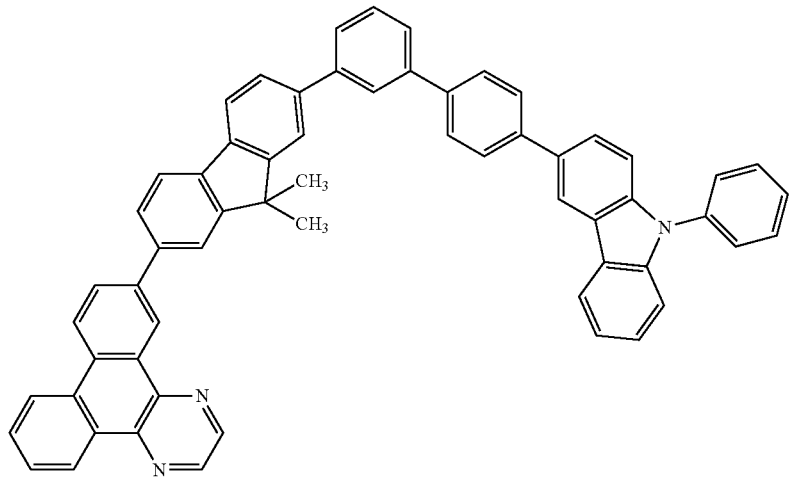
(951)
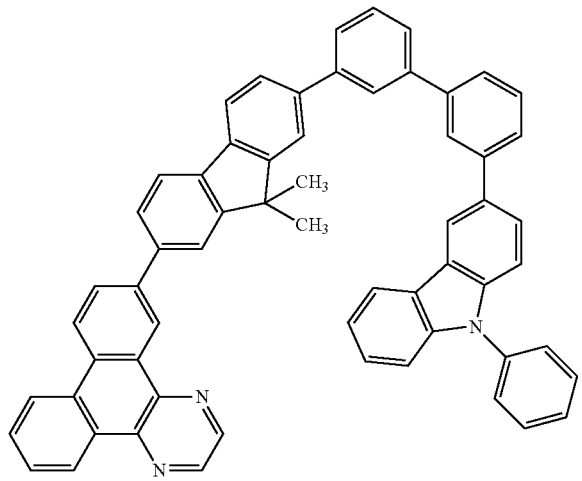
[Chemical formula 198]
(952)
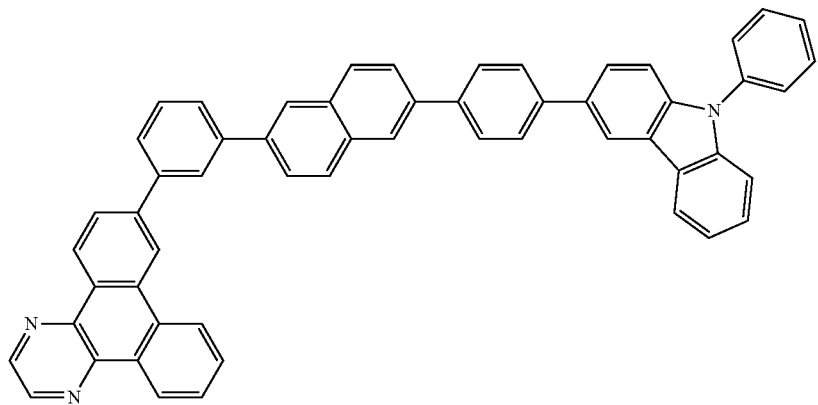

-continued
(953)
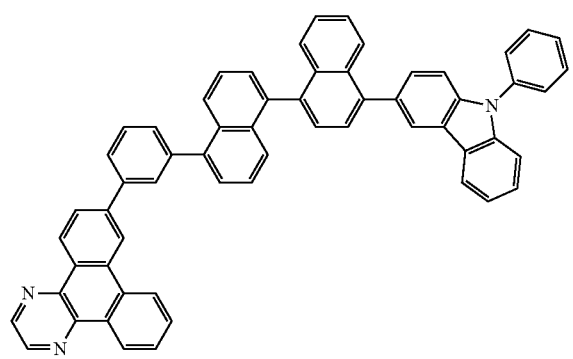
(954)
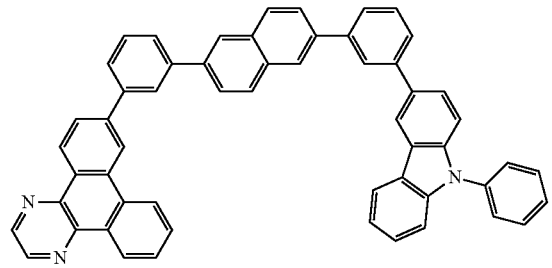
(955)
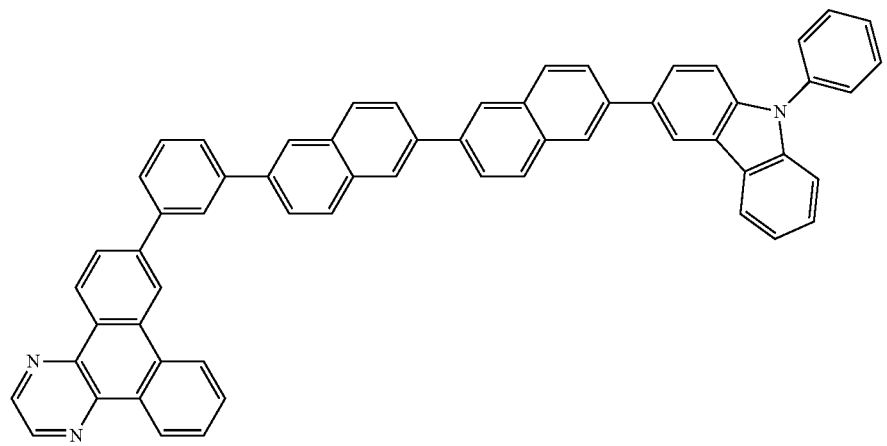
(956)
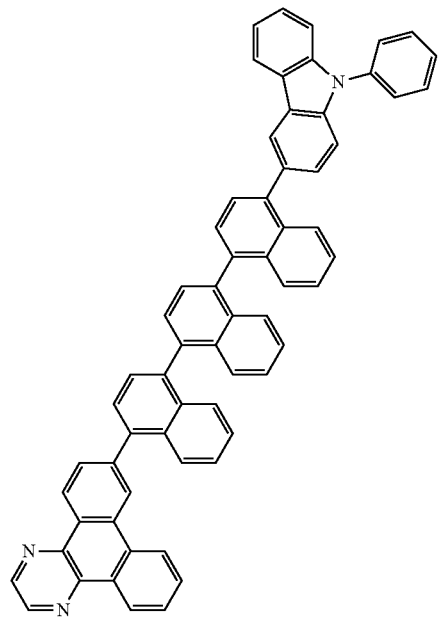
(957)
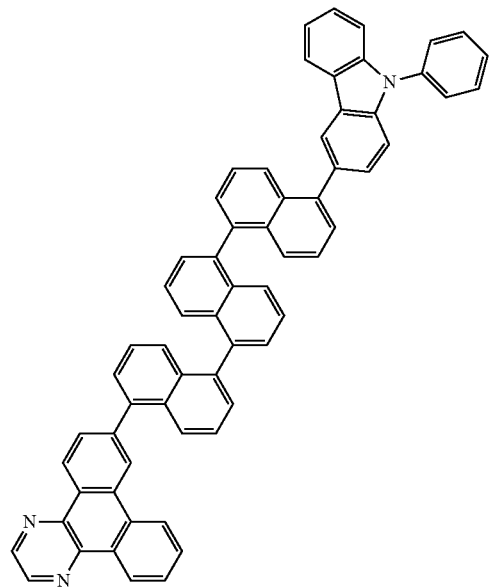

-continued
(958)
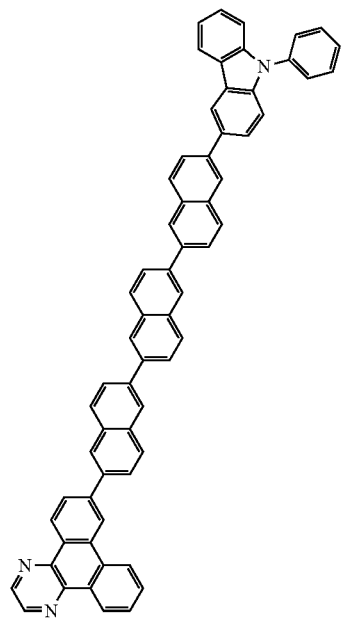
(959)
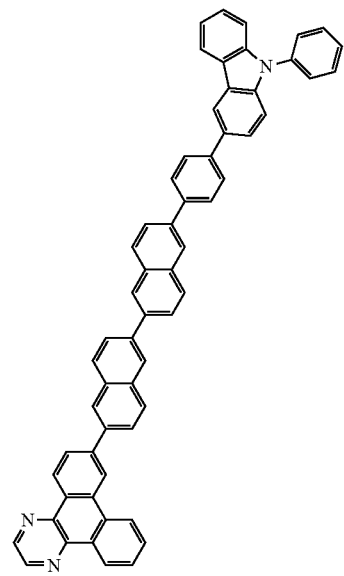
(960)
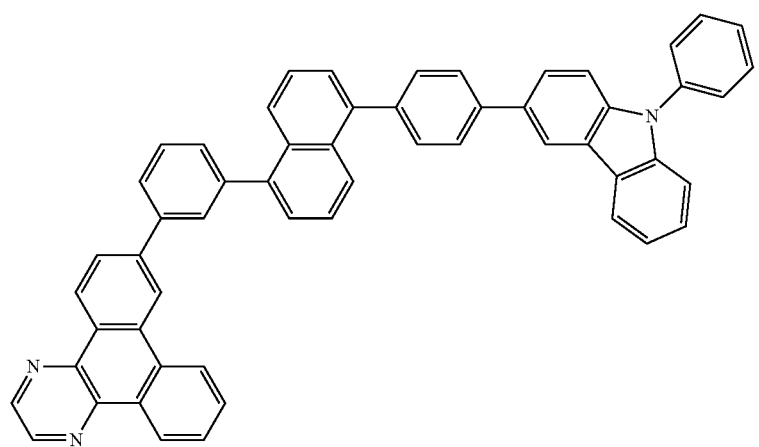
[Chemical formula 199]
(961)
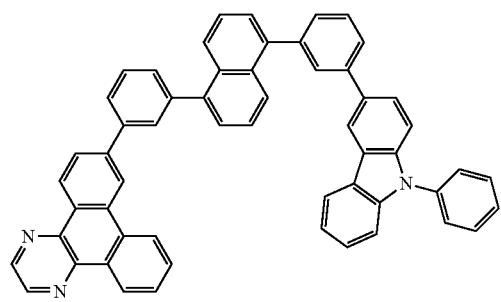
(962)
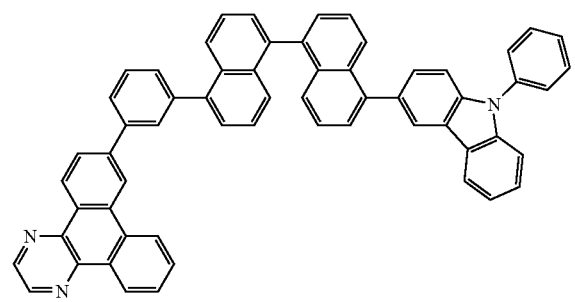

-continued
(963)
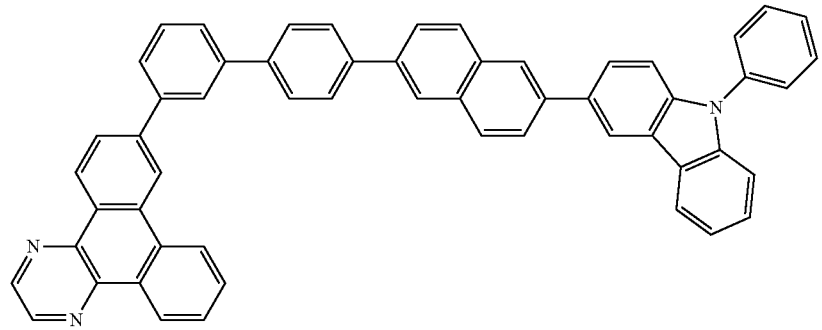
(964)
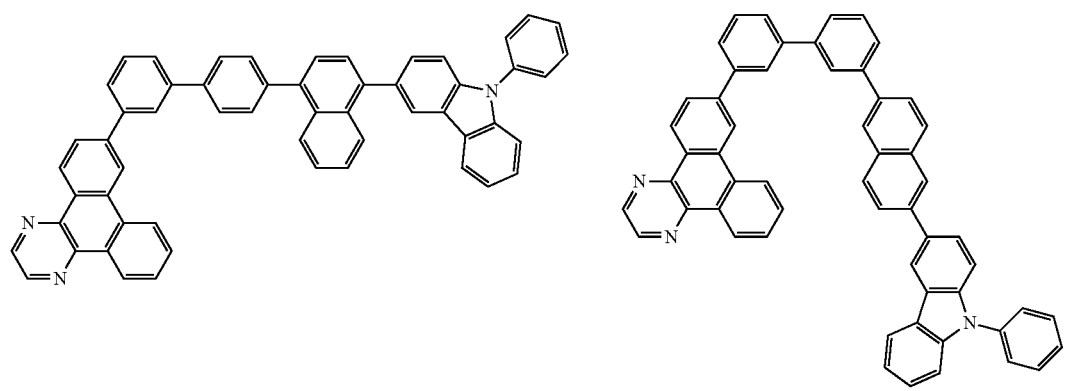
(965)
(966)
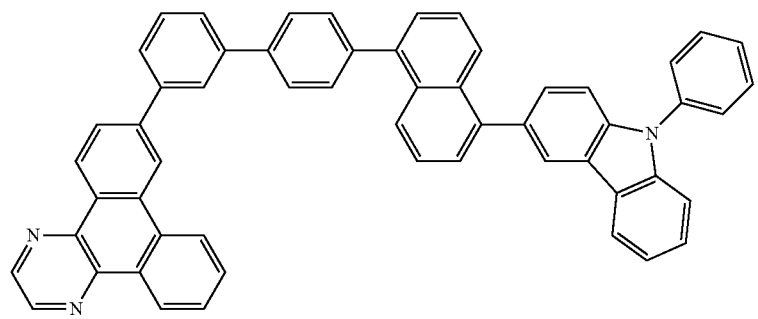
(967)
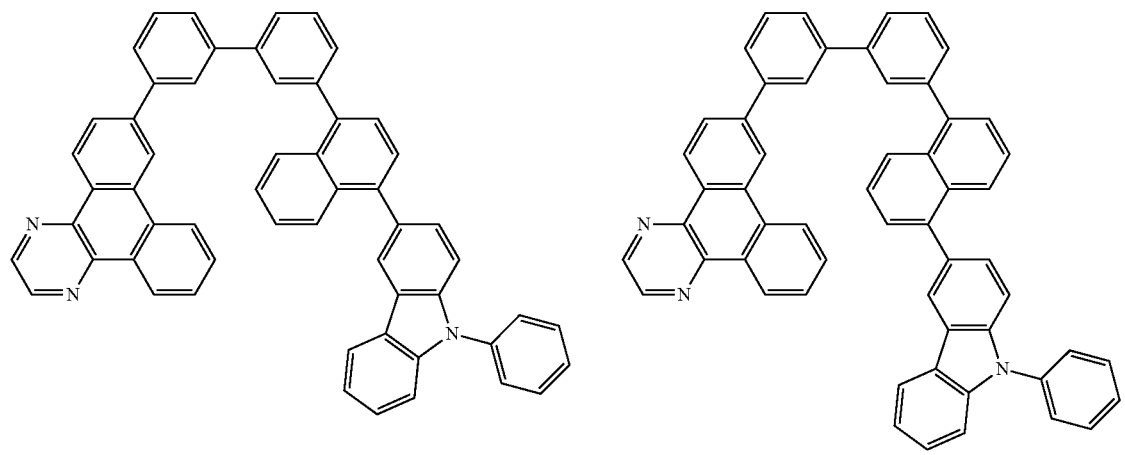
(968)

[Chemical formula 200]
(969)
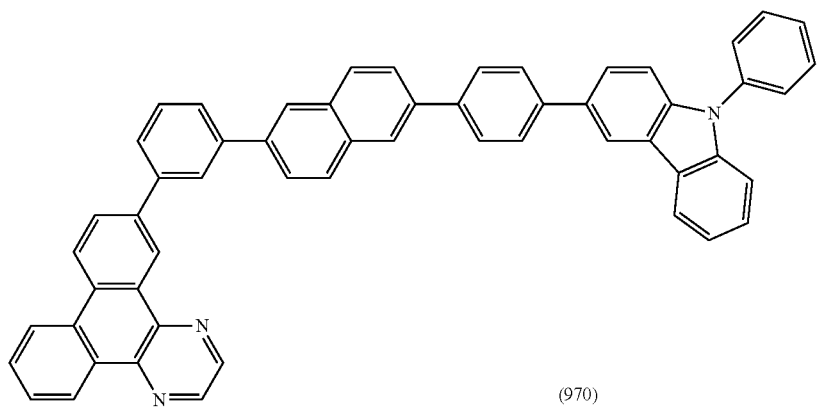
(970)
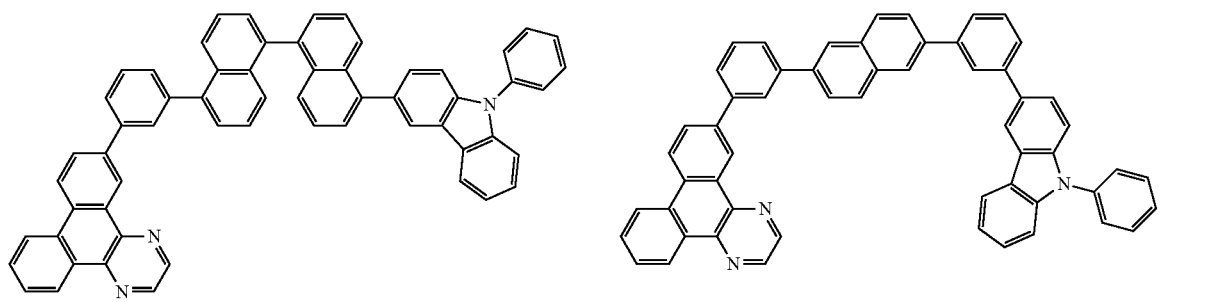
(971)
(972)
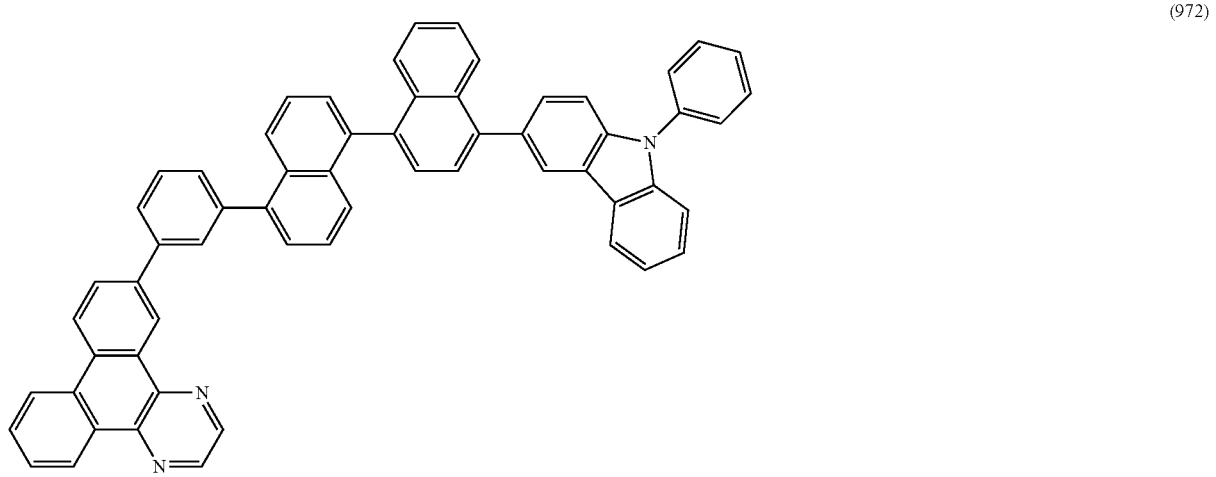
(973)
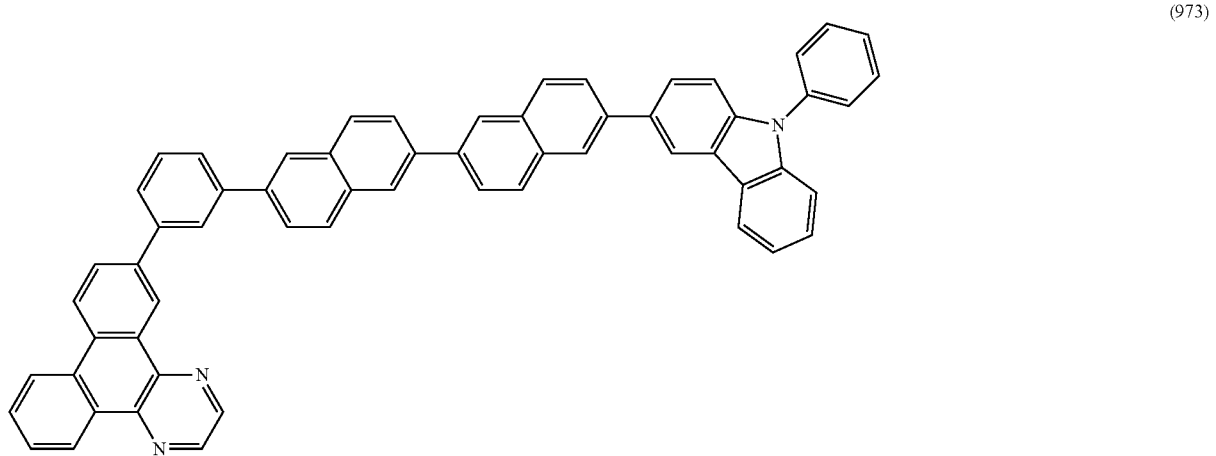

-continued
(974)
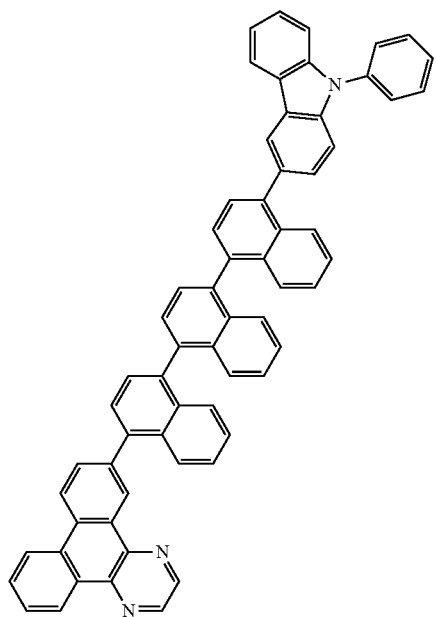
(975)
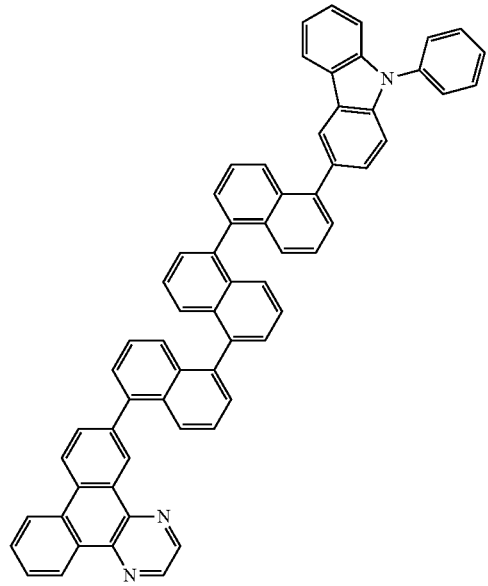
(976)
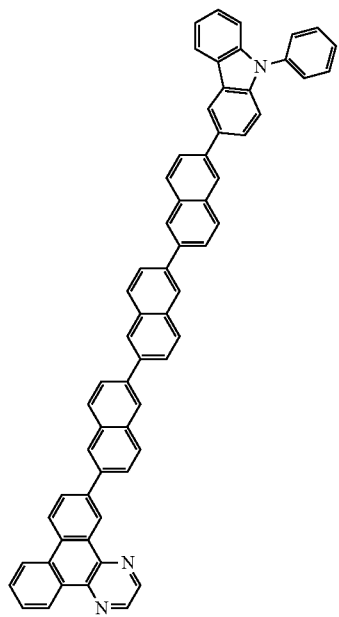
(977)
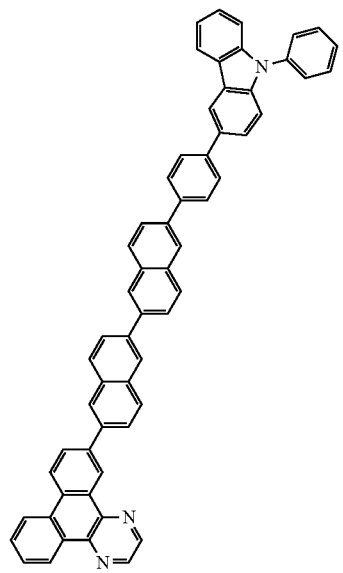
[Chemical formula 201]
(978)
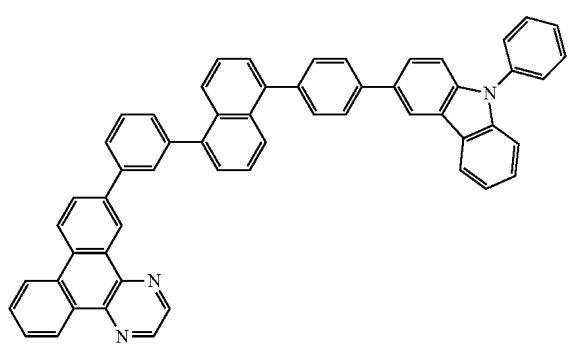
(979)
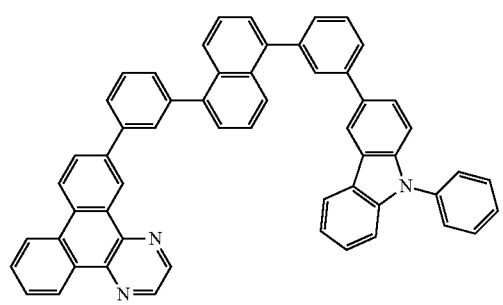

(980)
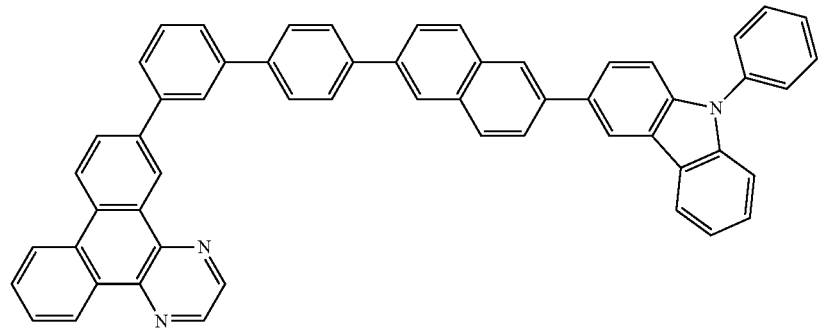
(981)
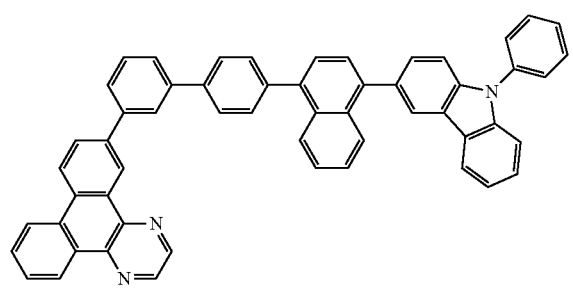
(982)
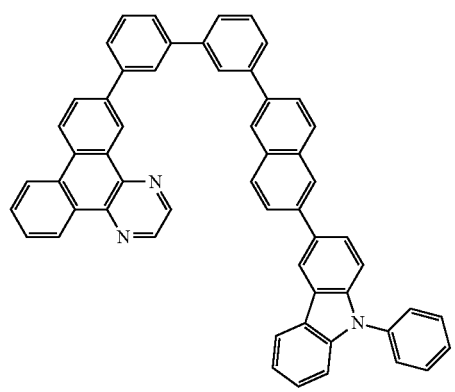
(983)
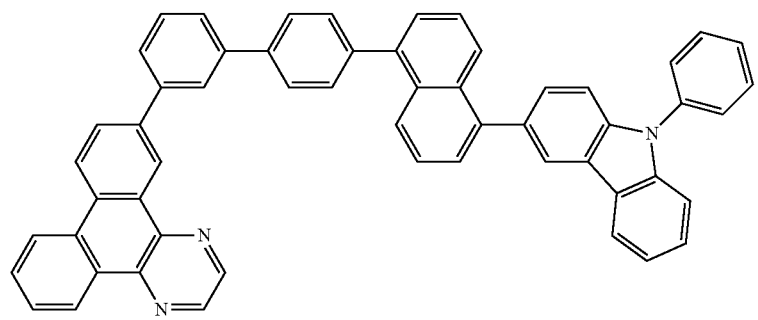
(984)
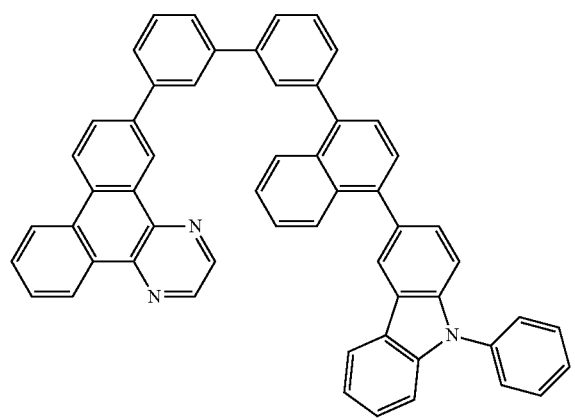
(985)
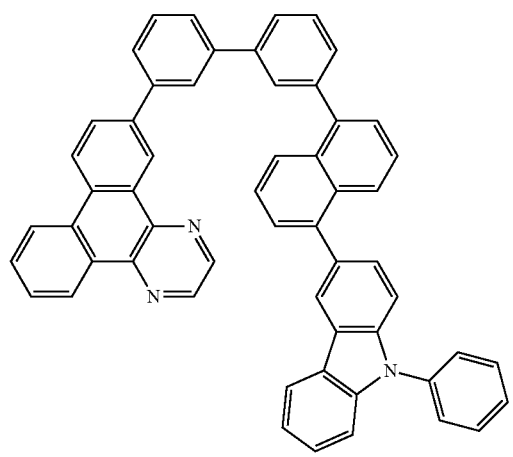

[Chemical formula 202]
(986)
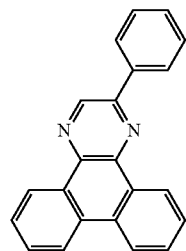 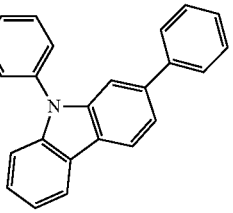
(987)
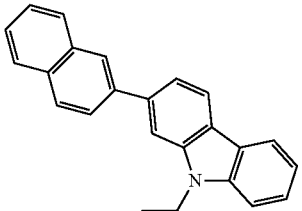
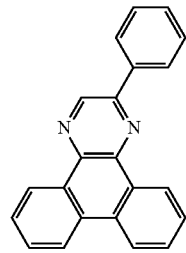
(988)
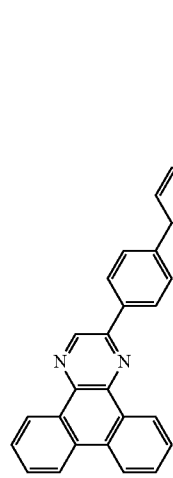 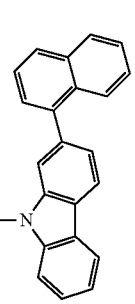
(989)
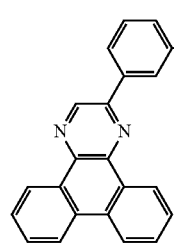 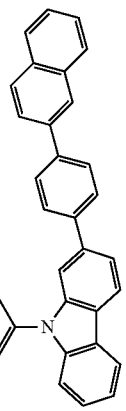

-continued
(990)
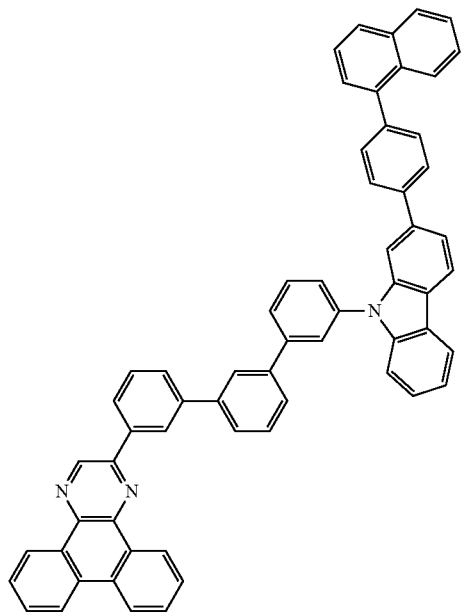
[Chemical formula 203]
(991)
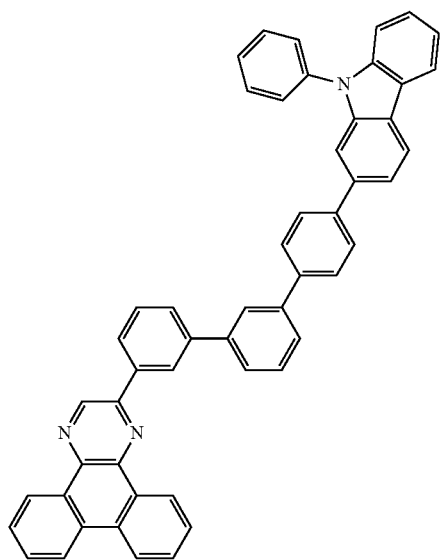
(992)
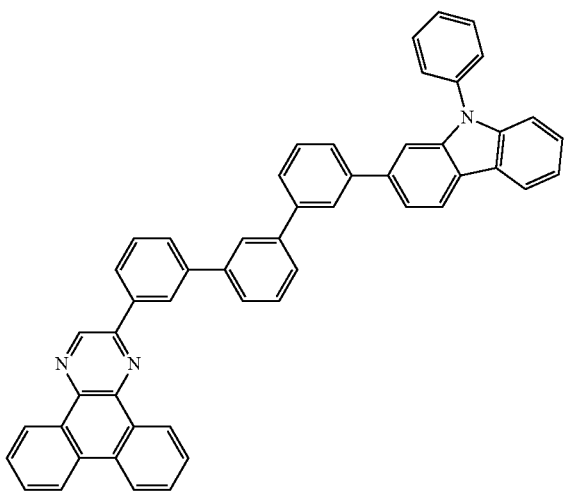

-continued
(993)
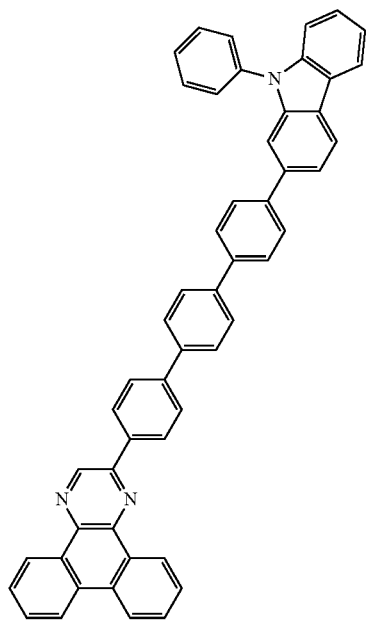
(994)
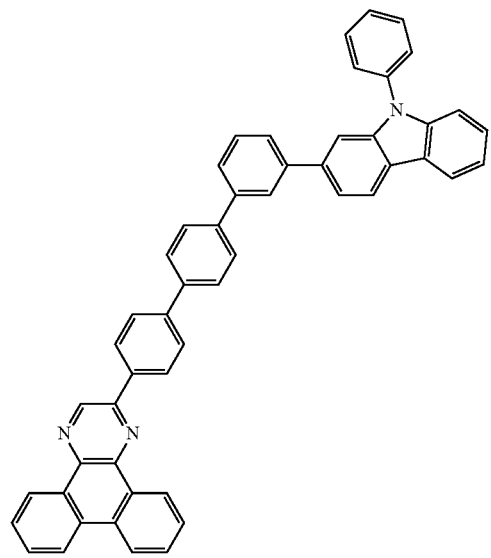
(995)
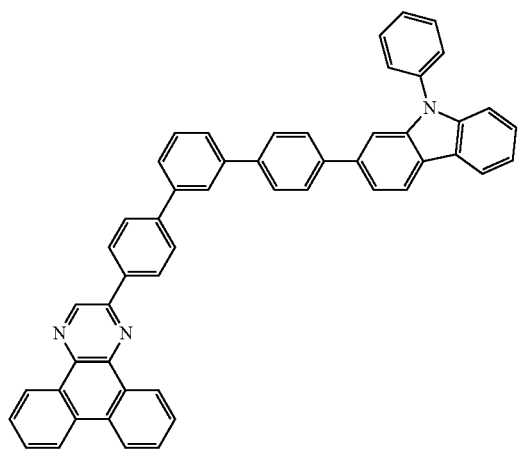
(996)
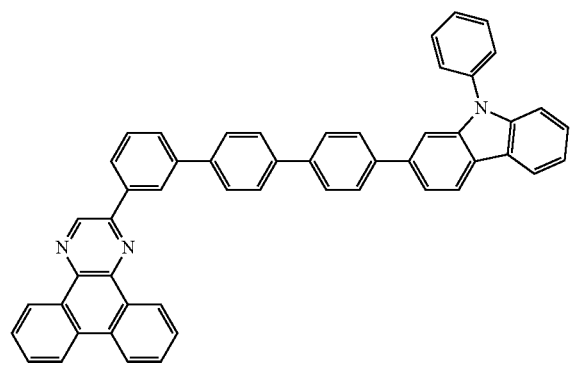
(997)
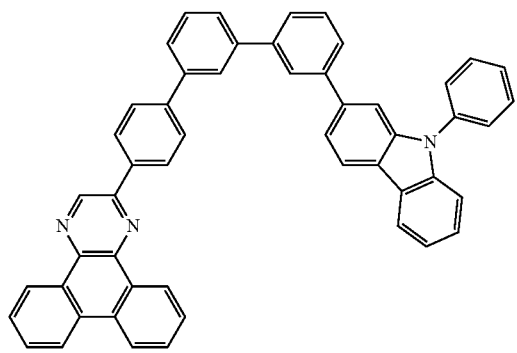
(998)
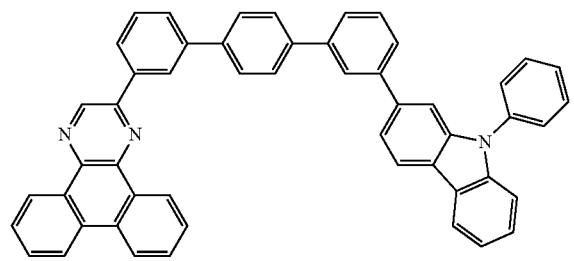

453 454
-continued
(999)
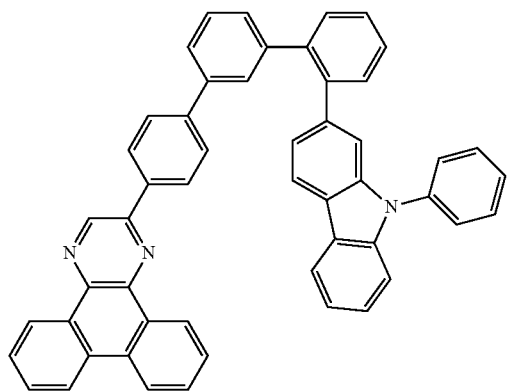
(1000)
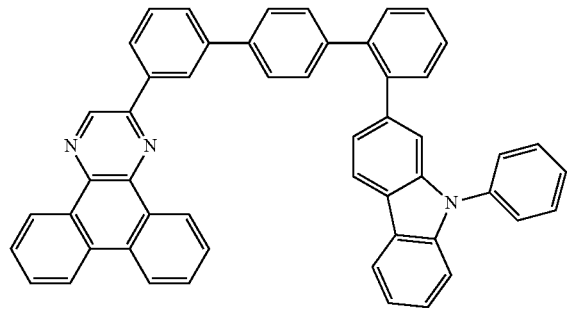
[Chemical formula 204]
(1001)
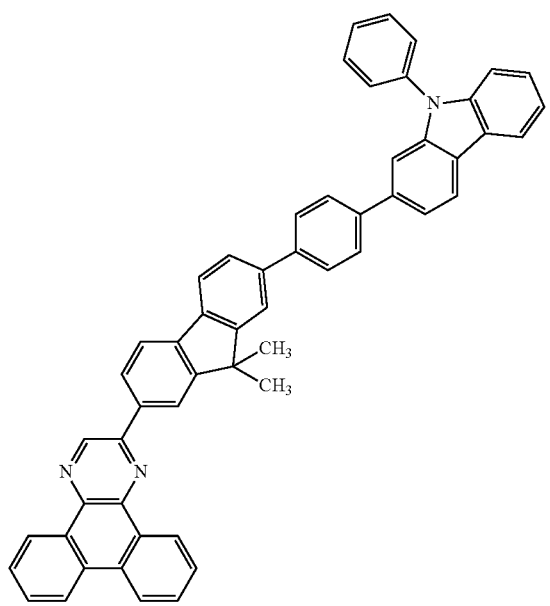
(1002)
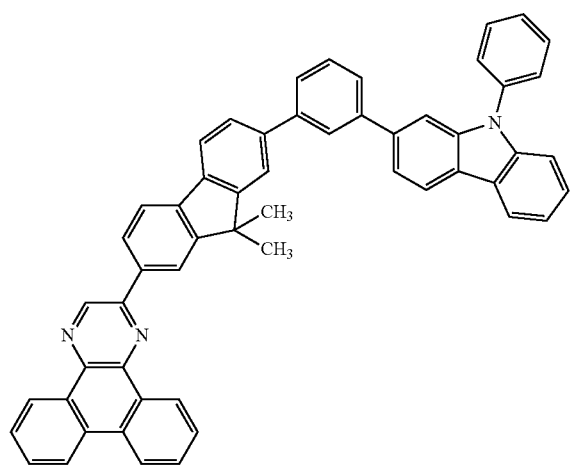

-continued
(1003)
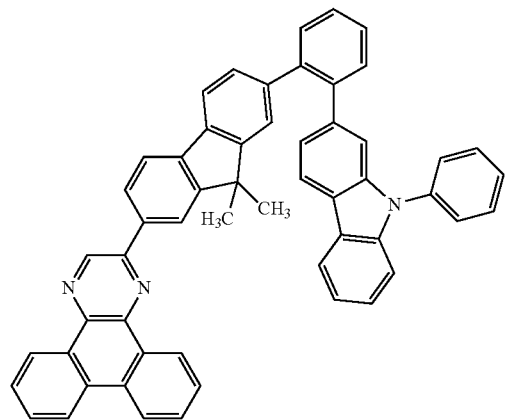
(1004)
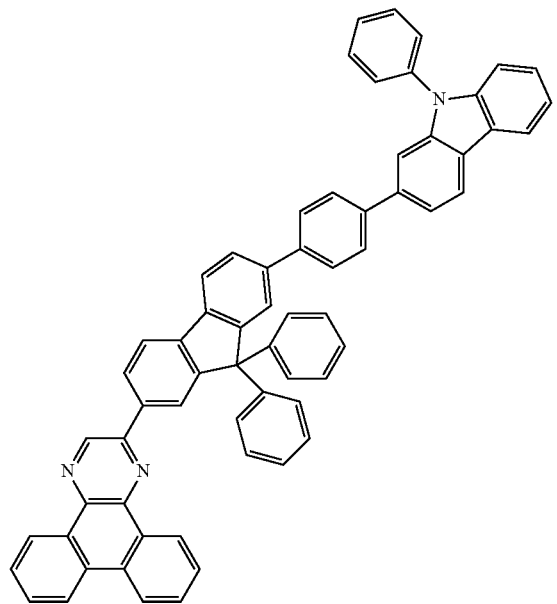
(1005)
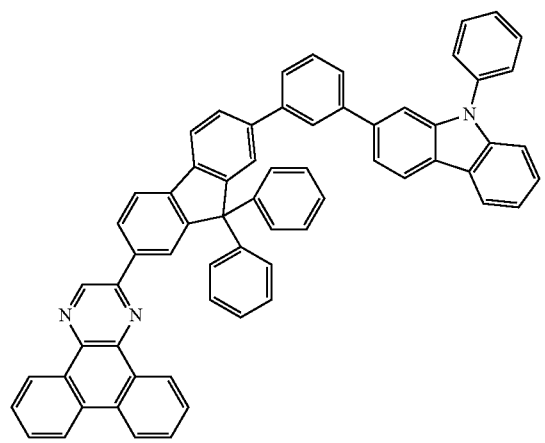
(1006)
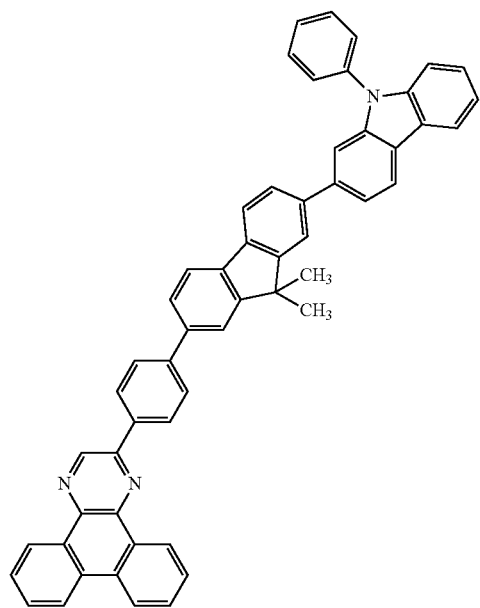

-continued
(1007)
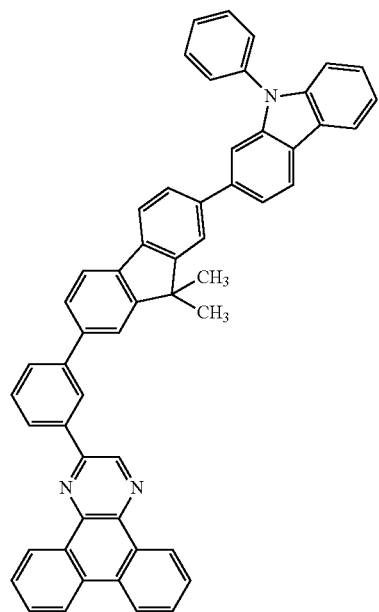
[Chemical formula 205]
(1008)
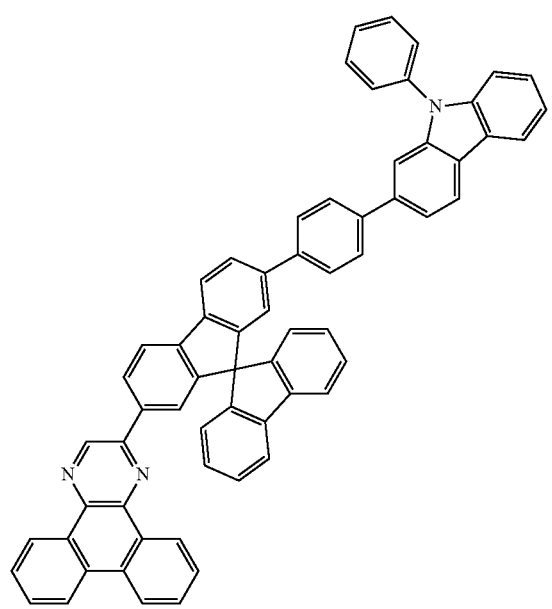
(1009)
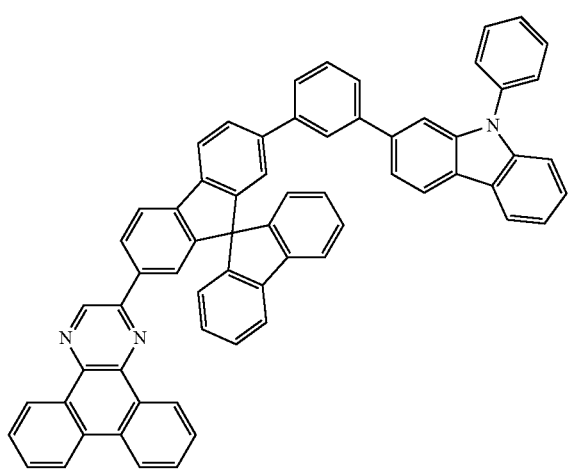

-continued
(1010)
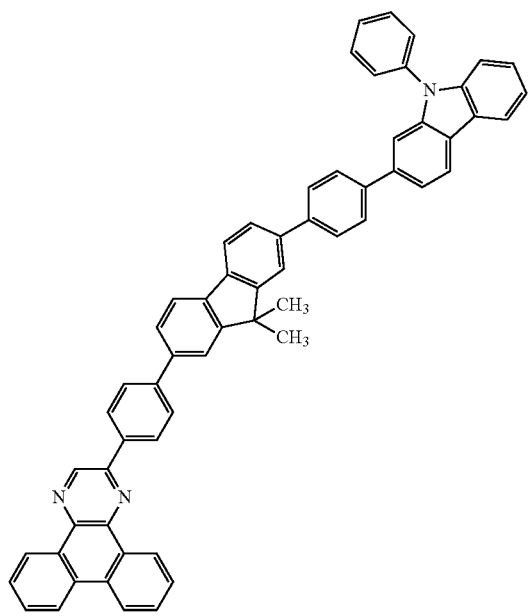
(1011)
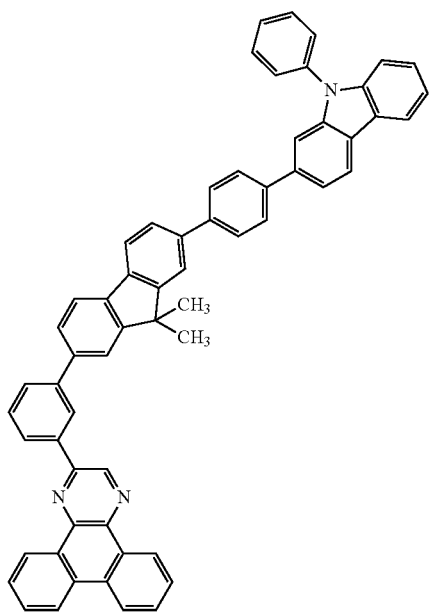
(1012)
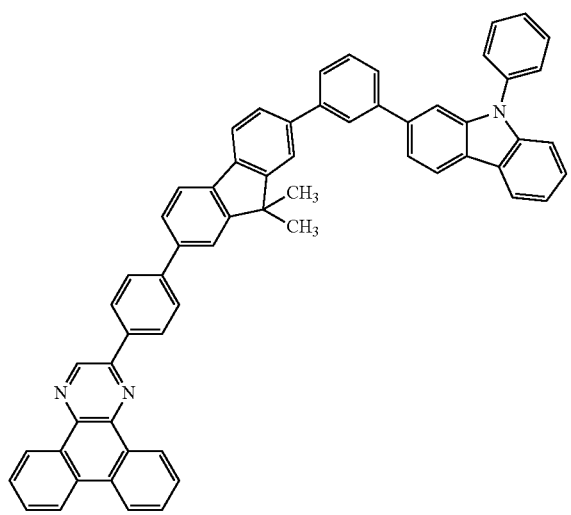
(1013)
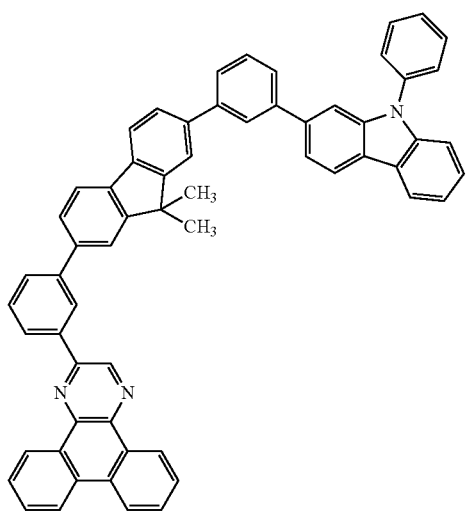
(1014)
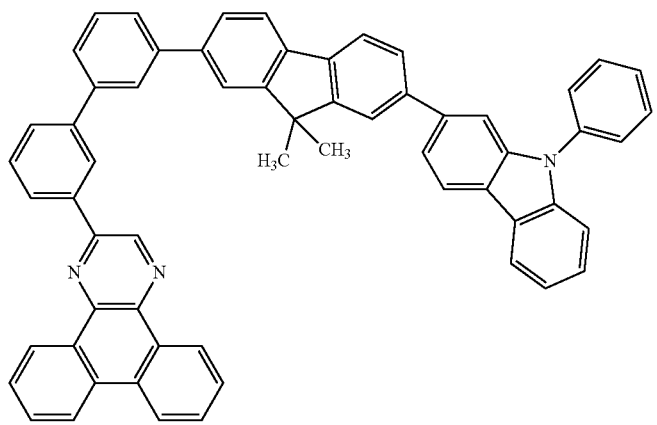

[Chemical formula 206]
(1015)
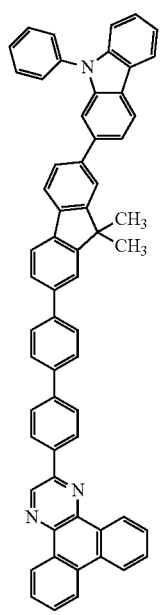
(1016)
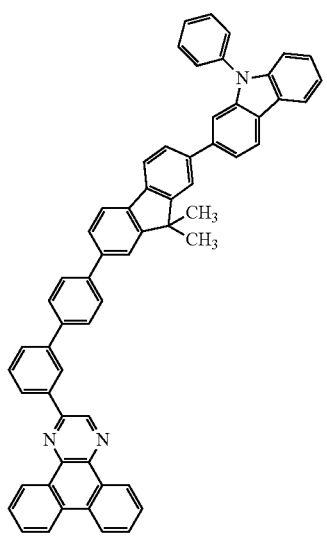
(1017)
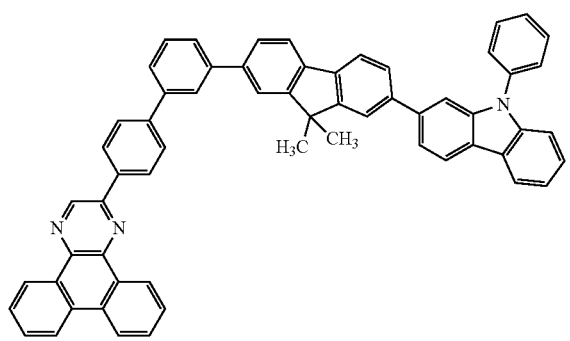
(1018)
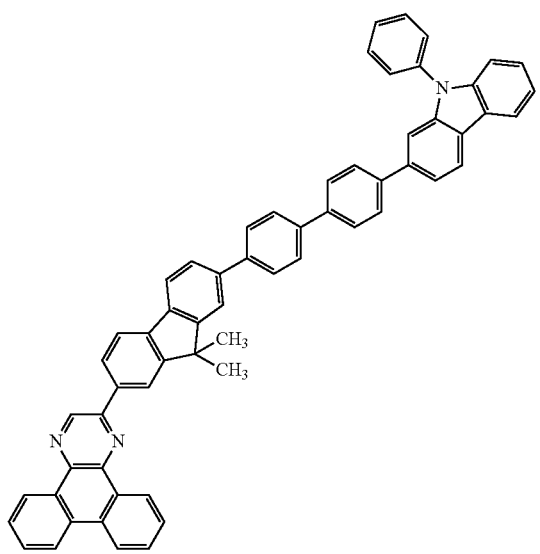
(1019)
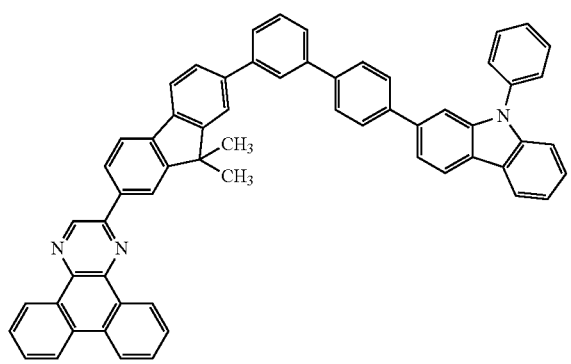
(1020)
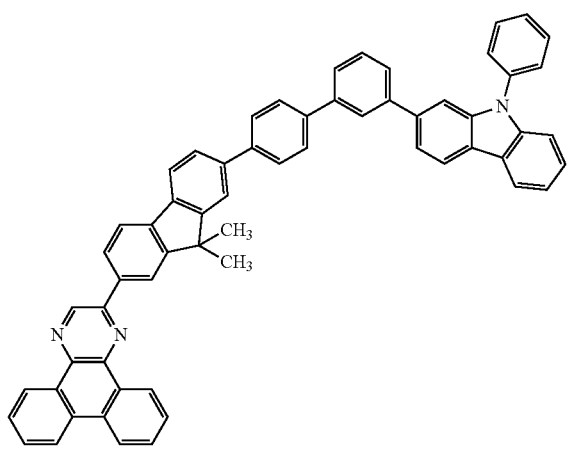

(1021)
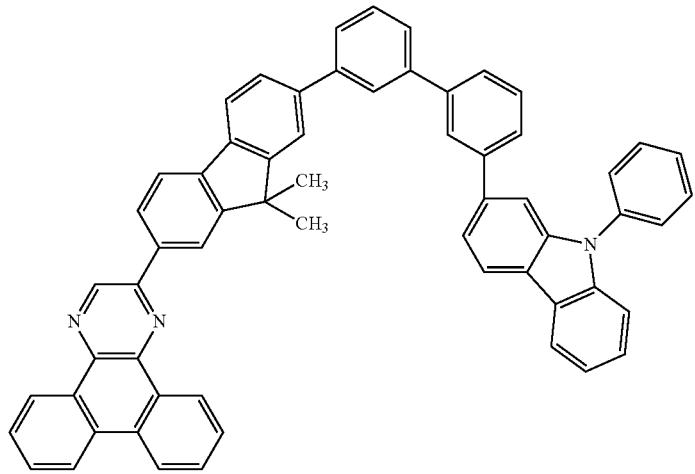
[Chemical formula 207]
(1022)
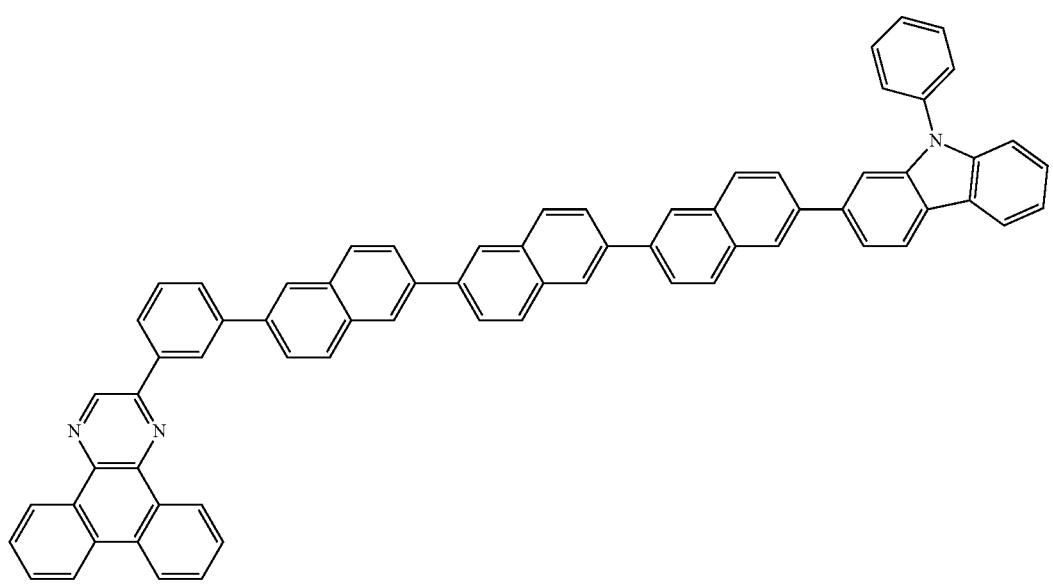
(1023)
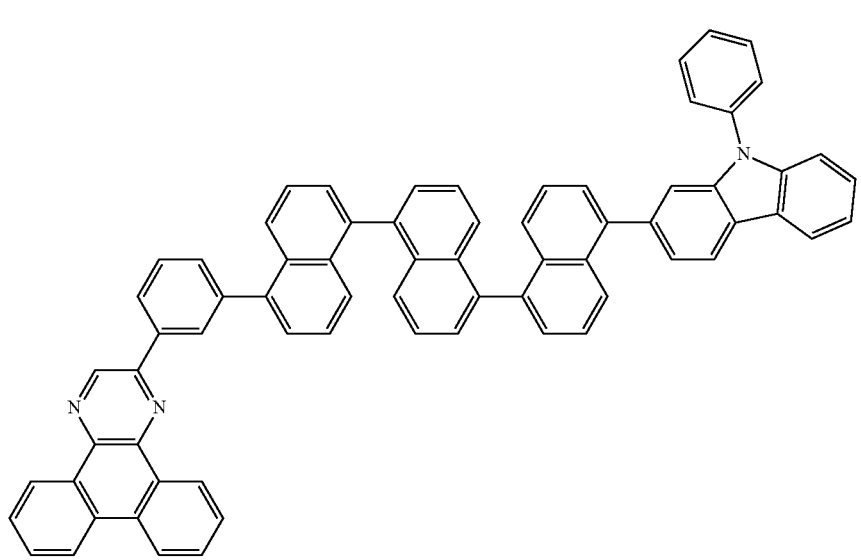

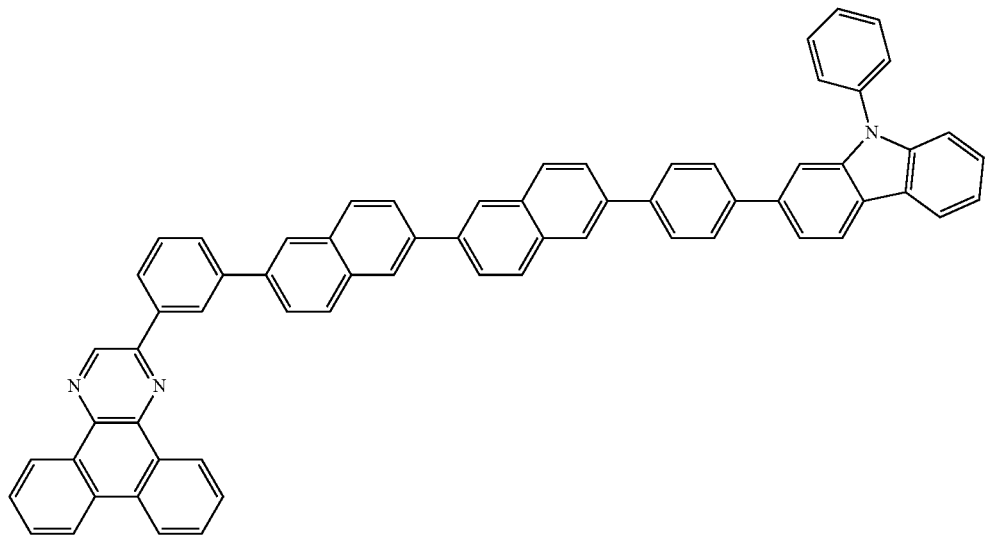
(1024)
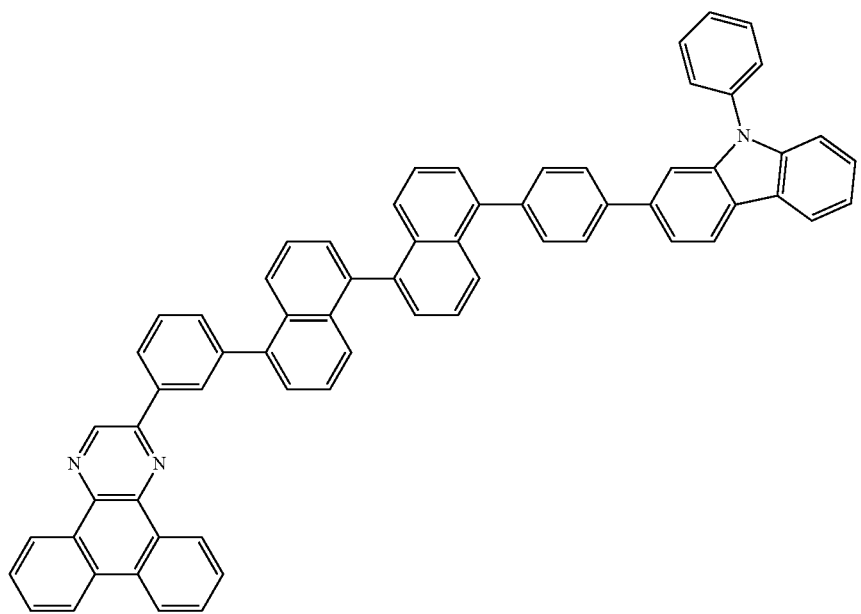
(1025)

-continued
(1026)
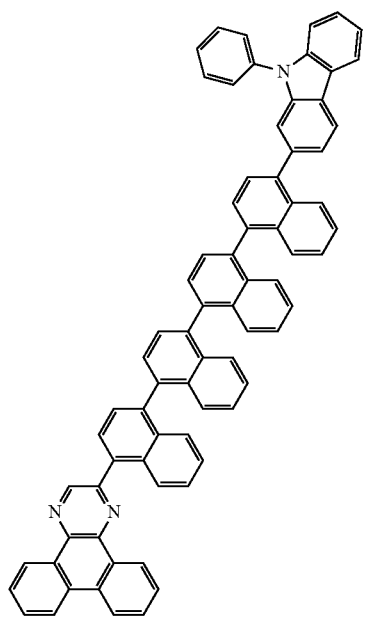
(1027)
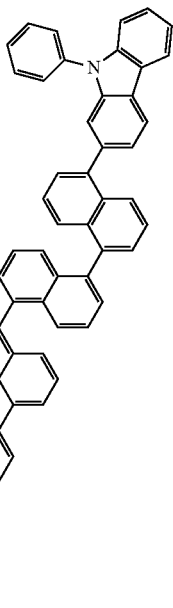
(1028)
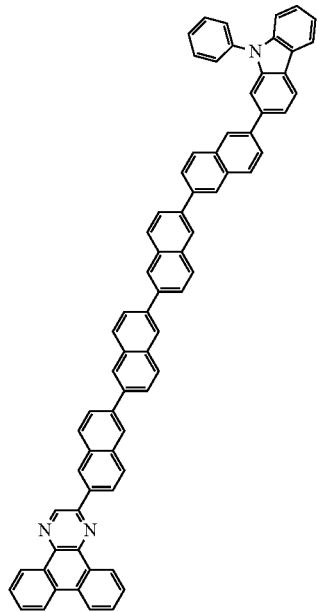

[Chemical formula 208]
(1029)
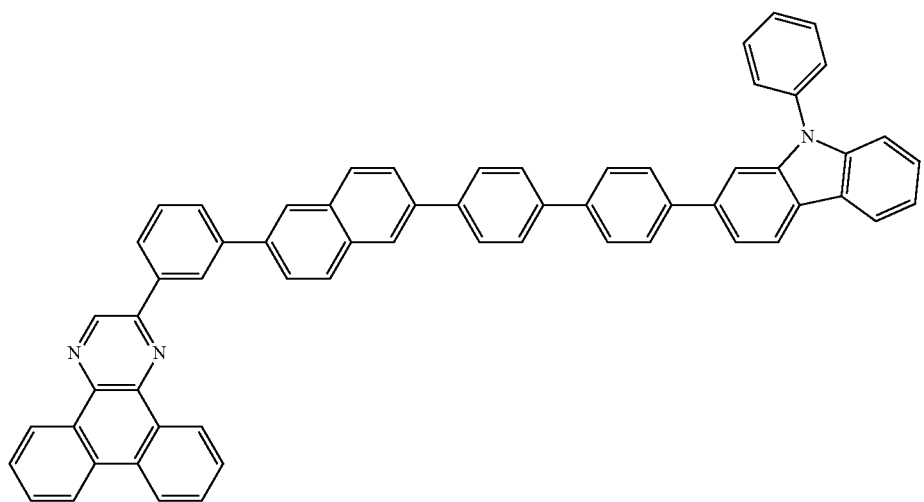
(1030)
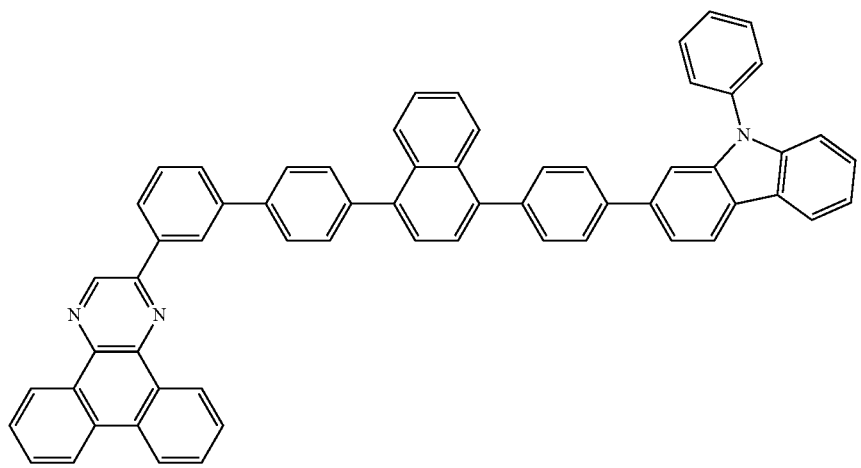
(1031)
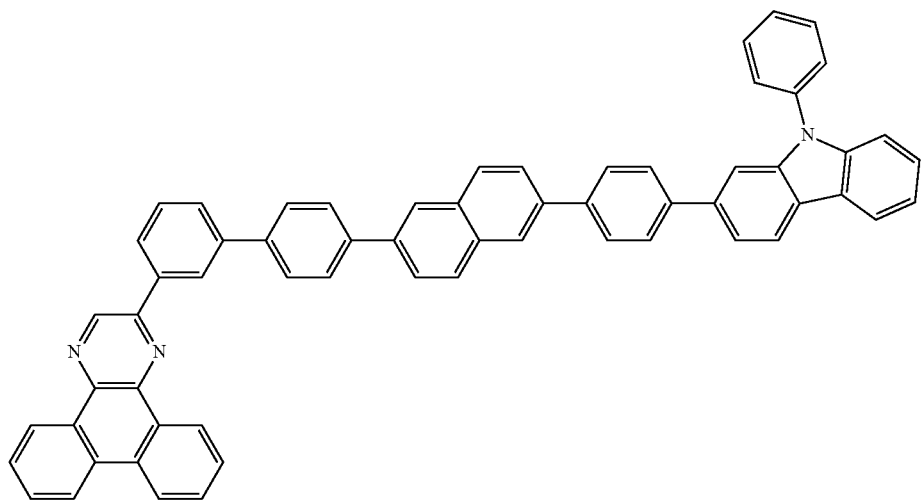

-continued
(1032)
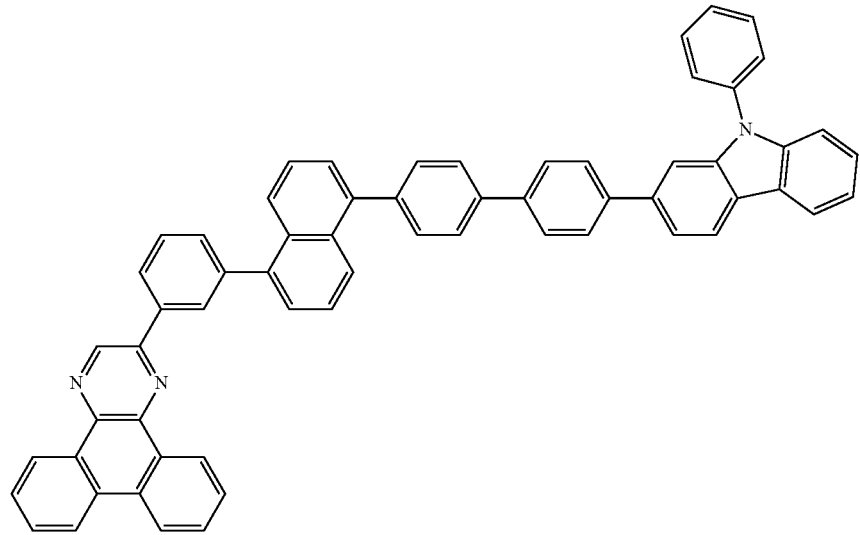
(1033) (1034)
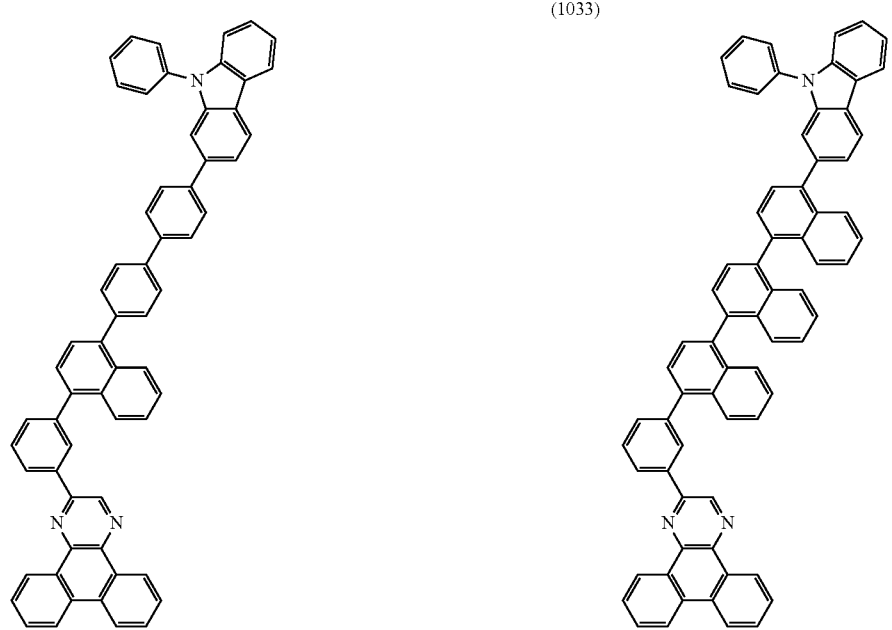

-continued
(1035)
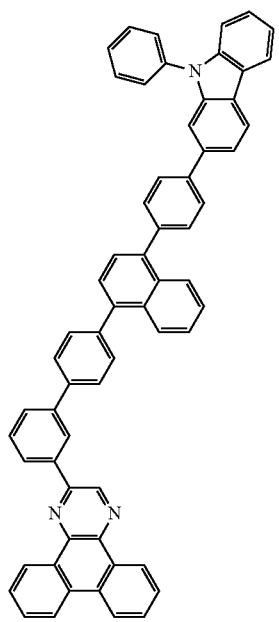
(1036)
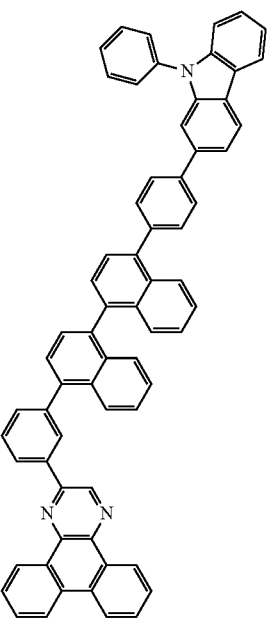
[Chemical formula 209]
(1037)
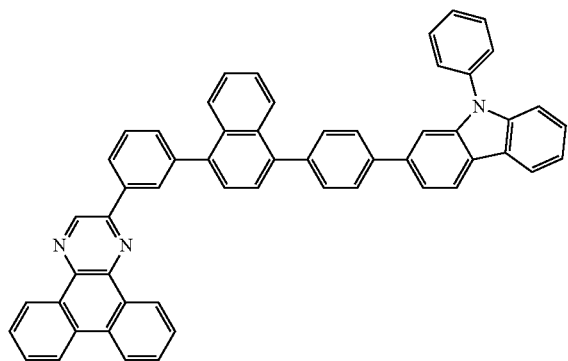
(1038)
(1039)
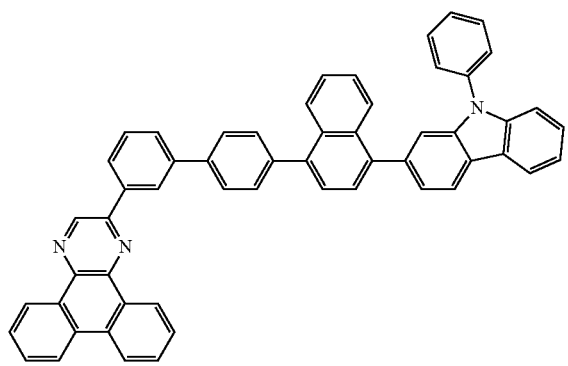
(1040)
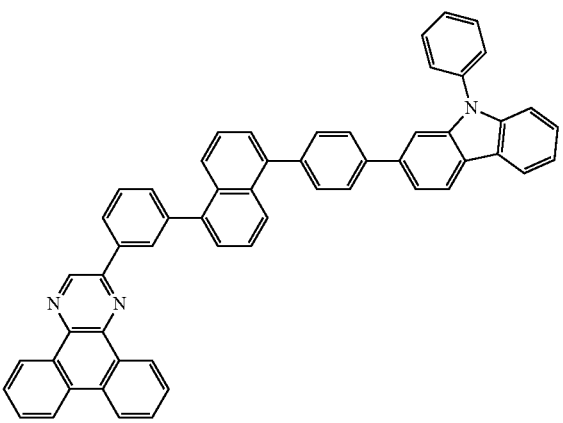

475
476
-continued
(1041)
(1042)
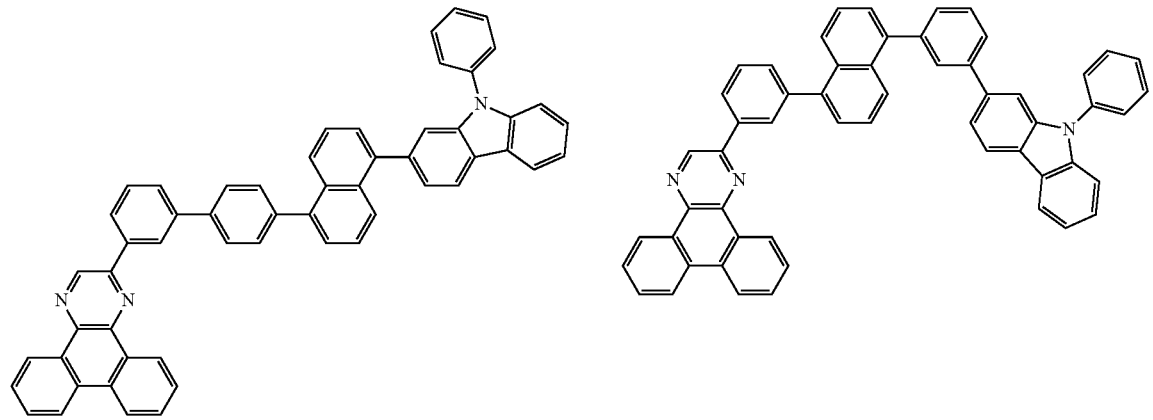
(1043)
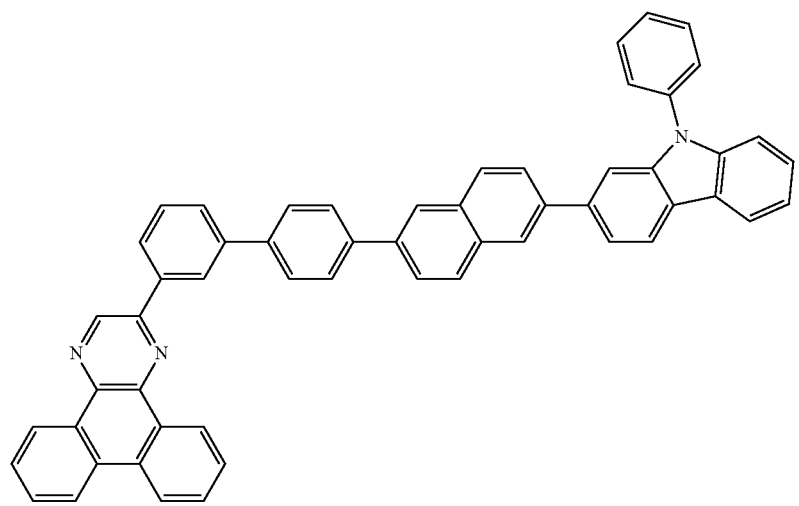
(1044)
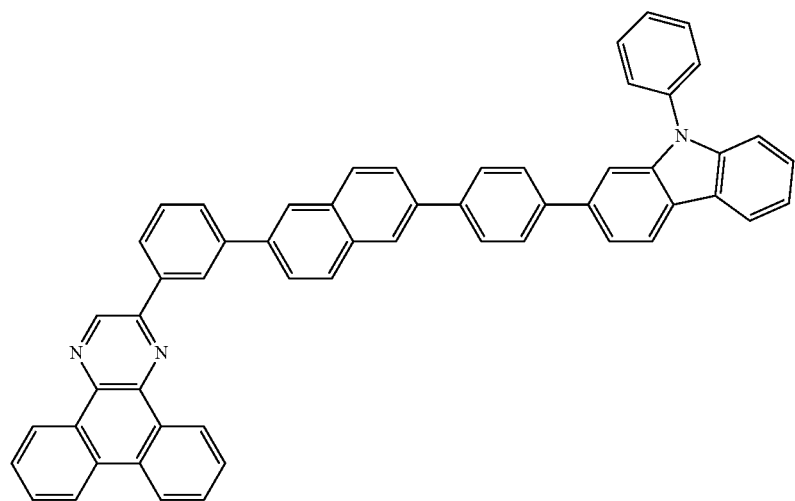

(1045)
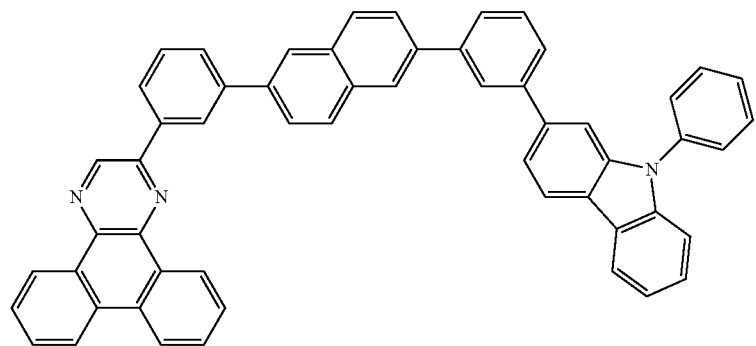
[Chemical formula 210]
(1046)
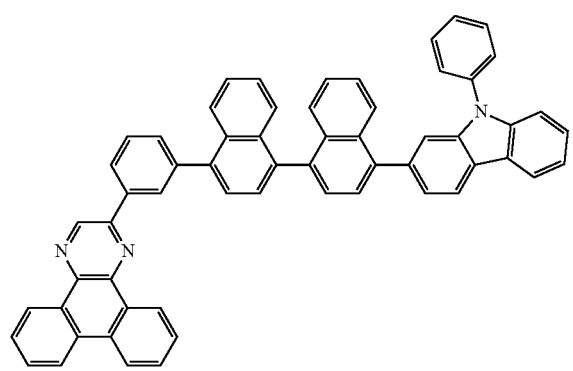
(1047)
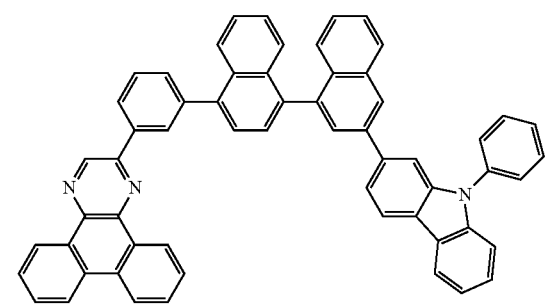
(1048)
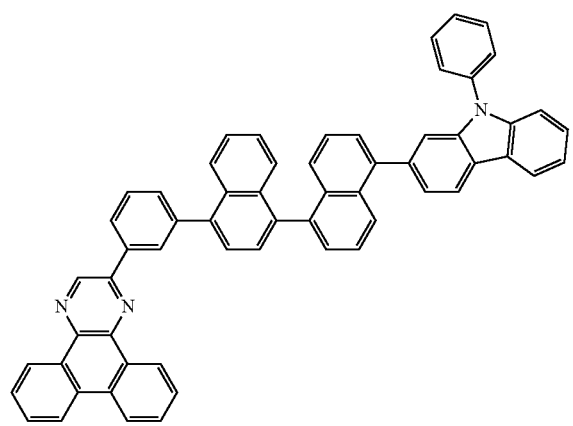
(1049)
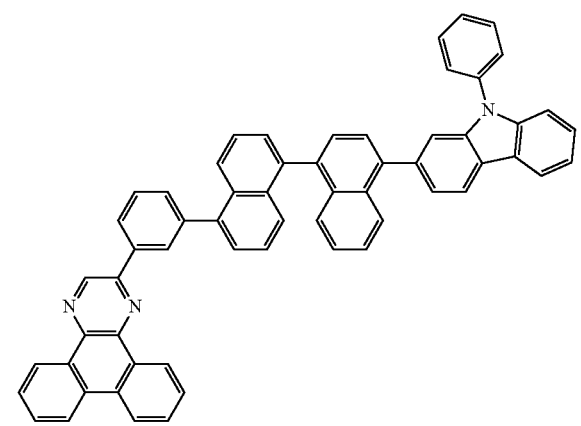

-continued
(1050)
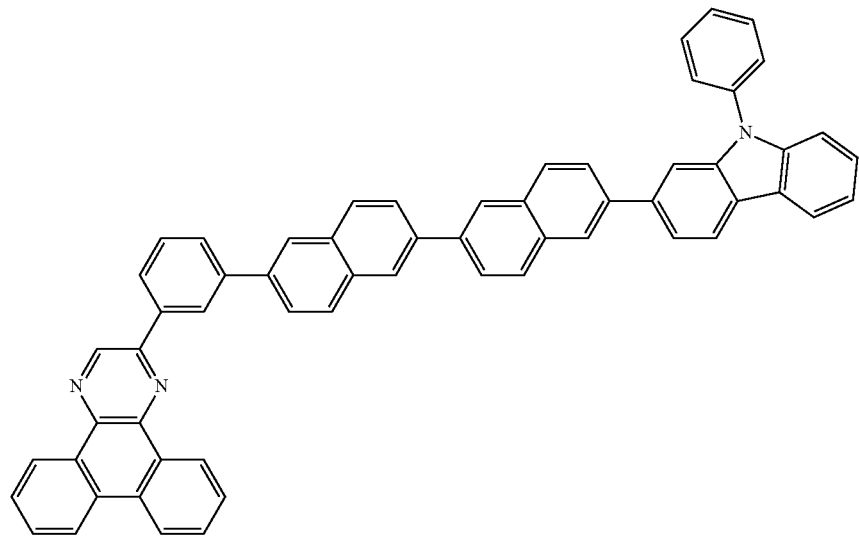
(1051)
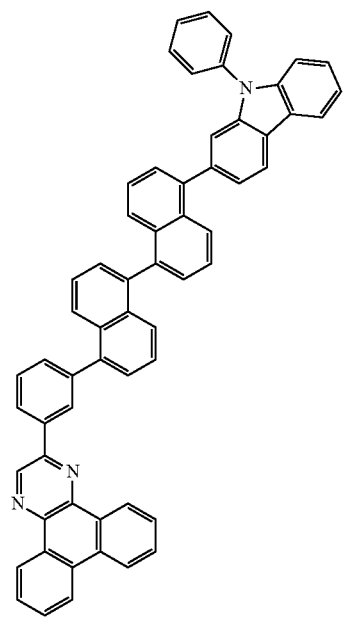
(1052)
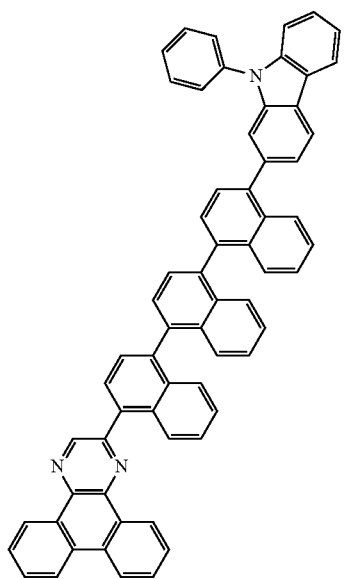

[Chemical formula 211]
(1053)
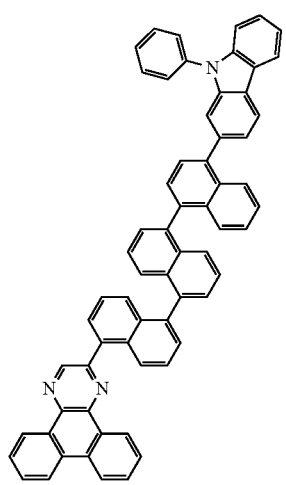
(1054)
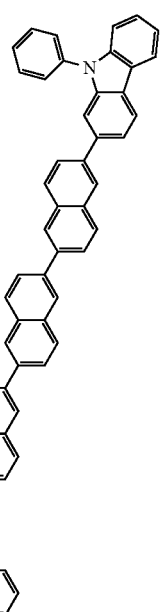
(1055)
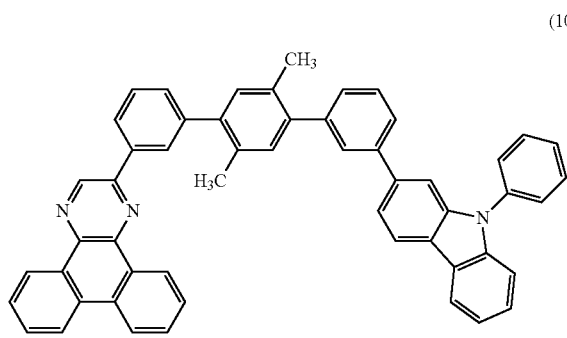
(1056)
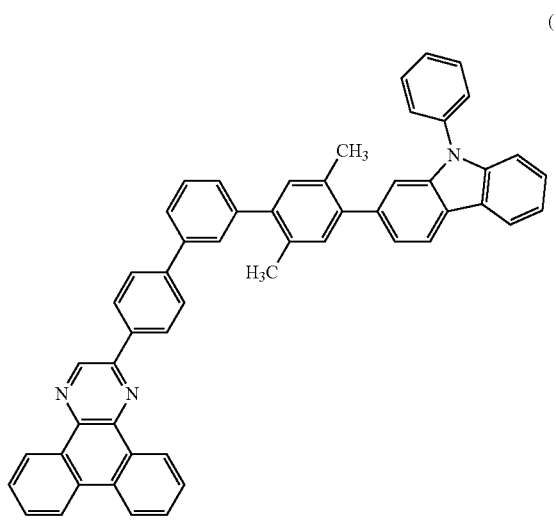
(1057)
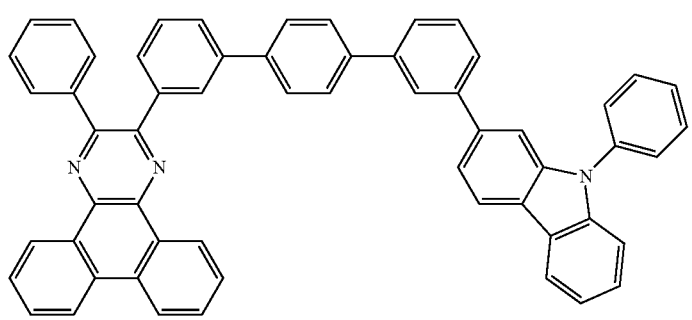

[Chemical formula 212]
(1058)
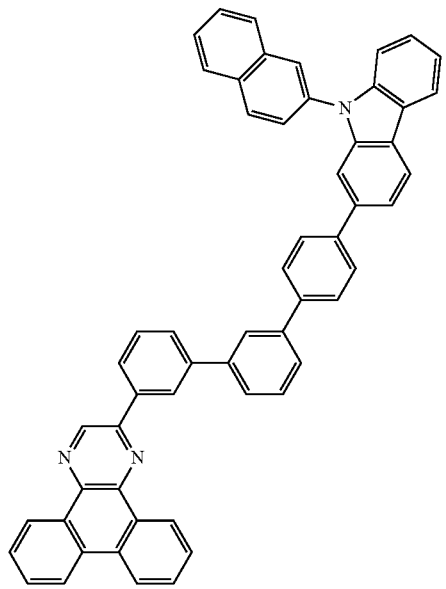
(1059)
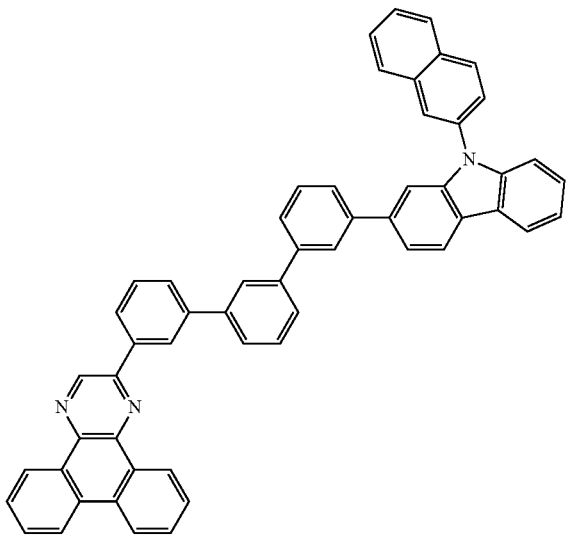
(1060)
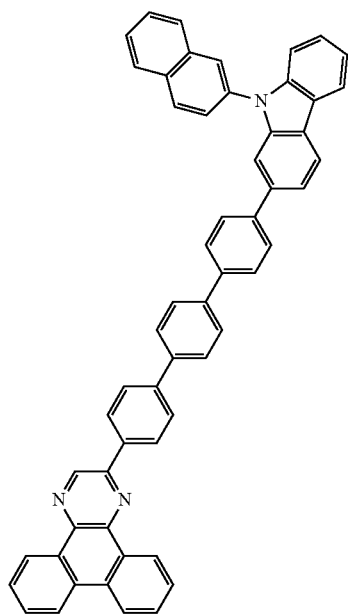
(1061)
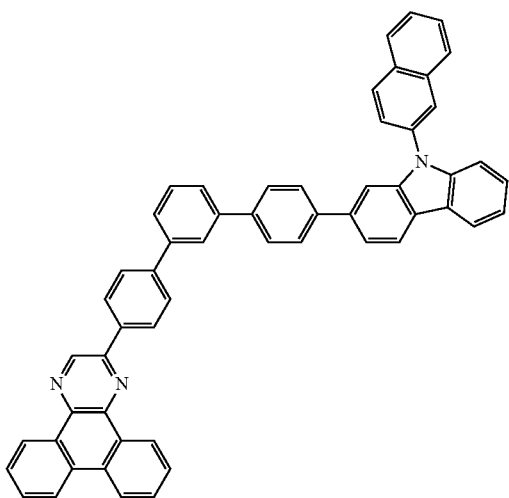

-continued
(1062)
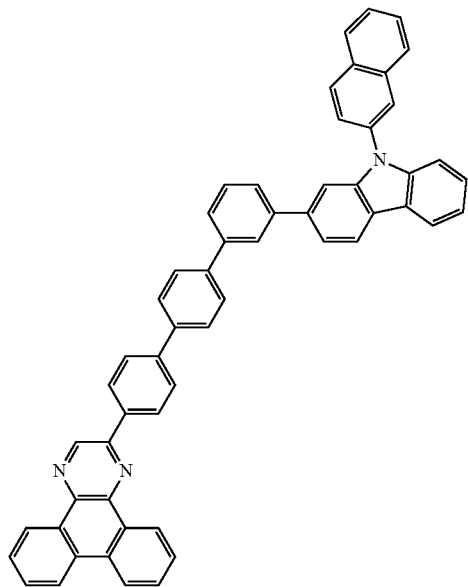
(1063)
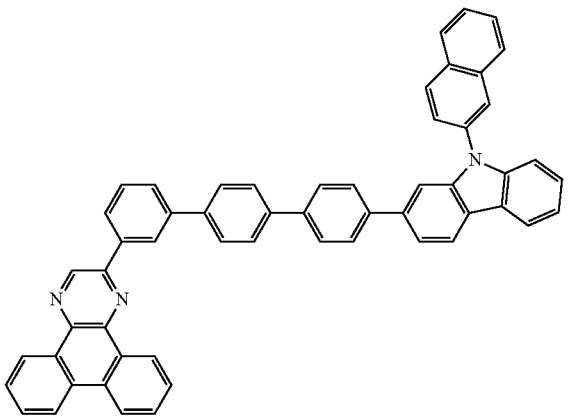
(1064)
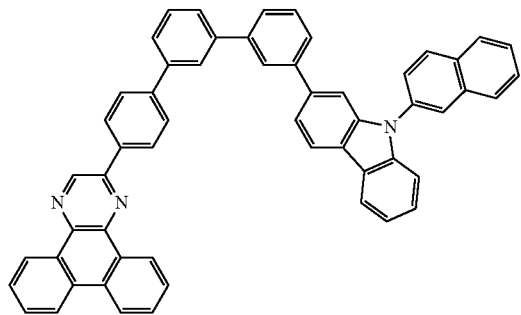
(1065)
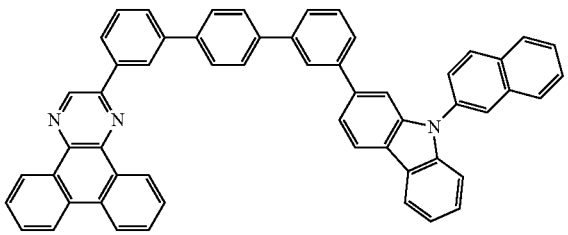
[Chemical formula 213]
(1066)
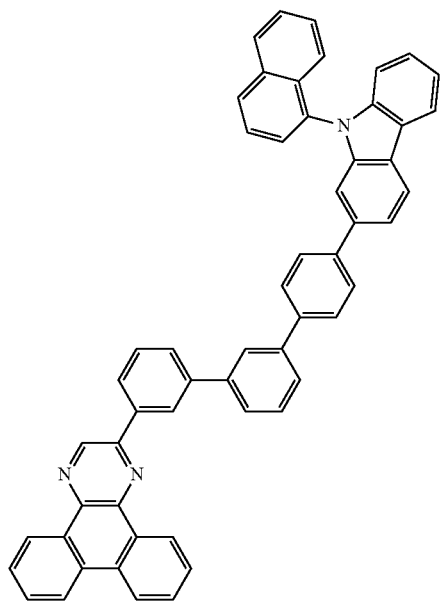
(1067)
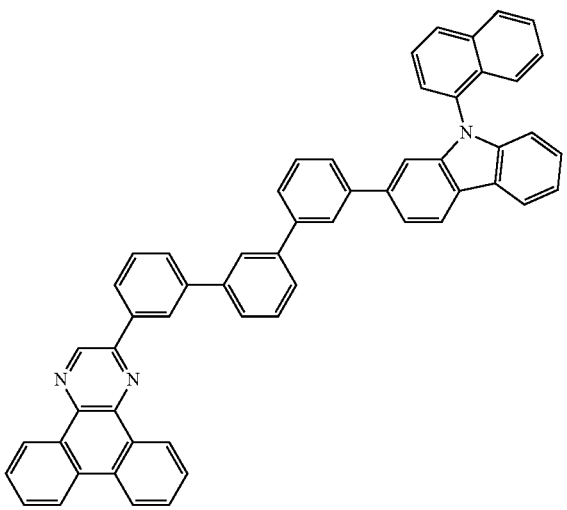

487                                         488
-continued
(1068)
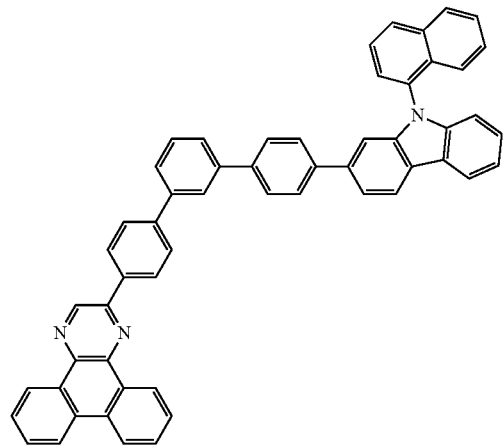
(1069)
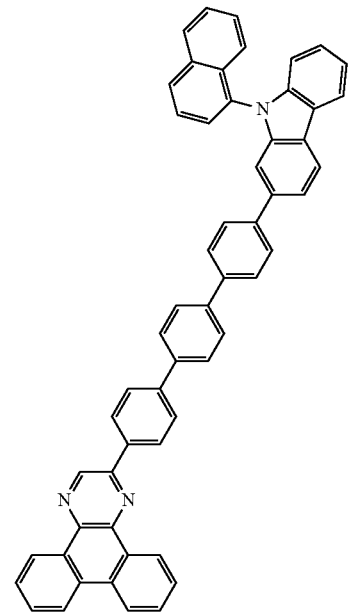
(1070)
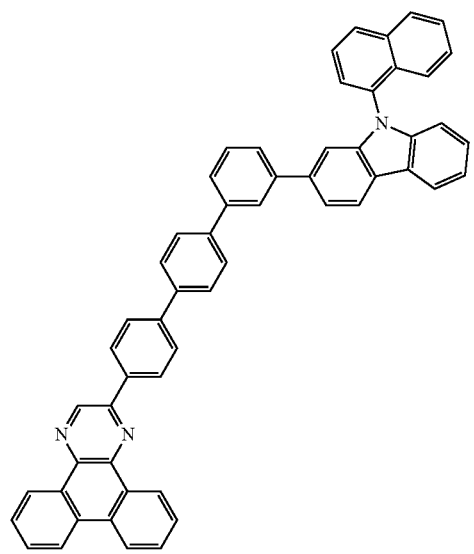
(1071)
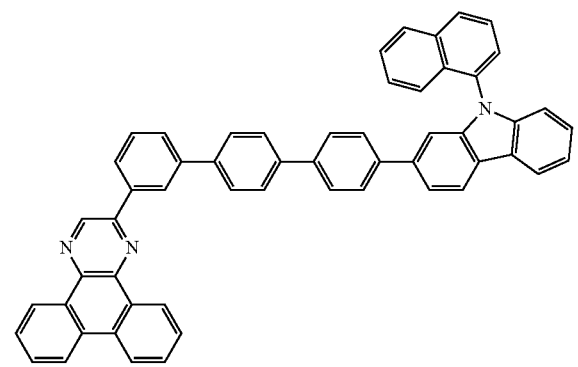
(1072)
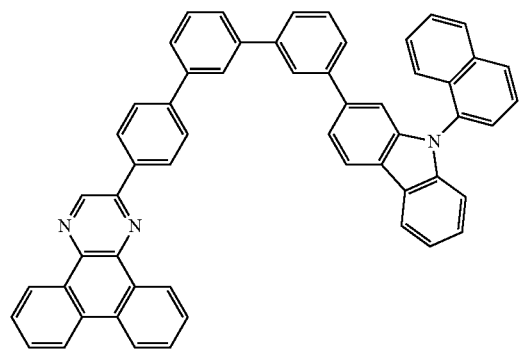
(1073)
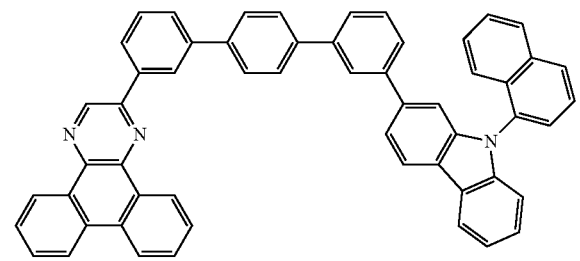

[Chemical formula 214]
(1074)
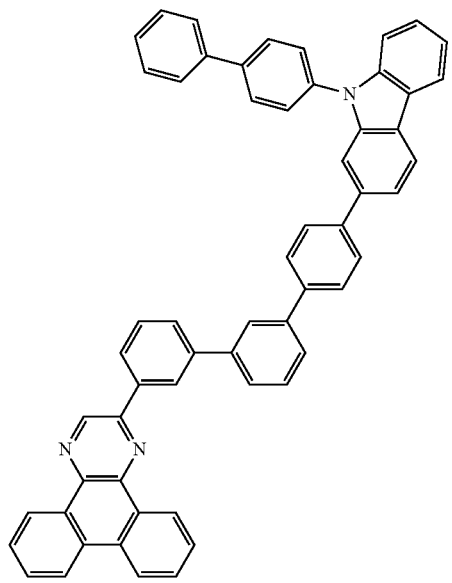
(1075)
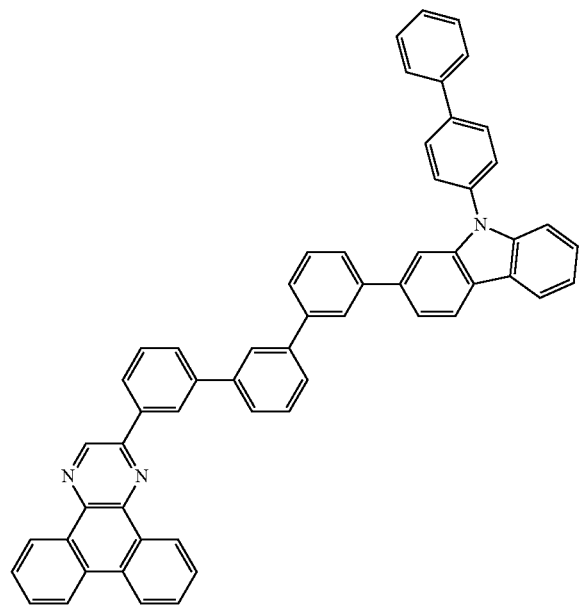
(1076)
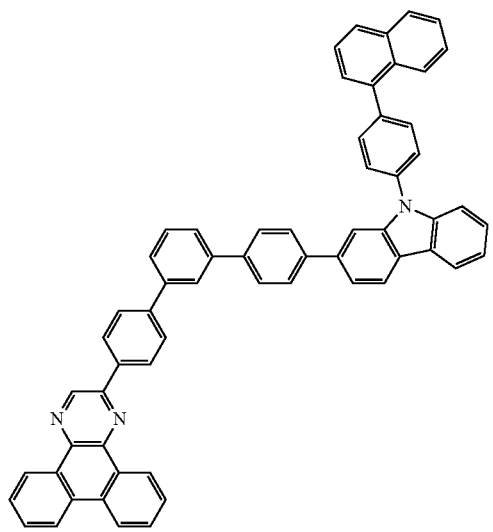
(1077)
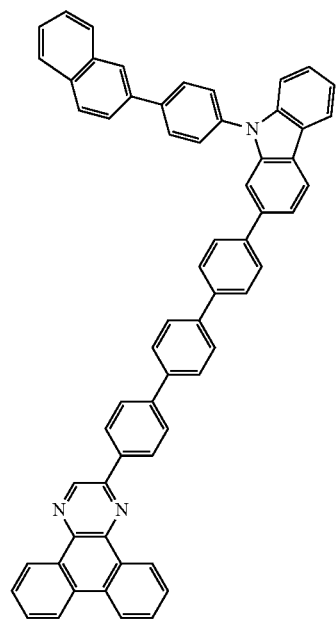

(1078)
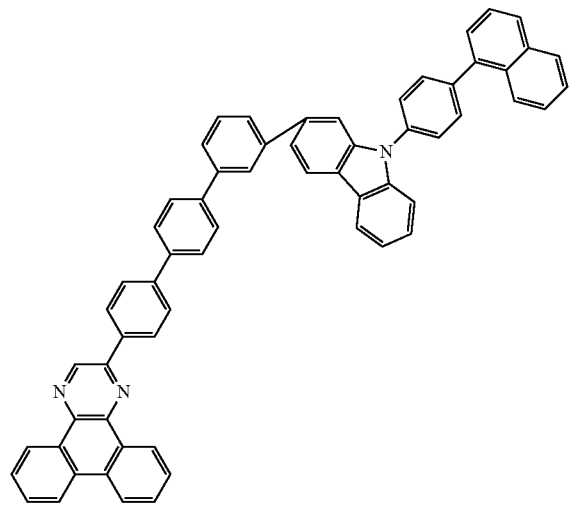
(1079)
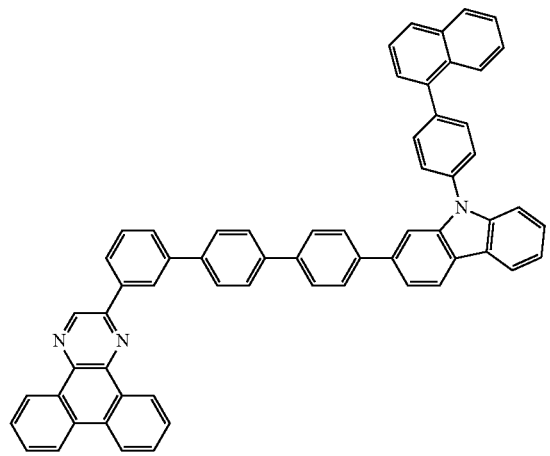
(1080)
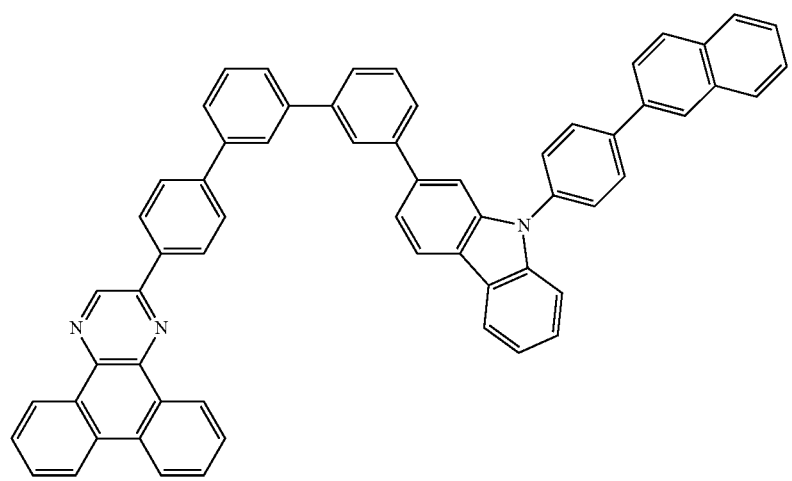
(1081)
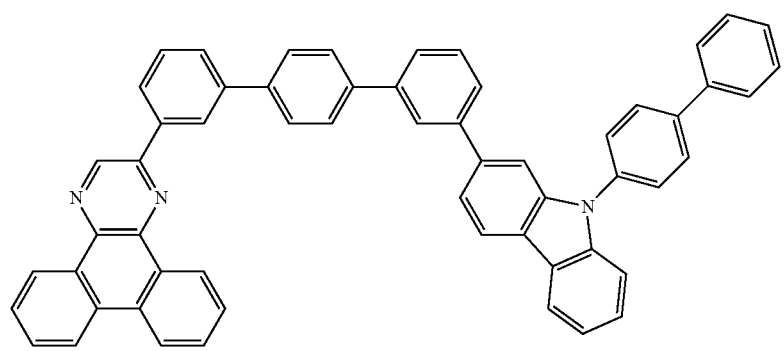

-continued
(1082)
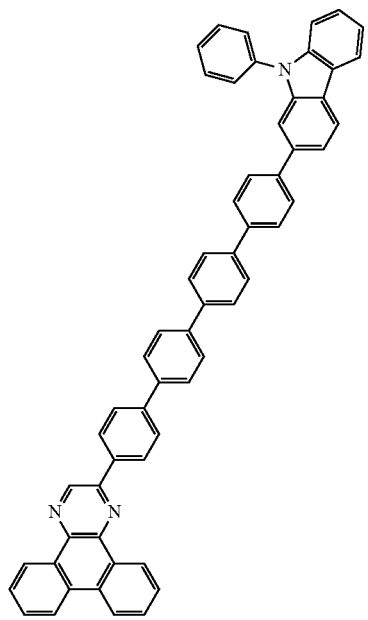
(1083)
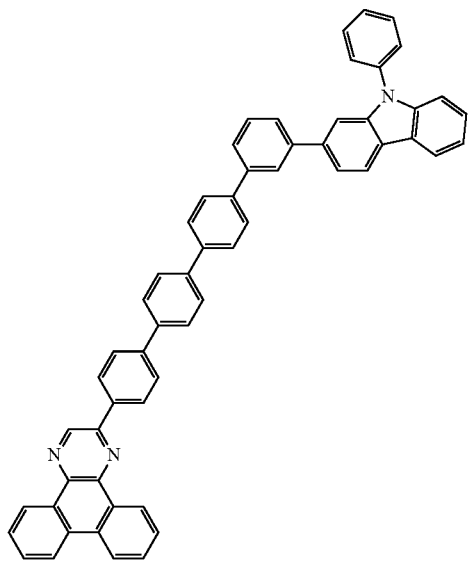
(1084)
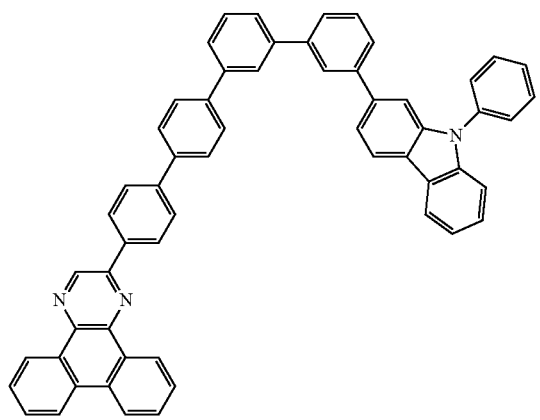
(1085)
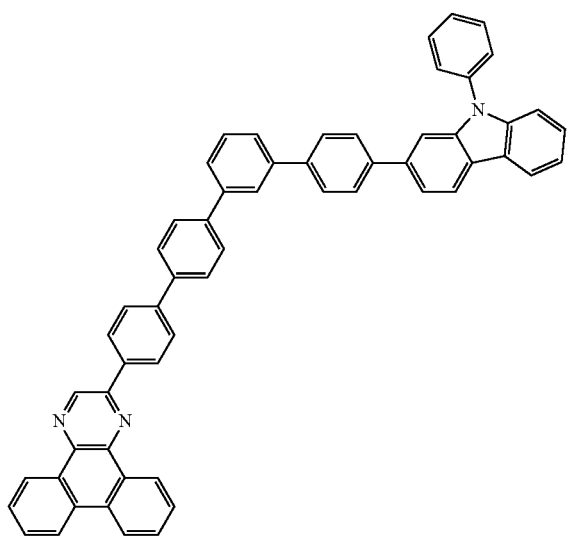

(1086)
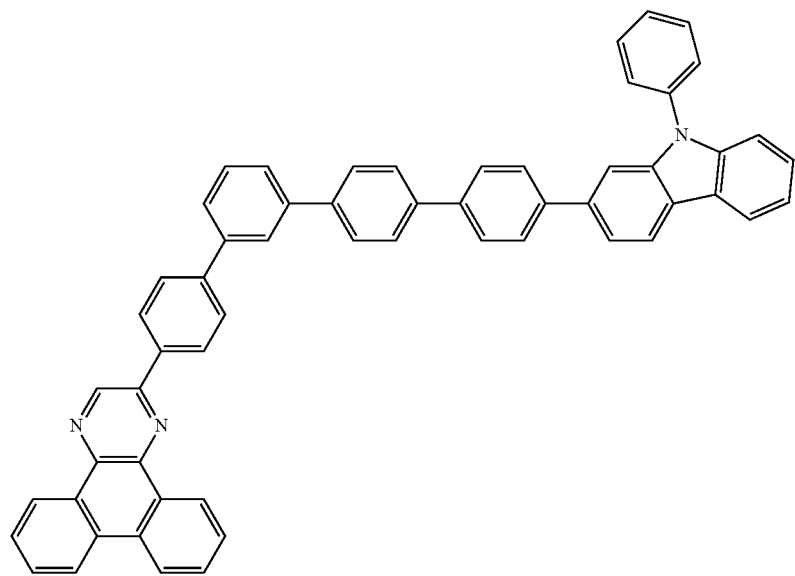
(1087)
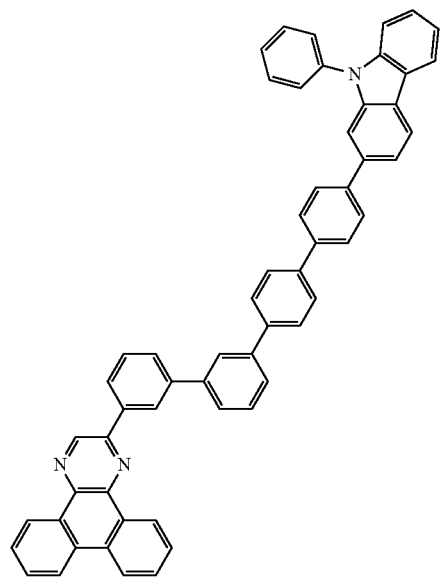
(1088)
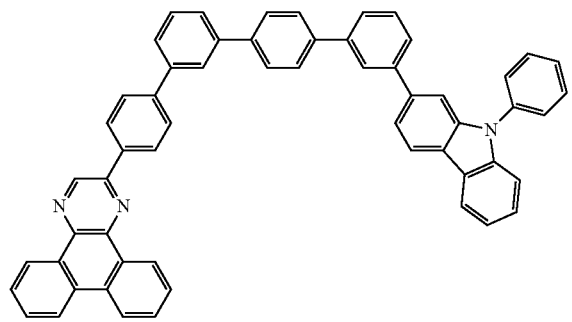

[Chemical formula 216]
(1089)
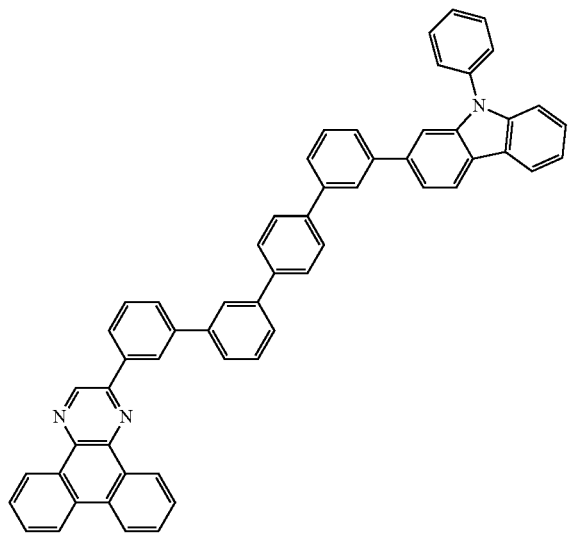
(1090)
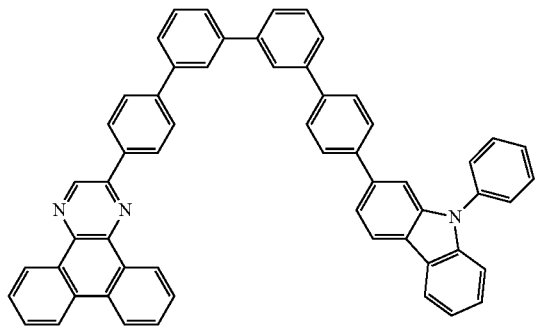
(1091)
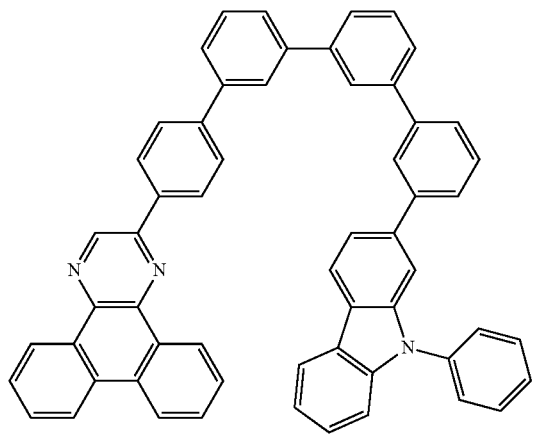
(1092)
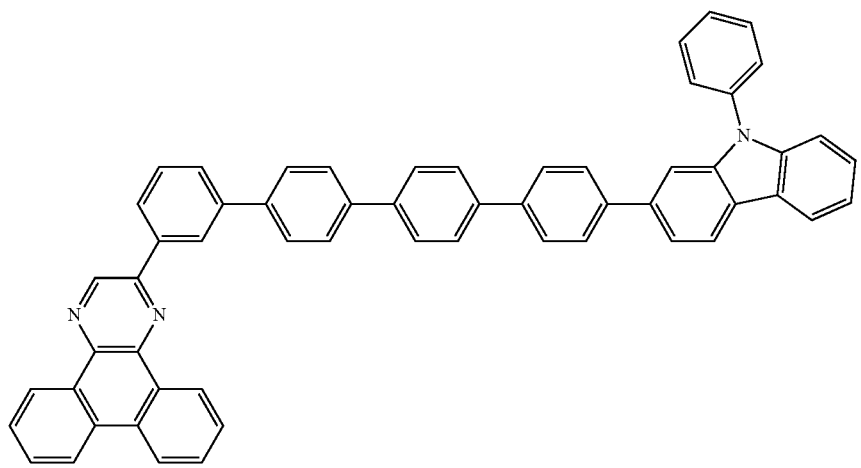

(1093)
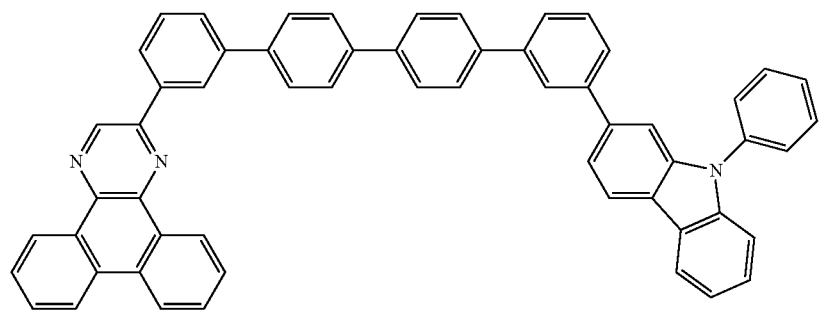
(1094)
(1095)
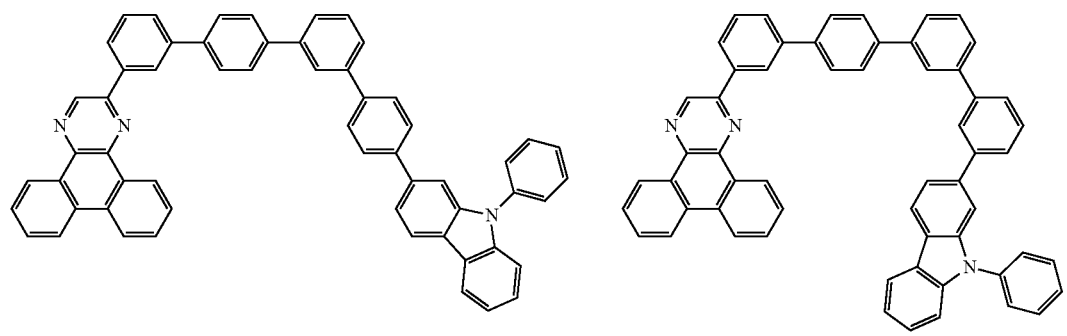
[Chemical formula 217]
(1096)
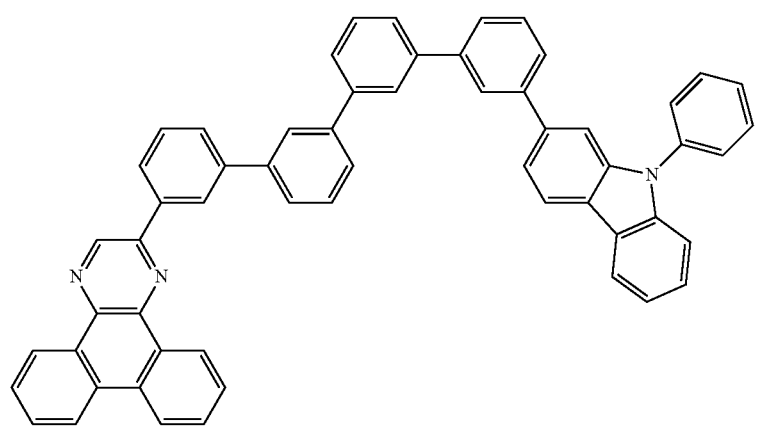

-continued
(1097)
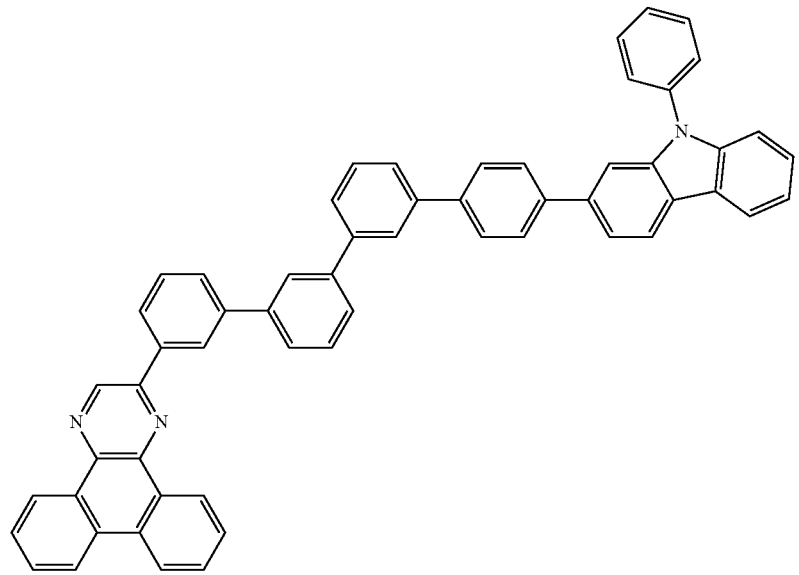
(1098)
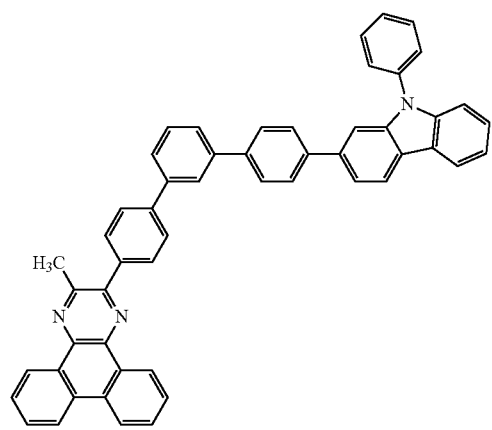
(1099)
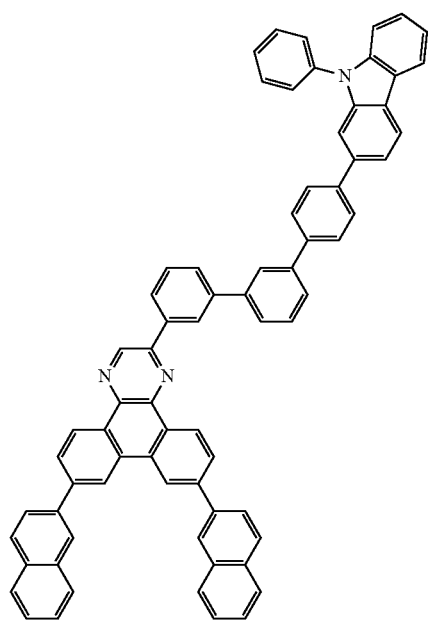

-continued
(1100)
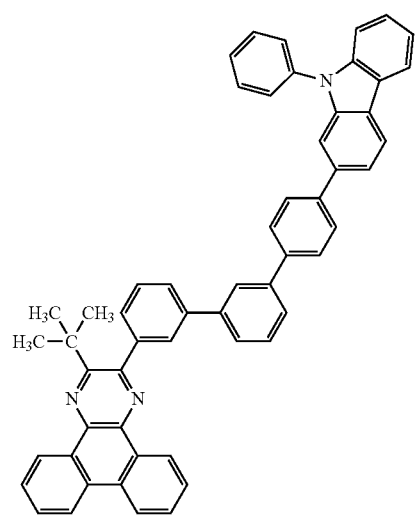
(1101)
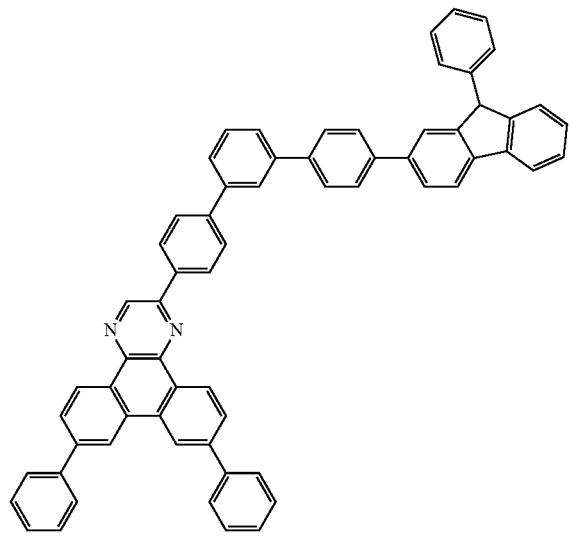
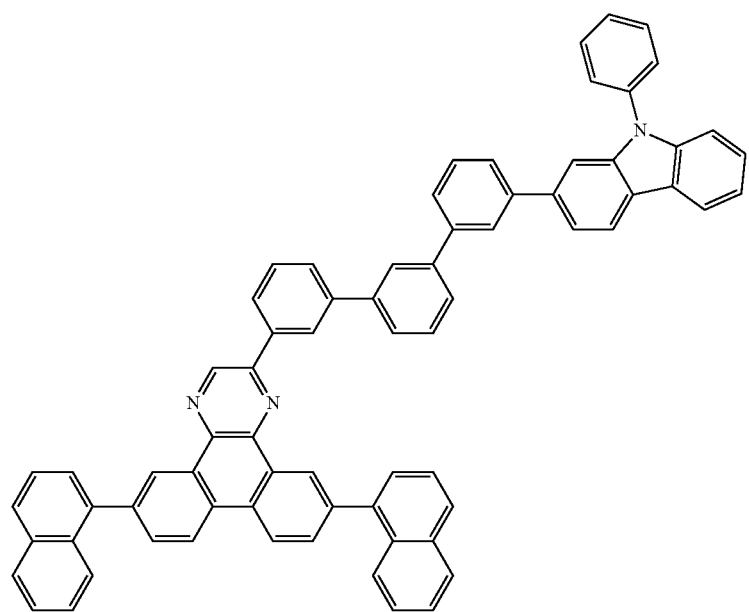
(1102)

[Chemical formula 218]
(1103)
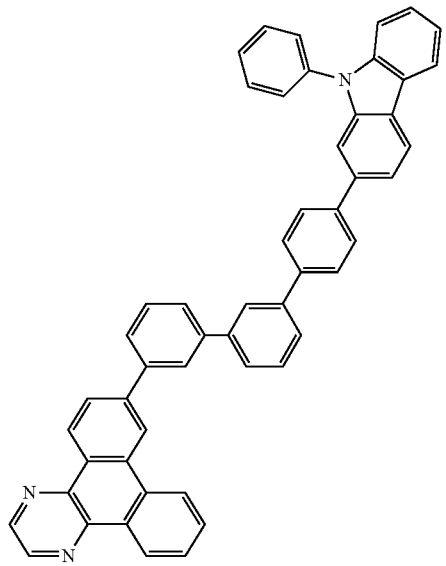
(1104)
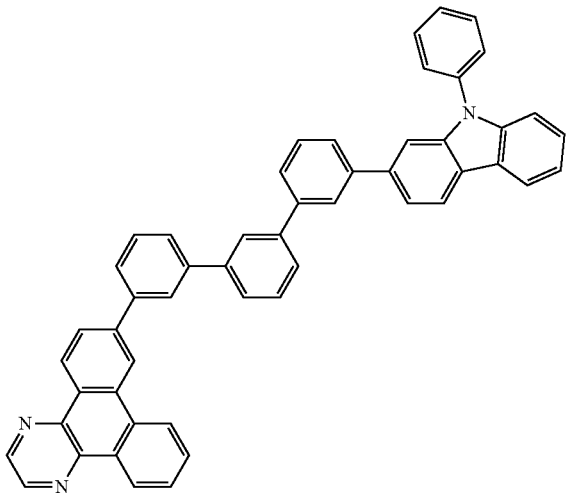
(1105)
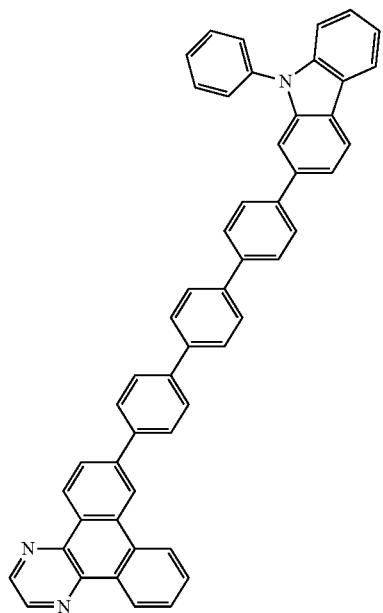
(1106)
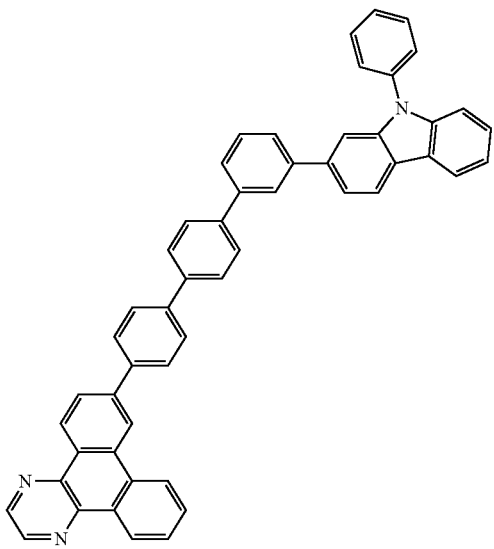

-continued
507
(1107)
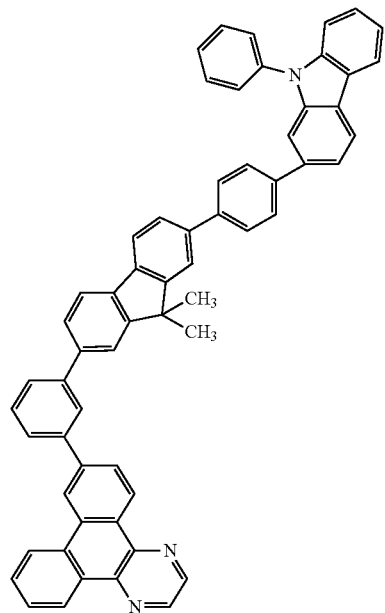
508
(1108)
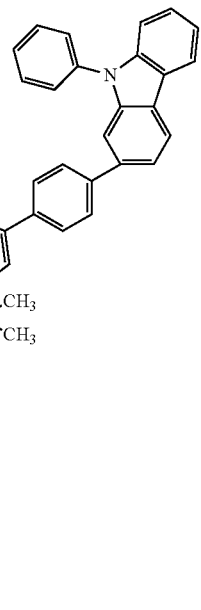
(1109)
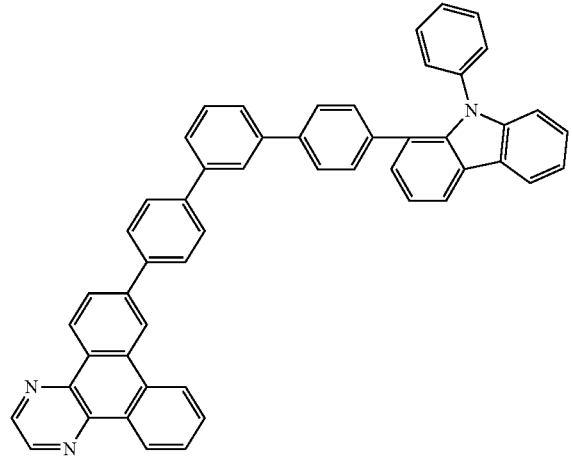
(1110)
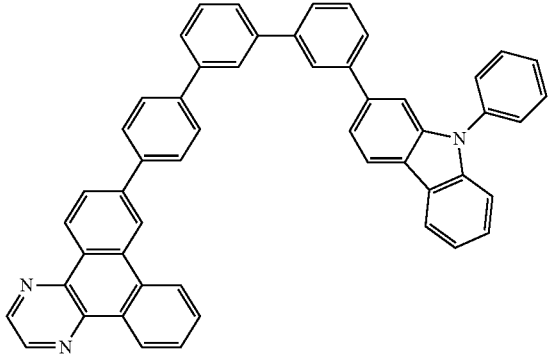

-continued
(1111)
(1112)
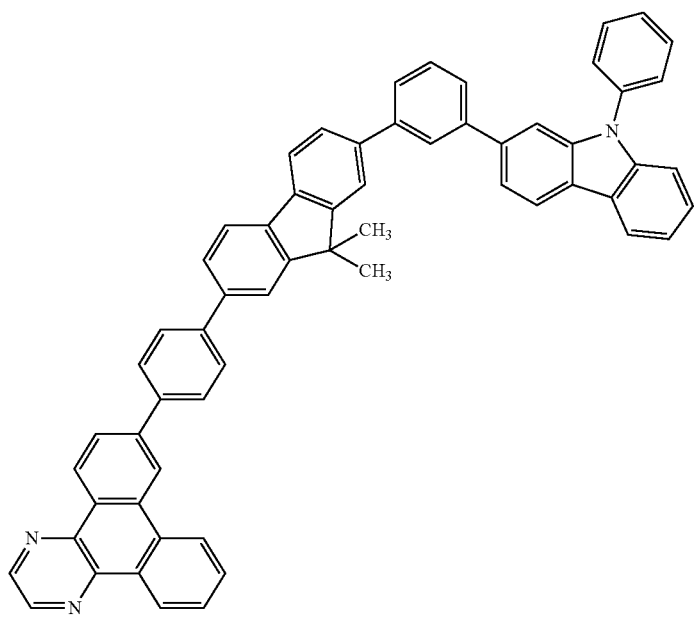
[Chemical formula 219]
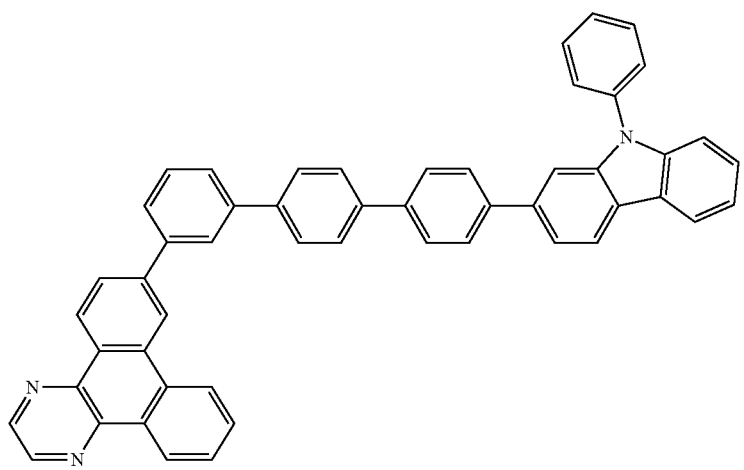
(1113)                                    (1114)
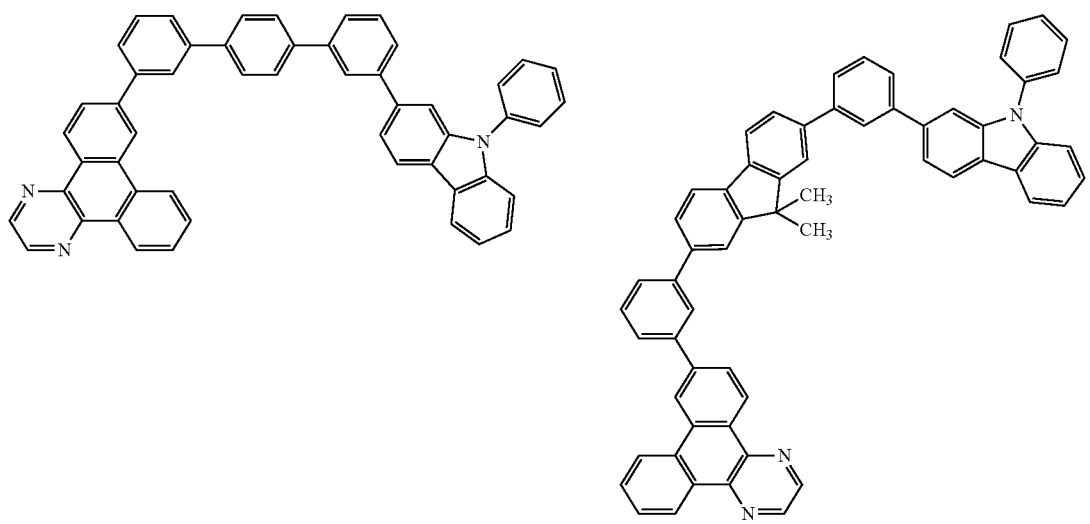

511
512
-continued
(1115)
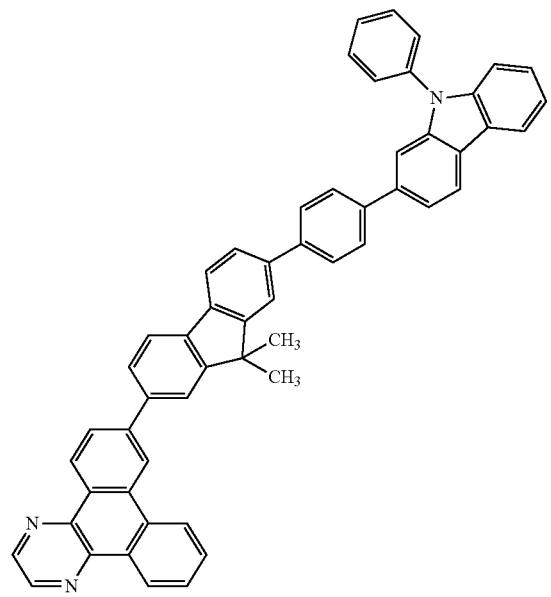
(1116)
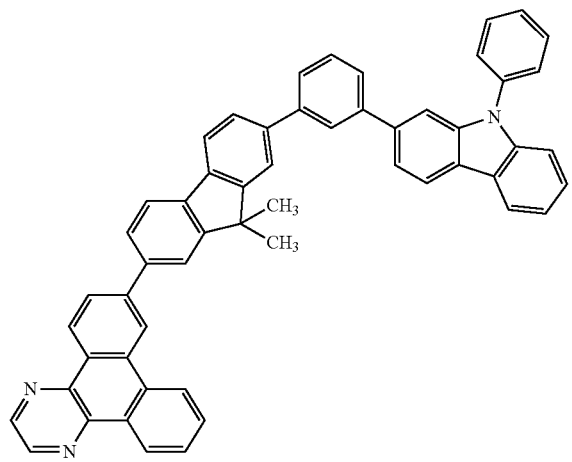
(1117)
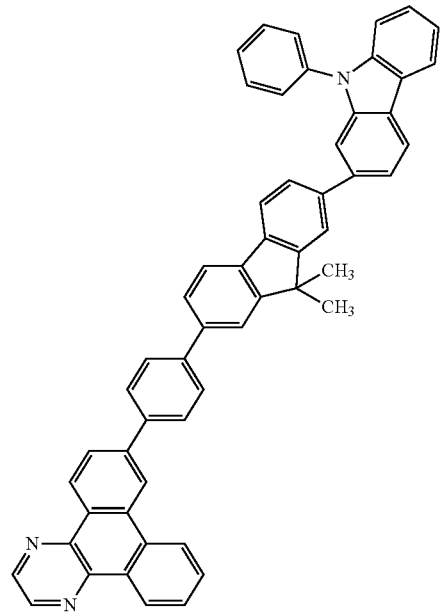
(1118)
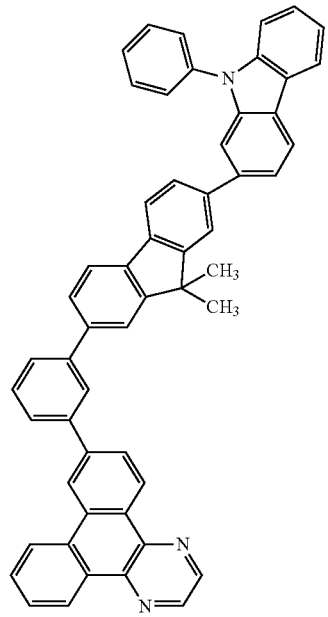

[Chemical formula 220]
(1119)
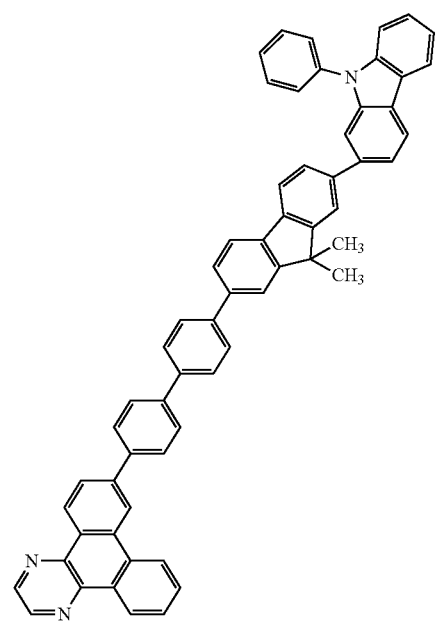
(1120)
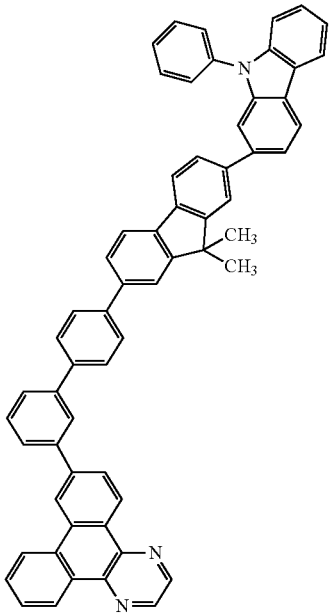
(1121)
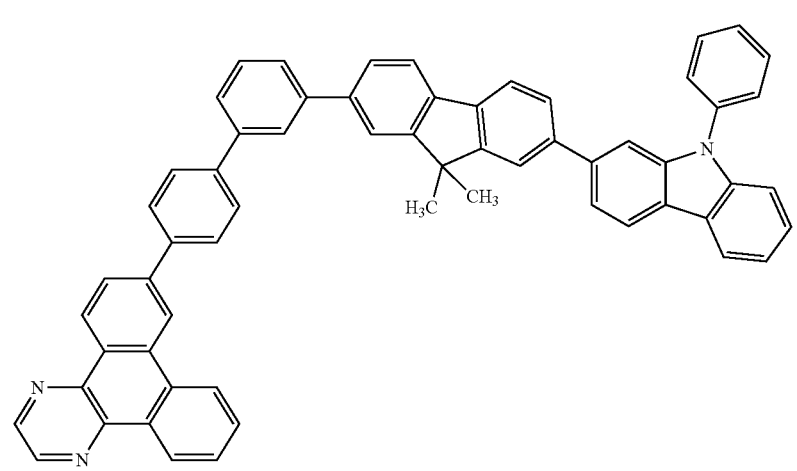

-continued
(1122)
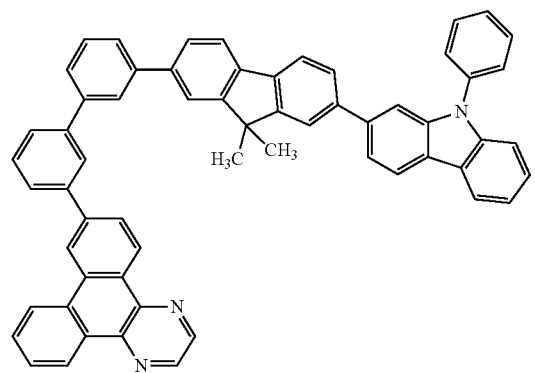
(1123)
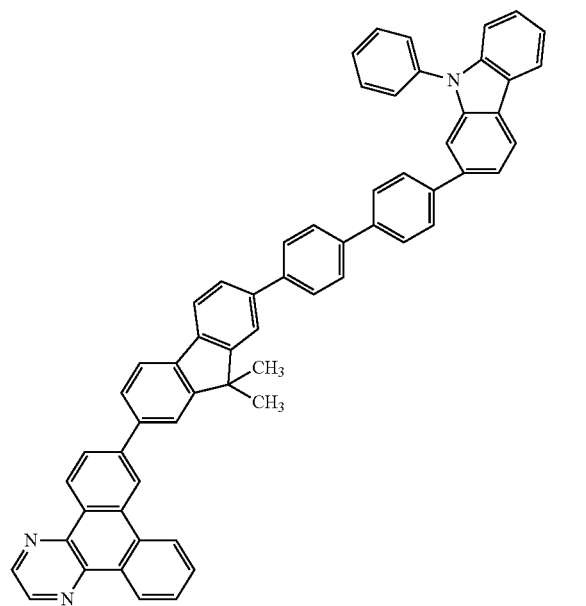
(1124)
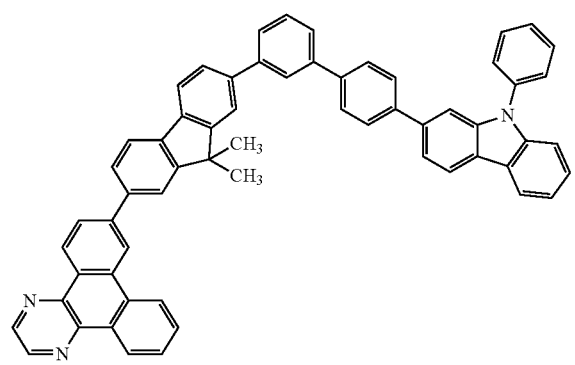
(1125)
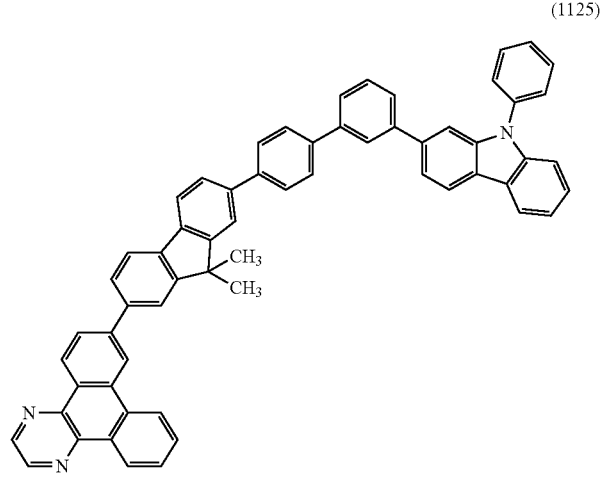

[Chemical formula 221]
(1126)
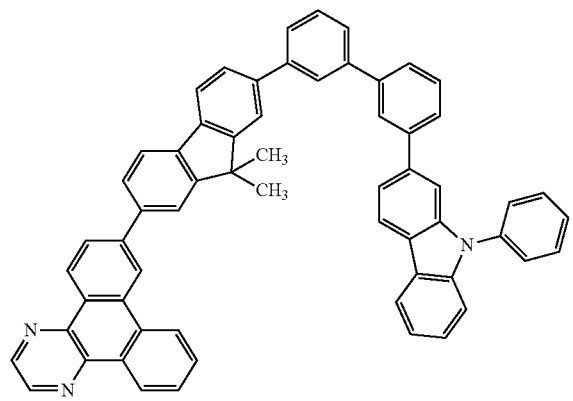
(1127)
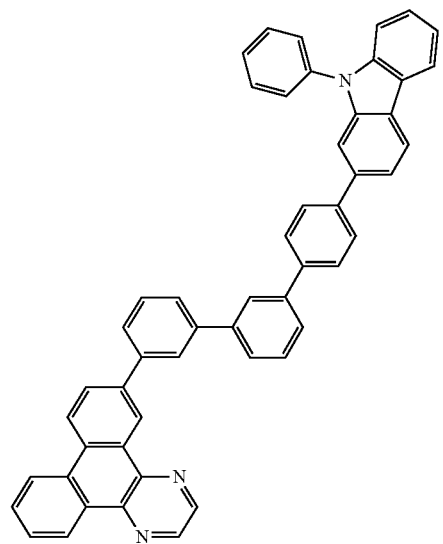
(1128)
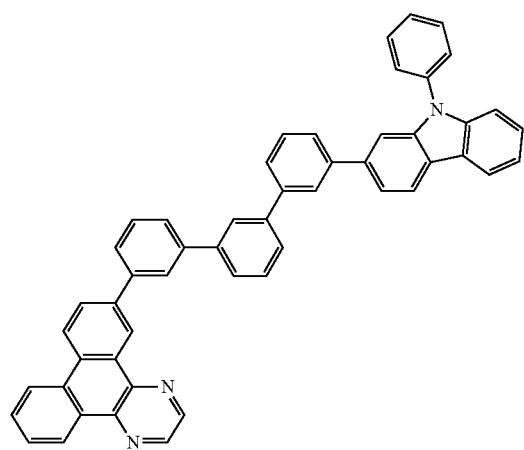
(1129)
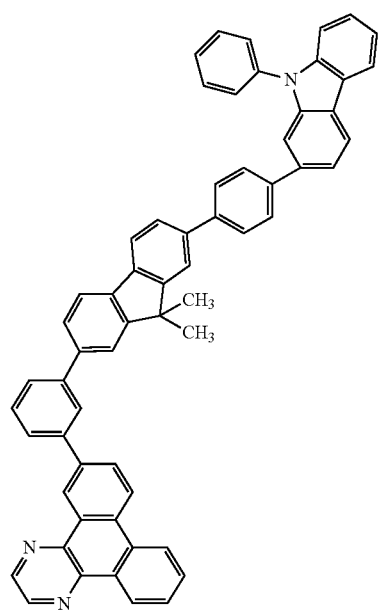

-continued
(1130)
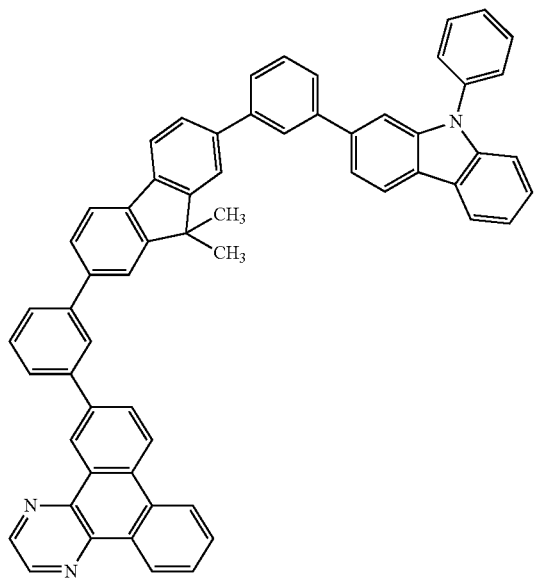
[Chemical formula 222]
(1131)
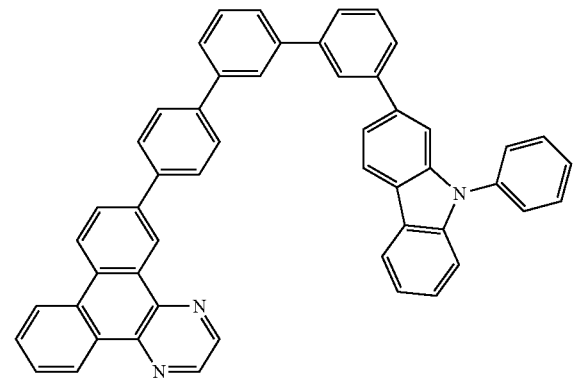
(1132)
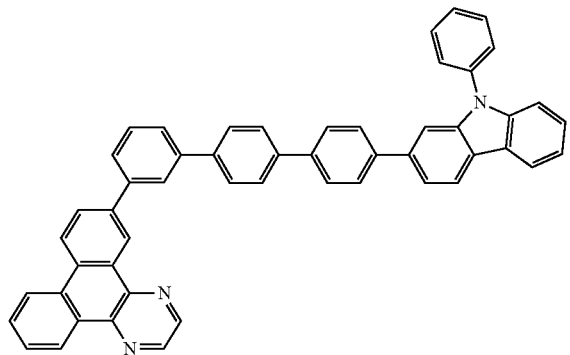
(1133)
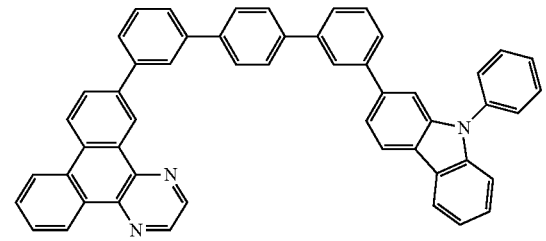
(1134)
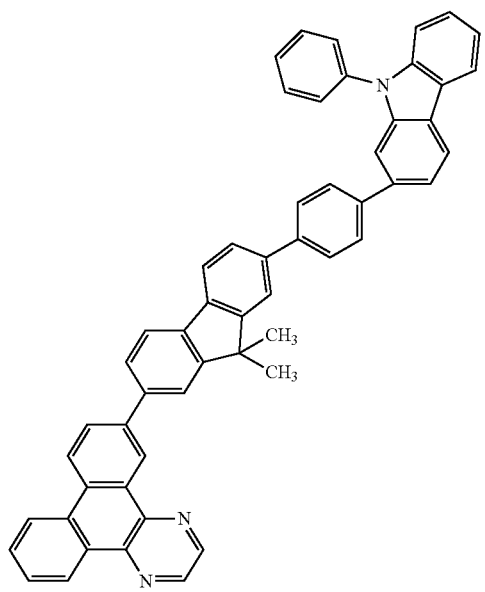
(1135)
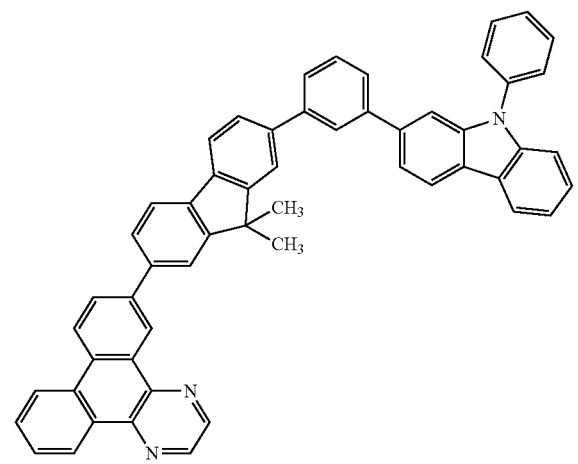

521
-continued
(1136)
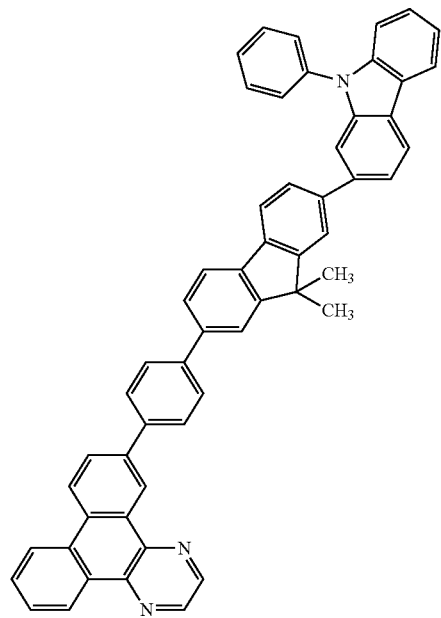
522
(1137)
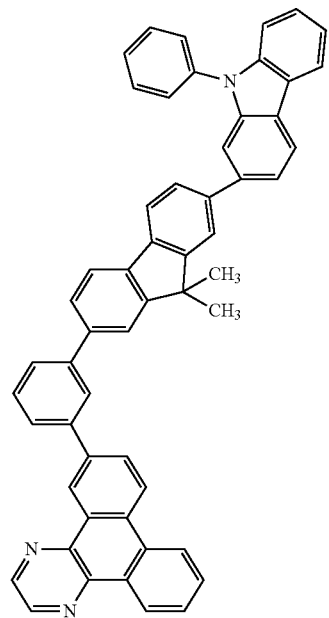
[Chemical formula 223]
(1138)
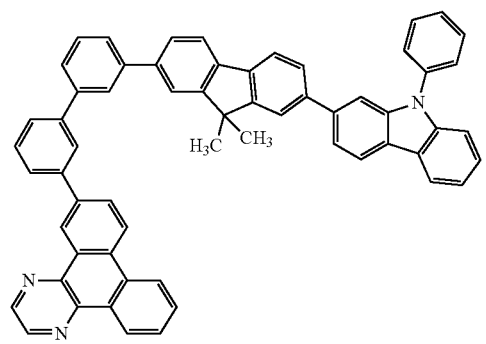
(1139)
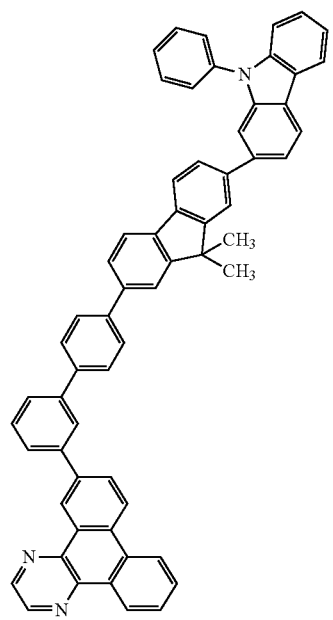

-continued
(1140)
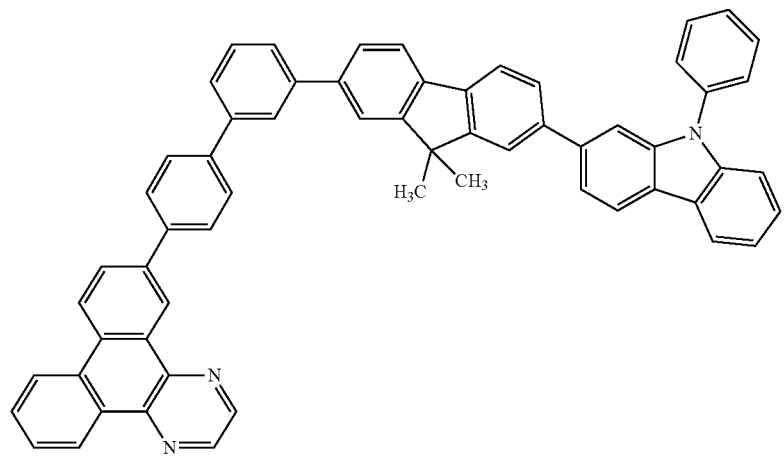
(1141) (1142)
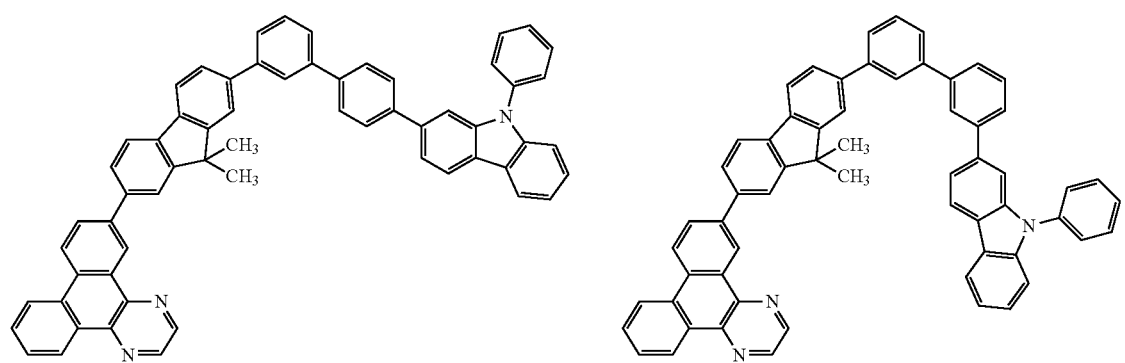
[Chemical formula 224]
(1143)
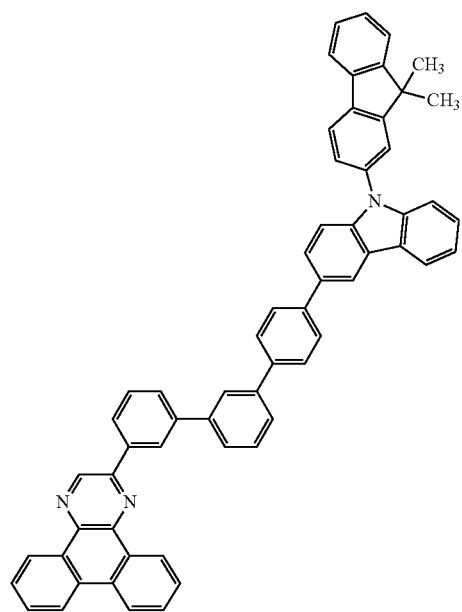

(1144)
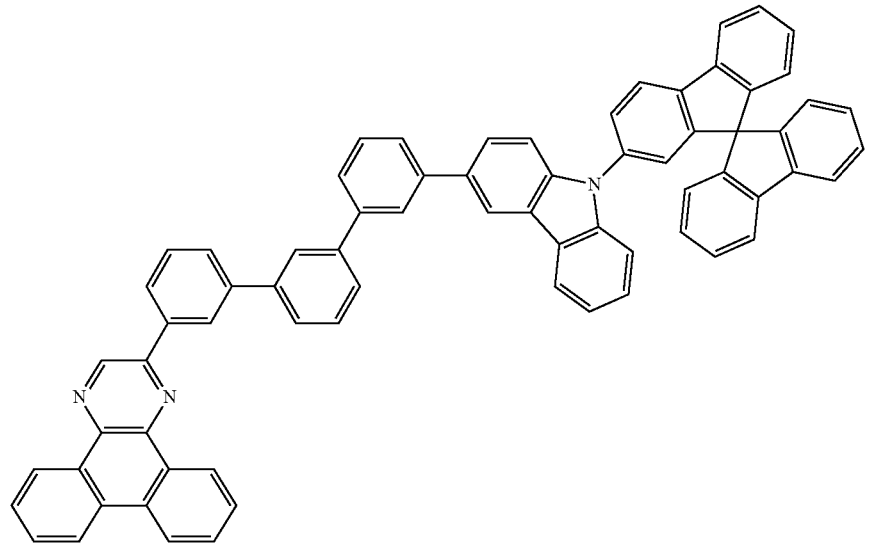
(1145)
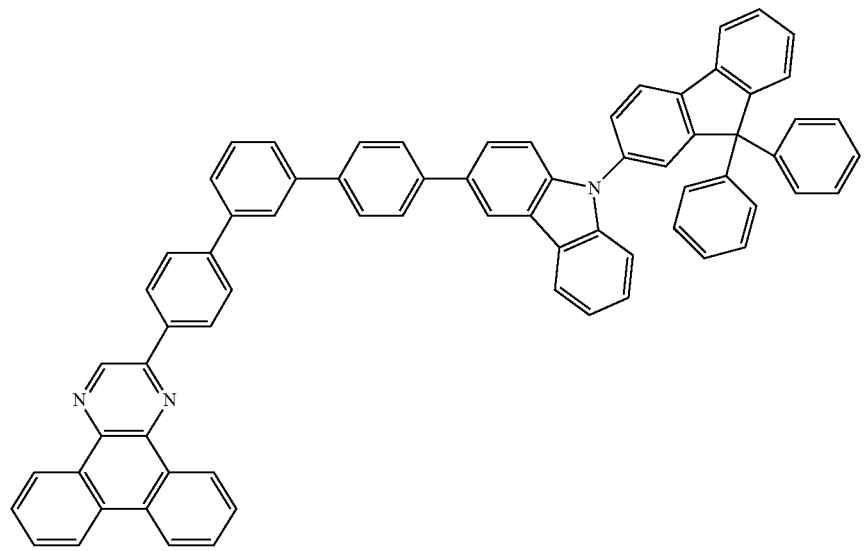

-continued
(1146)
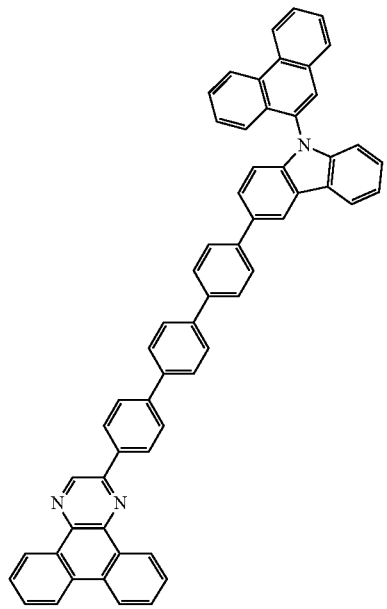
(1147)
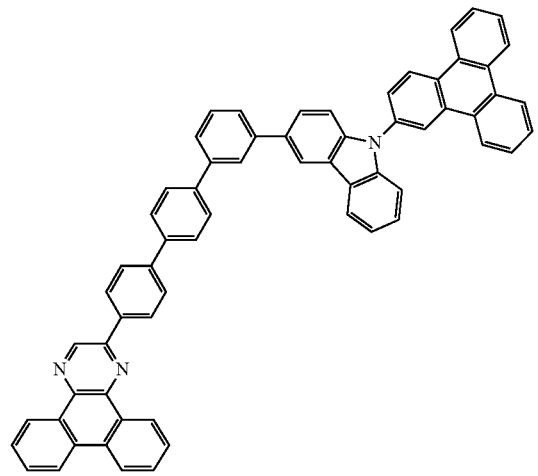
(1148)
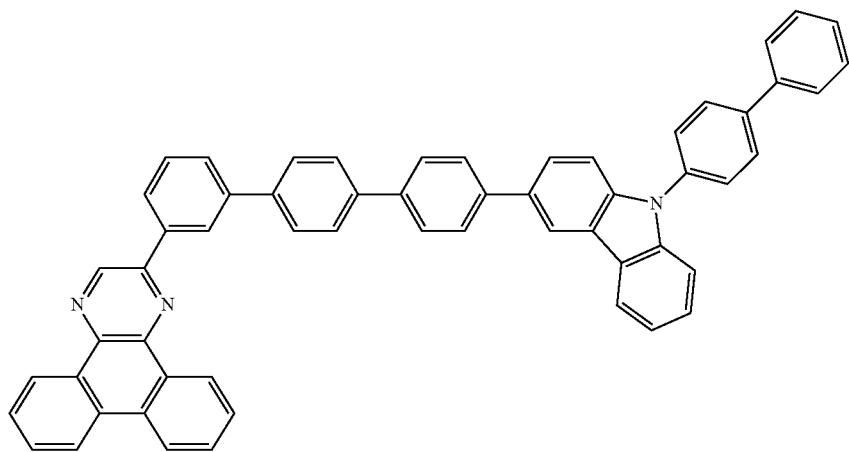
(1149)
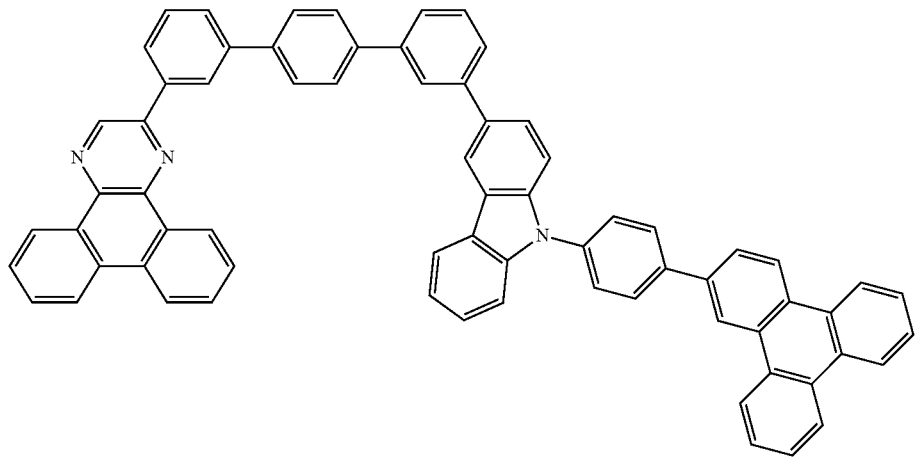

-continued

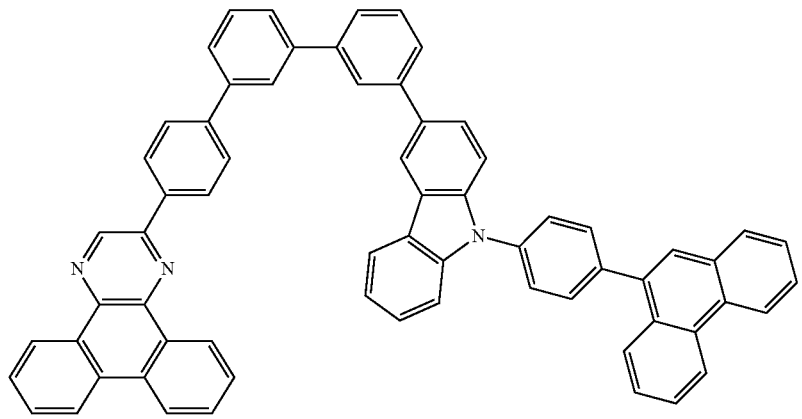

(1150)

The heterocyclic compound of one embodiment of the present invention has a structure in which a dibenzothiophenyl group, a dibenzofuranyl group, or a carbazolyl group and a dibenzo[f,h]quinoxalinyl group are bonded through three or more arylene groups. The heterocyclic compound of one embodiment of the present invention can be used as a host material in a light-emitting layer included in an EL layer.

Out of the properties and functions demanded for a host material in a light-emitting layer, an important property is high heat resistance. When the glass transition point (Tg) of a material is used as an index of the heat resistance of the material, a host material with a higher glass transition point (Tg) can be regarded as having higher heat resistance. The glass transition point (Tg) of a material is roughly proportional to the molecular mass thereof. Therefore, the molecular mass of a material may be increased to improve the heat resistance thereof.

An organic material with a high molecular mass usually tends to have a high glass transition point (Tg). However, because of the improved heat resistance, the sublimation temperature or boiling point in sublimation purification or distillation performed in a purification step also tends to be high. Many of typical low molecular organic compounds are decomposed at 400° C. or higher. In addition, simply increasing molecular mass increases the sublimation temperature or boiling point. Accordingly, higher temperatures are needed in a film formation step such as deposition by evaporation, or a purification step such as sublimation purification or distillation, and decomposition might be caused.

That is, simply increasing the molecular mass of a host material to improve its thermophysical properties increases the possibility of decomposition in a purification step or a film formation step, which sometimes makes it difficult to use a highly purified organic compound for an element.

In contrast, although the heterocyclic compound of one embodiment of the present invention has an increased molecular mass to improve thermophysical properties, the decomposition temperature of the heterocyclic compound is high and its heat resistance can be drastically improved only by adding at least one benzene ring. Therefore, decomposition does not easily occur in a purification step or an evaporation step and a material maintaining high purity can be used for an element. That is, an element having both high heat resistance and favorable characteristics can be provided.

An organic material having a high molecular mass usually tends to have a high refractive index, too. When the molecular mass of a host material used in a light-emitting layer is made high, not only the glass transition point (Tg) but also the refractive index of the light-emitting layer tend to become high.

The light generated in the light-emitting layer passes through an EL layer and a transparent electrode and is transmitted through a glass substrate, a resin film, and the like to travel into air. When the light crosses the boundary between these members, a difference in refractive index causes various optical phenomena. That is, depending on the angle at which the light is incident on the boundary, the magnitude relation of the refractive indices of the members through which the light is transmitted, or the degree of the difference between the refractive indices, the light emitted from the EL layer returns in the direction of the EL layer (total reflection) or is refracted in an unexpected direction, for example. As a result, the intensity of the light reaching the outside of the light-emitting element decreases, reducing the light extraction efficiency or external quantum efficiency of the light-emitting element.

In other words, simply increasing the molecular mass of a host material to improve its thermophysical properties causes a problem because this leads to an increased refractive index and a light-emitting element whose light-emitting layer uses this host material accordingly has reduced light extraction efficiency or reduced external quantum efficiency.

However, although the heterocyclic compound of one embodiment of the present invention has an increased molecular mass to improve thermophysical properties, the use of the heterocyclic compound as a host material in a light-emitting layer of a light-emitting element does not reduce the light extraction efficiency or external quantum efficiency of the light-emitting element.

The heterocyclic compound of one embodiment of the present invention has a molecular structure in which three or more arylene groups that are linked serve as a major axis. When a film of the heterocyclic compound is formed as a host material in a light-emitting layer, the orientation in the formed film tends to be such that the major axes of the molecules are inclined to be roughly parallel with a substrate. A molecule with a major axis sometimes has refractive index anisotropy, and the heterocyclic compound of one embodiment of the present invention also tends to have refractive index anisotropy.

When three or more arylene groups are used to increase the molecular mass, probably the molecule becomes large in the major-axis direction and the refractive index in the major-axis direction becomes high, but the molecular size in the minor-axis direction does not considerably change. Therefore, the refractive index in the minor-axis direction hardly changes. When the heterocyclic compound of one embodiment of the present invention is used for a light-emitting layer, the film of the heterocyclic compound tends to be formed with its minor axis aligned in the light-extraction direction; thus, the effective refractive index of the light-emitting layer is not significantly different from that of a light-emitting layer using a heterocyclic compound with a smaller number of arylene groups. However, since the molecule becomes large in the long-axis direction and the molecular mass becomes high, the thermophysical properties are improved.

For example, the heterocyclic compound of one embodiment of the present invention is different from 2-[3'-(dibenzothiophen-4-yl)biphenyl-3-yl]dibenzo[f,h]quinoxaline (abbreviation: 2mDBTBPDBq-II), which has excellent properties as a host material, in including three or more arylene groups, and thus has improved thermophysical properties with its effective refractive index maintained. Accordingly, a reduction in light extraction efficiency or external quantum efficiency of a light-emitting element is not caused.

Furthermore, when the heterocyclic compound of one embodiment of the present invention is oriented in a light-emitting layer, a dopant molecule (also referred to as a guest material) tends to be oriented, too. In the cases of some dopant molecules, when they are oriented in a particular direction, the light directed to the outside of a light-emitting element has increased emission intensity, whereby the external quantum efficiency of the light-emitting element is improved. This is because the light emitted by the dopant molecule has anisotropy like the refractive index. That is, a host material in a light-emitting element preferably improves the orientation of a dopant. In other words, the heterocyclic compound of one embodiment of the present invention can control the orientation of a dopant molecule to further increase the external quantum efficiency of a light-emitting element.

Thus, the heterocyclic compound of one embodiment of the present invention has excellent properties as a host material.

This embodiment can be combined with any of other embodiments as appropriate.

Embodiment 2

In this embodiment, a method for synthesizing the organic compound represented by General Formula (G1) is described.

[Chemical formula 225]

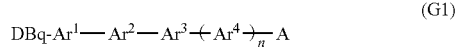

(G1)

A variety of reactions can be applied to the method for synthesizing the organic compound represented by General Formula (G1). For example, synthesis reactions described below enable the synthesis of the organic compound represented by General Formula (G1). Note that the method for synthesizing the organic compound of one embodiment of the present invention represented by General Formula (G1) is not limited to the following synthesis method.

<Method for Synthesizing Organic Compound Represented by General Formula (G1)>

The organic compound of one embodiment of the present invention represented by General Formula (G1) can be synthesized by Synthesis Scheme (a-1) shown below. That is, the compound represented by General Formula (G1) can be obtained by coupling a dibenzo[f,h]quinoxaline compound (compound 1) with a dibenzothiophene compound or a dibenzofuran compound (compound 2).

[Chemical formula 226]

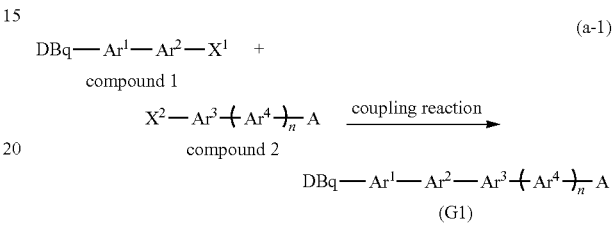

In Synthesis Scheme (a-1), DBq represents a substituted or unsubstituted dibenzo[f,h]quinoxalinyl group, n is 0 or 1, A represents any of a substituted or unsubstituted dibenzothiophenyl group and a substituted or unsubstituted dibenzofuranyl group, and each of $Ar^1$, $Ar^2$, $Ar^3$, and $Ar^4$ independently represents an arylene group having 6 to 10 carbon atoms. The arylene group may have one or more substituents. The substituents may be bonded to each other to form a ring. In $Ar^1$ to $Ar^4$, the adjacent arylene groups may be linked to each other through a methylene group to form a structure including a fluorene skeleton.

When a Suzuki-Miyaura coupling reaction using a palladium catalyst is performed in Synthesis Scheme (a-1), each of $X^1$ and $X^2$ independently represents a halogen, a boronic acid group, an organoboron group, or a triflate group, and the halogen is preferably iodine, bromine, or chlorine. In the reaction, a palladium compound such as bis(dibenzylideneacetone)palladium(0), palladium(II) acetate, [1,1'-bis(diphenylphosphino)ferrocene]palladium(II) dichloride, or tetrakis(triphenylphosphine)palladium(0) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, or tri(ortho-tolyl)phosphine can be used. In the reaction, an organic base such as sodium tert-butoxide, an inorganic base such as potassium carbonate, cesium carbonate, or sodium carbonate, or the like can be used. Furthermore, in the reaction, toluene, xylene, benzene, tetrahydrofuran, dioxane, ethanol, methanol, water, or the like can be used as a solvent. Note that reagents that can be used in the reaction are not limited to the above reagents.

The reaction performed under Synthesis Scheme (a-1) is not limited to a Suzuki-Miyaura coupling reaction, and a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like can also be employed. In the case of using the Migita-Kosugi-Stille coupling reaction, one of $X^1$ and $X^2$ represents an organotin group and the other represents a halogen. That is, one of the compounds 1 and 2 represents an organotin compound. In the case of using the Kumada-Tamao-Corriu coupling reaction, one of $X^1$ and $X^2$ represents a magnesium halide group and the other represents a halogen. That is, one of the compounds 1 and 2 represents a Grignard reagent. In the case of using the Negishi coupling reaction, one of $X^1$ and $X^2$ represents an organozinc group and the other represents a halogen. That is, one of the compounds 1 and 2 represents an organozinc compound.

Note that in the synthesis of the organic compound of one embodiment of the present invention represented by General Formula (G1), the synthesis method is not limited to Synthesis Scheme (a-1). For example, the synthesis can be conducted under any of Synthesis Schemes (a-2) to (a-4). That is, the compound represented by General Formula (G1) can be obtained by coupling a dibenzo[f,h]quinoxaline compound (compound 3, 5, or 7) with a dibenzothiophene compound or a dibenzofuran compound (compound 4, 6, or 8).

[Chemical formula 227]

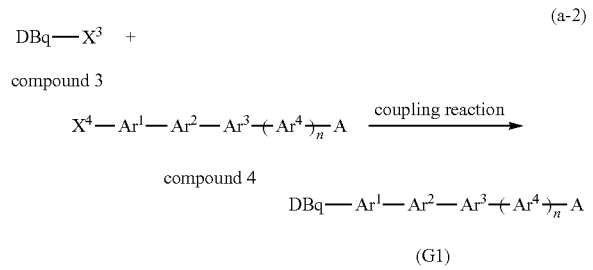

[Chemical formula 228]

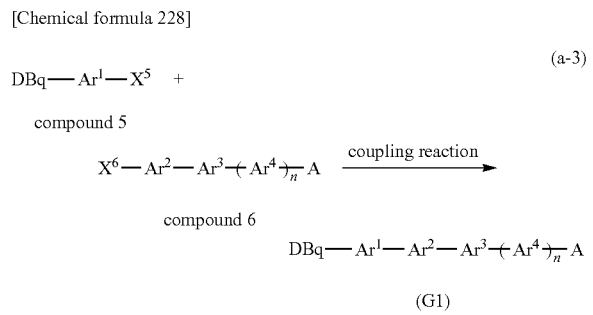

[Chemical formula 229]

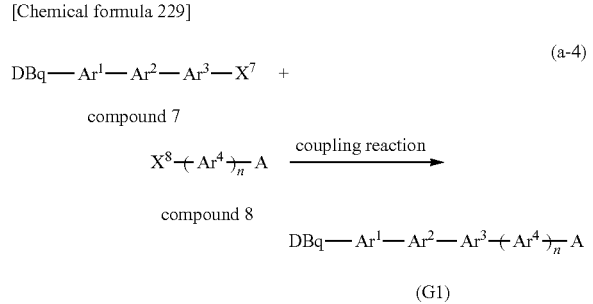

In Synthesis Schemes (a-2) to (a-4), DBq represents a substituted or unsubstituted dibenzo[f,h]quinoxalinyl group, n is 0 or 1, A represents any of a substituted or unsubstituted dibenzothiophenyl group and a substituted or unsubstituted dibenzofuranyl group, and each of $Ar^1$, $Ar^2$, $Ar^3$, and $Ar^4$ independently represents an arylene group having 6 to 10 carbon atoms. The arylene group may have one or more substituents. The substituents may be bonded to each other to form a ring. In $Ar^1$ to $Ar^4$, the adjacent arylene groups may be linked to each other through a methylene group to form a structure including a fluorene skeleton.

When a Suzuki-Miyaura coupling reaction using a palladium catalyst is performed in Synthesis Schemes (a-2) to (a-4), each of $X^3$ to $X^8$ independently represents a halogen, a boronic acid group, an organoboron group, or a triflate group, and the halogen is preferably iodine, bromine, or chlorine. Reagents that can be used here are similar to, but not limited to, those that can be used for Synthesis Scheme (a-1).

The reaction performed under Synthesis Schemes (a-2) to (a-4) is not limited to a Suzuki-Miyaura coupling reaction, and a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like can also be employed.

When the above reactions are used, $X^3$ to $X^8$ are similar to $X^1$ and $X^2$ in Synthesis Scheme (a-1). In other words, in the case of using the Migita-Kosugi-Stille coupling reaction, in each of the above reactions, one X represents an organotin group and the other X represents a halogen. That is, one of the compounds 3 and 4, one of the compounds 5 and 6, and one of the compounds 7 and 8 represent organotin compounds in the respective reactions. In the case of $X^3$ to $X^8$ when the Kumada-Tamao-Corriu coupling reaction is used, one X represents a magnesium halide group and the other X represents a halogen in each of the above reactions. That is, one of the compounds 3 and 4, one of the compounds 5 and 6, and one of the compounds 7 and 8 represent Grignard reagents and the others represent halogens in the respective reactions. In the case of $X^3$ to $X^8$ when the Negishi coupling reaction is used, one X represents an organozinc group and the other X represents a halogen in each of the above reactions. That is, one of the compounds 3 and 4, one of the compounds 5 and 6, and one of the compounds 7 and 8 represent organozinc compounds in the respective reactions.

In the case of conducting a coupling reaction between a dibenzo[f,h]quinoxaline compound and a dibenzothiophene compound or a dibenzofuran compound, the coupling may be caused at any of DBq, $Ar^1$ to $Ar^4$, and A. Note that a method for synthesizing the heterocyclic compound of one embodiment of the present invention is not limited to the above.

The above is the description of the example of a method for synthesizing the compound of one embodiment of the present invention; however, the present invention is not limited thereto and any other synthesis method may be employed.

In Embodiment 2, one embodiment of the present invention has been described. Other embodiments of the present invention are described in Embodiments 1 and 3 to 6. Note that one embodiment of the present invention is not limited to the above examples. For example, although an example in which a dibenzothiophenyl group, a dibenzofuranyl group, or a carbazolyl group and a dibenzo[f,h]quinoxalinyl group are bonded through three or more arylene groups has been described as one embodiment of the present invention, one embodiment of the present invention is not limited to this example. In one embodiment of the present invention, depending on circumstances or conditions, a skeleton other than the structure in which a dibenzothiophenyl group, a dibenzofuranyl group, or a carbazolyl group and a dibenzo [f,h]quinoxalinyl group are bonded through three or more arylene groups may be included. For example, in one embodiment of the present invention, depending on circumstances or conditions, the structure in which a dibenzothiophenyl group, a dibenzofuranyl group, or a carbazolyl group and a dibenzo[f,h]quinoxalinyl group are bonded through three or more arylene groups is not necessarily included.

This embodiment can be combined with any of other embodiments as appropriate.

Embodiment 3

In this embodiment, one mode of a light-emitting element that contains a heterocyclic compound of one embodiment of the present invention will be described with reference to FIG. 1A.

A light-emitting element of this embodiment includes a plurality of layers between a pair of electrodes. In this embodiment, the light-emitting element includes a first electrode 101, a second electrode 102, and an EL layer 103 provided between the first electrode 101 and the second electrode 102. Note that in FIG. 1A, the first electrode 101 functions as an anode and the second electrode 102 functions as a cathode. That is, when voltage is applied between the first electrode 101 and the second electrode 102 such that the potential of the first electrode 101 is higher than that of the second electrode 102, light emission can be obtained. Needless to say, a structure in which the first electrode functions as a cathode and the second electrode functions as an anode can be employed. In that case, the stacking order of layers in the EL layer is reversed from the above-mentioned order. Note that in the light-emitting element of this embodiment, at least one of layers in the EL layer 103 contains the heterocyclic compound of one embodiment of the present invention. A layer that contains the heterocyclic compound is preferably used as a light-emitting layer or an electron-transport layer because the characteristics of the heterocyclic compound can be utilized and the light-emitting element can have favorable characteristics.

For the electrode functioning as an anode, any of metals, alloys, conductive compounds, and mixtures thereof which have a high work function (specifically, a work function of 4.0 eV or more) or the like is preferably used. Specific examples are indium tin oxide (ITO), indium tin oxide containing silicon or silicon oxide, indium oxide-zinc oxide, indium oxide containing tungsten oxide and zinc oxide (IWZO), and the like. Films of these conductive metal oxides are usually formed by a sputtering method but may be formed by a sol-gel method or the like. For example, indium oxide-zinc oxide can be formed by a sputtering method using a target in which zinc oxide is added to indium oxide at higher than or equal to 1 wt % and lower than or equal to 20 wt %. Moreover, indium oxide containing tungsten oxide and zinc oxide (IWZO) can be formed by a sputtering method using a target in which tungsten oxide is added to indium oxide at higher than or equal to 0.5 wt % and lower than or equal to 5 wt % and zinc oxide is added to indium oxide at higher than or equal to 0.1 wt % and lower than or equal to 1 wt %. Other examples are gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like. Graphene may also be used.

There is no particular limitation on the stacked structure of the EL layer 103. The EL layer 103 can be formed by combining a layer containing a substance having a high electron-transport property, a layer containing a substance having a high hole-transport property, a layer containing a substance having a high electron-injection property, a layer containing a substance having a high hole-injection property, a layer containing a bipolar substance (a substance having a high electron-transport and hole-transport property), a layer having a carrier-blocking property, and the like as appropriate. In this embodiment, the EL layer 103 has a structure in which a hole-injection layer 111, a hole-transport layer 112, a light-emitting layer 113, an electron-transport layer 114, and an electron-injection layer 115 are stacked in this order over the electrode functioning as an anode. Materials contained in the layers are specifically given below.

The hole-injection layer 111 is a layer containing a substance having a high hole-injection property. As the substance having a high hole-injection property, for example, molybdenum oxide, vanadium oxide, ruthenium oxide, tungsten oxide, a manganese oxide can be used. The hole-injection layer 111 can also be formed using a phthalocyanine-based compound such as phthalocyanine (abbreviation: $H_2Pc$) or copper phthalocyanine (abbreviation: CuPc); an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD); a high molecular compound such as poly(ethylenedioxythiophene)/poly(styrenesulfonic acid) (PEDOT/PSS); or the like.

The hole-injection layer 111 can be formed using a composite material in which a substance exhibiting an electron-accepting property (hereinafter, simply referred to as "electron-accepting substance) with respect to a substance having a hole-transport property is contained in the substance having a hole-transport property. In this specification, the composite material refers to not a material in which two materials are simply mixed but a material in the state where charge transfer between the materials can be caused by a mixture of a plurality of materials. This charge transfer includes the charge transfer that occurs only when an electric field exists.

Note that by using the composite material in which the electron-accepting substance is contained in the substance having a hole-transport property, a material used for forming the electrode can be selected regardless of the work function of the material. In other words, besides a material having a high work function, a material having a low work function can be used for the electrode functioning as an anode. Examples of the electron-accepting substance are 7,7,8,8-tetracyano-2,3,5,6-tetrafluoroquinodimethane (abbreviation: $F_4$-TCNQ), chloranil, and the like. A transition metal oxide can also be used. In particular, an oxide of a metal belonging to any of Groups 4 to 8 of the periodic table can be suitably used. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable as the electron-accepting substance because it is stable in the air, has a low hygroscopic property, and is easily handled.

As the substance with a hole-transport property used for the composite material, any of a variety of organic compounds such as an aromatic amine compound, a carbazole compound, an aromatic hydrocarbon, and a high molecular compound (such as an oligomer, a dendrimer, or a polymer) can be used. The organic compound used for the composite material is preferably an organic compound having a high hole-transport property. Specifically, a substance having a hole mobility of $1\times10^{-6}$ $cm^2/Vs$ or higher is preferably used. Note that any other substance may be used as long as it has a hole-transport property. Specific examples of the organic compound that can be used as a substance having a hole-transport property in the composite material are given below.

Examples of the aromatic amine compound are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole compound that can be used for the composite material are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole compound that can be used for the composite material are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon that can be used for the composite material are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Other examples are pentacene, coronene, and the like. The aromatic hydrocarbon having a hole mobility of $1 \times 10^{-6}$ cm$^2$/Vs or more and having 14 to 42 carbon atoms is particularly preferable.

The aromatic hydrocarbon that can be used for the composite material may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Other examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N'-bis(4-butylphenyl)-N,N'-bis(phenyl)benzidine] (abbreviation: poly-TPD).

Note that the composite material may contain the compound in Embodiment 1 that has a structure in which a dibenzothiophenyl group, a dibenzofuranyl group, or a carbazolyl group and a dibenzo[f,h]quinoxalinyl group are bonded through three or more arylene groups.

The hole-transport layer 112 is a layer containing a substance having a hole-transport property. As the substance having a hole-transport property, those given above as the substances having hole-transport properties, which can be used for the above composite material, can be used. Note that detailed description is omitted to avoid repetition. Refer to the description of the composite material. Note that the hole-transport layer may contain the compound in Embodiment 1 that has a structure in which a dibenzothiophenyl group, a dibenzofuranyl group, or a carbazolyl group and a dibenzo[f,h]quinoxalinyl group are bonded through three or more arylene groups.

The light-emitting layer 113 is a layer containing a light-emitting substance. The light-emitting layer 113 may be formed using a film containing only a light-emitting substance or a film in which an emission center substance is dispersed in a host material.

There is no particular limitation on a material that can be used as the light-emitting substance or the emission center substance in the light-emitting layer 113, and light emitted from the material may be either fluorescence or phosphorescence. Examples of the above light-emitting substance and emission center substance are fluorescent substances and phosphorescent substances. Examples of the fluorescent substance are N,N'-diphenyl-N,N'-bis[4-(9-phenyl-9H-fluoren-9-yl)phenyl]pyrene-1,6-diamine (abbreviation: 1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)etheny]}-4H-pyran-4-ylidene 1propanedinitrile (abbreviation: DCJTB), 2-(2,6-bis{2-[4-

(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl) ethenyl]-4H-pyran-4-ylidene}propanedinitrile (abbreviation: BisDCJTM), and the like. Examples of blue-emissive phosphorescent substances include an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: Ir(mpptz-dmp)$_3$), tris(5-methyl-3,4-diphenyl-4H-1,2,4-triazolato)iridium(III) (abbreviation: Ir(Mptz)$_3$), or tris[4-(3-biphenyl)-5-isopropyl-3-phenyl-4H-1,2,4-triazolato]iridium(III) (abbreviation: Ir(iPrptz-3b)$_3$); an organometallic iridium complex having a 1H-triazole skeleton, such as tris[3-methyl-1-(2-methylphenyl)-5-phenyl-1H-1,2,4-triazolato]iridium(III) (abbreviation: Ir(Mptz1-mp)$_3$) or tris(1-methyl-5-phenyl-3-propyl-1H-1,2,4-triazolato)iridium(III) (abbreviation: Ir(Prptz1-Me)$_3$); an organometallic iridium complex having an imidazole skeleton, such as fac-tris[1-(2,6-diisopropylphenyl)-2-phenyl-1H-imidazole]iridium(III) (abbreviation: Ir(iPrpmi)$_3$) or tris[3-(2,6-dimethylphenyl)-7-methylimidazo[1,2-f]phenanthridinato]iridium(III) (abbreviation: Ir(dmpimpt-Me)$_3$); and an organometallic iridium complex in which a phenylpyridine compound having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: Ir(CF$_3$ppy)$_2$(pic)), or bis[2-(4',6'-difluorophenyl)pyridinato-N,C$^{2'}$]iridium(III) acetylacetonate (abbreviation: FIr(acac)). Note that an organometallic iridium complex having a 4H-triazole skeleton has excellent reliability and emission efficiency and thus is especially preferable. Examples of green-emissive phosphorescent substances include an organometallic iridium complex having a pyrimidine skeleton, such as tris(4-methyl-6-phenylpyrimidinato)iridium(III) (abbreviation: Ir(mppm)$_3$), tris(4-t-butyl-6-phenylpyrimidinato)iridium(III) (abbreviation: Ir(tBuppm)$_3$), (acetylacetonato)bis(6-methyl-4-phenylpyrimidinato)iridium(III) (abbreviation: Ir(mppm)$_2$(acac)), (acetylacetonato)bis(6-tert-butyl-4-phenylpyrimidinato)iridium(III) (abbreviation: Ir(tBuppm)$_2$(acac)), (acetylacetonato)bis[6-(2-norbornyl)-4-phenylpyrimidinato]iridium(III) (abbreviation: Ir(nbppm)$_2$(acac)), (acetylacetonato)bis[5-methyl-6-(2-methylphenyl)-4-phenylpyrimidinato]iridium(III) (abbreviation: Ir(mpmppm)$_2$(acac)), or (acetylacetonato)bis(4,6-diphenylpyrimidinato)iridium(III) (abbreviation: Ir(dppm)$_2$(acac)); an organometallic iridium complex having a pyrazine skeleton, such as (acetylacetonato)bis(3,5-dimethyl-2-phenylpyrazinato)iridium(III) (abbreviation: Ir(mppr-Me)$_2$(acac)) or (acetylacetonato)bis(5-isopropyl-3-methyl-2-phenylpyrazinato)iridium(M) (abbreviation: Ir(mppr-iPr)$_2$(acac)); an organometallic iridium complex having a pyridine skeleton, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C$^{2'}$)iridium(III) (abbreviation: Ir(pq)$_3$), or bis(2-phenylquinolinato-N,C$^{2'}$)iridium(III) acetylacetonate (abbreviation: Ir(pq)$_2$(acac)); and a rare earth metal complex such as tris(acetylacetonato)(monophenanthroline)terbium(III) (abbreviation: Tb(acac)$_3$(Phen)). Note that an organometallic iridium complex having a pyrimidine skeleton has distinctively high reliability and emission efficiency and thus is especially preferable. Examples of red-emissive phosphorescent substances include an organometallic iridium complex having a pyrimidine skeleton, such as (diisobutyrylmethanato)bis[4,6-bis(3-methylphenyl)pyrimidinato]iridium(III) (abbreviation: Ir(5mdppm)$_2$(dibm)), bis[4,6-bis(3-methylphenyl)pyrimidinato](dipivaloylmethanato)iridium(III) (abbreviation: Ir(5mdppm)$_2$(dpm)), or bis[4,6-di(naphthalen-1-yl)pyrimidinato](dipivaloylmethanato)iridium(III) (abbreviation: Ir(dlnpm)$_2$(dpm)); an organometallic iridium complex having a pyrazine skeleton, such as (acetylacetonato)bis(2,3,5-triphenylpyrazinato)iridium(III) (abbreviation: Ir(tppr)$_2$(acac)), bis(2,3,5-triphenylpyrazinato)(dipivaloylmethanato)iridium(III) (abbreviation: Ir(tppr)$_2$(dpm)), or (acetylacetonato)bis[2,3-bis(4-fluorophenyl)quinoxalinato]iridium(III) (abbreviation: Ir(Fdpq)$_2$(acac)); an organometallic iridium complex having a pyridine skeleton, such as tris(1-phenylisoquinolinato-N,C$^{2'}$)iridium(III) (abbreviation: Ir(piq)$_3$) or bis(1-phenylisoquinolinato-N,C$^{2'}$)iridium(III) acetylacetonate (abbreviation: Ir(piq)$_2$(acac)); a platinum complex such as 2,3,7,8,12,13,17,18-octaethyl-21H,23H-porphyrin platinum(II) (abbreviation: PtOEP); and a rare earth metal complex such as tris(1,3-diphenyl-1,3-propanedionato)(rnonophenanthroline)europium(III) (abbreviation: Eu(DBM)$_3$(Phen)) or tris[1-(2-thenoyl)-3,3,3-trifluoroacetonato](monophenanthroline)europium(III) (abbreviation: Eu(TTA)$_3$(Phen)). Note that an organometallic iridium complex having a pyrazine skeleton has distinctively high reliability and emission efficiency and thus is especially preferable. Further, because an organometallic iridium complex having a pyrazine skeleton can provide red light emission with favorable chromaticity, the use of the organometallic iridium complex in a white light-emitting element improves a color rendering property of the white light-emitting element. Note that the compound of one embodiment of the present invention having a structure in which a dibenzothiophenyl group, a dibenzofuranyl group, or a carbazolyl group and a dibenzo[f,h]quinoxalinyl group are bonded through three or more arylene groups exhibits light, and thus can be used as an emission center material.

The material that can be used as the light-emitting substance may be selected from various substances as well as from the substances given above.

As a host material in which the emission center substance is dispersed, the heterocyclic compound of one embodiment of the present invention is preferably used.

Since the heterocyclic compound has a wide band gap and a high triplet excitation level, the compound can be suitably used as not only a host material in which an emission center substance emitting fluorescence in the visible region is dispersed but also a host material in which an emission center substance emitting high-energy light (such as an emission center substance emitting phosphorescence in the visible region) is dispersed. In particular, the compound can be suitably used as a host material in which an emission center substance emitting blue phosphorescence is dispersed. Needless to say, the compound can also be used as a host material in which an emission center substance emitting fluorescence having a longer wavelength than blue light or an emission center substance emitting phosphorescence having a longer wavelength than green light is dispersed. The carrier-transport property (specifically, the electron-transport property) of the compound is high; accordingly, a light-emitting element driven at low voltage can be provided.

When the heterocyclic compound is used as a host material, the high orientation allows a guest material to be oriented. As a result, the light extraction efficiency increases and the external quantum efficiency becomes high. Furthermore, the heterocyclic compound has a relatively high molecular mass and thus is excellent in thermal stability, thereby prolonging the lifetime of a light-emitting element.

In addition, it is effective to use the compound as a material of a carrier-transport layer (preferably an electron-transport layer) adjacent to a light-emitting layer. Since the compound has a wide band gap or a high triplet excitation level, even when the emission center material is a material emitting high-energy light, such as a material emitting blue fluorescence or a material emitting green to blue phosphorescence, the energy of carriers that have recombined in a host material can be effectively transferred to the emission center substance. Thus, a light-emitting element having high emission efficiency can be fabricated. Note that in the case where the compound is used as a host material or a material of a carrier-transport layer, the emission center material is preferably, but not limited to, a substance having a narrower band gap between the HOMO level and the LUMO level than the compound or a substance having a lower singlet excitation level or a lower triplet excitation level than the compound.

Examples of materials that can be used as the host material in the case where the heterocyclic compound is not used as the host material are described below.

The following are examples of materials having an electron-transport property: a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); a heterocyclic compound having a polyazole skeleton such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2′,2″-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II); a heterocyclic compound having a diazine skeleton such as 2-[3-(dibenzothiophen-4-yl)phenyl]dibenzo[f,h]quinoxaline (abbreviation: 2mDBTPDBq-II), 2-[3′-(dibenzothiophen-4-yl)biphenyl-3-yl]dibenzo[f,h]quinoxaline (abbreviation: 2mDBTBPDBq-II), 2-[3′-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyridine (abbreviation: 4,6mDBTP2Pm-II); and a heterocyclic compound having a pyridine skeleton such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB). Among the above materials, a heterocyclic compound having a diazine skeleton and a heterocyclic compound having a pyridine skeleton have high reliability and are thus preferable. Specifically, a heterocyclic compound having a diazine (pyrimidine or pyrazine) skeleton has a high electron-transport property to contribute to a reduction in driving voltage. Note that the above compound with a benzothienopyrimidine skeleton has a relatively high electron-transport property, and is classified as a material having an electron-transport property.

The following are examples of materials which have a hole-transport property: a compound having an aromatic amine skeleton such as 4,4′-bis[N-(1-naphthyl)-N-phenylamino]biphenyl (abbreviation: NPB), N,N′-bis(3-methylphenyl)-N,N′-diphenyl-[1,1′-biphenyl]-4,4′-diamine (abbreviation: TPD), 4,4′-bis[N-(spiro-9,9′-bifluoren-2-yl)-N-phenylamino]biphenyl (abbreviation: BSPB), 4-phenyl-4′-(9-phenylfluoren-9-yl)triphenylamine (abbreviation: BPAFLP), 4-phenyl-3′-(9-phenylfluoren-9-yl)triphenylamine (abbreviation: mBPAFLP), 4-phenyl-4′-(9-phenyl-9H-carbazol-3-yl)triphenylamine (abbreviation: PCBA1BP), 4,4′-diphenyl-4″-(9-phenyl-9H-carbazol-3-yl)triphenylamine (abbreviation: PCBBi1BP), 4-(1-naphthyl)-4′-(9-phenyl-9H-carbazol-3-yl)triphenylamine (abbreviation: PCBANB), 4,4′-di(1-naphthyl)-4″-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9′-bifluoren-2-amine (abbreviation: PCBASF); a compound having a carbazole skeleton such as 1,3-bis(N-carbazolyl)benzene (abbreviation: mCP), 4,4′-di(N-carbazolyl)biphenyl (abbreviation: CBP), 3,6-bis(3,5-diphenylphenyl)-9-phenylcarbazole (abbreviation: CzTP), or 3,3′-bis(9-phenyl-9H-carbazole) (abbreviation: PCCP); a compound having a thiophene skeleton such as 4,4′,4″-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton such as 4,4′,4″-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high electron-transport properties to contribute to a reduction in driving voltage.

Note that when the emission center substance is a phosphorescent substance, a substance having a higher triplet excitation level than the phosphorescent substance is preferably selected as the host material, and when the light-emitting substance is a fluorescent substance, a substance having a wider band gap than the fluorescent substance is preferably selected as the host material. The light-emitting layer may contain a third substance in addition to the host material and the phosphorescent substance. Note that this statement does not exclude the possibility that the light-emitting layer contains a component other than the host materials, the phosphorescent substances, and the third substance.

Here, to achieve high emission efficiency of a light-emitting element that uses a phosphorescent substance, energy transfer between the host material and the phosphorescent substance will be considered. Carrier recombination occurs in both the host material and the phosphorescent substance; thus, efficient energy transfer from the host material to the phosphorescent substance is preferable to increase emission efficiency.

In this embodiment, a phosphorescent compound is used as the guest material. In an absorption spectrum of the phosphorescent compound, an absorption band that is considered to contribute to light emission most greatly is at an absorption wavelength corresponding to direct transition from a ground state to a triplet excited state and a vicinity of the absorption wavelength, which is on the longest wavelength side. Therefore, it is considered preferable that the emission spectrum (a fluorescence spectrum and a phosphorescence spectrum) of the host material overlap with the absorption band on the longest wavelength side in the absorption spectrum of the phosphorescent compound.

For example, most organometallic complexes, especially light-emitting iridium complexes, have a broad absorption band around 500 nm to 600 nm as the absorption band on the longest wavelength side. This absorption band is mainly based on a triplet MLCT (metal to ligand charge transfer) transition. Note that it is considered that the absorption band also includes absorptions based on a triplet $\pi$-$\pi^*$ transition and a singlet MLCT transition, and that these absorptions overlap each other to form a broad absorption band on the longest wavelength side in the absorption spectrum. Therefore, when an organometallic complex (especially iridium complex) is used as the guest material, it is preferable to make the broad absorption band on the longest wavelength side have a large overlap with the emission spectrum of the host material as described above.

Here, first, energy transfer from a host material in a triplet excited state will be considered. From the above-described discussion, it is preferable that, in energy transfer from a triplet excited state, the phosphorescence spectrum of the host material and the absorption band on the longest wavelength side of the guest material have a large overlap.

However, a question here is energy transfer from the host molecule in the singlet excited state. In order to efficiently perform not only energy transfer from the triplet excited state but also energy transfer from the singlet excited state, the host material is preferably designed such that not only its phosphorescence spectrum but also its fluorescence spectrum overlaps with the absorption band on the longest wavelength side of the guest material. In other words, when the host material is designed so as to have its fluorescence spectrum in a position similar to that of its phosphorescence spectrum, it is possible to achieve efficient energy transfer from the host material in both the singlet excited state and the triplet excited state.

However, in general, the S1 level differs greatly from the T1 level (S1 level>T1 level); therefore, the fluorescence emission wavelength also differs greatly from the phosphorescence emission wavelength (fluorescence emission wavelength<phosphorescence emission wavelength). For example, 4,4'-di(N-carbazolyl)biphenyl (abbreviation: CBP), which is commonly used in a light-emitting element containing a phosphorescent compound, has a phosphorescence spectrum around 500 nm and has a fluorescence spectrum around 400 nm, which are largely different by about 100 nm. This example also shows that it is extremely difficult to design a host material so as to have its fluorescence spectrum in a position similar to that of its phosphorescence spectrum.

Also, since fluorescence is emitted from an energy level higher than that of phosphorescence, the T1 level of a host material whose fluorescence spectrum corresponds to a wavelength close to an absorption spectrum of a guest material on the longest wavelength side is lower than the T1 level of the guest material.

Thus, in the case where a phosphorescent substance is used as the emission center substance, it is preferable that the light-emitting layer include a third substance in addition to the host material and the emission center substance and a combination of the host material and the third substance form an exciplex (also referred to as an excited complex).

In that case, at the time of recombination of carriers (electrons and holes) in the light-emitting layer, the host material and the third substance form an exciplex. A fluorescence spectrum of the exciplex is on a longer wavelength side than a fluorescence spectrum of the host material alone or the third substance alone. Therefore, energy transfer from a singlet excited state can be maximized while the T1 levels of the host material and the third substance are kept higher than the T1 level of the guest material. In addition, the exciplex is in a state where the T1 level and the S1 level are close to each other; therefore, the fluorescence spectrum and the phosphorescence spectrum exist at substantially the same position. Accordingly, both the fluorescence spectrum and the phosphorescence spectrum of the exciplex can have a large overlap with an absorption corresponding to transition of the guest molecule from the singlet ground state to the triplet excited state (a broad absorption band of the guest molecule existing on the longest wavelength side in the absorption spectrum), and thus a light-emitting element having high energy transfer efficiency can be obtained.

As the third substance, the above material which can be used as the host material or additives can be used. There is no particular limitation on the host materials and the third substance as long as they can form an exciplex; a combination of a compound which readily accepts electrons (a compound having an electron-transport property) and a compound which readily accepts holes (a compound having a hole-transport property) is preferably employed.

In the case where a compound having an electron-transport property and a compound having a hole-transport property are used for the host material and the third substance, carrier balance can be controlled by the mixture ratio of the compounds. Specifically, the ratio of the host material to the third substance (or additive) is preferably from 1:9 to 9:1. Note that in that case, the following structure may be employed: a light-emitting layer in which one kind of an emission center substance is dispersed is divided into two layers, and the two layers have different mixture ratios of the host material to the third substance. With this structure, the carrier balance of the light-emitting element can be optimized, so that the lifetime of the light-emitting element can be improved. Furthermore, one of the light-emitting layers may be a hole-transport layer and the other of the light-emitting layers may be an electron-transport layer.

In the case where the light-emitting layer having the above-described structure is formed using a plurality of materials, the light-emitting layer can be formed using co-evaporation by a vacuum evaporation method; or an inkjet method, a spin coating method, a dip coating method, or the like using a solution of the materials.

The electron-transport layer 114 is a layer containing a substance having an electron-transport property. For example, the electron-transport layer 114 is formed using a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato) beryllium (abbreviation: BeBq$_2$), or bis(2-methyl-8-quinolinolato)(4-phenylphenolato)aluminum (abbreviation: BAlq), or the like. A metal complex having an oxazole-based or thiazole-based ligand, such as bis[2-(2-hydroxyphenyl)benzoxazolato]zinc (abbreviation: Zn(BOX)$_2$) or bis [2-(2-hydroxyphenyl)benzothiazolato]zinc (abbreviation: Zn(BTZ)$_2$), or the like can also be used. Other than the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances given here are mainly ones having an electron mobility of $10^{-6}$ cm$^2$/Vs or higher. Note that any substance other than the above substances may be used for the electron-transport layer as long as the substance has an electron-transport property higher than a hole-transport property.

The heterocyclic compound may be used as a material contained in the electron-transport layer 114. Since the heterocyclic compound has a wide band gap and a high T1 level, excitation energy in the light-emitting layer can be prevented from transferring to the electron-transport layer 114 and a decrease in emission efficiency due to the energy transfer can be suppressed, so that a light-emitting element with high emission efficiency can be provided. Moreover, the compound of one embodiment of the present invention has a high carrier-transport property; thus, a light-emitting element driven at low voltage can be provided.

The electron-transport layer is not limited to a single layer, and may be a stack including two or more layers containing any of the above substances.

Between the electron-transport layer and the light-emitting layer, a layer that controls transport of electron carriers may be provided. This is a layer formed by addition of a small amount of a substance having a high electron-trapping property to the aforementioned materials having a high electron-transport property, and the layer is capable of adjusting carrier balance by retarding transport of electron carriers. Such a structure is very effective in preventing a problem (such as a reduction in element lifetime) caused when electrons pass through the light-emitting layer.

It is preferable that the host material in the light-emitting layer and a material of the electron-transport layer have the same skeleton, in which case transfer of carriers can be smooth and thus the driving voltage can be reduced. Moreover, it is effective that the host material and the material of the electron-transport layer be the same material.

The electron-injection layer 115 may be provided in contact with the second electrode 102 between the electron-transport layer 114 and the second electrode 102. For the electron-injection layer 115, lithium, calcium, lithium fluoride (LiF), cesium fluoride (CsF), calcium fluoride (CaF$_2$), or the like can be used. A composite material of a substance having an electron-transport property and a substance exhibiting an electron-donating property (hereinafter, simply referred to as electron-donating substance) with respect to the substance having an electron-transport property can also be used. Examples of the electron-donating substance include an alkali metal, an alkaline earth metal, compounds thereof, and an electride. Examples of the electride include an electride in which electrons are added at high concentration to calcium oxide-aluminum oxide. Note that such a composite material is preferably used for the electron-injection layer 115, in which case electrons are injected efficiently from the second electrode 102. With this structure, a conductive material as well as a material having a low work function can be used for the cathode.

For the electrode functioning as a cathode, any of metals, alloys, electrically conductive compounds, and mixtures thereof which have a low work function (specifically, a work function of 3.8 eV or less) or the like can be used. Specific examples of such a cathode material include elements that belong to Groups 1 and 2 of the periodic table, i.e., lithium (Li), cesium (Cs), magnesium (Mg), calcium (Ca), and strontium (Sr), alloys thereof (e.g., MgAg or AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium tin oxide containing silicon or silicon oxide can be used regardless of the work function. Films of these conductive materials can be formed by a sputtering method, an inkjet method, a spin coating method, or the like.

Any of a variety of methods can be used to form the EL layer 103 regardless of whether it is a dry process or a wet process. For example, a vacuum evaporation method, an inkjet method, a spin coating method, or the like may be used. Different formation methods may be used for the electrodes or the layers.

In addition, the electrode may be formed by a wet method using a sol-gel method, or by a wet method using paste of a metal material. Alternatively, the electrode may be formed by a dry method such as a sputtering method or a vacuum evaporation method.

Note that the structure of the EL layer provided between the first electrode 101 and the second electrode 102 is not limited to the above structure. However, it is preferable that a light-emitting region where holes and electrons recombine be positioned away from the first electrode 101 and the second electrode 102 so as to prevent quenching due to the proximity of the light-emitting region and a metal used for an electrode or a carrier-injection layer.

Further, in order that transfer of energy from an exciton generated in the light-emitting layer can be inhibited, preferably, the hole-transport layer and the electron-transport layer which are in direct contact with the light-emitting layer, particularly a carrier-transport layer in contact with a side closer to the light-emitting region in the light-emitting layer 113 is formed with a substance having a wider energy gap than the light-emitting substance of the light-emitting layer or the emission center substance included in the light-emitting layer.

In the light-emitting element having the above-described structure, current flows due to a potential difference provided between the first electrode 101 and the second electrode 102, and holes and electrons recombine in the light-emitting layer 113 which contains a substance having a high light-emitting property, so that light is emitted. In other words, a light-emitting region is formed in the light-emitting layer 113.

Light is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light is extracted from the substrate side through the first electrode 101. In contrast, when only the second electrode 102 is a light-transmitting electrode, light is extracted from the side opposite to the substrate side through the second electrode 102. In the case where both the first electrode 101 and the second electrode 102 are light-transmitting electrodes, light is extracted from both the substrate side and the side opposite to the substrate side through the first electrode 101 and the second electrode 102.

Since the light-emitting element in this embodiment is formed using the compound of one embodiment of the present invention, the light-emitting element can have high external quantum efficiency. Since the heterocyclic compound of one embodiment of the present invention has high heat resistance, the light-emitting element has favorable thermophysical properties.

Such a light-emitting element may be fabricated using a substrate made of glass, plastic, or the like as a support. A plurality of such light-emitting elements are formed over one substrate, thereby forming a passive matrix light-emitting device. Alternatively, a transistor may be formed over a substrate made of glass, plastic, or the like, and the light-emitting element may be fabricated over an electrode electrically connected to the transistor. In this manner, an active matrix light-emitting device in which the driving of the light-emitting element is controlled by the transistor can be fabricated. Note that a structure of the transistor is not particularly limited. Either a staggered TFT or an inverted staggered TFT may be employed. In addition, the crystallinity of a semiconductor used for the TFT is not particularly limited. In addition, a driver circuit formed in a TFT substrate may be formed with n-channel TFTs and p-channel TFTs, or with either n-channel TFTs or p-channel TFTs. The semiconductor layer for forming the TFTs may be formed using any material as long as the material exhibits semiconductor characteristics; for example, an element belonging to Group 14 of the periodic table such as silicon (Si) and germanium (Ge), a compound such as gallium arsenide and indium phosphide, an oxide such as zinc oxide and tin oxide, and the like can be given. For the oxide exhibiting semiconductor characteristics (oxide semiconductor), a composite oxide of an element selected from indium, gallium, aluminum, zinc, and tin can be used. Examples thereof are zinc oxide (ZnO), indium oxide containing zinc oxide (indium zinc oxide), and an oxide containing indium oxide, gallium oxide, and zinc oxide (IGZO: indium gallium zinc oxide). An organic semiconductor may also be used. The semiconductor layer may have either a crystalline structure or an amorphous structure. Specific examples of the crystalline semiconductor layer are a single crystal semiconductor, a polycrystalline semiconductor, and a microcrystalline semiconductor.

As described above, the heterocyclic compound of one embodiment of the present invention can be used for a light-emitting element.

This embodiment can be combined with any of other embodiments as appropriate.

Embodiment 4

In this embodiment is described one mode of a light-emitting element having a structure in which a plurality of light-emitting units are stacked (hereinafter, also referred to as stacked-type element), with reference to FIG. 1B. This light-emitting element includes a plurality of light-emitting units between a first electrode and a second electrode. Each light-emitting unit can have the same structure as the EL layer 103 which is described in Embodiment 2. In other words, the light-emitting element described in Embodiment 2 is a light-emitting element having one light-emitting unit while the light-emitting element described in this embodiment is a light-emitting element having a plurality of light-emitting units.

Figure 1B:
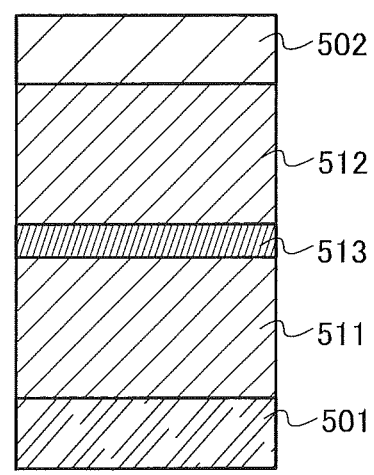

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 respectively correspond to the first electrode 101 and the second electrode 102 in Embodiment 2, and materials described in Embodiment 2 can be used. Further, the structures of the first light-emitting unit 511 and the second light-emitting unit 512 may be the same or different.

The charge generation layer 513 includes a composite material of an organic compound and a metal oxide. As this composite material of an organic compound and a metal oxide, the composite material that can be used for the hole-injection layer and described in Embodiment 2 can be used. As the organic compound, any of a variety of compounds such as aromatic amine compounds, carbazole compounds, aromatic hydrocarbons, and high molecular compounds (oligomers, dendrimers, polymers, or the like) can be used. Note that the organic compound preferably has a hole mobility of $1\times10^{-6}$ $cm^2$/Vs or more. However, any other substance may be used as long as the substance has a hole-transport property higher than an electron-transport property. Since a composite material of an organic compound and a metal oxide is excellent in carrier-injection property and carrier-transport property, low voltage driving and low current driving can be achieved. Note that in the light-emitting unit whose anode side surface is in contact with the charge generation layer, a hole-transport layer is not necessarily provided because the charge generation layer can also function as the hole-transport layer.

The charge generation layer 513 may have a stacked-layer structure of a layer containing the composite material of an organic compound and a metal oxide and a layer containing another material. For example, a layer containing the composite material of an organic compound and a metal oxide may be combined with a layer containing a compound of a substance selected from electron-donating substances and a compound having a high electron-transport property. Moreover, the charge generation layer 513 may be formed by combining a layer containing the composite material of an organic compound and a metal oxide with a transparent conductive film.

The charge generation layer 513 provided between the first light-emitting unit 511 and the second light-emitting unit 512 may have any structure as long as electrons can be injected to a light-emitting unit on one side and holes can be injected to a light-emitting unit on the other side when a voltage is applied between the first electrode 501 and the second electrode 502. For example, in FIG. 1B, any layer can be used as the charge generation layer 513 as long as the layer injects electrons into the first light-emitting unit 511 and holes into the second light-emitting unit 512 when a voltage is applied such that the potential of the first electrode is higher than that of the second electrode.

Although the light-emitting element having two light-emitting units is described in this embodiment, the present invention can be similarly applied to a light-emitting element in which three or more light-emitting units are stacked. With a plurality of light-emitting units partitioned by the charge generation layer between a pair of electrodes, as in the light-emitting element according to this embodiment, light with high luminance can be obtained while current density is kept low; thus, a light-emitting element having a long lifetime can be obtained. In addition, a low power consumption light-emitting device which can be driven at low voltage can be achieved.

By making the light-emitting units emit light of different colors from each other, the light-emitting element can provide light emission of a desired color as a whole. For example, by forming a light-emitting element having two light-emitting units such that the emission color of the first light-emitting unit and the emission color of the second light-emitting unit are complementary colors, the light-emitting element can provide white light emission as a whole. Note that the word "complementary" means color relationship in which an achromatic color is obtained when colors are mixed. In other words, when lights obtained from substances which emit light of complementary colors are mixed, white light emission can be obtained. Further, the same can be applied to a light-emitting element having three light-emitting units. For example, the light-emitting element as a whole can provide white light emission when the emission color of the first light-emitting unit is red, the emission color of the second light-emitting unit is green, and the emission color of the third light-emitting unit is blue. Alternatively, in the case of employing a light-emitting element in which a phosphorescent emission center substance is used for a light-emitting layer of one light-emitting unit and a fluorescent emission center substance is used for a light-emitting layer of the other light-emitting unit, both fluorescence and phosphorescence can be efficiently emitted from the light-emitting element. For example, when red phosphorescence and green phosphorescence are obtained from one light-emitting unit and blue fluorescence is obtained from the other light-emitting unit, white light with high emission efficiency can be obtained.

Since the light-emitting element of this embodiment contains the compound having a structure in which a dibenzothiophenyl group, a dibenzofuranyl group, or a carbazolyl group and a dibenzo[f,h]quinoxalinyl group are bonded through three or more arylene groups, the light-emitting element can have high emission efficiency or operate at low driving voltage. In addition, since light emission with high color purity which is derived from the emission center substance can be obtained from the light-emitting unit including the heterocyclic compound, color adjustment of the light-emitting element as a whole is easy.

This embodiment can be combined with any of other embodiments as appropriate.

Embodiment 5

In this embodiment, a light-emitting device that uses a light-emitting element including the compound having a structure in which a dibenzothiophenyl group, a dibenzofuranyl group, or a carbazolyl group and a dibenzo[f,h]quinoxalinyl group are bonded through three or more arylene groups is described.

In this embodiment, explanation will be given with reference to FIGS. 2A and 2B of an example of the light-emitting device fabricated using a light-emitting element including the compound having a structure in which a dibenzothiophenyl group, a dibenzofuranyl group, or a carbazolyl group and a dibenzo[f,h]quinoxalinyl group are bonded through three or more arylene groups. Note that FIG. 2A is a top view of the light-emitting device and FIG. 2B is a cross-sectional view taken along the lines A-B and C-D in FIG. 2A. This light-emitting device includes a driver circuit portion (source side driver circuit) 601, a pixel portion 602, and a driver circuit portion (gate side driver circuit) 603, which control light emission of a light-emitting element and denoted by dotted lines. A reference numeral 604 denotes a sealing substrate; 625, a desiccant; 605, a sealing material; and 607, a space surrounded by the sealing material 605.

A lead wiring 608 is a wiring for transmitting signals to be input to the source side driver circuit 601 and the gate side driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is explained with reference to FIG. 2B. The driver circuit portion and the pixel portion are formed over an element substrate 610; here, the source side driver circuit 601, which is a driver circuit portion, and one of the pixels in the pixel portion 602 are shown.

As the source side driver circuit 601, a CMOS circuit in which an n-channel TFT 623 and a p-channel TFT 624 are combined is formed. In addition, the driver circuit may be formed with any of a variety of circuits such as a CMOS circuit, a PMOS circuit, and an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching TFT 611, a current controlling TFT 612, and a first electrode 613 electrically connected to a drain of the current controlling TFT 612. Note that to cover an end portion of the first electrode 613, an insulator 614 is formed, for which a positive photosensitive resin film is used here.

In order to improve coverage of a film formed over the insulator 614, the insulator 614 is formed to have a curved surface with curvature at its upper or lower end portion. For example, in the case where a positive photosensitive acrylic resin is used for a material of the insulator 614, only the upper end portion of the insulator 614 preferably has a surface with a curvature radius (0.2 μm to 3 μm). As the insulator 614, either a negative photosensitive material or a positive photosensitive material can be used.

An EL layer 616 and a second electrode 617 are formed over the first electrode 613. As a material used for the first electrode 613 which functions as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack including a titanium nitride film and a film containing aluminum as its main component, a stack including three layers of a titanium nitride film, a film containing aluminum as its main component, and a titanium nitride film, or the like can be used. The stacked structure achieves low wiring resistance, a favorable ohmic contact, and a function as an anode.

The EL layer 616 is formed by any of a variety of methods such as an evaporation method using an evaporation mask, an inkjet method, and a spin coating method. The EL layer 616 contains the compound having a structure in which a dibenzothiophenyl group, a dibenzofuranyl group, or a carbazolyl group and a dibenzo[f,h]quinoxalinyl group are bonded through three or more arylene groups. Further, for another material included in the EL layer 616, any of low molecular compounds and high molecular compounds (including oligomers and dendrimers) may be used.

As a material used for the second electrode 617, which is formed over the EL layer 616 and functions as a cathode, a material having a low work function (e.g., Al, Mg, Li, Ca, or an alloy or compound thereof, such as MgAg, MgIn, or AlLi) is preferably used. In the case where light generated in the EL layer 616 passes through the second electrode 617, a stack including a thin metal film and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that the light-emitting element is formed with the first electrode 613, the EL layer 616, and the second electrode 617. The light-emitting element has the structure described in Embodiment 3. In the light-emitting device of this embodiment, the pixel portion, which includes a plurality of light-emitting elements, may include both the light-emitting element with the structure described in Embodiment 3 and a light-emitting element with a structure other than those.

The sealing substrate 604 is attached to the element substrate 610 with the sealing material 605, so that the light-emitting element 618 is provided in the space 607 surrounded by the element substrate 610, the sealing substrate 604, and the sealing material 605. The space 607 is filled with a filler. The filler may be an inert gas (such as nitrogen or argon), or a resin and/or a desiccant.

An epoxy-based resin or glass frit is preferably used for the sealing material 605. It is preferable that such a material do not transmit moisture or oxygen as much as possible. As the sealing substrate 604, a glass substrate, a quartz substrate, or a plastic substrate formed of fiber reinforced plastic (FRP), poly(vinyl fluoride) (PVF), a polyester, an acrylic resin, or the like can be used.

As described above, the light-emitting device fabricated by using the light-emitting element including the compound having a structure in which a dibenzothiophenyl group, a dibenzofuranyl group, or a carbazolyl group and a dibenzo[f,h]quinoxalinyl group are bonded through three or more arylene groups can be obtained.

Figures 3A, 3B:
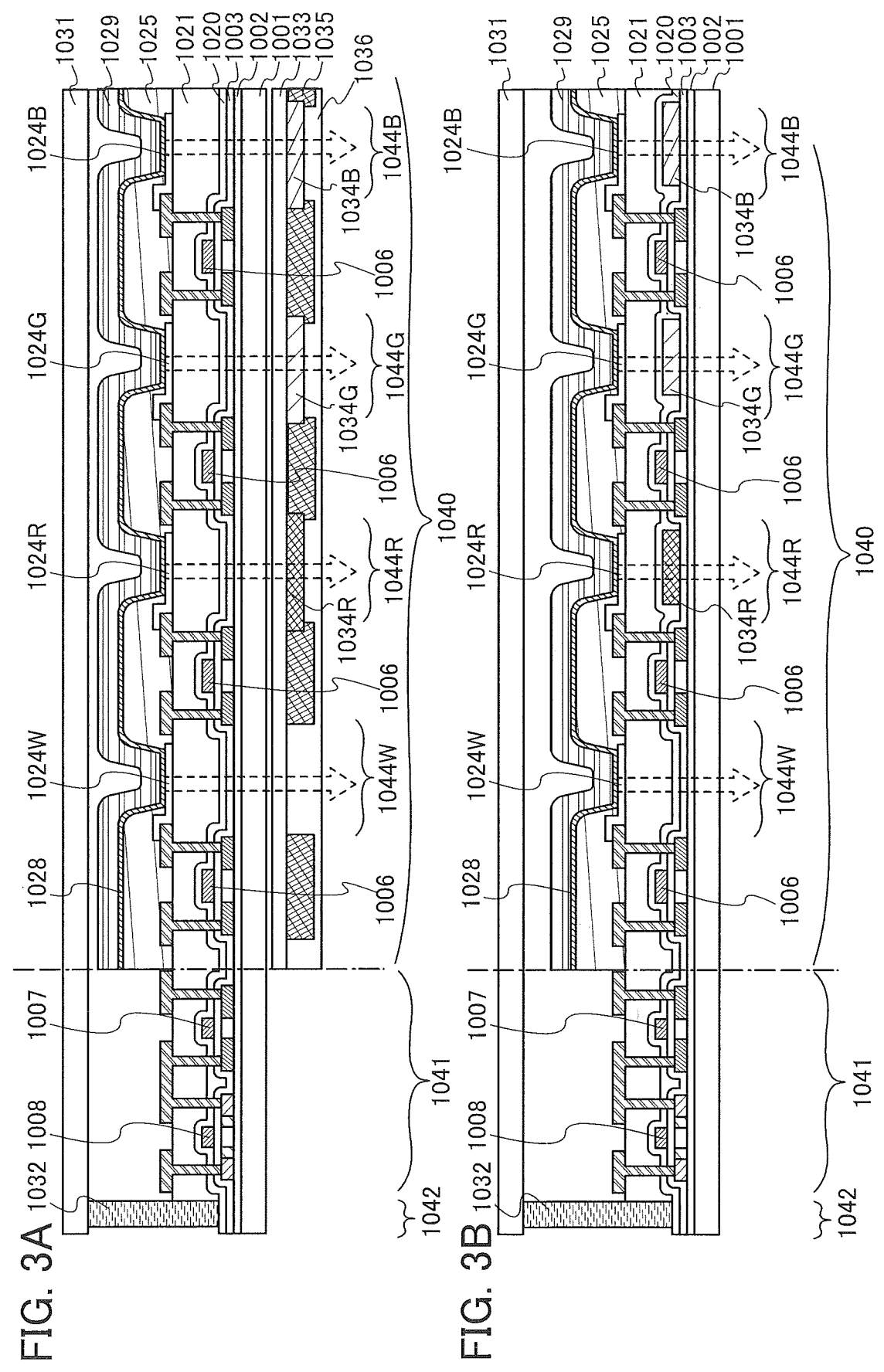

FIGS. 3A and 3B illustrate examples of light-emitting devices in which full color display is achieved by forming a light-emitting element exhibiting white light emission and providing a coloring layer (a color filter) and the like. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition wall 1025, an EL layer 1028, a second electrode 1029 of the light-emitting elements, a sealing substrate 1031, a sealant 1032, and the like are illustrated.

In FIG. 3A, coloring layers (a red coloring layer 1034R, a green coloring layer 1034G, and a blue coloring layer 1034B) are provided on a transparent base material 1033. Further, a black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 3A, light emitted from some of the light-emitting layers does not pass through the coloring layers, while light emitted from the others of the light-emitting layers passes through the coloring layers. Since light which does not pass through the coloring layers is white and light which passes through any one of the coloring layers is red, blue, or green, an image can be displayed using pixels of the four colors.

FIG. 3B illustrates an example in which coloring layers (a red coloring layer 1034R, a green coloring layer 1034G, and a blue coloring layer 1034B) are formed between the gate insulating film 1003 and the first interlayer insulating film 1020. As shown in FIG. 3B, the coloring layers may be provided between the substrate 1001 and the sealing substrate 1031.

Figure 4:
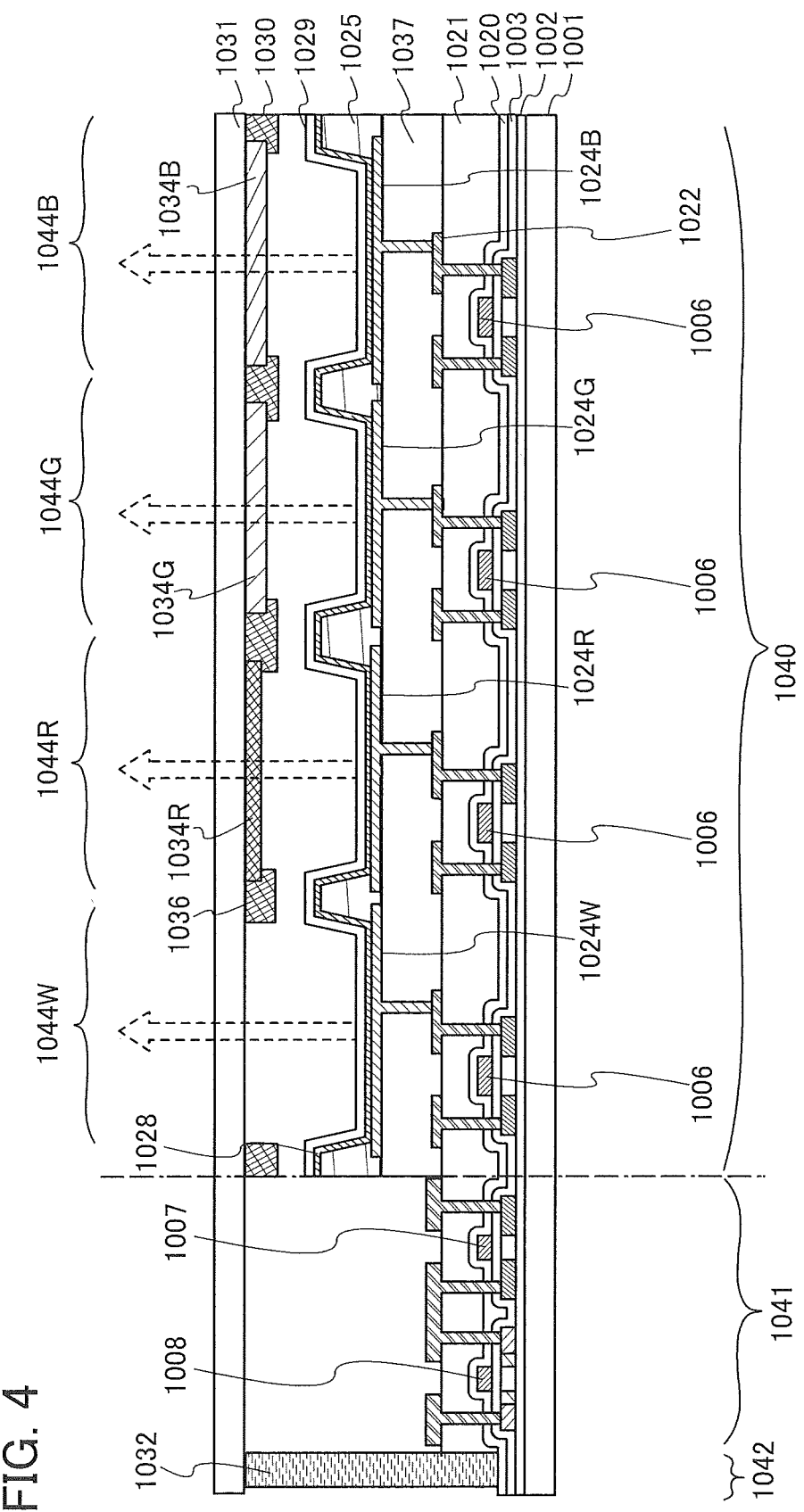
FIG. 4 is a schematic view of an active matrix light-emitting device.

The above-described light-emitting device has a structure in which light is extracted from the substrate 1001 side where the TFTs are formed (a bottom emission structure), but may have a structure in which light is extracted from the sealing substrate 1031 side (a top emission structure). FIG. 4 is a cross-sectional view of a light-emitting device having a top emission structure. In this case, a substrate which does not transmit light can be used as the substrate 1001. The process up to the step of forming a connection electrode which connects the TFT and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any other various materials.

The first electrodes 1024W, 1024R, 1024G, and 1024B of the light-emitting elements each serve as an anode here, but may serve as a cathode. Further, in the case of a light-emitting device having a top emission structure as illustrated in FIG. 4, the first electrodes are preferably reflective electrodes. The EL layer 1028 is formed to have a structure similar to the structure described in Embodiment 2, with which white light emission can be obtained.

In FIGS. 3A and 3B and FIG. 4, the structure of the EL layer for providing white light emission can be achieved by, for example, using a plurality of light-emitting layers or using a plurality of light-emitting units. Note that the structure to provide white light emission is not limited to the above.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with a black layer (the black matrix) 1030 which is positioned between pixels. The coloring layers (the red coloring layer 1034R, the green coloring layer 1034G, and the blue coloring layer 1034B) and the black layer (the black matrix) may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

Since the light-emitting device in this embodiment uses the light-emitting element described in Embodiment 3 (the light-emitting element including the compound having a structure in which a dibenzothiophenyl group, a dibenzofuranyl group, or a carbazolyl group and a dibenzo[f,h]quinoxalinyl group are bonded through three or more arylene groups), the light-emitting device can have favorable characteristics. Specifically, the compound having a structure in which a dibenzothiophenyl group, a dibenzofuranyl group, or a carbazolyl group and a dibenzo[f,h]quinoxalinyl group are bonded through three or more arylene groups has a wide energy gap and a high triplet excitation level and can inhibit energy transfer from a light-emitting substance; thus, a light-emitting element having high emission efficiency in a wide range of emission colors can be provided, leading to a light-emitting device having reduced power consumption and a favorable color rendering property. Furthermore, the compound having a structure in which a dibenzothiophenyl group, a dibenzofuranyl group, or a carbazolyl group and a dibenzo[f,h]quinoxalinyl group are bonded through three or more arylene groups has a high carrier-transport property, so that a light-emitting element driven at low voltage can be provided, leading to a light-emitting device driven at low voltage. The compound having a structure in which a dibenzothiophenyl group, a dibenzofuranyl group, or a carbazolyl group and a dibenzo[f,h]quinoxalinyl group are bonded through three or more arylene groups has favorable thermophysical properties, so that a light-emitting device with high heat resistance can be provided.

Figure 5A:
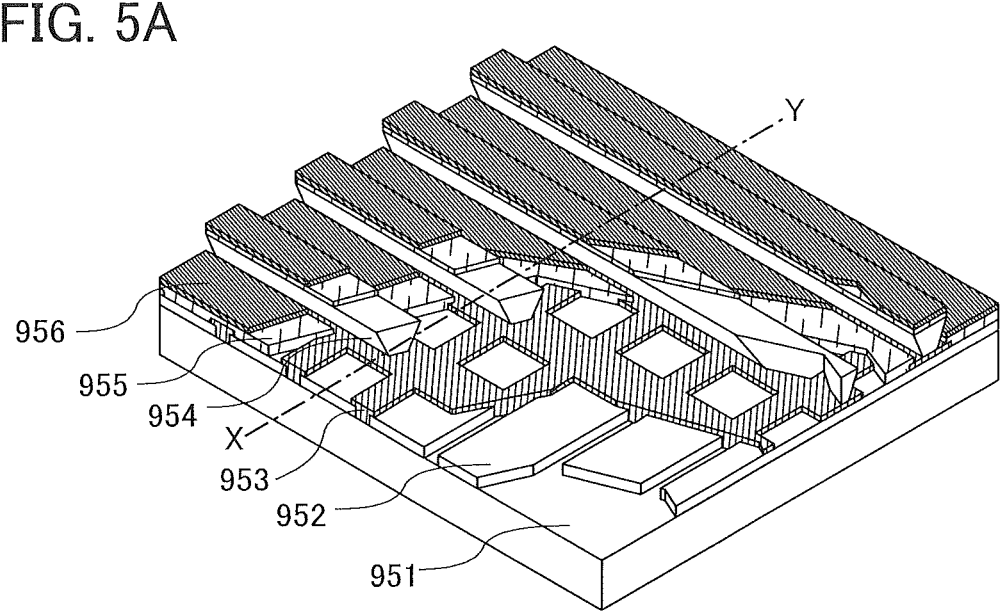
FIGS. 5A and 5B are schematic views of a passive matrix light-emitting device.
Figure 5B:
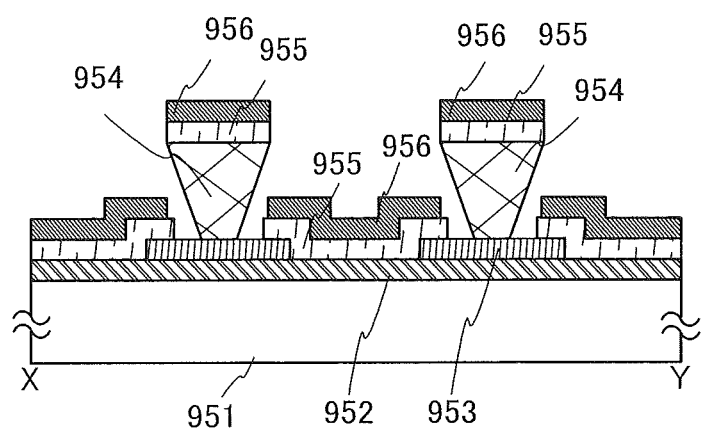

An active matrix light-emitting device is described above, whereas a passive matrix light-emitting device is described below. FIGS. 5A and 5B illustrate a passive matrix light-emitting device fabricated by application of one embodiment of the present invention. FIG. 5A is a perspective view of the light-emitting device, and FIG. 5B is a cross-sectional view of FIG. 5A taken along line X-Y. In FIGS. 5A and 5B, over a substrate 951, an EL layer 955 is provided between an electrode 952 and an electrode 956. An edge portion of the electrode 952 is covered with an insulating layer 953. A partition layer 954 is provided over the insulating layer 953. The sidewalls of the partition layer 954 slope so that the distance between one sidewall and the other sidewall gradually decreases toward the surface of the substrate. In other words, a cross section taken along the direction of the short side of the partition layer 954 is trapezoidal, and the base (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). By providing the partition layer 954 in such a manner, a defect of the light-emitting element due to static electricity or the like can be prevented. The passive matrix light-emitting device can also be driven with low power consumption, by including the light-emitting element described in Embodiment 3 (the light-emitting element including a compound having a structure in which a dibenzothiophenyl group, a dibenzofuranyl group, or a carbazolyl group and a dibenzo[f,h]quinoxalinyl group are bonded through three or more arylene groups) capable of operating at low driving voltage. In addition, the light-emitting device can have high heat resistance and high emission efficiency by including the light-emitting element with high heat resistance and high emission efficiency (the light-emitting element described in Embodiment 3) because the element includes the compound having a structure in which a dibenzothiophenyl group, a dibenzofuranyl group, or a carbazolyl group and a dibenzo[f,h]quinoxalinyl group are bonded through three or more arylene groups.

Note that in this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As examples of a glass substrate, a barium borosilicate glass substrate, an aluminoborosilicate glass substrate, a soda lime glass substrate, and the like can be given. Examples of the flexible substrate, the attachment film, the base film, and the like are substrates of plastics typified by polyethylene terephthalate (PET), polyethylene naphthalate (PEN), polyether sulfone (PES), and polytetrafluoroethylene (PTFE). Another example is a synthetic resin such as acrylic. Alternatively, polypropylene, polyester, polyvinyl fluoride, polyvinyl chloride, or the like can be used. Alternatively, polyamide, polyimide, aramid, epoxy, an inorganic vapor deposition film, paper, or the like can be used. Specifically, the use of semiconductor substrates, single crystal substrates, SOI substrates, or the like enables the manufacture of small-sized transistors with a small variation in characteristics, size, shape, or the like and with high current capability. A circuit using such transistors achieves lower power consumption of the circuit or higher integration of the circuit.

Alternatively, a flexible substrate may be used as the substrate, and the transistor or the light-emitting element may be provided directly on the flexible substrate. Still alternatively, a separation layer may be provided between the substrate and the transistor. The separation layer can be used when part or the whole of a semiconductor device formed over the separation layer is separated from the substrate and transferred onto another substrate. In such a case, the transistor can be transferred to a substrate having low heat resistance or a flexible substrate. For the separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of a substrate to which a transistor or a light-emitting element is transferred include, in addition to the above-described substrates over which transistors can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. When such a substrate is used, a transistor with excellent characteristics or a transistor with low power consumption can be formed, a device with high durability or high heat resistance can be provided, or reduction in weight or thickness can be achieved.

Since many minute light-emitting elements arranged in a matrix in the light-emitting device described above can each be controlled, the light-emitting device can be suitably used as a display device for displaying images.

This embodiment can be combined with any of other embodiments as appropriate.

Embodiment 6

In this embodiment, electronic devices each including the light-emitting element described in Embodiment 3 are described. The light-emitting element described in Embodiment 3 includes the compound of one embodiment of the present invention having a structure in which a dibenzothiophenyl group, a dibenzofuranyl group, or a carbazolyl group and a dibenzo[f,h]quinoxalinyl group are bonded through three or more arylene groups and thus has reduced power consumption; as a result, the electronic devices described in this embodiment can each include a display portion having reduced power consumption. In addition, the electronic devices can be driven at low voltage since the light-emitting element described in Embodiment 3 is driven at low voltage. The light-emitting element described in Embodiment 3 is also a light-emitting element having favorable thermophysical properties, whereby an electronic device having high heat resistance can be achieved.

Examples of the electronic device to which the above light-emitting element is applied include television devices (also referred to as TV or television receivers), monitors for computers and the like, cameras such as digital cameras and digital video cameras, digital photo frames, cellular phones (also referred to as mobile phones or mobile phone devices), portable game machines, portable information terminals, audio playback devices, and large game machines such as pachinko machines. Specific examples of these electronic devices are given below.

Figure 6A:
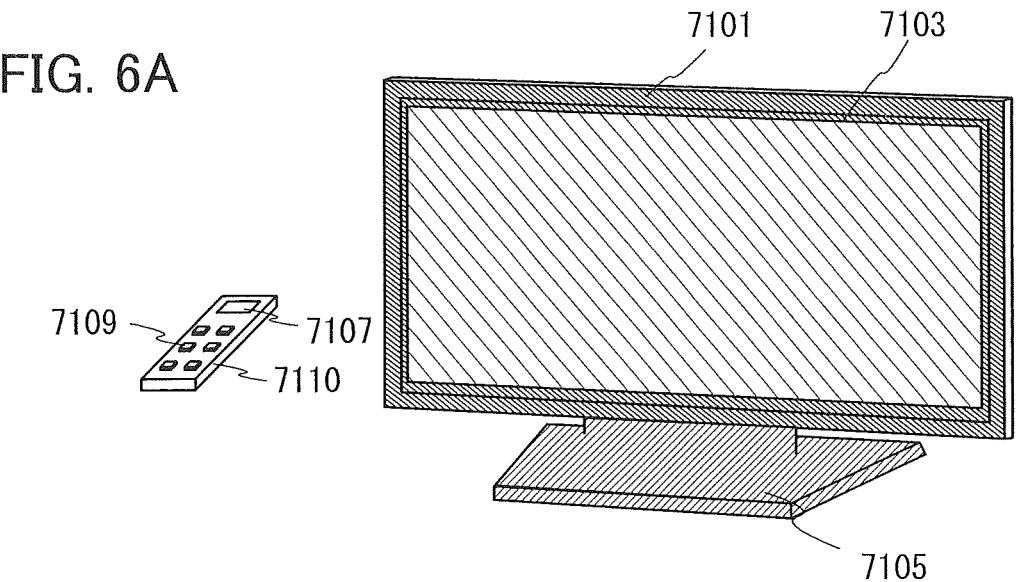
FIGS. 6A to 6D illustrate electronic devices.

FIG. 6A illustrates an example of a television device. In the television device, a display portion 7103 is incorporated in a housing 7101. In addition, here, the housing 7101 is supported by a stand 7105. The display portion 7103 enables display of images and includes light-emitting elements which are the same as the light-emitting element described in Embodiment 3 and arranged in a matrix. The light-emitting elements each include the compound having a structure in which a dibenzothiophenyl group, a dibenzofuranyl group, or a carbazolyl group and a dibenzo[f,h]quinoxalinyl group are bonded through three or more arylene groups and thus can have high emission efficiency and low driving voltage. Therefore, the television device including the display portion 7103 which is formed using the light-emitting elements can have reduced power consumption and low driving voltage.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

Figure 6B:
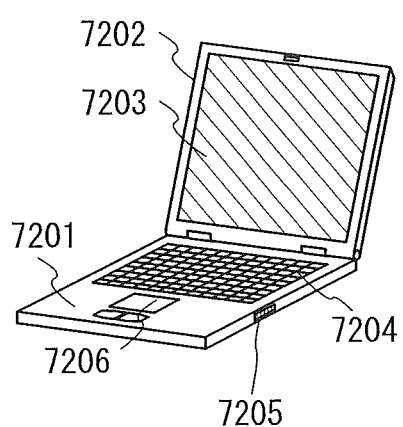

FIG. 6B illustrates a computer, which includes a main body 7201, a housing 7202, a display portion 7203, a keyboard 7204, an external connection port 7205, a pointing device 7206, and the like. Note that this computer is fabricated by using light-emitting elements arranged in a matrix in the display portion 7203, which are the same as the light-emitting element described in Embodiment 3. The light-emitting elements each include the compound of one embodiment of the present invention and thus can have high emission efficiency and low driving voltage. Therefore, the computer including the display portion 7203 which is formed using the light-emitting elements can have reduced power consumption and low driving voltage.

Figure 6C:
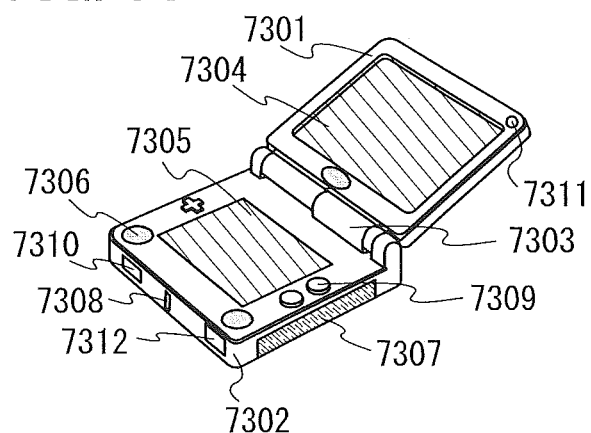

FIG. 6C illustrates a portable game machine having two housings, a housing 7301 and a housing 7302, which are connected with a joint portion 7303 so that the portable game machine can be opened or folded. A display portion 7304 including light-emitting elements which are the same as the light-emitting element described in Embodiment 3 and arranged in a matrix is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, an input unit (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as far as the display portion including light-emitting elements which are the same as the light-emitting element described in Embodiment 3 and arranged in a matrix is used as at least either the display portion 7304 or the display portion 7305, or both, and the structure can include other accessories as appropriate. The portable game machine illustrated in FIG. 6C has a function of reading out a program or data stored in a storage medium to display it on the display portion, and a function of sharing information with another portable game machine by wireless communication. The portable game machine illustrated in FIG. 6C can have a variety of functions without limitation to the above. Since the light-emitting elements used in the display portion 7304 have high emission efficiency by including the compound of one embodiment of the present invention having a structure in which a dibenzothiophenyl group, a dibenzofuranyl group, or a carbazolyl group and a dibenzo[f,h]quinoxalinyl group are bonded through three or more arylene groups, the portable game machine including the above-described display portion 7304 can be a portable game machine having reduced power consumption. Since the light-emitting elements used in the display portion 7304 each have low driving voltage by including the compound of one embodiment of the present invention, the portable game machine can also be a portable game machine having low driving voltage.

Figure 6D:
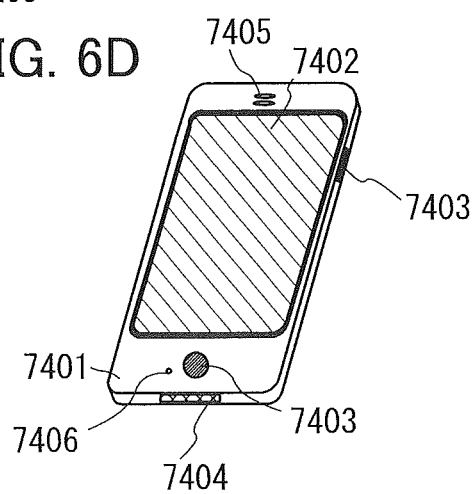

FIG. 6D illustrates an example of a cellular phone. A cellular phone is provided with a display portion 7402 incorporated in a housing 7401, operation buttons 7403, an external connection port 7404, a speaker 7405, a microphone 7406, and the like. Note that the cellular phone has the display portion 7402 including light-emitting elements which are the same as the light-emitting element described in Embodiment 3 and arranged in a matrix. The light-emitting elements each include the compound of one embodiment of the present invention and thus can have high emission efficiency and low driving voltage. Therefore, the cellular phone including the display portion 7402 which is formed using the light-emitting elements can have reduced power consumption and low driving voltage.

When the display portion 7402 of the cellular phone illustrated in FIG. 6D is touched with a finger or the like, data can be input into the cellular phone. In this case, operations such as making a call and creating e-mail can be performed by touching the display portion 7402 with a-finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone, display on the screen of the display portion 7402 can be automatically changed by determining the orientation of the cellular phone (whether the cellular phone is placed horizontally or vertically for a landscape mode or a portrait mode).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits near-infrared light in the display portion, an image of a finger vein, a palm vein, or the like can be taken.

Note that the structure described in this embodiment can be combined with any of the structures described in Embodiments 1 to 4 as appropriate.

As described above, the application range of the light-emitting device having the light-emitting element described in Embodiment 3 which includes the compound of one embodiment of the present invention is wide so that this light-emitting device can be applied to electronic devices in a variety of fields. By using the compound, an electronic device having reduced power consumption and low driving voltage can be obtained.

The light-emitting element including the compound of one embodiment of the present invention can also be used for a light source device. One mode is described with reference to FIG. 7. Note that the light source device includes a light-emitting element including the compound of one embodiment of the present invention as a light irradiation unit and at least includes an input-output terminal portion which supplies current to the light-emitting element. Further, the light-emitting element is preferably shielded from the outside atmosphere by sealing.

Figure 7:
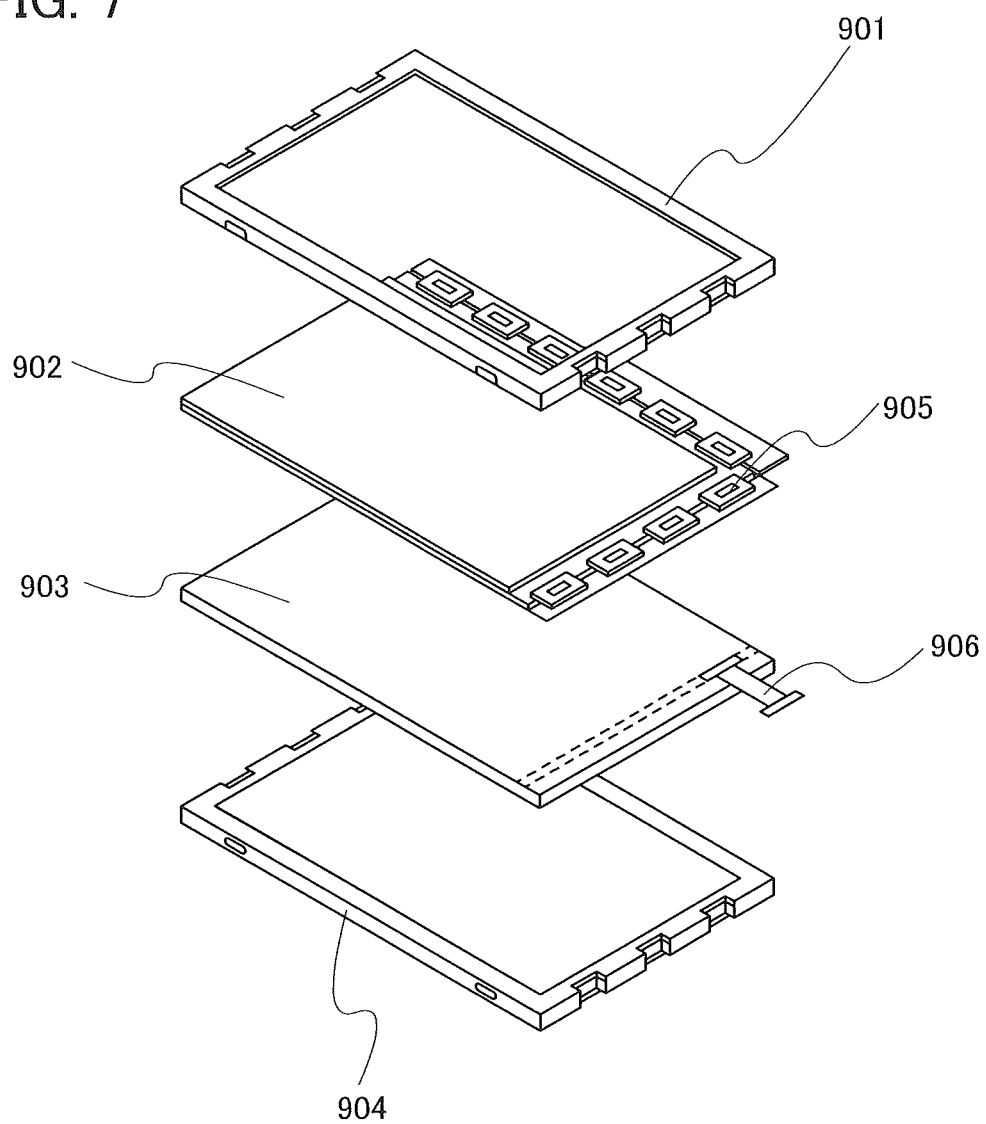
FIG. 7 illustrates a light source device.

FIG. 7 illustrates an example of a liquid crystal display device using the light-emitting elements including the compound of one embodiment of the present invention for a backlight. The liquid crystal display device illustrated in FIG. 7 includes a housing 901, a liquid crystal layer 902, a backlight 903, and a housing 904. The liquid crystal layer 902 is connected to a driver IC 905. The light-emitting element including the above compound is used in the backlight 903, to which current is supplied through a terminal 906.

The light-emitting element including the above compound is used for the backlight of the liquid crystal display device; thus, the backlight can have reduced power consumption. In addition, the use of the light-emitting element including the above compound enables fabrication of a planar-emission lighting device and further a larger-area planar-emission lighting device; therefore, the backlight can be a larger-area backlight, and the liquid crystal display device can also be a larger-area device. Furthermore, with the backlight using the light-emitting element including the above compound, the light-emitting device can be thinner than a conventional one; accordingly, the display device can also be thinner.

Figure 8:
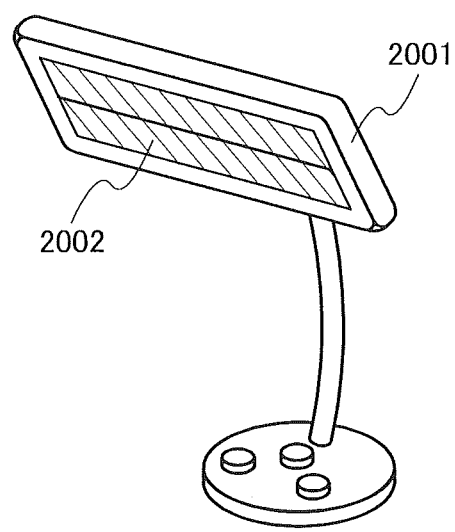
FIG. 8 illustrates a lighting device.

FIG. 8 illustrates an example in which the light-emitting element including the compound of one embodiment of the present invention is used for a table lamp which is a lighting device. The table lamp illustrated in FIG. 8 includes a housing 2001 and a light source 2002, and the light-emitting element including the above heterocyclic compound is used for the light source 2002.

Figure 9:
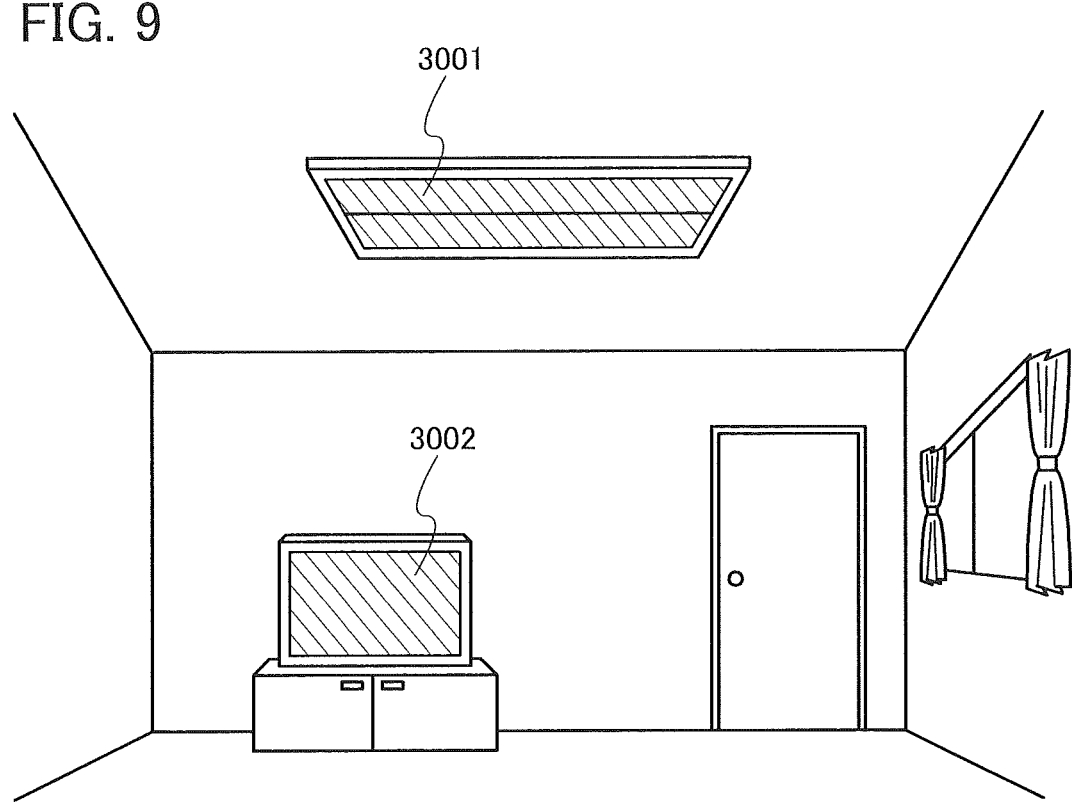
FIG. 9 illustrates a lighting device and an electronic device.

FIG. 9 illustrates an example in which the light-emitting element including the compound of one embodiment of the present invention is used for an indoor lighting device 3001. Since the light-emitting element including the above compound has reduced power consumption, a lighting device that has reduced power consumption can be obtained. Further, since the light-emitting element including the above compound can have a large area, the light-emitting element can be used for a large-area lighting device. Furthermore, since the light-emitting element including the above compound is thin, a lighting device having a reduced thickness can be fabricated. FIG. 9 also illustrates an example in which the light-emitting element including the compound of one embodiment of the present invention is used for a display device 3002.

Figure 10:
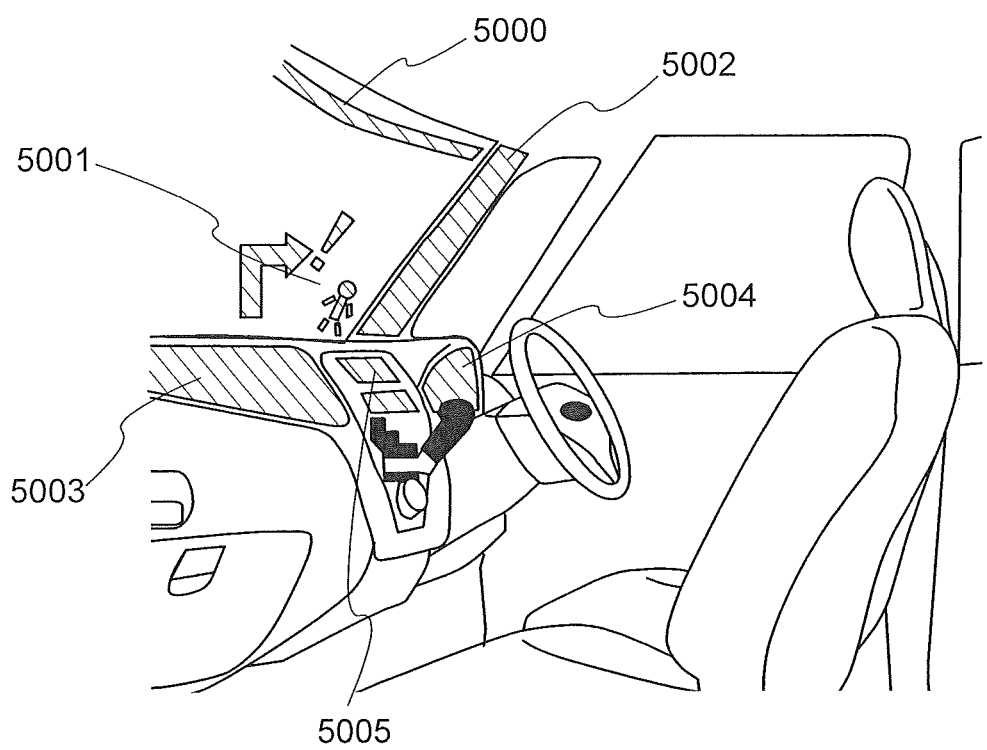
FIG. 10 illustrates in-vehicle display devices and lighting devices.

The light-emitting element including the compound of one embodiment of the present invention can also be used for an automobile windshield or an automobile dashboard. FIG. 10 illustrates one mode in which the light-emitting elements including the above heterocyclic compound are used for an automobile windshield and an automobile dashboard. Display regions 5000 to 5005 each include the light-emitting element including the above heterocyclic compound.

The display regions 5000 and 5001 are display devices which are provided in the automobile windshield and in which light-emitting elements including the above heterocyclic compound are incorporated. The light-emitting element including the above heterocyclic compound can be formed into a so-called see-through display device, through which the opposite side can be seen, by including a first electrode and a second electrode formed of electrodes having light-transmitting properties. Such see-through display devices can be provided even in the windshield of the car, without hindering the vision. Note that in the case where a transistor for driving the light-emitting element is provided, a transistor having a light-transmitting property, such as an organic transistor using an organic semiconductor material or a transistor using an oxide semiconductor, is preferably used.

The display region 5002 is a display device which is provided in a pillar portion and in which the light-emitting element including the above heterocyclic compound is incorporated. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedometer, a tachometer, a mileage, a fuel meter, a gearshift indicator, and air-condition setting. The content or layout of the display can be changed freely by a user as appropriate. Note that such information can also be shown by the display regions 5000 to 5003. The display regions 5000 to 5005 can also be used as lighting devices.

With the use of a light-emitting element that includes the compound having a structure in which a dibenzothiophenyl group, a dibenzofuranyl group, or a carbazolyl group and a dibenzo[f,h]quinoxalinyl group are bonded through three or more arylene groups, a light-emitting device with favorable thermophysical properties can be obtained. For that reason, the light-emitting device and the lighting device each of which includes the light-emitting element including the above compound can be suitably used as an in-vehicle light-emitting device or lighting device because these devices can be used even after exposed to high temperatures.

The compound of one embodiment of the present invention can be used for an electronic device such as an organic thin film solar cell. Specifically, the compound can be used in a carrier-transport layer or a carrier-injection layer since the compound has a carrier-transport property. The compound can be photoexcited and hence can be used in a power generation layer.

Example 1

Synthesis Example 1

In this synthesis example, a method for synthesizing 2-[3"-(dibenzothiophen-4-yl)-3,1':3',1"-terphenyl-1-yl]dibenzo[f,h]quinoxaline (abbreviation: 2mDBtTPDBq-II) (Structural Formula (2001)) that is the heterocyclic compound described in Embodiments 1 and 2 is described. The structural formula of 2mDBtTPDBq-II is shown below.

[Chemical formula 230]

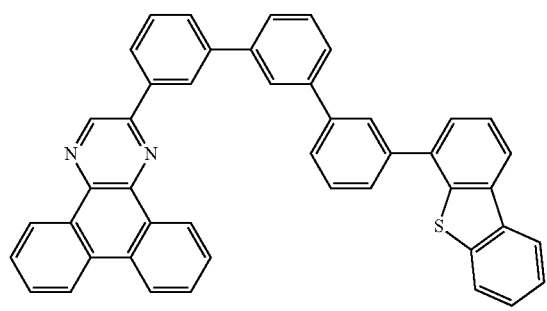

(2001)

Synthesis of 2-[3"-(dibenzothiophen-4-yl)-3,1':3',1"-terphenyl-1-yl]dibenzo[f,h]quinoxaline (Abbreviation: 2mDBtTPDBq-II)

Into a 100-mL three-neck flask were put 1.5 g (3.3 mmol) of 2-(3'-bromo-3,1'-biphenyl-1-yl)dibenzo[f,h]quinoxaline, 1.1 g (3.5 mmol) of 3-(dibenzothiophen-4-yl)phenylboronic acid, 20 mg (65 μmol) of tris(2-methylphenyl)phosphine, 20 mL of toluene, 5 mL of ethanol, and 5 mL of an aqueous solution of potassium carbonate (2 mol/L). The mixture in the flask was degassed under reduced pressure, a nitrogen gas was made to flow continuously in the system, and the mixture was heated to 80° C. After the heating, 7.0 mg (30 μmol) of palladium(II) acetate was added and stirring was performed at the same temperature for 12 hours. After the stirring, a precipitated solid was collected by suction filtration and the resulting solid was washed with water and ethanol, whereby 1.6 g of a powder of the target substance was obtained in a yield of 78%. The synthesis scheme of this step is shown in Formula (A-1).

[Chemical formula 231]

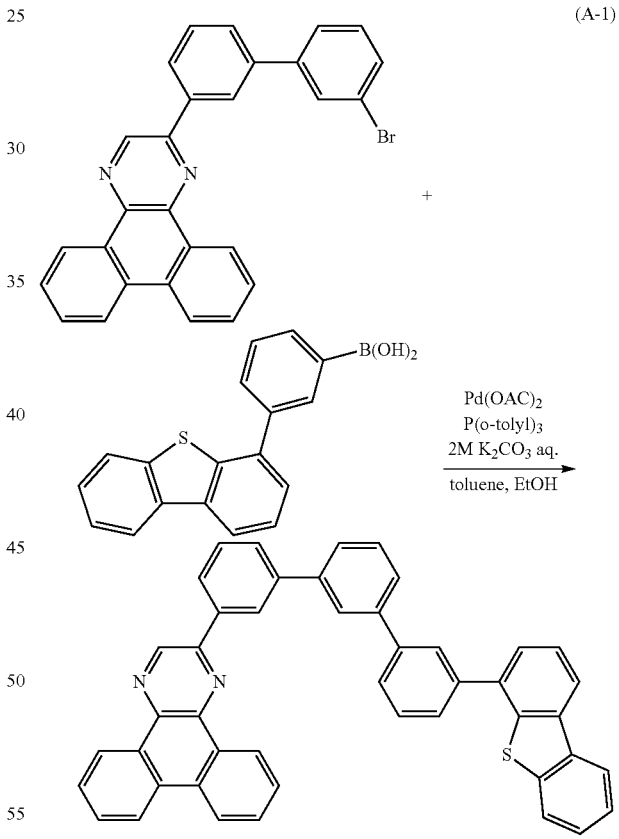

(A-1)

The obtained solid was subjected to nuclear magnetic resonance spectrometry ($^1$H NMR), and the results are shown below.

$^1$H NMR (chloroform-d, 500 MHz): δ=7.38-7.45 (m, 2H), 7.59 (d, J=4.5 Hz, 2H), 7.64-7.85 (m, 13H), 8.07 (s, 1H), 8.13 (s, 1H), 8.17-8.20 (m, 2H), 8.34 (d, J=8.0 Hz, 1H), 8.64-8.67 (m, 3H), 9.24 (d, J=8.0 Hz, 1H), 9.41 (d, J=8.0 Hz, 1H), 9.47 (s, 1H)

Figure 11A:
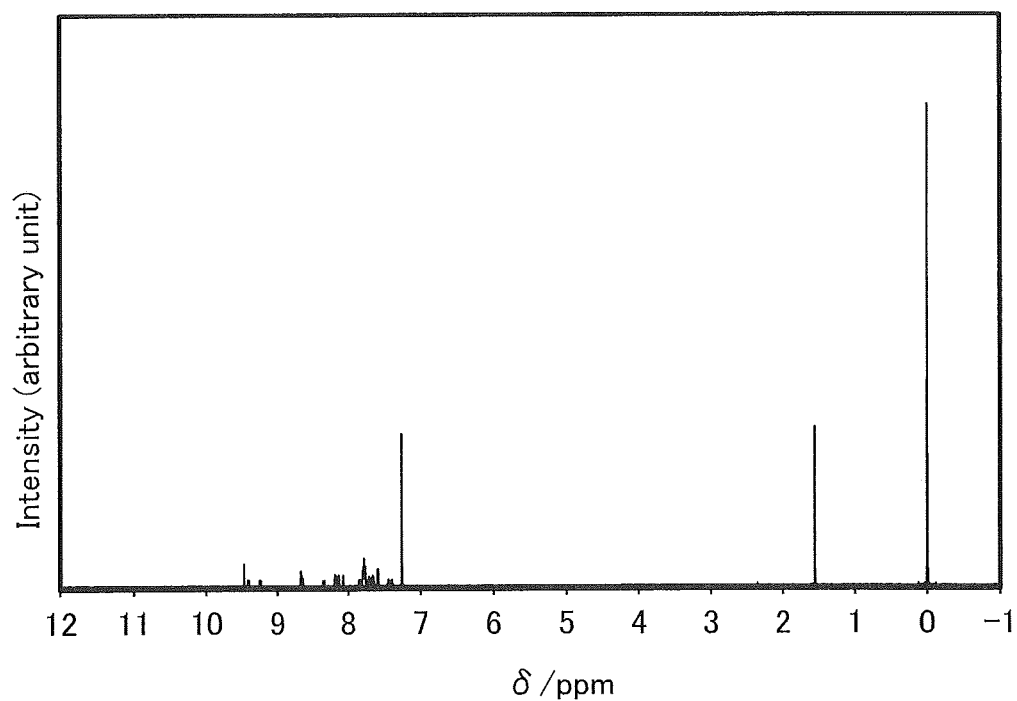
FIGS. 11A and 11B show NMR charts of 2mDBtTPDBq-II.
Figure 11B:
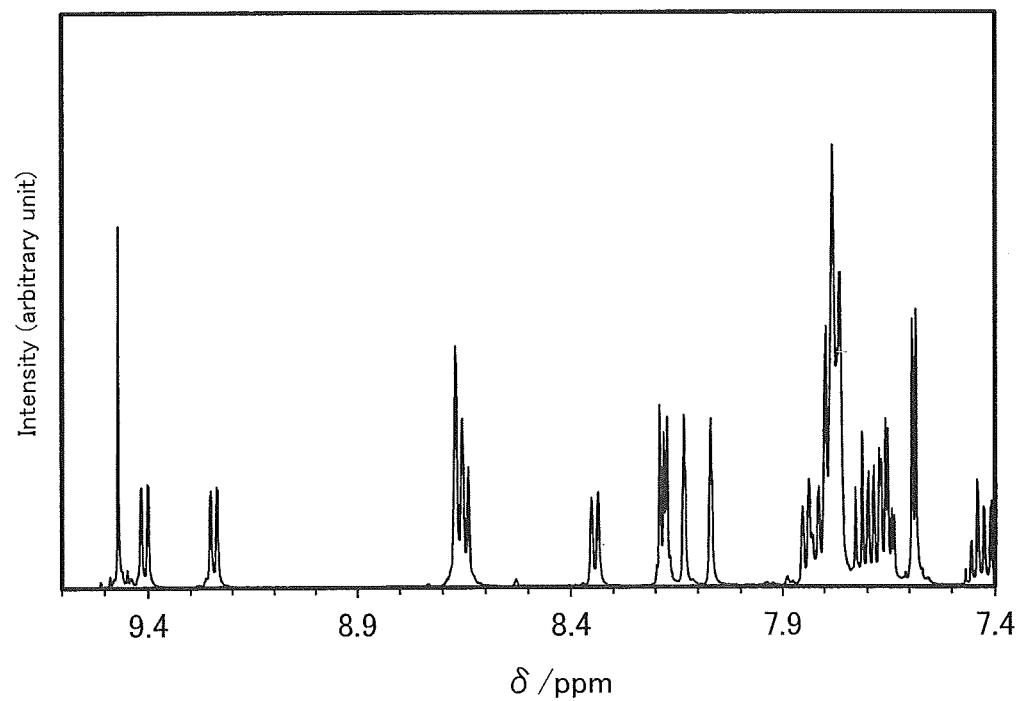

FIGS. 11A and 11B are $^1$H NMR charts. Note that FIG. 11B is a chart showing an enlarged part in the range of 7.4 ppm to 9.6 ppm of FIG. 11A. The results revealed that 2mDBtTPDBq-II, which was the target substance, was obtained.

By a train sublimation method, 1.6 g of the solid was purified. In the sublimation purification, the solid was heated at 340° C. for 15 hours under a pressure of 2.9 Pa with a flow rate of argon of 15 mL/min to give 1.1 g of a solid at a collection rate of 64%.

Physical Properties of 2-[3"-(dibenzothiophen-4-yl)-3,1':3',1"-terphenyl-1-yl]dibenzo[f,h]quinoxaline (Abbreviation: 2mDBtTPDBq-II)

Figure 12:
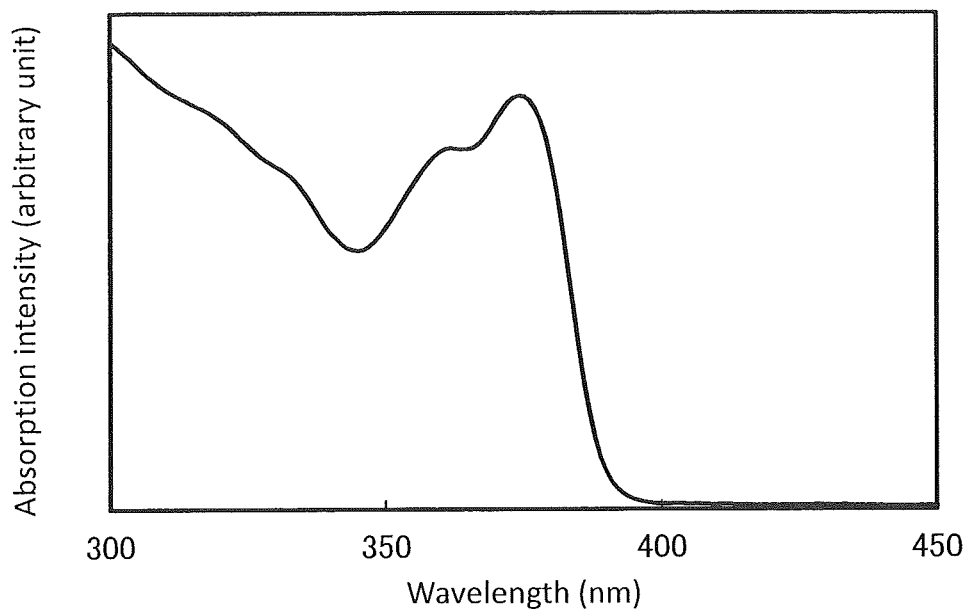
FIG. 12 shows an absorption spectrum of a solution of 2mDBtTPDBq-II.
Figure 13:
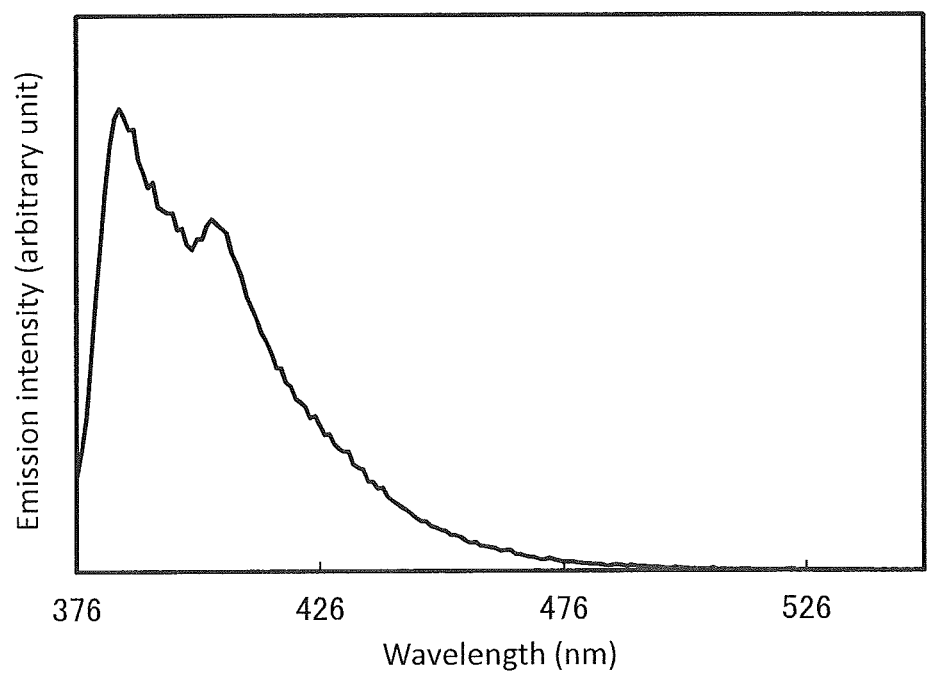
FIG. 13 shows an emission spectrum of a solution of 2mDBtTPDBq-II.
Figure 14:
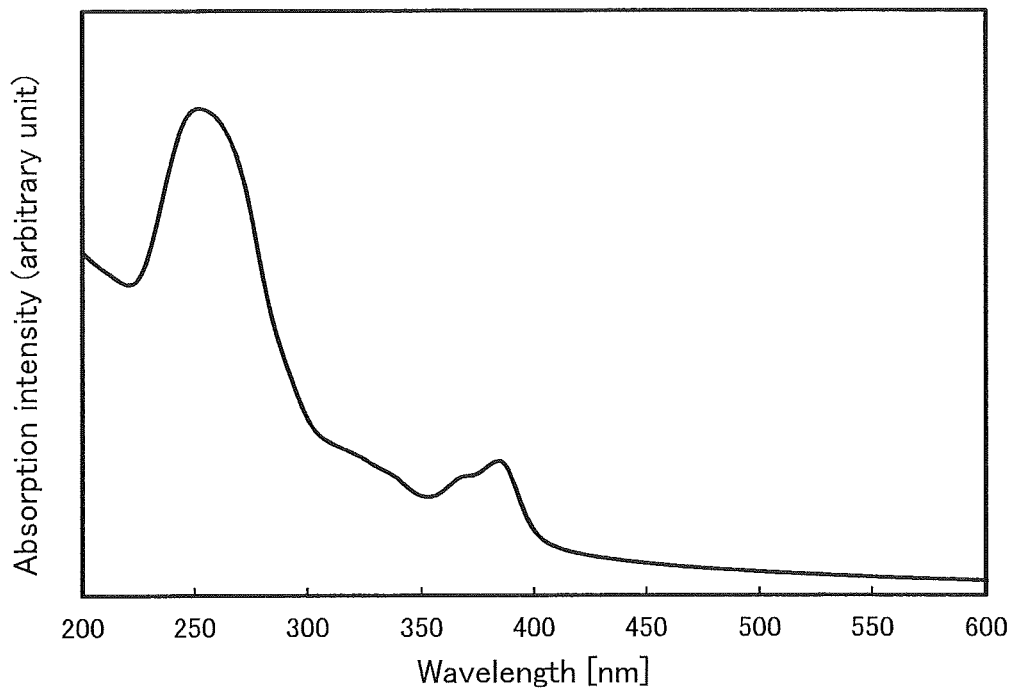
FIG. 14 shows an absorption spectrum of a thin film of 2mDBtTPDBq-II.
Figure 15:
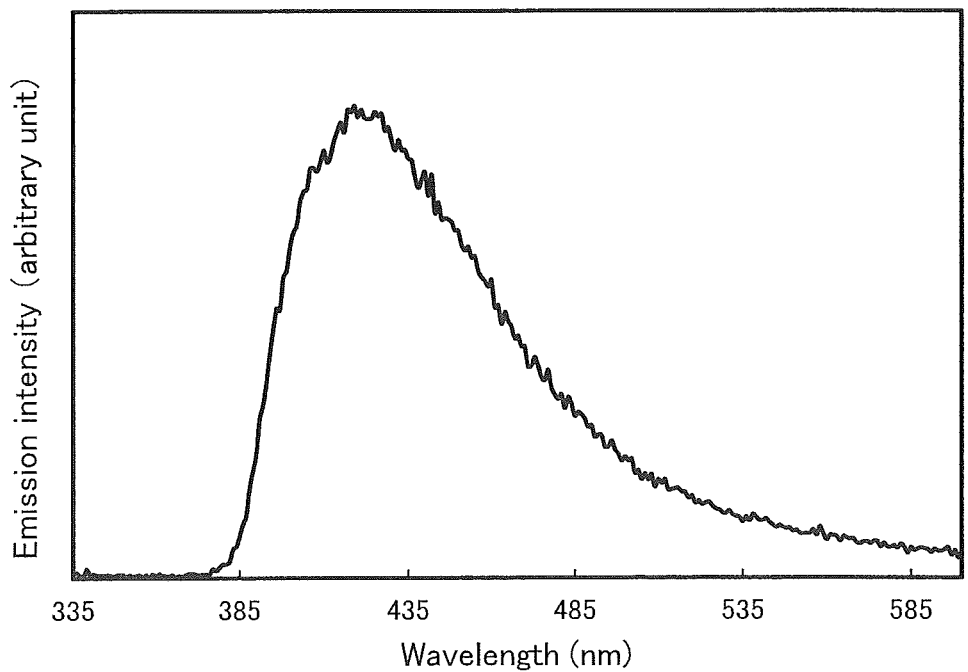
FIG. 15 shows an emission spectrum of a thin film of 2mDBtTPDBq-II.

FIG. 12 shows an absorption spectrum of a toluene solution of 2mDBtTPDBq-II, and FIG. 13 shows an emission spectrum thereof. FIG. 14 shows an absorption spectrum of a thin film of 2mDBtTPDBq-II, and FIG. 15 shows an emission spectrum thereof. The absorption spectra were measured with an ultraviolet-visible spectrophotometer (V-550, produced by JASCO Corporation). The emission spectra were measured with a fluorescence spectrophotometer (FS920, produced by Hamamatsu Photonics K.K.). The spectrum of the toluene solution was measured with the toluene solution of 2mDBtTPDBq-II put in a quartz cell. The spectrum of the thin film was measured with a sample prepared by deposition of 2mDBtTPDBq-II on a quartz substrate by evaporation. Note that the absorption spectrum of the toluene solution shown in the drawing was obtained by subtraction of the absorption spectra of the quartz cell and toluene from the measured spectrum, and the absorption spectrum of the thin film shown in the drawing was obtained by subtraction of the absorption spectrum of the quartz substrate from the measured spectrum.

As observed in FIG. 12 and FIG. 13, absorption peaks of the toluene solution of 2mDBtTPDBq-II are at approximately 374 nm, 362 nm, 333 nm, and 321 nm, and emission wavelength peaks thereof are at 384 nm and 403 nm (excitation wavelength: 378 nm). As observed in FIG. 14 and FIG. 15, absorption peaks of the thin film of 2mDBtTPDBq-II are at approximately 252 nm, 294 nm, 323 nm, 338 nm, 368 nm, and 384 nm, and an emission wavelength peak thereof is at approximately 421 nm (excitation wavelength: 321 nm). It was found that 2mDBtTPDBq-II emitted bluish purple light. The compound of one embodiment of the present invention can be used as a host material for a light-emitting substance or a host material for a substance emitting fluorescence in the visible region.

Figure 16:
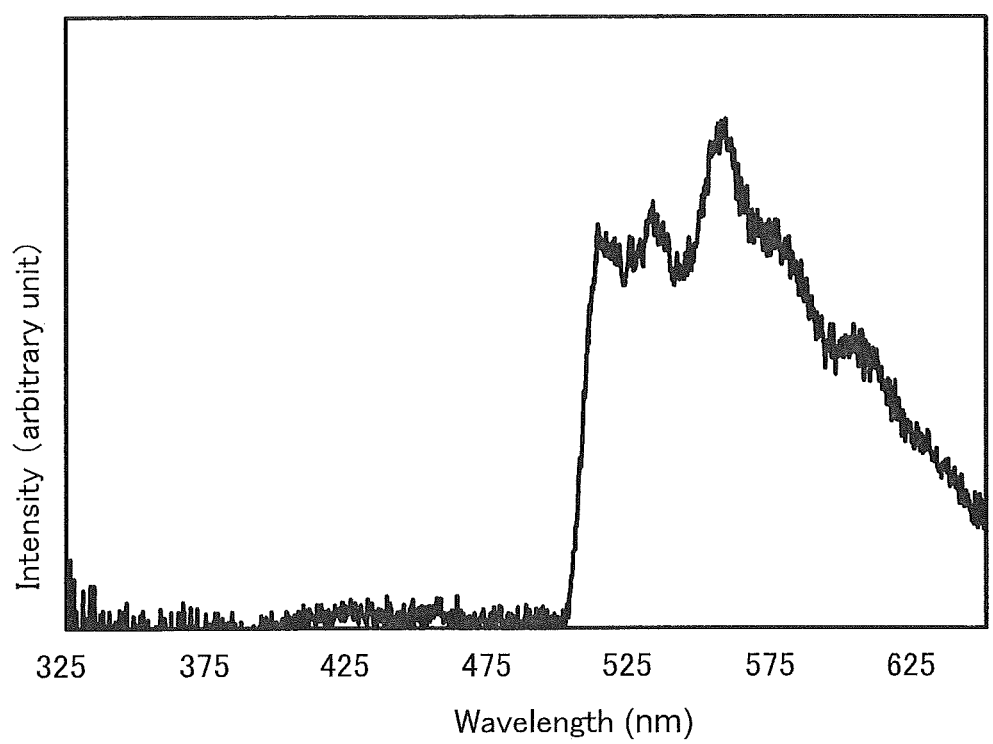
FIG. 16 shows a phosphorescence spectrum of 2mDBtTPDBq-II.

Phosphorescence of 2mDBtTPDBq-II was measured. The measurement was performed by using a PL microscope, LabRAM HR-PL (produced by HORIBA, Ltd.), a He—Cd laser (325 nm) as excitation light, and a CCD detector at a measurement temperature of 10 K. For the measurement, a thin film as a sample was formed over a quartz substrate to a thickness of approximately 50 nm and another quartz substrate was attached to the deposition surface in a nitrogen atmosphere. FIG. 16 shows the obtained phosphorescence spectrum. The results showed that the peak on the shortest wavelength side of the phosphorescence spectrum of 2mDBtTPDBq-II is at 514 nm, which means that 2mDBtTPDBq-II has a high $T_1$ level. It was found that aggregation of the thin film of 2mDBtTPDBq-II is not easily caused even under the air and the thin film suffers only a small change in shape and has high film quality.

The characteristics of oxidation-reduction reaction were examined by cyclic voltammetry (CV) measurement. An electrochemical analyzer (ALS model 600A or 600C, produced by BAS Inc.) was used for the measurement. The solution for the measurement was prepared by dissolving a supporting electrolyte of tetra-n-butylammonium perchlorate (n-Bu$_4$NClO$_4$) in a solvent of dehydrated dimethylformamide (DMF) such that the concentration became 100 mmol/L, and by further dissolving the measurement object such that the concentration became 2 mmol/L. In addition, a platinum electrode (PTE platinum electrode, produced by BAS Inc.) was used as a working electrode, a platinum electrode (Pt counter electrode for VC-3 (5 cm) produced by BAS Inc.) was used as an auxiliary electrode, and an Ag/Ag$^+$ electrode (RE-7 reference electrode for nonaqueous solvent, produced by BAS Inc.) was used as a reference electrode. The scan rate was set to 0.1 V/sec in all the measurement. According to the measurement results, the oxidation potential was −6.19 eV and the reduction potential was −2.94 eV. When the oxidation potential was regarded as a HOMO level and the reduction potential was regarded as a LUMO level, a gap between the HOMO level and the LUMO level was estimated to be 3.25 eV, which indicated that 2mDBtTPDBq-II has a wide band gap.

Example 2

Synthesis Example 2

In this synthesis example, a method for synthesizing 2-[3"-(dibenzothiophen-4-yl)-3,1':4',1"-terphenyl-1-yl]dibenzo[f,h]quinoxaline (abbreviation: 2DBtTPDBq) (Structural Formula (2002)) that is the heterocyclic compound described in Embodiments 1 and 2 is described. The structural formula of 2DBtTPDBq is shown below.

[Chemical formula 232]

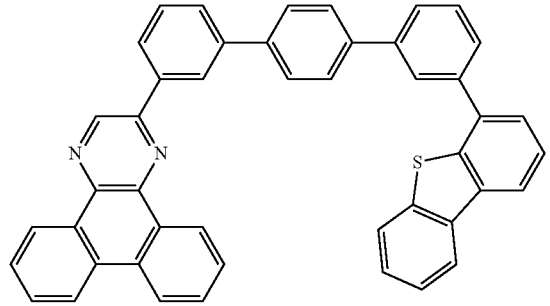

(2002)

Synthesis of 4-(4'-bromo-3,1'-biphenyl-1-yl)dibenzothiophene

Into a 200-mL three-neck flask were put 3.0 g (9.8 mmol) of 3-(dibenzothiophen-4-yl)phenylboronic acid, 2.8 g (2.8 mmol) of 4-bromoiodobenzene, 0.15 g (0.49 mmol) of tris(2-methylphenyl)phosphine, 50 mL of toluene, 5 mL of ethanol, and 15 mL of an aqueous solution of potassium carbonate (2 mol/L). The mixture was degassed under reduced pressure and a nitrogen gas was made to flow continuously in the system. The mixture was heated to 80° C. Then, 40 mg (0.18 mmol) of palladium(II) acetate was added and stirring was performed at the same temperature for 10 hours. After the stirring, the aqueous layer of the mixture was subjected to extraction with toluene three times, the solution of the extract and the organic layer were combined, and this mixture was washed with saturated brine and dried with anhydrous magnesium sulfate. The obtained mixture was gravity-filtered, and then the obtained filtrate was concentrated to give a brown oily substance. The obtained oily substance was purified by silica gel column chromatography (developing solvent: hexane) and recrystallized with chloroform/hexane; thus, 2.5 g of a white powder of the target substance was obtained in a yield of 60%. The synthesis scheme of this step is shown in Formula (B-1).

[Chemical formula 233]

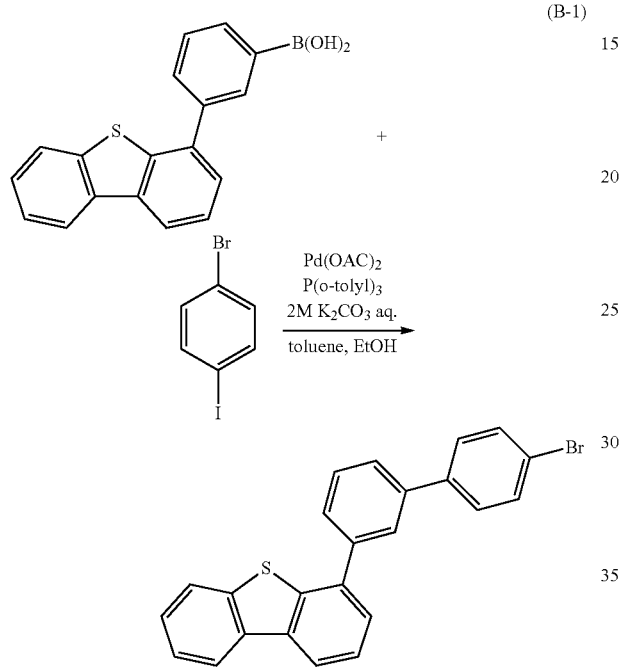

Synthesis of 3'-(dibenzothiophen-4-yl)-4,1'-biphenylboronic acid

Into a 300-mL three-neck flask was put 2.8 g (6.7 mmol) of 4-(4'-bromo-3,1'-biphenyl-1-yl)dibenzothiophene that was synthesized in the step shown by Formula (B-1). After a nitrogen gas was made to flow continuously in the system, 70 mL of dehydrated tetrahydrofuran was added. This solution was cooled down to −78° C., 5 mL (8.0 mmol) of an n-butyllithium hexane solution (1.6 mol/L) was dropped with a syringe, and then, stirring was performed at the same temperature for 1.5 hours. After the stirring, 1 mL (8.9 mmol) of trimethyl borate was added at the same temperature and the resulting solution was stirred at room temperature for 19 hours. After the stirring, 30 mL of hydrochloric acid (1 mol/L) was added and the aqueous layer of the resulting mixture was subjected to extraction with ethyl acetate. The obtained solution of the extract and the organic layer were combined, and this mixture was washed with an aqueous solution of sodium hydrogen carbonate and saturated brine and dried with anhydrous magnesium sulfate. The resulting mixture was gravity-filtered and the filtrate was concentrated to give a pale yellow solid. The solid was washed with chloroform/hexane, whereby 1.9 g of a powder of the target substance was obtained in a yield of 75%. The synthesis scheme of this step is shown in Formula (B-2).

[Chemical formula 234]

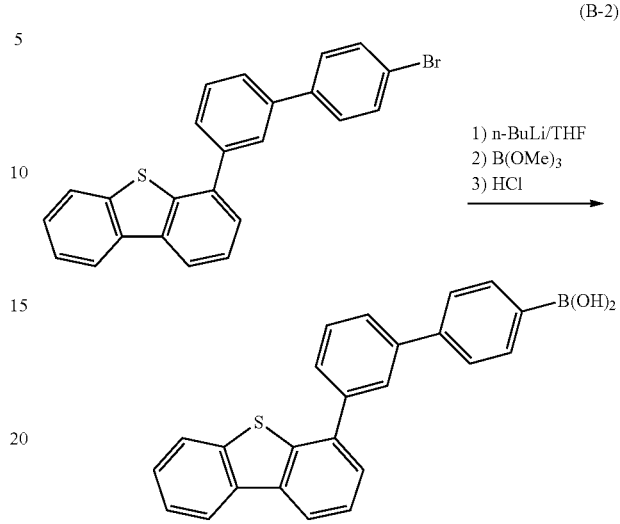

Method for Synthesizing 2-[3''-(dibenzothiophen-4-yl)-3,1':4',1''-terphenyl-1-yl]dibenzo[f,h]quinoxaline (abbreviation: 2DBtTPDBq)

Into a 100-mL three-neck flask were put 1.7 g (5.0 mmol) of 2-(3-chlorophenyl)dibenzo[f,h]quinoxaline, 1.9 g (5.0 mmol) of 3'-(dibenzothiophen-4-yl)-4,1'-biphenylboronic acid that was synthesized in the step shown by Formula (B-2), 3.2 g (15 mmol) of tripotassium phosphate, 0.10 g (0.28 mmol) of di(1-adamantyl)-n-butylphosphine, 2 mL of t-butyl alcohol, and 25 mL of diethylene glycol dimethyl ether. This mixture was degassed under reduced pressure and then, a nitrogen gas was made to flow continuously in the system. After this mixture was heated to 140° C., 30 mg (40 μmol) of [1,1'-bis(diphenylphosphino)ferrocene]palladium(II) dichloride was added and stirring was performed at the same temperature for 3.5 hours. After the stirring, the precipitated solid was collected by suction filtration, and the resulting solid was washed with ethanol and water. The resulting solid was subjected to heat filtration using chloroform and the filtrate was concentrated, whereby 2.0 g of a solid of the target substance was obtained in a yield of 63%. The synthesis scheme of this step is shown in Formula (B-3).

[Chemical formula 235]

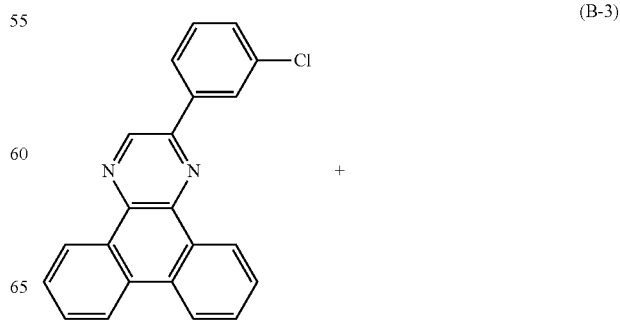

-continued

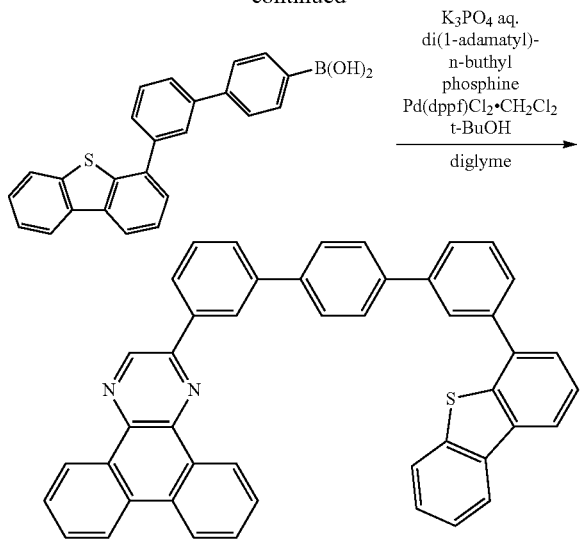

The obtained solid was subjected to nuclear magnetic resonance spectrometry ($^1$H NMR), and the results are shown below.

$^1$H NMR (tetrachloroethane-d$_2$, 500 MHz): δ=7.53-7.55 (m, 2H), 7.65-7.66 (m, 2H), 7.69 (t, J=8.0 Hz, 1H), 7.76 (t, J=8.0 Hz, 1H), 7.80-7.93 (m, 12H), 8.14 (s, 1H), 8.23-8.27 (m, 2H), 8.38 (d, J=8.0 Hz, 1H), 8.70-8.72 (m, 3H), 9.33 (d, J=8.0 Hz, 1H), 9.49 (d, J=8.0 Hz, 1H), 9.53 (s, 1H)

Figure 17A:
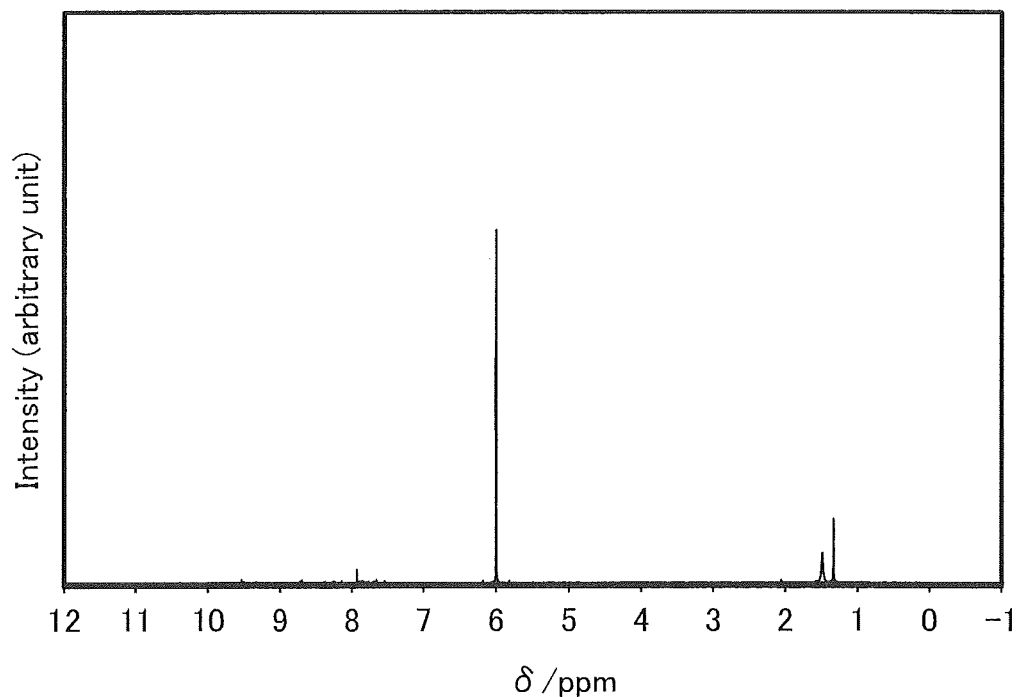
FIGS. 17A and 17B show NMR charts of 2DBtTPDBq.
Figure 17B:
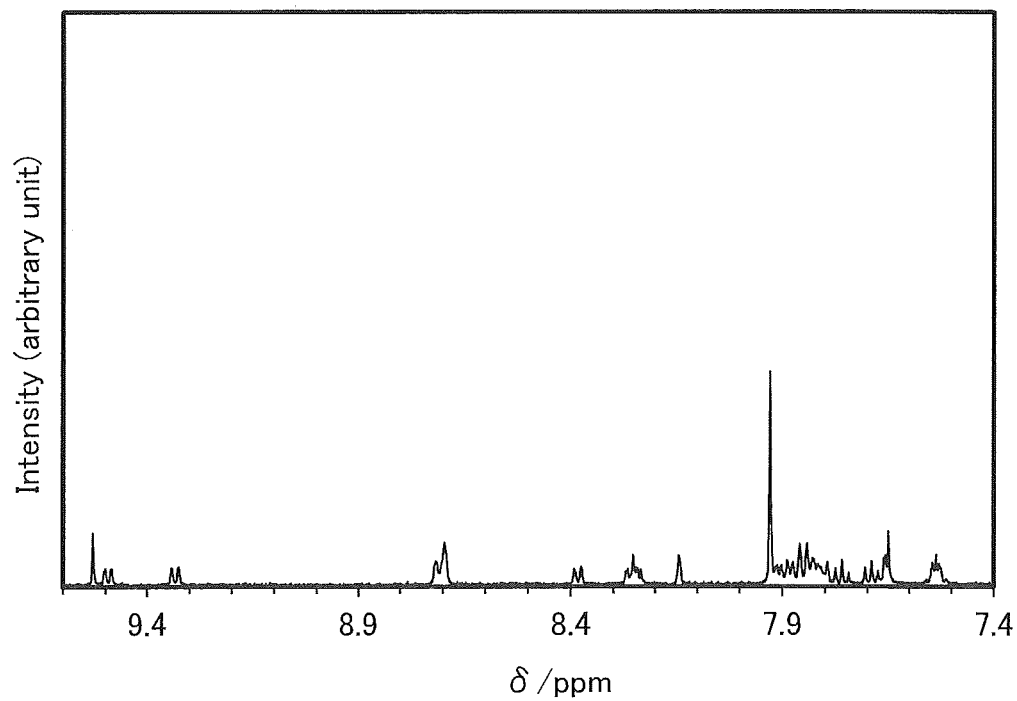

FIGS. 17A and 17B are $^1$H NMR charts. Note that FIG. 17B is a chart showing an enlarged part in the range of 7.4 ppm to 9.6 ppm of FIG. 17A. The results revealed that 2DBtTPDBq, which was the target substance, was obtained.

By a train sublimation method, 2.0 g of the solid was purified. In the sublimation purification, the solid was heated at 340° C. for 14 hours under a pressure of 2.9 Pa with a flow rate of argon of 15 mL/min. After the purification, 1.2 g of a powder of the target substance was obtained at a collection rate of 60%.

Physical Properties of 2-[3"-(dibenzothiophen-4-yl)-3,1':4',1"-terphenyl-1-yl]dibenzo[f,h]quinoxaline (Abbreviation: 2DBtTPDBq)

Figure 18:
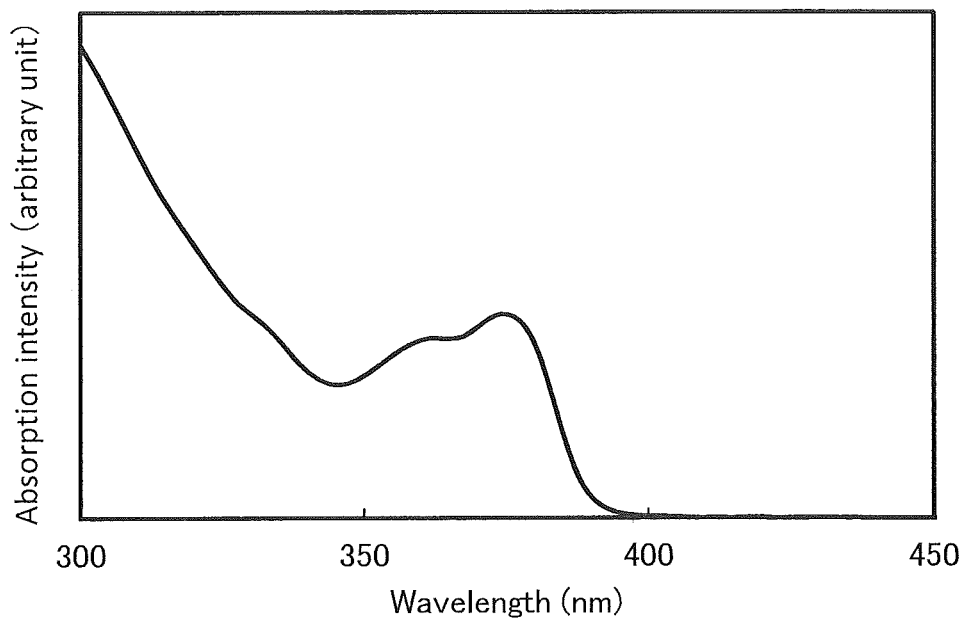
FIG. 18 shows an absorption spectrum of a solution of 2DBtTPDBq.
Figure 19:
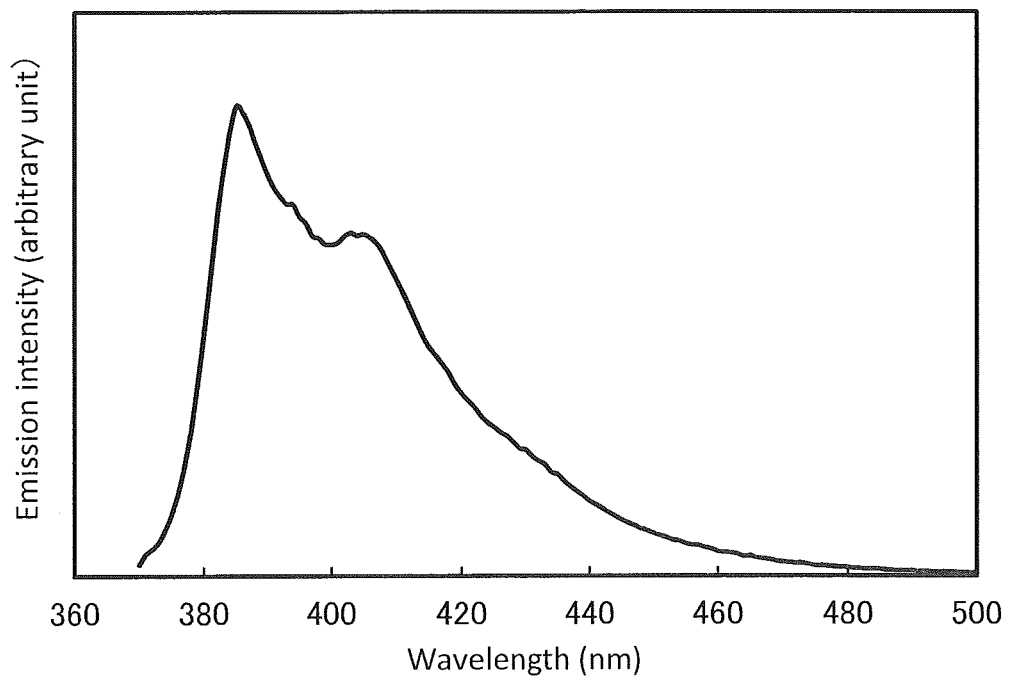
FIG. 19 shows an emission spectrum of a solution of 2DBtTPDBq.
Figure 20:
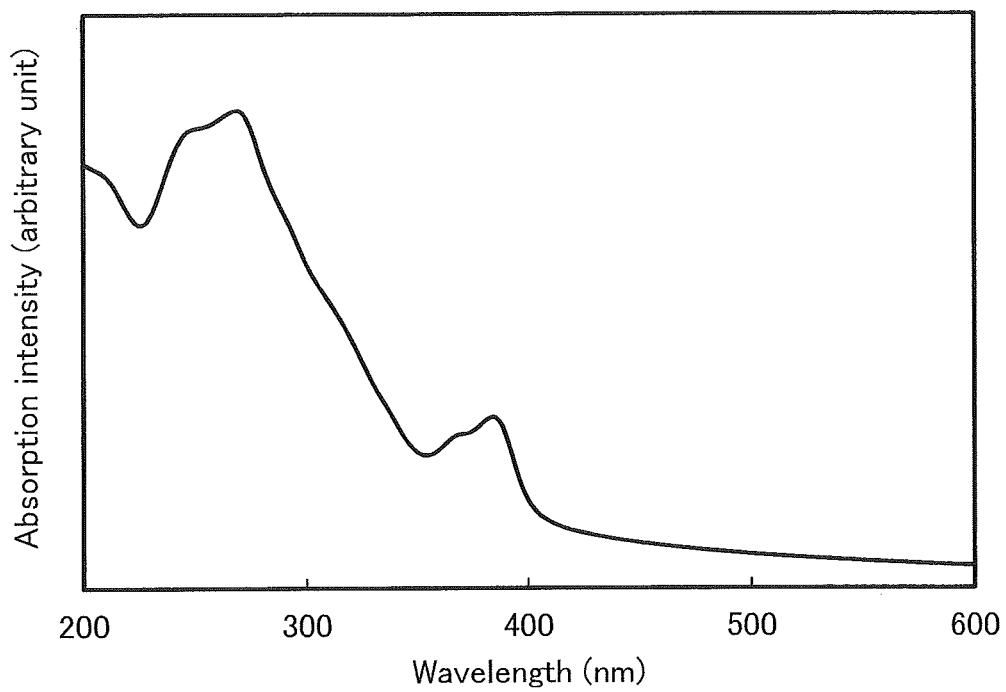
FIG. 20 shows an absorption spectrum of a thin film of 2DBtTPDBq.
Figure 21:
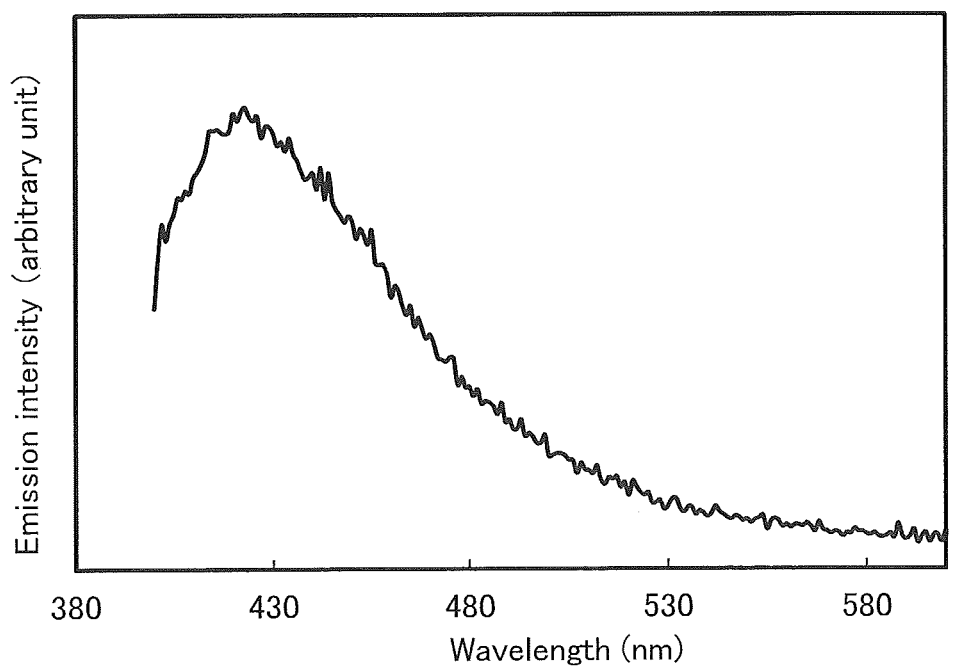
FIG. 21 shows an emission spectrum of a thin film of 2DBtTPDBq.

FIG. 18 shows an absorption spectrum of a toluene solution of 2DBtTPDBq that was measured by a method similar to that for 2mDBtTPDBq-II, and FIG. 19 shows an emission spectrum thereof. FIG. 20 shows an absorption spectrum of a thin film of 2DBtTPDBq that was measured by a method similar to that for 2mDBtTPDBq-II, and FIG. 21 shows an emission spectrum thereof.

As observed in FIG. 18 and FIG. 19, absorption peaks of the toluene solution of 2DBtTPDBq are at approximately 361 nm, 332 nm, and 282 nm, and emission wavelength peaks thereof are at 385 nm and 405 nm (excitation wavelength: 357 nm). As observed in FIG. 20 and FIG. 21, absorption peaks of the thin film of 2DBtTPDBq are at approximately 210 nm, 249 nm, 269 nm, 293 nm, 319 nm, 339 nm, 368 nm, and 384 nm, and an emission wavelength peak thereof is at approximately 423 nm (excitation wavelength: 385 nm). It was found that 2DBtTPDBq emitted bluish purple light. The compound of one embodiment of the present invention can be used as a host material for a light-emitting substance or a host material for a substance emitting fluorescence in the visible region.

Figure 22:
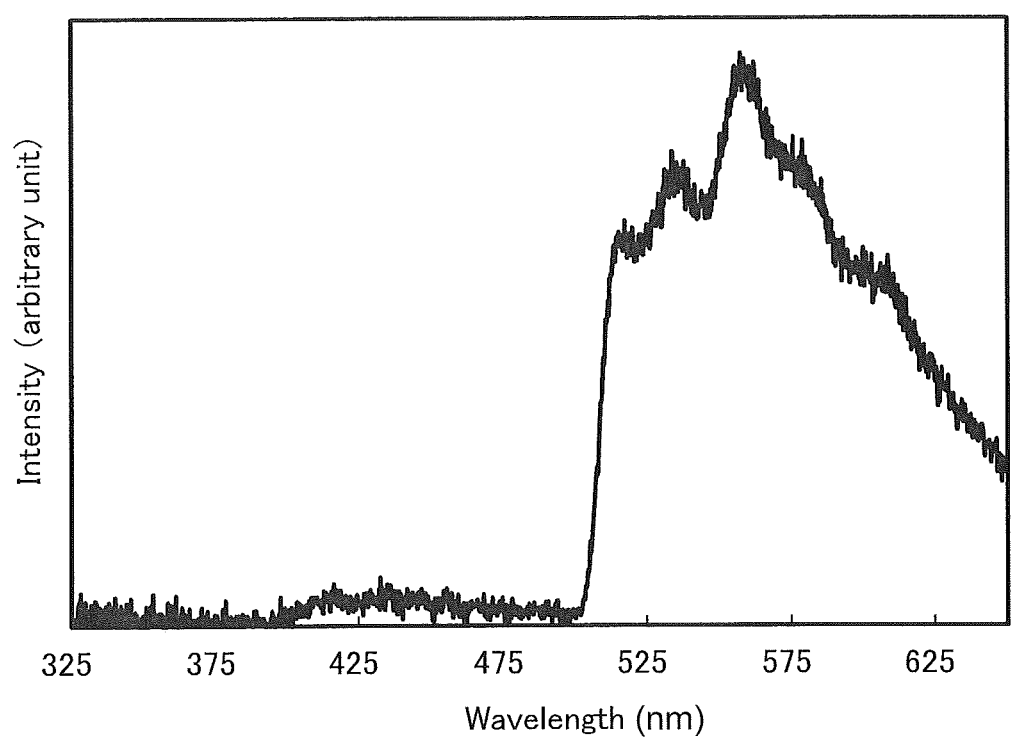
FIG. 22 shows a phosphorescence spectrum of 2DBtTPDBq.

Phosphorescence of 2DBtTPDBq was measured by a method similar to that for 2mDBtTPDBq-II. FIG. 22 shows the obtained phosphorescence spectrum. The results showed that the peak on the shortest wavelength side of the phosphorescence spectrum of 2DBtTPDBq is at 517 nm, which means that 2DBtTPDBq has a high T$_1$ level. It was found that aggregation of the thin film of 2DBtTPDBq is not easily caused even under the air and the thin film suffers only a small change in shape and has high film quality.

The characteristics of oxidation-reduction reaction were examined by cyclic voltammetry (CV) measurement. The measurement was performed by a method similar to that for 2mDBtTPDBq-II. According to the measurement results, the oxidation potential was not observed and the reduction potential was −2.99 eV.

Example 3

Synthesis Example 3

In this synthesis example, a method for synthesizing 2-[4"-(dibenzothiophen-4-yl)-3,1':4',1"-terphenyl-1-yl]dibenzo[f,h]quinoxaline (abbreviation: 2DBtTPDBq-03) (Structural Formula (2003)) that is the heterocyclic compound described in Embodiments 1 and 2 is described. The structural formula of 2DBtTPDBq-03 is shown below.

[Chemical formula 236]

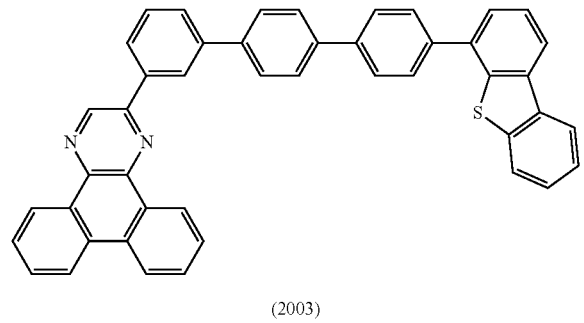

(2003)

Synthesis of 4-(4-bromophenyl)dibenzothiophene

Into a 300-mL three-neck flask were put 5.0 g (22 mmol) of dibenzothiophen-4-ylboronic acid, 6.2 g (22 mmol) of 4-bromoiodobenzene, 0.31 g (1.0 mmol) of tris(2-methylphenyl)phosphine, 110 mL of toluene, 10 mL of ethanol, and 30 mL of an aqueous solution of potassium carbonate (2 mol/L). The mixture was degassed under reduced pressure and then, a nitrogen gas was made to flow continuously in the system. The obtained mixture was heated to 80° C. Then, 100 mg (0.44 mmol) of palladium(II) acetate was added and stirring was performed for 11 hours. After the stirring, the aqueous layer of this mixture was subjected to extraction with toluene, the solution of the extract and the organic layer were combined, and this mixture was washed with saturated brine and dried with anhydrous magnesium sulfate. The resulting mixture was gravity-filtered, and then the obtained solution was concentrated to give a brown solid. The obtained solid was purified by silica gel column chromatography (developing solvent: hexane) and then recrystallized with hexane/chloroform; thus, 5.5 g of a white solid of the target substance was obtained in a yield of 74%. The synthesis scheme of this step is shown in Formula (C-1).

567

[Chemical formula 237]

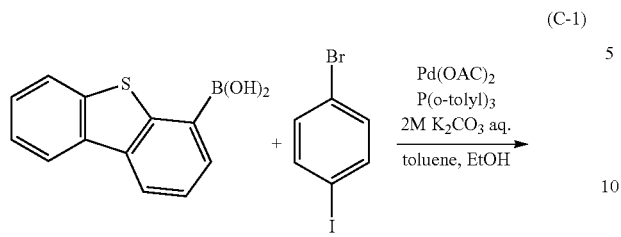

Synthesis of 4-(dibenzothiophen-4-yl)phenylboronic acid

Into a 300-mL three-neck flask was put 6.7 g (20 mmol) of 4-(4-bromophenyl)dibenzothiophene that was synthesized in the step shown by Formula (C-1). After a nitrogen gas was made to flow continuously in the system, 200 mL of dehydrated tetrahydrofuran was added. This solution was cooled down to −78° C., 15 mL (24.0 mmol) of an n-butyllithium hexane solution (1.6 mol/L) was dropped with a syringe, and then, stirring was performed at the same temperature for 1.5 hours. After the stirring, 3 mL (26.8 mmol) of trimethyl borate was added at the same temperature and the resulting solution was stirred at room temperature for 20 hours. After the stirring, 90 mL of hydrochloric acid (1 mol/L) was added and the aqueous layer of the resulting mixture was subjected to extraction with ethyl acetate. The obtained solution of the extract and the organic layer were combined, and this mixture was washed with an aqueous solution of sodium hydrogen carbonate and saturated brine and dried with anhydrous magnesium sulfate. The resulting mixture was gravity-filtered and the filtrate was concentrated to give a pale yellow solid. The solid was washed with chloroform/hexane, whereby 4.0 g of a white solid of the target substance was obtained in a yield of 77%. The synthesis scheme of this step is shown in Formula (C-2).

[Chemical formula 238]

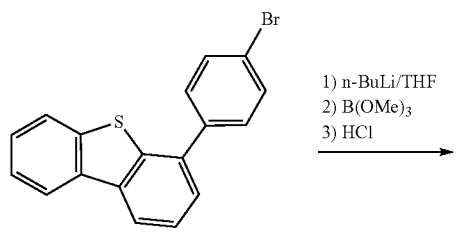

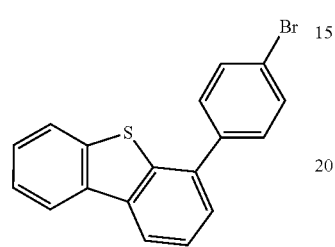

568

-continued

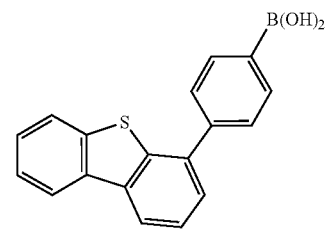

Synthesis of 4-(4'-bromo-4,1'-biphenyl-1-yl)dibenzothiophene

Into a 200-mL three-neck flask were put 3.7 g (12 mmol) of 4-(dibenzothiophen-4-yl)phenylboronic acid that was synthesized in the step shown by Formula (C-1), 3.4 g (12 mmol) of 4-bromoiodobenzene, 0.20 g (0.65 mmol) of tris(2-methylphenyl)phosphine, 20 mL of an aqueous solution of potassium carbonate (2 mol/L), 60 mL of toluene, and 6 mL of ethanol. The mixture was degassed under reduced pressure and then, a nitrogen gas was made to flow continuously in the system. The resulting mixture was heated to 80° C., 30 mg (0.13 mmol) of palladium(II) acetate was added, and stirring was performed at the same temperature for 7 hours. After the stirring, the aqueous layer of the mixture was subjected to extraction with chloroform, the solution of the extract and the organic layer were combined, and this mixture was washed with saturated brine and dried with anhydrous magnesium sulfate. The obtained mixture was gravity-filtered, and then the obtained filtrate was concentrated to give a solid. The obtained solid was purified by silica gel column chromatography (developing solvent: chloroform) and recrystallized with chloroform/hexane; thus, 3.3 g of a solid of the target substance was obtained in a yield of 66%. The synthesis scheme of this step is shown in Formula (C-3).

[Chemical formula 239]

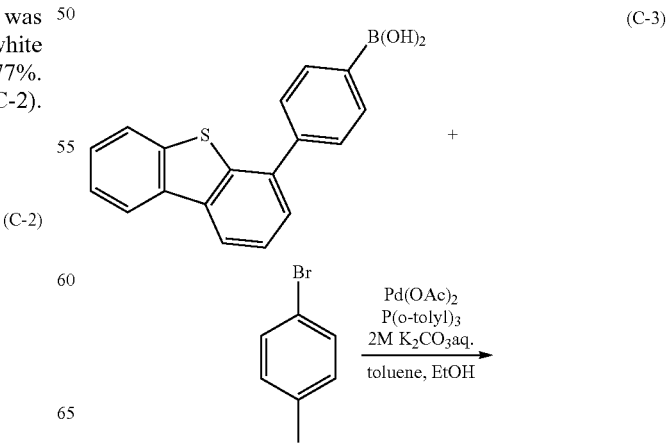

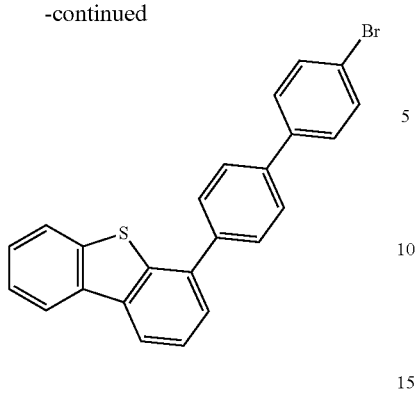

Synthesis of 4'-(dibenzothiophen-4-yl)-4,1'-biphenylboronic acid

Into a 200-mL three-neck flask was put 3.3 g (7.9 mmol) of 4-(4'-bromo-4,1'-biphenyl-1-yl)dibenzothiophene that was synthesized in the step shown by Formula (C-3). After a nitrogen gas was made to flow continuously in the system, 80 mL of dehydrated tetrahydrofuran was added. This solution was cooled down to −78° C., 5.5 mL (8.8 mmol) of an n-butyllithium hexane solution (1.6 mol/L) was dropped with a syringe, and then, stirring was performed at the same temperature for 1.5 hours. After the stirring, 1.1 mL (9.8 mmol) of trimethyl borate was added at the same temperature and the resulting solution was stirred at room temperature for 20 hours. After the stirring, 30 mL of hydrochloric acid (1 mol/L) was added and the aqueous layer of the resulting mixture was subjected to extraction with ethyl acetate. The obtained solution of the extract and the organic layer were combined, and this mixture was washed with an aqueous solution of sodium hydrogen carbonate and saturated brine and dried with anhydrous magnesium sulfate. The resulting mixture was gravity-filtered and the filtrate was concentrated to give a pale yellow solid. The solid was washed with chloroform/hexane, whereby 2.5 g of a white solid of the target substance was obtained in a yield of 83%. The synthesis scheme of this step is shown in Formula (C-4).

[Chemical formula 240]

(C-4)

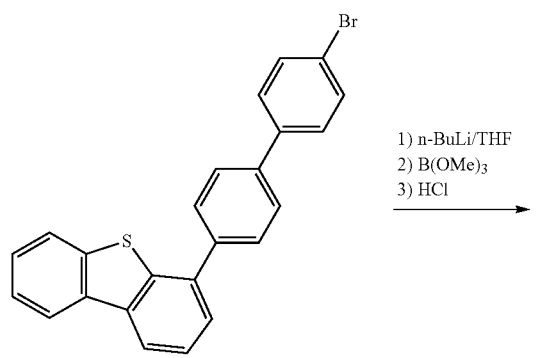

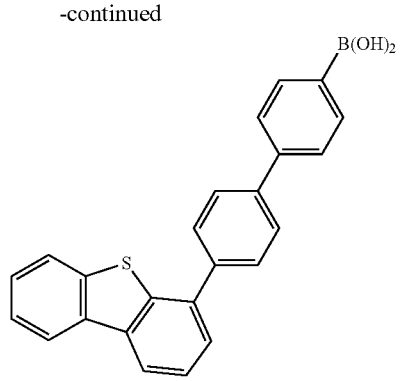

Method for Synthesizing 2-[4''-(dibenzothiophen-4-yl)-3,1':4',1''-terphenyl-1-yl]dibenzo[f,h]quinoxaline (Abbreviation: 2DBtTPDBq-03)

Into a 200-mL three-neck flask were put 2.3 g (6.7 mmol) of 2-(3-chlorophenyl)dibenzo[f,h]quinoxaline, 2.5 g (6.5 mmol) of 4'-(dibenzothiophen-4-yl)-4,1'-biphenylboronic acid that was synthesized in the step shown by Formula (C-4), 4.1 g (20 mmol) of tripotassium phosphate, 0.12 g (0.34 mmol) of di(1-adamantyl)-n-butylphosphine, 2 mL of t-butyl alcohol, and 30 mL of diethylene glycol dimethyl ether. This mixture was degassed under reduced pressure and then, a nitrogen gas was made to flow continuously in the system. After this mixture was heated to 140° C., 10 mg (65 μmol) of palladium(II) acetate was added and stirring was performed at the same temperature for 5 hours. After the stirring, the precipitated solid was collected by suction filtration and was washed with water and ethanol. After the washing, the resulting solid was subjected to heat filtration using chloroform and the filtrate was concentrated, whereby 2.0 g of a light black solid was obtained. The synthesis scheme of this step is shown in Formula (C-5).

[Chemical formula 241]

(C-5)

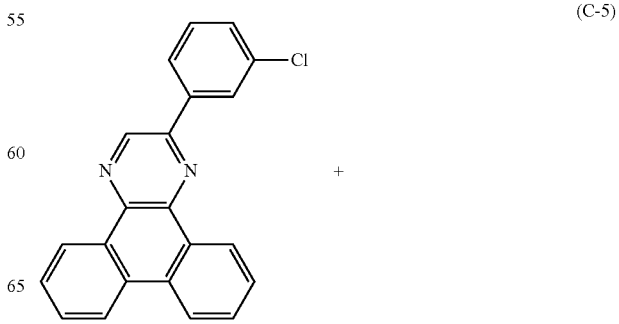

-continued

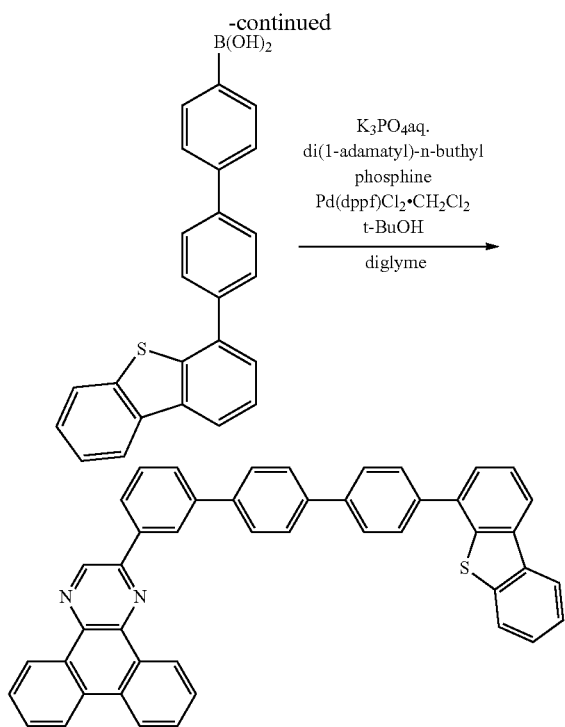

The obtained solid was subjected to nuclear magnetic resonance spectrometry (¹H NMR), and the results are shown below.

¹H NMR (chloroform-d, 500 MHz): δ=7.49-7.51 (m, 2H), 7.57-7.63 (m, 2H), 7.73 (t, J=8.0 Hz, 1H), 7.78-7.91 (m, 14H), 8.19-8.23 (m, 2H), 8.35 (d, J=8.0 Hz, 1H), 8.67-8.69 (m, 3H), 9.27 (d, J=8.0 Hz, 1H), 9.47 (d, J=8.0 Hz, 1H), 9.49 (s, 1H)

Figure 23A:
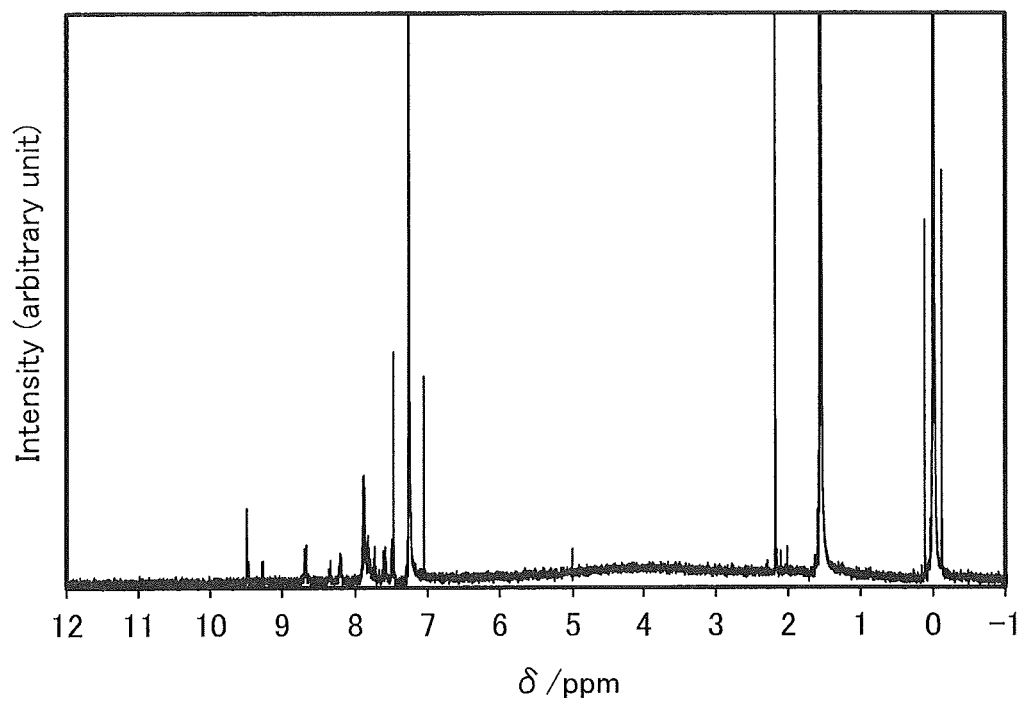
FIGS. 23A and 23B show NMR charts of 2DBtTPDBq-03.
Figure 23B:
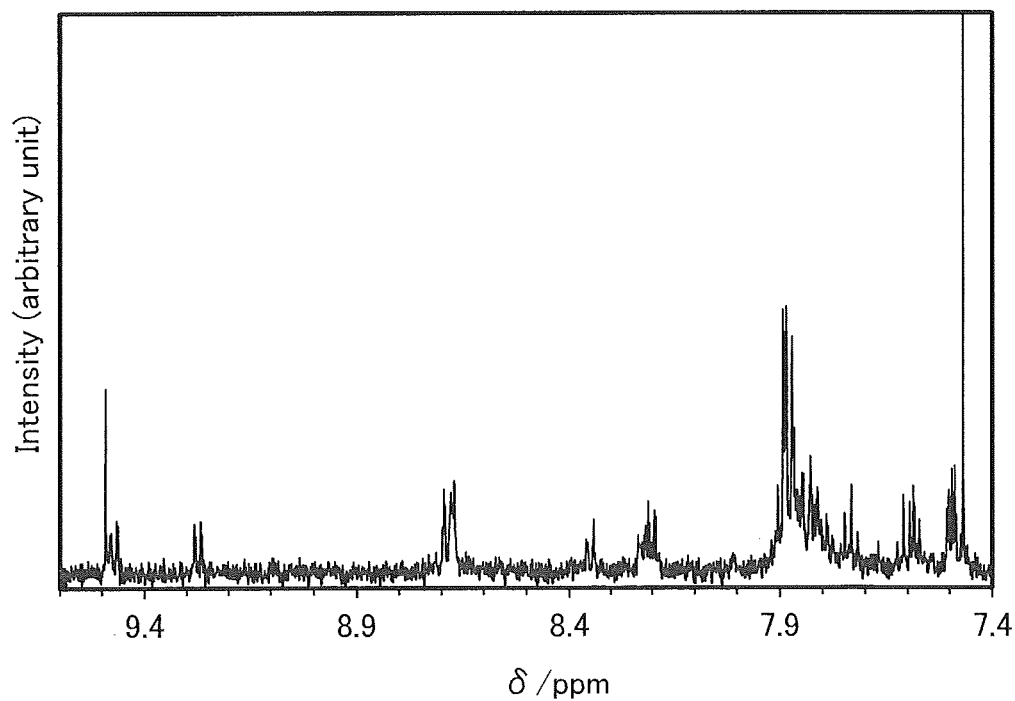

FIGS. 23A and 23B are ¹H NMR charts. Note that FIG. 23B is a chart showing an enlarged part in the range of 7.4 ppm to 9.6 ppm of FIG. 23A. The results revealed that 2DBtTPDBq-03, which was the target substance, was obtained.

By a train sublimation method, 2.0 g of the solid was purified. In the sublimation purification, the solid was heated at 365° C. for 14.5 hours under a pressure of 3.4 Pa with a flow rate of argon of 15 mL/min. After the purification, 1.4 g of a powder of the target substance was obtained at a collection rate of 71%.

Physical Properties of 2-[4"-(dibenzothiophen-4-yl)-3,1':4',1"-terphenyl-1-yl]dibenzo[f,h]quinoxaline (Abbreviation: 2DBtTPDBq-03)

Figure 24:
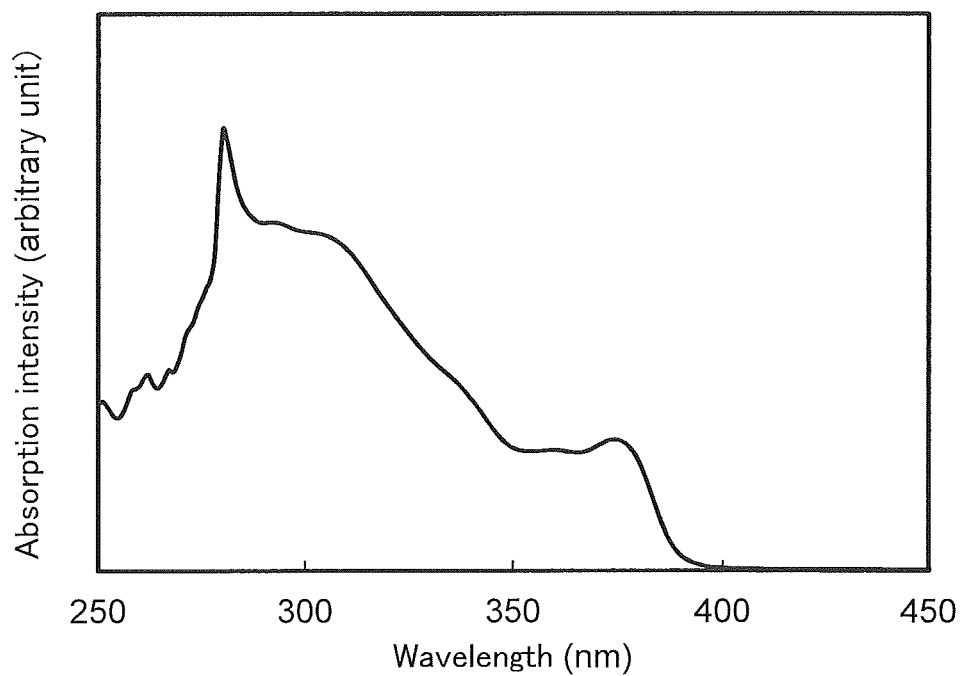
FIG. 24 shows an absorption spectrum of a solution of 2DBtTPDBq-03.
Figure 25:
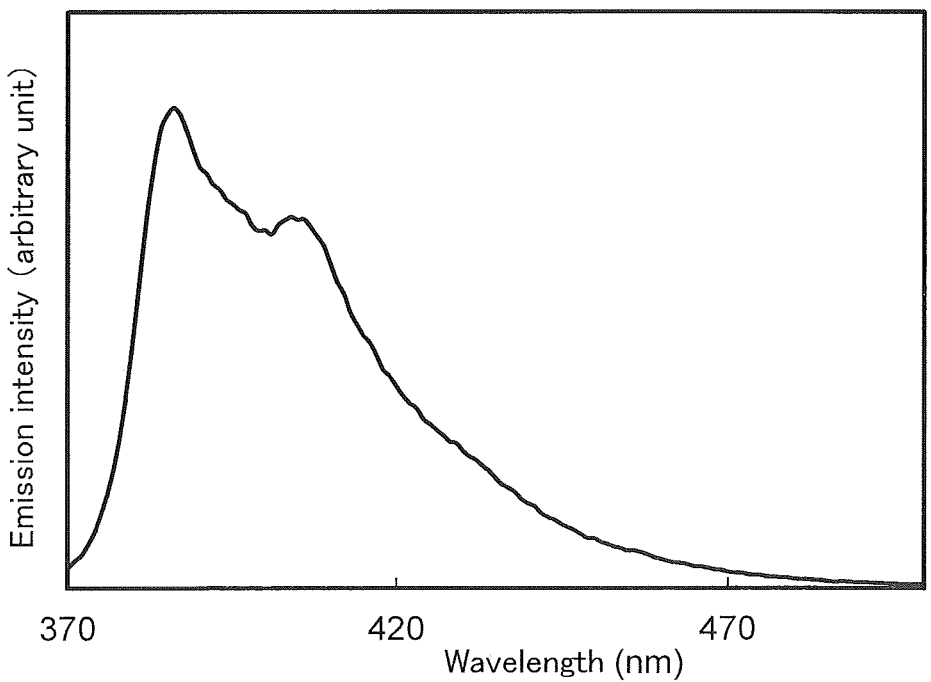
FIG. 25 shows an emission spectrum of a solution of 2DBtTPDBq-03.
Figure 26:
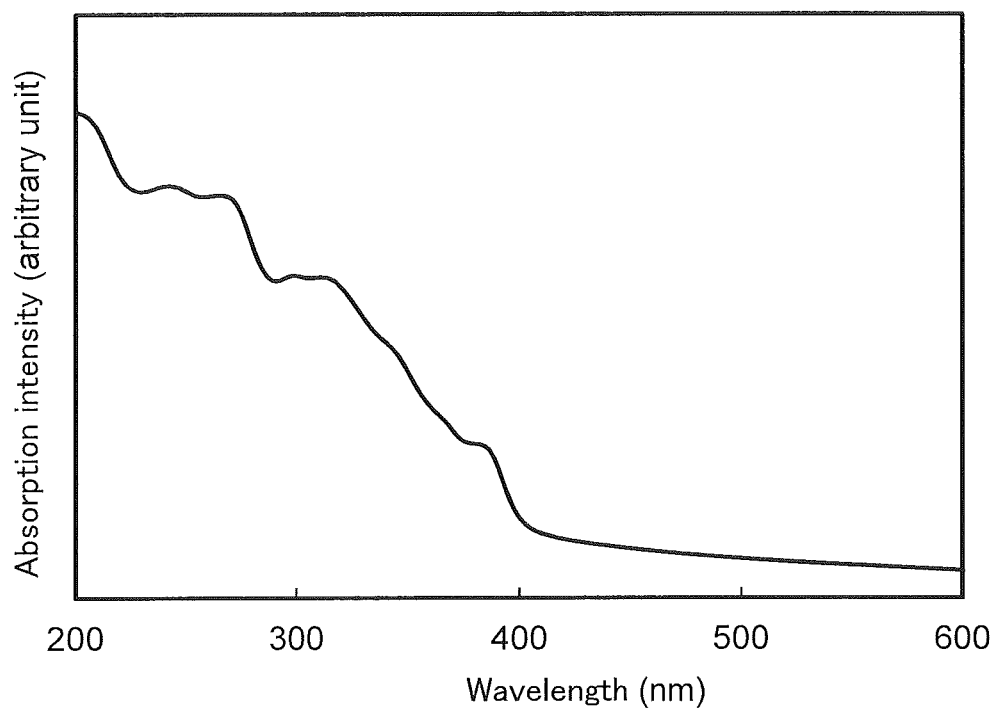
FIG. 26 shows an absorption spectrum of a thin film of 2DBtTPDBq-03.
Figure 27:
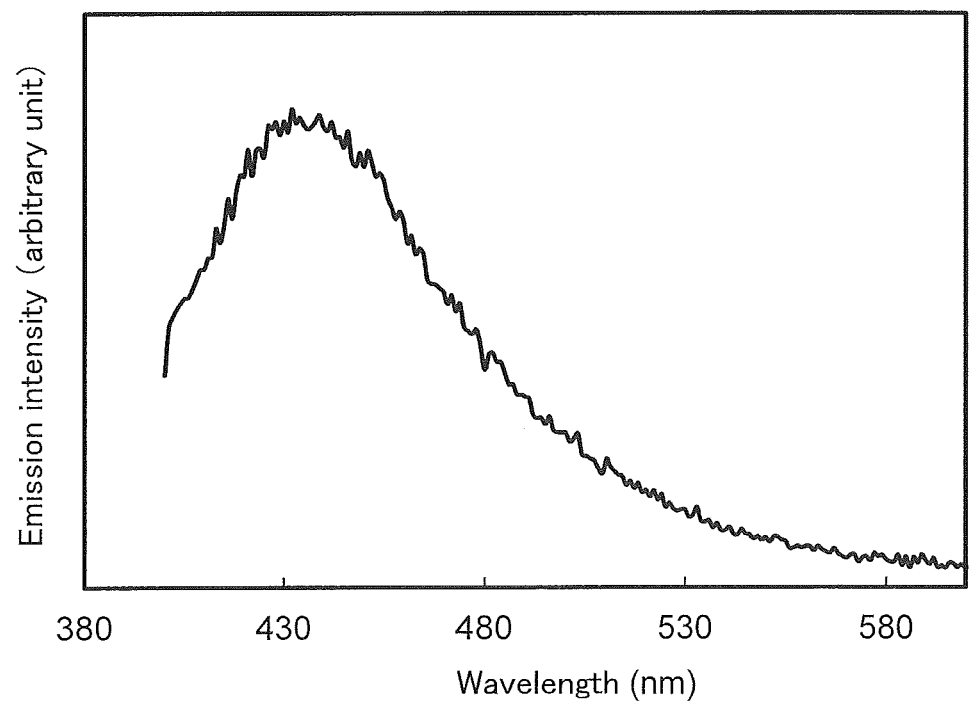
FIG. 27 shows an emission spectrum of a thin film of 2DBtTPDBq-03.

FIG. 24 shows an absorption spectrum of a toluene solution of 2DBtTPDBq-03 that was measured by a method similar to that for 2mDBtTPDBq-II, and FIG. 25 shows an emission spectrum thereof. FIG. 26 shows an absorption spectrum of a thin film of 2DBtTPDBq-03 that was measured by a method similar to that for 2mDBtTPDBq-II, and FIG. 27 shows an emission spectrum thereof.

As observed in FIG. 24 and FIG. 25, absorption peaks of the toluene solution of 2DBtTPDBq-03 are at approximately 294 nm, 304 nm, 361 nm, and 374 nm, and emission wavelength peaks thereof are at 378 nm and 405 nm (excitation wavelength: 360 nm). As observed in FIG. 26 and FIG. 27, absorption peaks of the thin film of 2DBtTPDBq-03 are at approximately 242 nm, 266 nm, 299 nm, 314 nm, 346 nm, 368 nm, and 383 nm, and an emission wavelength peak thereof is at approximately 436 nm (excitation wavelength: 383 nm). It was found that 2DBUPDBq-03 emitted bluish purple light. The compound of one embodiment of the present invention can be used as a host material for a light-emitting substance or a host material for a substance emitting fluorescence in the visible region.

Figure 28:
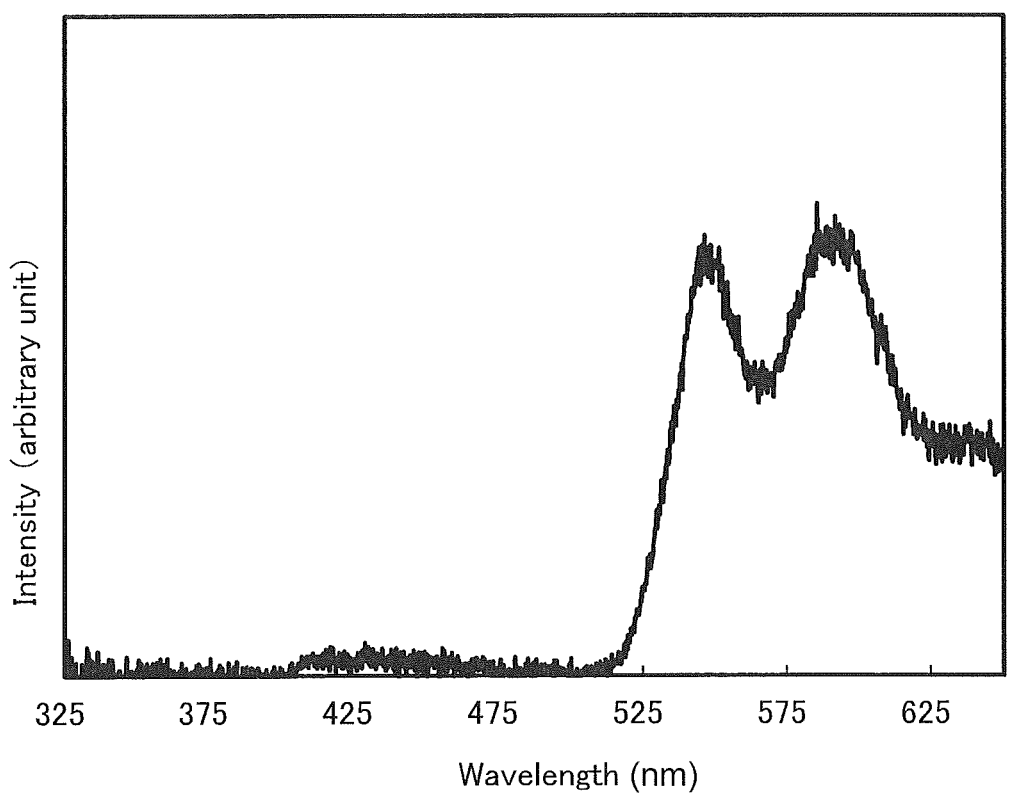
FIG. 28 shows a phosphorescence spectrum of 2DBtTPDBq-03.

Phosphorescence of 2DBtTPDBq-03 was measured by a method similar to that for 2mDBtTPDBq-II. FIG. 28 shows the obtained phosphorescence spectrum. The results showed that the peak on the shortest wavelength side of the phosphorescence spectrum of 2DBtTPDBq-03 is at 545 nm, which means that 2DBtTPDBq-03 has a high $T_1$ level. It was found that aggregation of the thin film of 2DBtTPDBq-03 is not easily caused even under the air and the thin film suffers only a small change in shape and has high film quality.

The characteristics of oxidation-reduction reaction were examined by cyclic voltammetry (CV) measurement. The measurement was performed by a method similar to that for 2mDBtTPDBq-II. According to the measurement results, the oxidation potential was −6.15 eV and the reduction potential was −2.95 eV. When the oxidation potential was regarded as a HOMO level and the reduction potential was regarded as a LUMO level, a gap between the HOMO level and the LUMO level was estimated to be 3.20 eV, which indicated that 2DBtTPDBq-03 has a wide band gap.

Example 4

Synthesis Example 4

In this synthesis example, a method for synthesizing 2-[4"-(dibenzothiophen-4-yl)-4,1':3',1"-terphenyl-1-yl]dibenzo[f,h]quinoxaline (abbreviation: 2DBtTPDBq-02) (Structural Formula (2004)) that is the heterocyclic compound described in Embodiments 1 and 2 is described. The structural formula of 2DBtTPDBq-02 is shown below.

[Chemical formula 242]

(2004)

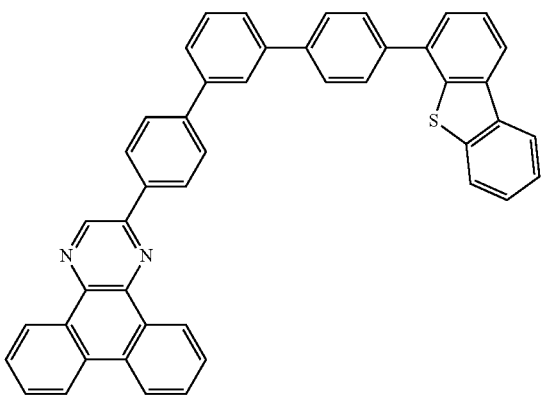

Method for Synthesizing 2-[4"-(dibenzothiophen-4-yl)-4,1':3',1"-terphenyl-1-yl]dibenzo[f,h]quinoxaline (Abbreviation: 2DBtTPDBq-02)

Into a 200-mL three-neck flask were put 1.2 g (3.5 mmol) of 2-(4-chlorophenyl)dibenzo[f,h]quinoxaline, 1.1 g (3.4 mmol) of 4'-(dibenzothiophen-4-yl)-4,1'-biphenylboronic acid whose synthesis method is described in the above example, 2.1 g (9.9 mmol) of tripotassium phosphate, 80 mg (0.22 mmol) of di(1-adamantyl)-n-butylphosphine, 1 mL of t-butyl alcohol, and 15 mL of diethylene glycol dimethyl ether. The mixture was degassed under reduced pressure and then, a nitrogen gas was made to flow continuously in the system. After that, the mixture was heated to 140° C., 20 mg (80 μmol) of palladium(II) acetate was added, and then, stirring was performed for 7 hours. After the stirring, the mixture was cooled down to room temperature and then, 10 mL of diethylene glycol dimethyl ether was added. Subsequently, 30 mg (40 μmol) of [1,1'-bis(diphenylphosphino)ferrocene]palladium(II) dichloride was added and the resulting mixture was stirred at 140° C. for 5.5 hours. After the stirring, the precipitated solid was collected by suction filtration and washed with water and ethanol. The resulting solid was subjected to heat filtration using chloroform and the filtrate was concentrated, whereby 1.3 g of a solid of the target substance was obtained in a yield of 58%. The synthesis scheme of this step is shown in Formula (D-1).

[Chemical formula 243]

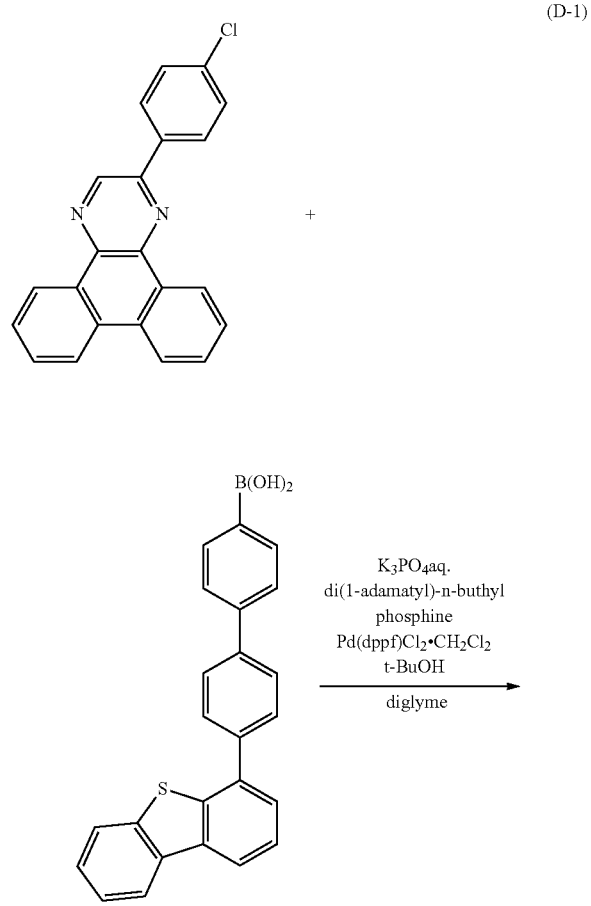

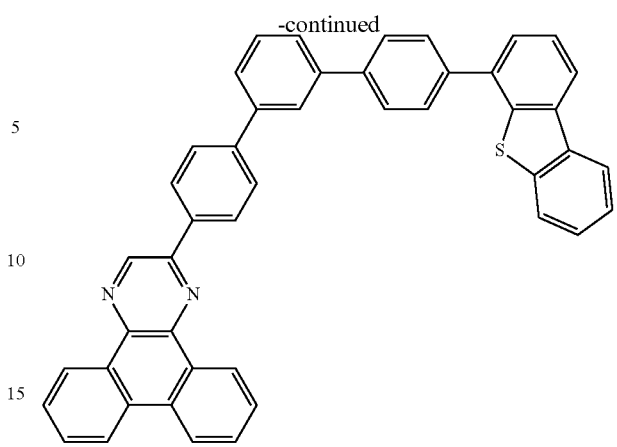

The obtained solid was subjected to nuclear magnetic resonance spectrometry ($^1$H NMR), and the results are shown below.

$^1$H NMR (tetrachloroethane-$d_2$, 500 MHz): δ=7.50-7.54 (m, 2H), 7.61-7.68 (m, 3H), 7.77-7.93 (m, 11H), 7.99 (d, J=8.0 Hz, 2H), 8.06 (s, 1H), 8.21-8.25 (m, 2H), 8.52 (d, J=8.0 Hz, 2H), 8.70 (d, J=8.0 Hz, 2H), 9.26 (d, J=8.0 Hz, 1H), 9.47 (d, J=8.0 Hz, 1H), 9.50 (s, 1H)

Figure 29A:
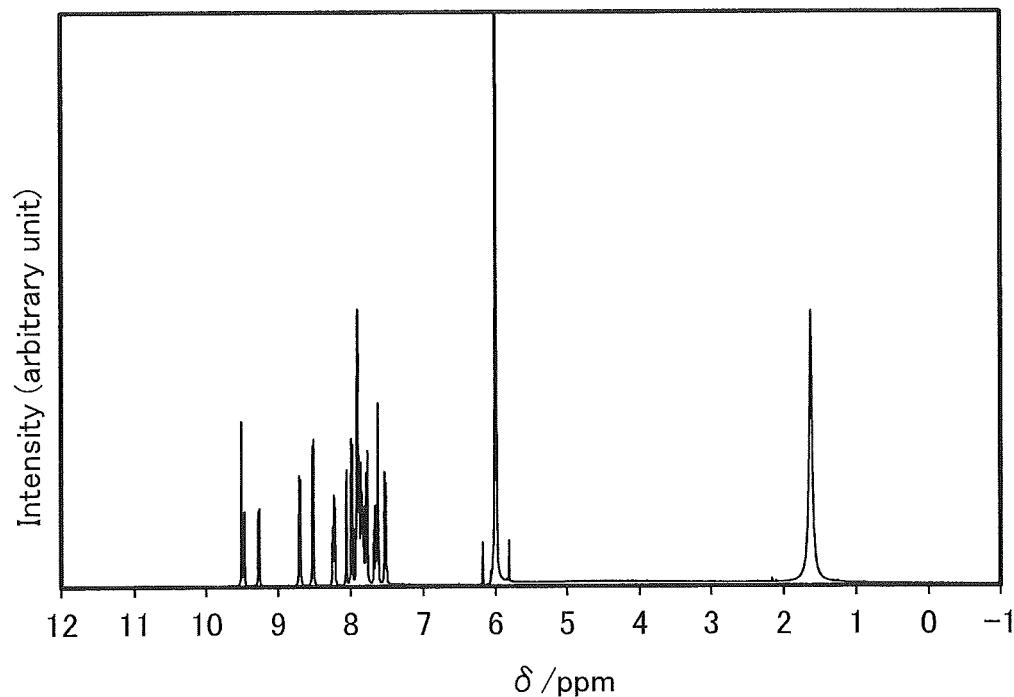
FIGS. 29A and 29B show NMR charts of 2DBtTPDBq-02.
Figure 29B:
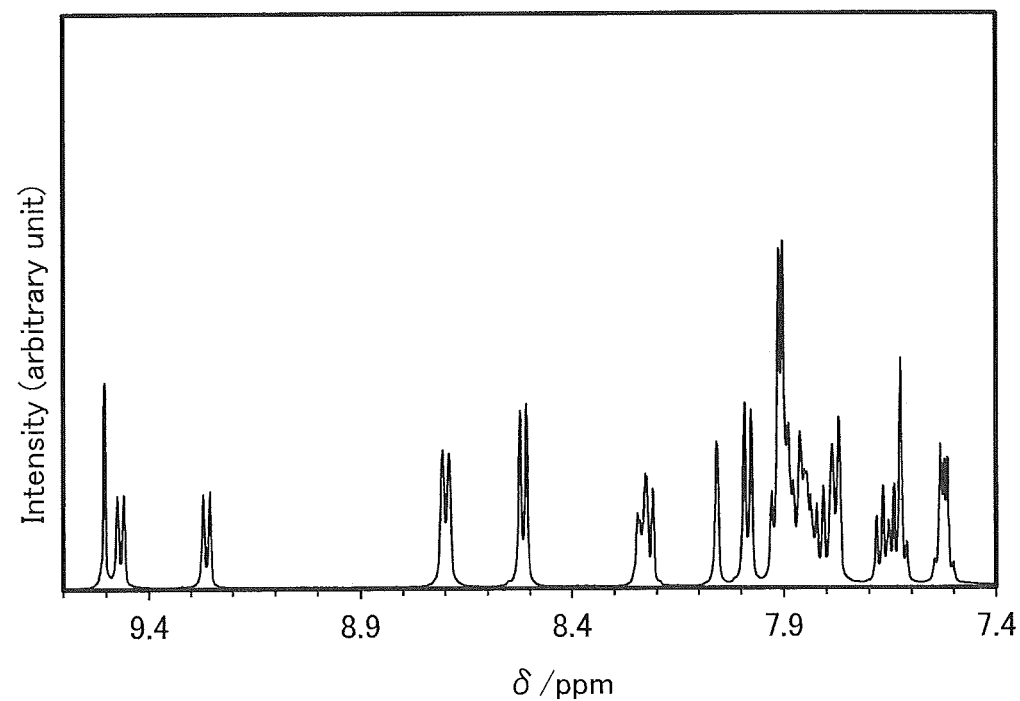

FIGS. 29A and 29B are $^1$H NMR charts. Note that FIG. 29B is a chart showing an enlarged part in the range of 7.4 ppm to 9.6 ppm of FIG. 29A. The results revealed that 2DBtTPDBq-02, which was the target substance, was obtained.

By a train sublimation method, 1.3 g of the solid was purified. In the sublimation purification, the solid was heated at 350° C. for 14.5 hours under a pressure of 2.9 Pa with a flow rate of argon of 15 mL/min. After the purification, 0.75 g of a solid of the target substance was obtained at a collection rate of 60%.

Physical Properties of 2-[4''-(dibenzothiophen-4-yl)-4,1':3',1''-terphenyl-1-yl]dibenzo[f,h]quinoxaline (Abbreviation: 2DBtTPDBq-02)

Figure 30:
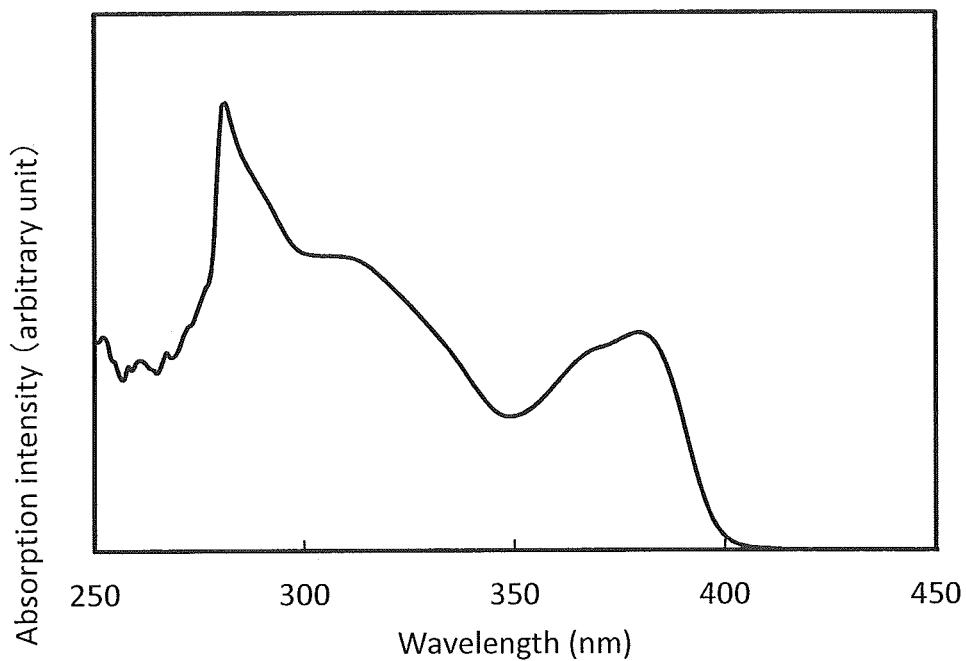
FIG. 30 shows an absorption spectrum of a solution of 2DBtTPDBq-02.
Figure 31:
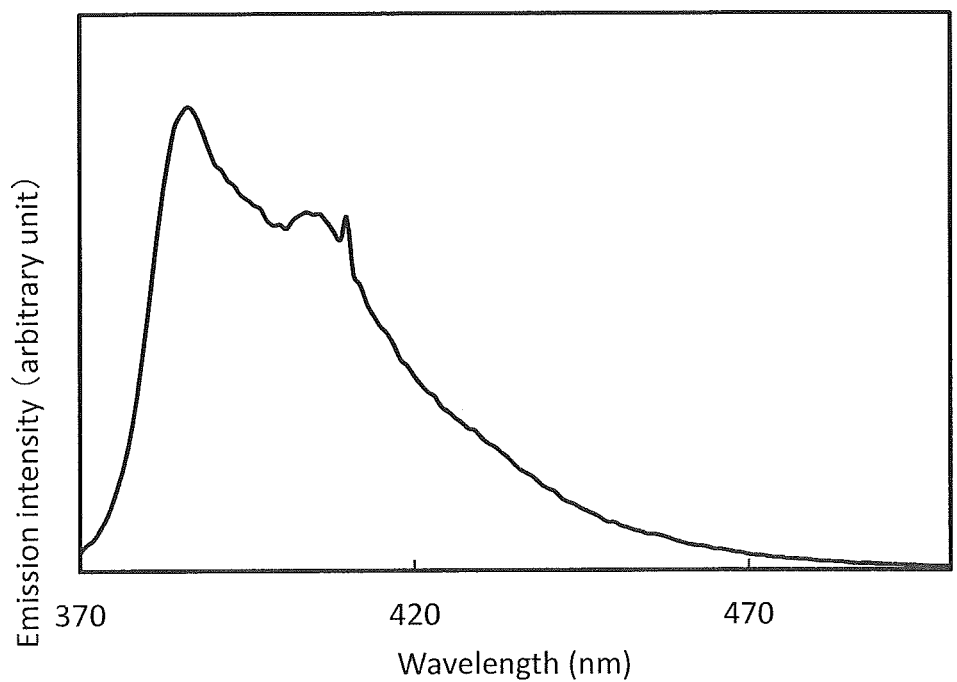
FIG. 31 shows an emission spectrum of a solution of 2DBtTPDBq-02.
Figure 32:
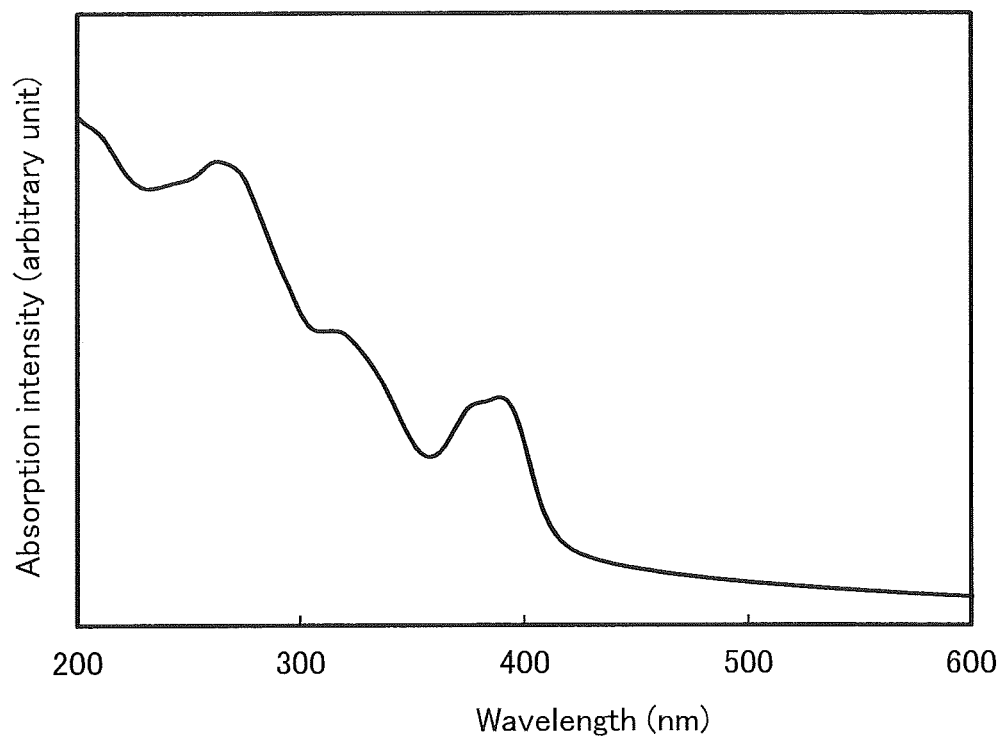
FIG. 32 shows an absorption spectrum of a thin film of 2DBtTPDBq-02.
Figure 33:
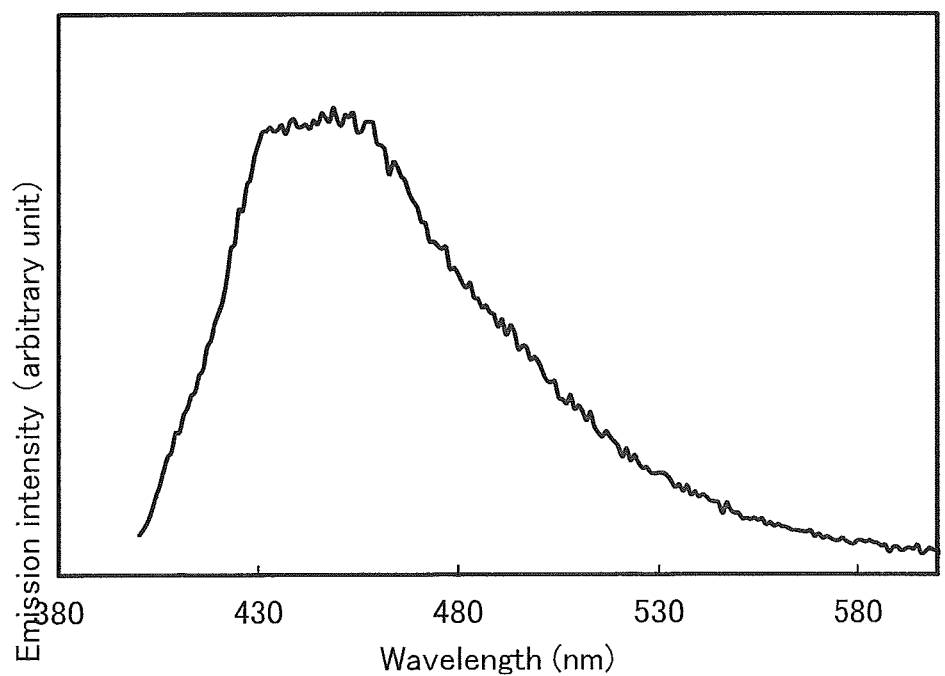
FIG. 33 shows an emission spectrum of a thin film of 2DBtTPDBq-02.

FIG. 30 shows an absorption spectrum of a toluene solution of 2DBtTPDBq-02 that was measured by a method similar to that for 2mDBtTPDBq-II, and FIG. 31 shows an emission spectrum thereof. FIG. 32 shows an absorption spectrum of a thin film of 2DBtTPDBq-02 that was measured by a method similar to that for 2mDBtTPDBq-II, and FIG. 33 shows an emission spectrum thereof.

As observed in FIG. 30 and FIG. 31, absorption peaks of the toluene solution of 2DBtTPDBq-02 are at approximately 281 nm, 311 nm, 368 nm, and 378 nm, and emission wavelength peaks thereof are at 386 nm and 405 nm (excitation wavelength: 360 nm). As observed in FIG. 32 and FIG. 33, absorption peaks of the thin film of 2DBtTPDBq-02 are at approximately 209 nm, 242 nm, 263 nm, 272 nm, 316 nm, 338 nm, 377 nm, and 389 nm, and emission wavelength peaks thereof are at approximately 450 nm and 439 nm (excitation wavelength: 439 nm). It was found that 2DBtTPDBq-02 emitted blue light. The compound of one embodiment of the present invention can be used as a host material for a light-emitting substance or a host material for a substance emitting fluorescence in the visible region.

Figure 34:
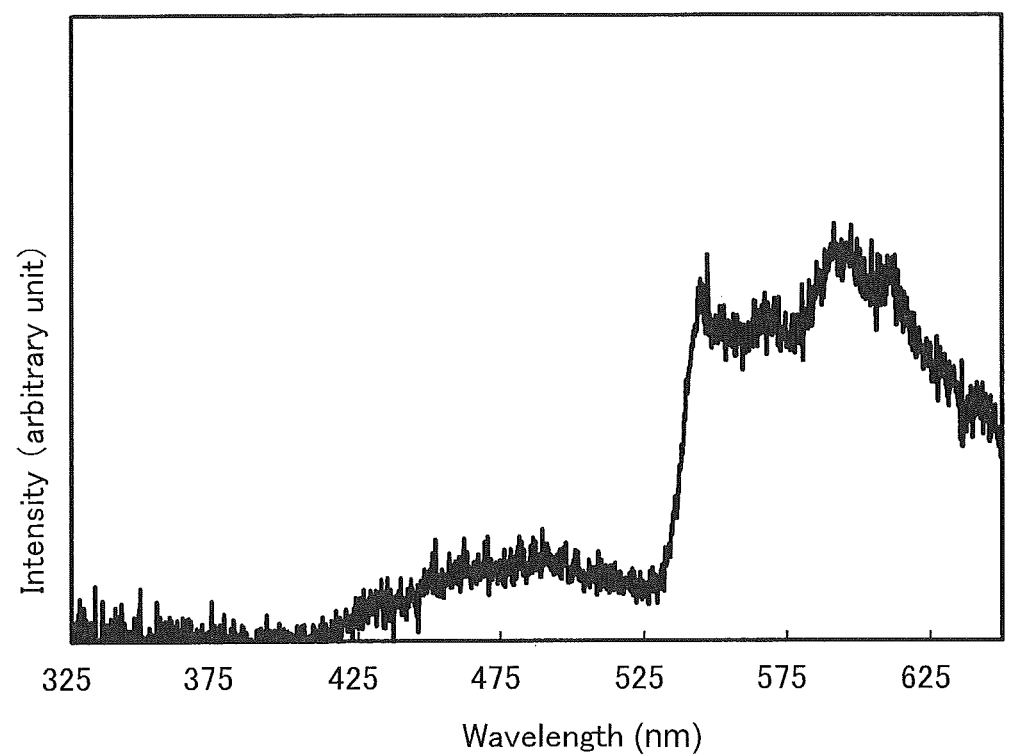
FIG. 34 shows a phosphorescence spectrum of 2DBtTPDBq-02.

Phosphorescence of 2DBtTPDBq-02 was measured by a method similar to that for 2mDBtTPDBq-II. FIG. 34 shows the obtained phosphorescence spectrum. The results showed that the peak on the shortest wavelength side of the phosphorescence spectrum of 2DBtTPDBq-02 is at 545 nm, which means that 2DBtTPDBq-02 has a high $T_1$ level. It was found that aggregation of the thin film of 2DBtTPDBq-02 is not easily caused even under the air and the thin film suffers only a small change in shape and has high film quality.

The characteristics of oxidation-reduction reaction were examined by cyclic voltammetry (CV) measurement. The measurement was performed by a method similar to that for 2mDBtTPDBq-H. According to the measurement results, the oxidation potential was −6.15 eV and the reduction potential was −2.94 eV. When the oxidation potential was regarded as a HOMO level and the reduction potential was regarded as a LUMO level, a gap between the HOMO level and the LUMO level was estimated to be 3.19 eV, which indicated that 2DBtTPDBq-02 has a wide band gap.

Example 5

Synthesis Example 5

In this synthesis example, a method for synthesizing 2-[4″-(dibenzothiophen-4-yl)-3,1′:3′,1″-terphenyl-1-yl]dibenzo[f,h]quinoxaline (abbreviation: 2DBtTPDBq-04) (Structural Formula (2005)) that is the heterocyclic compound described in Embodiments 1 and 2 is described. The structural formula of 2DBtTPDBq-04 is shown below.

[Chemical formula 244]

(2005)

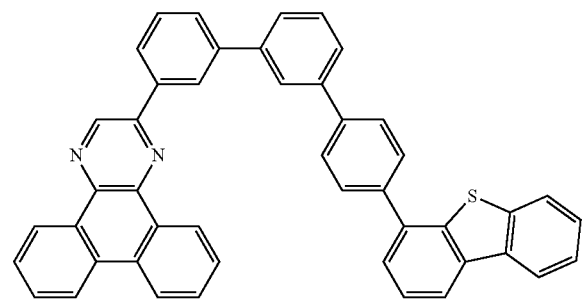

Synthesis of 4-(3′-bromo-4,1′-biphenyl-1-yl)dibenzothiophene

Into a 200-mL three-neck flask were put 3.9 g (13 mmol) of 4-(dibenzothiophen-4-yl)phenylboronic acid whose synthesis method is described in the above example, 3.6 g (13 mmol) of 3-bromoiodobenzene, 0.20 g (0.65 mmol) of tris(2-methylphenyl)phosphine, 20 mL of an aqueous solution of potassium carbonate (2 mol/L), 64 mL of toluene, and 6 mL of ethanol. The mixture was degassed under reduced pressure and then, a nitrogen gas was made to flow continuously in the system. The obtained mixture was heated to 80° C. Then, 30 mg (0.13 mmol) of palladium(II) acetate was added and stirring was performed at the same temperature for 6 hours. After the stirring, the aqueous layer of the mixture was subjected to extraction with chloroform, the solution of the extract and the organic layer were combined, and this mixture was washed with saturated brine and dried with anhydrous magnesium sulfate. The resulting mixture was gravity-filtered, and then the filtrate was concentrated to give a solid. The obtained solid was purified by silica gel column chromatography (developing solvent: chloroform) and then recrystallized with chloroform/hexane; thus, 3.8 g of a solid of the target substance was obtained in a yield of 71%. The synthesis scheme of this step is shown in Formula (E-1).

[Chemical formula 245]

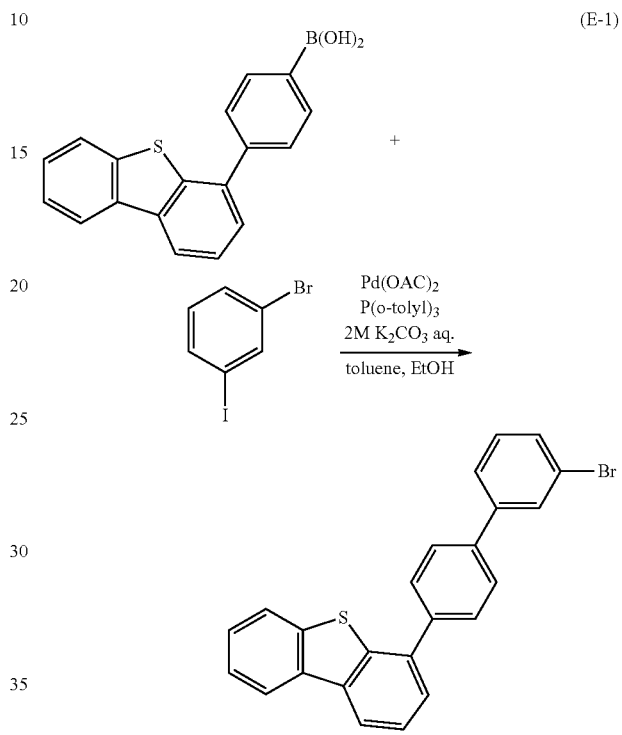

(E-1)

Synthesis of 4′-(dibenzothiophen-4-yl)-3,1′-biphenylboronic acid

Into a 200-mL three-neck flask was put 3.7 g (8.9 mmol) of 4-(3′-bromo-4,1′-biphenyl-1-yl)dibenzothiophene that was synthesized in the step shown by Formula (E-1). After a nitrogen gas was made to flow continuously in the system, 90 mL of dehydrated tetrahydrofuran was added. This solution was cooled down to −78° C., 6.1 mL (8.9 mmol) of an n-butyllithium hexane solution (1.6 mol/L) was dropped with a syringe, and then, stirring was performed at the same temperature for 1.5 hours. After the stirring, 1.2 mL (11 mmol) of trimethyl borate was added at the same temperature and the resulting solution was stirred at room temperature for 20 hours. After the stirring, 30 mL of hydrochloric acid (1 mol/L) was added and the aqueous layer of the resulting mixture was subjected to extraction with ethyl acetate. The obtained solution of the extract and the organic layer were combined, and this mixture was washed with an aqueous solution of sodium hydrogen carbonate and saturated brine and dried with anhydrous magnesium sulfate. The resulting mixture was gravity-filtered and the filtrate was concentrated to give a pale yellow solid. The solid was washed with chloroform/hexane, whereby 2.6 g of a white solid of the target substance was obtained in a yield of 78%. The synthesis scheme of this step is shown in Formula (E-2).

[Chemical formula 246]

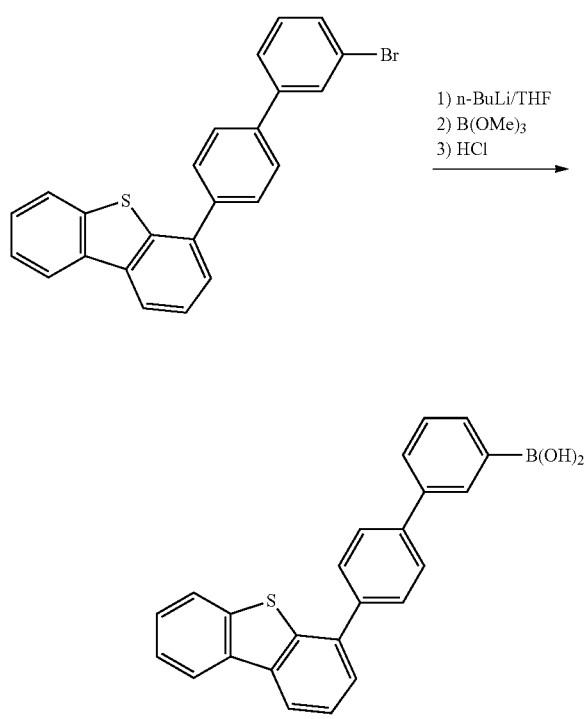

Synthesis of 2-[4''-(dibenzothiophen-4-yl)-3,1':3',1''-terphenyl-1-yl]dibenzo[f,h]quinoxaline (Abbreviation: 2DBtTPDBq-04)

Into a 200-mL three-neck flask were put 1.2 g (3.5 mmol) of 2-(3-chlorophenyl)dibenzo[f,h]quinoxaline, 1.1 g (3.4 mmol) of 4'-(dibenzothiophen-4-yl)-3,1'-biphenylboronic acid that was synthesized in the step shown by Formula (E-2), 2.1 g (9.9 mmol) of tripotassium phosphate, 70 mg (0.20 mmol) of di(1-adamantyl)-n-butylphosphine, 1 mL (11 mmol) of t-butyl alcohol, and 15 mL of diethylene glycol dimethyl ether. The mixture was degassed under reduced pressure and then, a nitrogen gas was made to flow continuously in the system. After that, 30 mg (40 μmol) of [1,1'-bis(diphenylphosphino)ferrocene]palladium(II) dichloride was added to this mixture, and the resulting mixture was stirred at 140° C. for 4.5 hours. After the stirring, the precipitated solid was collected by suction filtration and washed with water and ethanol to give a solid. The resulting solid was subjected to heat filtration using chloroform and the filtrate was concentrated, whereby 1.3 g of a solid of the target substance was obtained in a yield of 59%. The synthesis scheme of this step is shown in Formula (E-3).

[Chemical formula 247]

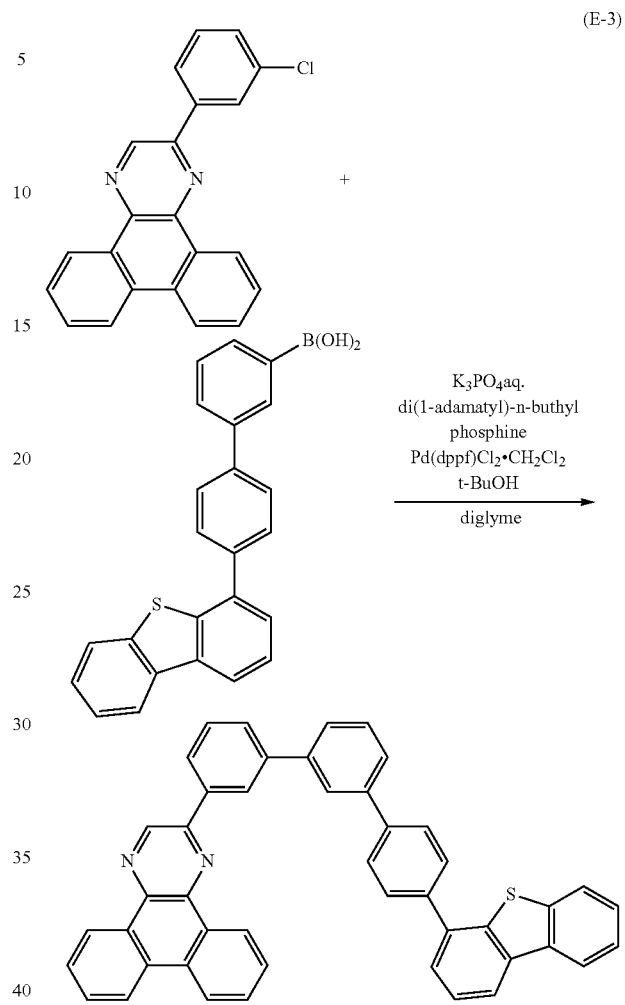

The obtained solid was subjected to nuclear magnetic resonance spectrometry ($^1$H NMR), and the results are shown below.

$^1$H NMR (chloroform-d, 500 MHz): δ=7.47-7.49 (m, 2H), 7.56-7.61 (m, 2H), 7.66 (t, J=8.0 Hz, 1H), 7.72-7.88 (m, 13H), 8.05 (s, 1H), 8.18-8.22 (m, 2H), 8.37 (d, J=8.0 Hz, 1H), 8.66-8.68 (m, 3H), 9.27 (d, J=8.0 Hz, 1H), 9.46 (d, J=8.0 Hz, 1H), 9.49 (s, 1H)

Figure 35A:
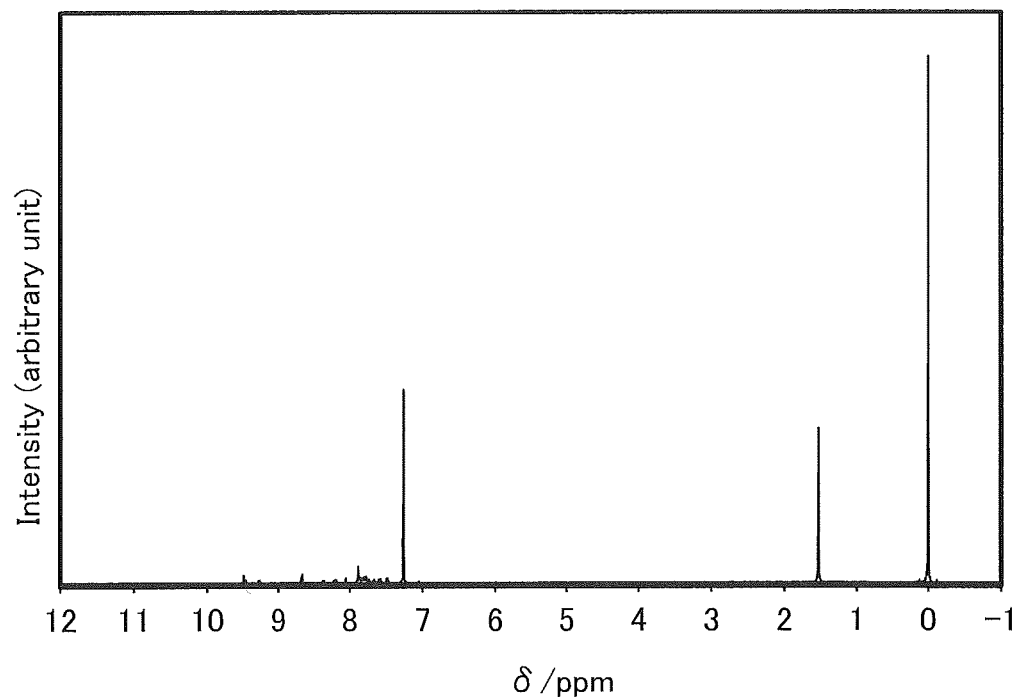
FIGS. 35A and 35B show NMR charts of 2DBtTPDBq-04.
Figure 35B:
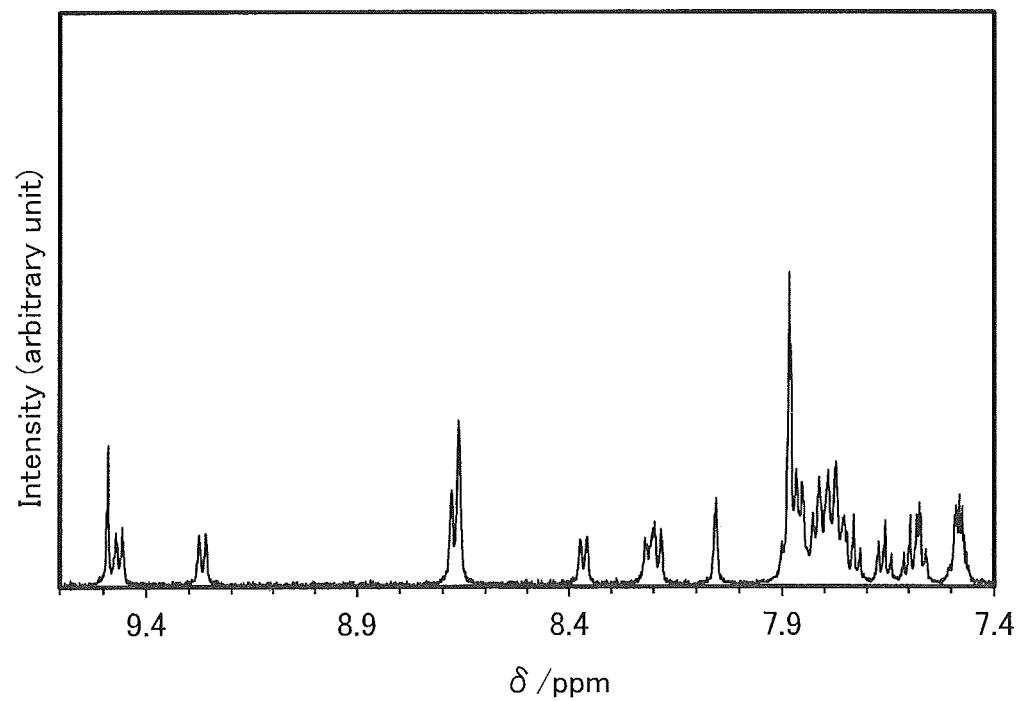

FIGS. 35A and 35B are $^1$H NMR charts. Note that FIG. 35B is a chart showing an enlarged part in the range of 7.4 ppm to 9.6 ppm of FIG. 35A. The results revealed that 2DBtTPDBq-04, which was the target substance, was obtained.

By a train sublimation method, 1.3 g of the solid was purified. In the sublimation purification, the solid was heated at 335° C. for 14.5 hours under a pressure of 2.9 Pa with a flow rate of argon of 15 mL/min. After the purification, 0.96 g of a solid of the target substance was obtained at a collection rate of 74%.

Physical Properties of 2-[4''-(dibenzothiophen-4-yl)-3,1':3',1''-terphenyl-1-yl]dibenzo[f,h]quinoxaline (Abbreviation: 2DBtTPDBq-04)

Figure 36:
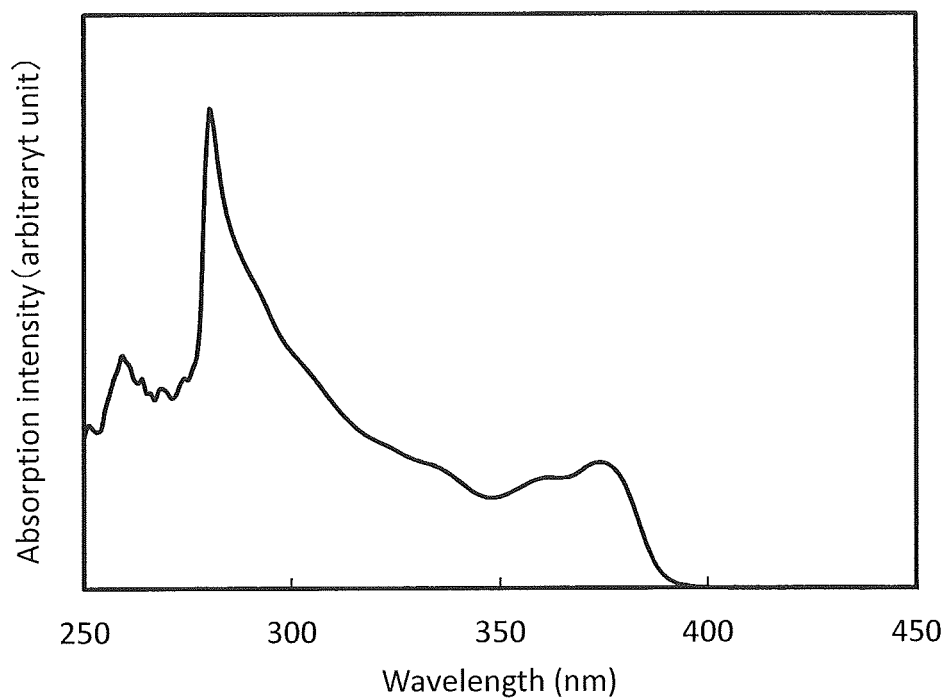
FIG. 36 shows an absorption spectrum of a solution of 2DBtTPDBq-04.
Figure 37:
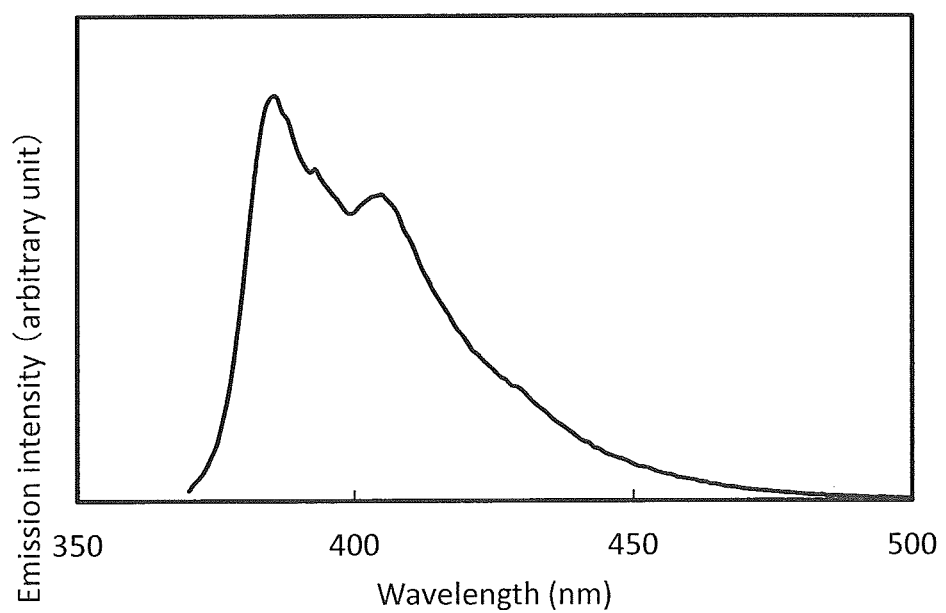
FIG. 37 shows an emission spectrum of a solution of 2DBtTPDBq-04.
Figure 38:
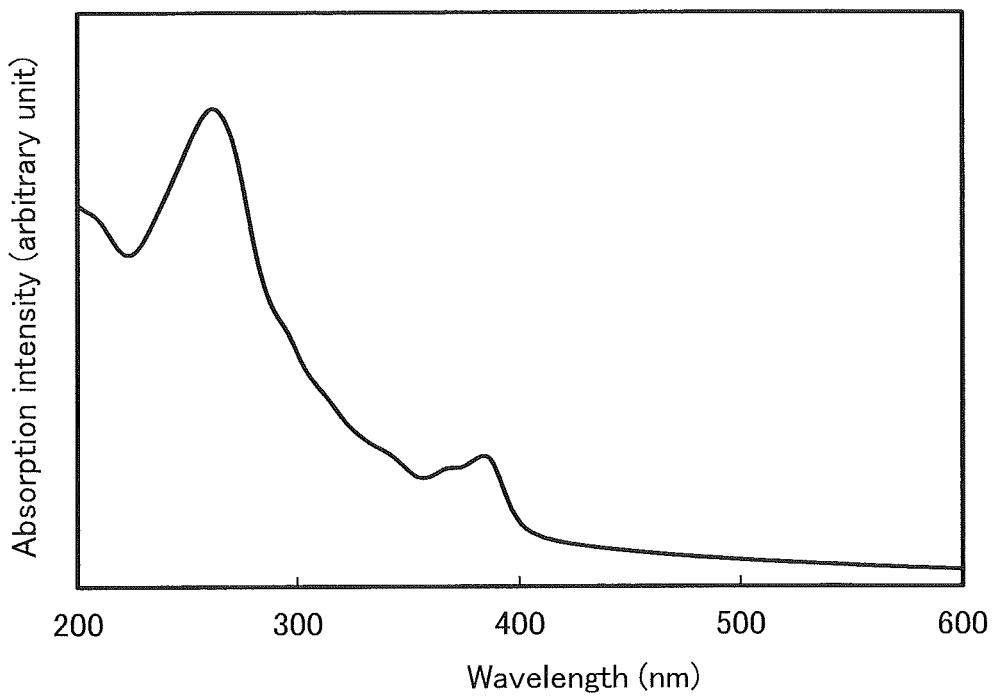
FIG. 38 shows an absorption spectrum of a thin film of 2DBtTPDBq-04.
Figure 39:
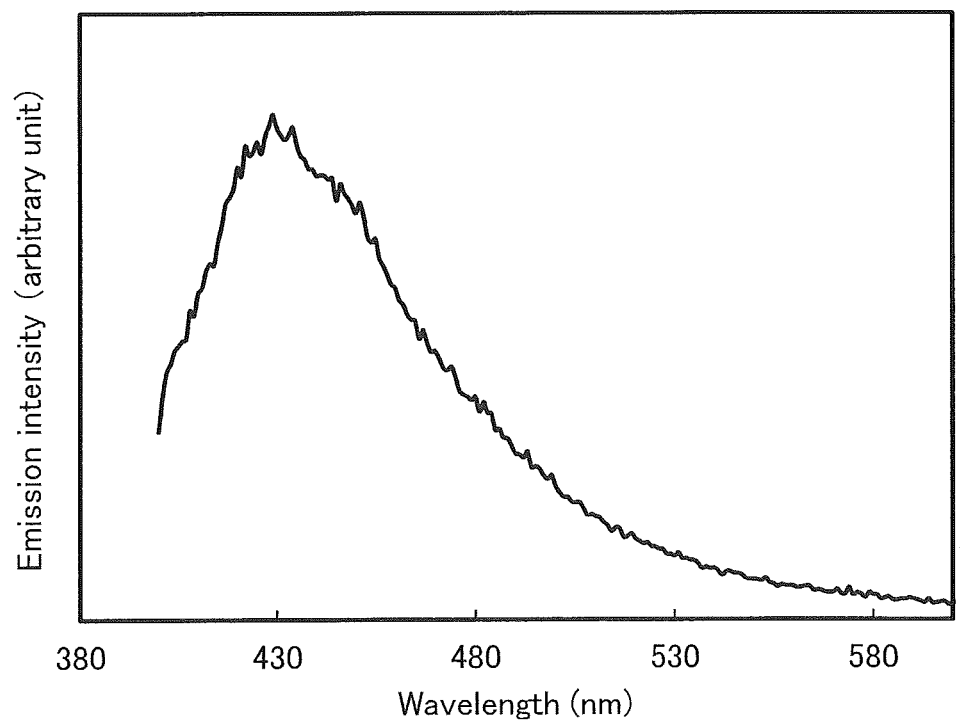
FIG. 39 shows an emission spectrum of a thin film of 2DBtTPDBq-04.

FIG. 36 shows an absorption spectrum of a toluene solution of 2DBtTPDBq-04 that was measured by a method similar to that for 2mDBtTPDBq-II, and FIG. 37 shows an emission spectrum thereof. FIG. 38 shows an absorption spectrum of a thin film of 2DBtTPDBq-04 that was measured by a method similar to that for 2mDBtTPDBq-II, and FIG. 39 shows an emission spectrum thereof.

As observed in FIG. 36 and FIG. 37, absorption peaks of the toluene solution of 2DBtTPDBq-04 are at approximately 280 nm, 332 nm, 361 nm, and 375 nm, and emission wavelength peaks thereof are at 385 nm and 404 nm (excitation wavelength: 360 nm). As observed in FIG. 38 and FIG. 39, absorption peaks of the thin film of 2DBtTPDBq-04 are at approximately 210 nm, 262 nm, 296 nm, 315 nm, 341 nm, 368 nm, and 384 nm, and emission wavelength peaks thereof are at approximately 429 nm and 446 nm (excitation wavelength: 385 nm). It was found that 2DBtTPDBq-04 emitted bluish purple light. The compound of one embodiment of the present invention can be used as a host material for a light-emitting substance or a host material for a substance emitting fluorescence in the visible region.

Figure 40:
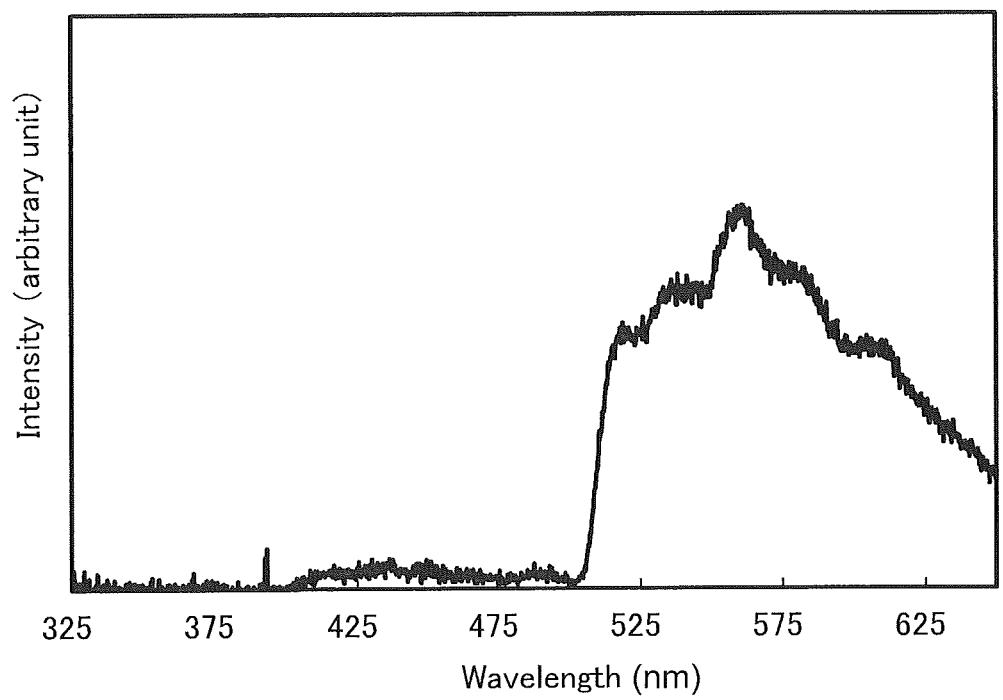
FIG. 40 shows a phosphorescence spectrum of 2DBtTPDBq-04.

Phosphorescence of 2DBtTPDBq-04 was measured by a method similar to that for 2mDBtTPDBq-II. FIG. 40 shows the obtained phosphorescence spectrum. The results showed that the peak on the shortest wavelength side of the phosphorescence spectrum of 2DBtTPDBq-04 is at 518 nm, which means that 2DBtTPDBq-04 has a high $T_1$ level. It was found that aggregation of the thin film of 2DBtTPDBq-04 is not easily caused even under the air and the thin film suffers only a small change in shape and has high film quality.

The characteristics of oxidation-reduction reaction were examined by cyclic voltammetry (CV) measurement. The measurement was performed by a method similar to that for 2mDBtTPDBq-II. According to the measurement results, the oxidation potential was −6.16 eV and the reduction potential was −2.94 eV. When the oxidation potential was regarded as a HOMO level and the reduction potential was regarded as a LUMO level, a gap between the HOMO level and the LUMO level was estimated to be 3.22 eV.

Example 6

Synthesis Example 6

In this synthesis example, a method for synthesizing 2-[3'''-(dibenzothiophen-4-yl)-3,1':3',1'':3'',1'''-quaterphenyl-1-yl]dibenzo[f,h]quinoxaline (abbreviation: 2mDBtQPDBq-II) (Structural Formula (2006)) that is the heterocyclic compound described in Embodiments 1 and 2 is described. The structural formula of 2mDBtQPDBq-II is shown below.

[Chemical formula 248]

(2006)

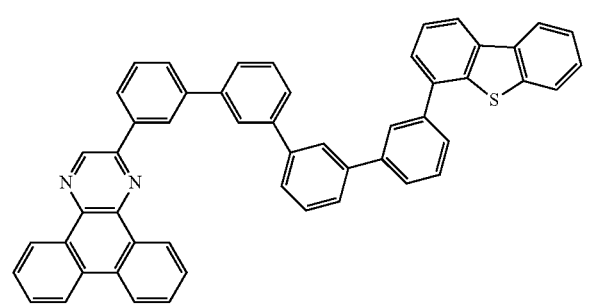

Synthesis of 4-(3'-bromo-3,1'-biphenyl-1-yl)dibenzothiophene

Into a 200-mL three-neck flask were put 3.0 g (9.8 mmol) of 3-(dibenzothiophen-4-yl)phenylboronic acid, 2.8 g (9.9 mmol) of 3-bromoiodobenzene, 0.16 g (0.53 mmol) of tris(2-methylphenyl)phosphine, 15 mL of an aqueous solution of potassium carbonate (2 mol/L), 50 mL of toluene, and 5 mL of ethanol. Then, the mixture was degassed under reduced pressure and a nitrogen gas was made to flow continuously in the system. The mixture was heated to 80° C. Then, 40 mg (0.18 mmol) of palladium(II) acetate was added and this mixture was stirred at the same temperature for 9 hours. After the stirring, the aqueous layer of the resulting mixture was subjected to extraction with toluene, the solution of the extract and the organic layer were combined, and this mixture was washed with saturated brine and dried with anhydrous magnesium sulfate. The mixture was gravity-filtered, and then the filtrate was concentrated to give 5 g of a brown oily substance. The obtained oily substance was purified by high performance liquid chromatography (developing solvent: chloroform); thus, 2.6 g of a colorless transparent oily substance of the target substance was obtained in a yield of 64%. The synthesis scheme of this step is shown in Formula (F-1).

[Chemical formula 249]

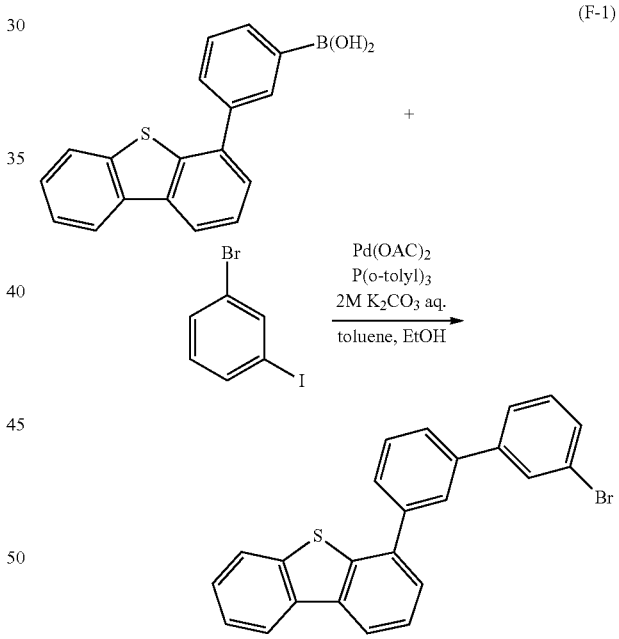

(F-1)

Method for Synthesizing 2-[3'''-(dibenzothiophen-4-yl)-3,1':3',1'':3'',1'''-quaterphenyl-1-yl]dibenzo[f,h]quinoxaline (Abbreviation: 2mDBtQPDBq-II)

Into a 100-mL three-neck flask were put 2.6 g (6.3 mmol) of 4-(3'-bromo-3,1'-biphenyl-1-yl)dibenzothiophene, 3.2 g (6.2 mmol) of 2-[3'-(2-dibenzo[f,h]quinoxalinyl)-1,1'-biphenyl-3-yl]-4,4,5,5-tetramethyl-1,3,2-dioxaborolane, 0.10 g (0.33 mmol) of tris(2-methylphenyl)phosphine, 30 mL of toluene, 3 mL of ethanol, and 10 mL of an aqueous solution of potassium carbonate (2 mol/L). The mixture was degassed under reduced pressure and then, a nitrogen gas was made to flow continuously in the system. After that, the mixture was heated to 80° C., 14 mg (60 mol) of palladium (II) acetate was added, and then, stirring was performed for 3 hours. After the stirring, the precipitated solid was collected by suction filtration, washed with water and ethanol, and recrystallized with toluene; thus, a solid of the target substance was obtained in a yield of 80%. The synthesis scheme of this step is shown in Formula (F-2).

[Chemical formula 250]

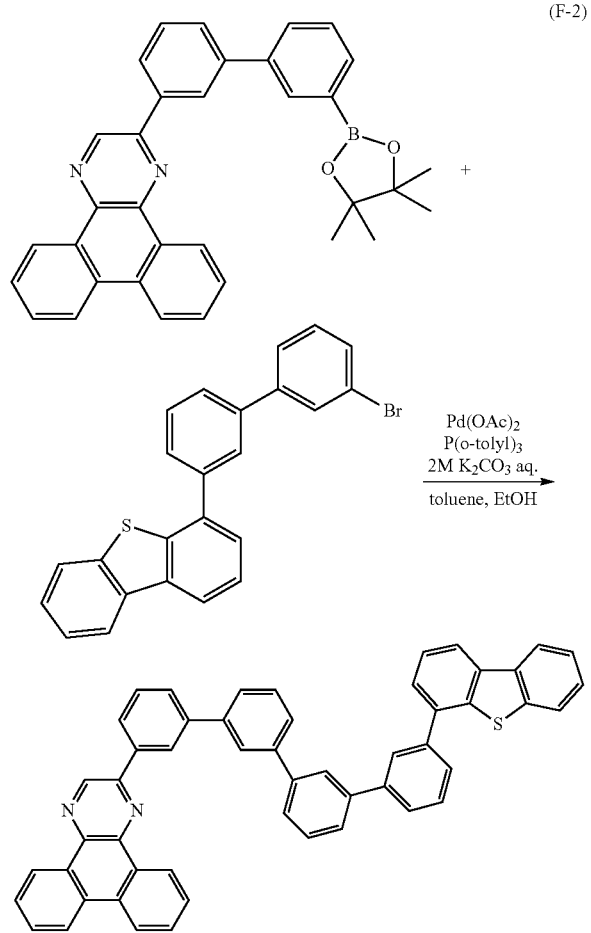

(F-2)

The obtained solid was subjected to nuclear magnetic resonance spectrometry ($^1$H NMR), and the results are shown below.

$^1$H NMR (tetrachloroethane-d$_2$, 500 MHz): δ=7.46-7.51 (in, 2H), 7.59-7.69 (m, 5H), 7.73-7.91 (m, 13H), 8.11 (d, J=8.0 Hz, 2H), 8.15 (s, 1H), 8.19 (t, J=8.0 Hz, 2H), 8.38 (d, J=8.0 Hz, 1H), 8.68-8.70 (m, 3H), 9.32 (d, J=8.0 Hz, 1H), 9.46 (d, J=8.0 Hz, 1H), 9.50 (s, 1H)

Figure 41A:
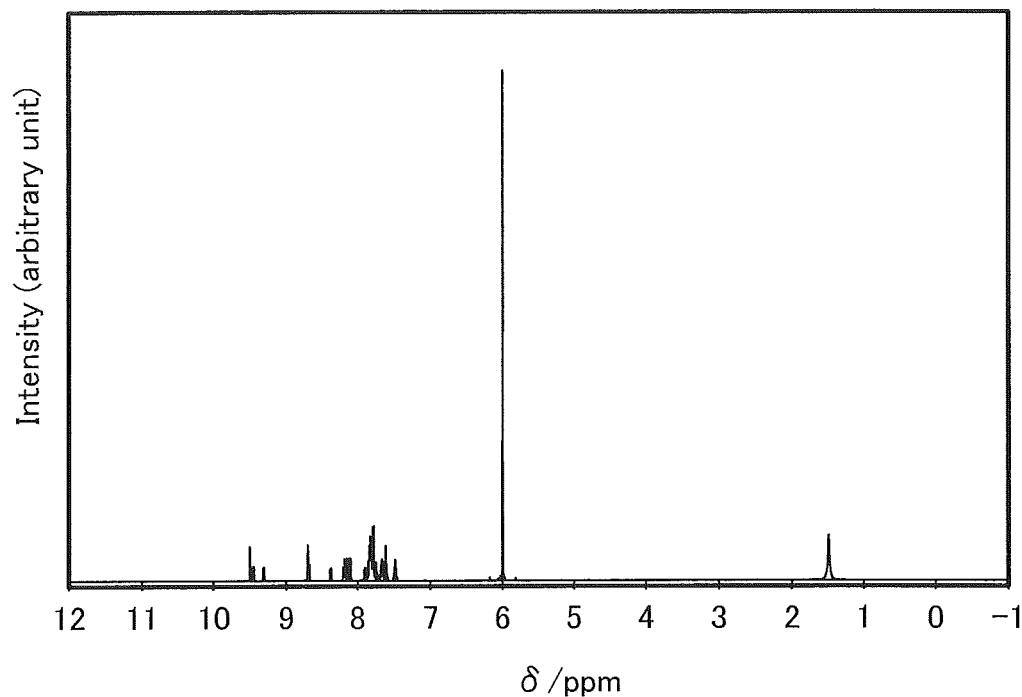
FIGS. 41A and 41B show NMR charts of 2mDBtQPDBq-II.
Figure 41B:
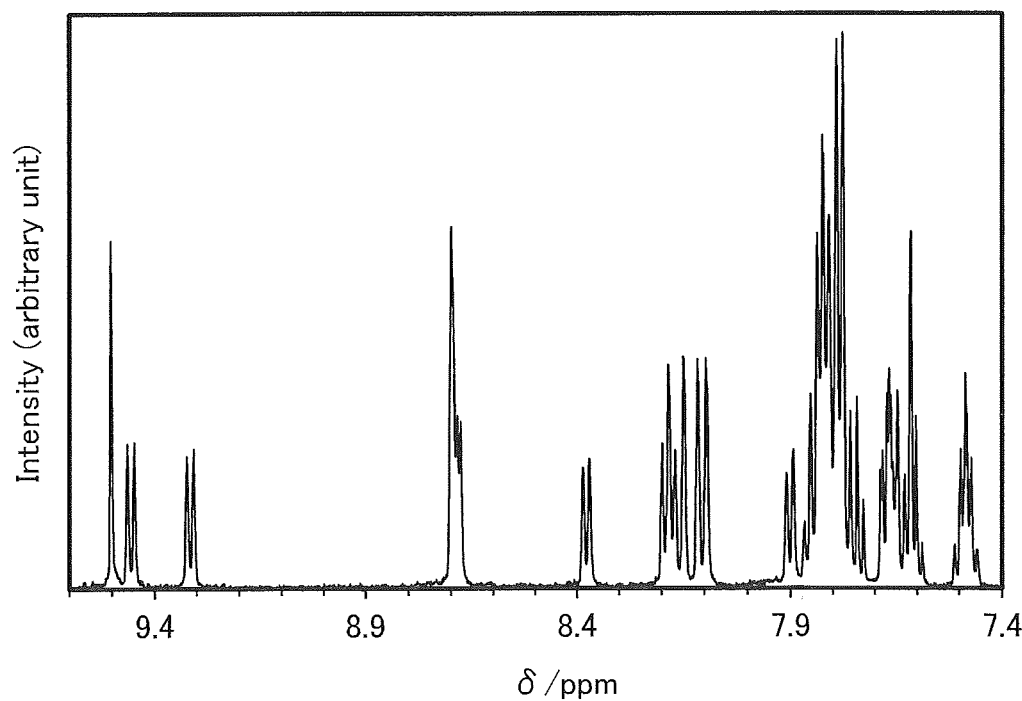

FIGS. 41A and 41B are $^1$H NMR charts. Note that FIG. 41B is a chart showing an enlarged part in the range of 7.4 ppm to 9.6 ppm of FIG. 41A. The results revealed that 2mDBtQPDBq-II, which was the target substance, was obtained.

By a train sublimation method, 3.6 g of the solid was purified. In the sublimation purification, the solid was heated at 395° C. for 17 hours under a pressure of 3.6 Pa with a flow rate of argon of 15 mL/min. After the purification, 2.6 g of a yellow solid of the target substance was obtained at a collection rate of 74%.

Physical Properties of 2-[3'''-(dibenzothiophen-4-yl)-3,1':3',1'':3'',1'''-quaterphenyl-1-yl]dibenzo[f,h]quinoxaline (Abbreviation: 2mDBtQPDBq-II)

Figure 42:
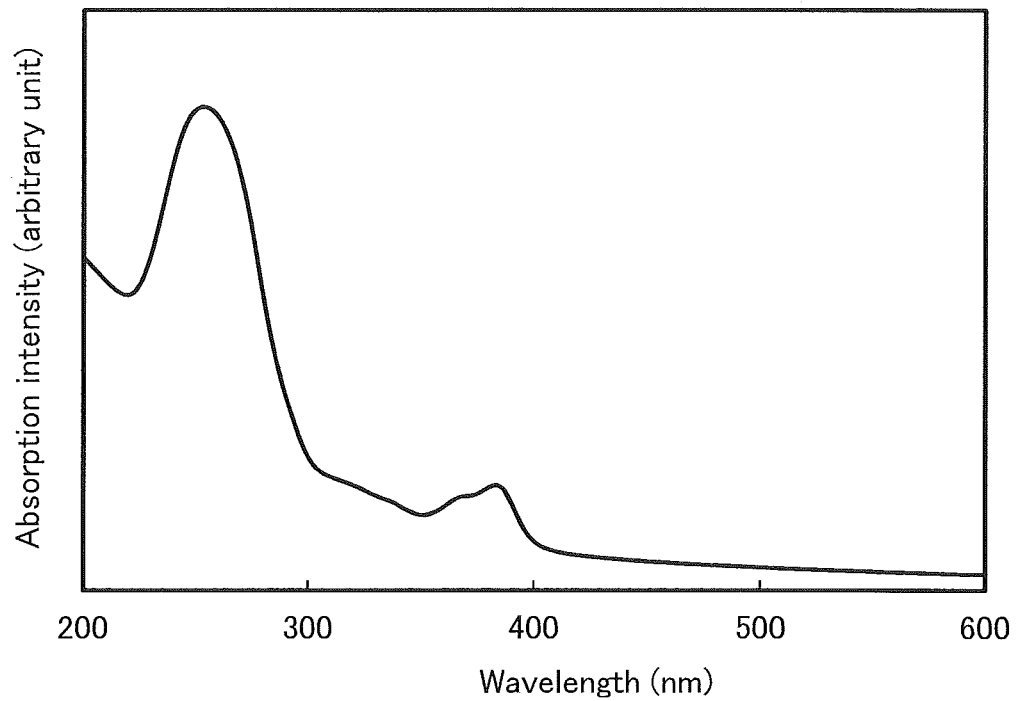
FIG. 42 shows an absorption spectrum of a thin film of 2mDBtQPDBq-II.
Figure 43:
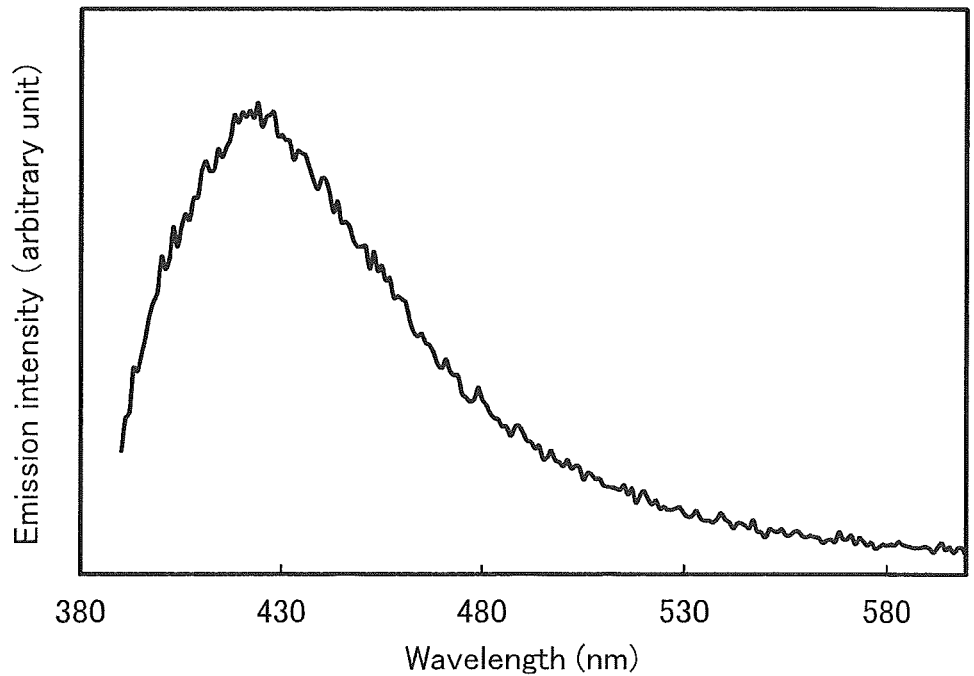
FIG. 43 shows an emission spectrum of a thin film of 2mDBtQPDBq-II.

FIG. 42 shows an absorption spectrum of a thin film of 2mDBtQPDBq-II that was measured by a method similar to that for 2mDBtTPDBq-II, and FIG. 43 shows an emission spectrum thereof.

As observed in FIG. 42 and FIG. 43, absorption peaks of the thin film of 2mDBtQPDBq-II are at approximately 253 nm, 318 nm, 337 nm, 367 nm, and 383 nm, and an emission wavelength peak thereof is at approximately 423 nm (excitation wavelength: 383 nm). It was found that 2mDBtQPDBq-II emitted bluish purple light. The compound of one embodiment of the present invention can be used as a host material for a light-emitting substance or a host material for a substance emitting fluorescence in the visible region.

Figure 44:
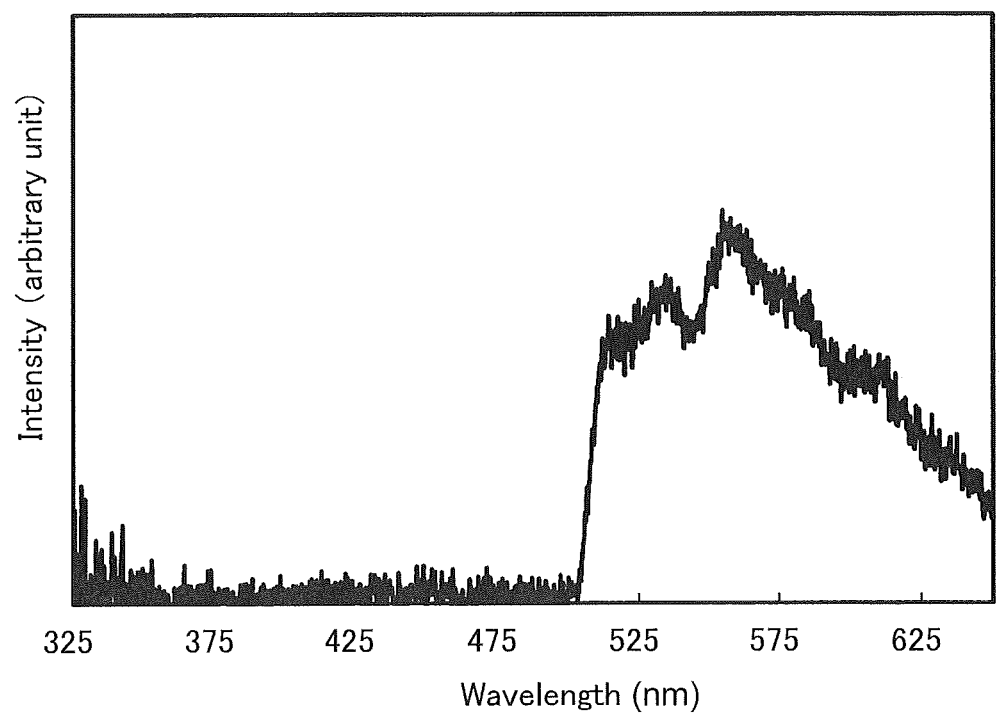
FIG. 44 shows a phosphorescence spectrum of 2mDBtQPDBq-II.

Phosphorescence of 2mDBtQPDBq-II was measured by a method similar to that for 2mDBtTPDBq-II. FIG. 44 shows the obtained phosphorescence spectrum. The results showed that the peak on the shortest wavelength side of the phosphorescence spectrum of 2mDBtQPDBq-II is at 514 nm, which means that 2mDBtQPDBq-II has a high T$_1$ level. It was found that aggregation of the thin film of 2mDBtQPDBq-II is not easily caused even under the air and the thin film suffers only a small change in shape and has high film quality.

The characteristics of oxidation-reduction reaction were examined by cyclic voltammetry (CV) measurement. The measurement was performed by a method similar to that for 2mDBtTPDBq-II. According to the measurement results, the oxidation potential was −6.19 eV and the reduction potential was −2.93 eV. When the oxidation potential was regarded as a HOMO level and the reduction potential was regarded as a LUMO level, a gap between the HOMO level and the LUMO level was estimated to be 3.26 eV.

Example 7

Synthesis Example 7

In this synthesis example, a method for synthesizing 2-[4''-(9-phenyl-9H-carbazol-3-yl)-1,1':3',1''-terphenyl-3-yl]dibenzo[f,h]quinoxaline (abbreviation: 2mmpPCTPDBq) (Structural Formula (2007)) that is the heterocyclic compound described in Embodiments 1 and 2 is described. The structural formula of 2mmpPCTPDBq is shown below.

[Chemical formula 251]

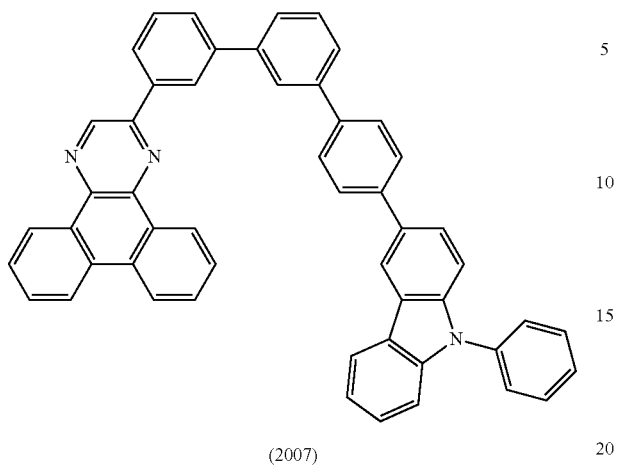

(2007)

(Step 1) Synthesis of 3-(3'-chloro-1,1'-biphenyl-4-yl)-9-phenyl-9H-carbazole

Into a 200-mL three-neck flask were put 4.0 g (10 mmol) of 3-(4-bromophenyl)-9-phenyl-9H-carbazole, 1.6 g (10 mmol) of 3-chlorophenylboronic acid, 0.61 g (2.0 mmol) of tri(ortho-tolyl)phosphine, 40 mL of toluene, 10 mL of ethanol, and 15 mL of an aqueous solution of potassium carbonate (2.0 mol/L). The mixture was degassed under reduced pressure and then, a nitrogen gas was made to flow continuously in the system. The mixture was heated to 60° C. Then, 87 mg (0.40 mmol) of palladium(II) acetate was added and the mixture was stirred at 80° C. for 12 hours. After the stirring, the organic layer of the resulting mixture was washed with water and the aqueous layer was subjected to extraction with toluene. The obtained solution of the extract and the organic layer were combined, the mixture was washed with saturated brine, and magnesium sulfate was added thereto. The resulting mixture was gravity-filtered, and then the obtained filtrate was concentrated to give 3.6 g of a brown oily substance of the target substance in a yield of 84%. The synthesis scheme of this step is shown in Formula (H-1).

[Chemical formula 252]

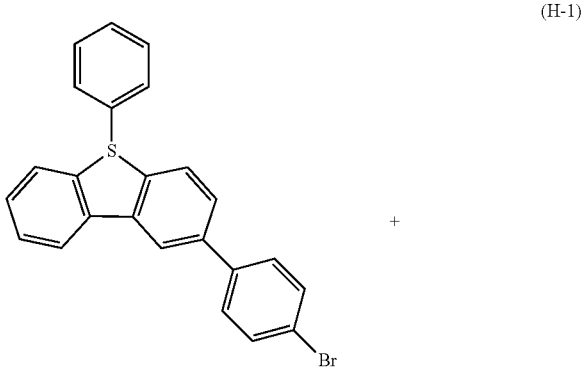

(H-1)

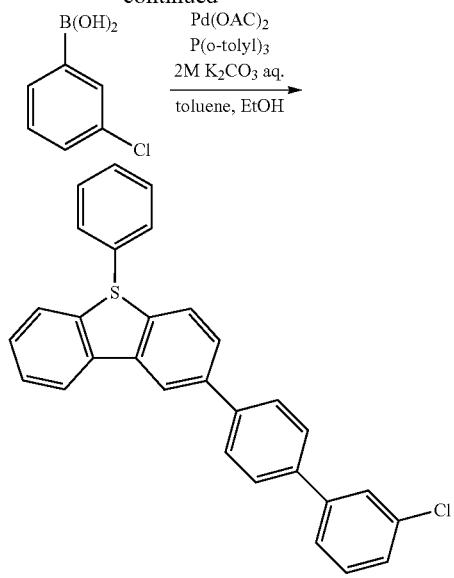

The obtained oily substance was subjected to nuclear magnetic resonance spectrometry ($^1$H NMR), and the results are shown below.

$^1$H NMR (chloroform-d, 500 MHz): δ=7.30-7.34 (m, 2H), 7.39 (t, J=8.0 Hz, 1H), 7.43 (d, J=3.5 Hz, 2H), 7.47-7.50 (m, 2H), 7.54 (d, J=7.5 Hz, 1H), 7.58-7.70 (m, 8H), 7.80 (d, J=8.5 Hz, 2H), 8.21 (d, J=8.0 Hz, 1H), 8.40 (d, J=2.0 Hz, 1H)

Figure 45A:
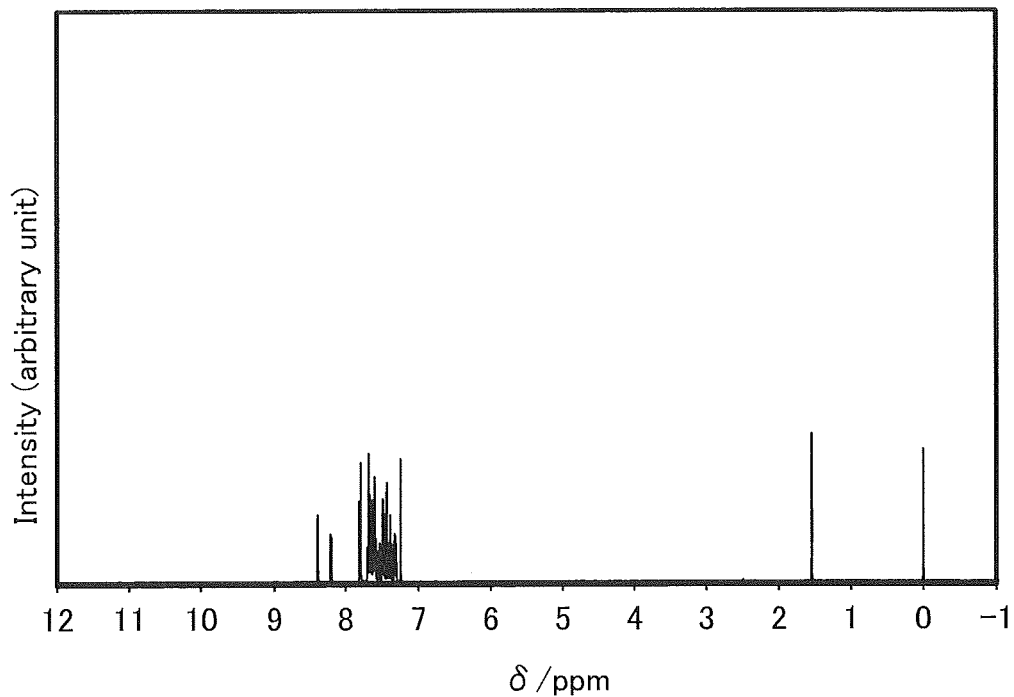
FIGS. 45A and 45B show NMR charts of 3-(3'-chloro-1,1'-biphenyl-4-yl)-9-phenyl-9H-carbazole.
Figure 45B:
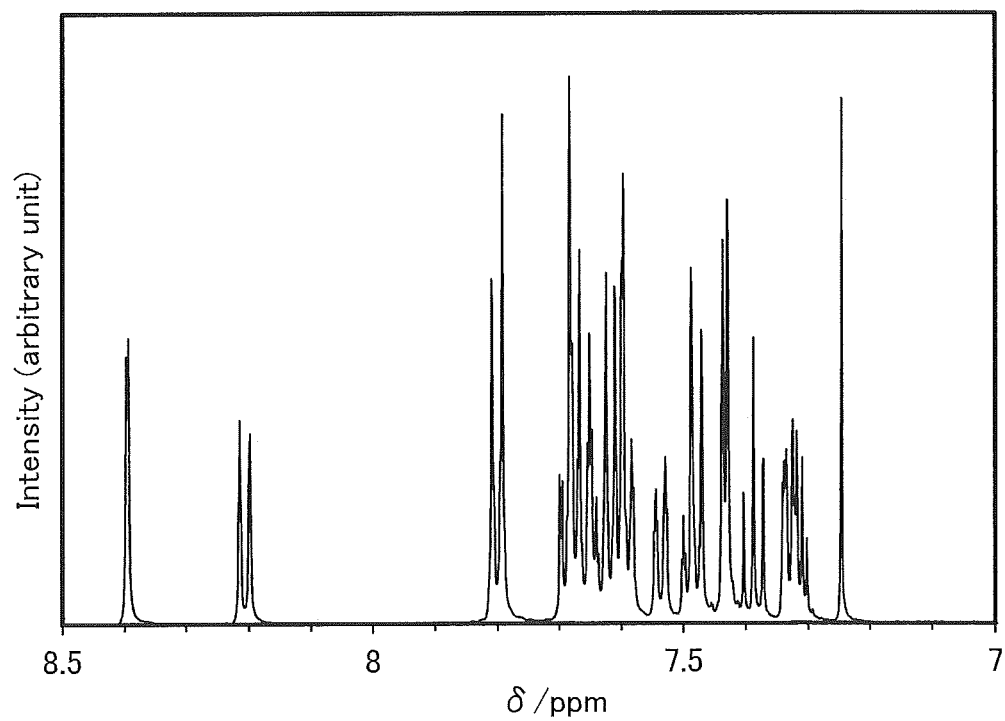

FIGS. 45A and 45B are $^1$H NMR charts of the obtained oily substance. Note that FIG. 45B is a chart showing an enlarged part in the range of 7.0 ppm to 8.5 ppm of FIG. 45A. The results revealed that 3-(3'-chloro-1,1'-biphenyl-4-yl)-9-phenyl-9H-carbazole, which was the target substance, was obtained.

(Step 2) Synthesis of 3-[3'-(4,4,5,5-tetramethyl-1,3,2-dioxaborolan-2-yl)-1,1'-biphenyl-4-yl]-9-phenyl-9H-carbazole Into a 200-mL three-neck flask were put 3.6 g (8.4 mmol) of 3-(3'-chloro-1,1'-biphenyl-4-yl)-9-phenyl-9H-carbazole, 2.2 g (8.4 mmol) of bis(pinacolato)diboron, 2.5 g (25 mmol) of potassium acetate, and 0.28 g (0.50 mmol) of 2-di-tert-butylphosphino-2',4',6'-triisopropyl-biphenyl (tBuxphos), and then the air in the system was replaced with nitrogen. After 42 mL of xylene was added to this mixture, the resulting mixture was degassed under reduced pressure and then, a nitrogen gas was made to flow continuously in the system. After this mixture was heated to 80° C., 0.16 g (0.2 mmol) of [1,1'-bis(diphenylphosphino)ferrocene]palladium (II) dichloride was added and this mixture was stirred at 150° C. for 27 hours. After the stirring, thin layer chromatography confirmed that 3-(3'-chloro-1,1'-biphenyl-4-yl)-9-phenyl-9H-carbazole had disappeared; then, the resulting mixture was cooled down to room temperature and as it is, Step 3 was performed. The synthesis scheme of this step is shown in Formula (H-2).

[Chemical formula 253]

(H-2)

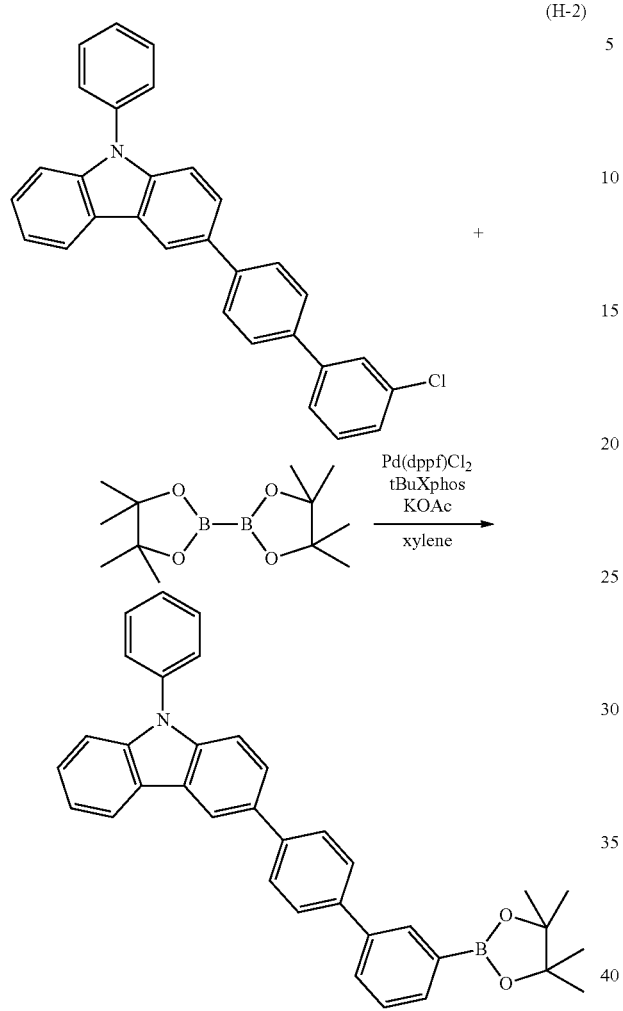

[Chemical formula 254]

(H-3)

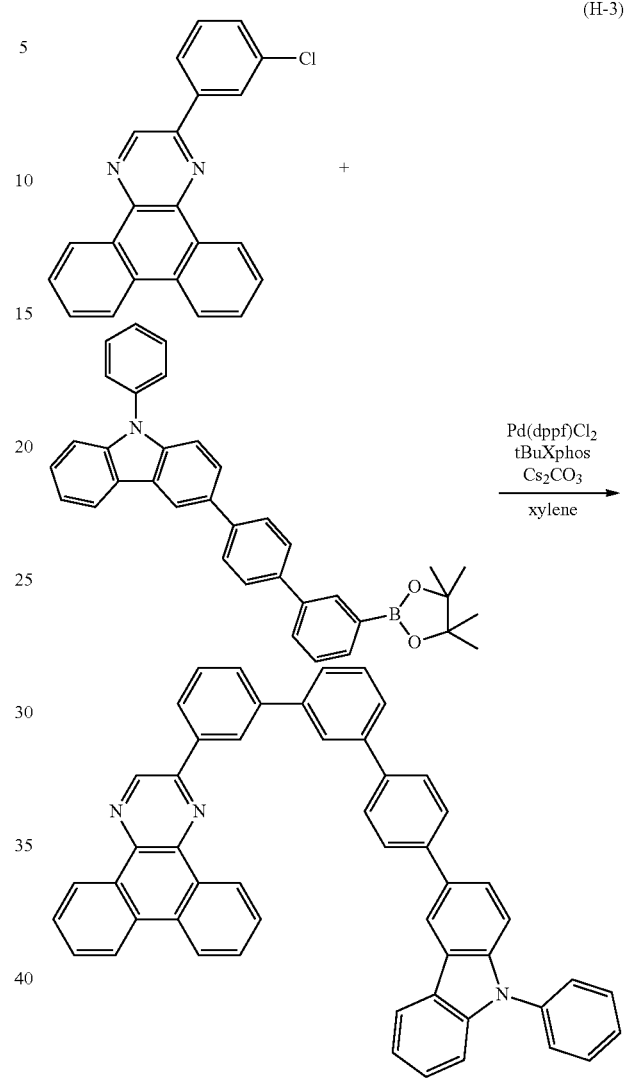

(Step 3) Synthesis of 2-[4"-(9-phenyl-9H-carbazol-3-yl)-1,1':3',1"-terphenyl-3-yl]dibenzo[f,h]quinoxaline (Abbreviation: 2mmpPCTPDBq)

To the mixture obtained in Step 2, 2.9 g (8.4 mmol) of 2-(3-chlorophenyl)dibenzo[f,h]quinoxaline, 0.55 g (1.5 mmol) of di(1-adamantyl)-n-butylphosphine, 4.3 g (20 mmol) of tripotassium phosphate, and 33 mL of diethylene glycol dimethyl ether were added. Then, this mixture was degassed under reduced pressure and a nitrogen gas was made to flow continuously in the system. The resulting mixture was heated to 80° C., 0.12 g (0.50 mmol) of palladium(II) acetate was added, and the mixture was stirred at 150° C. for 7 hours. After the stirring, a precipitated solid was collected by suction filtration and was washed with toluene, water, and ethanol, whereby 2.5 g of a brown powder of the target substance was obtained. The total yield for Steps 2 and 3 was 42%. The synthesis scheme of this step is shown in Formula (H-3).

The obtained solid was subjected to nuclear magnetic resonance spectrometry ($^1$H NMR), and the results are shown below.

$^1$H NMR (chloroform-d, 500 MHz): δ=7.31-7.34 (m, 1H), 7.44 (d, J=4.0 Hz, 1H), 7.50 (d, J=15 Hz, 2H), 7.60-7.66 (m, 5H), 7.72-7.87 (m, 14H), 8.04 (s, 1H), 8.22 (d, J=8.0 Hz, 1H), 8.36 (d, J=8.0 Hz, 1H), 8.43 (d, J=1.5 Hz, 1H), 8.65 (s, 1H), 8.67 (d, J=7.5 Hz, 2H), 9.26 (dd, J1=8.0 Hz, J2=2.0 Hz, 1H), 9.46 (dd, J1=8.0 Hz, J2=2.0 Hz, 1H), 9.48 (s, 1H)

Figure 46A:
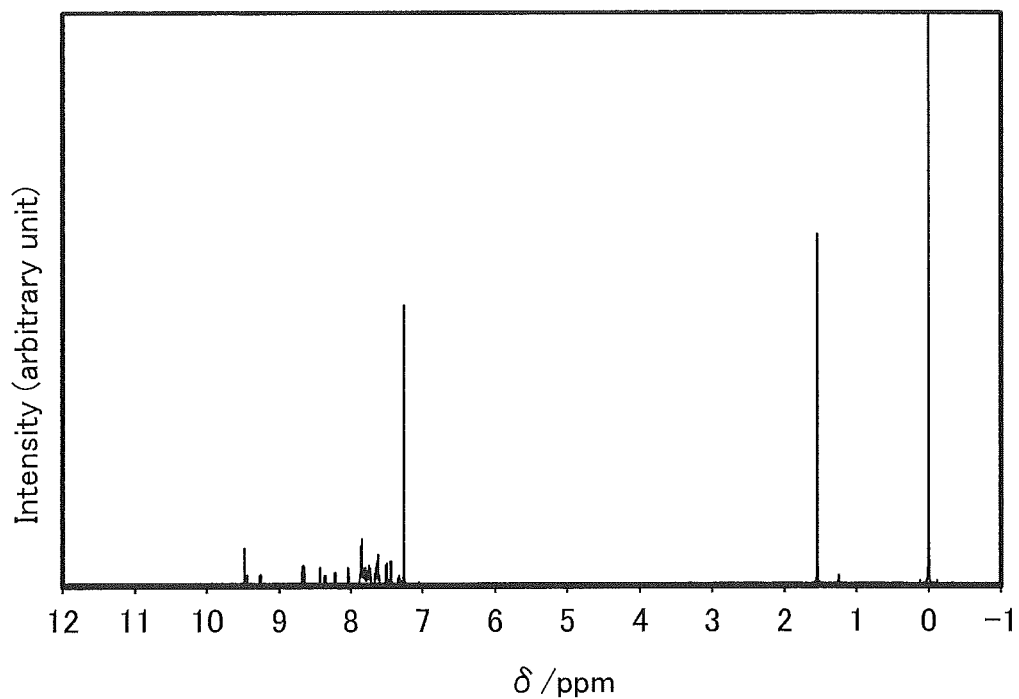
FIGS. 46A and 46B show NMR charts of 2mmpPCTPDBq.
Figure 46B:
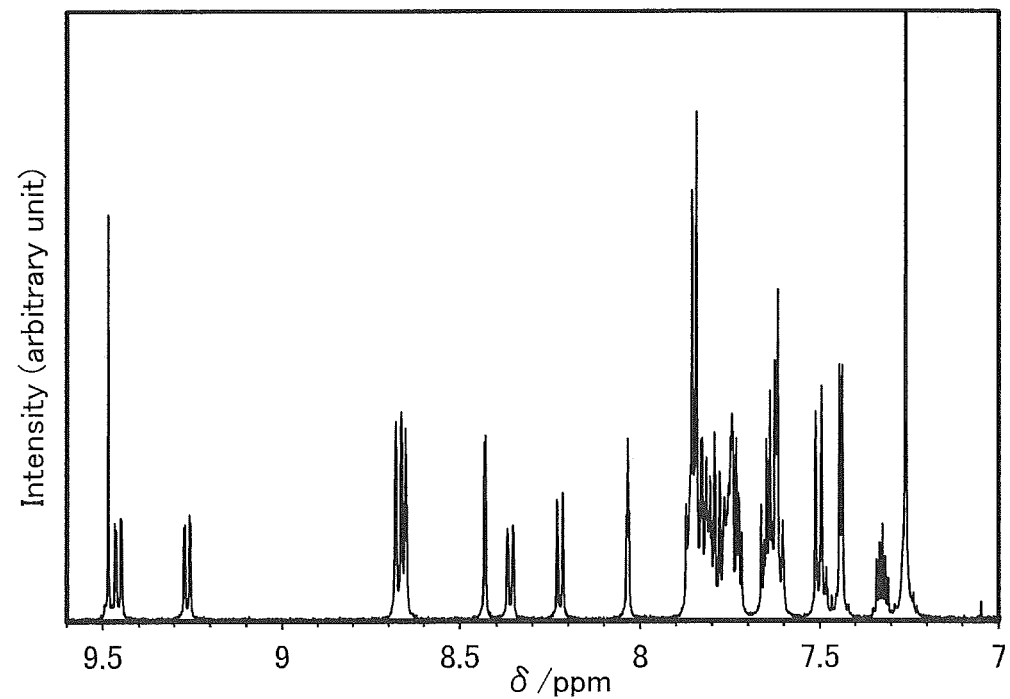

FIGS. 46A and 46B are $^1$H NMR charts of the obtained solid. Note that FIG. 46B is a chart showing an enlarged part in the range of 7.0 ppm to 9.6 ppm of FIG. 46A. The results revealed that 2-[4"-(9-phenyl-9H-carbazol-3-yl)-1,1':3',1"-terphenyl-3-yl]dibenzo[f,h]quinoxaline (abbreviation: 2mmpPCTPDBq), which was the target substance, was obtained.

By a train sublimation method, 2.5 g of the solid was purified. In the sublimation purification, the solid was heated at 375° C. for 15 hours under a pressure of 3.6 Pa with a flow rate of argon of 15 mL/min. After the sublimation purification, 2.2 g of a pale yellow solid of the target substance was obtained at a collection rate of 87%.

Physical Properties 2-[4"-(9-phenyl-9H-carbazol-3-yl)-1,1':3',1"-terphenyl-3-yl]dibenzo[f,h]quinoxaline (Abbreviation: 2mmpPCTPDBq)

Figure 47:
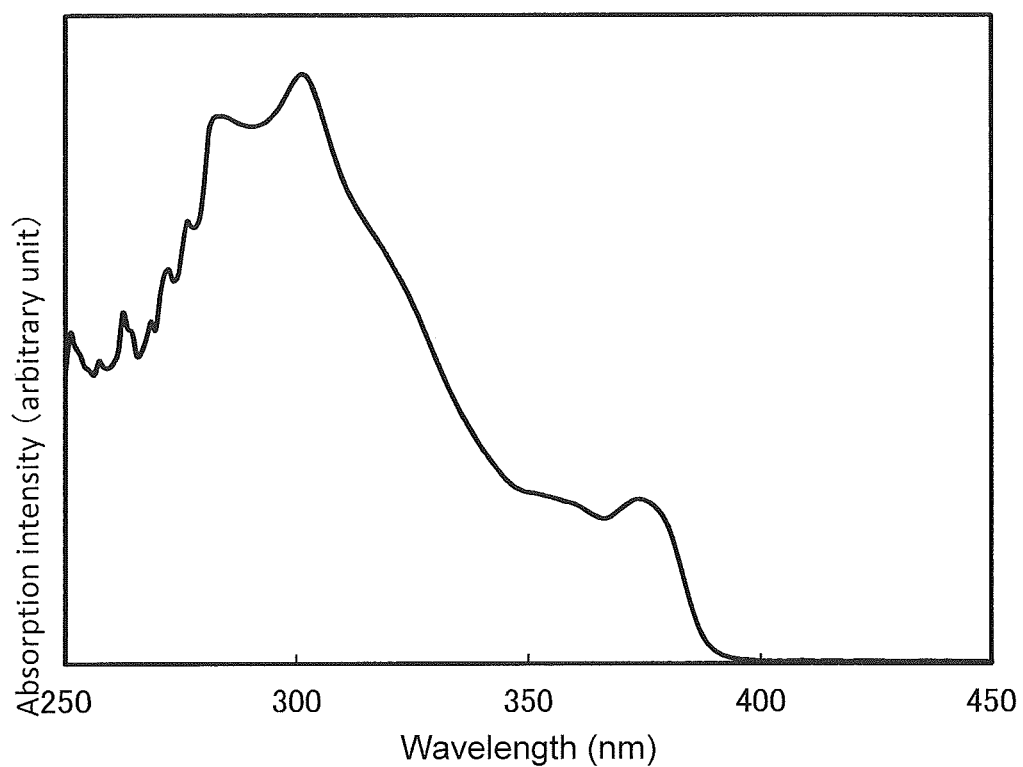
FIG. 47 shows an absorption spectrum of a solution of 2mmpPCTPDBq.
Figure 48:
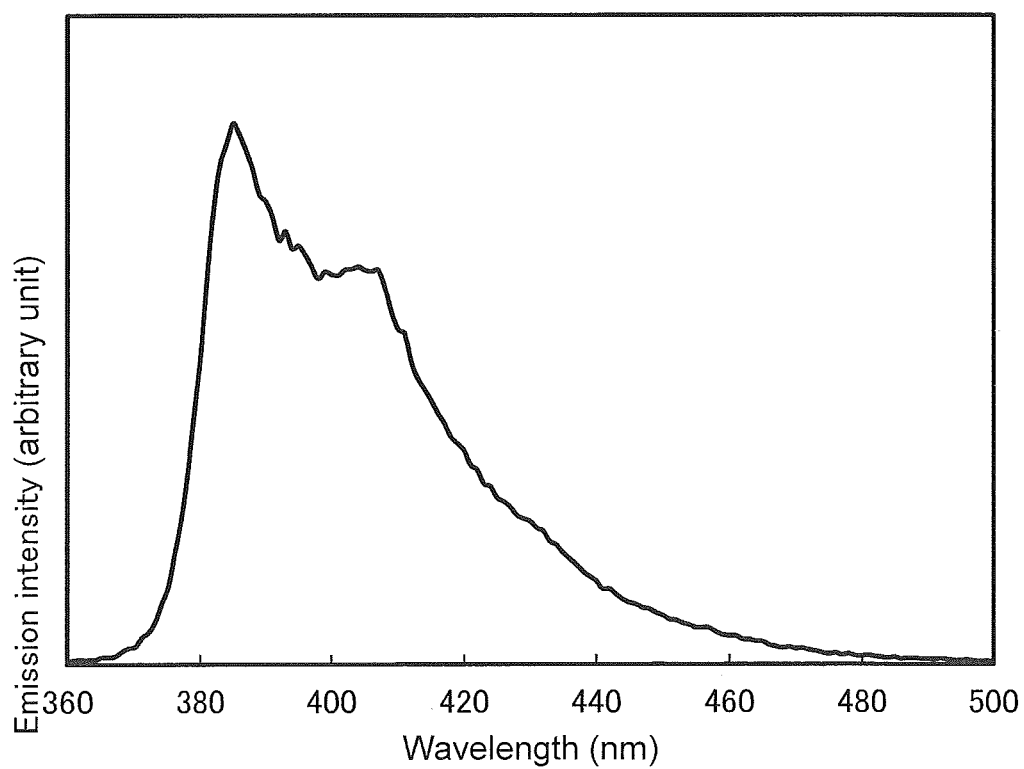
FIG. 48 shows an emission spectrum of a solution of 2mmpPCTPDBq.
Figure 49:
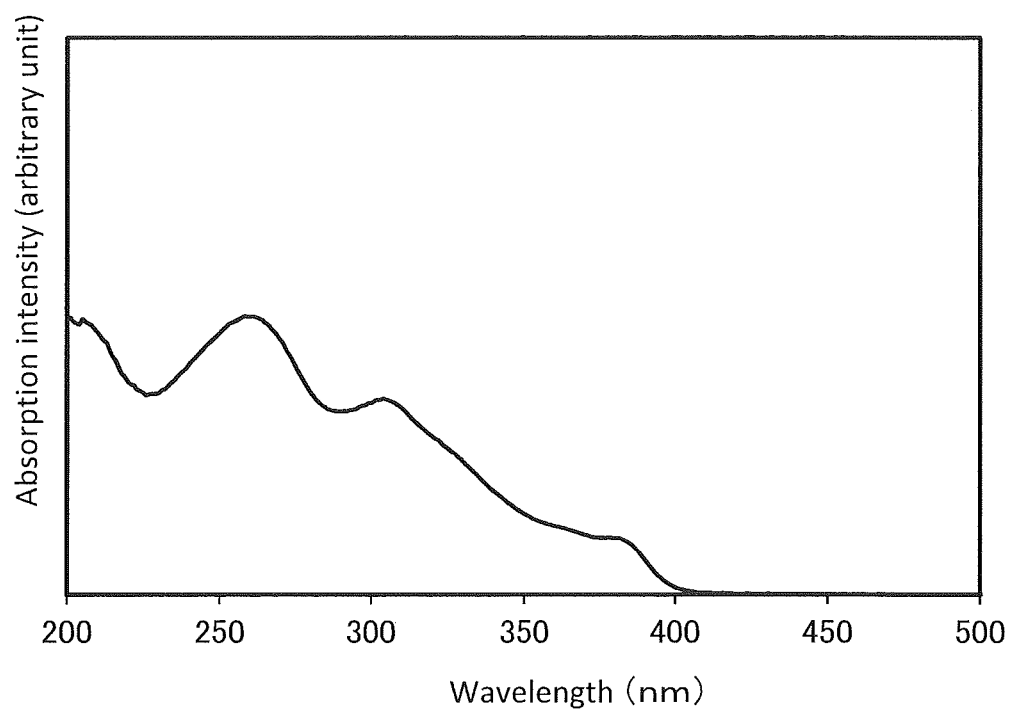
FIG. 49 shows an absorption spectrum of a thin film of 2mmpPCTPDBq.
Figure 50:
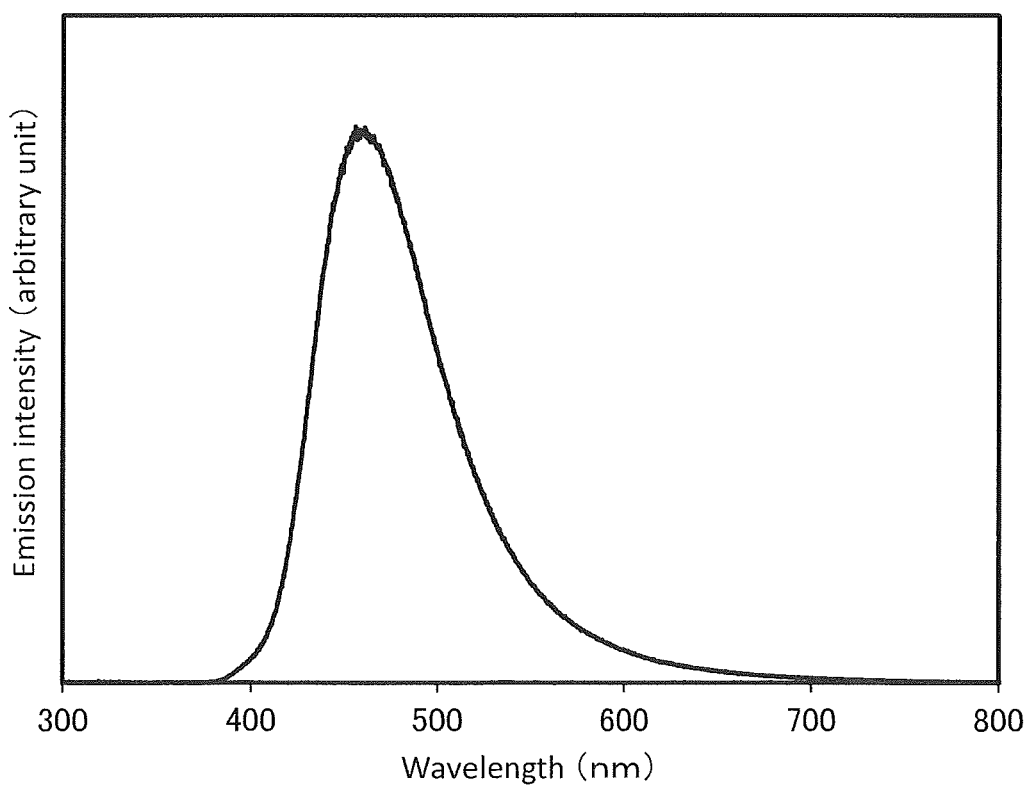
FIG. 50 shows an emission spectrum of a thin film of 2mmpPCTPDBq.

FIG. 47 shows an absorption spectrum of a toluene solution of 2mmpPCTPDBq, and FIG. 48 shows an emission spectrum thereof. FIG. 49 shows an absorption spectrum of a thin film of 2mmpPCTPDBq, and FIG. 50 shows an emission spectrum thereof. The solid thin film was formed over a quartz substrate by a vacuum evaporation method. The measurement of the absorption spectrum of the toluene solution was performed in a manner similar to that in Example 1. The absorption spectrum of the thin film was measured with a spectrophotometer (U-4100 Spectrophotometer, manufactured by Hitachi High-Technologies Corporation). The emission spectra were measured in a manner similar to that in Example 1.

As observed in FIG. 47 and FIG. 48, absorption peaks of the toluene solution of 2mmpPCTPDBq are at approximately 374 nm, 354 nm, and 302 nm, and emission wavelength peaks thereof are at 385 nm and 404 nm (excitation wavelength: 355 nm). As observed in FIG. 49 and FIG. 50, absorption peaks of the thin film of 2mmpPCTPDBq are at approximately 380 nm, 365 nm, 330 nm, 303 nm, and 258 nm, and an emission wavelength peak thereof is at approximately 459 nm (excitation wavelength: 325 nm). It was found that 2mmpPCTPDBq emitted bluish purple light. The compound of one embodiment of the present invention can be used as a host material for a light-emitting substance or a host material for a substance emitting fluorescence in the visible region.

Figure 51:
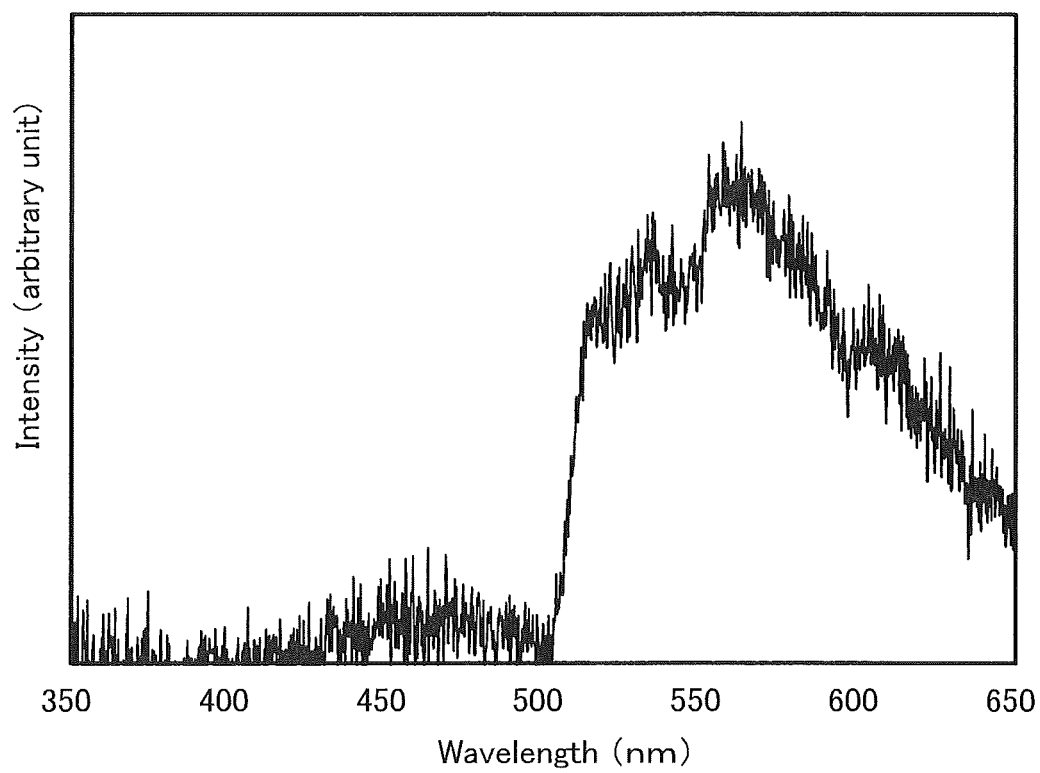
FIG. 51 shows a phosphorescence spectrum of 2mmpPCTPDBq.

Phosphorescence of 2mmpPCTPDBq was measured by the same method as in Example 1. FIG. 51 shows the obtained phosphorescence spectrum. The results showed that the peak on the shortest wavelength side of the phosphorescence spectrum of 2mmpPCTPDBq is at 514 nm, which means that 2mmpPCTPDBq has a high $T_1$ level. It was found that aggregation of the thin film of 2mmpPCTPDBq is not easily caused even under the air and the thin film suffers only a small change in shape and has high film quality.

The HOMO level and the LUMO level of 2mmpPCTPDBq were obtained through a cyclic voltammetry (CV) measurement. The measurement and calculation were performed by the same method as in Example 1.

Furthermore, the CV measurement was repeated 100 times, and the oxidation-reduction wave at the hundredth cycle and the oxidation-reduction wave at the first cycle were compared with each other to examine the electric stability of the compound.

As a result, in the measurement of an oxidation potential Ea [V] of 2mmpPCTPDBq, the HOMO level was −5.80 eV. Meanwhile, the LUMO level was found to be −2.94 eV. When the oxidation-reduction wave was repeatedly measured, in the Ea measurement, the peak intensity of the oxidation-reduction wave after the hundredth cycle was maintained to be 78% of that of the oxidation-reduction wave at the first cycle, and in the Ec measurement, the peak intensity of the oxidation-reduction wave after the hundredth cycle was maintained to be 90% of that of the oxidation-reduction wave at the first cycle; thus, resistance to oxidation and reduction of 2mmpPCTPDBq was found to be extremely high.

Example 8

Synthesis Example 8

In this synthesis example, a method for synthesizing 2-[3'-(9-phenyl-9H-carbazol-3-yl)-1,1'-biphenyl-3-yl]dibenzo[f,h]quinoxaline (abbreviation: 2mPCBPDBq) (Structural Formula (2008)) that was synthesized as a comparative substance for the heterocyclic compound of one embodiment of the present invention is described. The structural formula of 2mPCBPDBq is shown below.

[Chemical formula 255]

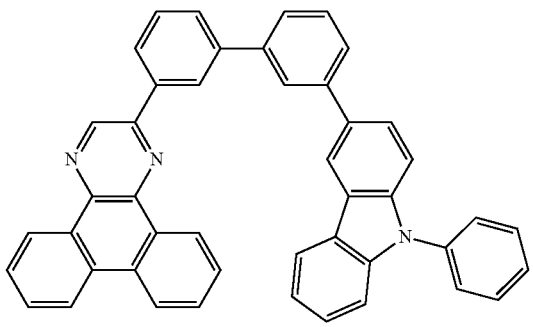

(2008)

<Synthesis of 2-[3'-(9-phenyl-9H-carbazol-3-yl)-1,1'-biphenyl-3-yl]dibenzo[f,h]quinoxaline (Abbreviation: 2mPCBPDBq)

Into a 200-mL three-neck flask were put 4.2 g (5 mmol) of 2-(3'-bromo-1,1'-biphenyl-3-yl)dibenzo[f,h]quinoxaline, 1.5 g (5 mmol) of 9-phenyl-9H-carbazol-3-ylboronic acid, 0.16 mg (0.50 mmol) of tri(ortho-tolyl)phosphine, 25 mL of toluene, 5 mL of ethanol, and 7.5 mL of an aqueous solution of potassium carbonate (2.0 mol/L). This mixture was degassed under reduced pressure and then, a nitrogen gas was made to flow continuously in the system. The mixture was heated to 60° C. Then, 52 mg (0.23 mmol) of palladium (II) acetate was added and this mixture was stirred at 90° C. for 32 hours. After the stirring, the precipitated solid was collected by suction filtration and washed with water, toluene, and ethanol to give 2.8 g of a brown solid of the target substance in a yield of 89%. The synthesis scheme of this step is shown in Formula (I-1).

[Chemical formula 256]

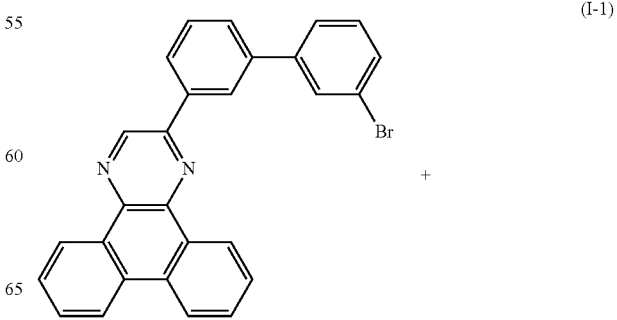

(I-1)

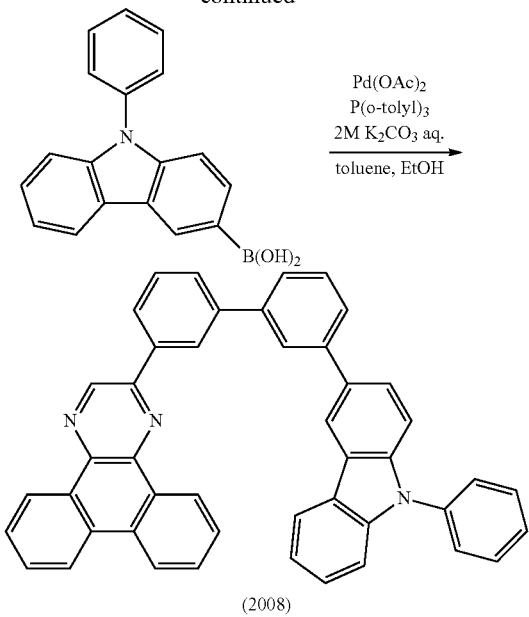

(2008)

The obtained solid was subjected to nuclear magnetic resonance spectrometry ($^1$H NMR), and the results are shown below.

$^1$H NMR (chloroform-d, 500 MHz): δ=7.29-7.33 (m, 1H), 7.42-7.45 (m, 2H), 7.50 (t, J=7.5 Hz, 1H), 7.52 (d, J=9.0 Hz, 1H), 7.61-7.82 (m, 8H), 7.88 (d, J=8.0 Hz, 1H), 8.08 (s, 1H), 8.23 (d, J=7.5 Hz, 1H), 8.36 (d, J=7.5 Hz, 1H), 8.47 (s, 1H), 8.67 (d, J=8.5 Hz, 2H), 8.67 (s, 1H), 9.26 (d, J=8.5 Hz, 1H), 9.46 (d, J=8.0 Hz, 1H), 9.49 (s, 1H)

Figure 52A:
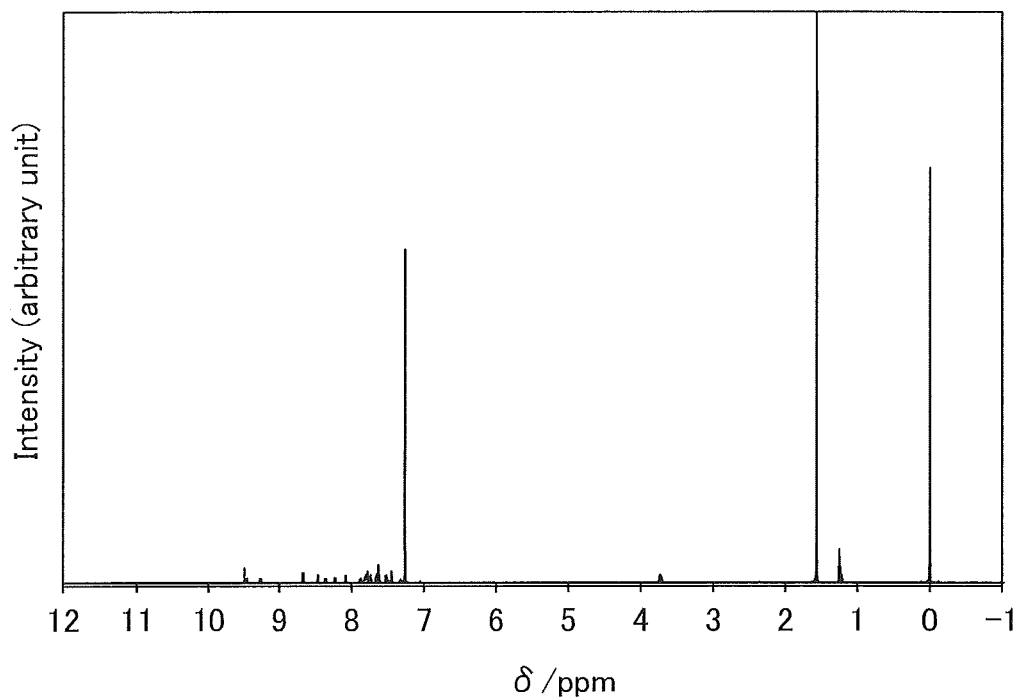
FIGS. 52A and 52B show NMR charts of 2mPCBPDBq.
Figure 52B:
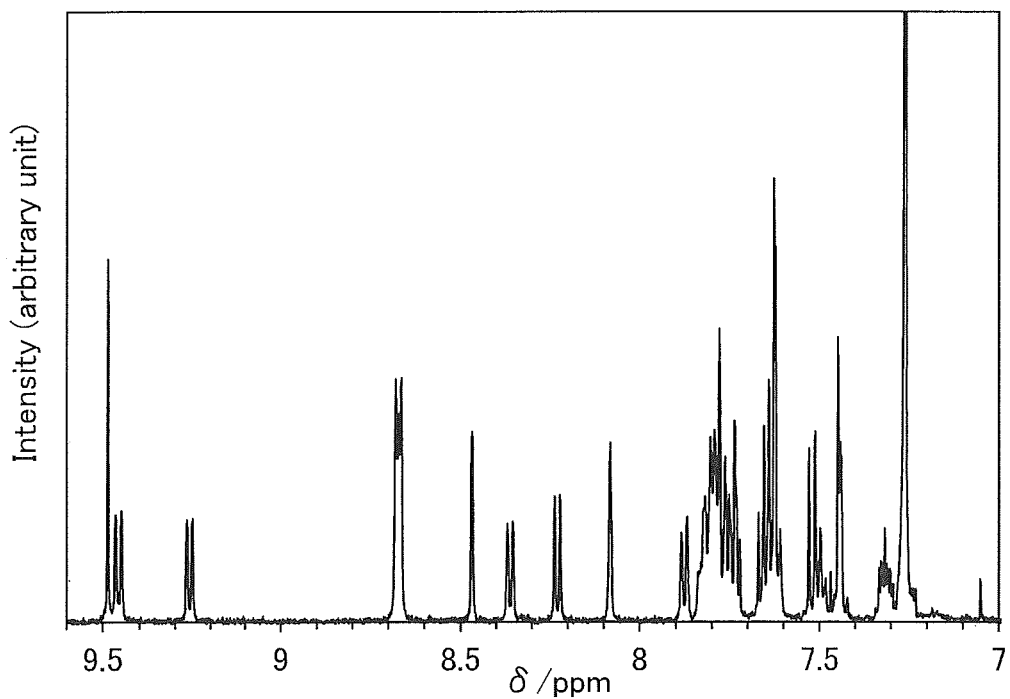

FIGS. 52A and 52B are $^1$H NMR charts of the obtained solid. Note that FIG. 52B is a chart showing an enlarged part in the range of 7.0 ppm to 9.6 ppm of FIG. 52A. The results revealed that 2-[3'-(9-phenyl-9H-carbazol-3-yl)-1,1'-biphenyl-3-yl]dibenzo[f,h]quinoxaline (abbreviation: 2mPCBPDBq), which was the target substance, was obtained.

By a train sublimation method, 2.1 g of the solid was purified. In the sublimation purification, the solid was heated at 330° C. for 15 hours under a pressure of 3.6 Pa with a flow rate of argon of 15 mL/min. After the sublimation purification, 1.9 g of a pale yellow solid of the target substance was obtained at a collection rate of 90%.

Physical Properties of 2-[3'-(9-phenyl-9H-carbazol-3-yl)-1,1'-biphenyl-3-yl]dibenzo[f,h]quinoxaline (Abbreviation: 2mPCBPDBq)

Phosphorescence of 2mPCBPDBq was measured by the same method as in Example 1. Although the obtained phosphorescence spectrum is not shown, it was revealed that the peak on the shortest wavelength side of the phosphorescence spectrum of 2mPCBPDBq is at 515 nm, which means that 2mPCBPDBq has a high $T_1$ level. It was found that aggregation of the thin film of 2mPCBPDBq is not easily caused even under the air and the thin film suffers only a small change in shape and has high film quality.

The HOMO level and the LUMO level of 2mPCBPDBq were obtained through a cyclic voltammetry (CV) measurement. The measurement and calculation were performed by the same method as in Example 1.

Furthermore, the CV measurement was repeated 100 times, and the oxidation-reduction wave at the hundredth cycle and the oxidation-reduction wave at the first cycle were compared with each other to examine the electric stability of the compound.

As a result, in the measurement of an oxidation potential Ea [V] of 2mPCBPDBq, the HOMO level was −5.84 eV. Meanwhile, the LUMO level was found to be −2.94 eV. When the oxidation-reduction wave was repeatedly measured, in the Ea measurement, the peak intensity of the oxidation-reduction wave after the hundredth cycle was maintained to be 78% of that of the oxidation-reduction wave at the first cycle, and in the Ec measurement, the peak intensity of the oxidation-reduction wave after the hundredth cycle was maintained to be 80% of that of the oxidation-reduction wave at the first cycle; thus, resistance to oxidation and reduction of 2mPCBPDBq was found to be extremely high.

The thermophysical properties of 2mPCBPDBq were measured. Thermogravimetry-differential thermal analysis (TG-DTA) of 2mPCBPDBq was carried out. The measurement was performed using a high vacuum differential type differential thermal balance (TG-DTA2410SA, manufactured by Bruker AXS K.K.). The measurement was performed under atmospheric pressure at a temperature rise rate of 10° C./min under a nitrogen stream (a flow rate of 200 mL/min). Furthermore, differential scanning calorimetry was performed by Pyris1DSC manufactured by PerkinElmer, Inc. In the differential scanning calorimetry, after the temperature was raised from 300° C. to 350° C. (temperatures at which the compound is not decomposed) at a temperature rise rate of 40° C./min, the temperature was held for 1 minute and then cooled to −10° C. at a temperature drop rate of 40° C./min. This operation was repeated twice successively.

In the thermogravimetry-differential thermal analysis, the temperature (decomposition temperature) at which the weight obtained by the thermogravimetry was reduced by 5% of the weight at the beginning of the measurement was found to be 500° C. or more. The glass transition point (Tg) observed in the second temperature increase in the differential scanning calorimetry was 119° C.

Example 9

In this example, the heterocyclic compounds of embodiments of the present invention obtained in Examples 1 to 5 and 7 were subjected to thermogravimetry-differential thermal analysis and differential scanning calorimetry. Note that the measurement methods are similar to those used in Example 8.

Table 1 lists the following data of the heterocyclic compounds of embodiments of the present invention obtained in Examples 1 to 5 and 7: the temperature (decomposition temperature) at which the weight obtained by thermogravimetry was reduced by 5% of the weight at the beginning of the measurement in the thermogravimetry-differential thermal analysis, the glass transition point (Tg) observed in the second temperature increase in the differential scanning calorimetry, the crystallization temperature (Tc), and the melting point (Tm).

TABLE 1

| | | Decomposition temperature (° C.) | Tg (° C.) | Tc (° C.) | Tm (° C.) |
|---|---|---|---|---|---|
| 2mDBtTPDBq-II | Example 1 | 487 | 116 | — | — |
| 2DBtTPDBq | Example 2 | 500 or more | 121 | — | 270 |
| 2DBtTPDBq-02 | Example 4 | 500 or more | 128 | 194 | 312 |
| 2DBtTPDBq-03 | Example 3 | 500 or more | — | — | 323 |
| 2DBtTPDBq-04 | Example 5 | 500 or more | 122 | — | 270 |
| 2mmpPCTPDBq | Example 7 | 500 or more | 132 | — | — |

*—: not observed

As can be observed from Table 1, the materials of embodiments of the present invention have glass transition points exceeding 100° C. and favorable thermophysical properties. Although 2mDBtTPDBq-II includes only meta-phenylene groups, each of 2DBtTPDBq, 2DBtTPDBq-02, 2DBtTPDBq-03, 2DBtTPDBq-04, and 2mmpPCTPDBq includes both a metaphenylene group and a paraphenylene group. It was thus revealed that among compounds having the same molecular mass, a compound whose skeleton has both a metaphenylene group and a paraphenylene group has higher heat resistance.

Example 10

In this example, the thermophysical properties of the heterocyclic compounds of embodiments of the present invention and the lifetimes of elements using the heterocyclic compounds were evaluated.

The evaluation of the thermophysical properties and the lifetimes of the elements was performed for the heterocyclic compounds of embodiments of the present invention that were synthesized in Examples 1 to 8 and the comparative heterocyclic compounds. Note that the comparative heterocyclic compounds are 2-[3'-(dibenzothiophen-4-yl)biphenyl-3-yl]dibenzo[f,h]quinoxaline (abbreviation: 2mDBTBPDBq-II) and 2-[3'-(9-phenyl-9H-carbazol-3-yl)-1,1'-biphenyl-3-yl]dibenzo[f,h]quinoxaline (abbreviation: 2mPCBPDBq), each of which has a smaller number of phenylene groups between the dibenzoquinoxaline ring and the dibenzothiophenyl group or the carbazolyl group and a lower molecular mass than the heterocyclic compounds of embodiments of the present invention. The structural formulae of 2mDBTBPDBq-II and 2mPCBPDBq are shown below.

[Chemical formula 257]

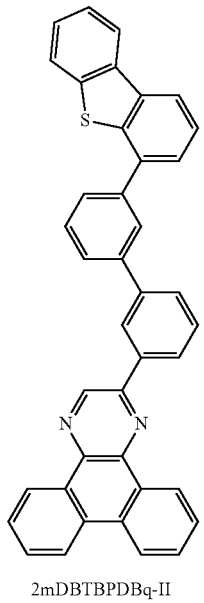

2mDBTBPDBq-II

-continued

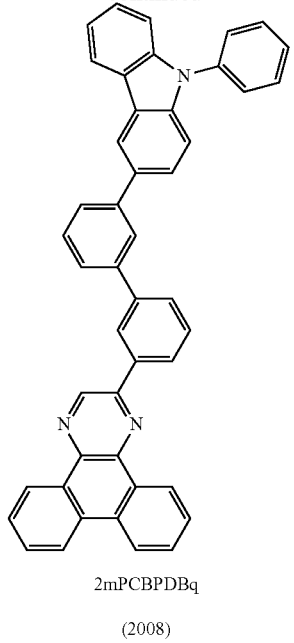

2mPCBPDBq (2008)

<Fabrication of Light-Emitting Elements 1 to 7 and Comparative Light-Emitting Element 8>

To evaluate the thermophysical properties and the lifetimes of elements, light-emitting elements whose EL layers contain the heterocyclic compounds were fabricated. The fabrication steps of the light-emitting elements are described. The light-emitting elements each have the stacked-layer structure illustrated in FIG. 1A.

First, as the first electrode 101, an ITSO film was formed to a thickness of 110 nm over a substrate. The electrode area of the first electrode 101 was set to 4 mm$^2$ (2 mm×2 mm).

Next, the EL layer 103 was formed over the first electrode 101. As the hole-injection layer 111, 1,3,5-tri(dibenzothiophen-4-yl)benzene (abbreviation: DBT3P-II) and molybdenum oxide were deposited by co-evaporation such that the formed layer had a weight ratio of DBT3P-II to molybdenum oxide of 2:1 and a thickness of 20 nm. Note that co-evaporation is an evaporation method in which a plurality of different substances are concurrently vaporized from different evaporation sources. As the hole-transport layer 112, 4-phenyl-4'-(9-phenylfluorene-9-yl)triphenylamine (abbreviation: BPAFLP) was deposited by evaporation to a thickness of 20 nm.

Then, the light-emitting layer 113 was formed. First, the heterocyclic compound, N-(1,1'-biphenyl-4-yl)-9,9-dimethyl-N-[4-(9-phenyl-9H-carbazol-3-yl)phenyl]-9H-fluoren-2-amine (abbreviation: PCBBiF), and (acetylacetonato)bis(6-tert-butyl-4-phenylpyrimidinato)iridium(III) (abbreviation: [Ir(tBuppm)$_2$(acac)]) were deposited by co-evaporation such that the formed layer had a weight ratio of the heterocyclic compound to PCBBiF to [Ir(tBuppm)$_2$(acac)] of 0.7:0.3:0.05 and a thickness of 20 nm. Over the layer, the heterocyclic compound, PCBBiF, and [Ir(tBuppm)$_2$ (acac)] were further deposited by co-evaporation such that the formed layer had a weight ratio of the heterocyclic compound to PCBBiF to [Ir(tBuppm)$_2$(acac)] of 0.8:0.2:0.05 and a thickness of 20 nm. In this manner, the light-emitting layer 113 was formed to have a total thickness of 40 nm. Note that in the light-emitting layer 113, the heterocyclic compound and PCBBiF were host materials and [Ir(tBuppm)$_2$(acac)] was a guest material.

Next, as the electron-transport layer 114, the heterocyclic compound and Bphen were deposited by evaporation in this order over the light-emitting layer 113 to have a thickness of 20 nm and a thickness of 10 nm, respectively. Next, as the electron-injection layer 115, lithium fluoride (LiF) was deposited by evaporation to a thickness of 1 nm.

As the electrode 102, aluminum (Al) was deposited to a thickness of 200 nm.

Next, in a glove box containing a nitrogen atmosphere, each light-emitting element was sealed by fixing a sealing substrate to the substrate provided with the EL layer 103 using a sealant for an organic EL device. Specifically, after the sealant was applied to surround the EL layer 103 over the substrate and the substrate was bonded to the sealing substrate, irradiation with ultraviolet light having a wavelength of 365 nm at 6 J/cm² and heat treatment at 80° C. for 1 hour were performed. Through the above steps, the light-emitting elements were obtained.

<Fabrication of Light-Emitting Element 9 and Comparative Light-Emitting Element 10>

A light-emitting element 9 and a comparative light-emitting element 10 were fabricated by the same method as the light-emitting elements 1 to 7 and the comparative light-emitting element 8 except for the step of forming the light-emitting layer 113.

For the light-emitting layer 113 of each of the light-emitting element 9 and the comparative light-emitting element 10, the heterocyclic compound, PCBBiF, and bis[2-(6-phenyl-4-pyrimidinyl-κN3)phenyl-κC](2,4-pentanedionato-κ²O,O')iridium(III) (abbreviation: Ir(dppm)₂(acac)) were deposited by co-evaporation such that the formed layer had a weight ratio of the heterocyclic compound to PCBBiF to [Ir(dppm)₂(acac)] of 0.7:0.3:0.05 and a thickness of 20 nm. Over the layer, the heterocyclic compound, PCBBiF, and [Ir(dppm)₂(acac)] were further deposited by co-evaporation such that the formed layer had a weight ratio of the heterocyclic compound to PCBBiF to [Ir(dppm)₂(acac)] of 0.8:0.2:0.05 and a thickness of 20 nm. In this manner, the light-emitting layer 113 was formed to have a total thickness of 40 nm. Note that in the light-emitting layer 113, the heterocyclic compound and PCBBiF were host materials and [Ir(dppm)₂(acac)] was a guest material.

The structures of the materials in the EL layers of the light-emitting elements other than the heterocyclic compounds of embodiments of the present invention are shown below.

[Chemical formula 258]

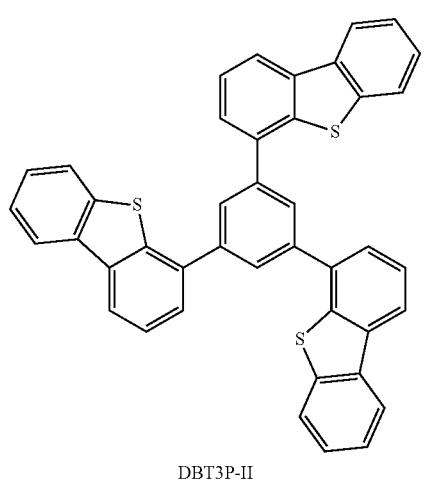

DBT3P-II (i)

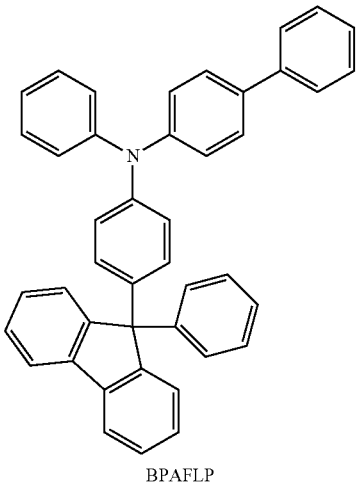

BPAFLP (ii)

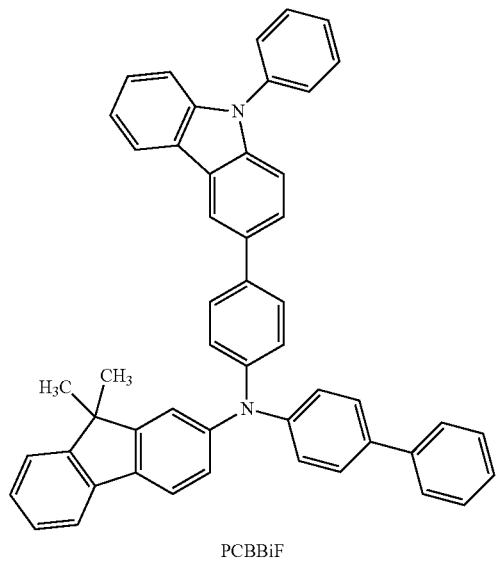

PCBBiF (iii)

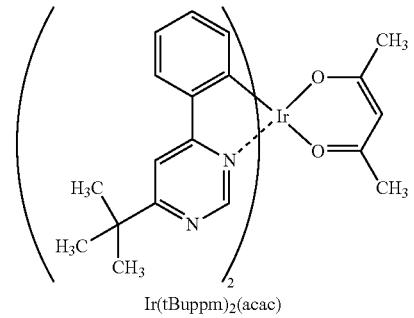

Ir(tBuppm)₂(acac)

(iv)

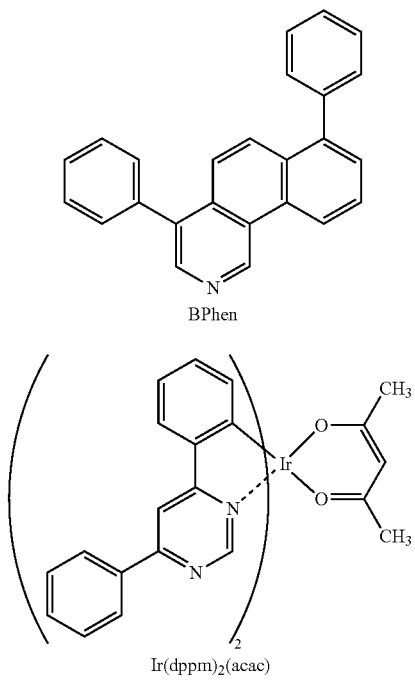

Note that in the light-emitting element 1, 2-[3"-(dibenzothiophen-4-yl)-3,1':3',1"-terphenyl-1-yl]dibenzo[f,h]quinoxaline (abbreviation: 2mDBtTPDBq-II) described in Example 1 was used as the heterocyclic compound in the light-emitting layer 113 and the electron-transport layer 114.

In the light-emitting element 2, 2-[3"-(dibenzothiophen-4-yl)-3,1':4',1"-terphenyl-1-yl]dibenzo[f,h]quinoxaline (abbreviation: 2DBtTPDBq) described in Example 2 was used as the heterocyclic compound in the light-emitting layer 113 and the electron-transport layer 114.

In the light-emitting element 3, 2-[4"-(dibenzothiophen-4-yl)-3,1':4',1"-terphenyl-1-yl]dibenzo[f,h]quinoxaline (abbreviation: 2DBtTPDBq-03) described in Example 3 was used as the heterocyclic compound in the light-emitting layer 113 and the electron-transport layer 114.

In the light-emitting element 4, 2-[4"-(dibenzothiophen-4-yl)-4,1':3',1"-terphenyl-1-yl]dibenzo[f,h]quinoxaline (abbreviation: 2DBtTPDBq-02) described in Example 4 was used as the heterocyclic compound in the light-emitting layer 113 and the electron-transport layer 114.

In the light-emitting element 5, 2-[4"-(dibenzothiophen-4-yl)-3,1':3',1"-terphenyl-1-yl]dibenzo[f,h]quinoxaline (abbreviation: 2DBtTPDBq-04) described in Example 5 was used as the heterocyclic compound in the light-emitting layer 113 and the electron-transport layer 114.

In the light-emitting element 6, 2-[3'''-(dibenzothiophen-4-yl)-3,1':3',1'':3'',1'''-quaterphenyl-1-yl]dibenzo[f,h]quinoxaline (abbreviation: 2mDBtQPDBq-II) described in Example 6 was used as the heterocyclic compound in the light-emitting layer 113 and the electron-transport layer 114.

In each of the light-emitting elements 7 and 9, 2-[4"-(9-phenyl-9H-carbazol-3-yl)-1,1':3',1"-terphenyl-3-yl]dibenzo[f,h]quinoxaline (abbreviation: 2mmpPCTPDBq) described in Example 7 was used as the heterocyclic compound in the light-emitting layer 113 and the electron-transport layer 114.

In the comparative light-emitting element 8, 2-[3'-(dibenzothiophen-4-yl)biphenyl-3-yl]dibenzo[f,h]quinoxaline (abbreviation: 2mDBTBPDBq-II) was used as the heterocyclic compound in the light-emitting layer 113 and the electron-transport layer 114.

In the comparative light-emitting element 10, 2-[3'''-(dibenzothiophen-4-yl)-3,1':3',1'':3'',1'''-quaterphenyl-1-yl]dibenzo[f,h]quinoxaline (abbreviation: 2mDBtQPDBq-II) described in Example 9 was used as the heterocyclic compound in the light-emitting layer 113 and the electron-transport layer 114.

Table 2 and Table 3 list the structures of the elements described in this example.

TABLE 2

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 1 | ITO (110 nm) | DBT3P-II: MoOx (4:2 20 nm) | BPAFLP (20 nm) | * | 2mDBtTPDBq-II (20 nm) | Bphen (10 nm) | LiF (1 nm) | Al (200 nm) |
| Light-emitting element 2 | ITO (110 nm) | DBT3P-II: MoOx (4:2 20 nm) | BPAFLP (20 nm) | ** | 2DBtTPDBq (20 nm) | Bphen (10 nm) | LiF (1 nm) | Al (200 nm) |
| Light-emitting element 3 | ITO (110 nm) | DBT3P-II: MoOx (4:2 20 nm) | BPAFLP (20 nm) | *** | 2DBtTPDBq-03 (20 nm) | Bphen (10 nm) | LiF (1 nm) | Al (200 nm) |
| Light-emitting element 4 | ITO (110 nm) | DBT3P-II: MoOx (4:2 20 nm) | BPAFLP (20 nm) | **** | 2DBtTPDBq-02 (20 nm) | Bphen (10 nm) | LiF (1 nm) | Al (200 nm) |
| Light-emitting element 5 | ITO (110 nm) | DBT3P-II: MoOx (4:2 20 nm) | BPAFLP (20 nm) | ***** | 2DBtTPDBq-04 (20 nm) | Bphen (10 nm) | LiF (1 nm) | Al (200 nm) |
| Light-emitting element 6 | ITO (110 nm) | DBT3P-II: MoOx (4:2 20 nm) | BPAFLP (20 nm) | ****** | 2mDBtQPDBq-II (20 nm) | Bphen (10 nm) | LiF (1 nm) | Al (200 nm) |
| Light-emitting element 7 | ITO (110 nm) | DBT3P-II: MoOx (4:2 20 nm) | BPAFLP (20 nm) | ******* | 2mmpPCTPDBq (20 nm) | Bphen (10 nm) | LiF (1 nm) | Al (200 nm) |

TABLE 2-continued

| | First electrode | Hole-injection layer | Hole-transport layer | Light-emitting layer | Electron-transport layer | | Electron-injection layer | Second electrode |
|---|---|---|---|---|---|---|---|---|
| Comparative light-emitting element 8 | ITO (110 nm) | DBT3P-II: MoOx (4:2 20 nm) | BPAFLP (20 nm) | ******** | 2mDBTBPDBq-II (20 nm) | Bphen (10 nm) | LiF (1 nm) | Al (200 nm) |

*2mDBtTPDBq-II:PCBBiF:[Ir(tBuppm)₂(acac)] (0.7:0.3:0.05 20 nm\0.8:0.2:0.05 20 nm)
**2DBtTPDBq:PCBBiF:[Ir(tBuppm)₂(acac)] (0.7:0.3:0.05 20 nm\0.8:0.2:0.05 20 nm)
***2DBtTPDBq-03:PCBBiF:[Ir(tBuppm)₂(acac)] (0.7:0.3:0.05 20 nm\0.8:0.2:0.05 20 nm)
****2DBtTPDBq-02:PCBBiF:[Ir(tBuppm)₂(acac)] (0.7:0.3:0.05 20 nm\0.8:0.2:0.05 20 nm)
*****2DBtTPDBq-04:PCBBiF:[Ir(tBuppm)₂(acac)] (0.7:0.3:0.05 20 nm\0.8:0.2:0.05 20 nm)
******2mDBtQPDBq-II:PCBBiF:[Ir(tBuppm)₂(acac)] (0.7:0.3:0.05 20 nm\0.8:0.2:0.05 20 nm)
*******2mmpPCTPDBq:PCBBiF:[Ir(tBuppm)₂(acac)] (0.7:0.3:0.05 20 nm\0.8:0.2:0.05 20 nm)
********2mDBTBPDBq-II:PCBBiF:[Ir(tBuppm)₂(acac)] (0.7:0.3:0.05 20 nm\0.8:0.2:0.05 20 nm)

TABLE 3

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 9 | ITO (110 nm) | DBT3P-II: MoOx (4:2 20 nm) | BPAFLP (20 nm) | ***** **** | 2mmpPCTPDBq (20 nm) | Bphen (10 nm) | LiF (1 nm) | Al (200 nm) |
| Comparative light-emitting element 10 | ITO (110 nm) | DBT3P-II: MoOx (4:2 20 nm) | BPAFLP (20 nm) | ***** ***** | 2mPCBPDBq (20 nm) | Bphen (10 nm) | LiF (1 nm) | Al (200 nm) |

*****2mmpPCTPDBq:PCBBiF:Ir(dppm)₂(acac) (0.7:0.3:0.05 20 nm\0.8:0.2:0.05 20 nm)
****
*****2mPCBPDBq:PCBBiF:Ir(dppm)₂(acac) (0.7:0.3:0.05 20 nm\0.8:0.2:0.05 20 nm)
*****

<Characteristics of Light-Emitting Elements 1 to 7 and Comparative Light-Emitting Element 8>

Table 4 lists the characteristics of the light-emitting elements 1 to 7 and the comparative light-emitting element 8. As can be seen from Table 4, the light-emitting elements 1 to 7 and the comparative light-emitting element 8 turned out to have favorable characteristics.

TABLE 4

| | Voltage (V) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|
| Light-emitting element 1 | 2.8 | 0.80 | (0.41, 0.58) | 900 | 115 | 130 | 30 |
| Light-emitting element 2 | 2.8 | 1.01 | (0.43, 0.56) | 1100 | 109 | 123 | 29 |
| Light-emitting element 3 | 2.8 | 0.84 | (0.42, 0.57) | 900 | 108 | 121 | 29 |
| Light-emitting element 4 | 2.7 | 1.08 | (0.42, 0.57) | 1100 | 103 | 120 | 27 |
| Light-emitting element 5 | 2.8 | 1.00 | (0.41, 0.58) | 1100 | 111 | 124 | 29 |
| Light-emitting element 6 | 3.0 | 1.11 | (0.43, 0.56) | 1100 | 101 | 106 | 27 |
| Light-emitting element 7 | 2.8 | 0.70 | (0.40, 0.59) | 800 | 114 | 128 | 30 |
| Comparative light-emitting element 8 | 2.8 | 0.88 | (0.41, 0.58) | 1000 | 112 | 126 | 29 |

Figure 53:
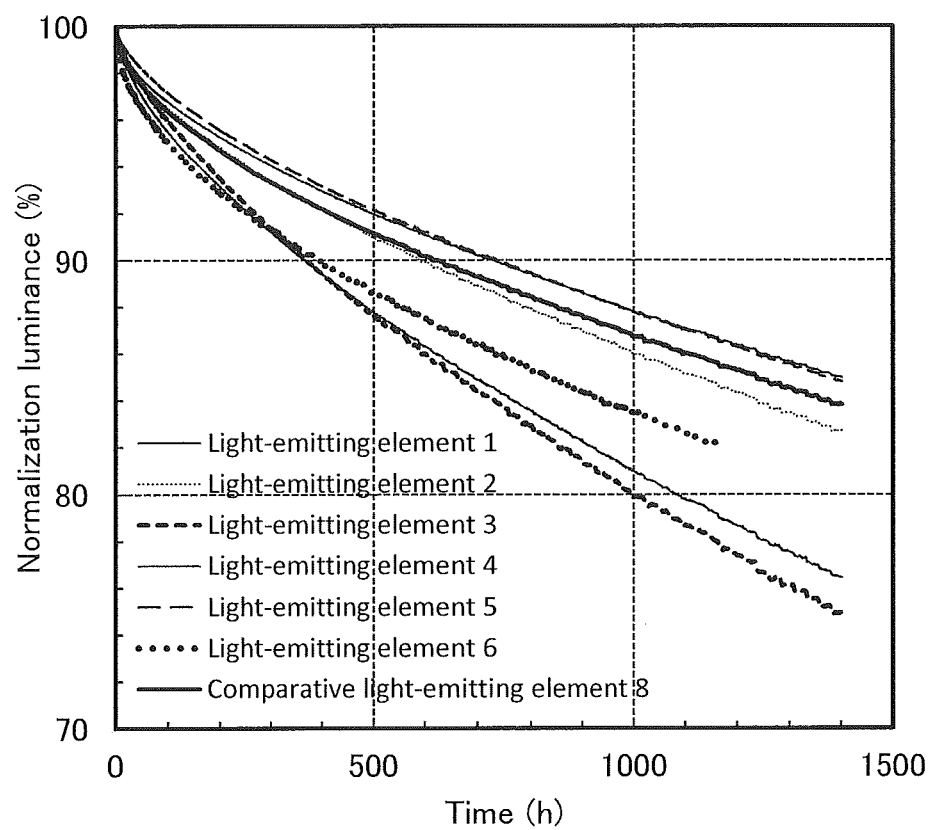
FIG. 53 shows results of reliability tests performed on light-emitting elements 1 to 6 and a comparative light-emitting element 8.

FIG. 53 shows the results of constant current driving tests performed on the light-emitting elements 1 to 6 and the comparative light-emitting element 8 at an initial luminance of 5000 cd/m². As can be seen from FIG. 53, the light-emitting elements 1 to 6 and the comparative light-emitting element 8 turned out to have high reliability. However, the slopes of the decay curves of the light-emitting elements 3 and 4 are a little sharp. Each of 2DBtTPDBq-03 used as the host material in the light-emitting element 3 and 2DBtTPDBq-02 used as the host material in the light-emitting element 4 has a molecular structure including one metaphenylene group and two paraphenylene groups as arylene groups. Meanwhile, 2mDBtTPDBq-II, 2DBtTPDBq, and 2DBtTPDBq-04 are used in the light-emitting layers in the light-emitting elements 1, 2, and 5, respectively, with extremely high reliability. These three materials each have a molecular structure including one or no paraphenylene group. Accordingly, to achieve both high reliability and high heat resistance, one paraphenylene group and two metaphenylene groups are preferably included in a molecular structure. Furthermore, a metabiphenyl-diyl group is preferably formed in such a manner that two metaphenylene groups are bonded successively from the dibenzo[f,h]quinoxaline skeleton side because higher reliability can be achieved and an element having higher reliability than the comparative light-emitting element 8 can be provided. In the case where a metabiphenyl-diyl group is formed in such a manner that two metaphenylene groups are bonded successively from the dibenzo[f,h]quinoxaline skeleton side, the third phenylene group from the dibenzo[f,h]quinoxaline skeleton side is more preferably bonded at a para-position because high heat resistance can be achieved.

<Characteristics of Light-Emitting Element 9 and Comparative Light-Emitting Element 10>

Table 5 lists the characteristics of the light-emitting element 9 and the comparative light-emitting element 10. As can be seen from Table 5, the light-emitting element 9 and the comparative light-emitting element 10 turned out to have favorable characteristics.

FIG. 55 shows the measurement results. Note that the horizontal axis of the graph represents the total preservation time (h) for which the light-emitting elements were put in the environment at 100° C. The vertical axis of the graph represents the retention rate (%) of the external quantum efficiency with the maximum external quantum efficiency at the start of the evaluation of the thermophysical properties assumed to be 100%. Note that the initial external quantum efficiencies of the elements were substantially the same, i.e., approximately 28%.

As shown in FIG. 55, the comparative light-emitting element 8 kept the initial external quantum efficiency for 5 hours from the start of preservation, but subsequently, the external quantum efficiency sharply decreased and reached 0% after a lapse of 25 hours. In contrast, the light-emitting element 1 kept the initial external quantum efficiency for 25 hours from the start of preservation, exhibiting thermophysical properties higher than those of the comparative light-emitting element 8. In addition, the light-emitting elements 2 and 5 substantially kept the initial external quantum efficiency even after 50 hours elapsed, indicating favorable thermophysical properties. Furthermore, the light-emitting elements 3 and 4 showed the retention rate higher than or equal to 85% even after 1000 hours elapsed, which means

TABLE 5

| | Voltage (V) | Current density ($mA/cm^2$) | Chromaticity (x, y) | Luminance ($cd/m^2$) | Current efficiency (cd/A) | Power efficiency (lm/W) | External quantum efficiency (%) |
|---|---|---|---|---|---|---|---|
| Light-emitting element 9 | 3.1 | 1.50 | (0.55, 0.44) | 1100 | 76 | 77 | 29 |
| Comparative light-emitting element 10 | 3 | 1.34 | (0.55, 0.44) | 1100 | 79 | 83 | 31 |

Figure 54:
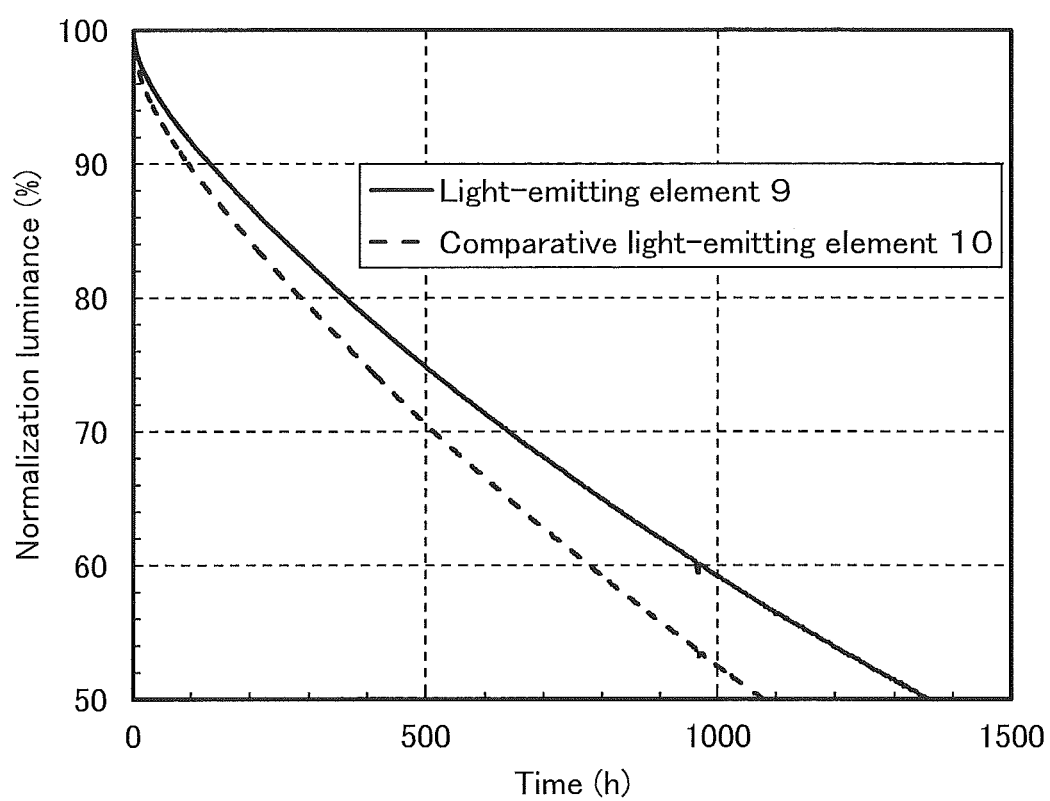
FIG. 54 shows results of reliability tests performed on a light-emitting element 9 and a comparative light-emitting element 10.

FIG. 54 shows the results of driving tests performed on the light-emitting element 9 and the comparative light-emitting element 10 at a constant current of 2 mA. From FIG. 54, it is found that $LT_{50}$ of each of the light-emitting element 9 and the comparative light-emitting element 10 exceeds 1000 hours, which means high reliability. Here, the slope of the decay curve of the light-emitting element 9 is gentler than that of the decay curve of the comparative light-emitting element 10; accordingly, the light-emitting element 9 has higher reliability than the comparative light-emitting element 10. As described above, it was thus shown that as the divalent group that links the dibenzo[f,h]quinoxaline skeleton and the carbazolyl group in the molecular structure, a terphenyl-diyl group in which three phenylene groups are successively bonded is preferred to a biphenyl-diyl group in which two phenylene groups are successively bonded in order to achieve high reliability.

<Evaluation of Heat Resistance>

Tests for evaluating thermophysical properties were conducted on the fabricated light-emitting elements. First, the light-emitting elements were preserved in an environment at 100° C. for a predetermined time. Then, the light-emitting elements were taken out of the environment to be cooled down to room temperature, and the external quantum efficiencies of the light-emitting elements were measured. After the measurement, the cycle of returning the light-emitting elements to the environment at 100° C., preserving them for a predetermined time, taking them out, and measuring the external quantum efficiencies was repeated.

extremely high thermophysical properties. The molecular structures of 2DBtTPDBq-03 and 2DBtTPDBq-02, which were respectively used as the host materials in the light-emitting element 3 and the light-emitting element 4, each have two metaphenylene groups and one paraphenylene group as arylene groups. Such a structure tends to result in high heat resistance. In the case where a molecular structure includes a terphenylene structure (a structure in which three phenylene groups are successively bonded), specifically a structure having two metaphenylene groups and one paraphenylene group as arylene groups, the whole molecule probably has high planarity and Tg also tends to be high. That is, a molecular structure with higher planarity is favorable in terms of heat resistance.

The heterocyclic compound of one embodiment of the present invention includes three or more phenylene groups at the middle and has a higher molecular mass than the heterocyclic compound used in the comparative light-emitting element 8. Therefore, a light-emitting element using the heterocyclic compound of one embodiment of the present invention can have favorable thermophysical properties.

Furthermore, when a light-emitting layer includes a compound with a high molecular mass, in general, the refractive index increases and thus, the external quantum efficiency tends to decrease. However, the light-emitting elements 1 to 5 and the comparative light-emitting element 8 showed substantially the same initial external quantum efficiency. It was thus confirmed that by being included in a light-emitting layer of a light-emitting element, the heterocyclic compound of one embodiment of the present invention enables the light-emitting element to have favorable thermophysical properties without causing a decrease in the external quantum efficiency of the light-emitting element.

REFERENCE NUMERALS

101: first electrode, 102: second electrode, 103: EL layer, 111: hole-injection layer, 112: hole-transport layer, 113: light-emitting layer, 114: electron-transport layer, 115: electron-injection layer, 501: first electrode, 502: second electrode, 511: first light-emitting unit, 512: second light-emitting unit, 513: charge generation layer, 601: driver circuit portion (source side driver circuit), 602: pixel portion, 603: driver circuit portion (gate side driver circuit), 604: sealing substrate, 605: sealing material, 607: space, 608: lead wiring, 609: FPC (flexible printed circuit), 610: element substrate, 611: switching TFT, 612: current controlling TFT, 613: first electrode, 614: insulator, 616: EL layer, 617: second electrode, 618: light-emitting element, 623: n-channel TFT, 624: p-channel TFT, 901: housing, 902: liquid crystal layer, 903: backlight, 904: housing, 905: driver IC, 906: terminal, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: interlayer insulating film, 1021: interlayer insulating film, 1022: electrode, 1024: electrode, 1025: partition wall, 1028: EL layer, 1029: electrode, 1030: black layer, 1031: sealing substrate, 1032: sealant, 1037: interlayer insulating film, 1040: pixel portion, 1041: driver circuit portion, 1042: peripheral portion, 2001: housing, 2002: light source, 3001: lighting device, 3002: display device, 5000: display region, 5001: display region, 5002: display region, 5003: display region, 5004: display region, 5005: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7401: housing, 7402: display portion, 7403: operation button, 7404: external connection port, 7405: speaker, 7406: microphone.

This application is based on Japanese Patent Application serial no. 2015-209351 filed with Japan Patent Office on Oct. 23, 2015, the entire contents of which are hereby incorporated by reference.

The invention claimed is:

1. A heterocyclic compound represented by Formula (G8-1):

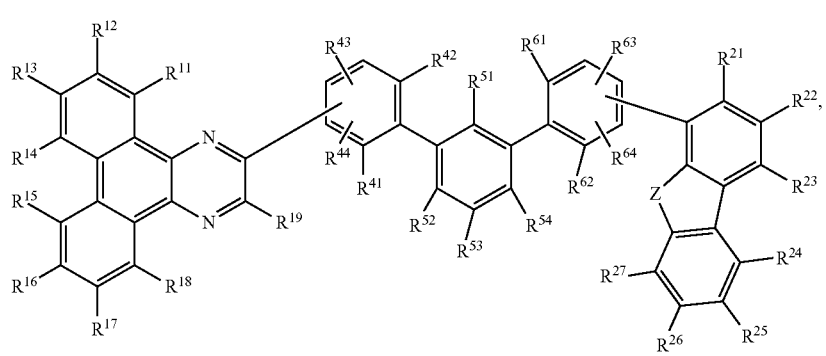

(G8-1)

wherein the dibenzo[f,h]quinoxaline group is bonded to the para position of the benzene ring bonding to $R^{41}$ to $R^{44}$ from the benzene ring bonding to $R^{51}$ to $R^{54}$, wherein the condensed ring comprising Z is bonded to the para position of the benzene ring bonding to $R^{61}$ to $R^{64}$ from the benzene ring bonding to $R^{51}$ to $R^{54}$, wherein Z represents sulfur, and wherein each of $R^{11}$ to $R^{19}$, $R^{21}$ to $R^{27}$, $R^{41}$ to $R^{44}$, $R^{51}$ to $R^{54}$, and $R^{61}$ to $R^{64}$ independently represents hydrogen, an alkyl group having 1 to 4 carbon atoms, or a substituted or unsubstituted aryl group having 6 to 13 carbon atoms.

2. A light-emitting device comprising:
a light-emitting portion; and
a substrate,
wherein the light-emitting portion comprises a light-emitting element comprising the heterocyclic compound according to claim 1.

3. An electronic device comprising:
a display portion; and
an antenna, a battery, a housing, a speaker, a microphone, or an operation key,
wherein the display portion comprises the light-emitting device according to claim 2.

4. A lighting device comprising:
the light-emitting device according to claim 2; and
a housing, a connection terminal, or a protective cover.

5. The heterocyclic compound according to claim 1, wherein each of $R^{11}$ to $R^{19}$, $R^{21}$ to $R^{27}$, $R^{41}$ to $R^{44}$, $R^{51}$ to $R^{54}$, and $R^{61}$ to $R^{64}$ is independently represented by any of Formulae (S01) to (S25):

(S01)

(S02)

(S03)

(S04)

-continued
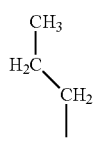 (S05)
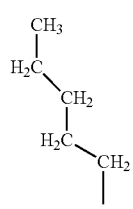 (S06)
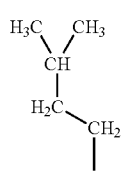 (S07)
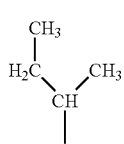 (S08)
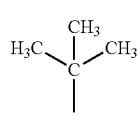 (S09)
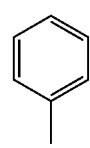 (S10)
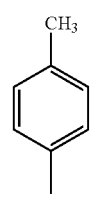 (S11)
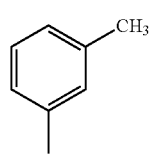 (S12)
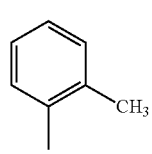 (S13)
-continued
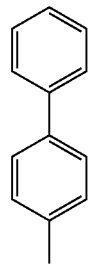 (S14)
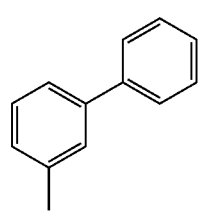 (S15)
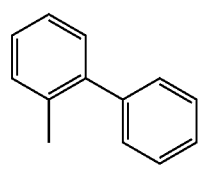 (S16)
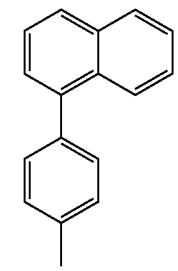 (S17)
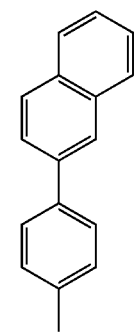 (S18)
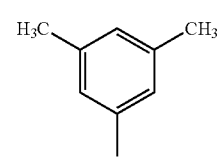 (S19)

605
-continued (S20) 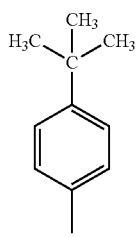

(S21) 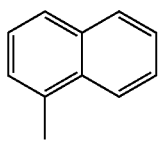

(S22) 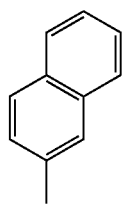

(S23) 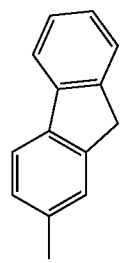

(S24) 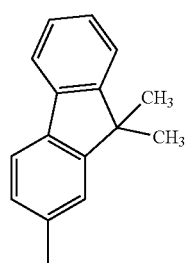

606
-continued (S25) 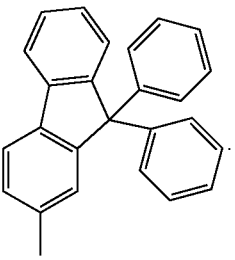

6. A heterocyclic compound represented by Formula (G1):

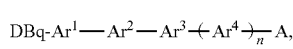

wherein A represents any of a substituted or unsubstituted dibenzothiophenyl group,
wherein DBq represents a substituted or unsubstituted dibenzo[f,h]quinoxalinyl group,
wherein n is 0,
wherein each of $Ar^1$, $Ar^2$ and $Ar^3$ independently represents one of a substituted or unsubstituted meta-phenylene group and a substituted or unsubstituted para-phenylene group, and
wherein $Ar^1$ is a meta-phenylene group, $Ar^2$ is a para-phenylene group, and $Ar^3$ is a meta-phenylene group in Formula (G1), or $Ar^1$ is a para-phenylene group, $Ar^2$ is a meta-phenylene group, and $Ar^3$ is a para-phenylene group in Formula (G1).

7. The heterocyclic compound according to claim 6, wherein $Ar^1$ represents a para-phenylene group.

8. The heterocyclic compound according to claim 6, wherein the heterocyclic compound is 2-[3"-(dibenzothiophen-4-yl)-3,1':4',1"-terphenyl-1-yl]dibenzo[f,h]quinoxaline.

9. A light-emitting device comprising:
a light-emitting portion; and
a substrate,
wherein the light-emitting portion comprises a light-emitting element comprising the heterocyclic compound according to claim 6.

10. The light-emitting device according to claim 9, wherein the heterocyclic compound is included in a light-emitting layer of the light-emitting element.

11. The light-emitting device according to claim 9, wherein the heterocyclic compound is included in an electron-transport layer.

12. An electronic device comprising:
a display portion; and
an antenna, a battery, a housing, a speaker, a microphone, or an operation key,
wherein the display portion comprises the light-emitting device according to claim 9.

13. A lighting device comprising:
the light-emitting device according to claim 9; and
a housing, a connection terminal, or a protective cover.

* * * * *